(12) United States Patent
Barry et al.

(10) Patent No.: US 7,998,671 B2
(45) Date of Patent: Aug. 16, 2011

(54) METHODS OF DETECTING PROSTATE CANCER USING BAP28-RELATED BIALLELIC MARKERS

(75) Inventors: Caroline Barry, Cheptainville (FR);
Lydie Bougueleret, Petit-Lancy (FR);
Ilya Chumakov, Vaux-le Penil (FR);
Annick Cohen-Akenine, Paris (FR)

(73) Assignee: Merck Serono Biodevelopment, Evry (FR)

( * ) Notice: Subject to any disclaimer, the term of this patent is extended or adjusted under 35 U.S.C. 154(b) by 817 days.

(21) Appl. No.: 11/776,964

(22) Filed: Jul. 12, 2007

(65) Prior Publication Data

US 2008/0168574 A1    Jul. 10, 2008

Related U.S. Application Data

(63) Continuation of application No. 09/603,665, filed on Jun. 23, 2000, now abandoned.

(60) Provisional application No. 60/176,880, filed on Jan. 18, 2000, provisional application No. 60/141,323, filed on Jun. 25, 1999.

(51) Int. Cl.
*C12Q 1/68* (2006.01)
*C07H 21/04* (2006.01)

(52) U.S. Cl. ............... 435/6; 536/23.1; 536/23.5

(58) Field of Classification Search .............. None
See application file for complete search history.

(56) References Cited

U.S. PATENT DOCUMENTS

| 5,696,234 | A | 12/1997 | Zurawski et al. |
| 5,811,267 | A | 9/1998 | Ring |
| 6,703,491 | B1 | 3/2004 | Homburger et al. |
| 6,759,192 | B1 * | 7/2004 | Blumenfeld et al. ............. 435/6 |

FOREIGN PATENT DOCUMENTS

| WO | WO 98/12327 A2 | 3/1998 |
| WO | WO 9964590 A1 * | 12/1999 |

OTHER PUBLICATIONS

Carninci, P. et al. "High-Efficiency Full-Length cDNA Cloning" *Methods in Enzymology*, 1999, pp. 19-44, vol. 303.
Eliasof, S. et al. "Localization and Function of Five Glutamate Transporters Cloned from the Salamander Retina" *Vision Research*, 1998, pp. 1443-1454, vol. 38.
Okano, S. et al. "Cloning of a Novel Ubiquitin-Conjugating Enzyme (E2) Gene from the Ciliate *Paramecium Tetraurelia*" *FEBS Letters*, 1996, pp. 1-4, vol. 391.
Vidalain, P.O. et al. "Increasing Specificity in High-Throughput Yeast Two-Hybrid Experiments" *Methods*, 2004, pp. 363-370, vol. 32.
GENBANK AA098827, Aug. 1, 1997.

(Continued)

*Primary Examiner* — Diana Johannsen
(74) *Attorney, Agent, or Firm* — Saliwanchik, Lloyd & Eisenschenk

(57) ABSTRACT

The present invention is directed to BAP28 polypeptides. BAP28 cDNA sequences encoding BAP28 polypeptides, to the genomic DNA sequence of the BAP28 gene as well as to regulatory regions located at the 5'- and 3'-ends of the BAP28 coding region. The invention also deals with antibodies directed specifically against such polypeptides that are useful as diagnostic reagents. The invention further encompasses biallelic markers of the BAP28 gene useful in genetic analysis. The invention concerns an association of the BAP28-related biallelic markers with prostate cancer. Therefore, the invention contemplates the diagnostic and treatment methods of prostate cancer.

1 Claim, 30 Drawing Sheets

PCTA-1

OTHER PUBLICATIONS

GENBANK AA320776, Apr. 19, 1997.
GENBANK AA357743, Apr. 21, 1997.
GENBANK AA424101, Oct. 16, 1997.
GENBANK AA437086, May 30, 1997.
GENBANK AA460031, Jun. 9, 1997.
GENBANK AA681616, Dec. 5, 1997.
GENBANK AA814857, Mar. 5, 1998.
GENBANK AA814859, Mar. 5, 1998.
GENBANK AA992680, Aug. 27, 1998.
GENBANK AI023607, Aug. 27, 1998.
GENBANK AI114709, Nov. 11, 1999.
GENBANK AI150773, Sep. 30, 1998.
GENBANK AI277866, Jan. 29, 1999.
GENBANK AI348668, Feb. 1, 1999.
GENBANK AI356180, Feb. 16, 1999.
GENBANK AI582623, Apr. 6, 1999.
GENBANK AI738790, Dec. 21, 1999.
GENBANK AI827817, Dec. 19, 1999.
GENBANK AI905672, Mar. 30, 2000.
GENBANK AK001857, Feb. 22, 2000.
GENBANK AL040338, Feb. 29, 2000.
GENBANK AV120680, Jul. 1, 1999.
GENBANK AW315340, Jan. 8, 2001.
GENBANK AW325866, Jul. 10, 2000.
GENBANK AW353291, Jul. 14, 2000.
GENBANK AW389900, Feb. 4, 2000.
GENBANK AW423202, Feb. 9, 2000.
GENBANK AW450486, Feb. 17, 2000.
GENBANK AW481398, Jul. 7, 2000.
GENBANK AW858897, May 19, 2000.
GENBANK AW858960, May 19, 2000.
GENBANK AW962967, Jun. 1, 2000.
GENBANK D77458, Oct. 7, 1996.
GENBANK N77431, Jan. 30, 1997.
GENBANK T85649, Mar. 17, 1995.

* cited by examiner

Alternative cDNAs of PCTA-1

| 0 | 1 | 2 | 3 | 4 | 5 | 6 | 7 | 8 | 9 |

| 0 | 1 | 2 | 3 | 4 | 5 | 6 | 6$^b$ | 7 | 8 | 9 |

| 0 | 1 | 2 | 3 | 4 | 5 | 6 | 7 | 8 | 9$^{bis}$ | 9$^{ter}$ |

| A | 0 | 1 | 2 | 3 | g$^{bis}$ | g$^{ter}$ |

Alternative 5' end of PCTA-1 cDNAs

| C | A | .... |

| B | 0 | 1 | 2 | .... |

| A | 1 | 2 | .... |

| A | D | 0 | 1 | 2 | .... |

```
H    -MTSLAQQLQRLALPQSDASLLSRD----EVASLLFDPKEAATIDRDTAFAIGCTGLEEL
D    MSTALAQQLQKLAAPQSSVTLADAR----SRASILFDPKEAATKDRRSIYEIGLTGLQEL
A    MSSSIVSQLQALKSVLQADTEPSKRP--FTRPSILFSPKEAADFDIESIYELGLKGLEVL
S    MASSLQKQLKNIQSNNVLKINKIRR-----APSLLYDPKVAADMDLEEIYVTAVSGFHEL
Y    -MSSLSDQLAQVASNNATVALDRKRRQKLHSASLIYNSKTAATQDYDFIFENASKALEEL
C    MATSLTSQLENLRTSAARHLTVEKR-----HVSLLFDRKEANKLSNETAHRIGVAGLEQM
            ::: .**    :              *::: . * *       .  .:   :

H    LGIDPSFE-QFEAPLFSQLAKTLERSVQTKAVNKQLDENISLFLIHLSPYFLLKPAQKCL
D    TDFNPAFK-EFQLTLFDEATLTLERSVELPEINKMLDAAIAKFLRLLSPYLLLRPAHMAF
A    GNKDERFK-NYMNDLFSHKSKEIDRELLGKEENARIDSSISSYLRLLSGYLQFRASLETL
S    AVHEPRLL-YFEKTLLGEQSVQVDRVLLNRTENEKIDLECVQILRLLAPFFTEKNALKVL
Y    SQIEPKFA-IFSRTLFSESSISLDRNVQTKEEIKDLDNAINAYLLLASSKWYLAPTLHAT
C    KRIDPVFDTEFANDLFSEERVDFVRSMLEKGANEELNKQIEKLLLELSPYLQHFACQQVL
            :     :     *:..    . * :        ::       *     :

H    EWLIHRFHIHLYNQDSLIACVLPYHETRIFVRVIQLLKINNSKHR-WFWLLPVKQSGVPL
D    EWLLRRFQVHEYNRSEVMALILPYHETMIFVQIVKTMRLRSSDGD-WYWLRPLQRPGVPL
A    EYLIRRYKIHIYNLEDVVLCALPYHDTHAFVRIVQLLSTGNSK---WKFLDGVKNSGAPP
S    EWLIRRFSIHEYVSDEFILSFLPFHDHPFFARILGCSKPKSRP---LLFLENAIKMPVTL
Y    EWLVRRFQIHVKNTEMLLLSTLNYYQTPVFKRILSIIKLPPLF----NCLSNFVRSEKPP
C    EFLIHTYQIYSFNAETLLLTFLPFHETKVYSRLLRILDFDWKRSKEWQFMQQFTKTETPI
      *:*::  : ::      . .:    * :::    . :::              :  .

H    AKGTLITHCYK-DLGFMDFICSLVTKSVKVFAEYPGSSAQLRVLLAFYASTIVSALVAAE
D    AKTAIINRAAS-NPAFLGFICQSTQKAVKELGPR---AHQLQAQINFYATVVVGALQTAK
A    PRSVIVQQCIR-DKQVLEALCDYASR-TKKYQPS------KPV-VSFSTAVVVGVLGSVP
S    SRADIVHALSR-DKEFFAMFAQFVQNTAESHNMY-------PELARFWAGTMMEVLVAWH
Y    TALTMIKLFN--DMDFLKLYTSYLDQCIKHNATY-------TNQLLFTTCCFINVVAFNS
C    PFTSIARATLSSKHSIITCITDHIRHAVEIVGSD-YLEIKHPILFNFHAKILLSMFTDPE
       . :          .:   .  .:         :                *  :  .: .

H    D-VSDNIIAKLFPYIQKGLKS---SLPDYRAATYMIICQISVKVTMENTFVNSLASQIIK
D    P-LQDWHITTILESLLRGLIS---DNIDFMAAAYVIVAQLVSRTKLKSKVCNALLERVAN
A    T-VDGDIVKTILPFVDSGLQSGVKGCLDQQAGALMVVGMLANRAVLNTNLIKRLMRSIID
S    SSNEDPNVLLDRFFLRVSYAVSYVSSIDFQIAGFMLLSSIAASLPLSPSIIPPLVSAITD
Y    N-NDEKLNQLVPILLEISAKLLASKSKDCQIAAHTILVVFATALPLKKTIILAAMETILS
C    K-VDEMMLAKLMPFIENGIKS---PMKSFRYSAMVVISQLVLTVKLKDEVLNSMCKLLIT
              .          :   ,         ::  :    :.    :

H    T-LTKIPSLIKDGLSCLIVLLQRQKPESLGKKPFPHLCNVPDLITILHGISE-TYDVSPL
D    CPFERLHSESLLLLVCIYGKQQAALP-HFKPETILNLVGKKWLISTLSSLAKGNIAIQSI
A    I--GREHAKE------------SSDP-HSLRLSLMALINFVQLQSVDLIPRK--------
S    R----LSFDN------------IKP---ALICVGHLLQFCSSFEFDHEQLE--------
Y    NLDAKEAKHS-----------ALLTICKLFQTLKGQGNVDQLPSKIFKLFD--------
C    K----MRSDT----------------AAASLSTLMVVFQQQNVQSLSKN--------
                                           .    .

H    LRYMLPHLVVSIIHHVTG--EETEGMDGQIYKRHLEAILTKISLKNNLDHLLAS-LLFEE
D    CMPLMTGAVAAIRDDDASSNSCKLFLDNLLSEVPMPKPTAQQLINCFLDTYVETAIDAPE
A    ----ALDLFNEISSSDDK---CCEVLASIIETVP---------VSNLVDHLISK-VFSLC
S    K---LESFGASSLLIELS----QEHRLDEFFVSYW---------VS-----LIKS-RKQKD
Y    ----SKFDTVSILTFLDK--EDKPVCDKFITSYT----------RS--IARYDRS--KLNI
C    --------TLKKLLRHEEG--IDVWKILKELSERT---------DT-----TKFFNVLWKE
                     :                                 .
```

Figure 3 (following)

```
H    YISYSSQEE------MDSN-KVSLLNEQFLPLIRLLESK-YPRTLDVVLEEHLKEIAD--L
D    PMETNSNEDDDTIVIDSDDEIETEKTTFQAWYSTYLEK-LERRYPEAFDLSVKEALR--S
A    MTQYQKNSD-----FRSS----TSGSWAKKFLVVVSKK-YPAELRAAVPKFLEATEVQ-S
S    KKRLISLLD-----TSIS-QIRVTHEQAKFLLSVIPVN-QDFKALQSYRRILDSVIQP-E
Y    ILSLLKKIR-----LERY-EVRLIITDLIYLSEILEDKSQLVELFEYFISINEDLVLK-C
C    LIVLSKDAES----EDNTLAIDVLIETIEDASILTGDQ-AGTILKLILQEGMDGNIFDNK

H    KKQELFHQFVSLSTSGGKYQFLADSDTSLMLSLNHPLAPVRILAMNHLKKIMKTSKEG-V
D    KSSTSNRQKALKLALGFRLNTTDEKAKHAYEKLYHYSADWRLSAVQKLLQNLNVTKKRER
A    KKEDLKLEMLSCMLDGNSDMSHPFVDSKLWFRLHHPRAAVRCAALSSLNGVLKDDSSKAE
S    RKEGKLDNLINTLQDKKKSSTFSKKDREVLLKKIS-----EIDSQTSFEQCLAYADSAAD
Y    LKSLGLTGELFEIRLTTSLFTNADVNTDIVKQLSDPVETTKKDTASFQTFLDKHSELINT
C    KKLKSNIRAIGMRFAKQFDAIHAELKAKDKKTLKNVLKEYQIEDIVQFASEAVAATQSEE

H    DESFIKEAVLARLGDDNIDVVLSAISA-FEIFKEHFSSEVTISNLLNLFQRAELSKNGEW
D    SVKLLQECLPDRINDDSGAVVSTLLSLPTEELAEMLGPLPLAQTLCHLLYRAQSEKDEEW
A    NLVTIQDAILRQLWDDDLAVVQAALSF--DKLPNIITSSGLLDALLHVVKRCVGILVSGV
S    LDSSVFISLLSKFG-DKIPFLLFCIAN--------GSERIIILSLIELRKTIEENKDVDY
Y    TNVSMLTETGERYK-KVLSLFTEAIGK----G--YKASSFLTSFFTTLESRITFLLRVTI
C    SIEIISEEAPSSKK-IKLTASEKAQKL--AQ--SSEFAKREVFSGDPINKATEWLNGEKW

H    YEVLKIAADILIKEEILSENDQLSNQVVVCLLPFVVINNDDTESAEMKIAIYLSKSGICS
D    QPVVPLAVRHLTSALVSGSYD--TNLVLLALMPLLFPGEALAEHQHKALRILLG-SDFVS
A    SHNVQLAVDVVALSLKIAVSSFGNQTDSTEKVTSAMFPFLLIQPKTWNLNLLVLKLGKDV
S    QIILPVVLYSLQSKDTEVRSR-----ALNLILTFLELRN-----ENLEFSIIYG------
Y    SPAAPTALKLISLNNIAKYIN--S--IEKEVNIFTLVPCLICALRDASIKVRTG------
C    DKVEWALNEMAQRGEKYFSRK-----VEDDVEQFVLEIVKVVG--VGGVKQIDG------

H    LHPLLRGWEEALENVIKSTKPGKLIGVANQKMIELLAD-NINLGDPS-SMLKMVEDLISV
D    KVPFLA--ELKVSNKFSDFN----VGEHRQHFLDIIASSNQELSSQERALLQSVEDHG--
A    NWPLFK--NLAADDGMKKLP-----DIMSTNLSSISMDIINDLG----EALSLDPDER--
S    ----MD------DNDNKNLR-----WLSPVETKYYCSD--LLLD----------------
Y    ----VK----KILSLIAKRP-----STKHYFLSDKLYGENVTIP-----MLN--------
C    ----GS-----VKAALAGAN------LNPQFVADLLTK-FDGVS----------------

H    GEEESFNLKQKVTFHVILSVLVSCCSS-LKETHFPFAIRVFSLLQKKIKKLESVITAVEI
D    GELYIQKASQLTHLLLLLTAYAKRELQPRESLHMLEKIGLYSRRLQFRVVNGSQNTQNCA
A    RIELIERACNYKLSEVLETCSNIKCSE---QDRNKLQKGLLIRESVSALNIDVINKLVEA
S    RSSEIGLDGTYLFSYIPERLFTEKKPK-----NASKEIAVTSFLSSHAACSKLSNVRVLL
Y    PKDSEAWLSGFLNEYVTENYDISRILT-----PKRNEKVFLMFWANQALLIPSPYAKTVL
C    EIAPKRTKGAQKKNLVEKTFGTEESWE-----AFNQRVVFVLDLLNARQIIPSSEKVLAA

H    PSEWHIELMLDRGIPVELWAHYVEELNSTQRVAVEDSVFLVFSLK-KFIYALKAPKSFPK
D    PLQLYVDFLLT-LVKNTKWT----ALASTPWNQMTDELRLCLRLL-EIICAQVFSEKADQ
A    -------FMMH-PADYIQWL--------TTEWEELEVEVDVSLKELSKSNCQELLYQLLDT
S    ---------------LEILTRV---------HGKVEDAKMQILLPRL--EQLSEFNSEKFKT
Y    ---------------LDNLKS-------PTYASSYSSLFEEFISHYLENRSSWEKSCIANK
C    ---------------LFAVVKQVN-------SKSDVESSSYQQHLAVN-AIRKILEHPEKTKI
```

Figure 3 (following)

```
H    GDIWWNPEQLKEDSRDYLHLLIGLFEMMLNGADAVHFRVLMKLFIKVHLEDVFQLFKFCS
D    ------PERQ-EWTRALQQSLQLILPEAQ---D------------RLEVLSNFYVFERLP
A    ------SDFTALNSKDVKAAAINCIEALFN----------------LRAA---IYGSSFDE
S    ------------VSKREVEALVNCFNHTS-------------------FTSLLSFLSSNI
Y    ------------TNFEHFERSLVNLVSPKE-----------------KQSFMIDFVLSALNS
C    ---------------GASEVDMDCVIETM---------------------RSTHNHH
                          .

H    VLWTYGSSLSNPLNCSVKTVLQTQALYVGCAMLSSQKTQCKHQLASISSPVVTSLLINLG
D    ELWPRDSDYA---------VFRLQGFIILEAVLSNPKSQIDCGLVHVLR-----VANACG
A    LLG--------------MIVQQRRLILSDNKFFA--SYLTSLLSSTTN----DLLVPVG
S    VLS---------------QAICRRIVEIQSHLKD--PQRLEFVKAVIS------QDEQ
Y    DYEQ-LA----------NIAAERLISIFASLNN--AQKLKIVQNIVD----SSSNVES
C    LLR----------------DCLRLIVAAAKHTP--NSVVKHVMSVFT------FMGNG
                     :                                       :

H    SPVKEVRRAAIQCLQALSG--VASPFYLIIDHLISKAEEITSD-AAYVIQDLATLFEELQ
D    SPLQTLRVQAINILQLISNRKLVSHVEQLVRSLLQRKSELSMDHEQYALILYTILEPEKA
A    LQKRFDQSTKENILSVILLCAEDLPAYGKLRVLSLLKDLGIMLMRDEIVKLLSQLLDK--
S    PHYYVDVLDSIKIPDTVFK-----KLIGSVRLVKEKNPAIAKR-----KRIDSHIFDG--
Y    SYDTVGVLQSLPLDSDIFVS---ILNQNSISNEMDQTDFSKRR-RRRSSTSKNAFLKEEV
C    MLRKDNELTLSIVEKTVES------LFSTIINSSGQAVLTKQQ-QTEKLIELARLFAASA
                . :       :                                   :

H    REKKLKSHQKLSETLKNLLSCVYSCPSYIAKDLMKVLQGVNGEMVLSQLLPMAEQLLEKI
D    TAKERLVLSKLKRSVLALASDPKQSP-ICTASLLAALKHVNDENFLNELLPLGLDSLKTI
A    RSQYYYKLDKTSQPLSDTEVDLLCLLLECSMMRTSSFKGQS----LDDHILSALNVDCMA
S    -------DVQRLTRILELLETKNAASYPKLASPLFEVLNSVIA---LKEDIVSSNYLLQLL
Y    SQLAELHLRKLTIILEALDKVRNVGSEKLLFTLLSLLSDLET---LDQDGGLPVLYAQET
C    IDIPAHRRARIAQAIARAVQAENAST--VVLVLVSSFCARWQ---RSSDAAAQEAMKRGS
                :  :                           :           ..

H    QK-EPTAVLKDEAMVLHLTLGKYNE-FSVSLLNEDPKSLDIFIKAVHTTKELY-AGMPTI
D    TAGEDNQNIKQLPWPHSEIYKSVIERFEGRVALNVLLRKDLAWKLFEDSFAQY-DTYVQL
A    SE-RPAVISPCLTILEKLSNRFYDE----LQT-------DVQIRFFHKLVSMFRSSNGSI
S    LG-------LLYEMIGASPITELSP-------------SIRIDTLVGCIRST--NNPQI
Y    LI---SCTLNTITYLKEHGCTELTN---------------VRADILVSAIRNS--ASPQV
C    DQ-------DAYDDLAIELLSALNP---------------FEQLSSVLEMCEYVRRLGGDK

H    QITALEKITKPFFAAISDEKVQQKLLRMLFDLLVNCKNSHCAQTVSSVFKGIS-VNAEQV
D    EQ-KLQPLPCVLLNSLPETFEQMHAKHKIALIKLIVESATNSDNDSIFLASH-RLLKRC
A    QNGAKEAVLRLKLSSSTVVLALDRITQQDTLVIGSLSKKKKQKKNSKSCPEED-INSEEF
S    QN--KALLLVSALANAAPEAVLHGVMPIFTFMGSTVLSRDDAFSIHVIEQTVKTVISALI
Y    QN--KLLLVIGSLATLSSEVILHSVMPIFTFMGAHSIRQDDEFTTKVVERTILTVVPALI
C    PA--KSTTTKKDLDTMIFDRTAQTLPRIRHFRYVVVTLISRIFSNRVLIERLAAYDDEEL
                :    .

H    RIELEPP-DKAKPLGTVQQKRRQK-MQQKKSQDLESVQEVGGS-Y-WQRVTLILELLQHK
D    RLDCQP---LVPILLEMANTKVEK-KQPVKRRSVQATQLDLTSPY-WKQGMTLLELLEHK
A    RSGEKAL-SFIASLLDMLLLKKDLTHRESLIRPLFKLLQRSMSKE-WVKIAFSIEETSLQ
S    RLGKDF---DSSLLVSCFVNAFPHIPQHRRLRLYRLVLQTIGS----NRFLSVVLIQFAE
Y    KNSKGNEKEEMEFLLLSFTTALQHVPRHRRVKLFSTLIKTLDPVKALGSFLFLIAQQYSS
C    LKNALP---LGKRLIECSVELDEFANKEANDQDGSDPQAQRYWVAFASRTEVVSEKLRHL
               *                    :                      :
```

Figure 3 (following)

```
H    XKLRSPQILVPTLFNLLSRCLEPLPQEQGNMEYTKQLILSCLLNICQKLSPDGGKIPKDI
D    KQLVGAELLIPPLFELLQACLT--MEEHSAAEYPKQLILSSLLHCCQTAQSAGVQLVKAM
A    PPQ-DVRETTPTFISSIQQTLL---------------LILKDIFDSLNMN-PLKAEVANEI
S    KML---LAKSTNVVAIHDFCLT------------------L--VQSF-----SVADRI
Y    ALVNFKIGEARILIEFIKALLV----------D-------LHVNEELS--G--LNDLL
C    LPG---GVAARLIADVLQECVN--------------------DKK------MSYKM
                .    .  :                              :       :   :

H    LDEEKFNVELIVQCIRLSEMPQTHHHALLLLGTVAGIFPDKVLHNIMSIFTFMGANVMRL
D    P-ESSFRIELVVQSLRNTRNPQTQQHALLFLTHCAGMYPQQVLHKIVEIFTFVGSTVARH
A    N------VKMLVELAHSSNDGVTRNHIFSLFTAIVKFVPDKVLDHIISILTLVGESTVTQ
S    G-------SIN-QCSRFCLKSLEEQSNSDSNGKAVSLIKLDELPMDVDLATLGSLRVKVL
Y    D-----IIKLLTSSKSSSEKKKSLESRVLFSNGVLNFSESEFLTFMNNTFEFIN-KITEE
C    C-------EKVLQLANIKLG-----HDRYLFA-DSGINEKELITLAQALNKFIVAETKSE
                .       .        :       .

H    DDTYSFQVINKTVKMVIPALIQSDSGDSIEVSRNVEEIVVKIISVFVDALPHVPEHRRLP
D    DDAFSLHIIHNVVESIIPILLN-TG--------HNELVIPVLKVFADICTDVPVHRRLP
A    IDSHSKSIFEGFISMVIPFWLSK-----------TKSEEQLLQIFVKVLPDIVEHRRRS
S    ELISLVSKAKNPAFDLAKIMENS------------------VDSFVEIQAGLFES--IK
Y    TDQDYYDVRRNLRLKVYSVLLDETSD---------KKLIRNIREEFGTLLEGVLFF-INS
C    EKMRMCQNSAYTLKLIAKNLPSQ-------------------SESLVLADTMQR-CVS
                :          .

H    ILVQLVDTLGAEKFLWILLILLFEQYVTKTVLAAAYGEKDAILEADTEFWFSVCCEFSVQ
D    LYATLFRVLEPKEHLWQFLCIIFES----QVLLEQVPQKVSTDKSRLDFARELTLMFEDP
A    IVAYLLGVVTS-------------------LLQQ---------------------------
S    LLITLSQQSSNE-----------------MELG---------------------------
Y    VELTFSCITSQE-----------------NEEAS--------------------------
C    IVSQYQKLDEN------------------------------------------------
            :

H    -HQIQSLMNILQYLLKLPEEKEETIPKAVSFNKSESQEEMLQVFNVETHTSKQLRHFKFL
D    TVAIQTCIRLLDYLAKLPATKSSLSGGSGSSVLSTEQ----QLFDVRTRTFKQLRHYKYL
A    ----QTDYNGTKKVLGLISERAKDTS---SS-----------------KMKHKRKI
S    ----HVYVALRSVIHLLPNELFCTVLG------------------------KLLHDERA
Y    ----DSETSLSDHTTEIKEILFKVLGN-----------------------VLQILPVDEFV
C    ---------LTGNVLLLAGELIRS-------------------------HNMRS
                :

H    SVSFMSQLLSSNNFLKKVVESGGPEILKGLEERLLETVLGYISAVAQSMERNADKLTVK-
D    IMDFLSGISSCNEWEKKMKRPDPNELLPYYQEFILKT-LAYVGVLNGALEAASETPSLEK
A    S------N--QK-----GRN------------------S-------
S    LLR----------RK------ALS------------------IVQ-----------
Y    NAVLPLLSTSTNEDIR-------YHLT----------------LVIGS------------
C    T-----------------------------------------I------------

H    FWRALLSKAYDLLDKVNALLPTETFIPVIRGLVGNPLPSVRRKALDLLNNKLQQNISWKK
D    FWRVLANHAHDVLDNAIGLLAPQHFISVITELLKHDHVYVRIKVMDLLVTKLSPSSDYFQ
A    -WLNLDEVAVDSFGKMCEEIV--HLINATDDESGVPVKRAAISTLEVLAGRFP----SGH
S    -QRVQQGSKVSALTALIPDVT--YNISNYSDE---ETTQLAMDCLAVMAKRFS-------
Y    KFELEGSEAIPIVNNVMKVLL--DRMPLESKS--VVISQVILNTMTALVSKYG-------
C    ------H-HATSLLKTCLATVQ--ECIARFSKP---QYDSAASPGSSVAGGRGN------
                .       :         :                             :
```

Figure 3 (following)
```
H       -TIVTRFLKLVPDLLAIVQ--RKKKEGEEEQAINRQTALYTLKLLCKNFGAENPDPFVPV
D       QSNAEHFGVLFAPLQEIINGILEGSSNSAQQAKLQQTALHALQLLALRHGRDYIEECRSL
A       ----PIFRKCLAAVAECIS---------------------------SKNLGVS--SSCLRT
S       ----ASPELFISPIEVVS-----------------------------GPYGLKN-SARDVQ
Y       ---KKLEGSILTQALTLAT----------------------------EKVSSD---MTEVK
C       ------RG-HRIRQQSLGG----------------------------NKFGSD-----TLL
                                                        . .

H       LSTAVKLIAPERKEEKNVLGSALLCIAEVTSTLEALAIPQLPSLMPSLLTTMKN----TS
D       LATLTKITKRRANVPKAVVGNVVLTLVEICASLKAHALAQLPKFAPQLTELLKEQVHQMA
A       TGALINVLG-----PKALIELPCIMKNLVKQSLEVSFASQS---G-------RN------
S       VSAIVCITV-----LTNTLAARILPYLADIVNYSLSILDDAR----------KD------
Y       ISSLALITN-----CVQVLGVKSIAFYPKIVPPSIKLFDASLADS-------SN------
C       ICSLTCIQR-----VYDQFASFVVESTGDVIIRYCRLIARFG----------D------
            :      :        .    :                                :

H       ELVSSEVYLLSALA-ALQKVVETLPHFISPYLEGILS----QVIHLEKITSEMGSASQAN
D       SLKQGPDYVCSTLVTALHKLFLGPYLVDIIGGLARLSVQLENPQLLQDKRTQVL
A       ATAEEQLLMLSVLV-TLEAVIDKLGGFLNPHLGDIMK------IMVLHPEYVSDFDKNLK
S       --PEGDLLELACFS-MMIDFFKVLPEFSSSYVEPTIK---------CALASDRAFEHDAI
Y       --PLKEQLQVAILL-LFAGLIKRIPSFLMSNILDVLH---------VIYFSREVDSSIR
C       ---PSELLALNQPS--SSTTAAFQGGSQTSGFGSKTG---------IHHRLSLIRRSLLS
                   .  .

H       IR-LTSLKKTLATTLAPRVLLPAIKKTYK-QIEKNWKNHMGPFMS-ILQEHIGAMKKEEL
D       KQKLADVWSAVAQGVEVRILVPSCAKAFSSLLEQQAYDELGHLMQQLLLQSVRHNSAAQL
A       SK-ANAIRRLLTDKIPVRLTLQPLLRIYNEAVSSGNASLVIAFNM--LEDLVVKMDRSSI
S       GE---LLFETIANFIPTRLLMKSIFAAWPECARLGSTAALRLLEL--IELALQNSSRSAI
Y       LS----VISLIIENIDLKEVLKVLFRIWSTEIATSNDTVAVSLFLSTLESTVENIDKKSA
C       IE-----LRVLPAHIVKTVGELKTEKKALS--ALFNLLTGYIETQH--Q-QKPEILRKSVI
                  :        :        :

H       TSHQSQLTAFFLEALDFRAQHSEN--DLEEVGKTENCIIDCLVAMVVKLSEVTFRPLFFK
D       QPVQDPLSELFLQALNFRLQVRGLGLQRQLVSDVEASITETFVTWILKLSETSFRPMYSR
A       VSSHGKIFDQCLVALDIRRLNPAA---IQNIDDAERSVTSAMVALTKKLTESEFRPLFIR
S       GTVYKSIFKFFLDSFDSRRSLLFA----EDVDNVETQAVNVFLKFVMKLSDTTFRPLFLH
Y       TSQSPIFFKLLLSLFEFRSISSFD--N-NTISRIEASVHEISNSYVLKMNDKVFRPLFVI
C       QLRRTFVSDVITPTLIVRSQERQSD-QFENVEKLEHTVFNFVISIASILSEVEFRTVVNE
                .           :  :        *        :         :.:  **.:

H       LFDWAKTEDAP----K----DRLLTFYNLADCIAEKLKGLFT----LFAGHLVKPFADTL
D       VHKWALESTSR----E----TRLTYFL-LTNRIAEALKSLFV----LFASDFVEDSSRLL
A       SIDWAESDVVDGSGSENKSIDRAISFYGLVDRLCESHRSIFVPYFKYVLDGIVAHLTTAE
S       LHSWALEDLYETD--PSGIVSRQTFFYNFLTIFLDTLKSIVT-------N-YYAYVLDDT
Y       LVRWAFDGEGVTN-AGITETERLLAFFKFFNKLQENLRGIIT----SYFTYLLEPVDMLL
C       LVAWAEPGLEAKA--DLAARLRLVSLLHFANDLYTSFNSLALP----YFGRILEISALVL
          **              *    :    :    :      ..:

H       DQVNISKTDEAFFDSENDPE--KCCLLLQFILNCLYKIFLFDT--QHFISKERAGALMMP
D       TEHNSIRPEFEVEEREDD------VDLLMAILNTLHHVFLYCS--EDFINDHRFNVLMPP
A       ASVSTRKKKKAKIQQTSDSIQPKSWHLRALVLSCLKNCFLHDTGSLKFLDTNNFQVLLKP
S       IELLSSK-D------TNS------EVR-HLVNSSLVSAFENDT-EEFWMVPARFGKISPV
Y       KRFISKD-------MEN-------VNLRRLVINSLTSSLKFDR-DEYWKSTSRFELISVS
C       KKCNATLLLGTDELLLSGKRGSIEALETDLALTLAIDVISNAARHRDFFTVDRCQLVSDV
                                    .             .        .   .  :
```

Figure 3 (following)

```
H    LVDQLENRLG-GEEKFQERVTKHLIP-----CIAQFSVAMADDSLWKPLNYQILLKTRDS
D    LVNQLENDLVLGNESLQQVLSN---------CIAQFAVATN-DVMWKQLNSQVLLKTRTS
A    IVSQLVVEPPSSLKEHPHVPSVDEVDDLLVSCIGQMAVASGSDLLWKPLNHEVLMQTRSE
S    LIEQIQYAPLLDDKVLVKAIVE-----------L-ASVASS-SDNFRSMNTQLLQYLRSS
Y    LVNQLSNIENSIGKYLVKAIGA------------LASNNSGVDEHNQILNKLIVEHMKAS
C    IVNELVNTKVEGHEKRCSDHLVP----------AIYRIGNADPDSFPELLNKIMLKTRDS
     ::.::        :                              ::   :  .

H    SP-KVRFAALITVLALAEKLKENYIVLLPES IPFLAELMEDECEEVEHQCQK-TIQQLET
D    NP-EVRILAFNSCVAIARKLGESYAALLPE TVPFIAELLEDEHQRVEKNTRT-GVQELET
A    SV-RSRMLSLRSVKQMLDNLKEEYLVLLAE TIPFLAELLEDVELSVKSLAQD-IIKQMEE
S    NI-NARLLAIQIQTQLYGRLGENWISTLPQ SVPFIAELMEDDDDQVETATAE-LVRIIDD
Y    CSSNEKLWAIRAMKLIYSKIGESWLVLLPQ LVPVIAELLEDDDEEIEREVRTGLVKVVEN
C    RA-KIRYRALIVLELLIKEIGDGVQPHLSI LLPFLNELIEDENKQVEAQCQK-VINSLQH
       . :  ::       :  .: :    *.  :*.: **:**    ::     :..::
                                                          HEAT REPEAT
H    VLGE--RLQSYF---
D    ILGE--SVQKYL---
A    MSGE--SLAEYL---
S    RLGENESLQDYLT--
Y    VLGE--PFDRYLD--
C    KFGE--TFWSGGSSA
        **       .:.
```

Figure 4

```
BAP28       MTSLAQQLQRLALPQSDASLLSRDEVASLLFDPKEAATIDRDTAFAIGCTGLEELLGIDP
BAP28       SFEQFEAPLFSQLAKTLERSVQTKAVNKQLDENISLFLIHLSPYFLLKPAQKCLEWLIHR
BAP28       FHIHLYNQDSLIACVLPYHETRIFVRVIQLLKINNSKHRWFWLLPVKQSGVPLAKGTLIT
BAP28       HCYKDLGFMDFICSLVTKSVKVFAEYPGSSAQLRVLLAFYASTIVSALVAAEDVSDNIIA
BAP28       KLFPYIQKGLKSSLPDYRAATYMIICQISVKVTMENTFVNSLASQIIKTLTKIPSLIKDG
BAP28       LSCLIVLLQRQKPESLGKKPFPHLCNVPDLITILHGISETYDVSPLLRYMLPHLVVSIIH
BAP28       HVTGEETEGMDGQIYKRHLEAILTKISLKNNLDHLLASLLFEEYISYSSQEEMDSNKVSL
BAP28       LNEQFLPLIRLLESKYPRTLDVVLEEHLKEIADLKKQELFHQFVSLSTSGGKYQFLADSD
BAP28       TSLMLSLNHPLAPVRILAMNHLKKIMKTSKEGVDESFIKEAVLARLGDDNIDVVLSAISA
BAP28       FEIFKEHFSSEVTISNLLNLFQRAELSKNGEWYEVLKIAADILIKEEILSENDQLSNQVV
BAP28       VCLLPFVVINNDDTESAEMKIAIYLSKSGICSLHPLLRGWEEALENVIKSTKPGKLIGVA
BAP28       NQKMIELLADNINLGDPSSMLKMVEDLISVGEEESFNLKQKVTFHVILSVLVSCCSSLKE
BAP28       THFPFAIRVFSLLQKKIKKLESVITAVEIPSEWHIELMLDRGIPVELWAHYVEELNSTQR
BAP28       VAVEDSVFLVFSLKKFIYALKAPKSFPKGDIWWNPEQLKEDSRDYLHLLIGLFEMMLNGA
BAP28       DAVHFRVLMKLFIKVHLEDVFQLFKFCSVLWTYGSSLSNPLNCSVKTVLQTQALYVGCAM

BAP28       LSSQKTQCKHQLASISSPVVTSLLINLGSPVKEVRRAAIQCLQALS-GVASPFYLIIDHL
Tetraodon1  ------------------FPSLLCCLSSPVQEVRRVSLGALQSLSRARASPFWPIMEKL
                              ..***  *.***:****.::  .**:**  . ****: *:::*

BAP28       ISKAEEITSDAAYVIQDLATLFEELQREKKLKSHQKLSETLKNLLSCVYSCFSYIAKDLM
Tetraodon1  LRTTDELLADPSYLSQVRRRSPASGDLRFWLLTPSVCVCCLG-----YRPSRRRPGLVLI
             : .::*: :*.:*: *     .  .  . *:. *           .   .    *:

BAP28       KVLQGVNGEMVLSQLLPMAEQLLEKIQKEPTAVLKDEAMVLHLTLGKYNEFSVSLLNEDP
Tetraodon1  PVVV-VFCQSILSALLPLLERLLEQSSPDTPNQLRDEAQLALLILSKYNEASAPLLAKDE
             *:  *  :  :** ***: *:*** . ...  *:***  :  * *.****  *:.**  :*

BAP28       KSLDIFIKAVHTTKELYAGMPTIQITALEKITKPFFAAISDEKVQQKLLRMLFDLLVNCK
Tetraodon1  NCLDLFIRALRNSTQQHLDIPSCQIFALEQITKSFFSAIESETVXQKLLSVMFDLLAENX
            :.**:**:*:::.::    :  .:*:  ** ***:***.**:**.,*.*  **** ::****.:

BAP28       NSHCAQTVSSVFKGISVNAEQVRIELEPPDKAKPLGTVQQKRRQKMCQKKSQDLESVQEV
Tetraodon1  XPLVAITIGSVFKRITVDAQLVANELAPADKASISMTVQQSRRSRMIL------------
             . * *:.**** *:*:*:  *  ** *.***.   ****.**.:*

BAP28       GGSYWQRVTLILELLQHKXKLRSPQILVPTLFNLLSRCLEPLPQEQGNMEYTKQLILSCLL
BAP28       NICQKLSPDGGKIFKDILDEEKFNVELIVQCIRLSEMPQTHHHALLLLGTVAGIFPDKVL
BAP28       HNIMSIFTFMGANVMRLDDTYSFQVINKTVKMVIPALIQSDSGDSIEVSRNVEEIVVKII

BAP28       SVFVDALPHVPEHRRLPILVQLVDTLGAEKFLWILLILLFEQYVTKTVLAAAYGEKDAIL
Tetraodon2  ----------------LPVLVQLVETLGPARFLWVLMLLLFKLHATHTANTASE--KDAAV
                             **:***** ***. :***:*::***:  :.*:*. :*:   *** :

BAP28       EADTEFWFSVCCEFSVQHQIQSLMNILQYLLKLPEEKEETIPKAVSFNKSESQEE-----
Tetraodon2  EKDVDFWISLCSQFKVGEQLASLNHILGFLLQLPEDKDEAASKHATGRRTTQKKEKEEQG
            * *.:**:*:*.*. * * .* ****.**: *** .:* ** :*

BAP28       ---MLQVFNVETHTSKQLRHFKFLSVSFMSQLLSSNNFLKKVVESGGP-EILKGLEERLL
Tetraodon2  DKMEELIFSVEAHSSKELRHFKFISVSFMAQLLGSASFIGKVSEITTSNSLLLSLKRMLL
               :*..**:*:**:****:*****.*****  :** .*::* ****

BAP28       ETVLGYISAVAQSMERNADKLTVKFWRALLSKAYDLLDKVNALLPTETFIPVIRGLVGNP
Tetraodon2  EDLLRYIHSIARSVEENAMKPTAKFWRVLLNKAYDVLDKVNSLLPTDTFIVVMKGLMGND
            * :* ** ::*:*:*.** * *.**** *.*****:**** *****:*** *::**:**:
```

Figure 4 (following)

```
BAP28       LPSVRRKALDLLNNKLQQNISWKKTIVTRFLKLVPDLLAIVQRKKKEGEEEQAINRQTAL
Tetraodon2  LPSVRRKAMELLNNKL--------------------------------------------
            ********:.******

BAP28
    YTLKLLCKNFGAENPDPFVPVLSTAVKLIAPERKEEKNVLGSALLCIAEVTSTLEALAIPQLPSLMPSL
BAP28       LTTMKNTSELVSSEVYLLSALAALQKVVETLPHFISPYLEGILSQVIHLEKITSEMGSAS
BAP28       QANIRLTSLKKTLATTLAPRVLLPAIKKTYKQIEKNWKNHMGPFM6ILQEHIGAMKKEEL
BAP28       TSHQSQLTAFFLEALDFRAQHSENDLEEVGKTENCIIDCLVAMVVKLSEVTFRPLFFKLF

BAP28       DWAKTEDAPKDRLLTFYNLADCIAEKLKGLFTLFAGHLVKPFADTLDQVNISKTDEAFFD
Tetraodon3  ---------------------------------------------------EVLFE
                                                               *.:*:

BAP28       SENDPEKCCLLLQFILNCLYKIFLFDTQHFISKERAGALMMPLVDQLENRLGGEEKFQER
Tetraodon3  SSHADQKVALXLQYVLXCLHKIFLYDTQRFLSKERADTLMNPLLDQLENFAGGPQTYQQR
            *.:   :*  .*  **::* **:****:***.*:*****..:** **:***** ** :.:*:*

BAP28       VTKHLIPCIAQFSVAMADDSLWKPLNYQILLKTRDSSPKVRFAALITVLALAEKLKENYI
Tetraodon3  VTQHLVPCLGQFAVALADDTQWKTLNYXXXLKSRHSDAKVRFSSLLMLMXLTSKLKENYM
            **:**:**:.**:**:***:*** ***    **:*.*. .****::*:  ::  *:..******:

BAP28       VLLPESIPFLAELMEDECEEVEHQCQKTIQQLETVLGEPLQSYF
Tetraodon3  VLLPETIPFLAELME----------------------------
            *****:*********
```

HAPLOTYPE ANALYSIS SORTED BY INDIVIDUAL HAPLOTYPE TEST (2 markers)
491 CASES vs 313 CONTROLS

| MARKERS | 99-16017402 | 99-137798/284 | 5-377/227 | 5-376/266 | 5-375/200 | 5-373/164 | 5-382/316 | 5-381/133 | 99-7182/49 | HAPLOTYPE FREQUENCY TEST | | | | | OMNIBUS LR TEST | | |
|---|---|---|---|---|---|---|---|---|---|---|---|---|---|---|---|---|---|
| POLYMORPHISM | A/T | A/G | A/G | A/G | A/G | C/T | C/G | A/G | C/T | Estimation frequency of haplotype | | | Odds ratio | Statistical test | | Likelihood Ratio | omnibus test |
| cases / controls | 480 vs 305 | 423 vs 278 | 449 vs 307 | 453 vs 298 | 455 vs 307 | 433 vs 298 | 448 vs 304 | 446 vs 304 | 415 vs 287 | cases (%) | control (%) | difference | | pvalue (1df) | Nb of permut | LR Test | Pvalue (3 df) | Pvalue (100 permut) |
| frequency % (case/controls) | 37/32 (T) | 58/53 (A) | 33/31 (G) | 33/31 (A) | 33/31 (A) | 34/31 (T) | 39/34 (G) | 37/34 (A) | 39/36 (T) | | | | | | | | |
| diff freq all (cases-controls) | 4,4 | 5,8 | 2,4 | 2,2 | 1,8 | 2,8 | 4,9 | 2,6 | 2,9 | | | | | | | | |
| pvalue | 7,40E-02 | 3,80E-02 | 3,20E-01 | 3,70E-01 | 4,40E-01 | 2,50E-01 | 5,40E-02 | 2,90E-01 | 2,70E-01 | | | | | | | | |
| Odds ratio | 1,20 | 1,20 | 1,10 | 1,10 | 1,10 | 1,10 | 1,20 | 1,10 | 1,10 | | | | | | | | |
| | 0,00 | 0,00 | 0,00 | 0,00 | 0,00 | 0,00 | 0,01 | 0,03 | 0,02 | | | | | | | | |
| | 0,01 | 0,00 | -0,02 | -0,02 | -0,02 | -0,01 | -0,02 | 0,01 | 0,01 | | | | | | | | |
| Test Hardy Weinberg cases vs controls | | | | | | | | | | | | | | | | | |
| haplotype 1 | T | A | G | A | A | T | G | A | T | 15,60 | 9,30 | 6,3 | 1,80 | 3,90E-04 | 0/100 | 10,10 | 1,70E-02 | 5,00E-02 S |
| haplotype 2 | | A | | | | | | | | 20,30 | 12,90 | 7,4 | 1,73 | 3,90E-04 | 0/100 | 11,51 | 8,90E-03 | 2,00E-02 S |
| haplotype 3 | T | | | | | T | | | | 18,80 | 12,50 | 7,3 | 1,73 | 4,10E-04 | 0/100 | 11,30 | 1,00E-02 | 1,00E-02 S |
| haplotype 4 | T | | | A | | | | | | 17,20 | 10,60 | 6,6 | 1,75 | 4,30E-04 | 0/100 | 9,81 | 1,90E-02 | 1,00E-02 S |
| haplotype 5 | T | A | | | | T | | | | 23,00 | 15,40 | 7,6 | 1,64 | 7,30E-04 | 0/100 | 10,19 | 1,70E-02 | 1,00E-02 S |
| haplotype 6 | T | | | | A | | | | | 15,20 | 9,30 | 5,9 | 1,75 | 8,20E-04 | 0/100 | 9,13 | 2,70E-02 | 2,00E-02 S |
| haplotype 7 | T | | | | | T | | | | 15,80 | 9,70 | 6,1 | 1,75 | 8,20E-04 | 0/100 | 8,79 | 3,20E-02 | 3,00E-02 S |
| haplotype 8 | T | | | | A | | | | | 15,10 | 9,30 | 5,8 | 1,75 | 9,10E-04 | 1/100 | 9,12 | 2,70E-02 | 4,00E-02 S |

HAPLOTYPE ANALYSIS SORTED BY INDIVIDUAL HAPLOTYPE TEST (2 markers)
91 FAMILY CASES having less than 65 years old vs 313 CONTROLS

HAPLOTYPE ANALYSIS SORTED BY INDIVIDUAL HAPLOTYPE TEST (2 markers)
70 SPORADICS CASES (Informatifs) vs 313 CONTROLS Figure 11B: HAPLOTYPE ANALYSIS SORTED BY INDIVIDUAL HAPLOTYPE TEST (3 markers) — 70 SPORADICS CASES (Informatifs) vs 313 CONTROLS

| MARKERS | 99-1572/440 | 5-171/204 |
|---|---|---|
| HAPLOTYPE 1 | T | T |
| pvalue (1df) frequency difference (sample sizes) | 1,10E-02 | 5,40E-02 |
| | 10.1 (89 vs 304) | 7.2 (89 vs 307) |

| | sample sizes cases vs controls | HAPLOTYPE FREQUENCY TEST | | | Statistical test | | OMNIBUS LR TEST | | |
|---|---|---|---|---|---|---|---|---|---|
| HAPLOTYPE 1 | | cases(%) | controls(%) | % frequency difference | Odds ratio | Pvalue(1df) | Pvalue (1000 permut) | Likelihood Ratio Test | Pvalue (3 df) | Pvalue (1000 permut) | omnibus test |

| HAPLOTYPE 1 | sample sizes cases vs controls | cases(%) | controls(%) | % freq diff | Odds ratio | Pvalue(1df) | Pvalue (1000 permut) | Likelihood Ratio Test | Pvalue (3 df) | Pvalue (1000 permut) | omnibus test |
|---|---|---|---|---|---|---|---|---|---|---|---|
| cases vs controls | 464 vs 300 | 50,1 | 44,2 | 5,9 | 1.26 | 2,50E-02 | 2,E-02 | 4,81 | 1,80E-01 | 1,80E-01 | NS |
| cases (<=65 years) vs controls | 177 vs 300 | 54,5 | 44,2 | 10,3 | 1.51 | 2,10E-03 | 3,E-03 | 8,62 | 3,40E-02 | 4,60E-02 | S |
| cases (>65 years) vs controls | 283 vs 300 | 46,7 | 44,2 | 2,5 | 1.11 | 3,70E-01 | 2,E-01 | 1,11 | 7,50E-01 | 7,60E-01 | NS |
| sporadic cases vs controls | 280 vs 300 | 45,5 | 44,2 | 1,3 | 1.05 | 6,50E-01 | 5,E-01 | 1,32 | 7,10E-01 | 7,40E-01 | NS |
| sporadic cases (<=65 years) vs controls | 89 vs 300 | 45,4 | 44,2 | 1,2 | 1.05 | 7,50E-01 | 7,E-01 | 1,19 | 7,50E-01 | 7,30E-01 | NS |
| sporadic cases (>65 years) vs controls | 187 vs 300 | 45,0 | 44,2 | 0,8 | 1.03 | 7,50E-01 | 7,E-01 | 0,85 | 8,30E-01 | 8,40E-01 | NS |
| sporadic informatif vs controls | 67 vs 300 | 43,4 | 44,2 | 0,8 | 0.97 | 7,50E-01 | 8,E-01 | 3,29 | 3,50E-01 | 3,30E-01 | NS |
| familial cases vs controls | 184 vs 300 | 57,1 | 44,2 | 12,9 | 1.68 | 9,70E-05 | <1.0e-03 | 14,30 | 2,40E-03 | 4,00E-03 | S |
| familial cases (<=65 years) vs controls | 88 vs 300 | 64,4 | 44,2 | 20,2 | 2.28 | 2,50E-06 | <1.0e-03 | 21,42 | 8,30E-05 | 1,00E-03 | S |
| familial cases (>65 years) vs controls | 95 vs 300 | 50,1 | 44,2 | 5,9 | 1.26 | 1,50E-01 | 9,E-02 | 2,04 | 5,50E-01 | 5,50E-01 | NS |
| familial cases (>=3caP) vs controls | 83 vs 300 | 58,6 | 44,2 | 14,4 | 1.79 | 9,60E-04 | 1,E-03 | 10,98 | 1,20E-02 | 1,00E-02 | S |

Figure 12A

| MARKERS | 5-370/197 | 5-381/133 |
|---|---|---|
| HAPLOTYPE 1 | G | A |
| pvalue (1df) | 2.10E-01 | 3.60E-08 |
| % frequency difference (sample sizes) | 6.3 (62 vs 287) | 21.3 (69 vs 304) |

HAPLOTYPE FREQUENCY TEST

| HAPLOTYPE 1 | Estimation frequency of haplotype | | | Statistical test | | | | | Likelihood Ratio | | | Omnibus test |
|---|---|---|---|---|---|---|---|---|---|---|---|---|
| | sample sizes cases vs controls | frequency cases (%) | frequency controls (%) | frequency difference (%) | Odds ratio | p-excess | Chi-S | pvalue (1df) | Pvalue (1000 permutat) | Nb of permut | LR Test | Pvalue (3 df) | Pvalue (1000 permutations) |
| cases vs controls | 422 vs 287 | 14.5 | 10.5 | 4 | 1.45 | 4.52 | 4.98 | 2.50E-02 | 2.E-02 | 18/1000 | 5.54 | 1.30E-01 | 1.70E-01 NS |
| cases (<=65 years) vs controls | 159 vs 287 | 15.2 | 10.5 | 4.7 | 1.53 | 6.22 | 4.20 | 4.00E-02 | 3.E-02 | 34/1000 | 4.66 | 2.00E-01 | 2.70E-01 NS |
| cases (>65 years) vs controls | 260 vs 287 | 13.9 | 10.5 | 3.4 | 1.38 | 3.84 | 3.03 | 7.80E-02 | 6.E-02 | 84/1000 | 3.78 | 2.80E-01 | 4.10E-01 NS |
| sporadic cases vs controls | 276 vs 287 | 17.0 | 10.5 | 6.5 | 1.75 | 7.25 | 10.08 | 1.50E-03 | 2.E-03 | 2/1000 | 11.53 | 8.90E-03 | 8.00E-03 S |
| sporadic cases (<=65 years) vs controls | 87 vs 287 | 17.4 | 10.5 | 8.9 | 1.80 | 7.71 | 5.99 | 1.40E-02 | 2.E-02 | 16/1000 | 6.28 | 9.80E-02 | 1.20E-01 NS |
| sporadic cases (>65 years) vs controls | 186 vs 287 | 16.5 | 10.5 | 6 | 1.69 | 6.74 | 7.35 | 6.50E-03 | 6.E-03 | 8/1000 | 8.49 | 3.70E-02 | 4.50E-02 S |
| sporadic informatif vs controls | 62 vs 287 | 28.6 | 10.5 | 18.1 | 3.43 | 20.30 | 28.48 | 8.40E-08 | <1.0e-03 | 0/1000 | 31.46 | 6.70E-07 | 1.00E-03 S |
| familial cases vs controls | 146 vs 287 | 9.9 | 10.5 | 0.6 | 0.94 | -0.61 | 0.06 | 7.50E-01 | 8.E-01 | 776/1000 | 1.13 | 7.50E-01 | 9.20E-01 NS |
| familial cases (<=65 years) vs controls | 72 vs 287 | 12.5 | 10.5 | 2 | 1.22 | 2.26 | 0.49 | 4.80E-01 | 5.E-01 | 488/1000 | 1.83 | 6.80E-01 | 6.10E-01 NS |
| familial cases (>65 years) vs controls | 74 vs 287 | 7.4 | 10.5 | 3.1 | 0.69 | -3.40 | 1.23 | 2.50E-01 | 3.E-01 | 286/1000 | 1.80 | 5.80E-01 | 6.70E-01 NS |
| familial cases (>=3caP) vs controls | 61 vs 287 | 7.4 | 10.5 | 3.1 | 0.68 | -3.45 | 1.08 | 2.90E-01 | 3.E-01 | 322/1000 | 2.85 | 4.10E-01 | 4.20E-01 NS |

Figure 12 B

| MARKERS | 99-1601/402 | 5-382/316 |
|---|---|---|
| HAPLOTYPE 1 | T | G |
| pvalue (1df) | 7,70E-03 | 4,40E-03 |
| % frequency difference (sample sizes) | 7.4 (286 vs 305) | 7.4 (286 vs 305) |

HAPLOTYPE FREQUENCY TEST

| HAPLOTYPE 1 | sample sizes cases vs controls | Estimation frequency of haplotype | | | Statistical test | | | | OMNIBUS LR TEST | | | |
|---|---|---|---|---|---|---|---|---|---|---|---|---|
| | | frequency cases (%) | frequency controls (%) | frequency difference (%) | Odds ratio | p-access | Chi-S | pvalue (1df) | Pvalue (1000 permutations) | Nb of permutations | Likelihood Ratio Test | Pvalue (3 df) | pvalue (1000 permutations) | omnibus test |

| | sample sizes cases vs controls | freq cases | freq ctrl | freq diff | Odds ratio | p-access | Chi-S | pvalue (1df) | Pvalue (1000 perm) | Nb of perm | LR Test | Pvalue (3 df) | Pvalue (1000 perm) | omnibus |
|---|---|---|---|---|---|---|---|---|---|---|---|---|---|---|
| cases vs controls | 440 vs 298 | 17.2 | 10.6 | 6.6 | 1.75 | 7.35 | 12.37 | 4,30E-04 | <1.0e-03 | 0/1000 | 9.81 | 1,90E-02 | 9,00E-03 | S |
| cases (<=65 years) vs controls | 165 vs 298 | 17.6 | 10.8 | 7 | 1.80 | 7.85 | 9.18 | 2,40E-03 | 8,E-03 | 8/1000 | 6.64 | 8,20E-02 | 7,80E-02 | NS |
| cases (>65 years) vs controls | 271 vs 298 | 16.7 | 10.8 | 6.1 | 1.69 | 8.81 | 9.00 | 2,60E-03 | 7,E-03 | 7/1000 | 8.28 | 4,00E-02 | 4,90E-02 | S |
| sporadic cases vs controls | 281 vs 298 | 19.9 | 10.8 | 9.3 | 2.09 | 10.37 | 18.44 | 1,00E-05 | <1.0e-03 | 0/1000 | 17.90 | 4,40E-04 | 1,00E-03 | S |
| sporadic cases (<=65 years) vs controls | 90 vs 298 | 22.8 | 10.8 | 12 | 2.48 | 13.40 | 17.10 | 3,40E-05 | <1.0e-03 | 0/1000 | 11.47 | 9,30E-03 | 4,00E-03 | S |
| sporadic cases (>65 years) vs controls | 189 vs 298 | 18.5 | 10.6 | 7.9 | 1.91 | 8.77 | 12.07 | 5,00E-04 | 2,E-03 | 2/1000 | 13.61 | 3,30E-03 | 4,00E-03 | S |
| sporadic cases informatif vs controls | 70 vs 298 | 25.8 | 10.6 | 15.2 | 2.94 | 17.03 | 22.60 | 2,00E-06 | <1.0e-03 | 0/1000 | 25.83 | 1,00E-05 | 1,00E-03 | S |
| familial cases vs controls | 157 vs 298 | 11.9 | 10.6 | 1.3 | 1.14 | 1.46 | 0.38 | 6,30E-01 | 6,E-01 | 568/1000 | 1.46 | 6,80E-01 | 6,70E-01 | NS |
| familial cases (<=65 years) vs controls | 75 vs 298 | 11.8 | 10.8 | 1 | 1.11 | 1.11 | 0.12 | 6,50E-01 | 7,E-01 | 740/1000 | 2.30 | 5,10E-01 | 4,80E-01 | NS |
| familial cases (>65 years) vs controls | 82 vs 298 | 12.4 | 10.6 | 1.8 | 1.19 | 1.96 | 0.41 | 4,80E-01 | 6,E-01 | 559/1000 | 1.72 | 6,10E-01 | 8,20E-01 | NS |
| familial cases (>=3 caP) vs controls | 64 vs 298 | 7.9 | 10.6 | -2.7 | 0.72 | -3.03 | 0.85 | 3,40E-01 | 4,E-01 | 394/1000 | 2.58 | 4,80E-01 | 4,30E-01 | NS |

Figure 12 C

SEQUENCE LISTING

```
<160> NUMBER OF SEQ ID NOS: 73

<210> SEQ ID NO 1
<211> LENGTH: 97662
<212> TYPE: DNA
<213> ORGANISM: Homo sapiens
<220> FEATURE:
<221> NAME/KEY: misc_feature
<222> LOCATION: 2996..4996
<223> OTHER INFORMATION: 5'regulatory region BAP28
<220> FEATURE:
```

```
<221> NAME/KEY: exon
<222> LOCATION: 4997..5076
<223> OTHER INFORMATION: exon 01 BAP28
<220> FEATURE:
<221> NAME/KEY: exon
<222> LOCATION: 5371..5544
<223> OTHER INFORMATION: exon 02 BAP28
<220> FEATURE:
<221> NAME/KEY: exon
<222> LOCATION: 6121..6337
<223> OTHER INFORMATION: exon 03 BAP28
<220> FEATURE:
<221> NAME/KEY: exon
<222> LOCATION: 9877..10018
<223> OTHER INFORMATION: exon 04 BAP28
<220> FEATURE:
<221> NAME/KEY: exon
<222> LOCATION: 11522..11623
<223> OTHER INFORMATION: exon 05 BAP28
<220> FEATURE:
<221> NAME/KEY: exon
<222> LOCATION: 12521..12661
<223> OTHER INFORMATION: exon 06 BAP28
<220> FEATURE:
<221> NAME/KEY: exon
<222> LOCATION: 13453..13664
<223> OTHER INFORMATION: exon 07 BAP28
<220> FEATURE:
<221> NAME/KEY: exon
<222> LOCATION: 13824..13957
<223> OTHER INFORMATION: exon 08 BAP28
<220> FEATURE:
<221> NAME/KEY: exon
<222> LOCATION: 15376..15478
<223> OTHER INFORMATION: exon 09 BAP28
<220> FEATURE:
<221> NAME/KEY: exon
<222> LOCATION: 16855..16965
<223> OTHER INFORMATION: exon 10 BAP28
<220> FEATURE:
<221> NAME/KEY: exon
<222> LOCATION: 17378..17495
<223> OTHER INFORMATION: exon 11 BAP28
<220> FEATURE:
<221> NAME/KEY: exon
<222> LOCATION: 18535..18642
<223> OTHER INFORMATION: exon 12 BAP28
<220> FEATURE:
<221> NAME/KEY: exon
<222> LOCATION: 21446..21541
<223> OTHER INFORMATION: exon 13 BAP28
<220> FEATURE:
<221> NAME/KEY: exon
<222> LOCATION: 21999..22087
<223> OTHER INFORMATION: exon 14 BAP28
<220> FEATURE:
<221> NAME/KEY: exon
<222> LOCATION: 23036..23247
<223> OTHER INFORMATION: exon 15 BAP28
<220> FEATURE:
<221> NAME/KEY: exon
<222> LOCATION: 23546..23667
<223> OTHER INFORMATION: exon 16 BAP28
<220> FEATURE:
<221> NAME/KEY: exon
<222> LOCATION: 24270..24461
<223> OTHER INFORMATION: exon 17 BAP28
<220> FEATURE:
<221> NAME/KEY: exon
<222> LOCATION: 26287..26470
<223> OTHER INFORMATION: exon 18 BAP28
<220> FEATURE:
<221> NAME/KEY: exon
<222> LOCATION: 26611..26747
<223> OTHER INFORMATION: exon 19 BAP28
<220> FEATURE:
<221> NAME/KEY: exon
<222> LOCATION: 28068..28260
<223> OTHER INFORMATION: exon 20 BAP28
<220> FEATURE:
```

-continued

```
<221> NAME/KEY: exon
<222> LOCATION: 32540..32709
<223> OTHER INFORMATION: exon 21 BAP28
<220> FEATURE:
<221> NAME/KEY: exon
<222> LOCATION: 33112..33270
<223> OTHER INFORMATION: exon 22 BAP28
<220> FEATURE:
<221> NAME/KEY: exon
<222> LOCATION: 34586..34828
<223> OTHER INFORMATION: exon 23 BAP28
<220> FEATURE:
<221> NAME/KEY: exon
<222> LOCATION: 35156..35287
<223> OTHER INFORMATION: exon 24 BAP28
<220> FEATURE:
<221> NAME/KEY: exon
<222> LOCATION: 36660..36763
<223> OTHER INFORMATION: exon 25 BAP28
<220> FEATURE:
<221> NAME/KEY: exon
<222> LOCATION: 36934..37077
<223> OTHER INFORMATION: exon 26 BAP28
<220> FEATURE:
<221> NAME/KEY: exon
<222> LOCATION: 37803..37921
<223> OTHER INFORMATION: exon 27 BAP28
<220> FEATURE:
<221> NAME/KEY: exon
<222> LOCATION: 38017..38138
<223> OTHER INFORMATION: exon 28 BAP28
<220> FEATURE:
<221> NAME/KEY: exon
<222> LOCATION: 40365..40493
<223> OTHER INFORMATION: exon 29 BAP28
<220> FEATURE:
<221> NAME/KEY: exon
<222> LOCATION: 42618..42848
<223> OTHER INFORMATION: exon 30 BAP28
<220> FEATURE:
<221> NAME/KEY: exon
<222> LOCATION: 43452..43578
<223> OTHER INFORMATION: exon 31 BAP28
<220> FEATURE:
<221> NAME/KEY: exon
<222> LOCATION: 44836..44999
<223> OTHER INFORMATION: exon 32 BAP28
<220> FEATURE:
<221> NAME/KEY: exon
<222> LOCATION: 48223..48269
<223> OTHER INFORMATION: exon 33 BAP28
<220> FEATURE:
<221> NAME/KEY: exon
<222> LOCATION: 49656..49779
<223> OTHER INFORMATION: exon 34 BAP28
<220> FEATURE:
<221> NAME/KEY: exon
<222> LOCATION: 50358..50498
<223> OTHER INFORMATION: exon 35 BAP28
<220> FEATURE:
<221> NAME/KEY: exon
<222> LOCATION: 50964..51256
<223> OTHER INFORMATION: exon 36 BAP28
<220> FEATURE:
<221> NAME/KEY: exon
<222> LOCATION: 52148..52298
<223> OTHER INFORMATION: exon 37 BAP28
<220> FEATURE:
<221> NAME/KEY: exon
<222> LOCATION: 53235..53393
<223> OTHER INFORMATION: exon 38 BAP28
<220> FEATURE:
<221> NAME/KEY: exon
<222> LOCATION: 53554..53688
<223> OTHER INFORMATION: exon 39 BAP28
<220> FEATURE:
<221> NAME/KEY: exon
<222> LOCATION: 53838..53942
<223> OTHER INFORMATION: exon 40 BAP28
<220> FEATURE:
```

```
<221> NAME/KEY: exon
<222> LOCATION: 54029..54197
<223> OTHER INFORMATION: exon 41 BAP28
<220> FEATURE:
<221> NAME/KEY: exon
<222> LOCATION: 54741..54895
<223> OTHER INFORMATION: exon 42 BAP28
<220> FEATURE:
<221> NAME/KEY: exon
<222> LOCATION: 55754..55912
<223> OTHER INFORMATION: exon 43 BAP28
<220> FEATURE:
<221> NAME/KEY: exon
<222> LOCATION: 57386..57494
<223> OTHER INFORMATION: exon 44 BAP28
<220> FEATURE:
<221> NAME/KEY: exon
<222> LOCATION: 58504..58827
<223> OTHER INFORMATION: exon 45 BAP28
<220> FEATURE:
<221> NAME/KEY: exon
<222> LOCATION: 58504..59354
<223> OTHER INFORMATION: exon 45b BAP28
<220> FEATURE:
<221> NAME/KEY: exon
<222> LOCATION: 85947..86168
<223> OTHER INFORMATION: exon B' BAP28
<220> FEATURE:
<221> NAME/KEY: exon
<222> LOCATION: 91229..91851
<223> OTHER INFORMATION: exon A' BAP28
<220> FEATURE:
<221> NAME/KEY: misc_feature
<222> LOCATION: 91852..97662
<223> OTHER INFORMATION: 3'regulatory region BAP28
<220> FEATURE:
<221> NAME/KEY: misc_feature
<222> LOCATION: 55071..57071
<223> OTHER INFORMATION: 3'regulatory region PCTA
<220> FEATURE:
<221> NAME/KEY: exon
<222> LOCATION: 57072..58406
<223> OTHER INFORMATION: exon 9ter PCTA complement
<220> FEATURE:
<221> NAME/KEY: exon
<222> LOCATION: 57072..61478
<223> OTHER INFORMATION: exon 9 PCTA complement
<220> FEATURE:
<221> NAME/KEY: exon
<222> LOCATION: 61344..61478
<223> OTHER INFORMATION: exon 9bis PCTA complement
<220> FEATURE:
<221> NAME/KEY: exon
<222> LOCATION: 64578..64743
<223> OTHER INFORMATION: exon 8 PCTA complement
<220> FEATURE:
<221> NAME/KEY: exon
<222> LOCATION: 65844..65932
<223> OTHER INFORMATION: exon 7 PCTA complement
<220> FEATURE:
<221> NAME/KEY: exon
<222> LOCATION: 66452..66577
<223> OTHER INFORMATION: exon 6b PCTA complement
<220> FEATURE:
<221> NAME/KEY: exon
<222> LOCATION: 66705..66731
<223> OTHER INFORMATION: exon 6 PCTA complement
<220> FEATURE:
<221> NAME/KEY: exon
<222> LOCATION: 67782..67838
<223> OTHER INFORMATION: exon 5 PCTA complement
<220> FEATURE:
<221> NAME/KEY: exon
<222> LOCATION: 68810..68929
<223> OTHER INFORMATION: exon 4 PCTA complement
<220> FEATURE:
<221> NAME/KEY: exon
<222> LOCATION: 70404..70614
<223> OTHER INFORMATION: exon 3 PCTA complement
<220> FEATURE:
```

```
<221> NAME/KEY: exon
<222> LOCATION: 71931..72019
<223> OTHER INFORMATION: exon 2 PCTA complement
<220> FEATURE:
<221> NAME/KEY: exon
<222> LOCATION: 83433..83580
<223> OTHER INFORMATION: exon 1 PCTA complement
<220> FEATURE:
<221> NAME/KEY: exon
<222> LOCATION: 85486..85577
<223> OTHER INFORMATION: exon 0 PCTA complement
<220> FEATURE:
<221> NAME/KEY: exon
<222> LOCATION: 85923..86108
<223> OTHER INFORMATION: exon B PCTA complement
<220> FEATURE:
<221> NAME/KEY: exon
<222> LOCATION: 91043..91119
<223> OTHER INFORMATION: exon D PCTA complement
<220> FEATURE:
<221> NAME/KEY: exon
<222> LOCATION: 91259..91325
<223> OTHER INFORMATION: exon A PCTA complement
<220> FEATURE:
<221> NAME/KEY: exon
<222> LOCATION: 92449..92662
<223> OTHER INFORMATION: exon C PCTA complement
<220> FEATURE:
<221> NAME/KEY: misc_feature
<222> LOCATION: 92663..94662
<223> OTHER INFORMATION: 5'regulatory region PCTA
<220> FEATURE:
<221> NAME/KEY: allele
<222> LOCATION: 4972
<223> OTHER INFORMATION: 5-381-133   : polymorphic base A or G
<220> FEATURE:
<221> NAME/KEY: allele
<222> LOCATION: 5468
<223> OTHER INFORMATION: 5-382-162   : polymorphic base C or T
<220> FEATURE:
<221> NAME/KEY: allele
<222> LOCATION: 5616
<223> OTHER INFORMATION: 5-382-310   : polymorphic base C or T
<220> FEATURE:
<221> NAME/KEY: allele
<222> LOCATION: 5622
<223> OTHER INFORMATION: 5-382-316   : polymorphic base G or C
<220> FEATURE:
<221> NAME/KEY: allele
<222> LOCATION: 13158
<223> OTHER INFORMATION: 99-7190-213   : polymorphic base C or T
<220> FEATURE:
<221> NAME/KEY: allele
<222> LOCATION: 23761
<223> OTHER INFORMATION: 99-7203-282   : polymorphic base A or T
<220> FEATURE:
<221> NAME/KEY: allele
<222> LOCATION: 23765
<223> OTHER INFORMATION: 99-7203-286   : polymorphic base C or T
<220> FEATURE:
<221> NAME/KEY: allele
<222> LOCATION: 27928
<223> OTHER INFORMATION: 5-383-42   : polymorphic base A or G
<220> FEATURE:
<221> NAME/KEY: allele
<222> LOCATION: 28070
<223> OTHER INFORMATION: 5-383-184   : polymorphic base G or T
<220> FEATURE:
<221> NAME/KEY: allele
<222> LOCATION: 30061
<223> OTHER INFORMATION: 99-7205-228   : polymorphic base A or G
<220> FEATURE:
<221> NAME/KEY: allele
<222> LOCATION: 32750
<223> OTHER INFORMATION: 5-384-312   : polymorphic base G or C
<220> FEATURE:
<221> NAME/KEY: allele
<222> LOCATION: 48189
<223> OTHER INFORMATION: 5-379-80   : polymorphic base A or C
<220> FEATURE:
```

```
<221> NAME/KEY: allele
<222> LOCATION: 49615
<223> OTHER INFORMATION: 5-380-58   : polymorphic base G or T
<220> FEATURE:
<221> NAME/KEY: allele
<222> LOCATION: 49616
<223> OTHER INFORMATION: 5-380-59   : polymorphic base C or T
<220> FEATURE:
<221> NAME/KEY: allele
<222> LOCATION: 50304
<223> OTHER INFORMATION: 5-366-143  : polymorphic base A or G
<220> FEATURE:
<221> NAME/KEY: allele
<222> LOCATION: 51133
<223> OTHER INFORMATION: 5-370-197  : polymorphic base A or G
<220> FEATURE:
<221> NAME/KEY: allele
<222> LOCATION: 51183
<223> OTHER INFORMATION: 5-370-247  : polymorphic base C or T
<220> FEATURE:
<221> NAME/KEY: allele
<222> LOCATION: 53534
<223> OTHER INFORMATION: 5-373-98   : polymorphic base C or T
<220> FEATURE:
<221> NAME/KEY: allele
<222> LOCATION: 53600
<223> OTHER INFORMATION: 5-373-164  : polymorphic base C or T
<220> FEATURE:
<221> NAME/KEY: allele
<222> LOCATION: 53658
<223> OTHER INFORMATION: 5-373-222  : polymorphic base A or G
<220> FEATURE:
<221> NAME/KEY: allele
<222> LOCATION: 54173
<223> OTHER INFORMATION: 5-375-200  : polymorphic base A or G
<220> FEATURE:
<221> NAME/KEY: allele
<222> LOCATION: 54232
<223> OTHER INFORMATION: 5-375-259  : polymorphic base C or T
<220> FEATURE:
<221> NAME/KEY: allele
<222> LOCATION: 54269
<223> OTHER INFORMATION: 5-375-296  : polymorphic base G or C
<220> FEATURE:
<221> NAME/KEY: allele
<222> LOCATION: 54372
<223> OTHER INFORMATION: 5-375-399  : polymorphic base G or C
<220> FEATURE:
<221> NAME/KEY: allele
<222> LOCATION: 54867
<223> OTHER INFORMATION: 5-376-266  : polymorphic base A or G
<220> FEATURE:
<221> NAME/KEY: allele
<222> LOCATION: 55689
<223> OTHER INFORMATION: 5-377-82   : polymorphic base C or T
<220> FEATURE:
<221> NAME/KEY: allele
<222> LOCATION: 55834
<223> OTHER INFORMATION: 5-377-227  : polymorphic base A or G
<220> FEATURE:
<221> NAME/KEY: allele
<222> LOCATION: 59937
<223> OTHER INFORMATION: 5-14-165   : polymorphic base A or G
<220> FEATURE:
<221> NAME/KEY: allele
<222> LOCATION: 60980
<223> OTHER INFORMATION: 5-11-158   : polymorphic base C or T
<220> FEATURE:
<221> NAME/KEY: allele
<222> LOCATION: 66492
<223> OTHER INFORMATION: 5-202-117  : polymorphic base A or T
<220> FEATURE:
<221> NAME/KEY: allele
<222> LOCATION: 66514
<223> OTHER INFORMATION: 5-202-95   : polymorphic base A or C
<220> FEATURE:
<221> NAME/KEY: allele
<222> LOCATION: 71834
<223> OTHER INFORMATION: 99-1605-112  : polymorphic base A or G
<220> FEATURE:
```

```
<221> NAME/KEY: allele
<222> LOCATION: 71993
<223> OTHER INFORMATION: 5-2-178  : polymorphic base A or G
<220> FEATURE:
<221> NAME/KEY: allele
<222> LOCATION: 85702
<223> OTHER INFORMATION: 5-171-204  : polymorphic base A or G
<220> FEATURE:
<221> NAME/KEY: allele
<222> LOCATION: 86504
<223> OTHER INFORMATION: 5-169-97  : polymorphic base G or C
<220> FEATURE:
<221> NAME/KEY: allele
<222> LOCATION: 87135
<223> OTHER INFORMATION: 99-1572-440  : polymorphic base A or G
<220> FEATURE:
<221> NAME/KEY: allele
<222> LOCATION: 91093
<223> OTHER INFORMATION: 5-403-325  : polymorphic base C or T
<220> FEATURE:
<221> NAME/KEY: allele
<222> LOCATION: 91124
<223> OTHER INFORMATION: 5-403-294  : polymorphic base A or G
<220> FEATURE:
<221> NAME/KEY: allele
<222> LOCATION: 91209
<223> OTHER INFORMATION: 5-403-209  : polymorphic base C or T
<220> FEATURE:
<221> NAME/KEY: allele
<222> LOCATION: 91262
<223> OTHER INFORMATION: 5-403-156  : polymorphic base C or T
<220> FEATURE:
<221> NAME/KEY: primer_bind
<222> LOCATION: 4840..4859
<223> OTHER INFORMATION: 5-381.pu
<220> FEATURE:
<221> NAME/KEY: primer_bind
<222> LOCATION: 5249..5266
<223> OTHER INFORMATION: 5-381.rp  complement
<220> FEATURE:
<221> NAME/KEY: primer_bind
<222> LOCATION: 5307..5324
<223> OTHER INFORMATION: 5-382.pu
<220> FEATURE:
<221> NAME/KEY: primer_bind
<222> LOCATION: 5710..5729
<223> OTHER INFORMATION: 5-382.rp  complement
<220> FEATURE:
<221> NAME/KEY: primer_bind
<222> LOCATION: 12946..12963
<223> OTHER INFORMATION: 99-7190.pu
<220> FEATURE:
<221> NAME/KEY: primer_bind
<222> LOCATION: 13471..13488
<223> OTHER INFORMATION: 99-7190.rp  complement
<220> FEATURE:
<221> NAME/KEY: primer_bind
<222> LOCATION: 23482..23501
<223> OTHER INFORMATION: 99-7203.pu
<220> FEATURE:
<221> NAME/KEY: primer_bind
<222> LOCATION: 23909..23929
<223> OTHER INFORMATION: 99-7203.rp  complement
<220> FEATURE:
<221> NAME/KEY: primer_bind
<222> LOCATION: 27887..27904
<223> OTHER INFORMATION: 5-383.pu
<220> FEATURE:
<221> NAME/KEY: primer_bind
<222> LOCATION: 28296..28315
<223> OTHER INFORMATION: 5-383.rp  complement
<220> FEATURE:
<221> NAME/KEY: primer_bind
<222> LOCATION: 29833..29853
<223> OTHER INFORMATION: 99-7205.rp
<220> FEATURE:
<221> NAME/KEY: primer_bind
<222> LOCATION: 30270..30288
<223> OTHER INFORMATION: 99-7205.pu complement
<220> FEATURE:
```

```
<221> NAME/KEY: primer_bind
<222> LOCATION: 32439..32457
<223> OTHER INFORMATION: 5-384.pu
<220> FEATURE:
<221> NAME/KEY: primer_bind
<222> LOCATION: 32858..32877
<223> OTHER INFORMATION: 5-384.rp   complement
<220> FEATURE:
<221> NAME/KEY: primer_bind
<222> LOCATION: 48110..48127
<223> OTHER INFORMATION: 5-379.pu
<220> FEATURE:
<221> NAME/KEY: primer_bind
<222> LOCATION: 48441..48460
<223> OTHER INFORMATION: 5-379.rp   complement
<220> FEATURE:
<221> NAME/KEY: primer_bind
<222> LOCATION: 49558..49577
<223> OTHER INFORMATION: 5-380.pu
<220> FEATURE:
<221> NAME/KEY: primer_bind
<222> LOCATION: 49958..49977
<223> OTHER INFORMATION: 5-380.rp   complement
<220> FEATURE:
<221> NAME/KEY: primer_bind
<222> LOCATION: 50162..50180
<223> OTHER INFORMATION: 5-366.pu
<220> FEATURE:
<221> NAME/KEY: primer_bind
<222> LOCATION: 50564..50583
<223> OTHER INFORMATION: 5-366.rp   complement
<220> FEATURE:
<221> NAME/KEY: primer_bind
<222> LOCATION: 50937..50955
<223> OTHER INFORMATION: 5-370.pu
<220> FEATURE:
<221> NAME/KEY: primer_bind
<222> LOCATION: 51341..51359
<223> OTHER INFORMATION: 5-370.rp   complement
<220> FEATURE:
<221> NAME/KEY: primer_bind
<222> LOCATION: 53437..53455
<223> OTHER INFORMATION: 5-373.pu
<220> FEATURE:
<221> NAME/KEY: primer_bind
<222> LOCATION: 53840..53858
<223> OTHER INFORMATION: 5-373.rp   complement
<220> FEATURE:
<221> NAME/KEY: primer_bind
<222> LOCATION: 53974..53993
<223> OTHER INFORMATION: 5-375.pu
<220> FEATURE:
<221> NAME/KEY: primer_bind
<222> LOCATION: 54375..54394
<223> OTHER INFORMATION: 5-375.rp   complement
<220> FEATURE:
<221> NAME/KEY: primer_bind
<222> LOCATION: 54602..54619
<223> OTHER INFORMATION: 5-376.pu
<220> FEATURE:
<221> NAME/KEY: primer_bind
<222> LOCATION: 55002..55021
<223> OTHER INFORMATION: 5-376.rp   complement
<220> FEATURE:
<221> NAME/KEY: primer_bind
<222> LOCATION: 55608..55625
<223> OTHER INFORMATION: 5-377.pu
<220> FEATURE:
<221> NAME/KEY: primer_bind
<222> LOCATION: 56025..56043
<223> OTHER INFORMATION: 5-377.rp   complement
<220> FEATURE:
<221> NAME/KEY: primer_bind
<222> LOCATION: 59673..59692
<223> OTHER INFORMATION: 5-14.rp
<220> FEATURE:
<221> NAME/KEY: primer_bind
<222> LOCATION: 60083..60100
<223> OTHER INFORMATION: 5-14.pu complement
<220> FEATURE:
```

-continued

```
<221> NAME/KEY: primer_bind
<222> LOCATION: 60718..60737
<223> OTHER INFORMATION: 5-11.rp
<220> FEATURE:
<221> NAME/KEY: primer_bind
<222> LOCATION: 61119..61137
<223> OTHER INFORMATION: 5-11.pu complement
<220> FEATURE:
<221> NAME/KEY: primer_bind
<222> LOCATION: 66177..66194
<223> OTHER INFORMATION: 5-202.rp
<220> FEATURE:
<221> NAME/KEY: primer_bind
<222> LOCATION: 66589..66608
<223> OTHER INFORMATION: 5-202.pu complement
<220> FEATURE:
<221> NAME/KEY: primer_bind
<222> LOCATION: 71723..71743
<223> OTHER INFORMATION: 99-1605.pu
<220> FEATURE:
<221> NAME/KEY: primer_bind
<222> LOCATION: 71735..71754
<223> OTHER INFORMATION: 5-2.rp
<220> FEATURE:
<221> NAME/KEY: primer_bind
<222> LOCATION: 72150..72169
<223> OTHER INFORMATION: 5-2.pu complement
<220> FEATURE:
<221> NAME/KEY: primer_bind
<222> LOCATION: 72150..72170
<223> OTHER INFORMATION: 99-1605.rp  complement
<220> FEATURE:
<221> NAME/KEY: primer_bind
<222> LOCATION: 85485..85502
<223> OTHER INFORMATION: 5-171.rp
<220> FEATURE:
<221> NAME/KEY: primer_bind
<222> LOCATION: 85887..85905
<223> OTHER INFORMATION: 5-171.pu complement
<220> FEATURE:
<221> NAME/KEY: primer_bind
<222> LOCATION: 86184..86203
<223> OTHER INFORMATION: 5-169.rp
<220> FEATURE:
<221> NAME/KEY: primer_bind
<222> LOCATION: 86581..86600
<223> OTHER INFORMATION: 5-169.pu complement
<220> FEATURE:
<221> NAME/KEY: primer_bind
<222> LOCATION: 86932..86952
<223> OTHER INFORMATION: 99-1572.rp
<220> FEATURE:
<221> NAME/KEY: primer_bind
<222> LOCATION: 87556..87574
<223> OTHER INFORMATION: 99-1572.pu complement
<220> FEATURE:
<221> NAME/KEY: primer_bind
<222> LOCATION: 91068..91085
<223> OTHER INFORMATION: 5-403.rp
<220> FEATURE:
<221> NAME/KEY: primer_bind
<222> LOCATION: 91398..91417
<223> OTHER INFORMATION: 5-403.pu complement
<220> FEATURE:
<221> NAME/KEY: primer_bind
<222> LOCATION: 4953..4971
<223> OTHER INFORMATION: 5-381-133.mis
<220> FEATURE:
<221> NAME/KEY: primer_bind
<222> LOCATION: 4973..4991
<223> OTHER INFORMATION: 5-381-133.mis complement
<220> FEATURE:
<221> NAME/KEY: primer_bind
<222> LOCATION: 5449..5467
<223> OTHER INFORMATION: 5-382-162.mis
<220> FEATURE:
<221> NAME/KEY: primer_bind
<222> LOCATION: 5469..5487
<223> OTHER INFORMATION: 5-382-162.mis complement
<220> FEATURE:
```

-continued

```
<221> NAME/KEY: primer_bind
<222> LOCATION: 5597..5615
<223> OTHER INFORMATION: 5-382-310.mis
<220> FEATURE:
<221> NAME/KEY: primer_bind
<222> LOCATION: 5603..5621
<223> OTHER INFORMATION: 5-382-316.mis
<220> FEATURE:
<221> NAME/KEY: primer_bind
<222> LOCATION: 5617..5635
<223> OTHER INFORMATION: 5-382-310.mis complement
<220> FEATURE:
<221> NAME/KEY: primer_bind
<222> LOCATION: 5623..5641
<223> OTHER INFORMATION: 5-382-316.mis complement
<220> FEATURE:
<221> NAME/KEY: primer_bind
<222> LOCATION: 13139..13157
<223> OTHER INFORMATION: 99-7190-213.mis
<220> FEATURE:
<221> NAME/KEY: primer_bind
<222> LOCATION: 13159..13177
<223> OTHER INFORMATION: 99-7190-213.mis complement
<220> FEATURE:
<221> NAME/KEY: primer_bind
<222> LOCATION: 23742..23760
<223> OTHER INFORMATION: 99-7203-282.mis
<220> FEATURE:
<221> NAME/KEY: primer_bind
<222> LOCATION: 23746..23764
<223> OTHER INFORMATION: 99-7203-286.mis
<220> FEATURE:
<221> NAME/KEY: primer_bind
<222> LOCATION: 23762..23780
<223> OTHER INFORMATION: 99-7203-282.mis complement
<220> FEATURE:
<221> NAME/KEY: primer_bind
<222> LOCATION: 23766..23784
<223> OTHER INFORMATION: 99-7203-286.mis complement
<220> FEATURE:
<221> NAME/KEY: primer_bind
<222> LOCATION: 27909..27927
<223> OTHER INFORMATION: 5-383-42.mis
<220> FEATURE:
<221> NAME/KEY: primer_bind
<222> LOCATION: 27929..27947
<223> OTHER INFORMATION: 5-383-42.mis complement
<220> FEATURE:
<221> NAME/KEY: primer_bind
<222> LOCATION: 28051..28069
<223> OTHER INFORMATION: 5-383-184.mis
<220> FEATURE:
<221> NAME/KEY: primer_bind
<222> LOCATION: 28071..28089
<223> OTHER INFORMATION: 5-383-184.mis complement
<220> FEATURE:
<221> NAME/KEY: primer_bind
<222> LOCATION: 30042..30060
<223> OTHER INFORMATION: 99-7205-228.mis
<220> FEATURE:
<221> NAME/KEY: primer_bind
<222> LOCATION: 30062..30080
<223> OTHER INFORMATION: 99-7205-228.mis complement
<220> FEATURE:
<221> NAME/KEY: primer_bind
<222> LOCATION: 32731..32749
<223> OTHER INFORMATION: 5-384-312.mis
<220> FEATURE:
<221> NAME/KEY: primer_bind
<222> LOCATION: 32751..32769
<223> OTHER INFORMATION: 5-384-312.mis complement
<220> FEATURE:
<221> NAME/KEY: primer_bind
<222> LOCATION: 48170..48188
<223> OTHER INFORMATION: 5-379-80.mis
<220> FEATURE:
<221> NAME/KEY: primer_bind
<222> LOCATION: 48190..48208
<223> OTHER INFORMATION: 5-379-80.mis complement
<220> FEATURE:
```

```
<221> NAME/KEY: primer_bind
<222> LOCATION: 49596..49614
<223> OTHER INFORMATION: 5-380-58.mis
<220> FEATURE:
<221> NAME/KEY: primer_bind
<222> LOCATION: 49597..49615
<223> OTHER INFORMATION: 5-380-59.mis
<220> FEATURE:
<221> NAME/KEY: primer_bind
<222> LOCATION: 49616..49634
<223> OTHER INFORMATION: 5-380-58.mis complement
<220> FEATURE:
<221> NAME/KEY: primer_bind
<222> LOCATION: 49617..49635
<223> OTHER INFORMATION: 5-380-59.mis complement
<220> FEATURE:
<221> NAME/KEY: primer_bind
<222> LOCATION: 50285..50303
<223> OTHER INFORMATION: 5-366-143.mis
<220> FEATURE:
<221> NAME/KEY: primer_bind
<222> LOCATION: 50305..50323
<223> OTHER INFORMATION: 5-366-143.mis complement
<220> FEATURE:
<221> NAME/KEY: primer_bind
<222> LOCATION: 51114..51132
<223> OTHER INFORMATION: 5-370-197.mis
<220> FEATURE:
<221> NAME/KEY: primer_bind
<222> LOCATION: 51134..51152
<223> OTHER INFORMATION: 5-370-197.mis complement
<220> FEATURE:
<221> NAME/KEY: primer_bind
<222> LOCATION: 51164..51182
<223> OTHER INFORMATION: 5-370-247.mis
<220> FEATURE:
<221> NAME/KEY: primer_bind
<222> LOCATION: 51184..51202
<223> OTHER INFORMATION: 5-370-247.mis complement
<220> FEATURE:
<221> NAME/KEY: primer_bind
<222> LOCATION: 53515..53533
<223> OTHER INFORMATION: 5-373-98.mis
<220> FEATURE:
<221> NAME/KEY: primer_bind
<222> LOCATION: 53535..53553
<223> OTHER INFORMATION: 5-373-98.mis complement
<220> FEATURE:
<221> NAME/KEY: primer_bind
<222> LOCATION: 53581..53599
<223> OTHER INFORMATION: 5-373-164.mis
<220> FEATURE:
<221> NAME/KEY: primer_bind
<222> LOCATION: 53601..53619
<223> OTHER INFORMATION: 5-373-164.mis complement
<220> FEATURE:
<221> NAME/KEY: primer_bind
<222> LOCATION: 53639..53657
<223> OTHER INFORMATION: 5-373-222.mis
<220> FEATURE:
<221> NAME/KEY: primer_bind
<222> LOCATION: 53659..53677
<223> OTHER INFORMATION: 5-373-222.mis complement
<220> FEATURE:
<221> NAME/KEY: primer_bind
<222> LOCATION: 54154..54172
<223> OTHER INFORMATION: 5-375-200.mis
<220> FEATURE:
<221> NAME/KEY: primer_bind
<222> LOCATION: 54174..54192
<223> OTHER INFORMATION: 5-375-200.mis complement
<220> FEATURE:
<221> NAME/KEY: primer_bind
<222> LOCATION: 54213..54231
<223> OTHER INFORMATION: 5-375-259.mis
<220> FEATURE:
<221> NAME/KEY: primer_bind
<222> LOCATION: 54233..54251
<223> OTHER INFORMATION: 5-375-259.mis complement
<220> FEATURE:
```

```
<221> NAME/KEY: primer_bind
<222> LOCATION: 54250..54268
<223> OTHER INFORMATION: 5-375-296.mis
<220> FEATURE:
<221> NAME/KEY: primer_bind
<222> LOCATION: 54270..54288
<223> OTHER INFORMATION: 5-375-296.mis complement
<220> FEATURE:
<221> NAME/KEY: primer_bind
<222> LOCATION: 54353..54371
<223> OTHER INFORMATION: 5-375-399.mis
<220> FEATURE:
<221> NAME/KEY: primer_bind
<222> LOCATION: 54373..54391
<223> OTHER INFORMATION: 5-375-399.mis complement
<220> FEATURE:
<221> NAME/KEY: primer_bind
<222> LOCATION: 54848..54866
<223> OTHER INFORMATION: 5-376-266.mis
<220> FEATURE:
<221> NAME/KEY: primer_bind
<222> LOCATION: 54868..54886
<223> OTHER INFORMATION: 5-376-266.mis complement
<220> FEATURE:
<221> NAME/KEY: primer_bind
<222> LOCATION: 55670..55688
<223> OTHER INFORMATION: 5-377-82.mis
<220> FEATURE:
<221> NAME/KEY: primer_bind
<222> LOCATION: 55690..55708
<223> OTHER INFORMATION: 5-377-82.mis complement
<220> FEATURE:
<221> NAME/KEY: primer_bind
<222> LOCATION: 55815..55833
<223> OTHER INFORMATION: 5-377-227.mis
<220> FEATURE:
<221> NAME/KEY: primer_bind
<222> LOCATION: 55835..55853
<223> OTHER INFORMATION: 5-377-227.mis complement
<220> FEATURE:
<221> NAME/KEY: primer_bind
<222> LOCATION: 59918..59936
<223> OTHER INFORMATION: 5-14-165.mis
<220> FEATURE:
<221> NAME/KEY: primer_bind
<222> LOCATION: 59938..59956
<223> OTHER INFORMATION: 5-14-165.mis complement
<220> FEATURE:
<221> NAME/KEY: primer_bind
<222> LOCATION: 60961..60979
<223> OTHER INFORMATION: 5-11-158.mis
<220> FEATURE:
<221> NAME/KEY: primer_bind
<222> LOCATION: 60981..60999
<223> OTHER INFORMATION: 5-11-158.mis complement
<220> FEATURE:
<221> NAME/KEY: primer_bind
<222> LOCATION: 66473..66491
<223> OTHER INFORMATION: 5-202-117.mis
<220> FEATURE:
<221> NAME/KEY: primer_bind
<222> LOCATION: 66493..66511
<223> OTHER INFORMATION: 5-202-117.mis complement
<220> FEATURE:
<221> NAME/KEY: primer_bind
<222> LOCATION: 66495..66513
<223> OTHER INFORMATION: 5-202-95.mis
<220> FEATURE:
<221> NAME/KEY: primer_bind
<222> LOCATION: 66515..66533
<223> OTHER INFORMATION: 5-202-95.mis complement
<220> FEATURE:
<221> NAME/KEY: primer_bind
<222> LOCATION: 71815..71833
<223> OTHER INFORMATION: 99-1605-112.mis
<220> FEATURE:
<221> NAME/KEY: primer_bind
<222> LOCATION: 71835..71853
<223> OTHER INFORMATION: 99-1605-112.mis complement
<220> FEATURE:
```

```
<221> NAME/KEY: primer_bind
<222> LOCATION: 71974..71992
<223> OTHER INFORMATION: 5-2-178.mis
<220> FEATURE:
<221> NAME/KEY: primer_bind
<222> LOCATION: 71994..72012
<223> OTHER INFORMATION: 5-2-178.mis complement
<220> FEATURE:
<221> NAME/KEY: primer_bind
<222> LOCATION: 85683..85701
<223> OTHER INFORMATION: 5-171-204.mis
<220> FEATURE:
<221> NAME/KEY: primer_bind
<222> LOCATION: 85703..85721
<223> OTHER INFORMATION: 5-171-204.mis complement
<220> FEATURE:
<221> NAME/KEY: primer_bind
<222> LOCATION: 86485..86503
<223> OTHER INFORMATION: 5-169-97.mis
<220> FEATURE:
<221> NAME/KEY: primer_bind
<222> LOCATION: 86505..86523
<223> OTHER INFORMATION: 5-169-97.mis complement
<220> FEATURE:
<221> NAME/KEY: primer_bind
<222> LOCATION: 87116..87134
<223> OTHER INFORMATION: 99-1572-440.mis
<220> FEATURE:
<221> NAME/KEY: primer_bind
<222> LOCATION: 87136..87154
<223> OTHER INFORMATION: 99-1572-440.mis complement
<220> FEATURE:
<221> NAME/KEY: primer_bind
<222> LOCATION: 91074..91092
<223> OTHER INFORMATION: 5-403-325.mis
<220> FEATURE:
<221> NAME/KEY: primer_bind
<222> LOCATION: 91094..91112
<223> OTHER INFORMATION: 5-403-325.mis complement
<220> FEATURE:
<221> NAME/KEY: primer_bind
<222> LOCATION: 91105..91123
<223> OTHER INFORMATION: 5-403-294.mis
<220> FEATURE:
<221> NAME/KEY: primer_bind
<222> LOCATION: 91125..91143
<223> OTHER INFORMATION: 5-403-294.mis complement
<220> FEATURE:
<221> NAME/KEY: primer_bind
<222> LOCATION: 91190..91208
<223> OTHER INFORMATION: 5-403-209.mis
<220> FEATURE:
<221> NAME/KEY: primer_bind
<222> LOCATION: 91210..91228
<223> OTHER INFORMATION: 5-403-209.mis complement
<220> FEATURE:
<221> NAME/KEY: primer_bind
<222> LOCATION: 91243..91261
<223> OTHER INFORMATION: 5-403-156.mis
<220> FEATURE:
<221> NAME/KEY: primer_bind
<222> LOCATION: 91263..91281
<223> OTHER INFORMATION: 5-403-156.mis complement
<220> FEATURE:
<221> NAME/KEY: misc_binding
<222> LOCATION: 4960..4984
<223> OTHER INFORMATION: 5-381-133.probe
<220> FEATURE:
<221> NAME/KEY: misc_binding
<222> LOCATION: 5456..5480
<223> OTHER INFORMATION: 5-382-162.probe
<220> FEATURE:
<221> NAME/KEY: misc_binding
<222> LOCATION: 5604..5628
<223> OTHER INFORMATION: 5-382-310.probe
<220> FEATURE:
<221> NAME/KEY: misc_binding
<222> LOCATION: 5610..5634
<223> OTHER INFORMATION: 5-382-316.probe
<220> FEATURE:
```

-continued

```
<221> NAME/KEY: misc_binding
<222> LOCATION: 13146..13170
<223> OTHER INFORMATION: 99-7190-213.probe
<220> FEATURE:
<221> NAME/KEY: misc_binding
<222> LOCATION: 23749..23773
<223> OTHER INFORMATION: 99-7203-282.probe
<220> FEATURE:
<221> NAME/KEY: misc_binding
<222> LOCATION: 23753..23777
<223> OTHER INFORMATION: 99-7203-286.probe
<220> FEATURE:
<221> NAME/KEY: misc_binding
<222> LOCATION: 27916..27940
<223> OTHER INFORMATION: 5-383-42.probe
<220> FEATURE:
<221> NAME/KEY: misc_binding
<222> LOCATION: 28058..28082
<223> OTHER INFORMATION: 5-383-184.probe
<220> FEATURE:
<221> NAME/KEY: misc_binding
<222> LOCATION: 30049..30073
<223> OTHER INFORMATION: 99-7205-228.probe
<220> FEATURE:
<221> NAME/KEY: misc_binding
<222> LOCATION: 32738..32762
<223> OTHER INFORMATION: 5-384-312.probe
<220> FEATURE:
<221> NAME/KEY: misc_binding
<222> LOCATION: 48177..48201
<223> OTHER INFORMATION: 5-379-80.probe
<220> FEATURE:
<221> NAME/KEY: misc_binding
<222> LOCATION: 49603..49627
<223> OTHER INFORMATION: 5-380-58.probe
<220> FEATURE:
<221> NAME/KEY: misc_binding
<222> LOCATION: 49604..49628
<223> OTHER INFORMATION: 5-380-59.probe
<220> FEATURE:
<221> NAME/KEY: misc_binding
<222> LOCATION: 50292..50316
<223> OTHER INFORMATION: 5-366-143.probe
<220> FEATURE:
<221> NAME/KEY: misc_binding
<222> LOCATION: 51121..51145
<223> OTHER INFORMATION: 5-370-197.probe
<220> FEATURE:
<221> NAME/KEY: misc_binding
<222> LOCATION: 51171..51195
<223> OTHER INFORMATION: 5-370-247.probe
<220> FEATURE:
<221> NAME/KEY: misc_binding
<222> LOCATION: 53522..53546
<223> OTHER INFORMATION: 5-373-98.probe
<220> FEATURE:
<221> NAME/KEY: misc_binding
<222> LOCATION: 53588..53612
<223> OTHER INFORMATION: 5-373-164.probe
<220> FEATURE:
<221> NAME/KEY: misc_binding
<222> LOCATION: 53646..53670
<223> OTHER INFORMATION: 5-373-222.probe
<220> FEATURE:
<221> NAME/KEY: misc_binding
<222> LOCATION: 54161..54185
<223> OTHER INFORMATION: 5-375-200.probe
<220> FEATURE:
<221> NAME/KEY: misc_binding
<222> LOCATION: 54220..54244
<223> OTHER INFORMATION: 5-375-259.probe
<220> FEATURE:
<221> NAME/KEY: misc_binding
<222> LOCATION: 54257..54281
<223> OTHER INFORMATION: 5-375-296.probe
<220> FEATURE:
<221> NAME/KEY: misc_binding
<222> LOCATION: 54360..54384
<223> OTHER INFORMATION: 5-375-399.probe
<220> FEATURE:
```

-continued

```
<221> NAME/KEY: misc_binding
<222> LOCATION: 54855..54879
<223> OTHER INFORMATION: 5-376-266.probe
<220> FEATURE:
<221> NAME/KEY: misc_binding
<222> LOCATION: 55677..55701
<223> OTHER INFORMATION: 5-377-82.probe
<220> FEATURE:
<221> NAME/KEY: misc_binding
<222> LOCATION: 55822..55846
<223> OTHER INFORMATION: 5-377-227.probe
<220> FEATURE:
<221> NAME/KEY: misc_binding
<222> LOCATION: 59925..59949
<223> OTHER INFORMATION: 5-14-165.probe
<220> FEATURE:
<221> NAME/KEY: misc_binding
<222> LOCATION: 60968..60992
<223> OTHER INFORMATION: 5-11-158.probe
<220> FEATURE:
<221> NAME/KEY: misc_binding
<222> LOCATION: 66480..66504
<223> OTHER INFORMATION: 5-202-117.probe
<220> FEATURE:
<221> NAME/KEY: misc_binding
<222> LOCATION: 66502..66526
<223> OTHER INFORMATION: 5-202-95.probe
<220> FEATURE:
<221> NAME/KEY: misc_binding
<222> LOCATION: 71822..71846
<223> OTHER INFORMATION: 99-1605-112.probe
<220> FEATURE:
<221> NAME/KEY: misc_binding
<222> LOCATION: 71981..72005
<223> OTHER INFORMATION: 5-2-178.probe
<220> FEATURE:
<221> NAME/KEY: misc_binding
<222> LOCATION: 85690..85714
<223> OTHER INFORMATION: 5-171-204.probe
<220> FEATURE:
<221> NAME/KEY: misc_binding
<222> LOCATION: 86492..86516
<223> OTHER INFORMATION: 5-169-97.probe
<220> FEATURE:
<221> NAME/KEY: misc_binding
<222> LOCATION: 87123..87147
<223> OTHER INFORMATION: 99-1572-440.probe
<220> FEATURE:
<221> NAME/KEY: misc_binding
<222> LOCATION: 91081..91105
<223> OTHER INFORMATION: 5-403-325.probe
<220> FEATURE:
<221> NAME/KEY: misc_binding
<222> LOCATION: 91112..91136
<223> OTHER INFORMATION: 5-403-294.probe
<220> FEATURE:
<221> NAME/KEY: misc_binding
<222> LOCATION: 91197..91221
<223> OTHER INFORMATION: 5-403-209.probe
<220> FEATURE:
<221> NAME/KEY: misc_binding
<222> LOCATION: 91250..91274
<223> OTHER INFORMATION: 5-403-156.probe

<400> SEQUENCE: 1
ccttcgaagg cattattttt atggcatttt tatgacacat ggaagctttc atgaaccaat      60
ttttagataa ttgtatataa ttttccattt taaaaagtgt gaaaactgat acttccataa    120
ggcaactggg gatacccctga atgccctctg gggtcaggaa aatgctttgg tgccacctgc    180
cggtttccaa agatgtttca ggaacttgct cctgttgatt ccaaatctt ttttttttt      240 tttaattcct agctccctcc cagtacattt caaaatacca aaaaaaaaa aaaaaaaaa      300 attataaatt ttttggtagc aagagcacaa gtgctcaagc ttataaaaat gcaaataaat    360
ttgtttggga tgcaatatga tgaaacacat acttctcaat catttaacta gtcaattttt    420
```

```
tttagcatat tgccaaaatg tagatttcat atgttgactt tacattgcta attacacaca    480
tcctatttct tttctcgtta ttttttcttt ctttcttatt tttacttttt gcgactccct    540
ctggtaccca ggctggagtt cagtggtgca atttcagctc acttcaacct ctgcctccca    600
ggctcaattg atcctcccag gctcaactga tcctcccatt ttcagcctcc cagggcgtgc    660
taccatgccc ggctaatttt tgtgctcatt gcagaggtgg agtttcccca tgttgctcag    720
actggtcttg aattcctggg ctcaagcgat atgccagcct tggcctctca accttgctgg    780
gtttacaagc gtgagccact gagcccagca acagatatat tttcaagtgg atggtatccc    840
atcagttgtg atatatgatg taaacactct actaataatt aaactttgaa gtttgtgaaa    900
attttacttt tattatagtt agaataattc taagttattc ctataataat gctacactta    960
ttcacttgaa ttctgataca catttcttga acaggaagga gatacagata cagcttatgc   1020
acatttatat tcattcattc attcgataaa taaatatgta ttgttaacca cgttccaggt   1080
actttatttg gtagttagga tttagtagta aacacgagaa agtcttcaac atcatcctta   1140
gatcgtgatc tctgcatatc acaaatcata caaaataaat ttgcttaaaa atgtgggaac   1200
ctgcctttca aaacctgcca tttagcacta ctgtggcata acctataaac ctaaacatag   1260
accctcatga tttatgcatt taagtttgtg ggaaataggt ctcttgtccc ttgtcctgaa   1320
agtaaaagac aaccctgtct gaatacactg aatatccgtg gattgtactg tttccggacg   1380
ctgcctaaga gcatagggag aatttgtttt tttgtttgtt ttttgtttcg ttttattttt   1440
gagacggagt ttcgctcttg ttgcccaggc tggagtgcaa acggcgcgat gtcggctcac   1500
tgcaacctcc acctcccggt tcaagagatt ctcctgcctc agcctcccta gtagctggga   1560
ttacaggcgt gcgccaccac gcccggccaa tttttttta gtagagtcag gattagtatt   1620
attagtagag atggggtttc accatgttgg ccaggctggt ctcaaactcc tgacctcagg   1680
tgagccgccc gcctcagcct ccaaagtgct gggttacagg catgagccac cgcacctggc   1740
cgggacccga ccaggatgct gaatacagaa atgcttaggt aagagaaaag aaaagttaat   1800
ttgtcacact tttcctttca aactacatga acatatttt gcattataaa gtattatatc    1860
taagtagttc caaacatgga atttcttatt tcctttttt ccccccaatt tatggttctg    1920
gatatactca ggaattagtg tagaattctc aacaatcaga tatggttgct gaggaacatt   1980
taacaatatt aaacaattca catgactctg aaatttgaaa ataggtagat acagacataa   2040
catgaacaaa gggtgatacc aattctttac actggcaact aggtggacat tgaatgatac   2100
gcttgtgagt aatttacttt aatgaacaat ttcattaagt aatatttacc aaaaaaacaa   2160
atacaacttt agatttattt aaattatttt acttaaaatt ttgtcactaa ttaaaccccg   2220
tctctactaa aaatacaaaa attagctggg tgtggtggca ggcacctgta atcccagcta   2280
cttgagaagc tgaggcagag gattgcttga acctgggagg cggaggttgc agtgagctga   2340
gatcacgcca ccacactcga gcctgggcga cagagcaaga ctccatctca aaacaaaaaa   2400
aaaatattgt cactaattat actttacatc ttataagaaa ggtaaatctt tgaaaaaag   2460 tgaaaaagat ttaatgtatt gcttttaat ttaatttata tttttattga acattcaaa    2520 ctatatgttt tgaatataat taaattttat ttttaatcct ttttgatcat tatttctgat   2580
agaacacaat tacatgaaaa tcttgatcaa acagcataca tggtaatttt gctgaaatga   2640
aggtaaattt tcatgggcta aatatatagg aaatgtatta actatagatg tctttatcac   2700
tcatccaaaa taatcagcca atcaatagga caccccggaca ggaatgatat aattaaatgc   2760
aatcagattt tgctgatttt catctatgta aaaacatttt tattttgcca ttataaatgt   2820
```

```
ttactcacca atattgagag ttatagcata tcctagttaa taatgtgtta agttaattta    2880
taacttttaa atatttacac ctacagcagt gagtccatct gtactctttc tcaggctcca    2940
taagtcttag ggatgggctt tatgccaacg tgctgaagcc aatattatag tgagggaata    3000
caagaaataa acaggtaaac aaacagacaa atcaggtcat ttcaagtagt gataatggct    3060
atgaagaaaa taccagcttg gtacatctgt ccgtcagata aaatatata attcaagatt    3120
attacatttt ttttaaaacc aaagcttttt ttaaaaaaaa aattacatttt atgaacatct   3180
gacttgtttt ccttttact ttccaaagta aaattcggca tggcactata caccatcaca    3240
gctgacatag gaaggactga gtcaaatctt tgtagcactt tttcaagttt cacttaaata    3300
aagcttttaa aaatatata gggtattttt taagcaaaaa aagcaaatta tcttatcaat    3360
gaaacagacc tggtgttcat ttctttaaa gtaccgaaag ctgattgctt ctgtaaaggt     3420
aaaactcctg tgacatgtta gaaagaaaaa aaaaattcct ttgagagata tgtttgtaag    3480
aatgaaatag gtactactag aattttcatg ttattctctg caaggcactc aacaccacat    3540
gaaaagaaga ttattaacag tcagtagaaa tactaataac tgaagaaaat atttggttgt    3600
tttaaatgct tttaaagcaa accaacaaca aaagattctg tttgtaaatg ggagagaatc    3660
tgcatgaggt atagacaacc agggcctcca aatttgtagc tgtgtttctg acattctcca    3720
gggaagacgg ttacagaaag acttgacccc ctggccccgc agagctcttc agagaaatta    3780
atgcatccag aaaagacaga gcatcagatc tcactccttc gtctggaaga cgtcagttca    3840
tcctagttct agcgcatacc ggtgttttgg aaacagatta gctatattca tacataagga    3900
tactcttccg caacactatc tgtagtgagg ccaagaccag tggttgcggg aatcttcgca    3960
aacaggcaag agacaatttt tagggggcgat ggaaactgtc attttgactg gggaggtcat   4020
tacacctata catgcatttg ctaaaagtca tcaaactctt ccactgacgt gggtgtaacc    4080
attgtttgta aattatacct caacaggatt cgattaattt atttattgag acagtctcgc    4140
tctgtggagt gcagtggtgc aatcttggcc cactgcaacc tccgactccc gggttccagc    4200
gattcttctg tctcagcttt cctagtagct gggattacag gcgcccgcca ccacgtccgg    4260
ctaattcttt tatttttagt agagacgggg tttcgctatg ttggccaggc tggtcccgaa    4320
ctcctgacct caggtgatca gctcgcctga gcttcccaaa gtgctcggat tacaggccgc    4380
gcctgactat gattcgtttt gaaagaaaaa aatatatgcc atttacccct cgggaatgga    4440
aacatagagg agtgacaaga tctccccccaa gctctggggc ggtggagtcc agcatttata   4500
gatcggtttg cactaggagc agaagctcct ttcacgacaa tctcggcctc ttcccacttt    4560
gtagagtgag taacaagctc ggagagatga aataatttgg tggcgttaac ccggccgaca    4620
ggcgccagcg ccaggatttg aacccaaacc acgtgacttc acaacccata gctttcaaca    4680
ctacgcggtg ctgctggcac ctagtaaagg ctggatcact actgaatgaa tgattctggc    4740
tacggatcct taaagcccac agaaggccca tccagagacc gaaagcttca gacacaagcc    4800
gcagagcaga ccgctaaacc ggagctacag aggcgaagct cagacttgag cctgagtccg    4860
gcgggctgag gggcgggctt tcgtctcggg aggcggagct gtctcgtcgc attcccggca    4920
agcttgaacc tcttcacttg ccgtagcgcc tgcagcagga agttgctcta crgcatgcct    4980
taggtttccg ggtgagggtt gggctccttg gtaccatgtg ggaagcgctg tgaagagttg    5040
ttgccttcca agatataccc aaattcccag ttccaggtaa gcggcacaga gccgcttgat    5100
gtggctgcgg atgggggcgg catatcgagg gagggtaaga gttttccgga tatctgcgga    5160
atcagggttg aaggaaagcc ttggcgcggt cgccgctact gtaattagtt gttaacgctg    5220
```

```
ctgccatcgt ctttgcatct ccggggtcca caaatctcag gacacccgcg ttgtgtgtcc    5280
atgacggtgc tgagtgcaga agagaattgt ttgtttacga ggcgccttat aatttcgtag    5340
aaacttatca aagtgcttac gttttttttag cccgtgtcat taaaaactccg ctggcgtgaa   5400 agatgacgtc cttagcccag cagctgcaac gactcgccct ccctcaaagt gatgccagcc    5460
tcttatcyag agatgaagtt gcttctttgt tatttgaccc taaggaagcg gccacaatcg    5520
acagggacac cgccttcgcc attggtgagc catcttttaa cttagaaaag ctcttggaag    5580
cgtttgtttt ctggatgtta ctgttttttt ttttyccct tsttttctct tctgtcccgt    5640
cctcttcctt agcagtttct agcatgttga tgtatatttt taagggaaag agaacataac    5700
agtcaggtgc ttggtgcttg aaatgcttat gagtagaggt atctggatt cacagatgaa    5760 gaaacaaaat tagagaggtc aactaatatg tcaaagagaa gaacagctaa aaggggatg    5820 gaggcagtga ctggggtgac ggagaagtcc tctcagagga ctggcctagt tattgtaggg    5880
gatatccaaa aaaaaaaaaa aaaagtgttc cctgccacga agtactttct gttctagtag    5940
atgagatagg atttactcta aaagttgaaa actagaaatc agtgtttggg actgtattat    6000
aaattatatg tacttaaaga attcagaaac ttcttagggg taagtaaaac tgtaaaagag    6060
gggtgggatg aatttgctta cgaagaattg ttaaataaac tggcctttttt tgaaatttag    6120 gatgtactgg cctggaagag ttgcttggaa ttgatccttc ctttgagcag tttgaagcac    6180
cgttgttcag tcagctagca aaaaccttgg agcgaagtgt tcagaccaaa gcagtaaaca    6240
aacagttgga tgaaaacatt tcattattcc ttattcactt gtcgccttac ttcctgctta    6300
agccagcaca gaagtgtctg gagtggttga ttcacaggta gctaatagaa ttacagaaat    6360
aactatgggt taatcacttt ggtcttgtaa aaaattaagt agttgagaac ttatcaaatt    6420
aaagctgaaa aattaggtat attaagagat tgatacaatg tccattgtgt gagataagca    6480
tgctcttctg ccttaaaatt cttttttgtt gatagtgaaa agtagaacta ctggtgattt    6540
tgagtaaatg gtctaacctc attagttttt ttttgagata gagtcttgct gggcactcag    6600
gctggagtgc aatattgaaa tcttggctca ctgcaacctc tgcctcccag gttcaagtga    6660
ttctcccacc tcagcctccc aagtagctgg gattacaggc acctgccata atgcctggat    6720
gagttttgtg ttttgtaga gatggagttt caccgtgtta gccaggctgg tctttaaccc    6780
ctgacctcag gtgatccacc cgcctcggcc tcccaaaata ctgggattac aggtgtgagc    6840
cacctcgccc agcctaacct cgttagttct gaagagccca tgctactttg ccattacagc    6900
ttgttcctgc acacttgagg cagtgagtac taagctgctt tcttggcaaa ataacaagat    6960
ggttggggaa gcaggcaatg ttatcctctg aaataccatt acttgagaaa aacaatgata    7020
gctaatgtgt ttttgagcat ttatacacta ggccctggta agcactttat ctgcattatc    7080
tcatttaatt ctcacagcat tcctctggtg agattatttg cattatcctt gttttacagt    7140
tgagaaaact gaggcttaga gggattaagt ttcttgagtc acacagctag taagtggcag    7200
agctaggata cagctgaagt ttatttccaa ggtctgatct tttatctgct ttgggaattg    7260
tctcagtaag cttagtttat tttctcacat attggtgtca catcacagca tacacatttt    7320
tgttttattt attctcccaa tatgtatgtc tttttttttt gagacagtct cacactgtcg    7380
cccaggctgg agtgcagtgg cacgatctca tctcactgca acctccacct cccaggttca    7440
agcaattctc ctgcctcagc ctcccaagta gctgggatta caggcacata ccactacgcc    7500
cagttaattt tttgtatttt ttttttttag taaagatggg gtttcatcac gttggccagg    7560
ctggtctcaa actcctgacc tcgtgatcca ctcgtccttag cctcccaaag tgctggtgtg    7620
```

```
agccaccaca gccactgcac acggctgtct ttttattttt attttattga gtgtcaggat    7680
ttcactcacc caggctggag tgcagtggtg tgatcgtggc ccactcgatc tccagggctc    7740
aaatgatcct ccgatctcag ccacccaagt agctgggatt acaggcatgc accaccatgc    7800
ccacctagtt ttttttttgtt tgtttgtttg ttttgttttt tgtttttcca tttttttgtag   7860 agacagtgtc tcactttgtt gcccaggctg gtctggaact cctggcctca agcgatcctc    7920
ctgccgagtc ggcctcccaa agtgctggg ttacaggcat gagccaccac atccagtcca    7980
acttacatgt tttaaaagta gatttctatt ccattaattg gagacatggc ttcaaggcca    8040
gcctggccag catggtaata cctgtctgtg tgaaaaatac aaaaattagc tgggtgcagt    8100
ggcgagcact tgtaattcta gctacttggg aggctgaggc aggagaattg cttgaatcca    8160
ggagacagat tttgcagtga gctgagatca cgccactgca ctccagcctg gtaacaggg    8220 agacgccgta tcaaaaaaaa aaaacaaaaa atggagacgt ggggataaac taatttttttt    8280 tcaagaagca agtgagtcat caagaaaaca tgattttaac ttgggtcttc tgattgtcag    8340
aacattaggg caatcagaca agaatatttt aaaagtctgt aatatttcca tctgttttct    8400
agcacctaac tttaccccca aatagatcat taatgtaagg aatacttttt gcatttgatt    8460
tttcatttta tgtcttcaga taacttattt attcagcaaa tactaagttc agtacataga    8520
taagtaggtt gccgttgatt actgttttga aataaatgcc ataataaagg attaagcaga    8580
gttttgtgga tatagttctg cctggaatag ttgaagaaag cttcatggaa aaagtaaccg    8640
ctaaaaccgt atgtcaaact aagaggctgg gttcagtggc tcacgcctgt aatcccagca    8700 cttttgagagg ctgaggcagg ccagtcactt gagatcagga gtttgagacg agcctgacca    8760
acatggtgaa tccctgtctc tactagaaat acaaaaaaaa attagctggt tgtggtgctg    8820
tgcacctgta attccagcta cttgggaggc tagggcatga gaatcgcttg aacttgggag    8880
gcgaaggttg cagtgagctg agatcacacc actgcactcc agcctgggtg accaagtaga    8940
ctctggaaaa aaaaaaaaat ctaataaaag gcaatgtatg gtactgttta aaaaaagtac    9000
ccgatgtaaa aggataggag agttttcaca gaagagggat cagttggcag aattagaaaa    9060
aacatcttag ccaggcatgg tggctcacac ctgtagtcct agcactttgg gaggctgagg    9120
caggtagatt gcctgagctc aggagttgga gaccagcctg gcaacatgg tgaaaccca    9180 tctctactaa agtaaaaaaa aaaaattagc tgggcatggt ggtatgcgtt tgtagtccca    9240
gctacttggg aggcggaggc aggagaatct tttaaacttg gaggtggagg ttgcagtgag    9300
ccgagattgt gccactgcac tccagcctgg gcaacagcaa gactccctct caaaaaaaaa    9360
aaaaaaaaaa aaaaaaaaaa aatgttgaca gaccagcctg gcaacacag ggagacctag    9420 tctctacaca gaaataaaaa attagccagc tgtgatggtg ctccctgtg gtcccagcta    9480 ctcaggagac ctaggtggga ggatcatttg agcctgggag gttgaggctg cagtgacccg    9540
tgatcgtgcc actgcactcc agcctgagtg gcagagcaag actctattca aaaaattaaa    9600
taaaaattgt aaagctgaga gaaagttaat gggatgtata ttttgatgta gaatattcaa    9660
agatattgca taggaattgg ctggaccatg ttgagggata tgtgaatgca aaattgggga    9720
ctttttaaat gctctgtatc ttataatttt gtgattttta ctgctactcg ttctaggttg    9780
ttttagctta ttaataatac agtttgggca tgtgaggaaa taggtgctta ttattaagtt    9840
ttgtgttcag ttggactgtt tgcttttttt ccccaggttc catatacatc tctataatca    9900
agatagcctc attgcttgtg ttctgccata ccacgagaca agaatatttg tgcgagtcat    9960
acagcttcta aaaattaata attcaaagca cagatggttc tggttgttgc cagttaaggt   10020
```

```
ataattgctg aatgacatat gtctgtaatc attacagatc ttgattaagg gatttaatta    10080
ggaaaaaata agtcattgct cctggggata gtccagataa ctacctccat cattttatt    10140 tcctgacttc caattgaaac tattattaat gttaataata tttagctttt atttagtatc    10200
tgacatcagg ctaggcaatg tacattatat tatcttggat tatcacaaaa cttcattttt    10260
acagatgagg acaggctact tgccaaagtt cacataacta taaagtggca gagttgagat    10320
ttgaacccaa atctgattcc agagtctgtg cctttgtatc gtaccatgcc gtttggcatt    10380
ttaaatttgg aactgagaac ttaaaaaaaa gttgaaggtg aagaaaggca gaaaatactt    10440
acaaaaatta aaaggataag gataacttca ggggtttcaa gaatttacta aagttgtgag    10500
gaagatgcta ggagttaatt tacagactaa gaaaaggatg cttgtgtaac aggaagggtc    10560
tgggtaagaa aagacagcat gctattgtag gaaaaccaac tgactaaccg ttagcacttt    10620
gtttgcaaca tatggtggag gaaagtagat gtatgttgtt agcaggaact tgactgcatg    10680
ttgggcatgg tgatccaggg tagggggggga ggcaaatggg gatgaaggta agctaacaga    10740
tcacgaggct gtgcacatta ggctgatgat ggtagtgggg tcagtgttca gaattagtaa    10800
gataggagta atgaggactt tttaattaga aggagaattt aagaatctga acgtaaagca    10860
cttgaactaa agaacgttgg agaaggccag cctttgataa agctcattaa ctgctcttcc    10920
caacattcac tctgcccata gcatcaaaat tattcttcct ctaatctacc ctggatcttg    10980
ctgctcccta ggcactctta ttccaggtag ccaaactcca ctcacctact aaagttcact    11040
taaaattctc ctttcattta tttaatcagt atttatggag catctattac ataccatgta    11100
caacgctaga tggtgggaat agtggtataa gttgtgcagt ttcctagtct atttctgttc    11160
ttagtgttat tgtaaagcaa tgacagaagc gtatcatagt ggctcagaaa ccaaatcgaa    11220
ccagtaaagt tactaagaat ctagagaatc cagattttga taaataacctt tcaaaatgtg    11280 acatacgata agcaaacatc tttcactaaa tacctctgcc ctcattgctg accttctctt    11340
ttgaatttct aagtttacat gattttatgt gttaatttca tcaccaccac cagttataag    11400
gagagattat attttttatt tatgaattgt agcagtatga agacattact agggtaaatg    11460
ctttaaaata aggatcagtt gatgaatgtt gctagtagtt tgttctttcc atcaataaca    11520
gcaatctgga gtgccgttag ctaaaggaac tttgattacc cactgctaca aagatcttgg    11580
attcatggat ttcatttgca gtttggtgac aaaatctgtg aaggtgagca gtctgtttca    11640
tgagtatata attttatgaa aagattgctt gctttgaatg aagaaaacat actaaaacat    11700
tccctaataa caatgatact ttggataaat ttattttgtt aaatggtctg gtgtttgaa    11760 gcaggagcag tttgagagtc cgtatctttt tttttttta agaatcagtc tttatcacc    11820 aaaggtgttt ttctacaaaa ataaatgtct attccttgcc agattctagt tacagtgact    11880
attcaaagag agtgtctaga aatgtcagga atattcaacc tgggaaagct gtttaaaaaa    11940
ttttaaggcc aggtgcggtg gctcacgcct gtaatcccaa cactttggga ggccaaggca    12000
ggcggatcac ttgaagtcag gagtttgaga ccagcctggc caacatggtg aaacaccgtc    12060
tctactaaaa atacgaaaat aaactgggca tggtggggca tgcctgtaat tccagctgct    12120
cgggaggctg aggcaggaaa atcgcttgaa cctgggaggc ggaggttgca gtgacccaag    12180
atcatgccac tgtactgcaa cctgggcgac agagactcca tctcaaaaaa aaaaaaaat    12240 tttttttta aataaaaatg ttaggaatat cattaggcag ttaattgttg tcacattgtg    12300
tattcattgt tgcaaaggta attcaggaga gctgtaaata taatttggcc tttcacttttt    12360 tttttttttt tggagacatg gacttgcttt gtcgcccagg ctagagtaca gtggtgccat    12420
```

```
catagttcgt tgaaatctca gccttgaact cctggcctca agcaatcctt ctacctccct   12480
ttcactgtta aatgtgtttt gtttgtgttc cttgtttcag gttttgctg  agtacccggg    12540
cagctcagct cagttgaggg tgctcttggc tttctatgct tctaccatag tgtcggcgct   12600
ggtagctgca gaggacgtat cagacaatat catcgccaaa ctatttccct atatccaaaa   12660
ggttggcact gctgatgtgt taagtagatt attttgtact taaaggaatt ttcttgcttt   12720
cgaaagtttt tttagattta agtgtttta  aattgacagt ttatttcaga tgatagctga   12780
gatttagcct ttaggttgaa aatatgacac ttttttatta gaaactcact ggactgggac   12840
cttaattagg actcttaaga ataaatattg gctgtctggt cctgcggcca tctcctagat   12900
tgatttccat agcagtcttt gtacctcact ggaaggagga cggagcagac agtctctttg   12960
aggcgtaagc agcctctcag tattctttgt gcactggctc ctgcctctca gcgtttctcc   13020
ttcccaagtg ccttcttgcc tgctgccttc ccaggtgccc tgtggaggta ctgctttcac   13080
ttcccaccag tgtcccaact tgtgaccttt catcagactt gtttcttcca ttagtgatct   13140
gattgaggtc tccctacyat aagtaggatt ttatgtataa aagaagagct tactggctcc   13200
tgtcaggaca tgtggtagat gtttgagttg ggaaattttc tgagatcctt tgtctcgttc   13260
aacagacttg tctcatctct gtatccactc tgaaaaaggg gtcagctcct ttattgttta   13320
tgtctgaaga gtgattgact atgcattagg ttgtattaat ctctatgaca tttctaattt   13380
gtcagattaa catttaaagt agcagaaaat aatatggttt atcattttc  cttatattta   13440
aaaaatattt agggattgaa atcatcttta ccagattaca gagctgcaac atacatgata   13500
atatgtcaga tttctgtgaa agtgaccatg gaaaatacct ttgtgaattc attggcatca   13560
cagatcatca aaacattgac caagattccc tctttgatca aggatgggtt aagttgcttg   13620
atagtgctcc tgcagagaca gaagccagag agccttggga aaaagtatgt acaattgaat   13680
tgagaaatgg tgctagtcag aggtgaataa aattatttg  aataattttt ttttgtgaga   13740
taagtgatta tatattttct tatattgtta ctcattgtct aacttgtaaa gtcaacacga   13800
tatgtacttt tgcttcttca aaggccattc cctcacttat gtaatgttcc tgatcttatt   13860
acaatacttc atgggatttc tgaaacttac gatgtcagtc ctcttctgcg ttacatgctt   13920
ccccatctgg tcgtctccat cattcatcat gttacaggtg tgtggtttta tattttttgt   13980
ccagaaattt tctaagattt gatcttaaaa tagtaaccat atcctggtta acagcttcaa   14040
aatatttaaa atttctgttt tccagttgtt cttgtgtaac ttgtctattt cttaagtgag   14100
aaacatctgg ggtggggagc aggttggttg aagaaagatc attgttaatt gagtaatttc   14160
ttagaatttt actttttta  agatctgtgt tcttaaatac ttaaatagtc tctacatgaa   14220
aaagactgga atacttttaa aatttattac tgagtaaacc tttgccttct catttaggta   14280
tttaatgaac tttagtgatt catttacaat gaatatctca tccagttgcc aaaaaagttt   14340
tttccctaga gtaattaaaa atataagacc aagaaaattt ttatacataa aaatccaaat   14400
tatgaaacaa agcaaaaagt aataattaga gggccaggtg gctcaaacct ataattctag   14460
cactttgaga aactgagatg ggcagatcat ggcaaaaccc cgtctctaca aaaatataca   14520
aaaattaacc gggcatggtg acatgcaact gtggtcccag ctgctcggga gactgaggtg   14580
ggaggatcac ctgagtccag ggagttcgag gctacaggga actgtgtttg tgccactgca   14640
gttcagcctg ggcgacagag tgagacccta tctcaaaaat aataataata attagaaagt   14700
gattatttgc attatgtctt ttaataaata cagaaaggct aggaagaaac atttggttct   14760
gttgctactt ggagaatact aagaaagact tctctaaact tatgtcagtc tactgaaaaa   14820
```

```
tgaggttttt gtaaccaaat cttggtttga acatgcattt tagaaaagtg actagcaaaa    14880
tgaaaatgta ttcttcctat tctgaaggta atgagtaatg tcccagtctt tgaaagcaag    14940
ggctaagatc agattcatat gtttattata aatctgaaat agatgacagc ttttggttca    15000
gtaagggggt gggtactgag ataaaagttt aacctctttt cagagatagt tgattggcac    15060
catcacaact aatttgtaat gtgacctggg gaaagactaa ttttggactt ttgttttgtt    15120
attgttataa gcatgatagt acttgttaaa aatagagaat tttagataaa agaaaaatga    15180
aggtgatcta tacaaaagag ctttaaaaaa tataaatgac taaataagtg gaatgcactt    15240
gtgcaaatag ataaaaagct ggatatcagt gtgtgtgttt tactctgaga acgattttct    15300
gctataagtg aatttaataa tgttagcttg caaaataaat ttttcccaac acaattttaa    15360
tttttacata ttaaggagaa gaaactgaag gaatggatgg tcaaatctac aagagacact    15420
tagaagctat acttacaaaa atatcactga agaacaactt agaccatttg ttggctaggt    15480
aagctattat ttttgacatg cttttgattt acattttgt gactcagtat aattttcaag     15540
attggttaga aatttcccag tattccttt taatgtatat cttgttttgc ctgtatcatt     15600
tcattaacta taagtactta atccagtaac tggcagcatt aaaagcaaaa gtaattttc     15660
ttgcatgtgt ttagtgctta tagatgaaaa tggaaagtta gtggttaaga caaatttggg    15720
taataactaa atgcagtttg tggccgtttg aagttttctc ttagtaaatg gaccataata    15780
tctgaaataa cacatcacaa ttaaaacgca gtaaatgtca tttagaaaca atattgaagg    15840
taagcataga gtaaggatta tttcttaaa gataattcag tcttttttt tttttttt       15900
ttttctctta atgggcaact cgatacagtg aaaagatgta ggcgttgtgg tcagacatag    15960
gtgtaaattc tgcgcctacc acttccaggg ctatagtaag ttttggaggt tagtctggat    16020
gtagctttgc cattttgtag gatcaagaga gtgcctgtgt gttggtgtgc atcattcatg    16080
cccctttgct cagagggttg gtttgtgaat taaggagag tatacacgtg tagtaatgtt     16140
gagaacatag gctctagaat cagactgggg cttaaaatgt gaaaccccac tctgtggcac    16200
agaagggctt actgaatgtt gccttttatt gctgttctca tgagcaaatt ggaagactta    16260
cactctagtt tctttcctt tttttttttt ctttaagatg gagtttcgct cttattgccc     16320
aggctggagt gcagtggcac aatctcggct cactgcaacc tccgcctccc aggttcaagc    16380
gattctcctg cctcagcctc cctggtagct gggattacag gcatgtgcca ccatgcccag    16440
ctaattttgt atatttagta gagacaaggt ttcaccatgt tggtcaggct gatctcgaac    16500
tcctgtcctc aggtgatccg cccacctcgg cctcccaaag tactgggatt acaggcgtga    16560
gccagcacca tttaagatag caatgtagtc ttgctgtgtt gttcagacag gtctcgaact    16620
cctgacctta agcagtcctc ctgccccggc tccgaaagt gctgggatta taatgccagt     16680
gatgtgaacc actacaccag gcctctagtt tctttatctg taaataagt attaaactat     16740
accttgtata agtatgacaa ttagagataa tatttctaaa gcacttagaa tatagtaggt    16800
actcaataaa tagtaactct tatgtatgct gatatttctg ttttttttt acagccttct     16860
atttgaagag tatatttcat atagttcaca ggaagaaatg gattctaata agtgtctttt    16920
gcttaatgaa caatttcttc cactcattag acttttagaa agcaagtaag ttatgtgtgt    16980
atgtttatgc tcttctaaag tacttcctgt tctataaaga tatgattcac aagtcacatc    17040
ttaatatact gaattgtaca gagactgtcc tttttaaatt tgttcttcaa gaaggggtga    17100
gtatcggaat caaaaatatt tgaaatataa gaggaaatag tggttgtgtg ggggctatgg    17160
agagtataat ttttttataga gagactatttt tgttattgga gtagtcatag taacacactt   17220
```

```
gaccaatgtc atttggtttt acctacaaca tttgttaaaa tttaagtcac agtctcagta    17280
atttttaaga ttttatgtct ttcctttata tgtgtatggt gtatgagatt aataaattta    17340
ttaagaataa tgaattcact ctttaattgc ttcccagata ccccagaaca ttagatgttg    17400
tattagagga acacttaaag gaaattgcag atctgaaaaa acaagagctt ttccatcagt    17460
ttgtttctct ttctacaagt ggaggaaagt atcaggtatg ttgttctcca aaggaattat    17520
gacaatttgg ggtacatttg tatgggtatg tgaagagctc cagaaggaaa tttgccactt    17580
ttttcccttg tgtggaaaat tttacagaga taaccttata cagtttgcct agttgcctga    17640
agtacggctc tgaggcagga atagaataat tggagaaagg tacaataatt tgtacataac    17700
tatgaacgtg atacttattt caggaaaagt attgtttgag aattttttta tgggatattc    17760
attaaggaat catcagagga cggcctcatg taggtttcta gcattctctg tctttcatct    17820
aggtctatgc tttccagtgt accagccaca gatggctata tattagatta gcaaggggga    17880
gatgggttct atttcatgat cacattaaaa cttgagaaat tttctggtga ttcaagccta    17940
aagctttata ctagaggtta gacatttaag caggagttct tatatttagc cttaaaaaca    18000
gataattatg aagagaaata tgattgtttt atatttctct tccataatta ctttcatttt    18060
taatggtgtt gcatttccaa atcttaggtt gatggataag actttctttt tagtctaatt    18120
gcgtaagtga actaagttgt cacgaatttg agtgtcacta tttgttatat catgtagatg    18180
agttgcattc tgtcttctgg aaggtgctaa acagggatt tatcttaggt gatttatcag    18240
atacgcatac aaaatacaaa attactttgt agaattactt gactaaatta aacctacaca    18300
tagacacaag tatacatgaa atcataccat taacaataca aattttttca tctattgcaa    18360
ctcatgtgat gttctagaaa caaagatttt gcatttttt gtttgttttc tgtagttaga    18420
tggttgttac tgaaaatgtt gggcaatttg gggtggtttt ctctgggttt tattcttgat    18480
catagactgt tcagattaag tgaaatcatt tgataactat gttgaaccct gtagttttta    18540
gcagattctg atacttcttt gatgctcagc ctgaatcatc cacttgctcc tgtgagaatt    18600
ctggccatga atcatttgaa aaagatcatg aaaacatcaa aggtttgttt cagatcgctt    18660
ttttatatgg ttttttttc ttatgatgag cagtgtaatt ctgaataaga aattgaagtt    18720
accacctaag tgggtaatga tacagatgag ttgaataaac ctcatgagag taccttagac    18780
taatatttag gactgtgtat gccagtcgtc cccattttaa caataaccta ataacaacta    18840
cttttatgtt tccacattga cagttgttta tctttagtgt ttttcaaact ggaatttgta    18900
gattaattca cgtaggttca ttaattatct gagaattttt ttagttttga aatttgattt    18960
tgggccggtc acagcagctc atgcctataa tcccagcact ctgtgagaag gatcacttga    19020
gcccaaacgt ttgagaccaa cctgggcaac atagggagac cccttctct gtaaaaagt    19080 tcaaaaaata aaaaattagc caagtttggt ggcacacgct ttggtcccag ctacttgaga    19140
ggctgaggta ggaggatctc ttgggtgtga gaggttgagg ctgcagcgag ccatgatcac    19200
gccactgctc tccagcctgg gtgacagggc aagactcttt caaaaaaaaa ccgagaaatt    19260
tgattttgat agtcttaatt ttagatgaag acatatttg ggacatttga atgataactt    19320
ttgaacactg ttccatgatt ttggtgcctg cagtttcgtt tgtctttaaa atgttagtgg    19380
tttcaaatat gtattgaggc tgactttatt tgtaaataat ttggtctaat ttgcatttat    19440
accaaaaggc attggtatga agacttggta atgatgcaca tagaatagta gtttccaaac    19500
tttagtcatt caagcagtcc ctgtacaatt tttgctaaat tacaaattac cactgatagt    19560
agtattattt tctcacaatt tttctttatt tcagatggac tcattatttt tttacatagc    19620
```

```
cttcaaattg tgggtgtgag gtgctaattg tatatgcatt ttactatagt tactataatt    19680
aaaataggaa tgctccatct gtgtcatatc taaaattatg caccgtgatt tgcatatttg    19740
agaaatttct ggaacagagt aaagcggtta acagagttta gtttccttgt agcacatggc    19800
agtgtaaacg tgccgaactc tagaacttgt gtcatagcaa ttagaagcag attcttacta    19860
caagtaaaat catatgatca gtaaaattta atttcagcta attacagcta atcacactaa    19920
gttcatcttc atttgaattt tattggtttt atagagtttt tagtatttcc cttgtagatt    19980
taaaaaaaaa ttttttgttt tatgtcatct atattttaag aaggagttat acttaatttt    20040
aagttgatat ataaacaaca aacaacattt agatctttga gaatgtttct ttgaaagtga    20100
ctgatgtaat attcaggttt gagaaatgtt gctttatttg atctgacatg aattctgctt    20160
ttgtaaactg ccaataggtt tattttgtcg atatgttaaa taaattcatt gaataatagt    20220
ctttgttgtg ataggaggat ttcagtgata agaaattctt ctagaataaa ggggagtcct    20280
ggaatcttct gtttctgaag ttattctcat ccttccttct tttactgcct ttctctcctg    20340
ttctctgggt ttggttcgtt tttcggtgaa gggccggccc tgcatacatt caacttacag    20400
gcttgaggat tgtaattgca gttgatgtcc tcctttgcat accatgtttc attttctttt    20460
ctccattgat gacaggacat aggttttatt ctaaactcca ggttcagata tatggctgct    20520
tattagctct tgaggatttg tttaaatgat ggggtcttgc tatgttatcc aggctggcct    20580
caaactcctg ggcttaagca atcctcccac ctcagcctcc agagtagctg ggattataga    20640
catgcaccac tgtgcctgac taacttaatt tttgtgaatt ctgtgaattt tcattttct    20700 cccaacagag tgacctatgt ttttatatt atttagttgc ctgccacata tagataggga    20760
tatattcagg ttgattagca gtcctagttt tcttttctg tgaatgaata tacattgttt    20820
tcttttattt gttatattta aaaaatgatc tctattttg gcagactggc tttgtagtac    20880
atgtccttat ccttgtaaaa atttagataa tactagctag cttttaacag tactatgtgt    20940
aaagcactgt gctacagact gacatgaatt ttttaatctt ctaacaaccc ttgcaggtag    21000
gtattattta ttagcaaacc tgttttatag gtgagaatag tgagatccag aaaggttaag    21060
tgacttgact aaagttacac aactagtaag tggtagagct aggatttaaa ttagacattc    21120 ttattctta gtctatatcc cgtcaatatc tgggctctca ctttaataag atgaactcct    21180
taactacaaa aactatattt ggagtatacc atatttacta tattttcact gaaaacttga    21240
aaaggatttg taccaaacaa ttattaatcc aaaaggccct ttagcgatta tctagttcta    21300
gtgtgtttca gtcctcatcc agagcagagc ctgtgttaga ctgtcattct ggagtgtttt    21360
tcacaaaacc atacttcctt tctagtgcaa agccttaaga gattttttggc aacagctaaa    21420 ttaatgttt tcttttattg ctcaggaggg tgttgatgaa tctttcataa aagaagctgt    21480
tttagcccga ttaggtgatg ataatataga tgttgttttg tcggctataa gtgcttttga    21540
ggtgagtgaa tttgtcattt gttgaggtat acaattttgt aaatttcctt gcccttctca    21600
cttgattctc tgcttgagac tagaatattt ttggaaatta ttttttccatg ggaaatttgt    21660 tctctggaga gcacagactt aagtctggtt aggagaaact cacagaaatt cacaatttga    21720
tatattaaat atatatggaa gttgttcaaa caggaaaaat gttttgtgaa tttttatatt    21780
gcttttaaca tattttatc aatagcaaat accttgggac ctgtggaaat tgtcttatga    21840
atgccacttt tgagaaatag atcttaaaac ttttaatttg tactaggatt cctgggagaa    21900
attccttata attcattctt tttaaaattc gcatttaaaa agcgccatac atgtttgaag    21960
caagtacaaa tctactctgg atattttttt cccttagat tttcaaagaa cacttcagtt    22020
```

```
cagaagtgac gatttcaaat cttctgaatc tctttcaaag agcagaactt tcaaagaatg    22080
gagaatggta tgtattcatt tctcctcata ctattttgaa ttgatgaagt tcttatatca    22140
agttctttct atttcttctt cttttttttt taaggctttg attacatgac ccttttgtcg    22200
tggtagtaga acagatctta ctgtaatact ctctttcatt atacagttaa ttaatttgtg    22260
tttgtgtgtg ttcattatac tgttctctat gtttggaatt tctcttaata aaatgcaaaa    22320
ggaagtatat aatgtatgat attgcattct gggaagtaag atgggtagga ctttctaatt    22380
tgctgcttta tgtaattttt actttataat taaaaacaaa taccaatgtg ttaaacaaat    22440
taaaaaataa gttcagagac acatgatacc atctgtggta agtttttaat gagctctgtt    22500
tatttcattt ttggcaccaa agcttttgc aagaaaaagt aagcaagctc catagggat     22560 gagagtgtgt cttacgtgtt tttgtatcta tcgtatgggt agatatctat catgtaggat    22620
gtgcttggtt cattttttt gagtgcctga gtgaacctga tttccggtag agttgagaca    22680
tctagtgtga tatgtcttat gttatagtta acctctagtg atttctctaa gaaaaattat    22740
tatttttttt ttaagattag acaggatgag cagattaaaa gtattgttgg ccaggcacag    22800
tggctcatgc ctgtaatccc agcacttgta caaaaaataa ataaataaaa atattgtcac    22860
agataactct gttattggca tggattttaa gtggtgtctt agtgtatctg aataatagtt    22920
ttggtcagga gaccaggata ttgtcagtta agctggagta atgtaatgat aaattttgc    22980 ccaattgaag ccttccaatg tgtctttcaa ccaagtgtgc ttgcatgtct tttaggtacg    23040
aggtacttaa gatagccgct gacatattaa ttaaagaaga gatactgagt gaaaatgatc    23100
agttgtcaaa tcaggtggtt gtatgtttgc tgccatttgt ggttatcaat aatgatgata    23160
cggaatctgc tgagatgaaa attgctatat atttatcaaa atcaggaatc tgctccctgc    23220
accctctatt aagaggctgg gaagaaggta aaaaattcag ttgttttttt agaaaaagtg    23280
aacagataac acaaagaaa acaaggaaaa tttaaaattt attgttggtc atgctatatg    23340
ccagtaaggt cttgtaaaat ttttgccaag ataaaagta tacagtgaaa aggaagccaa    23400
ttcatagaca aattcagaat cggatacaag gaaaaataaa aagcaaacct tcataaacaa    23460
tagtaaaatg tttgcctgaa ttcttcatgt gattctttga gtgttggtga cataagagct    23520
ctctgcattc gattttactt tacagctctt gaaaatgtaa ttaaaagcac aaagccagga    23580
aaactaatcg gtgtagcaaa tcagaagatg attgagttgt tggctgataa tataaattta    23640
ggagatcctt cttcaatgtt aaagatggta agtatgcttt gaaagtccac cccctggatt    23700
tctttctcat actcttatta aattctcagc ttttgcttta ctagattttt cttaaaaaaa    23760 wtttyttta ttcttgagta cttggtttta ctttaaacgt tgcagtgttg tttaatatat    23820
tctgtgcaat gtttgaaatc ttttaacatt ttatatattt tttcaatgtg gatccatatc    23880
acacccataa gataatatat ccttttacc accatttttt ctcattccca tttaaaatat    23940
tagtcttttt gttgttgttg ttgttaaaat agcaaaatat aatcccaaag aggagaaaat    24000
tatctttgcc ttattaaata aacctttgta aaggattaga tgtgtgattt aaatacatta    24060
accagttggc aagtgcaatt atgttcatta cagtttctga aattattatt ataattactt    24120
agaaatcagt gcttagtact ttataaaggt tttctatttg tcatctcact ttaaatgtaa    24180
aacacataat acctagatag acctgagttg aaaaaattgt tttatgaaaa tcaagagcaa    24240
ctggtaatag agtgtgttta tttttcaagg tggaggattt gataagcgtg ggtgaggagg    24300 agtccttaa cctgaagcag aaagtaacgt ttcatgtgat cctgtctgtg ctcgtctctt    24360
gttgttcatc tttaaaagaa acccacttc catttgcgat aagagtcttc agtttgttgc    24420
```

```
agaaaaaaat aaagaagctt gaaagtgtca ttactgcagt ggtaaggaaa gcagaatctc    24480
cagaaagtgg gatgttgaat aaaacaacag cctggcctat tagtcacagc aaaactgaaa    24540
atcagaggcg agatgttgag tctgtggata gtagctggat gaaatgtgaa gcagtcttgg    24600
gtagcagtga gatagtcaac taggcactcc cttgcttttg cggaaagttt agttgaatta    24660
taaaatttta gggttgcaat attttgtatc tgatgcctga ctctcctctc ttttattgtc    24720
tttattggat aattacccaa gctacaccta actacctcta gcgatgaaga attcacttgg    24780
cgtgttagtg cttgaacaaa atactatttc attcaattgt ttactaaaaa tagatctttt    24840
aggctttaaa taatgttaat attacataga tgtgtatccc tccagcctac tactatcttt    24900
catagtatta ctaagggaca tgtttcagct gtttacattt gacatgtttt gaggtagcaa    24960 gactttttt ttaatatctg ctatatgtaa ggattttgtt tttatttgtc ctccaaattt    25020
tagagggctt ctcattatag gatttactaa atgaattata tcttttcac atttacgtat    25080 acccgcagga ttttataagt tctgatcgtg gccattgtta gctaaaatgt gtaaacttta    25140 aaagagtaa agtcttcata ttttgaaaaa tagtccagat aggcccttct taacttttag    25200
tttcttggtg tcttttgtga agtatgatga cctgaactat actggttctc agtgttaaaa    25260
gtatggacaa atagagtgtt ttattataca tatgtagata acaggttatt ttatattgct    25320
ttacttttaa tacctttctc gaggtcatga gcatgttttc gcctgtagca gcatgttgag    25380
ttaatcaaat ccctcactgg agacgttaca ttgtaaatct ggctttggat tattttcctt    25440
ctaagttatt actctgtact gcttgtacag agtcacattt gtcattttct tacacctgtt    25500
ctgcattctt ttggcactta cagtataatt tctaaacacc taacattttg ctgcttgttt    25560
aaaatcatct gcaggtttgg agattttgc catgtacctt attcagatta gtggtaaaac    25620
agtgaaatga aagaattccc tttaactatg tcttggcaat ccaactgttt atcttcctgt    25680
tttgaaatat acctattttg gccaggcacg gtagctcacg cctataatcc cagcattttg    25740
ggaggccgag gcgggtggat catctgagga caggagttcg agaccaacct ggccaaaatg    25800
gtgaaaccta atctctacta aagatacaaa aattagccag gcatgatggc gggcacctgt    25860
aatccttcct actcgggagg ctgaagcagt agaattgctt gaacctggga gcggaggtt    25920 gcagtgagct gagattgtgc cgctgcactc cagcctgggt gacagagcaa gactccgtct    25980
caaaaaaaaa aaaaaaaga aatatgccta tttattccta ccctttattg gataaacagt    26040
tcatatgaat aaagtttgtt tttagagata atgtttcaag gtaagacata gataaaattt    26100
aactttgtct ttccttgtga atagtgataa acctctttaa aaatccgacc aaagcagttc    26160
tgttaatcct ttccccacca aaatgcacac ataaacaaaa cttttgcata ttatgcagag    26220
gaattcatat aacccatgtt cagaacccct agtttgtact agttttgtt tccttttaaca    26280 tttcaggaaa tcccctcaga atggcacatt gaactgatgt tagacagagg gatcccagta    26340
gagctgtggg cacattatgt agaagagctc aacagcactc agagggtggc cgtggaggac    26400
tcggtttttc ttgtattttc cttgaaaaaa tttatttatg cactgaaagc tcctaaatct    26460
tttcctaaag gtaagataca agctgtgaat cttttaaatg tgatactgtg caaaactgaa    26520
tgattgactc cacaatgact gtcttgaata aaaagctccc agcatgttca tgtaggatct    26580
agcatcattt ctcttttccat gtccttgtag gtgatatatg gtggaatcct gaacaactga    26640
aagaagacag caggggactat ctgcacttgc tcattgggct gtttgagatg atgctcaatg    26700
gtgccgatgc tgttcatttc agagttctga tgaaactttt cataaaggta caagcctcct    26760
ccttttcagg cgtactctac ccttaaagaa gatatggctg gcctgcaatc ccagcacttt    26820
```

```
gggaggccga ggcaggcgga tcacttgagg tcaggagttc aataccagcc tggccaacat   26880
agtgaaactc catttctact aaaaatacaa aaattagcca ggcatggtga tggggcctgt   26940
aatcccagcc acttgggagg cagaggcagg agaattcgct tgaacctggg aggcagaggt   27000
tgcagtgagc cgagatcaca ccaccgcact ccagcctggg tgacagagtg agactctgtc   27060
tcaaaaaaaa aagataggct gggcgcagta gctcacgcct ataatccgag cactttggga   27120
ggccgaggtg ggtggatcac gaggtcagga gatcgagacc atcctggcta acatggtgaa   27180
acgccgtctc tacgaaaaat acaaaaaaaa ttagctgggt gtggtggcgg gctcctgaag   27240
tcccagctac tcgggaggct gaggcaggag aatggcatga acctgggagg tggagcttgc   27300
agtgagcgga gatcgctcca ctgcactcca gcctgggcga cagagcgaga ctccatctca   27360
aaaaaaataa taaataaata aaaagatact gtgggttatt tgggttatga cagtttataa   27420
tgtaaacaaa agtagacttg taaacagtga agagtatata atagcacggg ccctgtaaaa   27480
gagtacaatc acaatactaa tcggtaggtt gaatagaaac taacattgct acactcctac   27540
taatatgtta ggcccattac tatatttaaa aataacaaca gcccagtctt tttgattggt   27600
taataccatt taaaaatgtg aatactggtg ttcagagagg ttatttagca cacgtgaagt   27660
tactcaggaa atttcatccc cagcaccagt gacctccatg ttgccaggcc cagtggtcag   27720
ttcctgttct tgcctgactt gttctctcta cagcatttga catggagttg gcattgctca   27780
gcacattgtt gaagtatttt cttaattagg cgtcccagat actgctcttg tcttggttct   27840
gtgttttcaa gtgcaaggtt atagtgaggc ttctgaatat cactcttcat tgacatcttc   27900
ccagttcatt aaaacatgga atatggarta atttgaaatg attagacaaa gcaaaacttt   27960
gccttaaatt atttgtttct ttataattgt acactagtga gaagaggatt tggaaccagc   28020
ttatttgagt aagaattaaa agtttgcttt ttttttttt taattaggtk catctagaag   28080
atgtttttca gttattcaag ttctgttctg ttttatggac ctatggttct agcctttcaa   28140
atccactaaa ctgcagtgtg aaaacagtgc tgcagactca agctctttat gtgggctgtg   28200
caatgctttc ttctcagaag acacagtgta aacaccaact ggcatccata tcttctccag   28260
gtattaaaag tagcattgtt atgttttgtc atgaccaact gttcatgctt tctctatatg   28320
gtttatgtag tttggaaaat tataacttaa aaaaaaata gcagagggca ggcgcggtat   28380
ctcacgcctg taatcccagc actttgggag gccgaagcag gcagatcatg aggtcaggag   28440
atcaagacca tcctgggcaa catggtgaaa ccccgtctct actaaaaata caaaaattag   28500
ctgggcgtgg tggcgtgtgc ctgtaatccc agctacttgg gaggctgagg ctggagaatt   28560
gcttgaacca gggagttgga ggttgcagtg agccgagatt gtgccactgc actccagcct   28620
ggtgacacag cgagactcca tctcaaaaaa aaaaaaaaaa atcgataaag gccaggcagg   28680
tggcttacac ctatagtctc agcactttgg gaggctaagg caggaggatc acttgaggcc   28740
aagagttcaa gaccagcttg gacaacgtga tgagatcctg cctctacaaa aaatacaaaa   28800
attagctggg cgtgatggta cgtgcctgta gtcccagcta ctcagttgcc tgaggtaggc   28860
agatggcttg tgcctgggag gtcaaggctg cagtgagctg tgattgcaca ctgcactcca   28920
aactgggcaa cagagcaaga ccctggctca aaaaaaaaa aaaaaaaaa gggctgtaca   28980 tctgtacata tttctggtca cttctaagta ttgcttttaa gttactggca ctagcaaaat   29040
ctcaccaaac acaaaagttt aataatagaa atggcaggtg attatatgag ttcttaataa   29100
tcagctattc attttctgag ctgtagcagc aatgggttag atatggaagt cagatcatca   29160
taatacaatt taataatgag ctaacaaaaa caaaaccctc ctgcatttat ctcttttatc   29220
```

```
gggcataaat catattcagg ttcggcattc tctaatgaaa taactgaaag ttaagttttt   29280
ttataatgta gaattgcaaa ttttgcaaaa gatgcagaat tcatgaaac aatgaatgcg    29340 atattgaaaa gtgggttgac ttacagagct attgacatga ggggatgtgg cagaattaga  29400
tcagagaaga atggttgaag atgaaaaaat tgattagaat aatggacatg attaatgctt  29460
caaactgtaa tgttattaat atcagaggca taggagtggc cctggggaaa tttgaagatg  29520
tccttggttt ttttttgttt tgtttcttgt ttttttttta attccaaaat tactcttgt   29580 aaatgttctg tgaaagcaag ttagatgatc gtatactttt ccctgaacaa ttcctcagtg  29640
tttatttttt gttagttctt tgaaagagca cataattaca tttgtaacca aattttgtta  29700
catttaaagt agttatgtaa tttcaagttt tatttctaaa ataaaattcc acaaaagtaa  29760
ttttttattc gcttacaaaa tttcggtctt tattttaggt gagttactg ttaaggtttt   29820 tctagttata tttggataag aacaactcta tacatttttt aactttaatt tttcaattaa  29880
tatggacatc tttccatatt aataaatgga aaaattatc ttttacaac tgcctgcaga    29940 gtattccatt gtatggagat agcaatttat taaaatagtt attttctgct aaacttgtgg  30000
gttttcaaaa aggtacatat atttattta gagataacta tttctgtttt ccaatttggt   30060
rttaaatgtt tactgtcctt tgacagtggc ctctgagtca tatatgtcat tttgactgta  30120
aatagcaaga tggaagaact tcagttttcc attggtattg ccctttgtgg gcatgcttgt  30180
gtggaagaat ttgggctttg tgaaaaagat acattgcagc tgcaggggc tgggagggtc   30240 ttttttttctg tggggacact gaataaacag ttgtatgcct gcattttcac tgcagcccgt 30300
cacatgaggt caggtgtgga attttccact tgtgtcatat tggtgctccg aaaatttgag  30360
attttggaat ttttggatca aggttgctca acctgtatga acttcttagg caggtttgaa  30420
accttgtcaa gctttatctt agtatttcag aaatggaaag tataatggaa aatttctagc  30480
aaaatataaa tgaccgtagt ttgctgcagt agatatgaaa taaagcttaa ataactaatt  30540
actgtaaaag gaatttagat atctctttgt tccaaagaca tcttttttaaa aaccctagcg 30600 cagttggtct cacagatgca ttcctactag atctttgaag cagattttt caatgttgtt   30660 gaactgggca gggcatagag aagggaagct tccagattct ttatttaaaa ctggcataac  30720
attgaaaatt gagaaagcct acagacaaaa actataggtc atgttgcttt gaataatatt  30780
atgtaaaaat cctaaagaaa atattcgcaa ataggctcta gcagcatatt tataaaaatc  30840
atttacctag ctagagttca tgcccagaat ataaaattgg ttcagtaaag gaactatgt   30900 taatataatt gactgtatca gtgaaggaca aaacccataa agtgtccaaa gatttgaaaa  30960
ggcattagcc aaaaatcagt aatcctgatt gacagcagaa taggagtaac atgatcaaaa  31020
attcctcaaa tcaaaagcta gcgttttcac ttcataattg ggaaaacaaa ggcattcctg  31080
ctgaaatcat cactctcatt gaacatgatt ctagaagtac tagccggcag aaatagacaa  31140
gtttcaaata cttatggaat gtatgaatat aataaaggca aaatcaaaga tctgtgagat  31200
ggttatgtgg attgttaaat gggacatctg gctatccatt tggaaacatt aggaagtttg  31260
actccaacct cattccttag atagaaattt catgtgaact aaagatttaa cataaactta  31320
gctctggcat tagaagaaag catgaggtac atatgatctc tcccctctaaa tatagagaga  31380 ggtactttct aaaattcactt agagtgagga gggcctttct aagcaccaga aaaaagtag   31440 aagaaaaact tgactctaac atttctctat caaaaagtaa aatcaaaaca caccagtctg   31500
ggaccaaata tttgtagagt acgatgcaca ggtgggtaat ttcccgtgca cgcttgtaca  31560
aggctgtatg tgcagcggtg tttgttgcag cattgttttg atgacaaaag aatagaaaca  31620
```

```
acctaaactt taccagtaag gtaccggttt ttaaaatatg gaaaatacat tggagtatac    31680
aattaaaaaa taatgatttg gccgggtttg atggctcaca cctataatcc cagcactttg    31740
ggaggccgag gtgggcggat cacctgaggt tgggagttcg agaccagcct gaccaacatg    31800
aagaaacccc gtctctacta aaaatacaaa attagccgga tgtggtggtg cgtgcctgta    31860
atcccagcta cttgggaggc tgaggcagga gaatcgcttg aatccaggag gcagaggttg    31920
cagtgagccg agatcgtgcc attgcactcc agcctgggca acaagaggaa aactccatct    31980
gaaaaaaaaa aaaagaatg atgtaatttg gatatgtatg tacttatgga aaacattcgc    32040
aagagtttag atgtgtctgt aatcccagca ctttgggagg ccaaggtggg tggctcactt    32100
gaggtcagga gttcgaaacc agcctggcca acatggtgaa acccagtctc tactaacaat    32160
accaaaatta gccaggcgtg tggcgtgcac ctgtaatccc agctgctcaa gaggctgagg    32220
caggagaatt gcttgaaccc aggaggtgga ggttgcagtg agccgagatt gcaccattga    32280
gcaatgtcca gctcatatgt gatagcagtt ggtgtagaac agagtttata gtacgctctt    32340
atttgtgtat tttcaaaaga atgcaccagg taacatatgc ctaacctttc tctggaatat    32400
taaatattca aacagtgaac agagaaggag tttgaattcg aagggaaact ttttatcaag    32460
tacctttggt actatgtaaa ttttgtactg tttcagtttt taaaattgtt tcttaaattt    32520
ttttttcctt tgattttagt ggtgacatct ttactcatta acctgggaag ccccgtaaaa    32580
gaagttcgta gggctgccat tcagtgtctc caggccctca gtggagtggc atccccgttt    32640
tatctgataa tagatcattt gatttctaaa gcagaggaga tcacttcaga tgctgcctat    32700
gttattcagg taagctcgtt agcaaagaag attgagtgtg ttcatgccts tgtgtactgg    32760
agcaattttc tccattctcg acatttcact gtgtagggat tttgatggac taagtcattg    32820
gatttaggaa ctgataggtc aatatctgta catctgtgtc cccctacttt tgaaaagata    32880
gcaatgtcat atttcaattt tgttcttttc attggataaa ggattagtgt gtagcttttc    32940
atagtaagcc agctgtgtgt ttttaataac gtttcttatt aaggttttaa ggagaaatgg    33000
aaaattataa acaatgtcac atcatttggg taagagtctt ccgtaattaa tatatttagc    33060
cttttgtagtt tcttaaccct tttttatcca attttctttt tggtatctta ggatttggct    33120
actttatttg aggaactaca gagagaaaag aaactgaaat ctcatcagaa gttgtctgaa    33180
actttgaaaa acttacttag ttgtgtgtat agttgcccat cttatatagc aaaagatttg    33240
atgaaagtac ttcagggagt caacggtgag gtatgtgcca tttaagtgga ttgtacattc    33300
ctgtgatgtt actaaagaat tgttgtaact gcttgtgggt gaagaagaca attgtaagag    33360
ttgcatgtgt gcactcagaa gagataaatg taatattaat ttgagagggg gatgagttga    33420
ggtagagaaa accagataca agatacaaag acaagtactg gtgagtttct ttttatttta    33480
aaattaagtg tgttgtccct gtctaatcat taagtttatt ttaaatgaac ttaacagtct    33540
cgtgtctcat ggggctgcac tgctgaaaga agctgttgct tcatctctgt ttttcaagtg    33600
aaaattctat acaaaggaat atatttggac acgagtctat gaaaattcca aaatcatttg    33660
ctcgtttatt atatatattt agagcttcca ttgtgttttc gaagaagctt gtgttacaaa    33720
agaaagcagt tgtgaaacac ttgttgatgt gatggcatgt gctgaccaac ataaaaaagg    33780
ttctttcatc ccagtgttac agaaatgcct gtgtgcttca tcagtcctag actgactgtg    33840
ggcttagaga actaaaatga gccaaatgga ttgaagacca tttgattaca ctttcttggt    33900
aggaacaaac aggttgcatt cagccctag ttgtccctgg tatagtttaa attaataatt     33960
gacaaatttc ttgggtaaag gaccagatag gaaatatttt atgctttcgg ggccacacag    34020
```

```
tctctgttgc agctactcat ctctgcagtt gtatcaggaa agcagccaca gacagggtgt   34080
aaacaaatga gcatggctgt gtttcagtaa ataaaattta caaaaacagg tggtctgttg   34140
aatttgacct gcaagccata atttgctggc ccctagttta gcagttaaag atttacatac   34200
ataatttgaa ttaatattaa ttataccaag ttggaaacat tgaaggacac atacagtgtt   34260
ttagggaatc ttaaacttta tttttattct ctaaagtttt agtttgtgtt ttctgttctc   34320
aagtcttgag gaatgctcac agattatctt tctgctcatc tctgaagggt ttagcacttt   34380
tgagcattac acatgaactg tcagaaagga cctgagtgcc ttagtgtgaa ttaatagctg   34440
tctccatgtc taagaagtta ccatcattgg gttttttcct ccaggctaaa ctcccatctt   34500
ccagcaggct ttgagtgtct ctgtagagtg agcaaaaaca tatcagtata cataactatt   34560
tactactaag tctttggatc tttagatggt gctttctcag ctattgccta tggctgaaca   34620
actgctagaa aagatccaga aggagcccac agctgtgctg aaagatgagg ccatggttct   34680
gcatctcact ctgggaaagt ataatgaatt ttcagtttcc cttttaaatg aggatccgaa   34740
gagtctagat atatttataa aagctgtgca cacaacaaag gaactttacg cgggaatgcc   34800
aaccattcag atcacagccc ttgaaaaggt cagtgatttc tttcagaaac taaggcatag   34860
catgttcaag catttaaagg tagaaggcaa caggaacagc gttaaaaaaa aaaagattaa   34920
tattttattt ggagaagata gttacaggtg gactagacgt tttaaaggaa aatgatgtat   34980
ttgacccatt tttgaaaact gaacgttgta catgggtcat taaaaagaat tgcattttaa   35040
ctgacaaaat taagtgggaa acaattttgt attttgagag aggttgatat aaaaattatt   35100
tctggaattt aaacttgttc actgaactca gttgcctttt ttctacccca tttagattac   35160
aaaaccattt tttgcagcca tatcagatga aaaagttcag cagaagcttt taagaatgtt   35220
gtttgattta ttggtgaact gtaaaaactc acattgtgct cagactgtca gcagtgtttt   35280
taaaggggta agctgcaaac ttcttgtaat tttttttatt aatgtttata gtctcttcca   35340
agggacacca tgtttaagag tcctgtattt tatagtgctt gtaagaggtc agatgttacc   35400
attaacaaaa atcatggaaa agtaagtcag agagaggcat aaaataaaaa ttttaaatct   35460
ttaccattat tttattttat gaagtatttg ttgataattt taaccagata ggatgtgtag   35520
gaatatgtgt gtgtgtgatc tttctcatat tagacggaat ctacctattc ctttatgcaa   35580
ggaataggaa tgagtcaatg gctcagtatt gaactgggta acattattct acttaattta   35640
aatagttgtt taatgacata taatggaatt gaaattctgc ttgttggttt tatacgtata   35700
ttgaaacctt gttattatca gaatagccac ctggttattc tcttttttga atatagaata   35760
atacaaagtt ctagtatcta gattcagcag ttctcagaat tttaacatat taatcttttt   35820
tccttctttt tctttgctga aatattttaa agtaaatctc ataatgtcat gcactttcat   35880
ccctctgtac ttcagtgtgc atcttttgaa aagtggatat gactacaatg ccattagaag   35940
taaaaaaaaa ataattcctt ggtattatct aatacctagt tcataatcat atttccatgg   36000
ttatcacaaa agtatttttt atagttgttt tctttgtatc agaatccaaa gatttagttg   36060
tgatgttaga accttataaa aagagatatc tggatcccac cccatatcta agaatctct   36120 ggggcagtaa atctgttttt gtgcatgtgt gtatatgtct tattccttcc tagctgatta   36180
gaatatacat atctgatccg gcacttggaa acaatcggta tggttgattc tgtattgcat   36240
tactagttgt ccactctaag ggatgagcgt gaaattgagt gactctggac tggagaagtg   36300
atactgtatc ataatcaagt aaagtgcagg gctgtaactt gagactccca agacaaattg   36360
tatagaaagc aagtgcatgg tagtaggaga gcttggttaa aatgaaaatc tgaagttgaa   36420
```

```
tttatgttgg ctagagcttt tagtgtatac tcttccctac tttgctttct tctcattctg    36480
gtttttcaag aagtctgtaa caaggtagta gcatccaatg ctggggggg ttcagatgca     36540 tatccagtaa gtcattcttc cctcttaatt gaataaatcc ttcctagggg ttaacattta   36600
ttgctctaat tttatcccaa tggattatat catcaactct tcttccttca atatttcaga   36660
tttccgttaa tgctgaacaa gtccgaatag aactggagcc accagataaa gctaaaccct   36720
tgggcacagt tcagcaaaaa agaaggcaaa aaatgcagca gaagtaagag ctacaaatgc   36780
attgagcaca tgctgttgtt ccctgactct gaatgttatg aaaccattgg aacttttga    36840 tactcatcga tttgctataa tcaggcacaa tggttttac ttagcacatg atagagtttg    36900
cttttccaac gttttgtctt ctccatttc cagaaaatca caagatctag aatctgttca   36960
ggaagttgga ggttcttact ggcaaagagt aactctcatc ctggaattac tgcagcacaa   37020
aaagaagctc agaagtcctc agatattggt gccaactctt tttaacttgc tatcaaggta   37080 atgcacttg gctttgatct gtgagagaat aggactctaa ttcttgccca tcttatctaa    37140
cattctcttt tcaacatact cttctcttgt gttagatagt ctgtaaaata aagcaagtac   37200
tataggtgaa attaaaagat tggttttagg tatccattgc tggtgcccca aactgacctt   37260
agtgtcctgt gtcatgtagt aaatggccac tcactgtaca gcctactttc ctctgaactt   37320
ttcagtagcg tgcctgggac gtcattactt gcatttcaag atatagtgtt gaatttatat  37380
agatatagat atgtgtgtat atagtgtttg ctatctaaat atattttcat atatatagat   37440
gtatatattc tatatacgta gatttgtgtg tgtgtgtgtg taaattgagt atgaattgta   37500
gcgtgtgctt tcatgtgaaa ggcaaagtaa ttctgaaggt tgtcctgtaa gattccagat   37560
aggctaatgg aaagtgcaat agagaggacg tggaatttga catagcgcct gtctatatga   37620
gagaaaatta gagttagaaa tcttatatct tatttctaga cttgatgttt aatgatagta   37680
ttttagttat tccttattga atgagttcct tattgaatga gttctggaca atggccatta   37740
atgtaacaat gaattgtaca acttttacat ttcccatcat ttctcttttg ggtgtcctga   37800
agatgtttag aacccttgcc acaagagcag ggaaatatgg aatacaccaa acaattaatt   37860
cttagttgtc tgctcaacat ctgccaaaaa ctatctccag atggtggcaa aatacccaaa   37920
ggtaggtact ttttggaagg aaaggttaga aaaattatct actttgagcg tgagtgtacc   37980
tgccacttag ggttttgtc tttctcacca ttgtagatat tttagatgag gagagagttca   38040 acgtggagtt gatagttcag tgcatccgcc tttcggagat gccgcagacc catcaccatg   38100 ccctttact tttgggcact gttgctggaa tatttccggt aagcgttaat gatataagat   38160
tttagcagat atttcagata ttttcttcc acagaaatgc actggcacct gttgattta    38220 aatttaatca attaggcttt ggaatcttcc agcactggtg agactctcag ccctgcctct   38280
tcatagctgg gactgtataa gccagttgat cttgctaagc tttggtttcc cttttttatca  38340 agtgggaata taaccttct tcactggatt gttgggggaa ttcagttgga taatttgtgg    38400
ttagtactta gcataatacc tggcacacta tctatctaat aaaacagtag gtattggtgt   38460
taattgggaa aagttaatat ctcatttatc ctcaagtaat cctcaaagta accttaacc    38520 agtgacttca gaaaattaat ttgatcataa actatgtcat ttaaagaaat cacgtccctt   38580
ttatgaaaaa tatcatttaa acatttgtaa agagattgaa gctatttca tattgaggat    38640 ttgagtcaaa gctccttaac ctggggttct ccatgagctt taggggatct taatctactg   38700
aaatcatatg caaagtttta tctgtatggg attttttttt ttcttgtaag agagtctgtg   38760
cttctcaaag gggttgataa tccagaaaca gttaagaatc attaatattt tttctgtttt   38820
```

```
tattgaaata tagttcagat gccataaaat tcacccattt aaggtataca attaagtgat   38880
tttagtatat tcacgaagtt tctgtaatca ccaccacgat ctacttgaag agtattttca   38940
tcaccccaga aaagaaaccc tacacccatt aactgtcact cttcctctcc ctcctccctg   39000
ccgctgccac cgtcaccacc agcaccacca ccaccaccat gaccaccacc ctgctcctgg   39060
ccactagtaa tccattttct gtctctctca atctgcctat gctggacatg tcatataaat   39120
tgagtcatac aatatgtggc cctctgtgtc tggtttcttt tgcttagcat aatgtttttg   39180
tttgtttgtt tgtttgtttt gagacggagt ctcgctctgt tgccgaggct ggagtgcagt   39240
ggcgcgatct cagctcactg caagctctgc ctcttgggtt cacgccattc tcctgcctcc   39300
gcctcccgag tagctgggac tacaggcacc cgccaccacg cccggctaat ttttttgtat   39360
ttttagtaga cgggggtttc accgtgtta gccaggatgg tctcgatctc ctgatgtcat   39420
gatccgcccg cctcggcctc ccaaagtgct ggaactacag gcgtgagcca ccgtgcccgg   39480
ctgcttagca taatgttttt gaggttcatt cttgttgaag cttgaatccg tattcctttt   39540
ataactgaat aatattgttg tatgtgtatg ccacattttg tttatctgtt catcggttga   39600
tggacatttg ggttgtttca actgtggggc tattataaat tatgttgcta tgaatattgt   39660
agacatggtt ttgtgtggac atgttttcat atctcctggg tatatatacc taggagtgga   39720
attgttgggt cacacggaat tttatgttta gctttggagt aacttgcaag actattttcc   39780
atagtggcca caccattttg cttccaccag cagcctgtaa agttcccaat ttcttcacat   39840
ccttgccagt acttgttact gtctttttta tcgccattct agtgggtgtg aagtagtatt   39900
tgtgcttata ttcttttcgt atgaattttt tctttgaaga aatgtctttt caaatccttt   39960
gcctgttttt taatcaggtt atttctcttt ttattggtga gttgtaatga atcgttgaaa   40020
tggaaaatgt tagcctgagc aggaatatca cttgtggcca ggagttcaag accagcctgg   40080
gagttcaaga ccagcctggg taacatagtg agaccccacc cttacaaaac agaaaaggaa   40140
aaaaaattag ctgggcaggg tagcatgcac ctgtagtcct agctactcag gaggctgagg   40200
tggaaggatt gcttgagctt aggagtccaa ggtttcagtg aactgtgatc acacaactgc   40260
actgcatccc agcctgaatg acggagcgag acgctatctc ttgaaaaaaa aattagtaga   40320
aattaacaga aataaaaaat gttgatagtt gtgttttctt tcaggataaa gttttacaca   40380
atatcatgtc tatttttaca tttatgggag ccaatgtcat gcgcctagat gatacttaca   40440
gttttcaagt tattaacaag acagtgaaaa tggttattcc cgcacttatt caggtaaggt   40500
ctctttatac catcgtgggg tttctttttt taatttaaaa atttttgcata taatgacatt   40560 taaaagcctt ttttttagtt ttttttttg ttttttttt ttttaatatc ctcaacagtt   40620
gtataaaagc cttctgaaa tgctcaagta cattgccctt aagttttaga acattgaagc   40680
taagaagcag tcttggcaat gtctttctca ataatataaa caaacgtgtt atagccggtt   40740
ctgctgtgct gtgagtgtgt aactgtaagt gtcttaacat cattcgggtg gggtaaattg   40800
acatccacca tctatttcag gacattgcat cagtttgata ataccttctt acatgttgat   40860
gaggctagga acttttagag ctacagtgac aaatttgtta acatgcagtt tagcaaatgt   40920
ttaccaagca ttctctaaga gctaaactca gagagagagg tgagatgttc tctctcccag   40980
taaggaatga acaattcaaa agttaaaagt agcctcaaga gtaaaagagc ttgttcatct   41040
acttgagttg tctatgtacc cttcacttgt taattaatgt ctttctcat gctattgacc   41100 ctctgaggga tgaccatatt cagcaccttc ttttaacctt agtattagat tggtgttctc   41160
agtgtccacc aagttggcaa gtataggata tatacctaaa aagaaaaata ataatatgca   41220
```

```
ttcatatgat cagtgccagt cgaataagta aatgctaaag agttcagaat aggggaaagt   41280
ctatatgggc caggatgacc agaaagttct ataagaaata gaatttgtac cggtgtgaaa   41340
gaaggatggg atttgttcag tgatggcaga gccaatagta tgagaaaagg catgatctag   41400
gaatgtgcac agcatgtttg aagaatgtaa tggtgattga ttgatggaga gcagagggtt   41460
gagacaggta gacgttggtt tattcattca ttcaagtgtt ttctgtcatt ctttctgtca   41520
tttattcaac aactatattt tgatcaccaa tacctggagt aaaatggttc aaactttatt   41580
ctgaaagcag caggaagttg ttggcctttt ctgtgctctg cttatcttca ttcttcttga   41640
ggcacaaccc aaatcctgtg tgatttgtgc agccttccca ggcagtctaa gcagacttgc   41700
tatcagtgtc acatatttgg catctgccat tactgcctcc tgttatcttt tcacacatgt   41760
attgtttctt ttgtttgttt gtttgagaca gagttttgct cttgttgccc aggctagagt   41820
gcaatggcat gatcttgggt cactgcaacc tctgcctcct ggtttcaagt gattctcctg   41880
cctcagcctc ctgagtagct gggactacag gcacgcacca ccacgcccgg ctaattttgt   41940 attttagta gagatgggtt taaccatgtt ggcctggctg gtcttgaact cctgacctta   42000
ggtgatctgc ccagcttggc ctcccaaagt gttgggatta caggcgtgag ccactgcgcc   42060
cagccatgta tcctgtttca tacagaaaat aaatctcctt tggggcaggg ctcatatcgt   42120
acactttgta ttccccttgg ggctaagtag cgcttgggac atgacaggta cttactgaat   42180
atttattgtt aggcctttga ttattaaaac tcttgtggct gagtgtggtg gcatgcacct   42240
gtaacaccag cactttggga ggctgaggtg ggattatttg aggccaggag tttgagaaca   42300
gcctggtcaa catagcaaaa ccccatctct acaaaaattt ttaaaaagtg gtggtggggt   42360
cctgggatgt cccagcttct tcggaggctg gggcaggagg atctctttga gctcaggaga   42420
tccaggctgc agtgagatat gatcacatca ctgcacttca gcctgggcca cggagaaaga   42480
ccctgtctct aaaaaaataa ataaaattct tctggcaatt tcttgggggcc catctaaaag   42540 ccttatcttg ttcacctaaa cttgttttgt ggaagattac ttgcacctac tcattgtctc   42600
tgcttgctgt tttgcagtct gatagtggag attctataga agtttcaaga aacgttgaag   42660
agattgtggt aaaaatcatt agtgtatttg tggatgcgct gccacacgtc ccggagcaca   42720
ggcgcctgcc catccttgtt caacttgttg atacactggg tgcagagaaa ttcctctgga   42780
ttctcctcat cttgcttttt gaacagtatg tcacaaaaac agtgctggcg gctgcctatg   42840
gcgaaaaggt cagaacctag ggtgggaaga taaggaaaat ggtgatttct cacacagatt   42900
ttatgatatt gtccagttta aacatgaggc tgatgatgcc taatgtgtgt tatttagaac   42960 cttttttgctc agaaccttt tcaaaaaggt ttttggcatt ttaaaaaatt gcattcagag   43020
cccatagcac tctgaatatc ctcagttgca gcaaaacatc ttctgaaggc gaattaactt   43080
ttctgagaaa cagttctgct gccacgcaag tggttctctt ttaagcccag cagagtatgg   43140
ctgaagagta atgaaacagt gtctcttcaa agcggttttg aaggcagttt gtggggaaat   43200
agaggagcgt ccgtgtccct gaagtcagta agacacaaac acaggtgatt gtttggataa   43260
agccctgttt ggataagtcg aggaccattt ttaaatgact tcttagacat gggatctggg   43320
agtagatctc gacccactgt aaataaagta gtatactctg ttctgctaga aatcctaacg   43380
cacattatcc tgaaattatg ccttcacaat tcctaagtac agatttgtta ccttttttctt   43440 tttctacaca ggatgctatt ttagaagcag acactgaatt ttggttttca gtctgttgtg   43500
agtttagtgt ccagcatcag atacaaagct tgatgaatat cctccagtac ttactaaagc   43560
tgccagagga aaaagaaggt aagcgtagat cgggtgtcac ttactgttca atctgaaagc   43620
```

```
taaagagaaa cagaagagaa tgcaggttat ccttagtaca tcttcagaag gattttaaa    43680
gtaagttaat cattttaatt tgattgtgta gtttcttgaa tccttatgga aaatagtcgg    43740
aattccattt gccattcctc acacattgtc ttttatacct ctgtgctctg cgctgacgtc    43800
ttggctgtgg aatgttgctg gtatccagga tgagttaggt tcaaatgaca gtaaatgatc    43860
aggacctcat tagctgtctc tcagcttctc attaaaatat ctgaagacat ttacatgaaa    43920
agaaaaaag taggtaccac aggagtggca gcaaaatatt aaaattgtac catgcagcag    43980
agccttgaag aaaatcccac gaactgcagc accactgagg ctggcttagg aaagggttga    44040
tgaagccagg tgtgatggtg ttagcctgtg gtcccagcta cccaggagaa tgagacagga    44100
ggatcacttt agcgcagttc aagaccagcc tgagcaacat agtaagacgc catctctaaa    44160
aaaaactttt tttcattaag aaagggttga cgtgttgata gttcttagtt ctctacaatt    44220
cgaagcagaa cgacaaggca cgttagaagg aaggtactct aagagctccg cagagactgt    44280
tttctgcgtg gccagccatt ggccctgtca tcactgtttg gcgaggcagt aacttgtccc    44340
atcctgcagt cagctcaggt ttggcaggga cagacgaggg aggtccctgg acagtatgtg    44400
gtgtatgtgg tatatgtggt gatgtgggta aggaagtgtc ttagcagtaa gtcattctat    44460
aggatagtgg tttttaacac tgcactgcca accccattta cattagacac attgaataaa    44520
gaaatctaca cctgcagttg gaagttcaga gactccttcc gtgatgtggt ttcttccatt    44580
tgattgtcca gtttccctgt tttgttttt gtcttaaaca ctcgcttctc agggccactg    44640
ggtactctct tggcaaatac actcacgttt tcactaatt tagaaggga gaaactggat    44700
gtaatagatg aacacatttc tctgggaaaa tgttatcccg ttaattgtcc tttacttgaa    44760
aggttatatc tgttaattct gtatgaagga ttcaggtgaa aatgagtaag gtcacttgtt    44820
ttattgctgt ttcagaaacc attcccaaag cagtgtcatt taataagagt gaatcacaag    44880
aagaaatgct acaggttttt aatgtagaga ctcacactag caagcaactg cggcatttta    44940
aattttttgtc agtgtccttc atgtctcagc tcctgtcttc caataatttt ctgaaaaagg    45000
taatgtgttc tttaaatgtg tttataaaaa ggtattctgc tgtctccaag gaactgttct    45060
caaccagtag aagtagcttg gtaaatggct catgaaaatg ggaggcacgc ctttaaagat    45120
aatagaacaa gaaagtacgt ttcaccatga aaagccgttc gtcatgatct actgagatgg    45180
aacataatgt aaactctgtg actcagtggt ttcattctta agtgttgtgt acccatcaga    45240
agtttatgaa cctgtacacc aaaaaaacta caagaatctt tataatattc ataacattct    45300
tcatggtagc acaaaactgg taacaactcc agtgtctacc agcagagtag ataaattgcc    45360
tgtatttat tttattttt gagacaggtc tcactccatg tcccaggctg aagtgcagta    45420
gagcaatcat ggctcactgc aacctgaaac tcctgggctc aagcaatcct cttgcctcag    45480
cctcccaagt agctgggact acaggcgtgt gccacctaca tctggctaat tttaaaactt    45540
tttttataga dacagggtct cgctctatta cccaggctga tgtcaaattc ctggcctcaa    45600
gcgatcctcc caactcgagt tcccatagtg ctgggattac aggcatgagc caccatgccc    45660
agcctttctt tacctggata tagtgagttc tgcatgtatg atttgtatac atctctgtt    45720
gtgtattaaa cttgttaaa caatgagaga aaggaagga aagaaaggaa tacgaccagg    45780
aatacaaaaa tggtttgaca ttagagtact gtaaagtcca ttaggtccta taatgcgtta    45840
acagatgaag aagggaaacc atatgatcat tttacatttc acagtgaaat aattcagcag    45900
actcaatgct tattcacaac ttaagagaga aaaatcctcg ctcacacctg taatcccagc    45960
actttgggag gccgaggcgg gcggatcatg aggtcaggag atcgagacca tcctggctaa    46020
```

```
catggtctct actaaaaaat acaaaaaatt agccaggcgt ggtggcgggc gcctgtagtc    46080
ccagctactc gggaggctga ggaaggagaa tggcgtgaac ccgggaggca tagcttgcag    46140
tgagccaaga tcgagccaat gcattccacc aacctgggtg acagagcgag actctgtctg    46200
aaaaaataaa aaaaataaaa aaaaggaaaa aactcctctc agcagtgcag gatagatggg    46260
aattactttg gcctaataaa ggtgacaatc tgaagcttgt ggtttatatc atacctaatg    46320
atgaaatatt aatggtgtgc ctgctacagt cagggacaag aatctcctct gtcattgttt    46380
ctattcagga aagaaatga agtgtaagaa tcaggaaaga agagaatcag caattagaac     46440
taataatgag ttcagtaagc ttgcttaaga gagatcagtg tagacactat ctagagatca    46500
gtgtaggttg tgatctgtat caagcaggct ggctgaacta attagtctca ccactgttat    46560
tgttattcct caaattagaa aacagagtag aaaaaaagat ttcctgtata atacaaacat    46620
aaacttacaa ggtaccaaga ataagcctga caaaaatatg tgcacaaata ttacagggga    46680
aatgtgcaag atatgaaggg acacagaaga aaacttggaa gaaatagaaa gagagacact    46740
gtgtttacgc atgaagaagc ctcactattt aaaggtggca gatctgccca gattggtcta    46800
gaaactcagt gtgcttttttc aattatatca tttttaagaaa tgatattgat acattgatac    46860
caaactgtaa ggggccaagg acagtggtat ggtgcaggag taatcagatg gatcaatgtg    46920
actgaacagt aggcccagaa acacatgcag gcataggtaa gaggtgcagc aggtgatttt    46980
acaaagcagt tggggggagag aatggtccaa gtgctggccc tggcatgatt tgtttcccat    47040
ttggggaaaa gtctgatgtc acaccttgta gaaaagacaa ctttagtcag agtaaaaact    47100
tcattgtaaa aaacaacagt tcaaatgttt agaagaaaat caaggagaac atgattgtga    47160
ctggaggata ggaaagaatt cctttaaaat tttgattcaa tagaaagcca caggctgaga    47220
gaagattatt gctctgcata aatcaaaaag cctcagtttc cattagaaca actggcaaag    47280
aatatgaatt cactgaagag gaattacaga tggccagtta atgtacaatg tcatttagcc    47340
tccagtaagc aggaaatgtg attaaatgtg atacccatca aattggcaaa actgttgaag    47400
tcgttagtac cagggatggg gtacgtagtg gcagacagtg tgattgttcc aaccactttta    47460 gaaagcaatt ggcaggatcc catgaggttg aaagttccag taattcctgt gatctggtca    47520
ttcccttcct taggtatata tgctgtaaaa acttcccaag atgatcaaag ggacataaaa    47580
atgttcttct ctagcattat tagtaaaagg ggaaaaatg gacataaact aaacatctaa     47640
caacagaggc aaatggatag ataagtggta tttatagagg aatatcatat gcagttaaaa    47700
tgaaggaact agaacataag tcaccatgca tagatctcaa aaatatgttt ccagaaaaac    47760
atgttgttcc gtgatatgta gtgtttgaaa catttggaag cagatttggg atgatggttt    47820
tgtttgtggg gcttggggta gagggagaat aggaccaagg agcagtactt ggggattcc     47880 agctgaatct gtaatgttta acttctcaac aaaggatatg tgagctcacc agatcagcat    47940
gtcatagaat tcgtagtgc taattgagtg ttgattgctg tattttttctg aaccattgta    48000 gtacttttta gatactacca gtagaatata attaaaataa attaagagaa atagagttac    48060
tacagtataa tgaagatgct atgaacctga ttaaattgta atgtcagaaa acagttgctg    48120
tggaaggttt cagtgaatgg tccgagtttc attgaactga cttgaaatga cttttattat    48180
tgacttccmt accgttctaa tgacgtcttc tttaaaaatt aggtagttga gagtggtggt    48240
cctgagattt taaaaggcct tgaagagagg tatgtttcct tttctttttt tacttttttat   48300 ttggaaatga cttcaaactt atagaaaacc tggaaaaaca gtacagaaaa ttcatatact    48360 cttttacaacc aggttcacca tttgataata ctttctgcca catttgcctt agcgttctcc   48420
```

```
ctatgtaggg ttttttctct gagccatttg aaagtaaatc atatacatta tgtctctaag    48480
aataagagat gttcttataa aaccacagta cattgatcaa attcagaaaa tttaacattg    48540
atccaatcca gtgatgtaat ctacagttca tactccagtc tccctaatta tcccaacact   48600
gtcctttaca ccgcatgtgt ttctgcatca tgatccatgt caagtctgtg tattgtattg   48660
agttgcagta tctgtttagt gtctcaatct ggccctgatt tctatgggct catgaattct   48720
ttattccgtg gattcaatc catatgctgc cattatatat ttgggtgcag gaattttcct    48780
ttctctccca tgtcctcggg gtttgcctcc tggccttgct gtgtacctcc ttttcagatg   48840
catggcattc ccagggccac tgtcctgccc cttccactgg aaagtgcctg ccctgcagcc   48900
aggaatgtga gctgctgagt tccagtcctg tgggctgact tgtagcgcta tgcgtaggac   48960
tttcgttttt ggagctgatt ttgtctgcgc cccttctcc cctcctctgc tgtgcggtgt    49020
caacttctgt ctccactctt ccctctagct ccccctcag gctggcagca gtgggggat    49080
ctccagtggc agctgtgttg gaatttggtg tgtgctttc taattacaag ttatttgaag    49140
tttgtagtct ttttttttgt ctcctaataa tgtgaaagaa gtgggttata tgttcatttc   49200
tattaatatt tctctttata taaatggtgt atggtgtgtg tgcatgtgta tgtgtgcgtg   49260
tgtgtgcctg tgtgtgtgtg cacgcacaca cctgccatta acctagggcc ataactccct   49320
gaacacccca cttggacagc ccagtgagat ccactgagca tgagctagat atgagtgagt   49380
tccttaaacg ctttcagcat ctgttgctta ttcagcacct cacagagtct gagcgaggtc   49440
gatgcttctg cacagaagcg cctagttact tcttgatgat ctctgtctat ggcaataatc   49500
cctcatttcc tttctttccg agtagttttt gaaataattt agtacagaat tatttaactc   49560
gtctttctac ttgaaacatt tagcataagg tagacatgaa caagttctct gagtkycttc   49620
agctgccgtt tgctgagcga gcctctgtgt ttcaggttgc tggagaccgt tctcggctat   49680
atcagtgcag ttgcacagtc catggaaagg aacgcagaca aactcaccgt gaagttctgg   49740
cgcgcgctcc ttagtaaagc ttacgacctg ttagataagg taggtgttca tttctccctg   49800
gaattactgt tttgttgctg ttttttaaat tattgtgaaa ttatgtaaag tttttaagaa   49860
taaacttagc aattccttt atgaatataa tgaagctcag attttcttta gaaaacaatc   49920
tcttgatgac tagaaatagt tttgtctgga aaaaattgtt tccttaccag ttatgagaac   49980
atgtacctcg tatatttaa taattaagtc atataatata tactgttcta ctttattcaa    50040
gtggaataaa ataaaagtat gaagtatatt acatacatat cactggcctc gaagttagga   50100
ttgctgattc aaatctagct cagtcattta gctgcatgcc tttggcactt cctcctgaca   50160
tcaggctttt gttttgttcg ataatgtgtg gttggtaatg cctacctgaa aggttatttt   50220
aagaattaaa taagaaaatg tgtgtggaag tgcctggtgc ctggaggtgt gcagtggaca   50280
gcagtctgtc ttaattgaag ttgrttttt ttaatttg ttttctttt catgttaaat       50340
ataaatttc tctttaggtc aatgccttgc tgcccacaga gacattcatt cctgtgatca   50400
gagggctggt gggcaatccc ctgccatctg ttcgccgcaa agcgctggac cttttgaata   50460
acaagctgca gcaaaatata tcctggaaga agacaatagt gagtgaagac ccaggacaca   50520
cccatttact gtactttgct ttatcaaaga gctgcattta actcccttca atttctctag   50580
tggtacaatt tcaaattgaa gtatattatt atctgaaatt aataccatga catgttttaa   50640
aatgtgacgt taattctaac gggaatatat gtgtgttgta agagctctta gaatggaatt   50700
tcagcctagt ggaattcttg cttactacag agcttacgtg gccttagcct tagcatagtt   50760
ctaagtccct tttactccag atcagtgggt gctttgtata agtgaaacac tggctagaac   50820
```

```
atgcacatcg cttagcatga ctgtgtgact caggacccccc gagtctgatt tccatttaga  50880
caatctcaag ctgtgacaat gggaaaatgg acaaacattt tttgcagctt taatgatttg  50940
gggattctgg ctgtcccctt caggttaccc gtttcctaaa actggttcca daccttttgg  51000
ccattgtgca gcgtaagaaa aaggaagggg aagaagaaca agcaatcaac agacagacag  51060
cgttgtatac cttaaagctt ttatgcaaga attttggtgc agaaaatcca gatcctttg   51120
tcccagtgct garcactgct gtgaaactga ttgctccaga gagaaaggag gagaagaatg  51180
tcytgggaag cgcgctgctg tgcatagcag aggtgacctc caccctggag gcgctggcca  51240
tcccccagct tcccaggtat gcggccgag acttggaaca ggagctgtta ccgcctggca  51300
cacattgaaa aataacactt tggtgacttt tttttttttt cctctgagta gacgttgcat  51360
aaaattggaa tttgttaaag aattgatctt gcagggtgtg gtggctcacg gctgtgatcc  51420
cagcactttg ggaggccaag gcagggagat catttgagcc caggagtttg aggctgcagt  51480
gagctatgac tgcaccactg cactgtagcc tgggcaacag agtgagaccc tgtctcttaa  51540
agaaataata ataaaaataa ttaatcttca aacagaaaga tgcagccttc ccgtttatct  51600
tcagatgcac tgcttttgcag tgttaatcgt cctccattct tccttccttt tgtctagtat  51660
agtcaaaaag cagtgggtga aggttcttgg cagagggggcc cacccagtta ggcaaggcca  51720
aagctgccctt ctgctgccaa atttggaagt tagaagctcc tggctgtggt agttccttac  51780
tgtacagcca gtatgttcct taacctgtta gagctttgct gtctataaaa cagagacagt  51840
atctacctca taggatttct gtagggcagt gcttgcaagg agttttgcat agtgcctgac  51900
acatagtaag tgttcagtta atgaaagaca ttgttatttt ttaaattact gttgtgtcca  51960
tactgttagc actgggagat ttcttgtgct tagccacata aaatgtatag acactgcttt  52020
ttaggctatg aggcagatag cgatgtaata ggcacagttt gctggttttt ttcataatgc  52080
cctctactcc attccctagc ctctgttttct gcttcaagtt cttctaaagc tcttactttg  52140
tttctagcct gatgccatcg ttgctgacaa caatgaagaa caccagcgag ctggtctcca  52200
gcgaggtcta cctgctcagt gccttggctg ctctgcagaa ggttgtggag actctcccgc  52260
acttcatcag cccctatctg gaaggcattc tctcccaggt gagccacgat agccacgaca  52320
tgctacgcag ggtggctggg gaaggtaaaa gatcacaaat gtagtgattt tgttttttct  52380
ttaagggtta gtttccgttt gacagaaagg agtcttattt ctgaagagat gtgcttgctt  52440
ttattaaatg tgtactttt ctcttccatc atccttgcca cttaatcttg aaattgatat  52500
gggggtcact tttagcgag atgcttctct tctttaattg tgcggaatgt attctggctt  52560
ttttttcttc tgtgagatct ttggagttgg gctggtagag ccgcctttta ttacttgtgg  52620
aaattgatgg gccctgtttc tactgtgaga ggtttaatcc taaggcatct tgcaaagcag  52680
aattttttgta ttgcacgtca gcggtttcct gtcaacacgc tagggccag tggtatttat  52740
gattgaagat gctcaagagt gttgagacct ggctgttcca ttgtgttgat catttgccat  52800
ttacaaggtt aggagccttc attaccatgg ggcaaatgat taaaccgctt cacttacacc  52860
acagccaggt tttaaaagta gccttctcag agaaagggggc ctgtgctctg aggagctttc  52920
tcagttttt agcaacttga ctcttgccgt ggtcccttgc attcctgtcc tctaagaaaa  52980
tcatctgtct gggtgctgtg tgtgcgtctg cgtctaccat cggccttcgt ccctgatcgc  53040
aagtttgggca agaggtgtct gcccagtttt atccactgac gtttagggct gactttaaaa  53100
ggaactctgt gtgtagttaa aaagtgctaa gcattttcca aacactagta cctcatcatg  53160
aagcctctct gtaagtgtgt gtttgtcagc gaagatctgc agtggccctg atcacttttt  53220
```

```
ttatattcct gtaggtgatt catctggaga aaatcactag tgaaatgggt tctgcgtcac   53280
aggctaatat ccgtctcaca tctcttaaaa agacactggc taccacactt gcaccccgag   53340
tcctgttgcc cgccatcaaa aaaacttaca agcagattga aagaactgg aaggttagat    53400 cttattgggt attaagactt tggagaaggg agaggtggta ctgcaatgtg taaactttga   53460
cttaaagaag aagatttagt ttttaaaaat acacaccgct gaactctagg aatcatttga   53520
aaatggcaca tctyttttcct gtgttattgg tagaatcaca tgggtccgtt tatgagcatc  53580
ttgcaagagc atattggggy gatgaagaag gaagagctca cctcccatca gtctcagcta   53640 accgccttt tcctggargc cctggacttc cgagcccagc actctgaggt aagctcaggt    53700
tcactcctcc aaatcctaaa gctgttatcc acctattgaa gagtccgaga acaatctagc   53760
cgtgtaacag tggtacttgc caaaataatt tacagtcagg tatcagcact ctaataaatg   53820
ggctcttctg ttttcagaac gatctggagg aagttggaaa aacggaaaat tgtatcattg   53880
actgtctagt agccatggtt gtcaaacttt ccgaggtcac attcaggccc ctgttcttca   53940
aggtgacgct ttcttcctct tcctctcttt tgtgctcaga tttaagtgac aagatgtcga   54000
agaaactaat actgtcttat ccttttcagct gtttgattgg gctaaaacag aagatgcccc  54060
aaaggacagg ttgttgacat tttacaactt ggcagattgc attgctgaaa agctgaaagg   54120 gcttttttact ctgtttgccg gccacttagt gaagcctttt gctgacacct tgraccaggt  54180
gaacatctcc aaaacaggtg ggtggtcgct tcagttcagc tgtcaccctt gycctgtgtg   54240
ccttatacaa ggtaccagta agacacaasc tagtgcttgg aagcaagatt ttagaggttc   54300
ttaagtccta agctaaggag ggtgaatttt ttacttcatt gttgtcagac agtgaagtgt   54360
tgttttagca tsatgagcga atgttataag tcacctcact tgggagaaag aataaagtaa   54420
atggccgtta ctgtcagtta ctggaagtaa cttaaaacg caaaaattaa gattagttta    54480
ttctctaatg ctaatacgtg acccacttga cagttgaggg aatttaactt gccagagtga   54540
gtgttagaat cttaactcta aaagaaggaa tcattcttcg agagaccatc cattgtgttc   54600
tgccttcgtc ctgattatga tttctagatc attttagact cttctgattt agttatttta   54660
atagtgattt caatgtaaac attggagatt aaatggttaa gttcagtgtt ttttcatttt   54720
tactcttccc acgtctacag atgaagcatt ttttgactct gaaaatgacc ctgaaaagtg   54780
ctgcttgctg ttgcagttta ttttgaactg tttatacaaa atcttccttt ttgatacccca  54840 gcatttttata agtaaagaga gagcagragc cttgatgatg cctctggtgg atcaggtaac  54900
caaacagaat catctttcgt tgctgaggaa gccatcactg ttcgagcttg gcaggtttta   54960
gatctgctca aatgacagct tgctaggatt tttctttgta aggttgtttt ttctggtctt   55020
tttaatgaaa tgtttatttt gaaaattgtt ttttcaaaga tataacttca ttgtggaatt   55080
tgagttttgt tttgttgttt tgagacaggg tcttgctctg tcacccaggc tggagtgcag   55140
tggtgcaatc tcggctcgct gcaacctcca cctcccgggt tcaagcaatt cttgtgcctc   55200
agcctcccga atagctggga tcacaggcgc ccgcctccac acctggctaa tttttgtatt   55260
tttagtaggg atgaggtttt gccatgttgg ccaggctggt ctcgaactcc tgacctcaag   55320
tgatccaccc accttggcct cccaaactgc tgggattaca ggcgtgagcc accatgcctg   55380
gccctgagtt atttttttatt ttttatttttt taaactgctc aaaagacaga catgatataa   55440
gctgtcatgg ttaatgtatt catttgtttt aactgggcct cactgagaac gtgtcagagc   55500
atggctgtcc tctggagcaa agagctcctc tgagatgttc tgctgagag aaaggggcga    55560 tgataaaggg tatgagattc catttgagtt ctagaaggca atacatttgc cctagagagt   55620
```

```
attagaataa tgcctggttt ttgaacctgc taatatcatg aaagatagta aaatatttgt   55680
atgttggaya tttttttcaaa cagaagaaag aaatgagact tgttgttcaa agtctttgtc   55740
ttactcttcc tagctggaaa acaggcttgg gggagaagag aaattccagg aacgggtgac   55800
aaagcacctg ataccatgca tcgcacagtt ttcrgtggcc atggcggatg actctctttg   55860
gaaaccactg aactaccaga ttctgctaaa gacgagagac tcctcgccta aggttaggaa   55920
ctgcgtgaca agtactgaaa ctgcatcttt tcactgcata gcctaaacag cctgcaggtg   55980
gtcacagatg taggccccct agtaaactgg cagggaagaa cattgctatt tgtcatccag   56040
tactagaggt ctggtctttt gtattaggca gaaatttgtg cctaagaaaa ttttgttttt   56100
tacttatagg ctatttgtaa agaatagcaa tgccctatcc ccaccccaat ggtgcgttgg   56160
gcagaagtac taaaatactt tctaaatact tttaaataac aaagatttga agtaattcct   56220
tctttttttaa gtgctattga aatgtcattg tgctccagag agaaatgcat tgaatttatc   56280
cacactatag tcttttgagt tagagcaata cattctgttg tttatagata ctaggcttat   56340
gatcttgttg agtaagtggt ggcagtggaa ataaaacatg ggtaggttga gtggaagtca   56400
aaatttgaca cccaagtgtt acaaatttca aactgtttta gcaatgagtc accatttctc   56460
aaactaatga ttgtattaga actttactgg ctataacaga ccaaagcaga atttttattaa   56520
taggatttat tagttcaaat tctttattag gatatgctaa caatgagact attatgatga   56580
acccccacat tttaaaccat aggtttttat acaagtagca gtatcaaatt tattgtaata   56640
ttttactttg cacaaatcaa ggaaatcctg attgaatcta ggtagttaca aatggttttt   56700
taataattca ctttgtactg tccagatatt ctttaattaa aatatccaaa attagaagac   56760
cagtagggct tttgtttcaa aagctaacaa tacccaacta ctgcttgctt tccttattat   56820
agacaaggca tgtgaggaac acctagacgt ttttaaagcc ccaaaactag gatattgtga   56880
cacagaatgt ttttttattca gtgctgagat gggagtttat cccaagcgat tgtcctggcc   56940
cctcatacaa ctatagtggt gaccagtcag gggctgtggg tgaggagacc tgccagaggt   57000
ggctggaggc actttattgc cagcctggcg ggctggcgag cgccaatgaa gtaaaatctg   57060
gtgacacact tgagtttgca tgtggcatttt tatttttattg gttttttttta aaggaagaga   57120
ttataaaaag acatttccaca ttaaagattt gcagtcctgg gacacagttt ggaaaacact   57180
atttataagg ttgcacatat tacaaacagc tcccaaatgg tgaaactggt attctaagat   57240
gaaagcttaa tgaacataat gaagtgaata aacgcgtgtg aactaatgtt taaaaagtta   57300
gagcttgtct caagtcagta cagctcttaa gataataaat acagtaacac tacttttttat   57360
ttctttgctc ttttatccct ttcaggttcg atttgctgct ttgattactg tgttagcact   57420
ggctgaaaaa ctaaaggaga attatattgt cttgctacca gaatccattc ctttcttagc   57480
agagttgatg gaaggtaatt cccaaactat tcccaaccat taaacaatta aggaataatt   57540
cagtaaaatt ctgtgaaaat gtgcccaatg ataatgcaga tttggatata acgtgactag   57600
cagttgatcc agtcctcata caggcagctc cagtctcaaa tacaggcagg ctcgagctcc   57660
tgttttgagt tgggtggagg gagcaagttg cgaagtgacc acctcctgat catttgagag   57720
tccgtttaca gtgtaatctt cacgatcttt tcttttgtgg tggtttgtga tcatacaagc   57780
agattacagt agtgtttttta attaacctca tacatttata tgattgaagt tttggtcccc   57840
agattgtatg gaaatgccta gtggcattaa ggatgcggta ggatgtccac ttttagtagc   57900
aaccgatgtt cattcactac tccatgtttag gtgcttact tggattatct cacttaaaaa   57960
ccacaacatt ttatctctgt tttacaaagg aagaaactag aggcttaaaa gatttcagtt   58020
```

```
atttgacaaa gatcacaagc tagtgggtgt gacatgggga gctgtgacag ttctggaaca   58080
taagtcttag gcccaggaaa taacagtaaa tgttattatt aagggagggg tggtggagca   58140
agtagatcag tcctttactg attcattgct tatctaagct acaaaagtac attctccttt   58200
gtttcttagc tcttggaggg gggaggtgtg agctactaaa ggggtggcat ccctaggaag   58260
tttgagtttt ggggattctt attcagcttc cagtgcaagc ctgtgggcaa ggaatgaagg   58320
cggaaggagc ggtgtggagg gaggcggtcc gtggcgcctc ctgctttgtt aatgtgcttc   58380
atttcactct tttgattgaa tgattgctgg aaagtgcaag gcattaagaa ttaaactaat   58440
gagaaccgag gcaggcagac tgactcagat tttaattttg attttttttt ttttttttt    58500
tagatgaatg tgaagaagta gaacatcagt gccaaaagac tattcagcaa ctggaaactg   58560
tcctgggaga gccactccag agctatttct aagactttct gtggtgtttc atactctact   58620
cagagttcac actcatattt catatttta tttttgggtg ttgggtgcca tgttactttt    58680
ggtgccttaa tacacctact tggattactt acaaatgttt tatcacttcg ttacaaaatc   58740
cccacctggc ttgtgctgcc acataagcct ctcctgccta tcgtatagag ctgcagaaag   58800
agtaaatgat acacggtatt tttatacaga ctgctgtgtt tgtttaaaca tttattattc   58860
tcttcctgat tgatggtaat aatattagac ttgttaattt tagcacccaa agctgacgcc   58920
tcatttgcac tgtaagcctt aactcttctg tacagcagta tcttatatac atggtatcca   58980
tgttgcagat ttcactcaaa gttgctctat ttcaagaaaa tgaagttatt tagcaatcaa   59040
cagaagtact tttgactgta aagcctactt ttcattttgg gtaggcgaac ttcagccttc   59100
gtttctttgt tgtgcccata aagagaagtg gttctggaat gctttttta acccaggagt    59160
gtgactgtca cctttatcct tgttctttt gggaacgggg agagatgaag gcaacacgct    59220
gcttctaaaa cagctcatac ctggctgctc acacagaggg cccagaaaca ctgggtggca   59280
cgaggaagct cctccaggat tcagaatgaa cccagttcca ttggtggtta actaagaact   59340
acttgtctaa gaaagtaagt atcagtagat ttttttcaat gctttgaagt gccctaatct   59400
ctagtactgg gtcatggtga agttggaaag tgagggttca aataaaatta gatctgcccc   59460
cttttttaaag gcatctaaga acatcccgta gaatgttcgc attgagttta aaagcctttg   59520
aagctaatat agaagtttaa tgcagaaatg tggcaagcaa aaggccaact tgcattttag   59580
agacagagct tgctagtata gaagtgcata tttctaagaa atgtctcagt aaaattcatt   59640
aataaatact aatagctttt taaattttt tcctccacgt aaaatgaaaa tgaacttaag    59700
acttacaagg aatgatgtga gtgggctatt ttttcctaa atgcctcaca gtctccaaca    59760
gctcagttaa gcactctgat ggtctttatg gagaaaaata actctgggg attctcgagt    59820
cttcttgcct tctacagctt tccctgtggc accctccacc cccaaccagt gtctttgagc   59880
ttggtgagac tctgcataca ttaatatgaa aagctggaaa agaattaagg gctagcratt   59940
tctacactga gtacttttaa aaaataaga ttgacaatgg tattcttttc aatatatgga    60000
tagaaataat atctaaaatc tgttctgaaa atattcctaa atcctggcag agttctgccc   60060
cagtctaatg tgataaaatg atcctcactg actgagcttt tttccctccc cactcccaaa   60120
cctttgaaat ttcctgtaac aagatctgac ctgtaaagat cccatataca tggaacttct   60180
gccaactccc ctcaaataat agaaaaatca cagaaatgga accatttaac ttgctgatac   60240
aggtttgatt ttaatcacgt aaagtggaag agtgctttga tctcagttgc taatgatgat   60300
ggactaatct ttgaagaac ggaggccttg attggtgatt tcatgggaac aaaacagatt    60360
tctgcattac ctctgcctgc tttgtgggtc ccttagttgg cgtacacttt ctgatagtgc   60420
```

```
ctgccttatg aatgcctgaa gtctaatcct gaccttactt tgttgcccat aaatatcttt    60480
caaattgaat gcatcttgcc tcttcctgaa actttctgta ggcgtctgtg tagactctga    60540
tttgccctaa gttcaaatac acagaaatca gctgccttgg gcttggcatc aagttaattt    60600
cagcaccatg tatttgtttt gctttggttt tttgccttaa tttctgtgct cagatgtcat    60660
gccaattact tggtaaagct tgcagctaat agagccacat gtttattacg ataaaatgat    60720
gtcagtcaac atcagtcctc agtgatggga tacggtagag cactggttat gacagtgatc    60780
actggggaag gagttgtgtc ttctgtaaat tagtgtcttc gggtgattta atagctgctt    60840
aactaatccc agaggacccc ttaggagttg atgtaatgcc tgtagaaaaa gcagtgcgca    60900
gcaatagagc acagaagagt cgaagctcaa gagaacaggg aacatactgg tttgtttcac    60960
caagtatata tcctagctcy tcacagtttt accaaaaaaa atctgtgctc aatacatgtt    61020
agctactgta ttatagtagg tactccataa atacttgttg aatggcattc ttgaagagtc    61080
agccaaagta ggagagaggg cagagtggct ttaactggct ataagtgttg ctgccccag     61140 tttccccatt cagtgctaga caccaccata cttcatggca aggactgaga cacccagca     61200 ggatctaatg gtgcacaagc tcattttaac aatataaaca atagaatgac agtgagatgc    61260
gtttcagcaa ggccagtatc acagaagcca ttctgtattt tggtttttgt agcagctgtg    61320
taggtaggct accagctcct tacttccagt aagtggatgt ctccattaat ttccagcgtg    61380
tcaatactgc tgagctcttt aaatctgtgt ttgtactcca ggctgtgtac gccatttact    61440
gcaaccttga attctctaac atcacagtaa attatcatct gaaggaaag gaaacatgcc     61500 attagtggtt ccccttagtt taaaattttg tgtttgttac atgctaacgg tgtcagagta    61560
aaccatttga ttatacatag aaaagttcca gcctgctgct gctgacttcc ttctgtgact    61620
tccaagaccc taatctaact aaagtgtccc tggtggtggc actgtctgcc tcatcccacc    61680
cagggaagtg actcggacat gtttggagcc tcacaccatc cccagggcct gcggccctcc    61740
tttcctcaac acagcccctc tccctcggcc gcatcctgcc ccttgctcct ggaaagccag    61800
agtgctgccc cctcctcgcc gatgctgggg actctcctaa agcaggaaaa ctcctaatat    61860
ggttgcttta gttcaccgag atgctgtttc cagctgtagc ctggaaccaa gggacttgga    61920
tcctgacttt tctgcctcaa actctaggac catgaacaaa ccagacaatt aatatgaaat    61980
ttcagcagct taaggcactt gctagggttt ttacagctgc ttggtgatcc tgatcctgat    62040
aagctcagca catcttggcc tcagtgtgtt tgtccaaagc cgtcaaagct gggtatcccg    62100
taagttggaa gtggtgcaca tactacaaat tcattcagat ccatcggcag tgttcgccct    62160
tcacagtcat ctatgcccaa aactcaaaca atgaaaaacc aaaaaaccta ctagccttt     62220 acatcacctt tacacctaca cttcatactt ctggtgccac gctgccagtg ccaggctggg    62280
tttccaccca ctctgagaag gccactggga ggccctgcac tgagctctcc ctgtgctcct    62340
cgcccccatg aaggcttcag aagaaagagg ggcagctcag ccttgctgct aacccggccc    62400
caccccgaga ggccagaaag aagcacaaaa cctgaatctg caaagcagca agttgagggt    62460
tttcattctt ttgattgata ggagcagtgg aaaggactgt caaggaaaat caggaagggg    62520
aggaaatttc agcccaagtc ctgcactctg ataacagagc tggccaagat gaagcttctg    62580
tggctacaga ggattgggga ataggtgta acctgagatt ctatccccac aagaatggtg     62640
ggaatcccag ttccaaccag gtagaaggga ccccagatat atttaacaaa atctcaagaa    62700
aacacaaaac acagcctg atgctatagc tcagaaggaa aaccaagttg gcagcagagg      62760
gagtcaatta gttacctgta ctgtatcaga gcaagtgcaa agccagtgaa ttacaagcaa    62820
```

```
gtggcaaaga aatgacatgc ttccgggtga gcagactact gcaaatgaaa agaaggcaca   62880
tcctttgcct agaagaaaac agaacaacag aatccctcac aaccatctga tgctgccgaa   62940
cagctgggag gaacacggat ttcatccaga ggaagagccc acagatgaaa ttacaacact   63000
gaatgagatt gttttaaaaa cactgtagat acaactaaag tgtatttgaa agagcaagaa   63060
gatttaaaat gaaagtaatg gcataatgga aagacctgag ataatctcaa tgcaagcata   63120
tttaaaaggc aagagatgga agccccggga aaggacctat cagtatagaa aatcgtcagc   63180
agtgatcaac acaaggataa ttactgctcc tgaattagaa aattaaatgg aaaagacgat   63240
tgttcaaaag catataacat tcatctattc attccttcag ccagccatcc ctttcactgt   63300
ctctgcaaaa aaacgcctgg aatgtggttc acctaatcct aatggtatgg tttgaattac   63360
gaagttggag gtattttcat cttagtattt ttcagcatta tttgaatgta tcattattat   63420
ccttttttat attaatatag cagatccaaa cttggggccc agataggtca aaaacaagtt   63480
acatcattgg tttcctgtca cccaccacaa ggctcaactt ccttctagag cactcatctc   63540
tgtttccctc cagtgaaccc caagtcaccc tttgcacctt gactcttgcc aagccaacaa   63600
ccctgtgctg cccttcccac ctctaaggac ttgttcaaat catgccctaa atctagaaaa   63660
gccaaccttc agccttccac atccttccca gctttctgaa ttcgaaacca atatccacaa   63720
cttccaggga accttccatg attagcccac atctgtctac actccacata ccagggcact   63780
gcattagact ggaacttagg gataaatacg aatgtcacat tgctatctat ttcgcctgat   63840
attcatgctt ttagtaacgg gttttgatga gtcctcaaga acccacatgg tccagacaat   63900
gtgtcagttt aaaatgctgt agaatgataa cctaaaccaa tgaccctaag tgactgtgtg   63960
aggcagtggc acctgagctg gtgattgagg ctggccaaac acccggcatc cacatcacaa   64020
ggagactatt ctctgctcag catcccagaa acatatttcg ggaaaggtat gtgttacaat   64080
attcacctat ctggggactc aggactgcat gccttttagt tccaagggac tgatgtattt   64140
ttccttgaat acatataaac aagactaact ccttaggaga aaggactgcc acctaccctg   64200
atgggagatg atggccagtg caagcaagca gttttagggt ctccagtcct caagtctgct   64260
tatatgatta aatgtgtgac tccagtcctg agacaagctt cctggttaaa ttcctatcaa   64320 tatgggcta cacaggaatt ttaatatgat gacaaatgtc aattccaatg tgcataattt   64380
gacactctac tggctttgcc atttatactg attgcccacg ttataaaaag gaaggggcaa   64440
attacaatct ccaagtaaac aaaaaacata cacaacctcc acatactgag ttaggacttg   64500
atttaaatgg accacttatc ccaccctgc tcccaggatt cttattgctg tcccattttc   64560
aaaaactgga acctcacctc aaagtacatc ccaggactaa atgggaaaga ggtaatattt   64620
ctctcttctt ctccccagga ctcctgaaga aaagaatttc ttacaaatgc tttaatattc   64680
aggcgtgggt tcaagtgtag agcaatatcc tttgattttc ctgctagtag gtcaacatta   64740
aagcttttga gaaagaaaga aaaaaaaaac cttaattaac caagtaggac agagtagtgg   64800
caatttcagc aatgttagtg accagacttg aactatgatt ctaactctat gaaacacacg   64860
tatccacatg gacatgggaa tgcaggtgaa gttgaaattt taaacccagt cagcattcca   64920
ctaattcgtt acttgcaaaa taaaaatacg aaaaaaaaaa cccctttaaa atcagcattg   64980
aggctgagat gtggttggac agaaatgaaa ggtttaacgc taaactgaat gactacttca   65040
ggctgcagga gcctgggatc ctctcaagca ggtattctct tttcatcatc tacccgtgtt   65100
ccttccttct tgaaagtatg ccactttcta ggaaatagct ctaatttcaa gctttcagaa   65160
ggctggacgt ctgtggaaaa agttgttaaa gcagaaattt tctaaatcac atgacaagag   65220
```

```
gggccctaaa aaatgttgcc tgggctgggc gtggcgactc acacctgtaa tcccagcact   65280
gggagggcga agtgggcgga tcacttgagg tcaggagttc cagaccagcc tggccaacat   65340
ggtgaacccc tgtctctact aaaaatacaa aaattcaaaa agtagctggg cgtggtggtg   65400
cgcctgtaat cccagctact ccagaggctg aggtaggaga atggcttgaa cacccaggaa   65460
gcggaggttg tggtgtgctg ggattgtgac actgcactcc agcctgggtg acacagtgag   65520
gctccatctc aaaaaaaaaa agaaaagatg ttgcctgatc ttacggggct gctctggagt   65580
tctacaaggc aaggataggc ctcgtggaca aaaatgctac tctcttgtct ggccagaaaa   65640
agccgaggtc agaacacggc cttagtcggc tctgctgccc actggctgtt cacaatctaa   65700
ccacctcctg cttgaatcat ctcactttgg aaatgaagat tctgacacta gccctacttc   65760
cagctcacag gaccgttcac gggtagaagg cggtaacagg cacggaagta tctgcactgt   65820
gactggtacc gaaggatact gaccttttgg catttgcatt cacttctcct ttaacgacga   65880
cagttcgtcc agggcccatg ggggtgttca accttgcagc gaatggcagg ctctgaaaag   65940
aagccacagt caggaccaag aggcctgcag aaagcgatct ccagggaaaa ctcgtgtcca   66000
aagaacacta cagaatgttt cagagccatg accctgtaaa tcccaggagg ggagagacag   66060
tctgccttgg tcccagctgg gtcccctgca gcagcactgt ccctggctcg aagcaaacac   66120
tcatgattac attttagacg atgaaatgag tgacagggtg ggacccgatg ccctctgtat   66180
gagtgaaaca cgccaggaag gccccctgtg cctggggtct gaggcagtac tgtgttctgc   66240
ctgaagggga agcagccaag cagggaggtg ctgaggaaat acacaggaat ggctcagagg   66300
caggcctggt tgactctcga atccatccag ggacggcaca caaatgcaga gggggctgct   66360
ttgggcttct attgtggata caggttactc gtaacagctc attacaactt aatttttata   66420
cagagttaag aaaatttggg gctcttcaaa cctttgacac atagttcata ggtggtattt   66480
tggtgcaagt cwaagtgtga ttgacagtcg aatmtttgct cttggtgtag acagttctgg   66540
gtgcgatttt agaaatgtct cctcctctat tactaggctg tagggaaaca gttctacagt   66600
aaggaatgga atgaatgaag ctgccctcca cggtttaaac tgttcatttt ctatgcaact   66660
ttataaaata ttccacatga aataacccag gcaaaaatac tcacaagctg gggcgtgcca   66720
gactttggaa cctattggaa aagaaacaaa acacaacaat gttagaaggg gaagaattat   66780
agtttataat ctgaagtctt ggttgtgctg agctgagcct ggccggagcc tgggatgttc   66840
ctgctccact ctggtgtgac ctccaggcag ctggtgcttt atgacggaat ggtatggtgt   66900
tgtgaagggc tacacgggtt gagaagagag tctgatatcc ctgttcatct gagtcctta   66960 tcctccacca taattaata attttcata gaactatatg aaatttttt aagagacagg   67020 gtcttactct gtcatccaca ctgggatgca gtggctcaat catggctcac tgcagcctca   67080
acctcctggg ctcaagtcat ccgcctactt cagccaccca aagctgggat cacagccatg   67140
cgccaccatg cccagataat ttttaattt tttgtagaga tgggttctc cctatgtggc   67200 ccaggctgat ctcaaactcc taggctcaag caatccccc acctcagcca aagcgctggg   67260 actacaggc tgagccacca ccttcaccca gcactacatg aacttcaaac gtgtcttagt   67320
tgtcctttcc agggtgcccc cagaatgcta agattctatt ctgtctgtga ggtgtgaacg   67380
tgccagtcgg taagacctca ctttctccat taataacagc gcattttaa attgcagtta   67440 ttctcccagg ggttgaagat acacatggaa gttcatttgc cagtgcactg gctgatgttc   67500
aatatttgga ataccccag aacagtacta ttcagcagtt aagagtgaga gagtgctttt   67560
tacataagaa cagtgagtgg cagttacaga aactgacagg tgaatcatca gcaaaaactt   67620
```

```
actgcgtgcc tggcaccaca agtatgtatc tcaattttca agtgattact tgcgttctaa    67680
aagcataatt ttcaaaaacc cagccttctt gccatttcat taacatggca gctaaaacaa    67740 cattttaaa  ccagtggctc attaaaagat ttaatattta cattttctct acttatctct    67800
gtcagttcca gactagatgc ttgggtactt tgtaagtcct gagaaaagat aataaagatt    67860
aatttgtaac atccagtaga aaatattttc tatatataac ctgtttgaca tataaaaaaa    67920
ttataaatgg tactaaaaat atgcttgaaa actatgatcc aaaaatatac ttgacactgg    67980
ggtcctttcc gccccccatc agattggcaa acattacaga gaataagatg taatgtcaac    68040
aagaaggtgg gagcatggct gttgagagtg caaactgttt ttacccttgt gaagggcgag    68100
ttagtatcta tcaaaatttt caatgcaaag acagtcatgt gttgcttaac aagggggta    68160 tgttctgaga aatgtgtcct tacatgactt ttgtcatcgt gcaaacatca cagaatatta    68220
cttaacaacc ttagatggta ctgccaacta cacacctagg ctgtagggtg tggcctatag    68280
ctcctggcca gtgaatctgt acagcaggca ctgtaccaaa tactgtaggc aaccagagca    68340
ggatggtaag tatttgtgca tataaactta cctaaacata gaaaaggtat ggtaaaaata    68400
cagtatatga caatcttatg ggaccacggt tgtatatgcg gttcatcttt gactgaactg    68460
tccttatgca acacatgact gtgctctttg actcagacac tcccagccta ggaacctgtc    68520
ttacagaaat actccatttt atgcccatgc aaaggaaata gctgctaccc agctaaaaac    68580
tgtgtgtgtt ttattaaaac cacactaggt ttgagatcct acagacaatg aagccctggc    68640
tgataaacag ccttctgcta gtgtgaacag ttcacttcca aaaaattaat actacagtca    68700
gggagatacg tccttttat  gtcaatagaa gtgttatttg aagattttt  ctaccatctc    68760 atcagaaacc atcctcataa aagaccccaa gctgtggaag gtcactcacc gagctgaagc    68820
taaaaccaat tgagtgaata ttcactttgc cataaatgcc cagagtgtct attttctctg    68880
ggccgatcct gtggccatag agcagagtat gttttccatt tacagccacc tagagagata    68940
cagaagacag agcccccccg ccaccaaaaa aaaacagtta ataaattaac ttattatcca    69000
aatttaaatg tttccttgcg tccaattta  tacctgttcc cacaggtctc cacacacgtg    69060
accaaatggt aaccgaaagc acccaaaaca ccagcagtgc ttccgaactt cttttgagtt    69120
cctgatttga ttaagcacca ggaactgtct ctccccagac aaacaggcag tcataagtat    69180
atgtgcgtgt gcttgtgtgc gcctctgcat acatgtgaga catctgggtt cgaaggtcgc    69240
ctggaagccc aggcacaggt gccctggaga ttgtgaaccc aggttaaaga tctgcctgcg    69300
agctccccac aacactgtcc ctggagacca cccatgtggc agacactcaa aatctgttgt    69360
atttgctaaa taaattaata tggacaagtt acccaacata tttgaattcg gttttcttat    69420
tctgaagtag gaacaatctc tacctcaaca gactacagta agatgacgag aaagtagctt    69480
ctgcaggtcc tcggcacgct acgagcctcc tccctccctc cctctcaaat gccaggtacc    69540
acgttaggtt ataggcagaa aacgcgagca gcatacaata tagtctctga ctcaaggagc    69600
tttaaatccc attgtggagg caaaataaac acataaagcc aaagcacaac tgttaaaaac    69660
tgtgaaaaag aatgatacag acacgggctc aaaaggccag agaagggaga ggtgaatgga    69720
gtttgggaga ttcagaaaga ctttcgggca ggagcagtat cccgaagatc agaaaggatc    69780
tgtgccagag gcatgtgagt cttctctcac gttggtacaa acctctactg tgggaaagct    69840
ccacaggcca gagggccagc aggtgtaaga gcttctggga ccaaattcaa ccatacacac    69900
gcgcgctagg tataagacac tccatgaagc cagagatgga actgacatca aggatttcta    69960
ggatgtcctc tgggtctaaa aatctcatga tcctacagaa ctgtcttgtg gcaagacttg    70020
```

```
aatttacaaa accccttctga tttctatgct gggattgccc ttgttagttc ttcaggtggt    70080
gacggttata ttataactta ccctcccatc atgaacataa tactgtgtca attcagaact    70140
cagccctgct aggagaaata ggatctaata aaaagatcta gtcacagtgg accatatttc    70200
tgcatggcaa caactggctg gagagtagtg gtgccacccc ctcatattta ggtgccttcc    70260
tggtcctttt atggagaaag actacaaagc caaactatat ctcaggtgta ggaaatacaa    70320
ggctgggctc acaaatgtga aaggcccccc tgtgcactcc tgctcactaa tgaggactca    70380
acctgtccct ctccaaaacc tacctggaat ttgtccttta gcaccataat cacgatctca    70440
aaagactttt ctcttttgaa aggcgtgtca taggtgatct cttcccgtcc ccattttca     70500 tttatcaaag tattgcaaac aatgcagccg gcccttttga acgaggatt  gaaatgaaag    70560 gccacatcgg ctcgaggttt cacactgctg ccattctgca gatccacctg gaatctatat    70620
gagggaagac acaggggcct catgagtgct cagaaaggaa agccaccagt aaaggcccag    70680
caggcactac actccaggcc cagtgacaag ggactgacca atccctcctc attcattcac    70740
tatgaggcct aaagagctga ctgtctaatc tttctgtct  tcctcagtaa aatagcccct    70800
gagtttgaac tgggtctgaa tctgcccaga ataaaaacct acctttccca gcctccctcg    70860
cagctaggcc tgcctgtgca gctaaagctc tgctgataag atggaagtga agtgctcagg    70920
gaaggctact agaaactgcc ttaaaagtca gcaagcactt gccttttgtc cagctctgtt    70980
tccccgcaaa caccacatgc acccatccag ctacccaaag cacagaagtg agggctggaa    71040
atctagctgc caaggataat gggaaagggg acctcacctc accctcaaga tagcagagtg    71100
gtaagctgga aggagtctac ttctctaacg acttgaagga gttaactgaa aaggcctggg    71160
ctgtctcctt gagacttaat tttcacatct taaaccactg ctcttcaggt gttaggtaca    71220
cagagctgag cccaacacta atgataccac agcttgtatc caaagcaagt attcagtaaa    71280
accatctgaa ctagatctgt gatgctgtgg gaatgtcaga ctaaaactag actctccctg    71340
tcatctgacc acaattcctt tctttaatga catacctaat tctttttctt tctttttttt    71400
tttttttttt tttttttttt tttgtcaccc aggctatagt gcagtggctc catcacagct    71460
cactgcaacc tcaaactcct gggctcaagg gatcctccta cctcagcccc ctgagtagct    71520
acaactacag gcgcacacca ccaagcccag ttaattttta attttttttt tttttttaac    71580
agatgggggg ggtctcacta tgttgcccag gctggtctcg aactcctggc ctcaaacaat    71640
cctcccgcct tggcctccca aagtgctgga aaagtatgtg taagtcacca catccagctg    71700
atagttctaa ttttttttata ctgaaatcag acttacagca atgaaataaa tcccaataac    71760
ctttatttag tcattcattc caatctcctc agcaccttgg ccagggctgc tgatgaaagc    71820
taattgggcc tcaragtatc aaatggtctc tcccgcctta ctctgttatc attccacaat    71880
cacaaaaaga cagcctattc atgctccttc ctttagcaca gtgatttac  ctgtctgcgt    71940 cactaggaac atgcccacat atcacaatca aagttccagg atccagctga tcrggaatgg    72000
tgccaacata cggattacc  taagaaaaaa aatttaacaa atgtacgttt acataaacaa    72060
aattacttac taagcaatta caacccacac tcattattga tagagaaaaa ctacactttt    72120
taaggctgca cataaatctc agaatccagc attttccaag tcatctttcc tattcaaaca    72180
gctataaaaa ggaactgcgg ccgggcgcgg tggctcacgc ctgtaatccc agcactttgg    72240
gaggccgagg caggaggatc acgaggtcag gagatcgaga ccatcctggc taacacggtg    72300
aaaccccgtc tctactaaaa atacaaaaat tagccgggtg tggtggcggg cgcctgtagt    72360
cccagctact cgggaggctg aggcaggaga atggcacgaa cccgggaggc ggagcttgca    72420
```

```
gtgagccgag atcgcgccac tatgctccag cctgggcgac agagcaaggc tccgtctcaa  72480
aaaaaaaaaa aaaacaaaaa aaaggaaccg cataccgcat ggccaggata tctgcaatag  72540
ctgcaaacca ctatgagttc tttggaaaga gacacaaggt aaatactatt catagtattt  72600
tgtatttggc tgagagtttg tgaagcaaaa cttctgctta atatgataat tctaacagaa  72660
aaaaaaaaaa agacttgttg caatgccatg tctactcatt ccttttccta ctgttccact  72720
gctgatccca acagaaggtt cgaggccaca ctaggcccaa agccaatgct gacgagacaa  72780
atgacaagca ctcactgcct ctgaaggaaa ctccacgtta agccacgccc ccacacctgg  72840
gattccaggg cctgctcttc tctgctggac tcccagactg caacccagac tgcactgtta  72900
gaaaccagag aactgcatga tcatgaggat gagtgggtgc ctgtgggtct tcaagacatg  72960
gcatccacct gccgtggacc agtccagtct gcaggcgtgg actctgacag ctggctccac  73020
ccagtattca ggtctcaacc tgcaccctca ctgcccagaa cccagcccct tttttctggg  73080
acctgccaca ctgccagatc ttgtcattcc ccttccccag agatgactac actgtcttcc  73140
cagtccactg gctggggacc tgtgctatgt ggctgcctct cctgcatcac aaccatctgc  73200
ctccatctgg agcatctgac caggatgtac agcccacaca ccgttaagcc tcacactaag  73260
ctcactcaaa ttacgatgtg catggtaaaa cctacccaag gtacttctga ttgtcaagaa  73320
ataagaaata aaataagacg ggccacagaa aagtggttat aaattggtgg ctcctaaacc  73380
gaaatcgcct tgaggcacag cctcctctgt ggagccttct tcaagctccc tgggctgctg  73440
agtcagcccc tctcagaggg ttcatgatag cactttggat tctgtttgtt tgcatgtagc  73500
tttgcctaga ctgtgagctg catggggcag aactggctcg tcacctttac ctccccagga  73560
cacaggtcaa gagacgatcg gtaactgcat ggtgaatgaa tgaactctca cctgtctgga  73620
aagtgggctc tggcaggcct cacacataca gaggagaggc aacaaagcag ctgctgaacc  73680
gcaagctgag cccacaagct ctctgttgcc ttaggcaata agatgagaaa ttacggaagc  73740
caattatcta tttgttgtca tggcaattgc taggagcagg gtgggaggca cgtgacacca  73800
gaaaacaaaa aatacaacag acagtgtaga ctggggctac agctgcacat cagagtatct  73860
gattttgtgt gtagagaatg gggaaggacc tacatcccta cattgatctt ttgggtcaca  73920
gctggttcca agaatatata gcagcaggtt tcatagcgtt aatctcttaa taaaatgaga  73980 agttttata acatcaaatt tcatcttaaa attatcttta tgcagaatat ttaataacac  74040
aaatgttagt aatataagag aaagtaatct atagagccat atatagtatg atctcaacta  74100
aataaatata aacattaaaa agaaaacctt gctaatacac actgtatcct gtatcaaaat  74160
atgccatata ccccataaat agatatacat actacatact caaaaaaatt aaaaattaaa  74220
aaaagaaaaa gagaaacact aaagaaatca gacaaaatg ataacaatag ttttcatggg  74280
ggatgatggc attttaattt ttttcttcat atattttcat actttgcaga tgtctataat  74340
aagcatcgat atttttatag ccagaaaaat attttaatt atatgtttca ttttagtgtt  74400
ggaaagagct ttttgagaca aaacaatcta ttcccatcac tttttttttt ttttttttt   74460 tttgagacag agactcactc tgtcccccag gctagagtgc agtggcgtga tctcagctca  74520
ctgcaacctc tgcctcccgg ttcaagcgat tctcctgcct cagccatcca gtagctggg   74580 actacaggca tgtgccacca tgcccagcta attttttgta gttttagaga tgggggttt   74640 tgccatgttg gccgggctgg tctggaactc ctgggctcaa agtgatcctc ccaaagtact  74700
ggggttgctt tgggaggtaa tgagctttgg gagaagctac cgcacccggc ccccatcact  74760 tctaataccct tgttcacaac tgtttatagg ttgttccagt ttgagaaaca actatgctaa  74820
```

```
gaacggtggc cacttgctgc tttagttttc tgggttcatc atgccttcta cttcagaaaa   74880
gatcctgcat tacttcagta atactttttt tttttttaa ctatgagaca cagtgccctg   74940
ccgctgactc atttaaccca cgactatgtg gcttctgtga aaacggagga catacattgt   75000
tttctaggct actccaagct actttggtga ttcacagatc attattaatt tacatttaaa   75060
aaattaaaat acagatctga tcacactgga gacaatacca caagcttacg ccacagtcag   75120
gtttgctgtt atttgccaaa acacccttgc tgattcatat tgctttgcct ttttgatgat   75180
taaatgcaag gctctctatt aggcagactg cagcttgaaa gaagcctaag agtcagacac   75240
ccaggaaaca taacagacac ccaggaaaca tggagtgaaa atgtgatact ctatttggct   75300
gctgaaaatt ggtatccctt tccatatctg aaaatcccct agcttatgaa cattagacct   75360
catctagact gcaacaaggt aagagcaggt gacaaaactg cccattagaa cttccagctc   75420
agcttttaag taagaaccag tgacaagaag aagccacaat gacgcagtat tcactctggc   75480
aaggggggcag ccgctatatc tgggtttgga gaaagctaca tctggggtca aaggcagcta   75540
catccggggt caggggcagc tatatcgagg gtcagaggga gctgcatcca gggtcagagg   75600
gagctgcatc caggggtcaga gggagctaca tctggggtca gagacagcag tggcattggt   75660
agagtagcag agacacagta ccatctgtgt ccagtggtga caacagatgc ctcttcatgg   75720
gaaccgtcct acagtatgct tgtgtatctg tggctaccta ttctccaagc ctggttcttc   75780
atcctgctag agattctgag aactctgcac tatcatttag caaattcctt ttctgcttaa   75840
agagttggct tctgttgctt gtaactacaa accctgacca attcaacatc tttaaaaaaa   75900
aaaaaaatgg gggtcaggcg cagtggctaa cacctgtaat cccagcattt tgggaggcga   75960
aggtgggcag atcacttgag gttgggagtt gaagaccagc ctgaccaacg tggagaaacc   76020
ccatctctac taaaaataca aaattagccg ggcatggtgg cacatgactg taatcccagc   76080
tactcaggag gctgaggcag gagaatcact tgaacccagg aggcggaggt tgcaatgagc   76140
cgagatcggg ccattgcact ccagcctggg caacaagcaa aattcagtct caaagaaaaa   76200
aaaaagggtg ggggagcagt aaagaagagt caaagaaatg cttcaggaaa atgggataag   76260
gaattctaac tgaggtagcc aaagacagtt tatgaagaag atatgatttc agttgccact   76320
tcaggtagaa atggcagttt acaaaagcag agaggcagga aaagacaaga cccatcttct   76380
ctcagcacgc agtcagggag tagttaaaga aaggtacagc cagggtcaga ttttagagtg   76440
acatacgaaa gaagtgttta ggaacaacag tccagtgggg gtgaaataag ccagaggtca   76500
ggaggtcatc tgggtgactg actgctgcca taagcctggc gtgaaacgat aaggacacat   76560
tccaggtcgg tggcaatggc cctggaagag cagagaagtc caagagatgt ttcaaaggaa   76620
actgtctaca taaggccact aaatacatga caaagctggg gagaaaacag gttttttgtt   76680
ttttgttttt tgttttcttt gagatggagt ttcacttttg ttgcccaggc tggagtgcaa   76740
tggcgtgatc tcggcttact gcaatctccg cctcccgggt tcaagcgatt ctcctgcctc   76800
agcctcctga atagctggga ttacaggtgc ctgccaccac gcctggctaa tttttttgta   76860
tttttcgtag agatggggtt ttaccaagtt ggccaggctg gtctcgaact cctgacctca   76920
ggtgatccac ccacctcggc ctcccaaagt actgggatta caagtgtgag ccaccgcgcc   76980
tggcctggga gacaggtttc aggaggaaga tgacgagttt agtttgtaat acttggtgtg   77040
aagcgttggc agagcatctg agagcaaatc tgctaagact tggagactca gaaccacacg   77100
ctaggtaat ggccagagca cacatttaaa agtcagggta aagatcattt gtaaagatat   77160
caaagtagat aaagaaatcg aaaagcagga caggtcaggc agcaaaggct cggtggtttc   77220
```

```
taaaattagg aggtatgcag aaaagaatta acattggcag gcctgactgc tgtcctggaa    77280
aggcctcctt acgaggcagg cccctggctg gtgtctggga acttgggatt tgagaagggc    77340
acccaccaac ctaactggta acggggattt cctgtacctg aactgttcat gcaaataata    77400
tggttatgct aaacacctgc tttccttctg ggggaccaga attttttgat atgtgtgagg    77460
gtgcttatgt gaccagcctc cagtaaaaac cctaggcact gaggctctga tgagcttccc    77520
tggcagtcca catttcacaa gtgttgtcac aactccttgc tggaggatgt aagcacatcc    77580
tatgtgactc cactgggagg cgaccttgga acttgcactg gatttcccct ggaattcacc    77640
ccaggtgcct ttccgtttgc aattttgctc tatatccttt caccgcaata aatcataggc    77700
acaagtacaa ctctatgctg gtgagtcatc aaaactgggt gtgaccttgg ggacctcaac    77760
atggggtgag aagagaaagg agagagaaga atcagtcagg ccagggcaat aatatcaagg    77820
gagtcaatgg atttataaat ttcagtaaga ggaaaactgt caatatcttt aacattgaag    77880
aagctaagaa ggatccaagc aaataaagat aataaaatgg ggccgggcgc ggtggctcac    77940
acctgtaatc ccagcacttt gggaggctga gatgggtgga tcacgaggtc aggagatcga    78000
gaccatcctg gctaacatgg tgaaaccccg tctctactaa aaatacaaaa aaattagcca    78060
ggcgtgggtg gcgggcgcct gtagtcccag ctactccgga ggctgaggca ggagaatggt    78120
gtgaacccgg gaggcggagc ttgcagtaag ccaagatcat gccactgcac tccagcctgg    78180
gcgacagagc aagactctgt ctcaaaaata aatgaataaa taaataaaat aaataagtaa    78240
agaaaatgga ccatcccctc tgacctagtg attccacttt tacagattta tcctacagaa    78300
atacgtagca caggcacacc aagatgcaca cacaaggatg tacactatag caccggatat    78360
aatcgcaaaa agacacagcc cttcacaagg gactgcttac ataagttta ctgctaatta     78420 tgcagctgtt aaaataaatg aggaagttct aaataaaatg acatttccaa aataggtcaa    78480
atagaaaaag cagggtagaa aacagtttat acggtaaaat gcatgcacgt aaagagacag    78540
gatatataaa aggtgatata cacaacacac acacttttgg atattcataa gtatctcagg    78600
aaggatatat ttctaaaaac cagtaaaaag tgattgccct tggggagtaa aactaagtac    78660
cagggtagaa ggaaaatgca tgtttcactg aaactcttaa atactgtttg aattttaaaa    78720
aaatgatttg cacatattat cttttaattt ttttaaaagg aaaagccact ggtttggaca    78780
taaatgtagt ttaaaatttt gaagacagac tatcttccaa ctattgggtg ctaggaaaca    78840
agggaggagg caaagttaa acagcagaag gatcctgctg cagaaaactg caagaggaaa     78900
gctggtttgg gaaggaagat gcaagtttgg ttttgaactc ctagtcttga agggctggct    78960
gagcaactga gagttggggg ttcacattag gtgaaaggtt ggaactggat acatatggaa    79020
aaaaaatttt atgagtgatc ggtaaagaca taaaagaaag agacattaaa gacaaaattt    79080
cactagtaaa accaaaaaag aaaagagagt gaaaaatcag agggcagagc cttagtgagg    79140
aaatccactc tcagtcagga aggcaggcag caaaaaaaga agaaaaacag cacaaaggct    79200
agaaggtacc tcacaggtta caaaagaaag acttgactgt gttgtgtttt aagactaaat    79260
tgtaaggtaa aaaaggagta cttagaatac taagcagaaa aggataaaca tggaagcaag    79320
gttcctaaga aaactgggta ccaggtagga tttatgttga caagcaactt attaacttgg    79380
agtaacaacc aattctgttt catttctaaa tgatttctta accagctagc atttaatcat    79440
atcttaagaa ctctataaac aatagcaaaa ttaaatatat aggtagataa tgaactgcca    79500
aacaagaaat ttcactggca gcattcctgg tatgaagtaa agatactgtc ttccaaatta    79560
ttcattcaaa ttcaatagaa agaaaagtaa gtggccagcc acggtggttc acgcctataa    79620
```

```
tcctagcact ttgggaggcc gaggcgggcg gattgcctga gctcaggagt tcgagaccag   79680
gctggccaac atggtgaaac cccgtctcta ctaaaataca aaagaacaat tagcggggcg   79740
tggcggtgtg cgcctgtagt cccagctact cgggaggctg aggcaggaga attgctagaa   79800
cccaggaggc aaaggtggca gtgagccgag attgcaccac tgcactccag catgggcaat   79860
agagcaagcc tccatctctt aaaaaaaaaa aaaaaagag aagaaaaag aaaaaaaaaa     79920 cagaaaagga agcctaactt ttttttttctt ttttttttttt tgagatgaag tatcactctg  79980
tcgcccagga tgcagtgcag ttgtgcaatc ttggctcatt acaacctcca cctcccgggt   80040
tcaagtgatt ctcctgcctc aacctcccat gtagctggga ttacaggcca ccgccaccat   80100
gcccggctaa ttttttgtatt tttagtagag acggggtttc actgtgttag tcaggctggt   80160
ctcgaactcc tgacctcaag tgatcctctc gcctcggctt cccaaagtgc tgggattaca   80220
ggcatgagcc gcagcacccg gactctgact ttttattttt attttttgaac atggttcttg   80280 ctctgtcacc cagaatgaag cacagtgtca aactcacagc tcactgcagc ctcaacctcc   80340
tgggctcaag caatcctccc acctcactct tcctcatagc tgggactaca gacatgcgcc   80400
acaatcccca gttaattttt gtattttttat agagagacaa ggtctcacta tgttgctcaa   80460
gctggtcttg aactcctggg ctcaagtgat ccactagcct tggcctccca cagtgctgga   80520
attacaggca tgagcctctg gacccagcct tagagcctga cttttttaag tcttggaatt   80580
ctatcagttg aactagtcaa agaaatatac taaatagggga aaaaaataca taggccagtt   80640
gcaatattta cttcatcttt tccaagaaaa cttaatgtgg acagttggtc taacaccaat   80700
gtggaccaaa atattagaaa taggccaggc atggtggctc atgcctgtaa tcccaacact   80760
ttgggaggcc gaggcgggag gagtgcttga ccagactgag aaacatggca aaactctgtc   80820
tttaccaaaa aaaatacaaa aattagccag gcatggtggt gcatgcctgt agtcccagct   80880
atttacaagg ctgagcccag gaggtggagg ttgcagtggg gtaagactgc accactccac   80940
tccagcctgg atgacagagc gagcctctgt cttaaaaaaa aaaaaaaaaa aaaaaaatt    81000 ggaaacatta atgaaataaa aattaaaaag tggcggtgtg tttataatgc ctaataaaga   81060
atacaacaga caataaatat atttacttat tgaacctatc agtaacaaaa caaccatgat   81120
tcaagaaaac aggttttgtg tgtgggggggg gttttttttt ttttgagatg gagtctcgct   81180
ctgtcaccca ggctggagtg cagtggcacc atctcggctc actgcaacct ccgcctccca   81240
ggttcaagtg attctcttgc ctcagcctcc cgagtagctg ggattacagg aggctgccat   81300
cacgcctggc taagttttgt attttttaagt agagacggag tttcgccatc ttggccaggc   81360
tggtcttgaa ctcctgacct cgtgatccac ctgcctcggc ctcccaaagt gctgggatta   81420
caggtgtgag ccaccatgcc cagctgaaaa cagtttttcct aagtctagct tataaaatat   81480
actaattgat tatctttaaa taactaagtt ggccaggcat ggtgcctcac gcctgtaatc   81540
ccagcacttt tggaggtcaa ggtgggcaca tcacctgagg tcaggagttt gagactaggc   81600
tggccaacac tgtgaaaccc catatctact aaaaacacaa aaattagccg ggcatggtag   81660
cacgtgcctg cagtcccagc tactcaggag gctgaggcac tagaattgct tgaacccggg   81720
aggcagaaat tgcagtaagc cgagattgca tcatttcact ccagcctggg tgaccagagg   81780
gaaactatat ctcaaaaaat ttaaaaaaaa aaattaattg aataaataaa ataagttatt   81840
tacagccttt tttttggaac attgaaaggg caactagcta caaatgagag aaattcagtg   81900
caatacaggc cctttatact ataaatattt tacagcagtg aaacgtaaag agagcgcaaa   81960 atgttttgc cattcagttc agtctacctc taaccttttcc gactcttttg tgagaactga   82020
```

```
taataaaaca gagaattttg aaaagaaaga aaaaaaagct atttgccaaa aatatctccc    82080
ttggaaatgc attatcctca gaacagcatc cagcccatgc cacaagactg aaggcatttt    82140
ctgctctagc gcagaactac ttctccagat ccccttcctc aagaaatgaa gtctacttat    82200
ttttgttcca cctcaatagt tgagagtact gaccccagaa actacaggaa tcagcagtat    82260
gctagaatca agatatgcac gaattttacc tataaaatta tcttcttttc tgtgtgaagg    82320
gcagaaatga acagtgtaac ctttatccat tctcccagct tgagccaaga tgatacttca    82380
gacacccgtg gcaggcagcc tagtttgttg ttgttgttgt tgttgttaag atctttgcag    82440
gaaatcagtt tacaaccttg ggatgttttt aactctaaca tgcgcaaagt catcttaaat    82500
gtctcacaag cttccgcttc aggaagtcat cttttttaaa cttactacca ctgaaaggct    82560
atttctccta aaactgactt tgcttgatac agcagcgata cctcattctt acacaatgac    82620
attaaaactt agggaaaaag gaaatacagc tataaagtaa atgacaaaaa cttgaaccca    82680
cacacactaa caaaactggt ttagggcctc attttaagga ttctcaccct tccttttgcc    82740
caagaatctt ctaggcggtt tactaaaaaa gtggctgtcc ttttttcagac ctcgattcag    82800 gattcagctt cagatacgtg gaaactagac attcctaaag attctcacca ccacataaaa    82860
ctaaaacaag ctctttactg ctcaggatta cagggcaatt ccagcaatt acagtcattc     82920 agggattcta ggacctgcct gaactgcacg agacccttac tacttcacac tctccatctc    82980
cccattggct tttgacattt tccctgctca agggccaagc agtatttgaa aggctgaggg    83040
aaagatcgag acattaactt ctcatggaca gctctaatta aaaagaaaa tgaaaaactt     83100 gtagagtaag aaatccattt tcctttaaaa actacaattt atgattagct gagcctcctc    83160
ccatcaccaa aagttggcat tccctccact ctacccagac gttccctgtt cataacactg    83220
tttcatcacg tcatattatc attgtgactt cttcctccac tagaggacaa gagctgtttc    83280
gtaatcagca cccaccacca tctctattac atagtaggtg ctttaaatat gttcactggc    83340
ttttattctt gccctgtctc ccaatggata attaatattc tattggatct gtcctggcat    83400
aggtaaaaag ttatcttata gaatcagtt accgggttat agatgatatt ctgtaggttg     83460
tttaaggaca acatcattct tttccagctt cttgtcgatt ggagtctctt ctgtgtatga    83520
cctaagattt taggcaagtt tcatttaaag gttacctgga ttgaaactga ggcactggcc    83580
ctgtgtaaag taaaaataga ggaaagaaa agtaagcatg tagcattttt cttcatatcc     83640
tattttaaaa tttaaattat atattatgtt actgatattt accaaataat agaatattat    83700
tacaatcaac gatctgcctc ccattcttac cagtgtgctc atatactaaa taattttgga    83760
ttgtgagtgt aggaaatatt gacttaaaaa atacatcagt agaaaatttc taacatggaa    83820
tttattatta aaaatactaa aataggccag gcatggtggc tcacacctgt aatcccagca    83880
ctttgggagg ccaaggcggg tggatcacct gaggttcagg agttggagac cagcctgacc    83940
aatatggtga aatcccatcc ctactaaaaa tacaaaaatt agccagacgt agtggcatgc    84000
acctgtagtc ccagctactc aggaggctga gacaggacaa ttgcttgaac ctgggagacg    84060
gaggttgaag tgagccgaga ttgtgccact gcactccagc ctgggcaaca gaacgagact    84120
ccatctcaaa aaaaaaaaaa atttaattaa ttaatggtaa atactaatca aacagtcccg    84180
tacaattatc agaggtattc atttaaattt tcatttccat aaaatgagaa ttacagtatt    84240
cacatcattg gtttgttctg aggattgagt taataaaaca gcgaaagagt aagcgctatg    84300
ttagctatta ttattgtgaa tagaaagaat tgctcttcct cctccaattt aaacaaatca    84360
aagtagggaa aaatccaata cttttaatac tattaagata cagttttctc tgttgcttaa    84420
```

```
aaaaataata atcacagggc aggggagtgt tggaaagcat cagccacatt ttttaagata    84480
aaagcactca tggacactac actacattta atagctccag gaaaaactcg actttaagca    84540
gaactaaagg ggaaatgaaa ccagagcttc ctgtatttta cttccagcaa ttctgtcatt    84600
atactgcaca ccaacaatac acaccgatca aatctatcac tttttcttta ttaagaaaaa    84660
aaactgtatc cctcttggtt taccacctaa atatagcccc atgtcattaa cttaattcgt    84720
tagtcaaaac ctcaaaactc tggctccgtg actcaattca ggaagtaaga acaagagcaa    84780
aaagaatgga tgccgagttg ccatacacat gtataataac aagccagtga cccaatttaa    84840
gccatctgct tgcattaaat cacgcaaccc ccgaagtatc cccagggaca ggtcccgcca    84900
gcatgaacac ttcgtatgca tcacaagcag ccatcactta agtttcacgt acggtcaaag    84960
gaagtcacat gacttgcgct ttgcaatgtt taacactgca gtcaaatgac tcggcatcct    85020
aaagagcgtg ttagaggcag ggaacgcaat ggaggtcact ccactgtcac tacaaattcc    85080
gggaaggaaa cttccccaga ttcctccact tggaggtggc gctcggcctc aggctaggag    85140
ggaacaggtg agaaagcagc ccaggtgggg tgggttttgca gcgaggagac accccagggc    85200
aaacagcctg accccagcca gggatgtcca agaaaggccg cgactcctga taatccctta    85260
tgccccggag cgcctcgcct gcagaggcag cgtccccgcc acccagcccc ggctctgccg    85320
cggtgaggac cggcgggtcg gggtggactg gacactgtcc cacccatcaa atggtgattt    85380
aggagccgtg acatccgaat gccatcctcc actggcgaga ccctcagagc agccacgcct    85440
ctagcgactg ccccgccacc cgaggccggg ggtcgcgcga ctcacccaaa gactggtgtt    85500
tcaggcgctc cacggagcag gttgtttgtc agcagctaag tgccgtcagg gttcccggct    85560
ctggcgtccg tgggcggcta cgggaagcga caggagtcag tcctcgttca cttcccggct    85620
cgcgcgcctc actgctgtgg tctccccacc ctccccgcgc ccgccttct gtgtctgggg    85680 cgtccctggc ggctctgctg grttttggac agggacccgc cgctgatcgc cacccagctc    85740
ggcctcctgc acagcctctg gagccttgga ccgcgactgg cttgctgtgg gacgagcaca    85800
gagggataag gacaaagaat gtgtcctggg tggatctggc tgcctttgcc cggaaggcgg    85860 agtgggtgg gaggtggtag gaaaatggga aggaaagaaa agaaaggtgg gccgacgtcc    85920
acctggctgt tccaggcctc caggtctagg agggagggcg ctcggggctg gacttttca    85980 ggaccagggt ggtcaccgca caggccccgc ctgcctggac caagcgctgg ccttcccggg    86040
gcgcccaggt ccacggggtc aacgccaggg ttttctcagc ttcctcgtct gcctcggatc    86100
caagtccaga cagtgccaga agagacttgg aggcgctgct ttttgacagt acacacctct    86160
gtatgcaggt gaaacggtgg gggaagggtt cagtacgctg gactgtgccc agcccaagct    86220
ccccatccgt tagtgataac ttggactcgc agccactccg cgtcactcgc cggttatcct    86280
gcgtgtgggt gttttctcca aattggacac ttagggaaca gtttaagcag tatggagcac    86340
aattctgtgc ctattagatg ctcttaaata cccgacttct cagggcccta cactgactga    86400
tagtttgacc tattggctgt aaacacacca gccagaaata caaataaagt taaacaaagt    86460
catgtcagcc acttggaatg gctggctgct tactgtttat tttstgttag ggacctcaaa    86520
gttctcatct tctctacttg gcttttatcc acatttgttt ggaaagatat attttagtgt    86580
cattaacgtg ggcttttctcc tccctggctt ttgttttcat tattttttgt tttaattgag    86640
gaattcatta caagtcccat aactgggaac tcatgttctg attcactgtt gcttttctct    86700
cctccttacc cattttccaa gcctgatgca cttctcaaga tccaatctga ataggtgaat    86760
ttacccttga catacactgc cttggattta tagctgtctt ttggtatgtg ttgtgtgttt    86820
```

```
tatctatcca actcgactgt agtttgagaa aaggaacttg tcttatacag tctccagtgc   86880
atagtgtaat gctttgcata aaatagatat caatgttagg ttgaaatgtt agattattga   86940
taaagtcagg agcaattgaa tatcttcaca attctgcctg agtctccccc cagccccgcc   87000
actttgagac agggtttccc tcaagtgatc ctcccacctc agcccagga gtagctggga    87060 ctatagacgc acaccactat gcccagctaa tttaaaaatt ttttttttgta gagacagggt   87120 ccactgtgtt gcccrggctg gtctcaaact cctgggctca caatatcttc ctgccttggc   87180
ctcccacaat gctgaaatta caggcatgag acaccaagct gggccctgag tcaaccttgt   87240 acttcttttac aaagctaaag taagttgaaa taagtacaca taaatgctgt gtttcttttg   87300
taagtcatat ttaggtgcaa acggggctga gtgaaagggc cagagagcag agttaacaaa   87360
gaaaatctgg attaaaatgt tcataaatcc taagaactta ttcctagaaa tatctccctc   87420
atttggcact gttgttcaat tagcccagtg tgttatttta aataagcaaa tattcactga   87480
atgcctatca tggccaggca cagcagtaaa gaatactagc atgcaaagga cctcatgggc   87540
ccttctagat agagtcccac atctcttaca ttattactgc agtatcctaa tcggtctccc   87600
tatatttgcc cttgccccctc tgcaatgtag tctcaacaca acagcagag aagtcatgac   87660 aaaacataat tcagatcatg ttaatccctt actaaaacct actttttttt ttttttgag    87720 gcagtctcac tctgttgccc aggttggagt ggagtacagt gttacattct cagctcactg   87780
cagcctctgc ctaccgtgtt caagtgattc atgtgcctca gcctcctgag tagctgggac   87840
tacaggtgcg cgccaccatg cccagctaag ttttgtattt ttagtagaga tgaggtttca   87900
ccatgttgcc caggctagtc ttgaactcct gacctcaagt gatccgcccg cctcggcctc   87960
ctgtaacctg ggattgcagg tgtgagccac tgcatccggc caaccgtcta ctaattttg    88020 ctcattcttt gagtaaagat ccagttctta cacgagcact tcctgatctg cccgaatcct   88080
cacacactgt gatttcatct cctactactt tccttctcac ttttttctgca gcagccacag   88140 cgactttgct attctcctag caggcctgtc acactcccat cctaaaatct ttactcaata   88200
tttccttttc cctttcaag tctactcaaa tgtcagttct cagtggggcc cttcctgacc    88260
accaatattt aaaattgcaa acactctccc aaaacacact catacacact ccctagcaac   88320
tcttccttgc tttatttctg gctaacattt gtcatgctaa tatactatat aaggtgcctt   88380 tttatttttat gttacttcac ccatcataag actataaact ccatgagggc aaggagtttt  88440
gattgttctt gtttcgagga agcttatact ctagttgagg acacatacag tgatgtgttt   88500
tagagaagat taaattggga gcacctgagt ggcaacctta gttgggtgac aaggaaagtc   88560
tctcagagga gtcaaagttt aagctgctgg tgagtgaaag aaaggaaaca gccatatgaa   88620
gatggtgggg aagagcattc cagccttagc gagcagctgc tgcaaagtcc ctgagggtct   88680
tgagaatgca ttaaatgtgt tcaggaaaca aaggccacca accagtatgg ctgaagcatg   88740
agggaagaat gatatgacat catgagattg gatggcacca cctaggagag tagtgggaga   88800
aaatcacctc ggacagccct ggggagataa gacaacgcca ataaatgaga ctgagaaggg   88860
acaaccaggg gaatttgctg agagtggtgt cacagatgcc aaagaaagag aaacagcctg   88920
tgtgccaagt gtgctgagag gccaaggagg acggaagtaa gcaatgggct taggaacatg   88980
gatgtcattg ctgactctga ctctgaagtg tgttgagaaa tggaggtga agaactggtg    89040 gaaaccatga ctataaagat ttcagaaagg tttgctgtga ggaggaatgg agaagcagca   89100
ttatagctga ggaaggagtg gagcaaaggg cagattcagg ttttctcctg ttgttttttt   89160 tttttttaa agagaagata ctacattggt gacttttaga cttcttttt ttcaagtgac     89220
```

```
ctgccataag aattacattt ccattgagac ttactacaca catacttaaa attacgaaaa    89280
caaaaatttt gaccaggcac gttggctcac tcctgtaatc ccagcacttt gggaagccga    89340
ggcaggtgga tcacttgagg tcaggagttt gagaccagcc tggccaatat ggtgaaaccc    89400
tgtttctact aaaaatacaa taattagctg ggccttgtgg cgcatgcctg taatttcagc    89460
tactcgggag gctgaggcat gagaatcgct tgaacccaga aggccgaggt tgcagtgagc    89520
tgagattgta ccactgtact ccagcctggg caacagagtg aaactgtgtc taaaaaaaaa    89580 aaaaaaaaa aaaattgta caaaacaata ctcctgttat gtgtaaaaca atctactttt     89640
tcattttaaa aaaatgctgc ttatagtcca ctaaaatgtt tgcaagcccc actaatgggc    89700
tgtgagctga agtttgaaga acactgggta gtatgttggt gttagctcat actggcttgt    89760
gacagccatt tttgtacata acttccatgt tgatacccttg aagttatcca gggcaactgc   89820
tagaacttag gacttttttc ccccaaagaa caagatctta aacatttacc agcacgctac    89880
tgactttact catgtgaatg atccgtggag aggagaaact gatcatgcag gagagggat    89940 ggtgttccca ataaaagttg cgaaaaccag tttcagaaca atagatattg ccaattattt    90000
gccacaactg cctgagagtt atgcagataa aaggatcact tctggtagga tcaatttctt    90060
tttcatctat attgtcctct ttccttgccc aagaagccac atttatatgg tataatatag    90120
ccacacattt agaaatagtc ttttttttt tttgagacag agtctcactc tattacccag     90180
gctggagtgt tgtggtacaa taatggctca ctgcagcagt gacctcctgg gctcaagtga    90240
tcctcccacc tcagcctccc aagtagctgg gactacaagt gcacaccacc atgcctgact    90300
aatttttttt tttttggta gtgatggggt cccactgtgt tgcccaggct ggtcttgaac     90360
tcctgggttc aagcagtcct cctgcctcaa cctcctgaag tgctaggatt acaggcatga    90420
gccaccatac ccaggcaaaa ttaagtctta caagcaaaat gttaaattat atatatagag    90480
cccacatttt ttaaaaaact agtaaaaaaa tcatgatttt agacatgaat tgtaagctct    90540
tgctacttag cagggttaac tgattaaaca gaaatagatg ccatattcta tcgatgtgaa    90600
ccgtattgtt tcaagctaag gaatactctg gcagtgattt tgcttattgt tttgttgctg    90660
tgttactttt gttaacataa ttgtaaaatt tttggacccc ctctccaacc atccatgaaa    90720
tagcggtgct aagtgctggg aaaatgtgct ccaactcaat aattttggaa tacaagttag    90780
atatgataaa agagtatcaa gaactttaaa gaactgcctt ggtatgctgt gaatttagaa    90840
accagaactc cgtcacagaa cctgtgacaa taatgataaa aaaaaatatg tgaaagcaaa    90900
aatttgccac aatggattat acatttgtga gcgccgagaa cacatacccct gctattctca   90960 tgagaaaatt aatcaaaata tgtaggtttt aaattatgca acatcttcag gaatgcattc    91020
tttacaaaac cacaatactc acatccttat acatacatct gcttccccag gaagtgtcat    91080
ggacggtgtc ttytacctct tccgattatc ttccccaatc taarggaatt catttctcct    91140
ttgaatcctc ttgctttgac ctaatctccc ctacacccca atactagccc catccatgag    91200
caccaaacyc ttttttttca ccctccagac cccctatgat ctgattcacc aggcttacct    91260
cygaagttct acaggatcat gtcccaaatc cagtcttttc aggtgggaga acaagcttc     91320 tagaactatg gttttgtcat aaaataaaag aatcttagtg acgagaggga tcttaggagg    91380
agtataaatt aattcatctc aatagctcaa aggatgagat agcctatttt gtgaaataca    91440
ttttttgaat ggcttacaga ctatgatgtt agtactaaaa aatgctgaat tatttgatat    91500
gaggaaaatg tatctgaaat tatgtaaaat gtaaagacaa aatgatacta aaaatgtata    91560
aatagtatac atgggccggg cgcggtggct tatgcctgta atcccagcac tttgggaggc    91620
```

```
cgaggcagat ggatcacgag gtcaggagtt cgagaccagc ctggacaaca tagtgaaacc    91680
ctgtctctac taaaaataca aaaattagcc aggagcggtg gcaggcgcct gtagtcccag    91740
ctactttgga ggctgagaca ggagaatcgc ttgaacctgg gaggcggaga ttgcagtgag    91800
ctgagactgc gccactgccc tccagcctag gtgacagagc aagctctgta aaaaaaaaaa    91860
aaaaaaaaaa aaaaaaaaaa acagtaaaaa aagtgcatat gtatatgctg tatatatcca    91920
gtaacagtca gacagtaatt tacatacaca tatttagcaa agtgcaaaag aatgatgttt    91980
aatgtagtgt tcattgttat cttttctctt gcaaaattac tgagattcat taaaaggctt    92040
ccctcagcaa ggcagtctca atatttaacc aacccttcca gcgcatagct gatctcttcc    92100
agcttgtgtt tacacagttc attgtaaagc aacaagtaaa acctcaggaa tttctatggc    92160
acgttagagc aagcaaaaaa attgaggtga ttttttttaaa ttaaaaaaaa gctgttgaat    92220
ccaaccaagt actcttccaa aaatatttta tctgggagta ttttaaaaca tacacaagag    92280
gacctcctct ttcggctttg gagcccccctc cctctgtctc tgtacggggg agcgtcttcc    92340
ttcagccttc tctttctttt cttgcctatt agactctctg ctccttaaaa ccaaaaccaa    92400
aaacaaacaa aaaacacac aaaagtagag agatggtgtg ataaataccct gtgctttcat    92460 cgcccagctc cagcaattat cgacgtggcc aatcttgttt cacctacacc tcacccactt    92520
cctccccacc actggttcat tttgaagcaa atctcagact tcatttaatc tgtaaaagct    92580
tcaaaactaa ttgttagatt taaaggtttta ataaggtccg gctgggctta attttttggc    92640
cagaagactt tacaggtgat atgtagctcc aattgcaact catcaggaga cagaaaatat    92700
ctggttgttt ttcttttat gacatcaaaa ccagttagtg gtttcagatg ttgttagcct    92760
gatccatctg ttacgaagtt cccatcagtg tttgatcaga tgattttagc atctagctat    92820
tgatggtcat tgcctagata cgttatttca ttaggaattg aaaatggtga tatttcaatt    92880
ctatcatttc tcctgcattt attagtaaga attcttttttc tcctttctct ttcttttttct    92940 ttcttttttc tttctttctt tccttctttc tttctttttc tctttctttc tcttttcttt    93000
ctctttcttc ctttcttcct ttcttttcctt tctctctctc tctctctttc tttgacaggg    93060
tctcactctg tcacccaggc tggagtgcag tggtgcgatc ttggctcact gcaacctgtg    93120
cctcccaggc tcaagcgatc ctcccacctc agcctctcga gtagctggga ctacaggtgc    93180
atgccaccat gcccggctaa ttttttgtatt tttgttagag atggggtttt gtcatgttac    93240
ccacgctggt cctgaactcc agagctcaag ccatctgcct tcctcagcct cccagggtgc    93300
tgggattaca ggcctgagcc attgcgcctg acctaagaat tatttttatta ggaaatagtg    93360 cttgataaat aatgcttctt tttgtatatt tgccacagtg tatctttaga tagattccta    93420
gaagctgcat ttttttgtgtc aaaggttaaa tgccatgtaa ttttgctaga tatgagtcca    93480
agcacttctt gagaattcat ttaaattctg tctctgctct accatagggg aaggtccggg    93540
ctgttctgat gggaaagagg tattggaggt gaggcccaag aggctgtagt gggaaacctc    93600
gcacctgaaa tgacaggaga atccaaattc agggagcgtg tgggatcagg agccacatga    93660
aaaaccaaag gccaggagcc aggaaggaaa tctgggaat ttcaaatagg gccaagagca    93720
gatatggaag cttccatcca ggaacataaa tgtgggaaaa atgaatacaa aaacaggctt    93780
ggaacaaatt ggggagggtc caaggtcatt acccccaaaca gcagctgctc ttttacaact    93840
atttttcttg gctggctgga acataagaca aaggcacagg gctgtttgca catgtttctg    93900
tcacgccgag ggcagctaac tgaaggagga tgtggtagct gaaacctagt ctgtacttta    93960
gccactgccc ctccacccccc aaaaggatag gagtgaaggg atgaagacca ccttttttcta    94020
```

```
atttgcacaa agatgcattt ggcctaacaa aatgggcaag aattatccca aatctccttc    94080
cacttttgca gttatattca tatctttctt cataatttag ctataccatg cacttttaa     94140 actcgatctg tagtaggaag gtgaggctaa atgttatggt cctttgcatt ttgatccgta    94200
agcaaacagt tgttgtttat tttagaaaaa tggtttccag gtgtaactgc caactgctga    94260
aaacttaggg ttatgtgagg tgaggcatgt tgatgcttta gtttatttgg agatggggga    94320
agcaggaaaa acagcaaacc attgcagtat ctggaattga tatggatctt tgtgtttaag    94380
acagggaact gaagcctggc tgtaccatac atactttaaa catttatgct tatgtaactg    94440
ctaatcgaat tttgaaaaac tatataactt ttcacacttt ttacaaggat gtttaggttt    94500
aatgagttga aaagatatac attctagaat attgtaaata tgacattttt aataaaaatt    94560
gttacaccac tcttttaaat gtattaaatg gggccggatg cagtggctca cacctgtaat    94620
cccagcactg tgggaggctg aggcagggag attgcttgag gccaggagtt tgaaaccagc    94680
ctggacaaca tagtgagatc ccacctctac agaaaatttt aaaattaatg tattaaatga    94740
aatattagca ccaaagtgat ttgatattca ccatcatcca atggaaaaaa agaaaaacac    94800
tgccaagctt ttctttaaaa gaaaccccca aggacaacca gcagaaggat tttacatctt    94860
cattttacat tgctcctttc tctcttgaaa atgtatttcc atcccattcc cgcaaataat    94920
tttatctagt gtaatatatt tttaacgctt aaaagccttt cgttgatcat tcattatgtc    94980
tctgcaacaa aaatattaat ataaattaat aattctgtgg tcttcaattc ctacagtctt    95040
aaggctctaa atgttcaaga ttcttttcaat ttagttattt ttacaagtct tttttattgtt   95100 accatgatcc atacacaatc aaaataaata aattttatca ttttgtaaat cattgttaaa    95160
caaaatttta ttggaaagta tcattttaat gagagagggt atttcagagc ctttgttaaa    95220
gaaggctctg caggcatcag cttgaatttc ctttacttgg gaaggtgggt tttttatatg    95280
tctcagggca ctgcataata ttaaaataaa ggatgggccg gtgcagtggc tcacacctgt    95340
aatcccagca atttgggaag tcgaggtgga aaagcgcttg agcccaggag ttcgagacca    95400
gcctgggcaa tacagtgaga ccaccatctc tacgaaaaat aaaataacta actgggtgtg    95460
gtgacacacg cctctagtcc cagccattca ggaagctgag gtggaagaat cacttgagcc    95520
gggaggtgca gtgagctgtc atcagccacc gaacttcagc ctgggcgaca gagtgagatg    95580
ctgtctcaaa aaatatgtat atactatata tatatacaca cacacatgca aacacatata    95640
tatacacaca cacatcttat atatatacat cacatatacg tatttgcgta catatacaca    95700
tatatagaca cacccatata tacatatata gacacacata tatgatgtat atatgtacac    95760
acacacgtgt atatatacac atatacacac atatacacat acacacatgt atatacacac    95820
tatatatgtt tacatagcat atatgtatat atcatatatg catacatata tatgatgtgt    95880
gtgcatgcat atgtagggta tgtatatata gaatatgtat ggggatatat atatatgatg    95940
gggggtgaaa gattttggta aagcaggaga agggcaatta tgaaatgaga aatagaaaaa    96000
gagccagctt aatgccttaa ttgcagggac tttctgtctc agaccaatgt tcagaaaaga    96060
gtacaaatgg aggttgatgg tccccacctg aagaccccag gcagggtcct cacctacccc    96120
tagggttgtg catacccaa ctggaagacc actggcccat gtaatattag gtgagatcct     96180
ttatctagaa atgagagta ataaaaccca ccttgcagag ttgtgaggac taaacaagag     96240
aatctctgtc cacagcttgc ttgtattatg ctgtgtaaac acagggtaaa tggacattgc    96300
tgtctgagtt gggcatttat tgttattgct attcttattg gtggtaaaca tgttatgaat    96360
aattaagata agggatgagg aatatttgtt gcaagttctc aatgtacctt tattctaacg    96420
```

-continued

```
gtagagttgt aattgtctgt tttcttgtct gtctctattc ccggacttgt tggctccttg   96480
ggttgggatt gtcagagttg tcattgtatt cccagaagtt aacagagggc ctgactacag   96540
gaagtgctca gtaaatgttt gttgactgaa ttaatgtgat ttctcctatt agtgtctatt   96600
taacattaaa acgagaaaca gcagtcatct aaaagaggta gaagccacta ggccaaacct   96660
atcccttcag aaaaatattc ccctttttgac tgatctggtt cttttcagag acccatacta   96720
agagaaagaa ccaattcttg ccacttattt ctctttgtca aaggaaaatg ggtttcataa   96780 ttgttttttgt ttgcactact gccaacatgg gccattgcaa agctcaggtt gagtgtttac   96840
atagacgtaa ggtatacttt agccttggga gcactataaa gacatgttgt tgtcttgata   96900 aaagaaaga aagggccagg tacggtggct catgcctgta atcccagcac ttcgggaggc   96960
ctaggcaggt ggagaatgag gtcaggagat caagaccatc ctggccaaca tggtaaaacc   97020
ccgtctctag aaaaataaaa aaattagctg gcgtggtggc acacacctgt agtctcagct   97080
actcaggagg ctgaggcagg agaattgctt gaacccggag gcggaggttg cagtgagcca   97140
agatcgcacc actgcattcc agcctggcga tagtgcaaga ctccatcaaa aaaaagaag   97200 aaagggagga aaaagaaag aaagagagac agagagagaa agaaaagaaa gaaaagaaaa   97260
gaaaaggctg ggcatggtgg ctcatgcctg tagtcccaga tactcagaag gctgaggcag   97320
gaggattact tgagccgggg aggtagaggc tgcagtgaac tatgatgacg tcactgcact   97380
tcggcctgga cgacagcaag accctatctc aaaaaaaaaa aaaagaaaga aagaaaatta   97440
acaagcaaag gaagaattct tttttaaaag tttgagagtt aatactctaa tgcgtaacta   97500
tgcttatctt aagtttagtt agtcaaattt tatcgaatcg aaactgaagc tgttaggttt   97560
ctgcatgtgt aaaacctggc tcctaaagaa ctccagattt ccttccagtt ctaaaattaa   97620
gtttatgcat caatttacgt ttatgcatag cacatgcatg cc                      97662
```

```
<210> SEQ ID NO 2
<211> LENGTH: 6782
<212> TYPE: DNA
<213> ORGANISM: Homo sapiens
<220> FEATURE:
<221> NAME/KEY: 5'UTR
<222> LOCATION: 1..112
<220> FEATURE:
<221> NAME/KEY: CDS
<222> LOCATION: 113..6547
<220> FEATURE:
<221> NAME/KEY: 3'UTR
<222> LOCATION: 6548..6782
<220> FEATURE:
<221> NAME/KEY: allele
<222> LOCATION: 178
<223> OTHER INFORMATION: 5-382-162  : polymorphic base C or T
<220> FEATURE:
<221> NAME/KEY: allele
<222> LOCATION: 2677
<223> OTHER INFORMATION: 5-383-184  : polymorphic base G or T
<220> FEATURE:
<221> NAME/KEY: allele
<222> LOCATION: 5193
<223> OTHER INFORMATION: 5-370-197  : polymorphic base A or G
<220> FEATURE:
<221> NAME/KEY: allele
<222> LOCATION: 5243
<223> OTHER INFORMATION: 5-370-247  : polymorphic base C or T
<220> FEATURE:
<221> NAME/KEY: allele
<222> LOCATION: 5673
<223> OTHER INFORMATION: 5-373-164  : polymorphic base C or T
<220> FEATURE:
<221> NAME/KEY: allele
<222> LOCATION: 5731
<223> OTHER INFORMATION: 5-373-222  : polymorphic base A or G
```

```
<220> FEATURE:
<221> NAME/KEY: allele
<222> LOCATION: 6011
<223> OTHER INFORMATION: 5-375-200  : polymorphic base A or G
<220> FEATURE:
<221> NAME/KEY: allele
<222> LOCATION: 6162
<223> OTHER INFORMATION: 5-376-266  : polymorphic base A or G
<220> FEATURE:
<221> NAME/KEY: allele
<222> LOCATION: 6271
<223> OTHER INFORMATION: 5-377-227  : polymorphic base A or G

<400> SEQUENCE: 2
ggttgggctc cttggtacca tgtgggaagc gctgtgaaga gttgttgcct tccaagatat      60
acccaaattc ccagttccag cccgtgtcat taaaactccg ctggcgtgaa ag atg acg     118
                                                         Met Thr
                                                           1 tcc tta gcc cag cag ctg caa cga ctc gcc ctc cct caa agt gat gcc       166
Ser Leu Ala Gln Gln Leu Gln Arg Leu Ala Leu Pro Gln Ser Asp Ala
          5                  10                  15 agc ctc tta tcy aga gat gaa gtt gct tct ttg tta ttt gac cct aag       214
Ser Leu Leu Ser Arg Asp Glu Val Ala Ser Leu Leu Phe Asp Pro Lys
 20                  25                  30 gaa gcg gcc aca atc gac agg gac acc gcc ttc gcc att gga tgt act       262
Glu Ala Ala Thr Ile Asp Arg Asp Thr Ala Phe Ala Ile Gly Cys Thr
35                  40                  45                  50 ggc ctg gaa gag ttg ctt gga att gat cct tcc ttt gag cag ttt gaa       310
Gly Leu Glu Glu Leu Leu Gly Ile Asp Pro Ser Phe Glu Gln Phe Glu
                55                  60                  65 gca ccg ttg ttc agt cag cta gca aaa acc ttg gag cga agt gtt cag       358
Ala Pro Leu Phe Ser Gln Leu Ala Lys Thr Leu Glu Arg Ser Val Gln
         70                  75                  80 acc aaa gca gta aac aaa cag ttg gat gaa aac att tca tta ttc ctt       406
Thr Lys Ala Val Asn Lys Gln Leu Asp Glu Asn Ile Ser Leu Phe Leu
     85                  90                  95 att cac ttg tcg cct tac ttc ctg ctt aag cca gca cag aag tgt ctg       454
Ile His Leu Ser Pro Tyr Phe Leu Leu Lys Pro Ala Gln Lys Cys Leu
100                 105                 110 gag tgg ttg att cac agg ttc cat ata cat ctc tat aat caa gat agc       502
Glu Trp Leu Ile His Arg Phe His Ile His Leu Tyr Asn Gln Asp Ser
115                 120                 125                 130 ctc att gct tgt gtt ctg cca tac cac gag aca aga ata ttt gtg cga       550
Leu Ile Ala Cys Val Leu Pro Tyr His Glu Thr Arg Ile Phe Val Arg
                135                 140                 145 gtc ata cag ctt cta aaa att aat aat tca aag cac aga tgg ttc tgg       598
Val Ile Gln Leu Leu Lys Ile Asn Asn Ser Lys His Arg Trp Phe Trp
         150                 155                 160 ttg ttg cca gtt aag caa tct gga gtg ccg tta gct aaa gga act ttg       646
Leu Leu Pro Val Lys Gln Ser Gly Val Pro Leu Ala Lys Gly Thr Leu
     165                 170                 175 att acc cac tgc tac aaa gat ctt gga ttc atg gat ttc att tgc agt       694
Ile Thr His Cys Tyr Lys Asp Leu Gly Phe Met Asp Phe Ile Cys Ser
180                 185                 190 ttg gtg aca aaa tct gtg aag gtt ttt gct gag tac ccg ggc agc tca       742
Leu Val Thr Lys Ser Val Lys Val Phe Ala Glu Tyr Pro Gly Ser Ser
195                 200                 205                 210 gct cag ttg agg gtg ctc ttg gct ttc tat gct tct acc ata gtg tcg       790
Ala Gln Leu Arg Val Leu Leu Ala Phe Tyr Ala Ser Thr Ile Val Ser
                215                 220                 225 gcg ctg gta gct gca gag gac gta tca gac aat atc atc gcc aaa cta       838
Ala Leu Val Ala Ala Glu Asp Val Ser Asp Asn Ile Ile Ala Lys Leu
         230                 235                 240
```

```
ttt ccc tat atc caa aag gga ttg aaa tca tct tta cca gat tac aga    886
Phe Pro Tyr Ile Gln Lys Gly Leu Lys Ser Ser Leu Pro Asp Tyr Arg
        245                 250                 255 gct gca aca tac atg ata ata tgt cag att tct gtg aaa gtg acc atg    934
Ala Ala Thr Tyr Met Ile Ile Cys Gln Ile Ser Val Lys Val Thr Met
260                 265                 270 gaa aat acc ttt gtg aat tca ttg gca tca cag atc atc aaa aca ttg    982
Glu Asn Thr Phe Val Asn Ser Leu Ala Ser Gln Ile Ile Lys Thr Leu
275                 280                 285                 290 acc aag att ccc tct ttg atc aag gat ggg tta agt tgc ttg ata gtg   1030
Thr Lys Ile Pro Ser Leu Ile Lys Asp Gly Leu Ser Cys Leu Ile Val
                295                 300                 305 ctc ctg cag aga cag aag cca gag agc ctt ggg aaa aag cca ttc cct   1078
Leu Leu Gln Arg Gln Lys Pro Glu Ser Leu Gly Lys Lys Pro Phe Pro
            310                 315                 320 cac tta tgt aat gtt cct gat ctt att aca ata ctt cat ggg att tct   1126
His Leu Cys Asn Val Pro Asp Leu Ile Thr Ile Leu His Gly Ile Ser
        325                 330                 335 gaa act tac gat gtc agt cct ctt ctg cgt tac atg ctt ccc cat ctg   1174
Glu Thr Tyr Asp Val Ser Pro Leu Leu Arg Tyr Met Leu Pro His Leu
340                 345                 350 gtc gtc tcc atc att cat cat gtt aca gga gaa gaa act gaa gga atg   1222
Val Val Ser Ile Ile His His Val Thr Gly Glu Glu Thr Glu Gly Met
355                 360                 365                 370 gat ggt caa atc tac aag aga cac tta gaa gct ata ctt aca aaa ata   1270
Asp Gly Gln Ile Tyr Lys Arg His Leu Glu Ala Ile Leu Thr Lys Ile
                375                 380                 385 tca ctg aag aac aac tta gac cat ttg ttg gct agc ctt cta ttt gaa   1318
Ser Leu Lys Asn Asn Leu Asp His Leu Leu Ala Ser Leu Leu Phe Glu
            390                 395                 400 gag tat att tca tat agt tca cag gaa gaa atg gat tct aat aaa gtg   1366
Glu Tyr Ile Ser Tyr Ser Ser Gln Glu Glu Met Asp Ser Asn Lys Val
        405                 410                 415 tct ttg ctt aat gaa caa ttt ctt cca ctc att aga ctt tta gaa agc   1414
Ser Leu Leu Asn Glu Gln Phe Leu Pro Leu Ile Arg Leu Leu Glu Ser
420                 425                 430 aaa tac ccc aga aca tta gat gtt gta tta gag gaa cac tta aag gaa   1462
Lys Tyr Pro Arg Thr Leu Asp Val Val Leu Glu Glu His Leu Lys Glu
435                 440                 445                 450 att gca gat ctg aaa aaa caa gag ctt ttc cat cag ttt gtt tct ctt   1510
Ile Ala Asp Leu Lys Lys Gln Glu Leu Phe His Gln Phe Val Ser Leu
                455                 460                 465 tct aca agt gga gga aag tat cag ttt tta gca gat tct gat act tct   1558
Ser Thr Ser Gly Gly Lys Tyr Gln Phe Leu Ala Asp Ser Asp Thr Ser
            470                 475                 480 ttg atg ctc agc ctg aat cat cca ctt gct cct gtg aga att ctg gcc   1606
Leu Met Leu Ser Leu Asn His Pro Leu Ala Pro Val Arg Ile Leu Ala
        485                 490                 495 atg aat cat ttg aaa aag atc atg aaa aca tca aag gag ggt gtt gat   1654
Met Asn His Leu Lys Lys Ile Met Lys Thr Ser Lys Glu Gly Val Asp
500                 505                 510 gaa tct ttc ata aaa gaa gct gtt tta gcc cga tta ggt gat gat aat   1702
Glu Ser Phe Ile Lys Glu Ala Val Leu Ala Arg Leu Gly Asp Asp Asn
515                 520                 525                 530 ata gat gtt gtt ttg tcg gct ata agt gct ttt gag att ttc aaa gaa   1750
Ile Asp Val Val Leu Ser Ala Ile Ser Ala Phe Glu Ile Phe Lys Glu
                535                 540                 545 cac ttc agt tca gaa gtg acg att tca aat ctt ctg aat ctc ttt caa   1798
His Phe Ser Ser Glu Val Thr Ile Ser Asn Leu Leu Asn Leu Phe Gln
            550                 555                 560
```

| | | |
|---|---|---|
| aga gca gaa ctt tca aag aat gga gaa tgg tac gag gta ctt aag ata<br>Arg Ala Glu Leu Ser Lys Asn Gly Glu Trp Tyr Glu Val Leu Lys Ile<br>565 570 575 | | 1846 |
| gcc gct gac ata tta att aaa gaa gag ata ctg agt gaa aat gat cag<br>Ala Ala Asp Ile Leu Ile Lys Glu Glu Ile Leu Ser Glu Asn Asp Gln<br>580 585 590 | | 1894 |
| ttg tca aat cag gtg gtt gta tgt ttg ctg cca ttt gtg gtt atc aat<br>Leu Ser Asn Gln Val Val Val Cys Leu Leu Pro Phe Val Val Ile Asn<br>595 600 605 610 | | 1942 |
| aat gat gat acg gaa tct gct gag atg aaa att gct ata tat tta tca<br>Asn Asp Asp Thr Glu Ser Ala Glu Met Lys Ile Ala Ile Tyr Leu Ser<br>615 620 625 | | 1990 |
| aaa tca gga atc tgc tcc ctg cac cct cta tta aga ggc tgg gaa gaa<br>Lys Ser Gly Ile Cys Ser Leu His Pro Leu Leu Arg Gly Trp Glu Glu<br>630 635 640 | | 2038 |
| gct ctt gaa aat gta att aaa agc aca aag cca gga aaa cta atc ggt<br>Ala Leu Glu Asn Val Ile Lys Ser Thr Lys Pro Gly Lys Leu Ile Gly<br>645 650 655 | | 2086 |
| gta gca aat cag aag atg att gag ttg ttg gct gat aat ata aat tta<br>Val Ala Asn Gln Lys Met Ile Glu Leu Leu Ala Asp Asn Ile Asn Leu<br>660 665 670 | | 2134 |
| gga gat cct tct tca atg tta aag atg gtg gag gat ttg ata agc gtg<br>Gly Asp Pro Ser Ser Met Leu Lys Met Val Glu Asp Leu Ile Ser Val<br>675 680 685 690 | | 2182 |
| ggt gag gag gag tcc ttt aac ctg aag cag aaa gta acg ttt cat gtg<br>Gly Glu Glu Glu Ser Phe Asn Leu Lys Gln Lys Val Thr Phe His Val<br>695 700 705 | | 2230 |
| atc ctg tct gtg ctc gtc tct tgt tgt tca tct tta aaa gaa acc cac<br>Ile Leu Ser Val Leu Val Ser Cys Cys Ser Ser Leu Lys Glu Thr His<br>710 715 720 | | 2278 |
| ttt cca ttt gcg ata aga gtc ttc agt ttg ttg cag aaa aaa ata aag<br>Phe Pro Phe Ala Ile Arg Val Phe Ser Leu Leu Gln Lys Lys Ile Lys<br>725 730 735 | | 2326 |
| aag ctt gaa agt gtc att act gca gtg gaa atc ccc tca gaa tgg cac<br>Lys Leu Glu Ser Val Ile Thr Ala Val Glu Ile Pro Ser Glu Trp His<br>740 745 750 | | 2374 |
| att gaa ctg atg tta gac aga ggg atc cca gta gag ctg tgg gca cat<br>Ile Glu Leu Met Leu Asp Arg Gly Ile Pro Val Glu Leu Trp Ala His<br>755 760 765 770 | | 2422 |
| tat gta gaa gag ctc aac agc act cag agg gtg gcc gtg gag gac tcg<br>Tyr Val Glu Glu Leu Asn Ser Thr Gln Arg Val Ala Val Glu Asp Ser<br>775 780 785 | | 2470 |
| gtt ttt ctt gta ttt tcc ttg aaa aaa ttt att tat gca ctg aaa gct<br>Val Phe Leu Val Phe Ser Leu Lys Lys Phe Ile Tyr Ala Leu Lys Ala<br>790 795 800 | | 2518 |
| cct aaa tct ttt cct aaa ggt gat ata tgg tgg aat cct gaa caa ctg<br>Pro Lys Ser Phe Pro Lys Gly Asp Ile Trp Trp Asn Pro Glu Gln Leu<br>805 810 815 | | 2566 |
| aaa gaa gac agc agg gac tat ctg cac ttg ctc att ggg ctg ttt gag<br>Lys Glu Asp Ser Arg Asp Tyr Leu His Leu Leu Ile Gly Leu Phe Glu<br>820 825 830 | | 2614 |
| atg atg ctc aat ggt gcc gat gct gtt cat ttc aga gtt ctg atg aaa<br>Met Met Leu Asn Gly Ala Asp Ala Val His Phe Arg Val Leu Met Lys<br>835 840 845 850 | | 2662 |
| ctt ttc ata aag gtk cat cta gaa gat gtt ttt cag tta ttc aag ttc<br>Leu Phe Ile Lys Val His Leu Glu Asp Val Phe Gln Leu Phe Lys Phe<br>855 860 865 | | 2710 |
| tgt tct gtt tta tgg acc tat ggt tct agc ctt tca aat cca cta aac<br>Cys Ser Val Leu Trp Thr Tyr Gly Ser Ser Leu Ser Asn Pro Leu Asn<br>870 875 880 | | 2758 |

| | |
|---|---|
| tgc agt gtg aaa aca gtg ctg cag act caa gct ctt tat gtg ggc tgt<br>Cys Ser Val Lys Thr Val Leu Gln Thr Gln Ala Leu Tyr Val Gly Cys<br>              885                  890                   895 | 2806 |
| gca atg ctt tct tct cag aag aca cag tgt aaa cac caa ctg gca tcc<br>Ala Met Leu Ser Ser Gln Lys Thr Gln Cys Lys His Gln Leu Ala Ser<br>900                  905                   910 | 2854 |
| ata tct tct cca gtg gtg aca tct tta ctc att aac ctg gga agc ccc<br>Ile Ser Ser Pro Val Val Thr Ser Leu Leu Ile Asn Leu Gly Ser Pro<br>915                  920                  925                  930 | 2902 |
| gta aaa gaa gtt cgt agg gct gcc att cag tgt ctc cag gcc ctc agt<br>Val Lys Glu Val Arg Arg Ala Ala Ile Gln Cys Leu Gln Ala Leu Ser<br>              935                  940                  945 | 2950 |
| gga gtg gca tcc ccg ttt tat ctg ata ata gat cat ttg att tct aaa<br>Gly Val Ala Ser Pro Phe Tyr Leu Ile Ile Asp His Leu Ile Ser Lys<br>                  950                  955                  960 | 2998 |
| gca gag gag atc act tca gat gct gcc tat gtt att cag gat ttg gct<br>Ala Glu Glu Ile Thr Ser Asp Ala Ala Tyr Val Ile Gln Asp Leu Ala<br>965                  970                   975 | 3046 |
| act tta ttt gag gaa cta cag aga gaa aag aaa ctg aaa tct cat cag<br>Thr Leu Phe Glu Glu Leu Gln Arg Glu Lys Lys Leu Lys Ser His Gln<br>            980                  985                  990 | 3094 |
| aag ttg tct gaa act ttg aaa aac tta ctt agt tgt gtg tat agt tgc<br>Lys Leu Ser Glu Thr Leu Lys Asn Leu Leu Ser Cys Val Tyr Ser Cys<br>995                  1000               1005              1010 | 3142 |
| cca tct tat ata gca aaa gat ttg atg aaa gta ctt cag gga gtc aac<br>Pro Ser Tyr Ile Ala Lys Asp Leu Met Lys Val Leu Gln Gly Val Asn<br>                1015               1020               1025 | 3190 |
| ggt gag atg gtg ctt tct cag cta ttg cct atg gct gaa caa ctg cta<br>Gly Glu Met Val Leu Ser Gln Leu Leu Pro Met Ala Glu Gln Leu Leu<br>                 1030               1035               1040 | 3238 |
| gaa aag atc cag aag gag ccc aca gct gtg ctg aaa gat gag gcc atg<br>Glu Lys Ile Gln Lys Glu Pro Thr Ala Val Leu Lys Asp Glu Ala Met<br>              1045               1050               1055 | 3286 |
| gtt ctg cat ctc act ctg gga aag tat aat gaa ttt tca gtt tcc ctt<br>Val Leu His Leu Thr Leu Gly Lys Tyr Asn Glu Phe Ser Val Ser Leu<br>1060                 1065               1070 | 3334 |
| tta aat gag gat ccg aag agt cta gat ata ttt ata aaa gct gtg cac<br>Leu Asn Glu Asp Pro Lys Ser Leu Asp Ile Phe Ile Lys Ala Val His<br>1075                 1080               1085               1090 | 3382 |
| aca aca aag gaa ctt tac gcg gga atg cca acc att cag atc aca gcc<br>Thr Thr Lys Glu Leu Tyr Ala Gly Met Pro Thr Ile Gln Ile Thr Ala<br>                 1095               1100               1105 | 3430 |
| ctt gaa aag att aca aaa cca ttt ttt gca gcc ata tca gat gaa aaa<br>Leu Glu Lys Ile Thr Lys Pro Phe Phe Ala Ala Ile Ser Asp Glu Lys<br>              1110               1115               1120 | 3478 |
| gtt cag cag aag ctt tta aga atg ttg ttt gat tta ttg gtg aac tgt<br>Val Gln Gln Lys Leu Leu Arg Met Leu Phe Asp Leu Leu Val Asn Cys<br>             1125               1130               1135 | 3526 |
| aaa aac tca cat tgt gct cag act gtc agc agt gtt ttt aaa ggg att<br>Lys Asn Ser His Cys Ala Gln Thr Val Ser Ser Val Phe Lys Gly Ile<br>1140                 1145               1150 | 3574 |
| tcc gtt aat gct gaa caa gtc cga ata gaa ctg gag cca cca gat aaa<br>Ser Val Asn Ala Glu Gln Val Arg Ile Glu Leu Glu Pro Pro Asp Lys<br>1155                 1160               1165               1170 | 3622 |
| gct aaa ccc ttg ggc aca gtt cag caa aaa aga agg caa aaa atg cag<br>Ala Lys Pro Leu Gly Thr Val Gln Gln Lys Arg Arg Gln Lys Met Gln<br>                 1175               1180               1185 | 3670 |
| cag aaa aaa tca caa gat cta gaa tct gtt cag gaa gtt gga ggt tct<br>Gln Lys Lys Ser Gln Asp Leu Glu Ser Val Gln Glu Val Gly Gly Ser<br>              1190               1195               1200 | 3718 |

```
                                               -continued tac tgg caa aga gta act ctc atc ctg gaa tta ctg cag cac aaa aag      3766
Tyr Trp Gln Arg Val Thr Leu Ile Leu Glu Leu Leu Gln His Lys Lys
        1205                1210                1215 aag ctc aga agt cct cag ata ttg gtg cca act ctt ttt aac ttg cta      3814
Lys Leu Arg Ser Pro Gln Ile Leu Val Pro Thr Leu Phe Asn Leu Leu
    1220                1225                1230 tca aga tgt tta gaa ccc ttg cca caa gag cag gga aat atg gaa tac      3862
Ser Arg Cys Leu Glu Pro Leu Pro Gln Glu Gln Gly Asn Met Glu Tyr
1235                1240                1245                1250 acc aaa caa tta att ctt agt tgt ctg ctc aac atc tgc caa aaa cta      3910
Thr Lys Gln Leu Ile Leu Ser Cys Leu Leu Asn Ile Cys Gln Lys Leu
                1255                1260                1265 tct cca gat ggt ggc aaa ata ccc aaa gat att tta gat gag gag aag      3958
Ser Pro Asp Gly Gly Lys Ile Pro Lys Asp Ile Leu Asp Glu Glu Lys
            1270                1275                1280 ttc aac gtg gag ttg ata gtt cag tgc atc cgc ctt tcg gag atg ccg      4006
Phe Asn Val Glu Leu Ile Val Gln Cys Ile Arg Leu Ser Glu Met Pro
        1285                1290                1295 cag acc cat cac cat gcc ctt tta ctt ttg ggc act gtt gct gga ata      4054
Gln Thr His His His Ala Leu Leu Leu Leu Gly Thr Val Ala Gly Ile
    1300                1305                1310 ttt ccg gat aaa gtt tta cac aat atc atg tct att ttt aca ttt atg      4102
Phe Pro Asp Lys Val Leu His Asn Ile Met Ser Ile Phe Thr Phe Met
1315                1320                1325                1330 gga gcc aat gtc atg cgc cta gat gat act tac agt ttt caa gtt att      4150
Gly Ala Asn Val Met Arg Leu Asp Asp Thr Tyr Ser Phe Gln Val Ile
                1335                1340                1345 aac aag aca gtg aaa atg gtt att ccc gca ctt att cag tct gat agt      4198
Asn Lys Thr Val Lys Met Val Ile Pro Ala Leu Ile Gln Ser Asp Ser
            1350                1355                1360 gga gat tct ata gaa gtt tca aga aac gtt gaa gag att gtg gta aaa      4246
Gly Asp Ser Ile Glu Val Ser Arg Asn Val Glu Glu Ile Val Val Lys
        1365                1370                1375 atc att agt gta ttt gtg gat gcg ctg cca cac gtc ccg gag cac agg      4294
Ile Ile Ser Val Phe Val Asp Ala Leu Pro His Val Pro Glu His Arg
    1380                1385                1390 cgc ctg ccc atc ctt gtt caa ctt gtt gat aca ctg ggt gca gag aaa      4342
Arg Leu Pro Ile Leu Val Gln Leu Val Asp Thr Leu Gly Ala Glu Lys
1395                1400                1405                1410 ttc ctc tgg att ctc ctc atc ttg ctt ttt gaa cag tat gtc aca aaa      4390
Phe Leu Trp Ile Leu Leu Ile Leu Leu Phe Glu Gln Tyr Val Thr Lys
                1415                1420                1425 aca gtg ctg gcg gct gcc tat ggc gaa aag gat gct att tta gaa gca      4438
Thr Val Leu Ala Ala Ala Tyr Gly Glu Lys Asp Ala Ile Leu Glu Ala
            1430                1435                1440 gac act gaa ttt tgg ttt tca gtc tgt tgt gag ttt agt gtc cag cat      4486
Asp Thr Glu Phe Trp Phe Ser Val Cys Cys Glu Phe Ser Val Gln His
        1445                1450                1455 cag ata caa agc ttg atg aat atc ctc cag tac tta cta aag ctg cca      4534
Gln Ile Gln Ser Leu Met Asn Ile Leu Gln Tyr Leu Leu Lys Leu Pro
    1460                1465                1470 gag gaa aaa gaa gaa acc att ccc aaa gca gtg tca ttt aat aag agt      4582
Glu Glu Lys Glu Glu Thr Ile Pro Lys Ala Val Ser Phe Asn Lys Ser
1475                1480                1485                1490 gaa tca caa gaa gaa atg cta cag gtt ttt aat gta gag act cac act      4630
Glu Ser Gln Glu Glu Met Leu Gln Val Phe Asn Val Glu Thr His Thr
                1495                1500                1505 agc aag caa ctg cgg cat ttt aaa ttt ttg tca gtg tcc ttc atg tct      4678
Ser Lys Gln Leu Arg His Phe Lys Phe Leu Ser Val Ser Phe Met Ser
            1510                1515                1520
```

```
cag ctc ctg tct tcc aat aat ttt ctg aaa aag gta gtt gag agt ggt      4726
Gln Leu Leu Ser Ser Asn Asn Phe Leu Lys Lys Val Val Glu Ser Gly
        1525                1530                1535 ggt cct gag att tta aaa ggc ctt gaa gag agg ttg ctg gag acc gtt      4774
Gly Pro Glu Ile Leu Lys Gly Leu Glu Glu Arg Leu Leu Glu Thr Val
    1540                1545                1550 ctc ggc tat atc agt gca gtt gca cag tcc atg gaa agg aac gca gac      4822
Leu Gly Tyr Ile Ser Ala Val Ala Gln Ser Met Glu Arg Asn Ala Asp
1555                1560                1565                1570 aaa ctc acc gtg aag ttc tgg cgc gcg ctc ctt agt aaa gct tac gac      4870
Lys Leu Thr Val Lys Phe Trp Arg Ala Leu Leu Ser Lys Ala Tyr Asp
                1575                1580                1585 ctg tta gat aag gtc aat gcc ttg ctg ccc aca gag aca ttc att cct      4918
Leu Leu Asp Lys Val Asn Ala Leu Leu Pro Thr Glu Thr Phe Ile Pro
            1590                1595                1600 gtg atc aga ggg ctg gtg ggc aat ccc ctg cca tct gtt cgc cgc aaa      4966
Val Ile Arg Gly Leu Val Gly Asn Pro Leu Pro Ser Val Arg Arg Lys
        1605                1610                1615 gcg ctg gac ctt ttg aat aac aag ctg cag caa aat ata tcc tgg aag      5014
Ala Leu Asp Leu Leu Asn Asn Lys Leu Gln Gln Asn Ile Ser Trp Lys
    1620                1625                1630 aag aca ata gtt acc cgt ttc cta aaa ctg gtt cca gac ctt ttg gcc      5062
Lys Thr Ile Val Thr Arg Phe Leu Lys Leu Val Pro Asp Leu Leu Ala
1635                1640                1645                1650 att gtg cag cgt aag aaa aag gaa ggg gaa gaa gaa caa gca atc aac      5110
Ile Val Gln Arg Lys Lys Lys Glu Gly Glu Glu Glu Gln Ala Ile Asn
                1655                1660                1665 aga cag aca gcg ttg tat acc tta aag ctt tta tgc aag aat ttt ggt      5158
Arg Gln Thr Ala Leu Tyr Thr Leu Lys Leu Leu Cys Lys Asn Phe Gly
            1670                1675                1680 gca gaa aat cca gat cct ttt gtc cca gtg ctg arc act gct gtg aaa      5206
Ala Glu Asn Pro Asp Pro Phe Val Pro Val Leu Xaa Thr Ala Val Lys
        1685                1690                1695 ctg att gct cca gag aga aag gag gag aag aat gtc ytg gga agc gcg      5254
Leu Ile Ala Pro Glu Arg Lys Glu Glu Lys Asn Val Leu Gly Ser Ala
    1700                1705                1710 ctg ctg tgc ata gca gag gtg acc tcc acc ctg gag gcg ctg gcc atc      5302
Leu Leu Cys Ile Ala Glu Val Thr Ser Thr Leu Glu Ala Leu Ala Ile
1715                1720                1725                1730 ccc cag ctt ccc agc ctg atg cca tcg ttg ctg aca aca atg aag aac      5350
Pro Gln Leu Pro Ser Leu Met Pro Ser Leu Leu Thr Thr Met Lys Asn
                1735                1740                1745 acc agc gag ctg gtc tcc agc gag gtc tac ctg ctc agt gcc ttg gct      5398
Thr Ser Glu Leu Val Ser Ser Glu Val Tyr Leu Leu Ser Ala Leu Ala
            1750                1755                1760 gct ctg cag aag gtt gtg gag act ctc ccg cac ttc atc agc ccc tat      5446
Ala Leu Gln Lys Val Val Glu Thr Leu Pro His Phe Ile Ser Pro Tyr
        1765                1770                1775 ctg gaa ggc att ctc tcc cag gtg att cat ctg gag aaa atc act agt      5494
Leu Glu Gly Ile Leu Ser Gln Val Ile His Leu Glu Lys Ile Thr Ser
    1780                1785                1790 gaa atg ggt tct gcg tca cag gct aat atc cgt ctc aca tct ctt aaa      5542
Glu Met Gly Ser Ala Ser Gln Ala Asn Ile Arg Leu Thr Ser Leu Lys
1795                1800                1805                1810 aag aca ctg gct acc aca ctt gca ccc cga gtc ctg ttg ccc gcc atc      5590
Lys Thr Leu Ala Thr Thr Leu Ala Pro Arg Val Leu Leu Pro Ala Ile
                1815                1820                1825 aaa aaa act tac aag cag att gag aag aac tgg aag aat cac atg ggt      5638
Lys Lys Thr Tyr Lys Gln Ile Glu Lys Asn Trp Lys Asn His Met Gly
            1830                1835                1840
```

| | | |
|---|---|---|
| ccg ttt atg agc atc ttg caa gag cat att ggg gyg atg aag aag gaa<br>Pro Phe Met Ser Ile Leu Gln Glu His Ile Gly Xaa Met Lys Lys Glu<br>    1845                1850                1855 | 5686 | |
| gag ctc acc tcc cat cag tct cag cta acc gcc ttt ttc ctg gar gcc<br>Glu Leu Thr Ser His Gln Ser Gln Leu Thr Ala Phe Phe Leu Glu Ala<br>1860                1865                1870 | 5734 | |
| ctg gac ttc cga gcc cag cac tct gag aac gat ctg gag gaa gtt gga<br>Leu Asp Phe Arg Ala Gln His Ser Glu Asn Asp Leu Glu Glu Val Gly<br>1875                1880                1885                1890 | 5782 | |
| aaa acg gaa aat tgt atc att gac tgt cta gta gcc atg gtt gtc aaa<br>Lys Thr Glu Asn Cys Ile Ile Asp Cys Leu Val Ala Met Val Val Lys<br>                1895                1900                1905 | 5830 | |
| ctt tcc gag gtc aca ttc agg ccc ctg ttc ttc aag ctg ttt gat tgg<br>Leu Ser Glu Val Thr Phe Arg Pro Leu Phe Phe Lys Leu Phe Asp Trp<br>    1910                1915                1920 | 5878 | |
| gct aaa aca gaa gat gcc cca aag gac agg ttg tta aca ttt tac aac<br>Ala Lys Thr Glu Asp Ala Pro Lys Asp Arg Leu Leu Thr Phe Tyr Asn<br>    1925                1930                1935 | 5926 | |
| ttg gca gat tgc att gct gaa aag ctg aaa ggg ctt ttt act ctg ttt<br>Leu Ala Asp Cys Ile Ala Glu Lys Leu Lys Gly Leu Phe Thr Leu Phe<br>    1940                1945                1950 | 5974 | |
| gcc ggc cac tta gtg aag cct ttt gct gac acc ttg rac cag gtg aac<br>Ala Gly His Leu Val Lys Pro Phe Ala Asp Thr Leu Xaa Gln Val Asn<br>1955                1960                1965                1970 | 6022 | |
| atc tcc aaa aca gat gaa gca ttt ttt gac tct gaa aat gac cct gaa<br>Ile Ser Lys Thr Asp Glu Ala Phe Phe Asp Ser Glu Asn Asp Pro Glu<br>                1975                1980                1985 | 6070 | |
| aag tgc tgc ttg ctg ttg cag ttt att ttg aac tgt tta tac aaa atc<br>Lys Cys Cys Leu Leu Leu Gln Phe Ile Leu Asn Cys Leu Tyr Lys Ile<br>    1990                1995                2000 | 6118 | |
| ttc ctt ttt gat acc cag cat ttt ata agt aaa gag aga gca gra gcc<br>Phe Leu Phe Asp Thr Gln His Phe Ile Ser Lys Glu Arg Ala Xaa Ala<br>    2005                2010                2015 | 6166 | |
| ttg atg atg cct ctg gtg gat cag ctg gaa aac agg ctt ggg gga gaa<br>Leu Met Met Pro Leu Val Asp Gln Leu Glu Asn Arg Leu Gly Gly Glu<br>    2020                2025                2030 | 6214 | |
| gag aaa ttc cag gaa cgg gtg aca aag cac ctg ata cca tgc atc gca<br>Glu Lys Phe Gln Glu Arg Val Thr Lys His Leu Ile Pro Cys Ile Ala<br>2035                2040                2045                2050 | 6262 | |
| cag ttt tcr gtg gcc atg gcg gat gac tct ctt tgg aaa cca ctg aac<br>Gln Phe Ser Val Ala Met Ala Asp Asp Ser Leu Trp Lys Pro Leu Asn<br>                2055                2060                2065 | 6310 | |
| tac cag att ctg cta aag acg aga gac tcc tcg cct aag gtt cga ttt<br>Tyr Gln Ile Leu Leu Lys Thr Arg Asp Ser Ser Pro Lys Val Arg Phe<br>    2070                2075                2080 | 6358 | |
| gct gct ttg att act gtg tta gca ctg gct gaa aaa cta aag gag aat<br>Ala Ala Leu Ile Thr Val Leu Ala Leu Ala Glu Lys Leu Lys Glu Asn<br>    2085                2090                2095 | 6406 | |
| tat att gtc ttg cta cca gaa tcc att cct ttc tta gca gag ttg atg<br>Tyr Ile Val Leu Leu Pro Glu Ser Ile Pro Phe Leu Ala Glu Leu Met<br>    2100                2105                2110 | 6454 | |
| gaa gat gaa tgt gaa gaa gta gaa cat cag tgc caa aag act att cag<br>Glu Asp Glu Cys Glu Glu Val Glu His Gln Cys Gln Lys Thr Ile Gln<br>2115                2120                2125                2130 | 6502 | |
| caa ctg gaa act gtc ctg gga gag cca ctc cag agc tat ttc taa<br>Gln Leu Glu Thr Val Leu Gly Glu Pro Leu Gln Ser Tyr Phe<br>                2135                2140 | 6547 | |
| gactttctgt ggtgtttcat actctactca gagttcacac tcatatttca tatttttatt | 6607 | |
| tttgggtgtt gggtgccatg ttactttttgg tgccttaata cacctacttg gattacttac | 6667 | |

-continued

```
aaatgtttta tcacttcgtt acaaaatccc cacctggctt gtgctgccac ataagcctct   6727
cctgcctatc gtatagagct gcagaaagag taaatgatac acggtatttt tatac        6782

<210> SEQ ID NO 3
<211> LENGTH: 7932
<212> TYPE: DNA
<213> ORGANISM: Homo sapiens
<220> FEATURE:
<221> NAME/KEY: 5'UTR
<222> LOCATION: 1..112
<220> FEATURE:
<221> NAME/KEY: CDS
<222> LOCATION: 113..6547
<220> FEATURE:
<221> NAME/KEY: 3'UTR
<222> LOCATION: 6548..7932
<220> FEATURE:
<221> NAME/KEY: allele
<222> LOCATION: 178
<223> OTHER INFORMATION: 5-382-162  : polymorphic base C or T
<220> FEATURE:
<221> NAME/KEY: allele
<222> LOCATION: 2677
<223> OTHER INFORMATION: 5-383-184  : polymorphic base G or T
<220> FEATURE:
<221> NAME/KEY: allele
<222> LOCATION: 5193
<223> OTHER INFORMATION: 5-370-197  : polymorphic base A or G
<220> FEATURE:
<221> NAME/KEY: allele
<222> LOCATION: 5243
<223> OTHER INFORMATION: 5-370-247  : polymorphic base C or T
<220> FEATURE:
<221> NAME/KEY: allele
<222> LOCATION: 5673
<223> OTHER INFORMATION: 5-373-164  : polymorphic base C or T
<220> FEATURE:
<221> NAME/KEY: allele
<222> LOCATION: 5731
<223> OTHER INFORMATION: 5-373-222  : polymorphic base A or G
<220> FEATURE:
<221> NAME/KEY: allele
<222> LOCATION: 6011
<223> OTHER INFORMATION: 5-375-200  : polymorphic base A or G
<220> FEATURE:
<221> NAME/KEY: allele
<222> LOCATION: 6162
<223> OTHER INFORMATION: 5-376-266  : polymorphic base A or G
<220> FEATURE:
<221> NAME/KEY: allele
<222> LOCATION: 6271
<223> OTHER INFORMATION: 5-377-227  : polymorphic base A or G
<220> FEATURE:
<221> NAME/KEY: allele
<222> LOCATION: 7343
<223> OTHER INFORMATION: 5-403-156  : polymorphic base C or T

<400> SEQUENCE: 3
ggttgggctc cttggtacca tgtgggaagc gctgtgaaga gttgttgcct tccaagatat   60
acccaaattc ccagttccag cccgtgtcat taaaactccg ctggcgtgaa ag atg acg  118
                                                            Met Thr
                                                             1 tcc tta gcc cag cag ctg caa cga ctc gcc ctc cct caa agt gat gcc   166
Ser Leu Ala Gln Gln Leu Gln Arg Leu Ala Leu Pro Gln Ser Asp Ala
        5                  10                  15 agc ctc tta tcy aga gat gaa gtt gct tct ttg tta ttt gac cct aag   214
Ser Leu Leu Ser Arg Asp Glu Val Ala Ser Leu Leu Phe Asp Pro Lys
 20                  25                  30 gaa gcg gcc aca atc gac agg gac acc gcc ttc gcc att gga tgt act   262
Glu Ala Ala Thr Ile Asp Arg Asp Thr Ala Phe Ala Ile Gly Cys Thr
 35                  40                  45                  50
```

```
ggc ctg gaa gag ttg ctt gga att gat cct tcc ttt gag cag ttt gaa      310
Gly Leu Glu Glu Leu Leu Gly Ile Asp Pro Ser Phe Glu Gln Phe Glu
            55                  60                  65 gca ccg ttg ttc agt cag cta gca aaa acc ttg gag cga agt gtt cag      358
Ala Pro Leu Phe Ser Gln Leu Ala Lys Thr Leu Glu Arg Ser Val Gln
        70                  75                  80 acc aaa gca gta aac aaa cag ttg gat gaa aac att tca tta ttc ctt      406
Thr Lys Ala Val Asn Lys Gln Leu Asp Glu Asn Ile Ser Leu Phe Leu
            85                  90                  95 att cac ttg tcg cct tac ttc ctg ctt aag cca gca cag aag tgt ctg      454
Ile His Leu Ser Pro Tyr Phe Leu Leu Lys Pro Ala Gln Lys Cys Leu
        100                 105                 110 gag tgg ttg att cac agg ttc cat ata cat ctc tat aat caa gat agc      502
Glu Trp Leu Ile His Arg Phe His Ile His Leu Tyr Asn Gln Asp Ser
115                 120                 125                 130 ctc att gct tgt gtt ctg cca tac cac gag aca aga ata ttt gtg cga      550
Leu Ile Ala Cys Val Leu Pro Tyr His Glu Thr Arg Ile Phe Val Arg
            135                 140                 145 gtc ata cag ctt cta aaa att aat aat tca aag cac aga tgg ttc tgg      598
Val Ile Gln Leu Leu Lys Ile Asn Asn Ser Lys His Arg Trp Phe Trp
        150                 155                 160 ttg ttg cca gtt aag caa tct gga gtg ccg tta gct aaa gga act ttg      646
Leu Leu Pro Val Lys Gln Ser Gly Val Pro Leu Ala Lys Gly Thr Leu
            165                 170                 175 att acc cac tgc tac aaa gat ctt gga ttc atg gat ttc att tgc agt      694
Ile Thr His Cys Tyr Lys Asp Leu Gly Phe Met Asp Phe Ile Cys Ser
        180                 185                 190 ttg gtg aca aaa tct gtg aag gtt ttt gct gag tac ccg ggc agc tca      742
Leu Val Thr Lys Ser Val Lys Val Phe Ala Glu Tyr Pro Gly Ser Ser
195                 200                 205                 210 gct cag ttg agg gtg ctc ttg gct ttc tat gct tct acc ata gtg tcg      790
Ala Gln Leu Arg Val Leu Leu Ala Phe Tyr Ala Ser Thr Ile Val Ser
            215                 220                 225 gcg ctg gta gct gca gag gac gta tca gac aat atc atc gcc aaa cta      838
Ala Leu Val Ala Ala Glu Asp Val Ser Asp Asn Ile Ile Ala Lys Leu
        230                 235                 240 ttt ccc tat atc caa aag gga ttg aaa tca tct tta cca gat tac aga      886
Phe Pro Tyr Ile Gln Lys Gly Leu Lys Ser Ser Leu Pro Asp Tyr Arg
            245                 250                 255 gct gca aca tac atg ata ata tgt cag att tct gtg aaa gtg acc atg      934
Ala Ala Thr Tyr Met Ile Ile Cys Gln Ile Ser Val Lys Val Thr Met
        260                 265                 270 gaa aat acc ttt gtg aat tca ttg gca tca cag atc atc aaa aca ttg      982
Glu Asn Thr Phe Val Asn Ser Leu Ala Ser Gln Ile Ile Lys Thr Leu
275                 280                 285                 290 acc aag att ccc tct ttg atc aag gat ggg tta agt tgc ttg ata gtg     1030
Thr Lys Ile Pro Ser Leu Ile Lys Asp Gly Leu Ser Cys Leu Ile Val
            295                 300                 305 ctc ctg cag aga cag aag cca gag agc ctt ggg aaa aag cca ttc cct     1078
Leu Leu Gln Arg Gln Lys Pro Glu Ser Leu Gly Lys Lys Pro Phe Pro
        310                 315                 320 cac tta tgt aat gtt cct gat ctt att aca ata ctt cat ggg att tct     1126
His Leu Cys Asn Val Pro Asp Leu Ile Thr Ile Leu His Gly Ile Ser
            325                 330                 335 gaa act tac gat gtc agt cct ctt ctg cgt tac atg ctt ccc cat ctg     1174
Glu Thr Tyr Asp Val Ser Pro Leu Leu Arg Tyr Met Leu Pro His Leu
        340                 345                 350 gtc gtc tcc atc att cat cat gtt aca gga gaa gaa act gaa gga atg     1222
Val Val Ser Ile Ile His His Val Thr Gly Glu Glu Thr Glu Gly Met
355                 360                 365                 370
```

```
                                    -continued
gat ggt caa atc tac aag aga cac tta gaa gct ata ctt aca aaa ata    1270
Asp Gly Gln Ile Tyr Lys Arg His Leu Glu Ala Ile Leu Thr Lys Ile
            375                 380                 385 tca ctg aag aac aac tta gac cat ttg ttg gct agc ctt cta ttt gaa    1318
Ser Leu Lys Asn Asn Leu Asp His Leu Leu Ala Ser Leu Leu Phe Glu
        390                 395                 400 gag tat att tca tat agt tca cag gaa gaa atg gat tct aat aaa gtg    1366
Glu Tyr Ile Ser Tyr Ser Ser Gln Glu Glu Met Asp Ser Asn Lys Val
                405                 410                 415 tct ttg ctt aat gaa caa ttt ctt cca ctc att aga ctt tta gaa agc    1414
Ser Leu Leu Asn Glu Gln Phe Leu Pro Leu Ile Arg Leu Leu Glu Ser
            420                 425                 430 aaa tac ccc aga aca tta gat gtt gta tta gag gaa cac tta aag gaa    1462
Lys Tyr Pro Arg Thr Leu Asp Val Val Leu Glu Glu His Leu Lys Glu
435                 440                 445                 450 att gca gat ctg aaa aaa caa gag ctt ttt cat cag ttt gtt tct ctt    1510
Ile Ala Asp Leu Lys Lys Gln Glu Leu Phe His Gln Phe Val Ser Leu
                455                 460                 465 tct aca agt gga gga aag tat cag ttt tta gca gat tct gat act tct    1558
Ser Thr Ser Gly Gly Lys Tyr Gln Phe Leu Ala Asp Ser Asp Thr Ser
            470                 475                 480 ttg atg ctc agc ctg aat cat cca ctt gct cct gtg aga att ctg gcc    1606
Leu Met Leu Ser Leu Asn His Pro Leu Ala Pro Val Arg Ile Leu Ala
        485                 490                 495 atg aat cat ttg aaa aag atc atg aaa aca tca aag gag ggt gtt gat    1654
Met Asn His Leu Lys Lys Ile Met Lys Thr Ser Lys Glu Gly Val Asp
                500                 505                 510 gaa tct ttc ata aaa gaa gct gtt tta gcc cga tta ggt gat gat aat    1702
Glu Ser Phe Ile Lys Glu Ala Val Leu Ala Arg Leu Gly Asp Asp Asn
515                 520                 525                 530 ata gat gtt gtt ttg tcg gct ata agt gct ttt gag att ttc aaa gaa    1750
Ile Asp Val Val Leu Ser Ala Ile Ser Ala Phe Glu Ile Phe Lys Glu
                535                 540                 545 cac ttc agt tca gaa gtg acg att tca aat ctt ctg aat ctc ttt caa    1798
His Phe Ser Ser Glu Val Thr Ile Ser Asn Leu Leu Asn Leu Phe Gln
            550                 555                 560 aga gca gaa ctt tca aag aat gga gaa tgg tac gag gta ctt aag ata    1846
Arg Ala Glu Leu Ser Lys Asn Gly Glu Trp Tyr Glu Val Leu Lys Ile
        565                 570                 575 gcc gct gac ata tta att aaa gaa gag ata ctg agt gaa aat gat cag    1894
Ala Ala Asp Ile Leu Ile Lys Glu Glu Ile Leu Ser Glu Asn Asp Gln
                580                 585                 590 ttg tca aat cag gtg gtt gta tgt ttg ctg cca ttt gtg gtt atc aat    1942
Leu Ser Asn Gln Val Val Val Cys Leu Leu Pro Phe Val Val Ile Asn
595                 600                 605                 610 aat gat gat acg gaa tct gct gag atg aaa att gct ata tat tta tca    1990
Asn Asp Asp Thr Glu Ser Ala Glu Met Lys Ile Ala Ile Tyr Leu Ser
                615                 620                 625 aaa tca gga atc tgc tcc ctg cac cct cta tta aga ggc tgg gaa gaa    2038
Lys Ser Gly Ile Cys Ser Leu His Pro Leu Leu Arg Gly Trp Glu Glu
            630                 635                 640 gct ctt gaa aat gta att aaa agc aca aag cca gga aaa cta atc ggt    2086
Ala Leu Glu Asn Val Ile Lys Ser Thr Lys Pro Gly Lys Leu Ile Gly
        645                 650                 655 gta gca aat cag aag atg att gag ttg ttg gct gat aat ata aat tta    2134
Val Ala Asn Gln Lys Met Ile Glu Leu Leu Ala Asp Asn Ile Asn Leu
                660                 665                 670 gga gat cct tct tca atg tta aag atg gtg gag gat ttg ata agc gtg    2182
Gly Asp Pro Ser Ser Met Leu Lys Met Val Glu Asp Leu Ile Ser Val
            675                 680                 685                 690
```

| | | |
|---|---|---|
| ggt gag gag gag tcc ttt aac ctg aag cag aaa gta acg ttt cat gtg<br>Gly Glu Glu Glu Ser Phe Asn Leu Lys Gln Lys Val Thr Phe His Val<br>695                                   700                          705 | 2230 |
| atc ctg tct gtg ctc gtc tct tgt tgt tca tct tta aaa gaa acc cac<br>Ile Leu Ser Val Leu Val Ser Cys Cys Ser Ser Leu Lys Glu Thr His<br>710                            715                         720 | 2278 |
| ttt cca ttt gcg ata aga gtc ttc agt ttg ttg cag aaa aaa ata aag<br>Phe Pro Phe Ala Ile Arg Val Phe Ser Leu Leu Gln Lys Lys Ile Lys<br>725                          730                         735 | 2326 |
| aag ctt gaa agt gtc att act gca gtg gaa atc ccc tca gaa tgg cac<br>Lys Leu Glu Ser Val Ile Thr Ala Val Glu Ile Pro Ser Glu Trp His<br>740                       745                       750 | 2374 |
| att gaa ctg atg tta gac aga ggg atc cca gta gag ctg tgg gca cat<br>Ile Glu Leu Met Leu Asp Arg Gly Ile Pro Val Glu Leu Trp Ala His<br>755                    760                     765                   770 | 2422 |
| tat gta gaa gag ctc aac agc act cag agg gtg gcc gtg gag gac tcg<br>Tyr Val Glu Glu Leu Asn Ser Thr Gln Arg Val Ala Val Glu Asp Ser<br>                        775                       780                   785 | 2470 |
| gtt ttt ctt gta ttt tcc ttg aaa aaa ttt att tat gca ctg aaa gct<br>Val Phe Leu Val Phe Ser Leu Lys Lys Phe Ile Tyr Ala Leu Lys Ala<br>                  790                       795                   800 | 2518 |
| cct aaa tct ttt cct aaa ggt gat ata tgg tgg aat cct gaa caa ctg<br>Pro Lys Ser Phe Pro Lys Gly Asp Ile Trp Trp Asn Pro Glu Gln Leu<br>805                          810                         815 | 2566 |
| aaa gaa gac agc agg gac tat ctg cac ttg ctc att ggg ctg ttt gag<br>Lys Glu Asp Ser Arg Asp Tyr Leu His Leu Leu Ile Gly Leu Phe Glu<br>820                          825                       830 | 2614 |
| atg atg ctc aat ggt gcc gat gct gtt cat ttc aga gtt ctg atg aaa<br>Met Met Leu Asn Gly Ala Asp Ala Val His Phe Arg Val Leu Met Lys<br>835                          840                       845                   850 | 2662 |
| ctt ttc ata aag gtk cat cta gaa gat gtt ttt cag tta ttc aag ttc<br>Leu Phe Ile Lys Val His Leu Glu Asp Val Phe Gln Leu Phe Lys Phe<br>                  855                       860                   865 | 2710 |
| tgt tct gtt tta tgg acc tat ggt tct agc ctt tca aat cca cta aac<br>Cys Ser Val Leu Trp Thr Tyr Gly Ser Ser Leu Ser Asn Pro Leu Asn<br>                  870                       875                   880 | 2758 |
| tgc agt gtg aaa aca gtg ctg cag act caa gct ctt tat gtg ggc tgt<br>Cys Ser Val Lys Thr Val Leu Gln Thr Gln Ala Leu Tyr Val Gly Cys<br>885                          890                       895 | 2806 |
| gca atg ctt tct tct cag aag aca cag tgt aaa cac caa ctg gca tcc<br>Ala Met Leu Ser Ser Gln Lys Thr Gln Cys Lys His Gln Leu Ala Ser<br>900                          905                       910 | 2854 |
| ata tct tct cca gtg gtg aca tct tta ctc att aac ctg gga agc ccc<br>Ile Ser Ser Pro Val Val Thr Ser Leu Leu Ile Asn Leu Gly Ser Pro<br>915                          920                       925                   930 | 2902 |
| gta aaa gaa gtt cgt agg gct gcc att cag tgt ctc cag gcc ctc agt<br>Val Lys Glu Val Arg Arg Ala Ala Ile Gln Cys Leu Gln Ala Leu Ser<br>                  935                       940                   945 | 2950 |
| gga gtg gca tcc ccg ttt tat ctg ata ata gat cat ttg att tct aaa<br>Gly Val Ala Ser Pro Phe Tyr Leu Ile Ile Asp His Leu Ile Ser Lys<br>950                          955                       960 | 2998 |
| gca gag gag atc act tca gat gct gcc tat gtt att cag gat ttg gct<br>Ala Glu Glu Ile Thr Ser Asp Ala Ala Tyr Val Ile Gln Asp Leu Ala<br>965                          970                       975 | 3046 |
| act tta ttt gag gaa cta cag aga gaa aag aaa ctg aaa tct cat cag<br>Thr Leu Phe Glu Glu Leu Gln Arg Glu Lys Lys Leu Lys Ser His Gln<br>                  980                       985                   990 | 3094 |
| aag ttg tct gaa act ttg aaa aac tta ctt agt tgt gtg tat agt tgc<br>Lys Leu Ser Glu Thr Leu Lys Asn Leu Leu Ser Cys Val Tyr Ser Cys<br>995                          1000                     1005                   1010 | 3142 |

```
cca tct tat ata gca aaa gat ttg atg aaa gta ctt cag gga gtc aac        3190
Pro Ser Tyr Ile Ala Lys Asp Leu Met Lys Val Leu Gln Gly Val Asn
            1015                1020                1025 ggt gag atg gtg ctt tct cag cta ttg cct atg gct gaa caa ctg cta        3238
Gly Glu Met Val Leu Ser Gln Leu Leu Pro Met Ala Glu Gln Leu Leu
        1030                1035                1040 gaa aag atc cag aag gag ccc aca gct gtg ctg aaa gat gag gcc atg        3286
Glu Lys Ile Gln Lys Glu Pro Thr Ala Val Leu Lys Asp Glu Ala Met
        1045                1050                1055 gtt ctg cat ctc act ctg gga aag tat aat gaa ttt tca gtt tcc ctt        3334
Val Leu His Leu Thr Leu Gly Lys Tyr Asn Glu Phe Ser Val Ser Leu
        1060                1065                1070 tta aat gag gat ccg aag agt cta gat ata ttt ata aaa gct gtg cac        3382
Leu Asn Glu Asp Pro Lys Ser Leu Asp Ile Phe Ile Lys Ala Val His
1075                1080                1085                1090 aca aca aag gaa ctt tac gcg gga atg cca acc att cag atc aca gcc        3430
Thr Thr Lys Glu Leu Tyr Ala Gly Met Pro Thr Ile Gln Ile Thr Ala
                1095                1100                1105 ctt gaa aag att aca aaa cca ttt ttt gca gcc ata tca gat gaa aaa        3478
Leu Glu Lys Ile Thr Lys Pro Phe Phe Ala Ala Ile Ser Asp Glu Lys
        1110                1115                1120 gtt cag cag aag ctt tta aga atg ttg ttt gat tta ttg gtg aac tgt        3526
Val Gln Gln Lys Leu Leu Arg Met Leu Phe Asp Leu Leu Val Asn Cys
        1125                1130                1135 aaa aac tca cat tgt gct cag act gtc agc agt gtt ttt aaa ggg att        3574
Lys Asn Ser His Cys Ala Gln Thr Val Ser Ser Val Phe Lys Gly Ile
        1140                1145                1150 tcc gtt aat gct gaa caa gtc cga ata gaa ctg gag cca cca gat aaa        3622
Ser Val Asn Ala Glu Gln Val Arg Ile Glu Leu Glu Pro Pro Asp Lys
1155                1160                1165                1170 gct aaa ccc ttg ggc aca gtt cag caa aaa aga agg caa aaa atg cag        3670
Ala Lys Pro Leu Gly Thr Val Gln Gln Lys Arg Arg Gln Lys Met Gln
                1175                1180                1185 cag aaa aaa tca caa gat cta gaa tct gtt cag gaa gtt gga ggt tct        3718
Gln Lys Lys Ser Gln Asp Leu Glu Ser Val Gln Glu Val Gly Gly Ser
        1190                1195                1200 tac tgg caa aga gta act ctc atc ctg gaa tta ctg cag cac aaa aag        3766
Tyr Trp Gln Arg Val Thr Leu Ile Leu Glu Leu Leu Gln His Lys Lys
        1205                1210                1215 aag ctc aga agt cct cag ata ttg gtg cca act ctt ttt aac ttg cta        3814
Lys Leu Arg Ser Pro Gln Ile Leu Val Pro Thr Leu Phe Asn Leu Leu
        1220                1225                1230 tca aga tgt tta gaa ccc ttg cca caa gag cag gga aat atg gaa tac        3862
Ser Arg Cys Leu Glu Pro Leu Pro Gln Glu Gln Gly Asn Met Glu Tyr
1235                1240                1245                1250 acc aaa caa tta att ctt agt tgt ctg ctc aac atc tgc caa aaa cta        3910
Thr Lys Gln Leu Ile Leu Ser Cys Leu Leu Asn Ile Cys Gln Lys Leu
                1255                1260                1265 tct cca gat ggt ggc aaa ata ccc aaa gat att tta gat gag gag aag        3958
Ser Pro Asp Gly Gly Lys Ile Pro Lys Asp Ile Leu Asp Glu Glu Lys
            1270                1275                1280 ttc aac gtg gag ttg ata gtt cag tgc atc cgc ctt tcg gag atg ccg        4006
Phe Asn Val Glu Leu Ile Val Gln Cys Ile Arg Leu Ser Glu Met Pro
        1285                1290                1295 cag acc cat cac cat gcc ctt tta ctt ttg ggc act gtt gct gga ata        4054
Gln Thr His His His Ala Leu Leu Leu Leu Gly Thr Val Ala Gly Ile
        1300                1305                1310 ttt ccg gat aaa gtt tta cac aat atc atg tct att ttt aca ttt atg        4102
Phe Pro Asp Lys Val Leu His Asn Ile Met Ser Ile Phe Thr Phe Met
        1315                1320                1325                1330
```

```
gga gcc aat gtc atg cgc cta gat gat act tac agt ttt caa gtt att    4150
Gly Ala Asn Val Met Arg Leu Asp Asp Thr Tyr Ser Phe Gln Val Ile
        1335                1340                1345 aac aag aca gtg aaa atg gtt att ccc gca ctt att cag tct gat agt    4198
Asn Lys Thr Val Lys Met Val Ile Pro Ala Leu Ile Gln Ser Asp Ser
        1350                1355                1360 gga gat tct ata gaa gtt tca aga aac gtt gaa gag att gtg gta aaa    4246
Gly Asp Ser Ile Glu Val Ser Arg Asn Val Glu Glu Ile Val Val Lys
        1365                1370                1375 atc att agt gta ttt gtg gat gcg ctg cca cac gtc ccg gag cac agg    4294
Ile Ile Ser Val Phe Val Asp Ala Leu Pro His Val Pro Glu His Arg
        1380                1385                1390 cgc ctg ccc atc ctt gtt caa ctt gtt gat aca ctg ggt gca gag aaa    4342
Arg Leu Pro Ile Leu Val Gln Leu Val Asp Thr Leu Gly Ala Glu Lys
1395                1400                1405                1410 ttc ctc tgg att ctc ctc atc ttg ctt ttt gaa cag tat gtc aca aaa    4390
Phe Leu Trp Ile Leu Leu Ile Leu Leu Phe Glu Gln Tyr Val Thr Lys
        1415                1420                1425 aca gtg ctg gcg gct gcc tat ggc gaa aag gat gct att tta gaa gca    4438
Thr Val Leu Ala Ala Ala Tyr Gly Glu Lys Asp Ala Ile Leu Glu Ala
        1430                1435                1440 gac act gaa ttt tgg ttt tca gtc tgt tgt gag ttt agt gtc cag cat    4486
Asp Thr Glu Phe Trp Phe Ser Val Cys Cys Glu Phe Ser Val Gln His
        1445                1450                1455 cag ata caa agc ttg atg aat atc ctc cag tac tta cta aag ctg cca    4534
Gln Ile Gln Ser Leu Met Asn Ile Leu Gln Tyr Leu Leu Lys Leu Pro
        1460                1465                1470 gag gaa aaa gaa gaa acc att ccc aaa gca gtg tca ttt aat aag agt    4582
Glu Glu Lys Glu Glu Thr Ile Pro Lys Ala Val Ser Phe Asn Lys Ser
1475                1480                1485                1490 gaa tca caa gaa gaa atg cta cag gtt ttt aat gta gag act cac act    4630
Glu Ser Gln Glu Glu Met Leu Gln Val Phe Asn Val Glu Thr His Thr
        1495                1500                1505 agc aag caa ctg cgg cat ttt aaa ttt ttg tca gtg tcc ttc atg tct    4678
Ser Lys Gln Leu Arg His Phe Lys Phe Leu Ser Val Ser Phe Met Ser
        1510                1515                1520 cag ctc ctg tct tcc aat aat ttt ctg aaa aag gta gtt gag agt ggt    4726
Gln Leu Leu Ser Ser Asn Asn Phe Leu Lys Lys Val Val Glu Ser Gly
        1525                1530                1535 ggt cct gag att tta aaa ggc ctt gaa gag agg ttg ctg gag acc gtt    4774
Gly Pro Glu Ile Leu Lys Gly Leu Glu Glu Arg Leu Leu Glu Thr Val
        1540                1545                1550 ctc ggc tat atc agt gca gtt gca cag tcc atg gaa agg aac gca gac    4822
Leu Gly Tyr Ile Ser Ala Val Ala Gln Ser Met Glu Arg Asn Ala Asp
1555                1560                1565                1570 aaa ctc acc gtg aag ttc tgg cgc gcg ctc ctt agt aaa gct tac gac    4870
Lys Leu Thr Val Lys Phe Trp Arg Ala Leu Leu Ser Lys Ala Tyr Asp
        1575                1580                1585 ctg tta gat aag gtc aat gcc ttg ctg ccc aca gag aca ttc att cct    4918
Leu Leu Asp Lys Val Asn Ala Leu Leu Pro Thr Glu Thr Phe Ile Pro
        1590                1595                1600 gtg atc aga ggg ctg gtg ggc aat ccc ctg cca tct gtt cgc cgc aaa    4966
Val Ile Arg Gly Leu Val Gly Asn Pro Leu Pro Ser Val Arg Arg Lys
        1605                1610                1615 gcg ctg gac ctt ttg aat aac aag ctg cag caa aat ata tcc tgg aag    5014
Ala Leu Asp Leu Leu Asn Asn Lys Leu Gln Gln Asn Ile Ser Trp Lys
        1620                1625                1630 aag aca ata gtt acc cgt ttc cta aaa ctg gtt cca gac ctt ttg gcc    5062
Lys Thr Ile Val Thr Arg Phe Leu Lys Leu Val Pro Asp Leu Leu Ala
1635                1640                1645                1650
```

-continued

| | | |
|---|---|---|
| att gtg cag cgt aag aaa aag gaa ggg gaa gaa gaa caa gca atc aac<br>Ile Val Gln Arg Lys Lys Lys Glu Gly Glu Glu Glu Gln Ala Ile Asn<br>          1655                      1660                1665 | 5110 | |
| aga cag aca gcg ttg tat acc tta aag ctt tta tgc aag aat ttt ggt<br>Arg Gln Thr Ala Leu Tyr Thr Leu Lys Leu Leu Cys Lys Asn Phe Gly<br>    1670                      1675                    1680 | 5158 | |
| gca gaa aat cca gat cct ttt gtc cca gtg ctg arc act gct gtg aaa<br>Ala Glu Asn Pro Asp Pro Phe Val Pro Val Leu Xaa Thr Ala Val Lys<br>1685                      1690                    1695 | 5206 | |
| ctg att gct cca gag aga aag gag gag aag aat gtc ytg gga agc gcg<br>Leu Ile Ala Pro Glu Arg Lys Glu Glu Lys Asn Val Leu Gly Ser Ala<br>    1700                      1705                    1710 | 5254 | |
| ctg ctg tgc ata gca gag gtg acc tcc acc ctg gag gcg ctg gcc atc<br>Leu Leu Cys Ile Ala Glu Val Thr Ser Thr Leu Glu Ala Leu Ala Ile<br>1715                      1720                    1725                1730 | 5302 | |
| ccc cag ctt ccc agc ctg atg cca tcg ttg ctg aca aca atg aag aac<br>Pro Gln Leu Pro Ser Leu Met Pro Ser Leu Leu Thr Thr Met Lys Asn<br>          1735                      1740                1745 | 5350 | |
| acc agc gag ctg gtc tcc agc gag gtc tac ctg ctc agt gcc ttg gct<br>Thr Ser Glu Leu Val Ser Ser Glu Val Tyr Leu Leu Ser Ala Leu Ala<br>                1750                    1755                  1760 | 5398 | |
| gct ctg cag aag gtt gtg gag act ctc ccg cac ttc atc agc ccc tat<br>Ala Leu Gln Lys Val Val Glu Thr Leu Pro His Phe Ile Ser Pro Tyr<br>          1765                      1770                1775 | 5446 | |
| ctg gaa ggc att ctc tcc cag gtg att cat ctg gag aaa atc act agt<br>Leu Glu Gly Ile Leu Ser Gln Val Ile His Leu Glu Lys Ile Thr Ser<br>1780                      1785                    1790 | 5494 | |
| gaa atg ggt tct gcg tca cag gct aat atc cgt ctc aca tct ctt aaa<br>Glu Met Gly Ser Ala Ser Gln Ala Asn Ile Arg Leu Thr Ser Leu Lys<br>1795                      1800                    1805                1810 | 5542 | |
| aag aca ctg gct acc aca ctt gca ccc cga gtc ctg ttg ccc gcc atc<br>Lys Thr Leu Ala Thr Thr Leu Ala Pro Arg Val Leu Leu Pro Ala Ile<br>                1815                    1820                  1825 | 5590 | |
| aaa aaa act tac aag cag att gag aag aac tgg aag aat cac atg ggt<br>Lys Lys Thr Tyr Lys Gln Ile Glu Lys Asn Trp Lys Asn His Met Gly<br>          1830                      1835                1840 | 5638 | |
| ccg ttt atg agc atc ttg caa gag cat att ggg gyg atg aag aag gaa<br>Pro Phe Met Ser Ile Leu Gln Glu His Ile Gly Xaa Met Lys Lys Glu<br>1845                      1850                    1855 | 5686 | |
| gag ctc acc tcc cat cag tct cag cta acc gcc ttt ttc ctg gar gcc<br>Glu Leu Thr Ser His Gln Ser Gln Leu Thr Ala Phe Phe Leu Glu Ala<br>          1860                      1865                1870 | 5734 | |
| ctg gac ttc cga gcc cag cac tct gag aac gat ctg gag gaa gtt gga<br>Leu Asp Phe Arg Ala Gln His Ser Glu Asn Asp Leu Glu Glu Val Gly<br>1875                      1880                    1885                1890 | 5782 | |
| aaa acg gaa aat tgt atc att gac tgt cta gta gcc atg gtt gtc aaa<br>Lys Thr Glu Asn Cys Ile Ile Asp Cys Leu Val Ala Met Val Val Lys<br>                1895                    1900                  1905 | 5830 | |
| ctt tcc gag gtc aca ttc agg ccc ctg ttc ttc aag ctg ttt gat tgg<br>Leu Ser Glu Val Thr Phe Arg Pro Leu Phe Phe Lys Leu Phe Asp Trp<br>          1910                      1915                1920 | 5878 | |
| gct aaa aca gaa gat gcc cca aag gac agg ttg ttg aca ttt tac aac<br>Ala Lys Thr Glu Asp Ala Pro Lys Asp Arg Leu Leu Thr Phe Tyr Asn<br>1925                      1930                    1935 | 5926 | |
| ttg gca gat tgc att gct gaa aag ctg aaa ggg ctt ttt act ctg ttt<br>Leu Ala Asp Cys Ile Ala Glu Lys Leu Lys Gly Leu Phe Thr Leu Phe<br>                1940                    1945                  1950 | 5974 | |
| gcc ggc cac tta gtg aag cct ttt gct gac acc ttg rac cag gtg aac<br>Ala Gly His Leu Val Lys Pro Phe Ala Asp Thr Leu Xaa Gln Val Asn<br>1955                      1960                    1965                1970 | 6022 | |

-continued

| | | |
|---|---|---|
| atc tcc aaa aca gat gaa gca ttt ttt gac tct gaa aat gac cct gaa<br>Ile Ser Lys Thr Asp Glu Ala Phe Phe Asp Ser Glu Asn Asp Pro Glu<br>         1975                  1980               1985 | | 6070 |
| aag tgc tgc ttg ctg ttg cag ttt att ttg aac tgt tta tac aaa atc<br>Lys Cys Cys Leu Leu Leu Gln Phe Ile Leu Asn Cys Leu Tyr Lys Ile<br>         1990                  1995               2000 | | 6118 |
| ttc ctt ttt gat acc cag cat ttt ata agt aaa gag aga gca gra gcc<br>Phe Leu Phe Asp Thr Gln His Phe Ile Ser Lys Glu Arg Ala Xaa Ala<br>         2005                  2010               2015 | | 6166 |
| ttg atg atg cct ctg gtg gat cag ctg gaa aac agg ctt ggg gga gaa<br>Leu Met Met Pro Leu Val Asp Gln Leu Glu Asn Arg Leu Gly Gly Glu<br>         2020                  2025               2030 | | 6214 |
| gag aaa ttc cag gaa cgg gtg aca aag cac ctg ata cca tgc atc gca<br>Glu Lys Phe Gln Glu Arg Val Thr Lys His Leu Ile Pro Cys Ile Ala<br>2035                  2040               2045               2050 | | 6262 |
| cag ttt tcr gtg gcc atg gcg gat gac tct ctt tgg aaa cca ctg aac<br>Gln Phe Ser Val Ala Met Ala Asp Asp Ser Leu Trp Lys Pro Leu Asn<br>         2055                  2060               2065 | | 6310 |
| tac cag att ctg cta aag acg aga gac tcc tcg cct aag gtt cga ttt<br>Tyr Gln Ile Leu Leu Lys Thr Arg Asp Ser Ser Pro Lys Val Arg Phe<br>         2070                  2075               2080 | | 6358 |
| gct gct ttg att act gtg tta gca ctg gct gaa aaa cta aag gag aat<br>Ala Ala Leu Ile Thr Val Leu Ala Leu Ala Glu Lys Leu Lys Glu Asn<br>         2085                  2090               2095 | | 6406 |
| tat att gtc ttg cta cca gaa tcc att cct ttc tta gca gag ttg atg<br>Tyr Ile Val Leu Leu Pro Glu Ser Ile Pro Phe Leu Ala Glu Leu Met<br>         2100                  2105               2110 | | 6454 |
| gaa gat gaa tgt gaa gaa gta gaa cat cag tgc caa aag act att cag<br>Glu Asp Glu Cys Glu Glu Val Glu His Gln Cys Gln Lys Thr Ile Gln<br>2115                  2120               2125               2130 | | 6502 |
| caa ctg gaa act gtc ctg gga gag cca ctc cag agc tat ttc taa<br>Gln Leu Glu Thr Val Leu Gly Glu Pro Leu Gln Ser Tyr Phe<br>         2135                  2140 | | 6547 |
| gactttctgt ggtgtttcat actctactca gagttcacac tcatatttca tattttatt | | 6607 |
| tttgggtgtt gggtgccatg ttacttttgg tgccttaata cacctacttg gattacttac | | 6667 |
| aaatgtttta tcacttcgtt acaaaatccc cacctggctt gtgctgccac ataagcctct | | 6727 |
| cctgcctatc gtatagagct gcagaaagag taaatgatac acggtatttt tatacagact | | 6787 |
| gctgtgtttg tttaaacatt tattattctc ttcctgattg atggtaataa tattagactt | | 6847 |
| gttaatttta gcacccaaag ctgacgcctc atttgcactg taagccttaa ctcttctgta | | 6907 |
| cagcagtatc ttatatacat ggtatccatg ttgcagattt cactcaaagt tgctctattt | | 6967 |
| caagaaaatg aagttattta gcaatcaaca gaagtacttt tgactgtaaa gcctacttt | | 7027 |
| cattttgggt aggcgaactt cagccttcgt ttctttgttg tgcccataaa gagaagtggt | | 7087 |
| tctggaatgc ttttttttaac ccaggagtgt gactgtcacc tttatccttt gttctttttgg | | 7147 |
| gaaacgggag atgaaggc aacacgctgc ttctaaaaca gctcatacct ggctgctcac | | 7207 |
| acagagggcc cagaaacact gggtggcacg aggaagctcc tccaggattc agaatgaacc | | 7267 |
| cagttccatt ggtggttaac taagaactac ttgtctaaga aacccccta tgatctgatt | | 7327 |
| caccaggctt acctcygaag ttctacagga tcatgtccca aatccagtct tttcaggtgg | | 7387 |
| gagaaacaag cttctagaac tatggttttg tcataaaata aaagaatctt agtgacgaga | | 7447 |
| gggatcttag gaggagtata aattaattca tctcaatagc tcaaggatg agatagccta | | 7507 |
| ttttgtgaaa tacattttttt gaatggctta cagactatga tgttagtact aaaaaatgct | | 7567 |
| gaattatttg atatgaggaa aatgtatctg aaattatgta aaatgtaaag acaaaatgat | | 7627 |

```
actaaaaatg tataaatagt atacatgggc cgggcgcggt ggcttatgcc tgtaatccca    7687
gcactttggg aggccgaggc agatggatca cgaggtcagg agttcgagac cagcctggac    7747
aacatagtga aaccctgtct ctactaaaaa tacaaaaatt agccaggagc ggtggcaggc    7807
gcctgtagtc ccagctactt ggaggctga dacaggagaa tcgcttgaac ctgggaggcg    7867
gagattgcag tgagctgaga ctgcgccact gccctccagc ctaggtgaca gagcaagctc    7927
tgtaa                                                                7932

<210> SEQ ID NO 4
<211> LENGTH: 845
<212> TYPE: DNA
<213> ORGANISM: Homo sapiens
<220> FEATURE:
<221> NAME/KEY: allele
<222> LOCATION: 256
<223> OTHER INFORMATION: 5-403-156  : polymorphic base C or T

<400> SEQUENCE: 4
taggagggag ggcgctcggg gctgggactt ttcaggacca gggtggtcac cgcacaggcc     60
ccgcctgcct ggaccaagcg ctggccttcc cggggcgccc aggtccacgg ggtcaacgcc    120
agggttttct cagcttcctc gtctgcctcg gatccaagtc cagacagtgc cagaagagac    180
ttggaggcgc tgcttttttga cagtacacac ctctgtatgc agacccccta tgatctgatt    240
caccaggctt acctcygaag ttctacagga tcatgtccca aatccagtct tttcaggtgg    300
gagaaacaag cttctagaac tatggttttg tcataaaata aaagaatctt agtgacgaga    360
gggatcttag gaggagtata aattaattca tctcaatagc tcaaaggatg agatagccta    420
ttttgtgaaa tacattttt gaatggctta cagactatga tgttagtact aaaaaatgct    480
gaattatttg atatgaggaa aatgtatctg aaattatgta aaatgtaaag acaaaatgat    540
actaaaaatg tataaatagt atacatgggc cgggcgcggt ggcttatgcc tgtaatccca    600
gcactttggg aggccgaggc agatggatca cgaggtcagg agttcgagac cagcctggac    660
aacatagtga aaccctgtct ctactaaaaa tacaaaaatt agccaggagc ggtggcaggc    720
gcctgtagtc ccagctactt ggaggctga dacaggagaa tcgcttgaac ctgggaggcg    780
gagattgcag tgagctgaga ctgcgccact gccctccagc ctaggtgaca gagcaagctc    840
tgtaa                                                                845

<210> SEQ ID NO 5
<211> LENGTH: 2144
<212> TYPE: PRT
<213> ORGANISM: Homo sapiens
<220> FEATURE:
<221> NAME/KEY: VARIANT
<222> LOCATION: 1694
<223> OTHER INFORMATION: Xaa=Ser or Asn
<220> FEATURE:
<221> NAME/KEY: VARIANT
<222> LOCATION: 1854
<223> OTHER INFORMATION: Xaa=Ala or Val
<220> FEATURE:
<221> NAME/KEY: VARIANT
<222> LOCATION: 1967
<223> OTHER INFORMATION: Xaa=Asp or Asn
<220> FEATURE:
<221> NAME/KEY: VARIANT
<222> LOCATION: 2017
<223> OTHER INFORMATION: Xaa=Gly or Glu

<400> SEQUENCE: 5

Met Thr Ser Leu Ala Gln Gln Leu Gln Arg Leu Ala Leu Pro Gln Ser
1               5                   10                  15
```

```
Asp Ala Ser Leu Leu Ser Arg Asp Glu Val Ala Ser Leu Leu Phe Asp
             20                  25                  30

Pro Lys Glu Ala Ala Thr Ile Asp Arg Asp Thr Ala Phe Ala Ile Gly
             35                  40                  45

Cys Thr Gly Leu Glu Glu Leu Gly Ile Asp Pro Ser Phe Glu Gln
 50                  55                  60

Phe Glu Ala Pro Leu Phe Ser Gln Leu Ala Lys Thr Leu Glu Arg Ser
 65                  70                  75                  80

Val Gln Thr Lys Ala Val Asn Lys Gln Leu Asp Glu Asn Ile Ser Leu
                 85                  90                  95

Phe Leu Ile His Leu Ser Pro Tyr Phe Leu Leu Lys Pro Ala Gln Lys
                100                 105                 110

Cys Leu Glu Trp Leu Ile His Arg Phe His Ile His Leu Tyr Asn Gln
                115                 120                 125

Asp Ser Leu Ile Ala Cys Val Leu Pro Tyr His Glu Thr Arg Ile Phe
        130                 135                 140

Val Arg Val Ile Gln Leu Leu Lys Ile Asn Asn Ser Lys His Arg Trp
145                 150                 155                 160

Phe Trp Leu Leu Pro Val Lys Gln Ser Gly Val Pro Leu Ala Lys Gly
                165                 170                 175

Thr Leu Ile Thr His Cys Tyr Lys Asp Leu Gly Phe Met Asp Phe Ile
                180                 185                 190

Cys Ser Leu Val Thr Lys Ser Val Lys Val Phe Ala Glu Tyr Pro Gly
        195                 200                 205

Ser Ser Ala Gln Leu Arg Val Leu Leu Ala Phe Tyr Ala Ser Thr Ile
        210                 215                 220

Val Ser Ala Leu Val Ala Ala Glu Asp Val Ser Asp Asn Ile Ile Ala
225                 230                 235                 240

Lys Leu Phe Pro Tyr Ile Gln Lys Gly Leu Lys Ser Ser Leu Pro Asp
                245                 250                 255

Tyr Arg Ala Ala Thr Tyr Met Ile Ile Cys Gln Ile Ser Val Lys Val
        260                 265                 270

Thr Met Glu Asn Thr Phe Val Asn Ser Leu Ala Ser Gln Ile Ile Lys
        275                 280                 285

Thr Leu Thr Lys Ile Pro Ser Leu Ile Lys Asp Gly Leu Ser Cys Leu
        290                 295                 300

Ile Val Leu Leu Gln Arg Gln Lys Pro Glu Ser Leu Gly Lys Lys Pro
305                 310                 315                 320

Phe Pro His Leu Cys Asn Val Pro Asp Leu Ile Thr Ile Leu His Gly
                325                 330                 335

Ile Ser Glu Thr Tyr Asp Val Ser Pro Leu Leu Arg Tyr Met Leu Pro
        340                 345                 350

His Leu Val Val Ser Ile Ile His His Val Thr Gly Glu Glu Thr Glu
        355                 360                 365

Gly Met Asp Gly Gln Ile Tyr Lys Arg His Leu Glu Ala Ile Leu Thr
370                 375                 380

Lys Ile Ser Leu Lys Asn Asn Leu Asp His Leu Leu Ala Ser Leu Leu
385                 390                 395                 400

Phe Glu Glu Tyr Ile Ser Tyr Ser Ser Gln Glu Glu Met Asp Ser Asn
                405                 410                 415

Lys Val Ser Leu Leu Asn Glu Gln Phe Leu Pro Leu Ile Arg Leu Leu
        420                 425                 430

Glu Ser Lys Tyr Pro Arg Thr Leu Asp Val Val Leu Glu Glu His Leu
```

```
                435                 440                 445
Lys Glu Ile Ala Asp Leu Lys Lys Gln Glu Leu Phe His Gln Phe Val
            450                 455                 460

Ser Leu Ser Thr Ser Gly Gly Lys Tyr Gln Phe Leu Ala Asp Ser Asp
465                 470                 475                 480

Thr Ser Leu Met Leu Ser Leu Asn His Pro Leu Ala Pro Val Arg Ile
                485                 490                 495

Leu Ala Met Asn His Leu Lys Lys Ile Met Lys Thr Ser Lys Glu Gly
            500                 505                 510

Val Asp Glu Ser Phe Ile Lys Glu Ala Val Leu Ala Arg Leu Gly Asp
            515                 520                 525

Asp Asn Ile Asp Val Val Leu Ser Ala Ile Ser Ala Phe Glu Ile Phe
            530                 535                 540

Lys Glu His Phe Ser Ser Glu Val Thr Ile Ser Asn Leu Leu Asn Leu
545                 550                 555                 560

Phe Gln Arg Ala Glu Leu Ser Lys Asn Gly Glu Trp Tyr Glu Val Leu
                565                 570                 575

Lys Ile Ala Ala Asp Ile Leu Ile Lys Glu Glu Ile Leu Ser Glu Asn
            580                 585                 590

Asp Gln Leu Ser Asn Gln Val Val Cys Leu Leu Pro Phe Val Val
            595                 600                 605

Ile Asn Asn Asp Asp Thr Glu Ser Ala Glu Met Lys Ile Ala Ile Tyr
            610                 615                 620

Leu Ser Lys Ser Gly Ile Cys Ser Leu His Pro Leu Leu Arg Gly Trp
625                 630                 635                 640

Glu Glu Ala Leu Glu Asn Val Ile Lys Ser Thr Lys Pro Gly Lys Leu
                645                 650                 655

Ile Gly Val Ala Asn Gln Lys Met Ile Glu Leu Leu Ala Asp Asn Ile
            660                 665                 670

Asn Leu Gly Asp Pro Ser Ser Met Leu Lys Met Val Glu Asp Leu Ile
            675                 680                 685

Ser Val Gly Glu Glu Glu Ser Phe Asn Leu Lys Gln Lys Val Thr Phe
            690                 695                 700

His Val Ile Leu Ser Val Leu Val Ser Cys Cys Ser Ser Leu Lys Glu
705                 710                 715                 720

Thr His Phe Pro Phe Ala Ile Arg Val Phe Ser Leu Leu Gln Lys Lys
                725                 730                 735

Ile Lys Lys Leu Glu Ser Val Ile Thr Ala Val Glu Ile Pro Ser Glu
            740                 745                 750

Trp His Ile Glu Leu Met Leu Asp Arg Gly Ile Pro Val Glu Leu Trp
            755                 760                 765

Ala His Tyr Val Glu Glu Leu Asn Ser Thr Gln Arg Val Ala Val Glu
            770                 775                 780

Asp Ser Val Phe Leu Val Phe Ser Leu Lys Lys Phe Ile Tyr Ala Leu
785                 790                 795                 800

Lys Ala Pro Lys Ser Phe Pro Lys Gly Asp Ile Trp Trp Asn Pro Glu
                805                 810                 815

Gln Leu Lys Glu Asp Ser Arg Asp Tyr Leu His Leu Ile Gly Leu
            820                 825                 830

Phe Glu Met Met Leu Asn Gly Ala Asp Ala Val His Phe Arg Val Leu
            835                 840                 845

Met Lys Leu Phe Ile Lys Val His Leu Glu Asp Val Phe Gln Leu Phe
            850                 855                 860
```

-continued

Lys Phe Cys Ser Val Leu Trp Thr Tyr Gly Ser Ser Leu Ser Asn Pro
865                 870                 875                 880

Leu Asn Cys Ser Val Lys Thr Val Leu Gln Thr Gln Ala Leu Tyr Val
            885                 890                 895

Gly Cys Ala Met Leu Ser Ser Gln Lys Thr Gln Cys Lys His Gln Leu
        900                 905                 910

Ala Ser Ile Ser Ser Pro Val Val Thr Ser Leu Leu Ile Asn Leu Gly
    915                 920                 925

Ser Pro Val Lys Glu Val Arg Arg Ala Ala Ile Gln Cys Leu Gln Ala
930                 935                 940

Leu Ser Gly Val Ala Ser Pro Phe Tyr Leu Ile Ile Asp His Leu Ile
945                 950                 955                 960

Ser Lys Ala Glu Glu Ile Thr Ser Asp Ala Ala Tyr Val Ile Gln Asp
            965                 970                 975

Leu Ala Thr Leu Phe Glu Glu Leu Gln Arg Glu Lys Lys Leu Lys Ser
        980                 985                 990

His Gln Lys Leu Ser Glu Thr Leu Lys Asn Leu Leu Ser Cys Val Tyr
    995                 1000                1005

Ser Cys Pro Ser Tyr Ile Ala Lys Asp Leu Met Lys Val Leu Gln Gly
    1010                1015                1020

Val Asn Gly Glu Met Val Leu Ser Gln Leu Leu Pro Met Ala Glu Gln
1025                1030                1035                1040

Leu Leu Glu Lys Ile Gln Lys Glu Pro Thr Ala Val Leu Lys Asp Glu
            1045                1050                1055

Ala Met Val Leu His Leu Thr Leu Gly Lys Tyr Asn Glu Phe Ser Val
        1060                1065                1070

Ser Leu Leu Asn Glu Asp Pro Lys Ser Leu Asp Ile Phe Ile Lys Ala
    1075                1080                1085

Val His Thr Thr Lys Glu Leu Tyr Ala Gly Met Pro Thr Ile Gln Ile
    1090                1095                1100

Thr Ala Leu Glu Lys Ile Thr Lys Pro Phe Phe Ala Ala Ile Ser Asp
1105                1110                1115                1120

Glu Lys Val Gln Gln Lys Leu Leu Arg Met Leu Phe Asp Leu Leu Val
            1125                1130                1135

Asn Cys Lys Asn Ser His Cys Ala Gln Thr Val Ser Ser Val Phe Lys
        1140                1145                1150

Gly Ile Ser Val Asn Ala Glu Gln Val Arg Ile Glu Leu Glu Pro Pro
    1155                1160                1165

Asp Lys Ala Lys Pro Leu Gly Thr Val Gln Gln Lys Arg Arg Gln Lys
    1170                1175                1180

Met Gln Gln Lys Lys Ser Gln Asp Leu Glu Ser Val Gln Glu Val Gly
1185                1190                1195                1200

Gly Ser Tyr Trp Gln Arg Val Thr Leu Ile Leu Glu Leu Leu Gln His
            1205                1210                1215

Lys Lys Lys Leu Arg Ser Pro Gln Ile Leu Val Pro Thr Leu Phe Asn
        1220                1225                1230

Leu Leu Ser Arg Cys Leu Glu Pro Leu Pro Gln Glu Gln Gly Asn Met
    1235                1240                1245

Glu Tyr Thr Lys Gln Leu Ile Leu Ser Cys Leu Leu Asn Ile Cys Gln
    1250                1255                1260

Lys Leu Ser Pro Asp Gly Gly Lys Ile Pro Lys Asp Ile Leu Asp Glu
1265                1270                1275                1280

Glu Lys Phe Asn Val Glu Leu Ile Val Gln Cys Ile Arg Leu Ser Glu
            1285                1290                1295

```
Met Pro Gln Thr His His His Ala Leu Leu Leu Gly Thr Val Ala
            1300                1305                1310

Gly Ile Phe Pro Asp Lys Val Leu His Asn Ile Met Ser Ile Phe Thr
            1315                1320                1325

Phe Met Gly Ala Asn Val Met Arg Leu Asp Asp Thr Tyr Ser Phe Gln
            1330                1335                1340

Val Ile Asn Lys Thr Val Lys Met Val Ile Pro Ala Leu Ile Gln Ser
1345                1350                1355                1360

Asp Ser Gly Asp Ser Ile Glu Val Ser Arg Asn Val Glu Glu Ile Val
            1365                1370                1375

Val Lys Ile Ile Ser Val Phe Val Asp Ala Leu Pro His Val Pro Glu
            1380                1385                1390

His Arg Arg Leu Pro Ile Leu Val Gln Leu Val Asp Thr Leu Gly Ala
            1395                1400                1405

Glu Lys Phe Leu Trp Ile Leu Ile Leu Leu Phe Glu Gln Tyr Val
            1410                1415                1420

Thr Lys Thr Val Leu Ala Ala Ala Tyr Gly Glu Lys Asp Ala Ile Leu
1425                1430                1435                1440

Glu Ala Asp Thr Glu Phe Trp Phe Ser Val Cys Cys Glu Phe Ser Val
            1445                1450                1455

Gln His Gln Ile Gln Ser Leu Met Asn Ile Leu Gln Tyr Leu Leu Lys
            1460                1465                1470

Leu Pro Glu Glu Lys Glu Glu Thr Ile Pro Lys Ala Val Ser Phe Asn
            1475                1480                1485

Lys Ser Glu Ser Gln Glu Glu Met Leu Gln Val Phe Asn Val Glu Thr
            1490                1495                1500

His Thr Ser Lys Gln Leu Arg His Phe Lys Phe Leu Ser Val Ser Phe
1505                1510                1515                1520

Met Ser Gln Leu Leu Ser Ser Asn Asn Phe Leu Lys Lys Val Val Glu
            1525                1530                1535

Ser Gly Gly Pro Glu Ile Leu Lys Gly Leu Glu Glu Arg Leu Leu Glu
            1540                1545                1550

Thr Val Leu Gly Tyr Ile Ser Ala Val Ala Gln Ser Met Glu Arg Asn
            1555                1560                1565

Ala Asp Lys Leu Thr Val Lys Phe Trp Arg Ala Leu Leu Ser Lys Ala
            1570                1575                1580

Tyr Asp Leu Leu Asp Lys Val Asn Ala Leu Leu Pro Thr Glu Thr Phe
1585                1590                1595                1600

Ile Pro Val Ile Arg Gly Leu Val Gly Asn Pro Leu Pro Ser Val Arg
            1605                1610                1615

Arg Lys Ala Leu Asp Leu Leu Asn Asn Lys Leu Gln Gln Asn Ile Ser
            1620                1625                1630

Trp Lys Lys Thr Ile Val Thr Arg Phe Leu Lys Leu Val Pro Asp Leu
            1635                1640                1645

Leu Ala Ile Val Gln Arg Lys Lys Lys Glu Gly Glu Glu Gln Ala
            1650                1655                1660

Ile Asn Arg Gln Thr Ala Leu Tyr Thr Leu Lys Leu Cys Lys Asn
1665                1670                1675                1680

Phe Gly Ala Glu Asn Pro Asp Pro Phe Val Pro Val Leu Xaa Thr Ala
            1685                1690                1695

Val Lys Leu Ile Ala Pro Glu Arg Lys Glu Glu Lys Asn Val Leu Gly
            1700                1705                1710

Ser Ala Leu Leu Cys Ile Ala Glu Val Thr Ser Thr Leu Glu Ala Leu
```

```
                    1715                1720                1725
Ala Ile Pro Gln Leu Pro Ser Leu Met Pro Ser Leu Leu Thr Thr Met
                    1730                1735                1740
Lys Asn Thr Ser Glu Leu Val Ser Ser Glu Val Tyr Leu Leu Ser Ala
1745                1750                1755                1760
Leu Ala Ala Leu Gln Lys Val Val Glu Thr Leu Pro His Phe Ile Ser
                    1765                1770                1775
Pro Tyr Leu Glu Gly Ile Leu Ser Gln Val Ile His Leu Glu Lys Ile
                    1780                1785                1790
Thr Ser Glu Met Gly Ser Ala Ser Gln Ala Asn Ile Arg Leu Thr Ser
                    1795                1800                1805
Leu Lys Lys Thr Leu Ala Thr Thr Leu Ala Pro Arg Val Leu Leu Pro
            1810                1815                1820
Ala Ile Lys Lys Thr Tyr Lys Gln Ile Glu Lys Asn Trp Lys Asn His
1825                1830                1835                1840
Met Gly Pro Phe Met Ser Ile Leu Gln Glu His Ile Gly Xaa Met Lys
                    1845                1850                1855
Lys Glu Glu Leu Thr Ser His Gln Ser Gln Leu Thr Ala Phe Phe Leu
                    1860                1865                1870
Glu Ala Leu Asp Phe Arg Ala Gln His Ser Glu Asn Asp Leu Glu Glu
            1875                1880                1885
Val Gly Lys Thr Glu Asn Cys Ile Ile Asp Cys Leu Val Ala Met Val
            1890                1895                1900
Val Lys Leu Ser Glu Val Thr Phe Arg Pro Leu Phe Phe Lys Leu Phe
1905                1910                1915                1920
Asp Trp Ala Lys Thr Glu Asp Ala Pro Lys Asp Arg Leu Leu Thr Phe
                    1925                1930                1935
Tyr Asn Leu Ala Asp Cys Ile Ala Glu Lys Leu Lys Gly Leu Phe Thr
            1940                1945                1950
Leu Phe Ala Gly His Leu Val Lys Pro Phe Ala Asp Thr Leu Xaa Gln
            1955                1960                1965
Val Asn Ile Ser Lys Thr Asp Glu Ala Phe Phe Asp Ser Glu Asn Asp
            1970                1975                1980
Pro Glu Lys Cys Cys Leu Leu Leu Gln Phe Ile Leu Asn Cys Leu Tyr
1985                1990                1995                2000
Lys Ile Phe Leu Phe Asp Thr Gln His Phe Ile Ser Lys Glu Arg Ala
                    2005                2010                2015
Xaa Ala Leu Met Met Pro Leu Val Asp Gln Leu Glu Asn Arg Leu Gly
                    2020                2025                2030
Gly Glu Glu Lys Phe Gln Glu Arg Val Thr Lys His Leu Ile Pro Cys
                    2035                2040                2045
Ile Ala Gln Phe Ser Val Ala Met Ala Asp Asp Ser Leu Trp Lys Pro
                    2050                2055                2060
Leu Asn Tyr Gln Ile Leu Leu Lys Thr Arg Asp Ser Ser Pro Lys Val
2065                2070                2075                2080
Arg Phe Ala Ala Leu Ile Thr Val Leu Ala Leu Ala Glu Lys Leu Lys
                    2085                2090                2095
Glu Asn Tyr Ile Val Leu Leu Pro Glu Ser Ile Pro Phe Leu Ala Glu
                    2100                2105                2110
Leu Met Glu Asp Glu Cys Glu Glu Val Glu His Gln Cys Gln Lys Thr
                    2115                2120                2125
Ile Gln Gln Leu Glu Thr Val Leu Gly Glu Pro Leu Gln Ser Tyr Phe
                    2130                2135                2140
```

```
<210> SEQ ID NO 6
<211> LENGTH: 5406
<212> TYPE: DNA
<213> ORGANISM: Homo sapiens
<220> FEATURE:
<221> NAME/KEY: 5'UTR
<222> LOCATION: 1..198
<220> FEATURE:
<221> NAME/KEY: CDS
<222> LOCATION: 199..1149
<220> FEATURE:
<221> NAME/KEY: 3'UTR
<222> LOCATION: 1150..5406
<220> FEATURE:
<221> NAME/KEY: polyA_signal
<222> LOCATION: 5384..5389

<400> SEQUENCE: 6
```

| | | |
|---|---|---|
| ccgcccacgg acgccagagc cgggaaccct gacggcactt agctgctgac aaacaacctg | | 60 |
| ctccgtggag cgcctgaaac accagtcttt ggggccagtg cctcagtttc aatccaggta | | 120 |
| acctttaaat gaaacttgcc taaaatctta ggtcatacac agaagagact ccaatcgaca | | 180 |

| agaagctgga aagaatg | atg ttg tcc tta aac aac cta cag aat atc atc | 231 |
|---|---|---|
| | Met Leu Ser Leu Asn Asn Leu Gln Asn Ile Ile | |
| | 1               5                  10 | |

| tat aac ccg gta atc ccg tat gtt ggc acc att ccc gat cag ctg gat | 279 |
|---|---|
| Tyr Asn Pro Val Ile Pro Tyr Val Gly Thr Ile Pro Asp Gln Leu Asp | |
|        15              20              25 | |

| cct gga act ttg att gtg ata tgt ggg cat gtt cct agt gac gca gac | 327 |
|---|---|
| Pro Gly Thr Leu Ile Val Ile Cys Gly His Val Pro Ser Asp Ala Asp | |
|        30              35              40 | |

| aga ttc cag gtg gat ctg cag aat ggc agc agt gtg aaa cct cga gcc | 375 |
|---|---|
| Arg Phe Gln Val Asp Leu Gln Asn Gly Ser Ser Val Lys Pro Arg Ala | |
| 45              50              55 | |

| gat gtg gcc ttt cat ttc aat cct cgt ttc aaa agg gcc ggc tgc att | 423 |
|---|---|
| Asp Val Ala Phe His Phe Asn Pro Arg Phe Lys Arg Ala Gly Cys Ile | |
| 60              65              70              75 | |

| gtt tgc aat act ttg ata aat gaa aaa tgg gga cgg gaa gag atc acc | 471 |
|---|---|
| Val Cys Asn Thr Leu Ile Asn Glu Lys Trp Gly Arg Glu Glu Ile Thr | |
|        80              85              90 | |

| tat gac acg cct ttc aaa aga gaa aag tct ttt gag atc gtg att atg | 519 |
|---|---|
| Tyr Asp Thr Pro Phe Lys Arg Glu Lys Ser Phe Glu Ile Val Ile Met | |
|        95              100             105 | |

| gtg cta aag gac aaa ttc cag gtg gct gta aat gga aaa cat act ctg | 567 |
|---|---|
| Val Leu Lys Asp Lys Phe Gln Val Ala Val Asn Gly Lys His Thr Leu | |
|        110             115             120 | |

| ctc tat ggc cac agg atc ggc cca gag aaa ata gac act ctg ggc att | 615 |
|---|---|
| Leu Tyr Gly His Arg Ile Gly Pro Glu Lys Ile Asp Thr Leu Gly Ile | |
|        125             130             135 | |

| tat ggc aaa gtg aat att cac tca att ggt ttt agc ttc agc tcg gac | 663 |
|---|---|
| Tyr Gly Lys Val Asn Ile His Ser Ile Gly Phe Ser Phe Ser Ser Asp | |
| 140             145             150             155 | |

| tta caa agt acc caa gca tct agt ctg gaa ctg aca gag ata agt aga | 711 |
|---|---|
| Leu Gln Ser Thr Gln Ala Ser Ser Leu Glu Leu Thr Glu Ile Ser Arg | |
|        160             165             170 | |

| gaa aat gtt cca aag tct ggc acg ccc cag ctt agc ctg cca ttc gct | 759 |
|---|---|
| Glu Asn Val Pro Lys Ser Gly Thr Pro Gln Leu Ser Leu Pro Phe Ala | |
|        175             180             185 | |

| gca agg ttg aac acc ccc atg ggc cct gga cga act gtc gtc gtt aaa | 807 |
|---|---|
| Ala Arg Leu Asn Thr Pro Met Gly Pro Gly Arg Thr Val Val Val Lys | |
|        190             195             200 | |

| gga gaa gtg aat gca aat gcc aaa agc ttt aat gtt gac cta cta gca | 855 |
|---|---|
| Gly Glu Val Asn Ala Asn Ala Lys Ser Phe Asn Val Asp Leu Leu Ala | |

```
                        205                 210                 215
gga aaa tca aag gat att gct cta cac ttg aac cca cgc ctg aat att    903
Gly Lys Ser Lys Asp Ile Ala Leu His Leu Asn Pro Arg Leu Asn Ile
220                 225                 230                 235 aaa gca ttt gta aga aat tct ttt ctt cag gag tcc tgg gga gaa gaa    951
Lys Ala Phe Val Arg Asn Ser Phe Leu Gln Glu Ser Trp Gly Glu Glu
                240                 245                 250 gag aga aat att acc tct ttc cca ttt agt cct ggg atg tac ttt gag    999
Glu Arg Asn Ile Thr Ser Phe Pro Phe Ser Pro Gly Met Tyr Phe Glu
            255                 260                 265 atg ata att tac tgt gat gtt aga gaa ttc aag gtt gca gta aat ggc   1047
Met Ile Ile Tyr Cys Asp Val Arg Glu Phe Lys Val Ala Val Asn Gly
        270                 275                 280 gta cac agc ctg gag tac aaa cac aga ttt aaa gag ctc agc agt att   1095
Val His Ser Leu Glu Tyr Lys His Arg Phe Lys Glu Leu Ser Ser Ile
    285                 290                 295 gac acg ctg gaa att aat gga gac atc cac tta ctg gaa gta agg agc   1143
Asp Thr Leu Glu Ile Asn Gly Asp Ile His Leu Leu Glu Val Arg Ser
300                 305                 310                 315 tgg tag cctacctaca cagctgctac aaaaaccaaa atacagaatg gcttctgtga   1199
Trp * tactggcctt gctgaaacgc atctcactgt cattctattg tttatattgt taaaatgagc   1259
ttgtgcacca ttagatcctg ctgggtgttc tcagtccttg ccatgaagta tggtggtgtc   1319
tagcactgaa tggggaaact gggggcagca acacttatag ccagttaaag ccactctgcc   1379
ctctctccta ctttggctga ctcttcaaga atgccattca acaagtattt atggagtacc   1439
tactataata cagtagctaa catgtattga gcacagattt ttttggtaa aactgtgagg   1499
agctaggata tacttggt gaaacaaacc agtatgttcc ctgttctctt gagcttcgac   1559
tcttctgtgc tctattgctg cgcactgctt tttctacagg cattacatca actcctaagg   1619
ggtcctctgg gattagttaa gcagctatta aatcacccga agacactaat ttacagaaga   1679
cacaactcct tccccagtga tcactgtcat aaccagtgct ctaccgtatc ccatcactga   1739
ggactgatgt tgactgacat cattttatcg taataaacat gtggctctat tagctgcaag   1799
ctttaccaag taattggcat gacatctgag cacagaaatt aaggcaaaaa accaaagcaa   1859
aacaaataca tggtgctgaa attaacttga tgccaagccc aaggcagctg atttctgtgt   1919
atttgaactt agggcaaatc agagtctaca cagacgccta cagaaagttt caggaagagg   1979
caagatgcat tcaatttgaa agatatttat gggcaacaaa gtaaggtcag gattagactt   2039
caggcattca taaggcaggc actatcagaa agtgtacgcc aactaaggga cccacaaagc   2099
aggcagaggt aatgcagaaa tctgttttgt tcccatgaaa tcaccaatca aggcctccgt   2159
tcttctaaag attagtccat catcattagc aactgagatc aaagcactct tccactttac   2219
gtgattaaaa tcaaacctgt atcagcaagt taaatggttc catttctgtg attttttctat   2279
tatttgaggg gagttggcag aagttccatg tatatgggat ctttacaggt cagatcttgt   2339
tacaggaaat ttcaaaggtt tgggagtggg gagggaaaaa agctcagtca gtgaggatca   2399
ttttatcaca ttagactggg gcagaactct gccaggattt aggaatattt tcagaacaga   2459
ttttagatat tatttctatc catatattga aaagaatacc attgtcaatc ttatttttt   2519
aaaagtactc agtgtagaaa ttgctagccc ttaattcttt tccagctttt catattaatg   2579
tatgcagagt ctcaccaagc tcaaagacac tggttggggg tggagggtgc cacagggaaa   2639
gctgtagaag gcaagaagac tcgagaatcc cccagagtta ttttctcca taaagaccat   2699
cagagtgctt aactgagctg ttggagactg tgaggcattt aggaaaaaaa tagcccactc   2759
```

```
acatcattcc ttgtaagtct aagttcatt ttcattttac gtggaggaaa aaaatttaaa    2819
aagctattag tatttattaa tgaattttac tgagacattt cttagaaata tgcacttcta    2879
tactagcaag ctctgtctct aaaatgcaag ttggccttt  gcttgccaca tttctgcatt    2939
aaacttctat attagcttca aaggctttta aactcaatgc gaacattcta cgggatgttc    2999
ttagatgcct ttaaaaaggg ggcagatcta attttatttg aaccctcact ttccaacttc    3059
accatgaccc agtactagag attagggcac ttcaaagcat tgaaaaaaat ctactgatac    3119
ttactttctt agacaagtag ttcttagtta accaccaatg gaactgggtt cattctgaat    3179
cctggaggag cttcctcgtg ccacccagtg tttctgggcc ctctgtgtga gcagccaggt    3239
atgagctgtt ttagaagcag cgtgttgcct tcatctctcc cgtttcccaa agaacaaag    3299 gataaaggtg acagtcacac tcctgggtta aaaaaagcat tccagaacca cttctcttta    3359
tgggcacaac aaagaaacga aggctgaagt tcgcctaccc aaaatgaaaa gtaggcttta    3419
cagtcaaaag tacttctgtt gattgctaaa taacttcatt ttcttgaaat agagcaactt    3479
tgagtgaaat ctgcaacatg gataccatgt atataagata ctgctgtaca gaagagttaa    3539
ggcttacagt gcaaatgagg cgtcagcttt gggtgctaaa attaacaagt ctaatattat    3599
taccatcaat caggaagaga ataataaatg tttaaacaaa cacagcagtc tgtataaaaa    3659
taccgtgtat catttactct ttctgcagct ctatacgata ggcaggagag cttatgtgg    3719 cagcacaagc caggtgggga ttttgtaacg aagtgataaa acatttgtaa gtaatccaag    3779
taggtgtatt aaggcaccaa aagtaacatg gcacccaaca cccaaaaata aaaatatgaa    3839
atatgagtgt gaactctgag tagagtatga acaccacag  aaagtcttag aaatagctct    3899
ggagtggctc tcccaggaca gtttccagtt gctgaatagt cttttggcac tgatgttcta    3959
cttcttcaca ttcatctaaa aaaaaaaaa  aaaaaaatca aaattaaaat ctgagtcagt    4019
ctgcctgcct cggttctcat tagtttaatt cttaatgcct tgcactttcc agcaatcatt    4079
caatcaaaag agtgaaatga agcacattaa caaagcagga ggcgccacgg accgcctccc    4139
tccacaccgc tccttccgcc ttcattcctt gcccacaggc ttgcactgga agctgaataa    4199
gaatccccaa aactcaaact tcctagggat gccacccctt tagtagctca cacctccccc    4259
ctccaagagc taagaaacaa aggagaatgt acttttgtag cttagataag caatgaatca    4319
gtaaaggact gatctacttg ctccaccacc cctcccttaa taataacatt tactgttatt    4379
tcctgggcct aagacttatg ttccagaact gtcacagctc cccatgtcac acccactagc    4439
ttgtgatctt tgtcaaataa ctgaaatctt ttaagcctct agtttcttcc tttgtaaaac    4499
agagataaaa tgttgtggtt tttaagtgag ataatccaag taaagcacct aacatggagt    4559
agtgaatgaa catcggttgc tactaaaagt ggacatccta ccgcatcctt aatgccacta    4619
ggcatttcca tacaatctgg ggaccaaaac ttcaatcata taaatgtatg aggttaatta    4679
aaaacactac tgtaatctgc ttgtatgatc acaaaccacc acaaagaaa  agatcgtgaa    4739 gattacactg taaacggact ctcaaatgat caggaggtgg tcacttcgca acttgctccc    4799
tccacccaac tcaaaacagg agctcgagcc tgcctgtatt tgagactgga gctgcctgta    4859
tgaggactgg atcaactgct agtcacgtta tatccaaatc tgcattatca ttgggcacat    4919
tttcacagaa ttttactgaa ttattcctta attgtttaat ggtgggaat  agtttgggaa    4979 ttaccttcca tcaactctgc taagaaagga atggattctg gtagcaagac aatataattc    5039
tcctttagtt tttcagccag tgctaacaca gtaatcaaag cagcaaatcg aacctgaaag    5099
ggataaaaga gcaaagaaat aaaaagtagt gttactgtat ttattatctt aagagctgta    5159
```

```
ctgacttgag acaagctcta acttttaaa cattagttca cacgcgttta ttcacttcat   5219
tatgttcatt aagctttcat cttagaatac cagtttcacc atttgggagc tgtttgtaat   5279
atgtgcaacc ttataaatag tgttttccaa actgtgtccc aggactgcaa atctttaatg   5339
tgaaatgtct ttttataatc tcttccttta aaaaaaacca ataaaataaa atgccacatg   5399
caaactc                                                              5406

<210> SEQ ID NO 7
<211> LENGTH: 5532
<212> TYPE: DNA
<213> ORGANISM: Homo sapiens
<220> FEATURE:
<221> NAME/KEY: 5'UTR
<222> LOCATION: 1..198
<220> FEATURE:
<221> NAME/KEY: CDS
<222> LOCATION: 199..1275
<220> FEATURE:
<221> NAME/KEY: 3'UTR
<222> LOCATION: 1276..5532
<220> FEATURE:
<221> NAME/KEY: polyA_signal
<222> LOCATION: 5510..5515

<400> SEQUENCE: 7
ccgcccacgg acgccagagc cgggaaccct gacggcactt agctgctgac aaacaacctg    60
ctccgtggag cgcctgaaac accagtcttt ggggccagtg cctcagtttc aatccaggta   120
acctttaaat gaaacttgcc taaaatctta ggtcatacac agaagagact ccaatcgaca   180
```

| agaagctgga aaagaatg atg ttg tcc tta aac aac cta cag aat atc atc<br>Met Leu Ser Leu Asn Asn Leu Gln Asn Ile Ile<br>1                5               10 | 231 |
|---|---|
| tat aac ccg gta atc ccg tat gtt ggc acc att ccc gat cag ctg gat<br>Tyr Asn Pro Val Ile Pro Tyr Val Gly Thr Ile Pro Asp Gln Leu Asp<br>           15               20               25 | 279 |
| cct gga act ttg att gtg ata tgt ggg cat gtt cct agt gac gca gac<br>Pro Gly Thr Leu Ile Val Ile Cys Gly His Val Pro Ser Asp Ala Asp<br>           30               35               40 | 327 |
| aga ttc cag gtg gat ctg cag aat ggc agc agt gtg aaa cct cga gcc<br>Arg Phe Gln Val Asp Leu Gln Asn Gly Ser Ser Val Lys Pro Arg Ala<br>     45               50               55 | 375 |
| gat gtg gcc ttt cat ttc aat cct cgt ttc aaa agg gcc ggc tgc att<br>Asp Val Ala Phe His Phe Asn Pro Arg Phe Lys Arg Ala Gly Cys Ile<br>60               65               70               75 | 423 |
| gtt tgc aat act ttg ata aat gaa aaa tgg gga cgg gaa gag atc acc<br>Val Cys Asn Thr Leu Ile Asn Glu Lys Trp Gly Arg Glu Glu Ile Thr<br>              80               85               90 | 471 |
| tat gac acg cct ttc aaa aga gaa aag tct ttt gag atc gtg att atg<br>Tyr Asp Thr Pro Phe Lys Arg Glu Lys Ser Phe Glu Ile Val Ile Met<br>           95               100              105 | 519 |
| gtg cta aag gac aaa ttc cag gtg gct gta aat gga aaa cat act ctg<br>Val Leu Lys Asp Lys Phe Gln Val Ala Val Asn Gly Lys His Thr Leu<br>             110              115              120 | 567 |
| ctc tat ggc cac agg atc ggc cca gag aaa ata gac act ctg ggc att<br>Leu Tyr Gly His Arg Ile Gly Pro Glu Lys Ile Asp Thr Leu Gly Ile<br>           125              130              135 | 615 |
| tat ggc aaa gtg aat att cac tca att ggt ttt agc ttc agc tcg gac<br>Tyr Gly Lys Val Asn Ile His Ser Ile Gly Phe Ser Phe Ser Ser Asp<br>140              145              150              155 | 663 |
| tta caa agt acc caa gca tct agt ctg gaa ctg aca gag ata agt aga<br>Leu Gln Ser Thr Gln Ala Ser Ser Leu Glu Leu Thr Glu Ile Ser Arg<br>             160              165              170 | 711 |

```
gaa aat gtt cca aag tct ggc acg ccc cag ctt cct agt aat aga gga      759
Glu Asn Val Pro Lys Ser Gly Thr Pro Gln Leu Pro Ser Asn Arg Gly
            175                 180                 185 gga gac att tct aaa atc gca ccc aga act gtc tac acc aag agc aaa      807
Gly Asp Ile Ser Lys Ile Ala Pro Arg Thr Val Tyr Thr Lys Ser Lys
            190                 195                 200 gat tcg act gtc aat cac act ttg act tgc acc aaa ata cca cct atg      855
Asp Ser Thr Val Asn His Thr Leu Thr Cys Thr Lys Ile Pro Pro Met
    205                 210                 215 aac tat gtg tca aag agc ctg cca ttc gct gca agg ttg aac acc ccc      903
Asn Tyr Val Ser Lys Ser Leu Pro Phe Ala Ala Arg Leu Asn Thr Pro
220                 225                 230                 235 atg ggc cct gga cga act gtc gtc gtt aaa gga gaa gtg aat gca aat      951
Met Gly Pro Gly Arg Thr Val Val Val Lys Gly Glu Val Asn Ala Asn
                240                 245                 250 gcc aaa agc ttt aat gtt gac cta cta gca gga aaa tca aag gat att      999
Ala Lys Ser Phe Asn Val Asp Leu Leu Ala Gly Lys Ser Lys Asp Ile
            255                 260                 265 gct cta cac ttg aac cca cgc ctg aat att aaa gca ttt gta aga aat     1047
Ala Leu His Leu Asn Pro Arg Leu Asn Ile Lys Ala Phe Val Arg Asn
        270                 275                 280 tct ttt ctt cag gag tcc tgg gga gaa gaa gag aga aat att acc tct     1095
Ser Phe Leu Gln Glu Ser Trp Gly Glu Glu Glu Arg Asn Ile Thr Ser
    285                 290                 295 ttc cca ttt agt cct ggg atg tac ttt gag atg ata att tac tgt gat     1143
Phe Pro Phe Ser Pro Gly Met Tyr Phe Glu Met Ile Ile Tyr Cys Asp
300                 305                 310                 315 gtt aga gaa ttc aag gtt gca gta aat ggc gta cac agc ctg gag tac     1191
Val Arg Glu Phe Lys Val Ala Val Asn Gly Val His Ser Leu Glu Tyr
                320                 325                 330 aaa cac aga ttt aaa gag ctc agc agt att gac acg ctg gaa att aat     1239
Lys His Arg Phe Lys Glu Leu Ser Ser Ile Asp Thr Leu Glu Ile Asn
            335                 340                 345 gga gac atc cac tta ctg gaa gta agg agc tgg tag cctacctaca           1285
Gly Asp Ile His Leu Leu Glu Val Arg Ser Trp *
        350                 355 cagctgctac aaaaaccaaa atacagaatg gcttctgtga tactggcctt gctgaaacgc   1345
atctcactgt cattctattg tttatattgt taaaatgagc ttgtgcacca ttagatcctg   1405
ctgggtgttc tcagtccttg ccatgaagta tggtggtgtc tagcactgaa tggggaaact   1465
gggggcagca acacttatag ccagttaaag ccactctgcc ctctctccta ctttggctga   1525
ctcttcaaga atgccattca acaagtattt atggagtacc tactataata cagtagctaa   1585
catgtattga gcacagattt ttttggtaa aactgtgagg agctaggata tatacttggt    1645
gaaacaaacc agtatgttcc ctgttctctt gagcttcgac tcttctgtgc tctattgctg   1705
cgcactgctt tttctacagg cattacatca actcctaagg ggtcctctgg gattagttaa   1765
gcagctatta aatcacccga agacactaat ttacagaaga cacaactcct tccccagtga   1825
tcactgtcat aaccagtgct ctaccgtatc ccatcactga ggactgatgt tgactgacat   1885
cattttatcg taataaacat gtggctctat tagctgcaag ctttaccaag taattggcat   1945
gacatctgag cacagaaatt aaggcaaaaa accaaagcaa aacaaataca tggtgctgaa   2005
attaacttga tgccaagccc aaggcagctg atttctgtgt atttgaactt agggcaaatc   2065
agagtctaca cagacgccta cagaaagttt caggaagagg caagatgcat tcaatttgaa   2125
agatatttat gggcaacaaa gtaaggtcag gattagactt caggcattca taaggcaggc   2185
actatcagaa agtgtacgcc aactaaggga cccacaaagc aggcagaggt aatgcagaaa   2245
```

```
tctgttttgt tcccatgaaa tcaccaatca aggcctccgt tcttctaaag attagtccat    2305
catcattagc aactgagatc aaagcactct tccactttac gtgattaaaa tcaaacctgt    2365
atcagcaagt taaatggttc catttctgtg attttttctat tatttgaggg gagttggcag   2425
aagttccatg tatatgggat ctttacaggt cagatcttgt tacaggaaat ttcaaaggtt    2485
tgggagtggg gagggaaaaa agctcagtca gtgaggatca ttttatcaca ttagactggg    2545
gcagaactct gccaggattt aggaatattt tcagaacaga ttttagatat tatttctatc    2605
catatattga aaagaatacc attgtcaatc ttatttttt aaaagtactc agtgtagaaa     2665
ttgctagccc ttaattcttt tccagctttt catattaatg tatgcagagt ctcaccaagc    2725
tcaaagacac tggttggggg tggagggtgc cacaggaaa gctgtagaag gcaagaagac     2785
tcgagaatcc cccagagtta ttttctcca taaagaccat cagagtgctt aactgagctg     2845
ttggagactg tgaggcattt aggaaaaaaa tagcccactc acatcattcc ttgtaagtct    2905
taagttcatt ttcattttac gtggaggaaa aaatttaaa aagctattag tatttattaa     2965
tgaattttac tgagacattt cttagaaata tgcacttcta tactagcaag ctctgtctct    3025
aaaatgcaag ttggccttt gcttgccaca tttctgcatt aaacttctat attagcttca    3085 aaggcttta aactcaatgc gaacattcta cgggatgttc ttagatgcct ttaaaaggg     3145 ggcagatcta atttttatttg aaccctcact ttccaacttc accatgaccc agtactagag   3205
attagggcac ttcaaagcat tgaaaaaaat ctactgatac ttactttctt agacaagtag    3265
ttcttagtta accaccaatg gaactgggtt cattctgaat cctggaggag cttcctcgtg    3325
ccacccagtg tttctgggcc ctctgtgtga gcagccaggt atgagctgtt ttagaagcag    3385
cgtgttgcct tcatctctcc cgtttcccaa aagaacaaag gataaaggtg acagtcacac    3445
tcctgggtta aaaaagcat tccagaacca cttctcttta tgggcacaac aaagaaacga    3505
aggctgaagt tcgcctaccc aaaatgaaaa gtaggcttta cagtcaaaag tacttctgtt    3565
gattgctaaa taacttcatt ttcttgaaat agagcaactt tgagtgaaat ctgcaacatg    3625
gataccatgt atataagata ctgctgtaca gaagagttaa ggcttacagt gcaaatgagg    3685
cgtcagcttt gggtgctaaa attaacaagt ctaatattat taccatcaat caggaagaga    3745
ataataaatg tttaaacaaa cacagcagtc tgtataaaaa taccgtgtat catttactct    3805
ttctgcagct ctatacgata ggcaggagag gcttatgtgg cagcacaagc caggtgggga    3865
ttttgtaacg aagtgataaa acatttgtaa gtaatccaag taggtgtatt aaggcaccaa    3925
aagtaacatg gcacccaaca cccaaaaata aaaatatgaa atatgagtgt gaactctgag    3985
tagagtatga acaccacag aaagtcttag aaatagctct ggagtggctc tcccaggaca    4045
gtttccagtt gctgaatagt cttttggcac tgatgttcta cttcttcaca ttcatctaaa    4105
aaaaaaaaaa aaaaaaatca aaattaaaat ctgagtcagt ctgcctgcct cggttctcat    4165
tagtttaatt cttaatgcct tgcactttcc agcaatcatt caatcaaaag agtgaaatga    4225
agcacattaa caaagcagga ggcgccacgg accgcctccc tccacaccgc tccttccgcc    4285
ttcattcctt gcccacaggc ttgcactgga agctgaataa gaatccccaa aactcaaact    4345
tcctagggat gccaccccctt tagtagctca cacctccccc ctccaagagc taagaaacaa    4405
aggagaatgt acttttgtag cttagataag caatgaatca gtaaaggact gatctacttg    4465
ctccaccacc cctcccttaa taataacatt tactgttatt tcctgggcct aagacttatg    4525
ttccagaact gtcacagctc cccatgtcac acccactagc ttgtgatctt tgtcaaataa    4585
ctgaaatctt ttaagcctct agtttcttcc tttgtaaaac agagataaaa tgttgtggtt    4645
```

```
tttaagtgag ataatccaag taaagcacct aacatggagt agtgaatgaa catcggttgc    4705
tactaaaagt ggacatccta ccgcatcctt aatgccacta ggcatttcca tacaatctgg    4765
ggaccaaaac ttcaatcata taatgtatg aggttaatta aaaacactac tgtaatctgc    4825
ttgtatgatc acaaccacc acaaaagaaa agatcgtgaa gattacactg taaacggact    4885
ctcaaatgat caggaggtgg tcacttcgca acttgctccc tccacccaac tcaaaacagg    4945
agctcgagcc tgcctgtatt tgagactgga gctgcctgta tgaggactgg atcaactgct    5005
agtcacgtta tatccaaatc tgcattatca ttgggcacat tttcacagaa ttttactgaa    5065
ttattcctta attgtttaat ggttgggaat agtttgggaa ttaccttcca tcaactctgc    5125
taagaaagga atggattctg gtagcaagac aatataattc tcctttagtt tttcagccag    5185
tgctaacaca gtaatcaaag cagcaaatcg aacctgaaag ggataaaaga gcaaagaaat    5245
aaaaagtagt gttactgtat ttattatctt aagagctgta ctgacttgag acaagctcta    5305 acttttaaa cattagttca cacgcgttta ttcacttcat tatgttcatt aagctttcat    5365
cttagaatac cagtttcacc atttgggagc tgtttgtaat atgtgcaacc ttataaatag    5425
tgttttccaa actgtgtccc aggactgcaa atctttaatg tgaaatgtct ttttataatc    5485 tcttcctta aaaaaaacca ataaaataaa atgccacatg caaactc                  5532
```

```
<210> SEQ ID NO 8
<211> LENGTH: 2469
<212> TYPE: DNA
<213> ORGANISM: Homo sapiens
<220> FEATURE:
<221> NAME/KEY: 5'UTR
<222> LOCATION: 1..198
<220> FEATURE:
<221> NAME/KEY: CDS
<222> LOCATION: 199..1305
<220> FEATURE:
<221> NAME/KEY: 3'UTR
<222> LOCATION: 1306..2469

<400> SEQUENCE: 8
```

```
ccgcccacgg acgccagagc cgggaaccct gacggcactt agctgctgac aaacaacctg     60
ctccgtggag cgcctgaaac accagtcttt ggggccagtg cctcagtttc aatccaggta    120
acctttaaat gaaacttgcc taaaatctta ggtcatacac agaagagact ccaatcgaca    180
agaagctgga aaagaatg atg ttg tcc tta aac aac cta cag aat atc atc       231
                    Met Leu Ser Leu Asn Asn Leu Gln Asn Ile Ile
                     1               5                  10 tat aac ccg gta atc ccg tat gtt ggc acc att ccc gat cag ctg gat       279
Tyr Asn Pro Val Ile Pro Tyr Val Gly Thr Ile Pro Asp Gln Leu Asp
         15                  20                  25 cct gga act ttg att gtg ata tgt ggg cat gtt cct agt gac gca gac       327
Pro Gly Thr Leu Ile Val Ile Cys Gly His Val Pro Ser Asp Ala Asp
     30                  35                  40 aga ttc cag gtg gat ctg cag aat ggc agc agt gtg aaa cct cga gcc       375
Arg Phe Gln Val Asp Leu Gln Asn Gly Ser Ser Val Lys Pro Arg Ala
 45                  50                  55 gat gtg gcc ttt cat ttc aat cct cgt ttc aaa agg gcc ggc tgc att       423
Asp Val Ala Phe His Phe Asn Pro Arg Phe Lys Arg Ala Gly Cys Ile
 60                  65                  70                  75 gtt tgc aat act ttg ata aat gaa aaa tgg gga cgg gaa gag atc acc       471
Val Cys Asn Thr Leu Ile Asn Glu Lys Trp Gly Arg Glu Glu Ile Thr
             80                  85                  90 tat gac acg cct ttc aaa aga gaa aag tct ttt gag atc gtg att atg       519
Tyr Asp Thr Pro Phe Lys Arg Glu Lys Ser Phe Glu Ile Val Ile Met
         95                 100                 105
```

-continued

```
                      95                      100                     105
gtg cta aag gac aaa ttc cag gtg gct gta aat gga aaa cat act ctg       567
Val Leu Lys Asp Lys Phe Gln Val Ala Val Asn Gly Lys His Thr Leu
            110                     115                     120 ctc tat ggc cac agg atc ggc cca gag aaa ata gac act ctg ggc att       615
Leu Tyr Gly His Arg Ile Gly Pro Glu Lys Ile Asp Thr Leu Gly Ile
125                     130                     135 tat ggc aaa gtg aat att cac tca att ggt ttt agc ttc agc tcg gac       663
Tyr Gly Lys Val Asn Ile His Ser Ile Gly Phe Ser Phe Ser Ser Asp
140                     145                     150                 155 tta caa agt acc caa gca tct agt ctg gaa ctg aca gag ata agt aga       711
Leu Gln Ser Thr Gln Ala Ser Ser Leu Glu Leu Thr Glu Ile Ser Arg
            160                     165                     170 gaa aat gtt cca aag tct ggc acg ccc cag ctt agc ctg cca ttc gct       759
Glu Asn Val Pro Lys Ser Gly Thr Pro Gln Leu Ser Leu Pro Phe Ala
            175                     180                     185 gca agg ttg aac acc ccc atg ggc cct gga cga act gtc gtc gtt aaa       807
Ala Arg Leu Asn Thr Pro Met Gly Pro Gly Arg Thr Val Val Val Lys
            190                     195                     200 gga gaa gtg aat gca aat gcc aaa agc ttt aat gtt gac cta cta gca       855
Gly Glu Val Asn Ala Asn Ala Lys Ser Phe Asn Val Asp Leu Leu Ala
205                     210                     215 gga aaa tca aag gat att gct cta cac ttg aac cca cgc ctg aat att       903
Gly Lys Ser Lys Asp Ile Ala Leu His Leu Asn Pro Arg Leu Asn Ile
220                     225                     230                 235 aaa gca ttt gta aga aat tct ttt ctt cag gag tcc tgg gga gaa gaa       951
Lys Ala Phe Val Arg Asn Ser Phe Leu Gln Glu Ser Trp Gly Glu Glu
            240                     245                     250 gag aga aat att acc tct ttc cca ttt agt cct ggg atg tac ttt gag       999
Glu Arg Asn Ile Thr Ser Phe Pro Phe Ser Pro Gly Met Tyr Phe Glu
            255                     260                     265 atg ata att tac tgt gat gtt aga gaa ttc aag gtt gca gta aat ggc      1047
Met Ile Ile Tyr Cys Asp Val Arg Glu Phe Lys Val Ala Val Asn Gly
            270                     275                     280 gta cac agc ctg gag tac aaa cac aga ttt aaa gag ctc agc agt att      1095
Val His Ser Leu Glu Tyr Lys His Arg Phe Lys Glu Leu Ser Ser Ile
285                     290                     295 gac acg ctg gaa att aat gga gac atc cac tta ctg gaa caa tca ttc      1143
Asp Thr Leu Glu Ile Asn Gly Asp Ile His Leu Leu Glu Gln Ser Phe
300                     305                     310                 315 aat caa aag agt gaa atg aag cac att aac aaa gca gga ggc gcc acg      1191
Asn Gln Lys Ser Glu Met Lys His Ile Asn Lys Ala Gly Gly Ala Thr
            320                     325                     330 gac cgc ctc cct cca cac cgc tcc ttc cgc ctt cat tcc ttg ccc aca      1239
Asp Arg Leu Pro Pro His Arg Ser Phe Arg Leu His Ser Leu Pro Thr
            335                     340                     345 ggc ttg cac tgg aag ctg aat aag aat ccc caa aac tca aac ttc cta      1287
Gly Leu His Trp Lys Leu Asn Lys Asn Pro Gln Asn Ser Asn Phe Leu
            350                     355                     360 ggg atg cca ccc ctt tag tagctcacac ctccccctc caagagctaa              1335
Gly Met Pro Pro Leu  *
365 gaaacaaagg agaatgtact tttgtagctt agataagcaa tgaatcagta aaggactgat    1395 ctacttgctc caccaccct cccttaataa taacatttac tgttatttcc tgggcctaag     1455 acttatgttc cagaactgtc acagctcccc atgtcacacc cactagcttg tgatctttgt    1515 caaataactg aaatctttta agcctctagt ttcttccttt gtaaaacaga gataaaatgt    1575 tgtggttttt aagtgagata atccaagtaa agcacctaac atggagtagt gaatgaacat    1635
```

```
cggttgctac taaaagtgga catcctaccg catccttaat gccactaggc atttccatac    1695
aatctgggga ccaaaacttc aatcatataa atgtatgagg ttaattaaaa acactactgt    1755
aatctgcttg tatgatcaca aaccaccaca aaagaaaaga tcgtgaagat tacactgtaa    1815
acggactctc aaatgatcag gaggtggtca cttcgcaact tgctccctcc acccaactca    1875
aaacaggagc tcgagcctgc ctgtatttga gactggagct gcctgtatga ggactggatc    1935
aactgctagt cacgttatat ccaaatctgc attatcattg gcacatttt cacagaatt     1995 tactgaatta ttccttaatt gtttaatggt tgggaatagt ttgggaatta ccttccatca    2055
actctgctaa gaaaggaatg gattctggta gcaagacaat ataattctcc tttagttttt    2115
cagccagtgc taacacagta atcaaagcag caaatcgaac ctgaaaggga taaagagca    2175 aagaaataaa aagtagtgtt actgtatta ttatcttaag agctgtactg acttgagaca    2235
agctctaact ttttaaacat tagttcacac gcgtttattc acttcattat gttcattaag    2295
ctttcatctt agaataccag tttcaccatt tgggagctgt ttgtaatatg tgcaaccta    2355 taaatagtgt tttccaaact gtgtcccagg actgcaaatc tttaatgtga aatgtctttt    2415
tataatctct tcctttaaaa aaaccaata aaataaaatg ccacatgcaa actc            2469

<210> SEQ ID NO 9
<211> LENGTH: 281
<212> TYPE: DNA
<213> ORGANISM: Homo sapiens

<400> SEQUENCE: 9
atatcacctg taaagtcttc tggccaaaaa attaagccca gccggacctt attaaacctt      60
taaatctaac aattagtttt gaagctttta cagattaaat gaagtctgag atttgcttca    120
aaatgaacca gtggtgggga ggaagtgggt gaggtgtagg tgaaacaaga ttggccacgt    180
cgataattgc tggagctggg cgatgaaagc acagttctag aagcttgttt ctcccacctg    240
aaaagactgg atttgggaca tgatcctgta gaacttcgga g                        281

<210> SEQ ID NO 10
<211> LENGTH: 515
<212> TYPE: DNA
<213> ORGANISM: Homo sapiens
<220> FEATURE:
<221> NAME/KEY: 5'UTR
<222> LOCATION: 1..384
<220> FEATURE:
<221> NAME/KEY: CDS
<222> LOCATION: 385..515

<400> SEQUENCE: 10
tggacttgga tccgaggcag acgaggaagc tgagaaaacc ctggcgttga ccccgtggac     60
ctgggcgccc cgggaaggcc agcgcttggt ccaggcaggc ggggcctgtg cggtgaccac    120
cctggtcctg aaagtccca gccccgagcg ccctccctcc tagacctgga ggcctggaac    180
agccagccgc ccacggacgc cagagccggg aaccctgacg gcacttagct gctgacaaac    240
aacctgctcc gtggagcgcc tgaaacacca gtctttgggg ccagtgcctc agtttcaatc    300 caggtaaccct ttaaatgaaa cttgcctaaa atcttaggtc atacacagaa gagactccaa   360
tcgacaagaa gctggaaaag aatg atg ttg tcc tta aac aac cta cag aat      411
                         Met Leu Ser Leu Asn Asn Leu Gln Asn
                          1               5 atc atc tat aac ccg gta atc ccg tat gtt ggc acc att ccc gat cag     459
Ile Ile Tyr Asn Pro Val Ile Pro Tyr Val Gly Thr Ile Pro Asp Gln
 10              15                  20                  25
```

```
ctg gat cct gga act ttg att gtg ata tgt ggg cat gtt cct agt gac    507
Leu Asp Pro Gly Thr Leu Ile Val Ile Cys Gly His Val Pro Ser Asp
                30                  35                  40 gca gac ag                                                          515
Ala Asp

<210> SEQ ID NO 11
<211> LENGTH: 304
<212> TYPE: DNA
<213> ORGANISM: Homo sapiens
<220> FEATURE:
<221> NAME/KEY: 5'UTR
<222> LOCATION: 1..173
<220> FEATURE:
<221> NAME/KEY: CDS
<222> LOCATION: 174..304

<400> SEQUENCE: 11
ttctagaagc ttgtttctcc cacctgaaaa gactggattt gggacatgat cctgtagaac    60
ttcggagggc cagtgcctca gtttcaatcc aggtaacctt taaatgaaac ttgcctaaaa   120
tcttaggtca tacacagaag agactccaat cgacaagaag ctggaaaaga atg atg     176
                                                        Met
                                                          1 ttg tcc tta aac aac cta cag aat atc atc tat aac ccg gta atc ccg    224
Leu Ser Leu Asn Asn Leu Gln Asn Ile Ile Tyr Asn Pro Val Ile Pro
            5                   10                  15 tat gtt ggc acc att ccc gat cag ctg gat cct gga act ttg att gtg    272
Tyr Val Gly Thr Ile Pro Asp Gln Leu Asp Pro Gly Thr Leu Ile Val
        20                  25                  30 ata tgt ggg cat gtt cct agt gac gca gac ag                         304
Ile Cys Gly His Val Pro Ser Asp Ala Asp
        35                  40

<210> SEQ ID NO 12
<211> LENGTH: 473
<212> TYPE: DNA
<213> ORGANISM: Homo sapiens
<220> FEATURE:
<221> NAME/KEY: 5'UTR
<222> LOCATION: 1..342
<220> FEATURE:
<221> NAME/KEY: CDS
<222> LOCATION: 343..473

<400> SEQUENCE: 12
ttctagaagc ttgtttctcc cacctgaaaa gactggattt gggacatgat cctgtagaac    60
ttcggagatt ggggaagata atcggaagag gtaaaagaca ccgtccatga cacttcctgg   120
ggaagcagat gtatgtataa ggatccgccc acggacgcca gagccgggaa ccctgacggc   180
acttagctgc tgacaaacaa cctgctccgt ggagcgcctg aaacaccagt ctttggggcc   240
agtgcctcag tttcaatcca ggtaacctttt aaatgaaact tgcctaaaat cttaggtcat   300
acacagaaga gactccaatc gacaagaagc tggaaaagaa tg atg ttg tcc tta     354
                                              Met Leu Ser Leu
                                                1 aac aac cta cag aat atc atc tat aac ccg gta atc ccg tat gtt ggc    402
Asn Asn Leu Gln Asn Ile Ile Tyr Asn Pro Val Ile Pro Tyr Val Gly
  5                 10                  15                  20 acc att ccc gat cag ctg gat cct gga act ttg att gtg ata tgt ggg    450
Thr Ile Pro Asp Gln Leu Asp Pro Gly Thr Leu Ile Val Ile Cys Gly
            25                  30                  35 cat gtt cct agt gac gca gac ag                                     473
His Val Pro Ser Asp Ala Asp
        40
```

<210> SEQ ID NO 13
<211> LENGTH: 2077
<212> TYPE: DNA
<213> ORGANISM: Homo sapiens
<220> FEATURE:
<221> NAME/KEY: 5'UTR
<222> LOCATION: 1..265
<220> FEATURE:
<221> NAME/KEY: CDS
<222> LOCATION: 266..913
<220> FEATURE:
<221> NAME/KEY: 3'UTR
<222> LOCATION: 914..2077

<400> SEQUENCE: 13

```
ttctagaagc ttgtttctcc cacctgaaaa gactggattt gggacatgat cctgtagaac      60
ttcggagccg cccacggacg ccagagccgg gaaccctgac ggcacttagc tgctgacaaa     120
caacctgctc cgtggagcgc ctgaaacacc agtctttggg gccagtgcct cagtttcaat     180
ccaggtaacc tttaaatgaa acttgcctaa aatcttaggt catacacaga agagactcca     240
atcgacaaga agctggaaaa gaatg atg ttg tcc tta aac aac cta cag aat       292
                            Met Leu Ser Leu Asn Asn Leu Gln Asn
                             1               5 atc atc tat aac ccg gta atc ccg tat gtt ggc acc att ccc gat cag       340
Ile Ile Tyr Asn Pro Val Ile Pro Tyr Val Gly Thr Ile Pro Asp Gln
 10              15                  20                  25 ctg gat cct gga act ttg att gtg ata tgt ggg cat gtt cct agt gac       388
Leu Asp Pro Gly Thr Leu Ile Val Ile Cys Gly His Val Pro Ser Asp
             30                  35                  40 gca gac aga ttc cag gtg gat ctg cag aat ggc agc agt gtg aaa cct       436
Ala Asp Arg Phe Gln Val Asp Leu Gln Asn Gly Ser Ser Val Lys Pro
         45                  50                  55 cga gcc gat gtg gcc ttt cat ttc aat cct cgt ttc aaa agg gcc ggc       484
Arg Ala Asp Val Ala Phe His Phe Asn Pro Arg Phe Lys Arg Ala Gly
     60                  65                  70 tgc att gtt tgc aat act ttg ata aat gaa aaa tgg gga cgg gaa gag       532
Cys Ile Val Cys Asn Thr Leu Ile Asn Glu Lys Trp Gly Arg Glu Glu
 75                  80                  85 atc acc tat gac acg cct ttc aaa aga gaa aag tct ttt gag atc gtg       580
Ile Thr Tyr Asp Thr Pro Phe Lys Arg Glu Lys Ser Phe Glu Ile Val
 90                  95                 100                 105 att atg gtg cta aag gac aaa ttc cag atg ata att tac tgt gat gtt       628
Ile Met Val Leu Lys Asp Lys Phe Gln Met Ile Ile Tyr Cys Asp Val
                110                 115                 120 aga gaa ttc aag gtt gca gta aat ggc gta cac agc ctg gag tac aaa       676
Arg Glu Phe Lys Val Ala Val Asn Gly Val His Ser Leu Glu Tyr Lys
            125                 130                 135 cac aga ttt aaa gag ctc agc agt att gac acg ctg gaa att aat gga       724
His Arg Phe Lys Glu Leu Ser Ser Ile Asp Thr Leu Glu Ile Asn Gly
        140                 145                 150 gac atc cac tta ctg gaa caa tca ttc aat caa aag agt gaa atg aag       772
Asp Ile His Leu Leu Glu Gln Ser Phe Asn Gln Lys Ser Glu Met Lys
    155                 160                 165 cac att aac aaa gca gga ggc gcc acg gac cgc ctc cct cca cac cgc       820
His Ile Asn Lys Ala Gly Gly Ala Thr Asp Arg Leu Pro Pro His Arg
170                 175                 180                 185 tcc ttc cgc ctt cat tcc ttg ccc aca ggc ttg cac tgg aag ctg aat       868
Ser Phe Arg Leu His Ser Leu Pro Thr Gly Leu His Trp Lys Leu Asn
                190                 195                 200 aag aat ccc caa aac tca aac ttc cta ggg atg cca ccc ctt tag           913
Lys Asn Pro Gln Asn Ser Asn Phe Leu Gly Met Pro Pro Leu *
            205                 210                 215
```

-continued

```
                205                 210                 215
tagctcacac ctcccccctc caagagctaa gaaacaaagg agaatgtact tttgtagctt      973
agataagcaa tgaatcagta aaggactgat ctacttgctc caccacccct cccttaataa     1033
taacatttac tgttatttcc tgggcctaag acttatgttc cagaactgtc acagctcccc     1093
atgtcacacc cactagcttg tgatctttgt caaataactg aaatcttttta agcctctagt     1153 ttcttccttt gtaaaacaga gataaaatgt tgtggttttt aagtgagata atccaagtaa     1213
agcacctaac atggagtagt gaatgaacat cggttgctac taaaagtgga catcctaccg     1273
catccttaat gccactaggc atttccatac aatctgggga ccaaaacttc aatcatataa     1333
atgtatgagg ttaattaaaa acactactgt aatctgcttg tatgatcaca aaccaccaca     1393
aaagaaaaga tcgtgaagat tacactgtaa acggactctc aaatgatcag gaggtggtca     1453
cttcgcaact tgctccctcc acccaactca aaacaggagc tcgagcctgc ctgtatttga     1513
gactggagct gcctgtatga ggactggatc aactgctagt cacgttatat ccaaatctgc     1573
attatcattg ggcacatttt cacagaattt tactgaatta ttccttaatt gtttaatggt     1633
tgggaatagt ttgggaatta ccttccatca actctgctaa gaaggaatg gattctggta     1693 gcaagacaat ataattctcc tttagttttt cagccagtgc taacacagta atcaaagcag     1753
caaatcgaac ctgaaaggga taaaagagca aagaaataaa aagtagtgtt actgtattta     1813
ttatcttaag agctgtactg acttgagaca agctctaact ttttaaacat tagttcacac     1873
gcgtttattc acttcattat gttcattaag ctttcatctt agaataccag tttcaccatt     1933
tgggagctgt ttgtaatatg tgcaaccta taaatagtgt tttccaaact gtgtcccagg     1993
actgcaaatc tttaatgtga aatgtctttt tataatctct tcctttaaaa aaaaccaata     2053
aaataaaatg ccacatgcaa actc                                            2077
```

<210> SEQ ID NO 14
<211> LENGTH: 316
<212> TYPE: PRT
<213> ORGANISM: Homo sapiens

<400> SEQUENCE: 14

```
Met Leu Ser Leu Asn Asn Leu Gln Asn Ile Ile Tyr Asn Pro Val Ile
1               5                   10                  15

Pro Tyr Val Gly Thr Ile Pro Asp Gln Leu Asp Pro Gly Thr Leu Ile
                20                  25                  30

Val Ile Cys Gly His Val Pro Ser Asp Ala Asp Arg Phe Gln Val Asp
            35                  40                  45

Leu Gln Asn Gly Ser Ser Val Lys Pro Arg Ala Asp Val Ala Phe His
        50                  55                  60

Phe Asn Pro Arg Phe Lys Arg Ala Gly Cys Ile Val Cys Asn Thr Leu
65                  70                  75                  80

Ile Asn Glu Lys Trp Gly Arg Glu Glu Ile Thr Tyr Asp Thr Pro Phe
                85                  90                  95

Lys Arg Glu Lys Ser Phe Glu Ile Val Ile Met Val Leu Lys Asp Lys
                100                 105                 110

Phe Gln Val Ala Val Asn Gly Lys His Thr Leu Leu Tyr Gly His Arg
            115                 120                 125

Ile Gly Pro Glu Lys Ile Asp Thr Leu Gly Ile Tyr Gly Lys Val Asn
        130                 135                 140

Ile His Ser Ile Gly Phe Ser Phe Ser Ser Asp Leu Gln Ser Thr Gln
145                 150                 155                 160
```

```
Ala Ser Ser Leu Glu Leu Thr Glu Ile Ser Arg Glu Asn Val Pro Lys
            165                 170                 175

Ser Gly Thr Pro Gln Leu Ser Leu Pro Phe Ala Ala Arg Leu Asn Thr
            180                 185                 190

Pro Met Gly Pro Gly Arg Thr Val Val Val Lys Gly Glu Val Asn Ala
            195                 200                 205

Asn Ala Lys Ser Phe Asn Val Asp Leu Leu Ala Gly Lys Ser Lys Asp
            210                 215                 220

Ile Ala Leu His Leu Asn Pro Arg Leu Asn Ile Lys Ala Phe Val Arg
225                 230                 235                 240

Asn Ser Phe Leu Gln Glu Ser Trp Gly Glu Glu Arg Asn Ile Thr
            245                 250                 255

Ser Phe Pro Phe Ser Pro Gly Met Tyr Phe Glu Met Ile Ile Tyr Cys
            260                 265                 270

Asp Val Arg Glu Phe Lys Val Ala Val Asn Gly Val His Ser Leu Glu
            275                 280                 285

Tyr Lys His Arg Phe Lys Glu Leu Ser Ser Ile Asp Thr Leu Glu Ile
            290                 295                 300

Asn Gly Asp Ile His Leu Leu Glu Val Arg Ser Trp
305                 310                 315

<210> SEQ ID NO 15
<211> LENGTH: 358
<212> TYPE: PRT
<213> ORGANISM: Homo sapiens

<400> SEQUENCE: 15

Met Leu Ser Leu Asn Asn Leu Gln Asn Ile Ile Tyr Asn Pro Val Ile
1               5                   10                  15

Pro Tyr Val Gly Thr Ile Pro Asp Gln Leu Asp Pro Gly Thr Leu Ile
            20                  25                  30

Val Ile Cys Gly His Val Pro Ser Asp Ala Asp Arg Phe Gln Val Asp
            35                  40                  45

Leu Gln Asn Gly Ser Ser Val Lys Pro Arg Ala Asp Val Ala Phe His
50                  55                  60

Phe Asn Pro Arg Phe Lys Arg Ala Gly Cys Ile Val Cys Asn Thr Leu
65                  70                  75                  80

Ile Asn Glu Lys Trp Gly Arg Glu Glu Ile Thr Tyr Asp Thr Pro Phe
            85                  90                  95

Lys Arg Gly Lys Ser Phe Glu Ile Val Ile Met Val Leu Lys Asp Lys
            100                 105                 110

Phe Gln Val Ala Val Asn Gly Lys His Thr Leu Leu Tyr Gly His Arg
            115                 120                 125

Ile Gly Pro Glu Lys Ile Asp Thr Leu Gly Ile Tyr Gly Lys Val Asn
130                 135                 140

Ile His Ser Ile Gly Phe Ser Phe Ser Ser Asp Leu Gln Ser Thr Gln
145                 150                 155                 160

Ala Ser Ser Leu Glu Leu Thr Glu Ile Ser Arg Glu Asn Val Pro Lys
            165                 170                 175

Ser Gly Thr Pro Gln Leu Pro Ser Asn Arg Gly Gly Asp Ile Ser Lys
            180                 185                 190

Ile Ala Pro Arg Thr Val Tyr Thr Lys Ser Lys Asp Ser Thr Val Asn
            195                 200                 205

His Thr Leu Thr Cys Thr Lys Ile Pro Pro Met Asn Tyr Val Ser Lys
            210                 215                 220
```

```
Ser Leu Pro Phe Ala Ala Arg Leu Asn Thr Pro Met Gly Pro Gly Arg
225                 230                 235                 240

Thr Val Val Val Lys Gly Glu Val Asn Ala Asn Ala Lys Ser Phe Asn
                245                 250                 255

Val Asp Leu Leu Ala Gly Lys Ser Lys Asp Ile Ala Leu His Leu Asn
            260                 265                 270

Pro Arg Leu Asn Ile Lys Ala Phe Val Arg Asn Ser Phe Leu Gln Glu
        275                 280                 285

Ser Trp Gly Glu Glu Arg Asn Ile Thr Ser Phe Pro Phe Ser Pro
    290                 295                 300

Gly Met Tyr Phe Glu Met Ile Ile Tyr Cys Asp Val Arg Glu Phe Lys
305                 310                 315                 320

Val Ala Val Asn Gly Val His Ser Leu Glu Tyr Lys His Arg Phe Lys
                325                 330                 335

Glu Leu Ser Ser Ile Asp Thr Leu Gly Ile Asn Gly Asp Ile His Leu
            340                 345                 350

Leu Glu Val Arg Ser Trp
            355

<210> SEQ ID NO 16
<211> LENGTH: 368
<212> TYPE: PRT
<213> ORGANISM: Homo sapiens

<400> SEQUENCE: 16

Met Leu Ser Leu Asn Asn Leu Gln Asn Ile Ile Tyr Asn Pro Val Ile
1               5                   10                  15

Pro Tyr Val Gly Thr Ile Pro Asp Gln Leu Asp Pro Gly Thr Leu Ile
            20                  25                  30

Val Ile Cys Gly His Val Pro Ser Asp Ala Asp Arg Phe Gln Val Asp
        35                  40                  45

Leu Gln Asn Gly Ser Ser Val Lys Pro Arg Ala Asp Val Ala Phe His
    50                  55                  60

Phe Asn Pro Arg Phe Lys Arg Ala Gly Cys Ile Val Cys Asn Thr Leu
65                  70                  75                  80

Ile Asn Glu Lys Trp Gly Arg Glu Glu Ile Thr Tyr Asp Thr Pro Phe
                85                  90                  95

Lys Arg Glu Lys Ser Phe Glu Ile Val Ile Met Val Leu Lys Asp Lys
            100                 105                 110

Phe Gln Val Ala Val Asn Gly Lys His Thr Leu Leu Tyr Gly His Arg
        115                 120                 125

Ile Gly Pro Glu Lys Ile Asp Thr Leu Gly Ile Tyr Gly Lys Val Asn
    130                 135                 140

Ile His Ser Ile Gly Phe Ser Phe Ser Ser Asp Leu Gln Ser Thr Gln
145                 150                 155                 160

Ala Ser Ser Leu Glu Leu Thr Glu Ile Ser Arg Glu Asn Val Pro Lys
                165                 170                 175

Ser Gly Thr Pro Gln Leu Ser Leu Pro Phe Ala Ala Arg Leu Asn Thr
            180                 185                 190

Pro Met Gly Pro Gly Arg Thr Val Val Val Lys Gly Glu Val Asn Ala
        195                 200                 205

Asn Ala Lys Ser Phe Asn Val Asp Leu Leu Ala Gly Lys Ser Lys Asp
    210                 215                 220

Ile Ala Leu His Leu Asn Pro Arg Leu Asn Ile Lys Ala Phe Val Arg
225                 230                 235                 240
```

```
Asn Ser Phe Leu Gln Glu Ser Trp Gly Glu Glu Arg Asn Ile Thr
            245                 250                 255

Ser Phe Pro Phe Ser Pro Gly Met Tyr Phe Glu Met Ile Ile Tyr Cys
        260                 265                 270

Asp Val Arg Glu Phe Lys Val Ala Val Asn Gly Val His Ser Leu Glu
        275                 280                 285

Tyr Lys His Arg Phe Lys Glu Leu Ser Ser Ile Asp Thr Leu Glu Ile
        290                 295                 300

Asn Gly Asp Ile His Leu Leu Glu Gln Ser Phe Asn Gln Lys Ser Glu
305                 310                 315                 320

Met Lys His Ile Asn Lys Ala Gly Gly Ala Thr Asp Arg Leu Pro Pro
                325                 330                 335

His Arg Ser Phe Arg Leu His Ser Leu Pro Thr Gly Leu His Trp Lys
                340                 345                 350

Leu Asn Lys Asn Pro Gln Asn Ser Asn Phe Leu Gly Met Pro Pro Leu
            355                 360                 365
```

<210> SEQ ID NO 17
<211> LENGTH: 215
<212> TYPE: PRT
<213> ORGANISM: Homo sapiens

<400> SEQUENCE: 17

```
Met Leu Ser Leu Asn Asn Leu Gln Asn Ile Ile Tyr Asn Pro Val Ile
1               5                   10                  15

Pro Tyr Val Gly Thr Ile Pro Asp Gln Leu Asp Pro Gly Thr Leu Ile
            20                  25                  30

Val Ile Cys Gly His Val Pro Ser Asp Ala Asp Arg Phe Gln Val Asp
        35                  40                  45

Leu Gln Asn Gly Ser Ser Val Lys Pro Arg Ala Asp Val Ala Phe His
    50                  55                  60

Phe Asn Pro Arg Phe Lys Arg Ala Gly Cys Ile Val Cys Asn Thr Leu
65                  70                  75                  80

Ile Asn Glu Lys Trp Gly Arg Glu Glu Ile Thr Tyr Asp Thr Pro Phe
                85                  90                  95

Lys Arg Glu Lys Ser Phe Glu Ile Val Ile Met Val Leu Lys Asp Lys
            100                 105                 110

Phe Gln Met Ile Ile Tyr Cys Asp Val Arg Glu Phe Lys Val Ala Val
        115                 120                 125

Asn Gly Val His Ser Leu Glu Tyr Lys His Arg Phe Lys Glu Leu Ser
    130                 135                 140

Ser Ile Asp Thr Leu Glu Ile Asn Gly Asp Ile His Leu Leu Glu Gln
145                 150                 155                 160

Ser Phe Asn Gln Lys Ser Glu Met Lys His Ile Asn Lys Ala Gly Gly
                165                 170                 175

Ala Thr Asp Arg Leu Pro Pro His Arg Ser Phe Arg Leu His Ser Leu
            180                 185                 190

Pro Thr Gly Leu His Trp Lys Leu Asn Lys Asn Pro Gln Asn Ser Asn
        195                 200                 205

Phe Leu Gly Met Pro Pro Leu
    210                 215
```

<210> SEQ ID NO 18
<211> LENGTH: 504
<212> TYPE: DNA
<213> ORGANISM: Homo sapiens
<220> FEATURE:

```
<221> NAME/KEY: allele
<222> LOCATION: 81
<223> OTHER INFORMATION: 99-7177-81 : polymorphic base C or T
<220> FEATURE:
<221> NAME/KEY: misc_binding
<222> LOCATION: 69..93
<223> OTHER INFORMATION: 99-7177-81.probe
<220> FEATURE:
<221> NAME/KEY: primer_bind
<222> LOCATION: 62..80
<223> OTHER INFORMATION: 99-7177-81.mis
<220> FEATURE:
<221> NAME/KEY: primer_bind
<222> LOCATION: 82..100
<223> OTHER INFORMATION: 99-7177-81.mis complement
<220> FEATURE:
<221> NAME/KEY: primer_bind
<222> LOCATION: 1..20
<223> OTHER INFORMATION: 99-7177.pu
<220> FEATURE:
<221> NAME/KEY: primer_bind
<222> LOCATION: 484..504
<223> OTHER INFORMATION: 99-7177.rp complement

<400> SEQUENCE: 18
aatcctgacc caccttctcc caagcacgca tgtagaggaa agaaagcaag agcgatagct      60
gaggggatca gcctactaga yggaggcagg tgtttcaaga tggtgttgga agggcaagcc     120
gagaactcta gtagcgggga ggggaaaact aaaactttat tactgtaagc aaatatcaca     180
gcaaatcagc cttaagtagg tataaaagaa cccataaaag aagacaaaat gtaaccaaag     240
ctcaccagac cacagaagag tcatcactgg agtcggaaga cagacgcgct ggatcctgca     300
gtaggagttg gggcatcccc cagcatagga caacagcaac cttcaatcct ccttcgtata     360
agctcctttt attaagtcca attgttactt tgggcaccct ctgttgtttg ctggtgaggg     420
cccttcccca gcaagcaaca ctgaaacagt ggttctggga gcagcgtcct gggacgcgtt     480
ccaggacttg agttaatttc tggg                                            504

<210> SEQ ID NO 19
<211> LENGTH: 488
<212> TYPE: DNA
<213> ORGANISM: Homo sapiens
<220> FEATURE:
<221> NAME/KEY: allele
<222> LOCATION: 345
<223> OTHER INFORMATION: 99-7212-346 : polymorphic base C or T
<220> FEATURE:
<221> NAME/KEY: misc_binding
<222> LOCATION: 333..357
<223> OTHER INFORMATION: 99-7212-346.probe
<220> FEATURE:
<221> NAME/KEY: primer_bind
<222> LOCATION: 326..344
<223> OTHER INFORMATION: 99-7212-346.mis
<220> FEATURE:
<221> NAME/KEY: primer_bind
<222> LOCATION: 346..364
<223> OTHER INFORMATION: 99-7212-346.mis complement
<220> FEATURE:
<221> NAME/KEY: primer_bind
<222> LOCATION: 1..20
<223> OTHER INFORMATION: 99-7212.pu
<220> FEATURE:
<221> NAME/KEY: primer_bind
<222> LOCATION: 470..488
<223> OTHER INFORMATION: 99-7212.rp complement

<400> SEQUENCE: 19
gctccttatg taattgaatg aatggtattt ttatcagatg cttttaaaa gtcagtacac       60 aattccatct atttcacagc aaattctaca gaaatagcag ctagacagca ggaagctgtg     120
```

```
gcttactgtt tagtgacttg tgattgtaat taaatgatta gtcttccact ccattccctc    180
caacttgtct tgggtctggg gaggtaggga ggacaaatgc aaaatccata gagtcaagga    240
tatagtgagg agtttacttt gccattgact ctgacaatca atcgtcagtg agacatgctg    300
attgtgatga aacatgact aaagacaaga ttccttcaag gtagygctct cacgttttca    360
ttcaatgaaa aactattggt gttgtataac ccaatgaatc attttgtat tttgaatctt    420 taaaaatata tacaagtgct attttgcttg aagtgctgtt tatttataag gttgacaatt    480
aaactgac                                                            488
```

```
<210> SEQ ID NO 20
<211> LENGTH: 542
<212> TYPE: DNA
<213> ORGANISM: Homo sapiens
<220> FEATURE:
<221> NAME/KEY: allele
<222> LOCATION: 226
<223> OTHER INFORMATION: 99-7193-228 : polymorphic base G or C
<220> FEATURE:
<221> NAME/KEY: misc_binding
<222> LOCATION: 214..238
<223> OTHER INFORMATION: 99-7193-228.probe
<220> FEATURE:
<221> NAME/KEY: primer_bind
<222> LOCATION: 207..225
<223> OTHER INFORMATION: 99-7193-228.mis
<220> FEATURE:
<221> NAME/KEY: primer_bind
<222> LOCATION: 227..245
<223> OTHER INFORMATION: 99-7193-228.mis complement
<220> FEATURE:
<221> NAME/KEY: primer_bind
<222> LOCATION: 1..20
<223> OTHER INFORMATION: 99-7193.pu
<220> FEATURE:
<221> NAME/KEY: primer_bind
<222> LOCATION: 522..542
<223> OTHER INFORMATION: 99-7193.rp complement

<400> SEQUENCE: 20
gaggtaaaaa tagcaggcag gagaacagat cttttaggat tgtgaattgt aatgtggaac     60
atgaaaactt catcatcttc tgtgtgctgg ctagtgtcag ttatcctttg ctgtataaaa    120
atcaccccca aaattagtga tttgaaacaa ctgtccccat ttatttactc atgattttgc    180
agttgctcag gacttggtgg ggataccttg actctgcttc tcgcastgtt gactgaggtc    240
atacttgcag ctacattcag ctggcagctt cattggggct ggaacagcaa agacagcttc    300
cctaacatac ctggcacctc agccaaggtg gctgcaatgg ctggaggctc actgggcctt    360
tcacttctgt gtggtttctc gtgatttcgt agtctatcct gaactccttt tcacggcaac    420
tggaatgcaa aaagatgaaa acagaagcta caatgtctgg gaacagaagt cctagaatgt    480
cacttctact acacctatta ctcactatta gtcaaaataa actcctctcc caatacttct    540
ca                                                                  542
```

```
<210> SEQ ID NO 21
<211> LENGTH: 528
<212> TYPE: DNA
<213> ORGANISM: Homo sapiens
<220> FEATURE:
<221> NAME/KEY: allele
<222> LOCATION: 212
<223> OTHER INFORMATION: 99-7186-212 : polymorphic base A or G
<220> FEATURE:
<221> NAME/KEY: misc_binding
<222> LOCATION: 200..224
<223> OTHER INFORMATION: 99-7186-212.probe
<220> FEATURE:
```

<221> NAME/KEY: primer_bind
<222> LOCATION: 193..211
<223> OTHER INFORMATION: 99-7186-212.mis
<220> FEATURE:
<221> NAME/KEY: primer_bind
<222> LOCATION: 213..231
<223> OTHER INFORMATION: 99-7186-212.mis complement
<220> FEATURE:
<221> NAME/KEY: primer_bind
<222> LOCATION: 1..19
<223> OTHER INFORMATION: 99-7186.pu
<220> FEATURE:
<221> NAME/KEY: primer_bind
<222> LOCATION: 510..528
<223> OTHER INFORMATION: 99-7186.rp complement

<400> SEQUENCE: 21

```
gagtgccatg tgtgcataga ttgttgtctg ggttttttcc tttttgttac ttctgcaata      60
tttagaacag tgactgacac atatcaggca ctcaataatt atttgctgaa tttctcaatg     120
tctcgatttg gcataaggat ttcatttttcc catggtatat tttcttccgt ggattgatgg    180
gctagtacta atttgcacgg gtgtcttggt grttcacaat catggtttta atgtcccagt    240
cccctttggc tacaggaggt acttgatcct aggtgactaa ggcagaaata aatagaatgt    300
gtaggactcc tctggtgtaa aaagtcatgg gttccaaaag ttcatttata agtcaattgt    360
ttggacatcc tgaacttatt ttcagaacac gattgggcac agctagttaa ctgcagggag    420
gcctgaggag actggaaggt gccagaacct ggaaccagat ctgcccacta ggacaggacc    480
agccctggaa ggacaggagc aggtgcactg gattctaaag gtgttcag              528
```

<210> SEQ ID NO 22
<211> LENGTH: 531
<212> TYPE: DNA
<213> ORGANISM: Homo sapiens
<220> FEATURE:
<221> NAME/KEY: allele
<222> LOCATION: 49
<223> OTHER INFORMATION: 99-7182-49 : polymorphic base C or T
<220> FEATURE:
<221> NAME/KEY: misc_binding
<222> LOCATION: 37..61
<223> OTHER INFORMATION: 99-7182-49.probe
<220> FEATURE:
<221> NAME/KEY: primer_bind
<222> LOCATION: 30..48
<223> OTHER INFORMATION: 99-7182-49.mis
<220> FEATURE:
<221> NAME/KEY: primer_bind
<222> LOCATION: 50..68
<223> OTHER INFORMATION: 99-7182-49.mis complement
<220> FEATURE:
<221> NAME/KEY: primer_bind
<222> LOCATION: 1..20
<223> OTHER INFORMATION: 99-7182.pu
<220> FEATURE:
<221> NAME/KEY: primer_bind
<222> LOCATION: 511..531
<223> OTHER INFORMATION: 99-7182.rp complement

<400> SEQUENCE: 22

```
gtgtgtagaa aagaaagatg gctgtcattt gagttgttaa gaacagcayg ctgcaatacc      60
aaaacatcaa gctgtacatc tcaaatatgt atgattttca tatgtgaatc acatctcaat    120
aaagctgtta gaaaaataaa attaccatta agtttaaaaa aaaaaagaaa aaagaaaaa     180
aacaaccaca gtcggggcaa gggccatgtt actagggcca gggatttggc caatgaagca    240
ggaacataga gatcctaggt ccataaggaa aagaagattc aaggaaggcc aggacatggg    300
agggaatgaa caaactccag tcctagaggt ttagcagaga ctagctggct tcttgcagtg    360
```

```
aattaataaa tgagaaaaaa atctgagatc acaataaaag atctttactg gtgcaagggc      420
cacttctcac cgctgtttga ctgctttggg tcattcttta gtaccttaag tttttttatat    480 tttgtgaaga ttttactatt ttttwatctg caagagagta agttcaatca a             531
```

```
<210> SEQ ID NO 23
<211> LENGTH: 546
<212> TYPE: DNA
<213> ORGANISM: Homo sapiens
<220> FEATURE:
<221> NAME/KEY: allele
<222> LOCATION: 372
<223> OTHER INFORMATION: 99-1585-373 : polymorphic base C or T
<220> FEATURE:
<221> NAME/KEY: misc_binding
<222> LOCATION: 360..384
<223> OTHER INFORMATION: 99-1585-373.probe
<220> FEATURE:
<221> NAME/KEY: primer_bind
<222> LOCATION: 353..371
<223> OTHER INFORMATION: 99-1585-373.mis
<220> FEATURE:
<221> NAME/KEY: primer_bind
<222> LOCATION: 373..391
<223> OTHER INFORMATION: 99-1585-373.mis complement
<220> FEATURE:
<221> NAME/KEY: primer_bind
<222> LOCATION: 1..20
<223> OTHER INFORMATION: 99-1585.pu
<220> FEATURE:
<221> NAME/KEY: primer_bind
<222> LOCATION: 527..546
<223> OTHER INFORMATION: 99-1585.rp complement
<220> FEATURE:
<221> NAME/KEY: misc_feature
<222> LOCATION: 52..53,55
<223> OTHER INFORMATION: n=a, g, c or t

<400> SEQUENCE: 23
cctgcaacat ttttwatgtg tagaattctg tgaatgaatc caacttcggc anntnttttt     60 ttctttctt ttttttaatc aaggaagtgg agacaagatg tgaaggggtg gcctgcccct    120
ccacacctgt ggatatttct agtcaggtgg gacgagagac tgagaaaata aataaaacac    180
agagacaaag tatagagaaa caacagtggg cccaggaac cggcgctcag cataccaagg    240
acctgcaccg gcaccatctc tgagttccct cagtttttat tgattattat cttcgttatt    300
tcagcaaaaa ggaatgtagt aggagagcag ggtgataata aggagaaggt cagcaacgaa    360
catgtgagca ayagaatcta cgtcataatk aagttcaagg gaaggtacta tgactggacg    420
tgcahgtaag ccagatttat gtttctctcc acccaaacat ctcggtggag taaagaataa    480
caaggcagca ttgctgcaaa catgtctcgc ctcccgccat agggcggttt ttctcctatc    540
tcagaa                                                               546
```

```
<210> SEQ ID NO 24
<211> LENGTH: 396
<212> TYPE: DNA
<213> ORGANISM: Homo sapiens
<220> FEATURE:
<221> NAME/KEY: allele
<222> LOCATION: 278
<223> OTHER INFORMATION: 99-1587-281 : polymorphic base A or G
<220> FEATURE:
<221> NAME/KEY: misc_binding
<222> LOCATION: 266..290
<223> OTHER INFORMATION: 99-1587-281.probe
<220> FEATURE:
<221> NAME/KEY: primer_bind
<222> LOCATION: 259..277
<223> OTHER INFORMATION: 99-1587-281.mis
<220> FEATURE:
```

```
<221> NAME/KEY: primer_bind
<222> LOCATION: 279..297
<223> OTHER INFORMATION: 99-1587-281.mis complement
<220> FEATURE:
<221> NAME/KEY: primer_bind
<222> LOCATION: 1..21
<223> OTHER INFORMATION: 99-1587.pu
<220> FEATURE:
<221> NAME/KEY: primer_bind
<222> LOCATION: 377..396
<223> OTHER INFORMATION: 99-1587.rp complement
<220> FEATURE:
<221> NAME/KEY: misc_feature
<222> LOCATION: 48
<223> OTHER INFORMATION: n=a, g, c or t

<400> SEQUENCE: 24
```

| | | | | | |
|---|---|---|---|---|---|
| taatggtagt | tgatgaggtc | ctatgtaata | tgcatttcct | tggttgcnaa | tagcaaatta | 60 |
| ctacacacac | agaaaggaaa | gccacactcc | ccgacacdwc | tacacacagg | aggactcaca | 120 |
| caggagggag | actcaaagaa | ggcacgtgac | ttttacattg | ttagggctta | catggtcctg | 180 |
| ggatttccca | ccagtactca | aaagatcaat | tgtatgaaca | agtcacctat | ttttacggca | 240 |
| ctaaataatt | attattcaac | aacatggaaa | atatgtgrta | gcagacctgg | attttccta | 300 |
| agagttattt | ttatgtggta | ctgcccctg | ctggaatata | acatctatac | acatcctttc | 360 |
| tggctgggct | gacatcctaa | aaccagccca | ggacca | | | 396 |

```
<210> SEQ ID NO 25
<211> LENGTH: 447
<212> TYPE: DNA
<213> ORGANISM: Homo sapiens
<220> FEATURE:
<221> NAME/KEY: allele
<222> LOCATION: 283
<223> OTHER INFORMATION: 99-13798-284 : polymorphic base A or G
<220> FEATURE:
<221> NAME/KEY: misc_binding
<222> LOCATION: 271..295
<223> OTHER INFORMATION: 99-13798-284.probe
<220> FEATURE:
<221> NAME/KEY: primer_bind
<222> LOCATION: 264..282
<223> OTHER INFORMATION: 99-13798-284.mis
<220> FEATURE:
<221> NAME/KEY: primer_bind
<222> LOCATION: 284..302
<223> OTHER INFORMATION: 99-13798-284.mis complement
<220> FEATURE:
<221> NAME/KEY: primer_bind
<222> LOCATION: 1..20
<223> OTHER INFORMATION: 99-13798.pu
<220> FEATURE:
<221> NAME/KEY: primer_bind
<222> LOCATION: 427..447
<223> OTHER INFORMATION: 99-13798.rp complement
<220> FEATURE:
<221> NAME/KEY: misc_feature
<222> LOCATION: 34,416
<223> OTHER INFORMATION: n=a, g, c or t

<400> SEQUENCE: 25
```

| | | | | | |
|---|---|---|---|---|---|
| gaggaaaagg | actttggatg | tctggtgtca | ctgnctgcac | accaggcaca | cagcaggtgc | 60 |
| tcaataagta | tttgatgaat | atatcaaatg | aatgaggagt | gtgacacagt | tcaagaagaa | 120 |
| aatcaaatga | aaaattaggc | ttcttagcag | cccgaaaaga | gctctttatc | tagaaattgt | 180 |
| caaaccagct | gatgcaagtt | tttttggtgt | taacaaggca | gccgcaagat | tgctatggag | 240 |
| aggacaccgt | gtaccatgga | gattaacggc | atgagcttta | gcrgcagcta | accccgtgca | 300 |
| gatgtgtgac | ttggacaggt | tactgagctt | gctaagcccc | tgtctcactc | tccaaacagg | 360 |

```
gataatgaca cctctctcac aaggtggttg tgaggattaa atgaggtaat cctttnaagc    420
tcccatccta gcacacgtaa gaagcat                                       447
```

<210> SEQ ID NO 26
<211> LENGTH: 506
<212> TYPE: DNA
<213> ORGANISM: Homo sapiens
<220> FEATURE:
<221> NAME/KEY: allele
<222> LOCATION: 402
<223> OTHER INFORMATION: 99-1601-402 : polymorphic base A or T
<220> FEATURE:
<221> NAME/KEY: misc_binding
<222> LOCATION: 390..414
<223> OTHER INFORMATION: 99-1601-402.probe
<220> FEATURE:
<221> NAME/KEY: primer_bind
<222> LOCATION: 383..401
<223> OTHER INFORMATION: 99-1601-402.mis
<220> FEATURE:
<221> NAME/KEY: primer_bind
<222> LOCATION: 403..421
<223> OTHER INFORMATION: 99-1601-402.mis complement
<220> FEATURE:
<221> NAME/KEY: primer_bind
<222> LOCATION: 1..18
<223> OTHER INFORMATION: 99-1601.pu
<220> FEATURE:
<221> NAME/KEY: primer_bind
<222> LOCATION: 486..506
<223> OTHER INFORMATION: 99-1601.rp complement

<400> SEQUENCE: 26

```
ttggcttggc agggcaacca gctcaccaga ctctctgcag acccgaagtc attacataca     60
gtatgataac agggaatgga cccgaccagc atttgctgga gatgatatct ggtgtcagcc    120
cgacaggccc ctacctgctt ctcttgatat gcaggaatcc cttcaagctc caacaagatc    180
tgtttaatag actggagagt cctttagttc cttcctctaa gggaaaatca gatcgttctg    240
gtttgcttgg taactcctta cttcatccct gatgggaagt ttatagaatg aggaaccagg    300
gctattacat gaaactataa aactgcctag agcacatact tggtattttt aacattgttg    360
agagggactc acttaattca gccttgcagc tattgcattc cwgtccaaac caacggcagg    420
ttctcaaaac aagcggtgaa agggttcctg ttgcagagct gtctggacat ttaaagaagg    480
gagaggaaat ctcargggt cggttg                                         506
```

<210> SEQ ID NO 27
<211> LENGTH: 546
<212> TYPE: DNA
<213> ORGANISM: Homo sapiens
<220> FEATURE:
<221> NAME/KEY: allele
<222> LOCATION: 79
<223> OTHER INFORMATION: 99-13808-80 : polymorphic base A or T
<220> FEATURE:
<221> NAME/KEY: misc_binding
<222> LOCATION: 67..91
<223> OTHER INFORMATION: 99-13808-80.probe
<220> FEATURE:
<221> NAME/KEY: primer_bind
<222> LOCATION: 60..78
<223> OTHER INFORMATION: 99-13808-80.mis
<220> FEATURE:
<221> NAME/KEY: primer_bind
<222> LOCATION: 80..98
<223> OTHER INFORMATION: 99-13808-80.mis complement
<220> FEATURE:
<221> NAME/KEY: primer_bind
<222> LOCATION: 1..20
<223> OTHER INFORMATION: 99-13808.pu
<220> FEATURE:

```
<221> NAME/KEY: primer_bind
<222> LOCATION: 526..546
<223> OTHER INFORMATION: 99-13808.rp complement
<220> FEATURE:
<221> NAME/KEY: allele
<222> LOCATION: 266
<223> OTHER INFORMATION: 99-13808-268 : polymorphic base A or C
<220> FEATURE:
<221> NAME/KEY: misc_binding
<222> LOCATION: 254..278
<223> OTHER INFORMATION: 99-13808-268.probe
<220> FEATURE:
<221> NAME/KEY: primer_bind
<222> LOCATION: 247..265
<223> OTHER INFORMATION: 99-13808-268.mis
<220> FEATURE:
<221> NAME/KEY: primer_bind
<222> LOCATION: 267..285
<223> OTHER INFORMATION: 99-13808-268.mis complement
<220> FEATURE:
<221> NAME/KEY: allele
<222> LOCATION: 419
<223> OTHER INFORMATION: 99-13808-425 : polymorphic base G or C
<220> FEATURE:
<221> NAME/KEY: misc_binding
<222> LOCATION: 407..431
<223> OTHER INFORMATION: 99-13808-425.probe
<220> FEATURE:
<221> NAME/KEY: primer_bind
<222> LOCATION: 400..418
<223> OTHER INFORMATION: 99-13808-425.mis
<220> FEATURE:
<221> NAME/KEY: primer_bind
<222> LOCATION: 420..438
<223> OTHER INFORMATION: 99-13808-425.mis complement
<220> FEATURE:
<221> NAME/KEY: allele
<222> LOCATION: 453
<223> OTHER INFORMATION: 99-13808-455 : polymorphic base A or G
<220> FEATURE:
<221> NAME/KEY: misc_binding
<222> LOCATION: 441..465
<223> OTHER INFORMATION: 99-13808-455.probe
<220> FEATURE:
<221> NAME/KEY: primer_bind
<222> LOCATION: 434..452
<223> OTHER INFORMATION: 99-13808-455.mis
<220> FEATURE:
<221> NAME/KEY: primer_bind
<222> LOCATION: 454..472
<223> OTHER INFORMATION: 99-13808-455.mis complement

<400> SEQUENCE: 27
gttgtgcctt aaagaatttg ctcatccaca gagtgccaac tgcattagaa agaaaacaac      60
tctcctttct aactcaccwg cattgatttt ctgttgttgg catgtagaag agtatttcaa     120
agaatgaatg aaagctataa tatttattag aagtaaaaaa gttctaaaga tatgctacct     180
tactgggatg cttagagacc atttgcaaac cctgttatg atctagaaat cctgtttttc      240 atttttatt tgtaaaactc tataamtctc aaaaaatttt aggtggatta tcatgtacct      300
aagggtaaaa tatagttgaa attattctta cctgattttt catatctgaa tttcgtgggc     360
agttcaaagt aattgtatca cattcttcag ctaggaaaaa aaaaagaaa gaaagaaasa      420 aacaaagtgt gattttaaaa agcacacact ccrtggtgta agacctaaaa ttaaggttca     480
gtgtcacatg ctgccttggc atctggtaaa atcagaagag ctggactaca aatycctctc     540
caaact                                                                546

<210> SEQ ID NO 28
<211> LENGTH: 476
<212> TYPE: DNA
<213> ORGANISM: Homo sapiens
<220> FEATURE:
```

```
<221> NAME/KEY: allele
<222> LOCATION: 212
<223> OTHER INFORMATION: 99-13810-214 : polymorphic base C or T
<220> FEATURE:
<221> NAME/KEY: misc_binding
<222> LOCATION: 200..224
<223> OTHER INFORMATION: 99-13810-214.probe
<220> FEATURE:
<221> NAME/KEY: primer_bind
<222> LOCATION: 193..211
<223> OTHER INFORMATION: 99-13810-214.mis
<220> FEATURE:
<221> NAME/KEY: primer_bind
<222> LOCATION: 213..231
<223> OTHER INFORMATION: 99-13810-214.mis complement
<220> FEATURE:
<221> NAME/KEY: primer_bind
<222> LOCATION: 1..18
<223> OTHER INFORMATION: 99-13810.pu
<220> FEATURE:
<221> NAME/KEY: primer_bind
<222> LOCATION: 458..476
<223> OTHER INFORMATION: 99-13810.rp complement
<220> FEATURE:
<221> NAME/KEY: allele
<222> LOCATION: 168
<223> OTHER INFORMATION: 99-13810-170 : polymorphic base A or T
<220> FEATURE:
<221> NAME/KEY: misc_binding
<222> LOCATION: 156..180
<223> OTHER INFORMATION: 99-13810-170.probe
<220> FEATURE:
<221> NAME/KEY: primer_bind
<222> LOCATION: 149..167
<223> OTHER INFORMATION: 99-13810-170.mis
<220> FEATURE:
<221> NAME/KEY: primer_bind
<222> LOCATION: 169..187
<223> OTHER INFORMATION: 99-13810-170.mis complement

<400> SEQUENCE: 28
gcattcccag attgtaacat agttttaagt aaacatccac tgaaagtctg catggaagaa      60
cacagaagcc agagcaagtt cagggctcct agaaagacga tgctggagct agccctagag     120
aatggctgag aattggatga actcagaaga agcagcaaag tagttgcwgg tggcaggcat     180
ggcaggagaa gggatcaggt ggctggaaga gyggagggta tagaactgaa acagagagtc     240
tgttggaggt ggacagagga aggcgggatt agatgagaaa tgacggaccc agtttctaag     300
aaagaccaag aaagataagc aaagggattt aggtgggatg cccttctagg ttctcgggaa     360
acttgctacc tgccttgcac tgactttgca tgagggaaga tggtcaacac agtcttgcaa     420
gaagtcagac aagcaggcaa tgacaattct ctgagatggc aaatagggat tgggct         476

<210> SEQ ID NO 29
<211> LENGTH: 454
<212> TYPE: DNA
<213> ORGANISM: Homo sapiens
<220> FEATURE:
<221> NAME/KEY: allele
<222> LOCATION: 127
<223> OTHER INFORMATION: 99-13790-129 : polymorphic base C or T
<220> FEATURE:
<221> NAME/KEY: misc_binding
<222> LOCATION: 115..139
<223> OTHER INFORMATION: 99-13790-129.probe
<220> FEATURE:
<221> NAME/KEY: primer_bind
<222> LOCATION: 108..126
<223> OTHER INFORMATION: 99-13790-129.mis
<220> FEATURE:
<221> NAME/KEY: primer_bind
<222> LOCATION: 128..146
<223> OTHER INFORMATION: 99-13790-129.mis complement
<220> FEATURE:
```

<221> NAME/KEY: primer_bind
<222> LOCATION: 1..20
<223> OTHER INFORMATION: 99-13790.pu
<220> FEATURE:
<221> NAME/KEY: primer_bind
<222> LOCATION: 434..454
<223> OTHER INFORMATION: 99-13790.rp complement

<400> SEQUENCE: 29

| | | | | | |
|---|---|---|---|---|---|
| gtcattttac | taagcctttc | agacagtaga | gagtgggatt | atacttgtcc | caacagctca | 60 |
| ccctcctaaa | ggtcaaacct | aaaccatttt | ggttctcttg | ttcaagttca | ggttgccagt | 120 |
| gaaaagyaaa | ggaacttgaa | attcatgtta | aacatttaac | atctttccat | atgaattgct | 180 |
| aggaagcaac | ttccattcca | aagttgtgtt | aacttcacag | ttttcccacc | tgtggtgaag | 240 |
| atggtacaaa | atagcttaaa | aactgatttt | gttccatcag | attctaatct | ttagtcacag | 300 |
| aattcaaggc | catactctaa | actttaaggt | tggcagaaat | atattataac | agaaatttta | 360 |
| gcaccatgta | aatgtttaaa | gttatttagc | cttaaataca | gaaccattta | actcagggtt | 420 |
| gaaaagtcag | gatgaagtga | gggwttgatt | gatt | | | 454 |

<210> SEQ ID NO 30
<211> LENGTH: 444
<212> TYPE: DNA
<213> ORGANISM: Homo sapiens
<220> FEATURE:
<221> NAME/KEY: allele
<222> LOCATION: 153
<223> OTHER INFORMATION: 99-13809-153 : polymorphic base A or G
<220> FEATURE:
<221> NAME/KEY: misc_binding
<222> LOCATION: 141..165
<223> OTHER INFORMATION: 99-13809-153.probe
<220> FEATURE:
<221> NAME/KEY: primer_bind
<222> LOCATION: 134..152
<223> OTHER INFORMATION: 99-13809-153.mis
<220> FEATURE:
<221> NAME/KEY: primer_bind
<222> LOCATION: 154..172
<223> OTHER INFORMATION: 99-13809-153.mis complement
<220> FEATURE:
<221> NAME/KEY: primer_bind
<222> LOCATION: 1..21
<223> OTHER INFORMATION: 99-13809.pu
<220> FEATURE:
<221> NAME/KEY: primer_bind
<222> LOCATION: 424..444
<223> OTHER INFORMATION: 99-13809.rp complement

<400> SEQUENCE: 30

| | | | | | |
|---|---|---|---|---|---|
| caactgagtg | aagagcaatg | ggaatttgta | gactttacag | atgacatcac | ccccatcata | 60 |
| cacgatgaag | ctcagcagac | agttgctgct | ttccatccct | taaccaggat | atccctgata | 120 |
| aaggaaggac | ccaagattag | caaaactggc | caracttcag | gcagtcatct | tattgctgga | 180 |
| tgtcctggcc | aacaaatcgc | cccatctgca | cagtttttat | aaattttttgg | accattgcct | 240 |
| aagagttgca | cccctttgtgg | taaagaactc | tcagaatctc | ttgcctcaaa | tacacccaaa | 300 |
| ctataaataa | agaaacagat | gtctctatgt | acagcaaggc | caccatacaa | ggcttcagca | 360 |
| gaacatttcc | agtctccttt | ggagtcccac | ttattactga | cagtgagcaa | gacactcatt | 420 |
| tctcttctaa | gaacatacaa | cgcc | | | | 444 |

<210> SEQ ID NO 31
<211> LENGTH: 693
<212> TYPE: DNA
<213> ORGANISM: Homo sapiens
<220> FEATURE:

```
<221> NAME/KEY: allele
<222> LOCATION: 162
<223> OTHER INFORMATION: 99-1597-162 : polymorphic base A or G
<220> FEATURE:
<221> NAME/KEY: misc_binding
<222> LOCATION: 150..174
<223> OTHER INFORMATION: 99-1597-162.probe
<220> FEATURE:
<221> NAME/KEY: primer_bind
<222> LOCATION: 143..161
<223> OTHER INFORMATION: 99-1597-162.mis
<220> FEATURE:
<221> NAME/KEY: primer_bind
<222> LOCATION: 163..181
<223> OTHER INFORMATION: 99-1597-162.mis complement
<220> FEATURE:
<221> NAME/KEY: primer_bind
<222> LOCATION: 1..19
<223> OTHER INFORMATION: 99-1597.pu
<220> FEATURE:
<221> NAME/KEY: primer_bind
<222> LOCATION: 675..693
<223> OTHER INFORMATION: 99-1597.rp complement
<220> FEATURE:
<221> NAME/KEY: misc_feature
<222> LOCATION: 582..615
<223> OTHER INFORMATION: n=a, g, c or t

<400> SEQUENCE: 31
tttaagatgc caagttgtca aactgggcag ctaggcccca ggctctttct aaattgtcaa      60
gactagcaaa gccgagtcat cccctgctc tagttctgga tgacaccaag cctaggaaat     120
aaagcacaat agatggggcc ctggtctctg aatgacagag trtgcatggg ggctaggagg    180
aaggaggaat ccagctctct aaaaggaagg tgcaggcggt gtgtgagggg tcaaagacaa    240
aggggcgtgt cccactgaag atacaaactc taggccgggc gcggtggctc atgcctgtaa    300
tcccagtact ttgggatgcc aaggcgggca gatcacaagg tcaggagatc gagaccatct    360
tggctaaggg ggtgaaaccc tgtctctact aaaaaaacta caaaaagtta gccaggtgtg    420
gtagcatacg cctgtagtcc cagctactca ggaggctgag gcaggagaat tgcttgaacc    480
cgggagatgg aggttgcagt gagccaagat cacgccactg cactccagcc tgggcaacag    540
agcgagactc tgtctcaaaa aggaaaagaa aagaaaaag annnnnnnnn nnnnnnnnn      600 nnnnnnnnnn nnnnaatag atttctgttt ccttgatgag gaaacaagat aaaactagtc    660
actatgtatt gggtggctac tttagcatca atc                                693

<210> SEQ ID NO 32
<211> LENGTH: 26
<212> TYPE: DNA
<213> ORGANISM: Artificial Sequence
<220> FEATURE:
<223> OTHER INFORMATION: oligonucleotide BAP283Ra6283

<400> SEQUENCE: 32
ggcggatgac tctctttgga aaccac                                         26

<210> SEQ ID NO 33
<211> LENGTH: 25
<212> TYPE: DNA
<213> ORGANISM: Artificial Sequence
<220> FEATURE:
<223> OTHER INFORMATION: oligonucleotide BAP283Ra6324n

<400> SEQUENCE: 33
tgctaaagac gagagactcc tcgcc                                          25

<210> SEQ ID NO 34
```

```
<211> LENGTH: 29
<212> TYPE: DNA
<213> ORGANISM: Artificial Sequence
<220> FEATURE:
<223> OTHER INFORMATION: oligonucleotide BAP28-exALF7311

<400> SEQUENCE: 34 cccctatga tctgattcac caggcttac                                      29

<210> SEQ ID NO 35
<211> LENGTH: 26
<212> TYPE: DNA
<213> ORGANISM: Artificial Sequence
<220> FEATURE:
<223> OTHER INFORMATION: oligonucleotide BAP28-exALF7319n

<400> SEQUENCE: 35
gatctgattc accaggctta cctccg                                        26

<210> SEQ ID NO 36
<211> LENGTH: 27
<212> TYPE: DNA
<213> ORGANISM: Artificial Sequence
<220> FEATURE:
<223> OTHER INFORMATION: oligonucleotide PCTAexALF12

<400> SEQUENCE: 36
cccacctgaa aagactggat ttgggac                                       27

<210> SEQ ID NO 37
<211> LENGTH: 27
<212> TYPE: DNA
<213> ORGANISM: Artificial Sequence
<220> FEATURE:
<223> OTHER INFORMATION: oligonucleotide PCTAexALF13n

<400> SEQUENCE: 37
ccacctgaaa agactggatt tgggaca                                       27

<210> SEQ ID NO 38
<211> LENGTH: 27
<212> TYPE: DNA
<213> ORGANISM: Artificial Sequence
<220> FEATURE:
<223> OTHER INFORMATION: oligonucleotide PCTAexALR60

<400> SEQUENCE: 38
ctccgaagtt ctacaggatc atgtccc                                       27

<210> SEQ ID NO 39
<211> LENGTH: 27
<212> TYPE: DNA
<213> ORGANISM: Artificial Sequence
<220> FEATURE:
<223> OTHER INFORMATION: oligonucleotide PCTAexALR12n

<400> SEQUENCE: 39
cccaaatcca gtcttttcag gtgggag                                       27

<210> SEQ ID NO 40
<211> LENGTH: 25
<212> TYPE: DNA
<213> ORGANISM: Artificial Sequence
<220> FEATURE:
<223> OTHER INFORMATION: oligonucleotide PCTAexBLF33

<400> SEQUENCE: 40
```

-continued gaaaaccctg gcgttgaccc cgtgg                                         25

<210> SEQ ID NO 41
<211> LENGTH: 25
<212> TYPE: DNA
<213> ORGANISM: Artificial Sequence
<220> FEATURE:
<223> OTHER INFORMATION: oligonucleotide PCTAexBLF120n

<400> SEQUENCE: 41
caccctggtc ctgaaaagtc cagcc                                         25

<210> SEQ ID NO 42
<211> LENGTH: 25
<212> TYPE: DNA
<213> ORGANISM: Artificial Sequence
<220> FEATURE:
<223> OTHER INFORMATION: oligonucleotide PCTAexBLR140

<400> SEQUENCE: 42
taggagggag ggagattcgg ggctg                                         25

<210> SEQ ID NO 43
<211> LENGTH: 26
<212> TYPE: DNA
<213> ORGANISM: Artificial Sequence
<220> FEATURE:
<223> OTHER INFORMATION: oligonucleotide PCTAexBLR40n

<400> SEQUENCE: 43
tccacggggt caacgccagg gttttc                                        26

<210> SEQ ID NO 44
<211> LENGTH: 27
<212> TYPE: DNA
<213> ORGANISM: Artificial Sequence
<220> FEATURE:
<223> OTHER INFORMATION: oligonucleotide PCTA5Ra220n

<400> SEQUENCE: 44
gggaatggtg ccaacatacg ggattac                                       27

<210> SEQ ID NO 45
<211> LENGTH: 26
<212> TYPE: DNA
<213> ORGANISM: Artificial Sequence
<220> FEATURE:
<223> OTHER INFORMATION: oligonucleotide PCTA5Ra230

<400> SEQUENCE: 45
gctgatcggg aatggtgcca acatac                                        26

<210> SEQ ID NO 46
<211> LENGTH: 25
<212> TYPE: DNA
<213> ORGANISM: Artificial Sequence
<220> FEATURE:
<223> OTHER INFORMATION: oligonucleotide PCTA_5Ra400

<400> SEQUENCE: 46
tcacctacac ctcacccact tcctc                                         25

<210> SEQ ID NO 47
<211> LENGTH: 25
<212> TYPE: DNA
<213> ORGANISM: Artificial Sequence
<220> FEATURE:

<223> OTHER INFORMATION: oligonucleotide PCTA_5Ran_400

<400> SEQUENCE: 47
cctacacctc acccacttcc tcccc                                              25

<210> SEQ ID NO 48
<211> LENGTH: 27
<212> TYPE: DNA
<213> ORGANISM: Artificial Sequence
<220> FEATURE:
<223> OTHER INFORMATION: oligonucleotide PCTA_5Ra_394

<400> SEQUENCE: 48
cctccccacc actggttcat tttgaag                                            27

<210> SEQ ID NO 49
<211> LENGTH: 25
<212> TYPE: DNA
<213> ORGANISM: Artificial Sequence
<220> FEATURE:
<223> OTHER INFORMATION: oligonucleotide PCTA_exD5Ra

<400> SEQUENCE: 49
tccccaggaa gtgtcatgga cggtg                                              25

<210> SEQ ID NO 50
<211> LENGTH: 27
<212> TYPE: DNA
<213> ORGANISM: Artificial Sequence
<220> FEATURE:
<223> OTHER INFORMATION: oligonucleotide PCTA_exD5Ran

<400> SEQUENCE: 50
ggaagtgtca tggacggtgt cttctac                                            27

<210> SEQ ID NO 51
<211> LENGTH: 29
<212> TYPE: DNA
<213> ORGANISM: Artificial Sequence
<220> FEATURE:
<223> OTHER INFORMATION: oligonucleotide PCTA_exC5Ra

<400> SEQUENCE: 51
gctttcatcg cccagctcca gcaattatc                                          29

<210> SEQ ID NO 52
<211> LENGTH: 25
<212> TYPE: DNA
<213> ORGANISM: Artificial Sequence
<220> FEATURE:
<223> OTHER INFORMATION: oligonucleotide PCTA_exC5Ran

<400> SEQUENCE: 52
tcgcccagct ccagcaatta tcgac                                              25

<210> SEQ ID NO 53
<211> LENGTH: 25
<212> TYPE: DNA
<213> ORGANISM: Artificial Sequence
<220> FEATURE:
<223> OTHER INFORMATION: oligonucleotide PCTAex9terLR330

<400> SEQUENCE: 53
acatggggag ctgtgacagt tctgg                                              25

<210> SEQ ID NO 54

```
<211> LENGTH: 29
<212> TYPE: DNA
<213> ORGANISM: Artificial Sequence
<220> FEATURE:
<223> OTHER INFORMATION: oligonucleotide PCTAex9terLR325n

<400> SEQUENCE: 54
ggggagctgt gacagttctg aacataag                                          29

<210> SEQ ID NO 55
<211> LENGTH: 27
<212> TYPE: DNA
<213> ORGANISM: Artificial Sequence
<220> FEATURE:
<223> OTHER INFORMATION: oligonucleotide PCTAexCLF120

<400> SEQUENCE: 55
cttcaaaatg aaccagtggt ggggagg                                           27

<210> SEQ ID NO 56
<211> LENGTH: 25
<212> TYPE: DNA
<213> ORGANISM: Artificial Sequence
<220> FEATURE:
<223> OTHER INFORMATION: oligonucleotide PCTAexCLF130n

<400> SEQUENCE: 56
accagtggtg gggaggaagt gggtg                                             25

<210> SEQ ID NO 57
<211> LENGTH: 20
<212> TYPE: DNA
<213> ORGANISM: Artificial Sequence
<220> FEATURE:
<223> OTHER INFORMATION: oligonucleotide BAP28polyTcourt

<400> SEQUENCE: 57
tttttttttt ttttttgtata                                                  20

<210> SEQ ID NO 58
<211> LENGTH: 25
<212> TYPE: DNA
<213> ORGANISM: Artificial Sequence
<220> FEATURE:
<223> OTHER INFORMATION: oligonucleotide BAP281LF12.1

<400> SEQUENCE: 58
ccatgtggga agcgctgtga agagt                                             25

<210> SEQ ID NO 59
<211> LENGTH: 26
<212> TYPE: DNA
<213> ORGANISM: Artificial Sequence
<220> FEATURE:
<223> OTHER INFORMATION: oligonucleotide BAP28LR6726.1

<400> SEQUENCE: 59
cagctctata cgataggcag gagagg                                            26

<210> SEQ ID NO 60
<211> LENGTH: 38
<212> TYPE: DNA
<213> ORGANISM: Artificial Sequence
<220> FEATURE:
<223> OTHER INFORMATION: oligonucleotide BAP28LF26SalI

<400> SEQUENCE: 60
```

```
cctgtgtcga ccgctgtgaa gagttgttgc cttccaag                                    38
```

<210> SEQ ID NO 61
<211> LENGTH: 36
<212> TYPE: DNA
<213> ORGANISM: Artificial Sequence
<220> FEATURE:
<223> OTHER INFORMATION: oligonucleotide BAP28LR6717SalI

<400> SEQUENCE: 61

```
actccgtcga ccgataggca ggagaggctt atgtgg                                      36
```

<210> SEQ ID NO 62
<211> LENGTH: 18
<212> TYPE: DNA
<213> ORGANISM: Artificial Sequence
<220> FEATURE:
<223> OTHER INFORMATION: sequencing oligonucleotide PrimerPU

<400> SEQUENCE: 62

```
tgtaaaacga cggccagt                                                          18
```

<210> SEQ ID NO 63
<211> LENGTH: 18
<212> TYPE: DNA
<213> ORGANISM: Artificial Sequence
<220> FEATURE:
<223> OTHER INFORMATION: sequencing oligonucleotide PrimerRP

<400> SEQUENCE: 63

```
caggaaacag ctatgacc                                                          18
```

<210> SEQ ID NO 64
<211> LENGTH: 2144
<212> TYPE: PRT
<213> ORGANISM: Homo sapiens
<220> FEATURE:
<221> NAME/KEY: misc_feature
<222> LOCATION: (1218)..(1218)
<223> OTHER INFORMATION: Xaa can be any naturally occurring amino acid

<400> SEQUENCE: 64

Met Thr Ser Leu Ala Gln Gln Leu Gln Arg Leu Ala Leu Pro Gln Ser
1               5                   10                  15

Asp Ala Ser Leu Leu Ser Arg Asp Glu Val Ala Ser Leu Leu Phe Asp
            20                  25                  30

Pro Lys Glu Ala Ala Thr Ile Asp Arg Asp Thr Ala Phe Ala Ile Gly
        35                  40                  45

Cys Thr Gly Leu Glu Glu Leu Leu Gly Ile Asp Pro Ser Phe Glu Gln
    50                  55                  60

Phe Glu Ala Pro Leu Phe Ser Gln Leu Ala Lys Thr Leu Glu Arg Ser
65                  70                  75                  80

Val Gln Thr Lys Ala Val Asn Lys Gln Leu Asp Glu Asn Ile Ser Leu
                85                  90                  95

Phe Leu Ile His Leu Ser Pro Tyr Phe Leu Leu Lys Pro Ala Gln Lys
            100                 105                 110

Cys Leu Glu Trp Leu Ile His Arg Phe His Ile His Leu Tyr Asn Gln
        115                 120                 125

Asp Ser Leu Ile Ala Cys Val Leu Pro Tyr His Glu Thr Arg Ile Phe
    130                 135                 140

Val Arg Val Ile Gln Leu Leu Lys Ile Asn Asn Ser Lys His Arg Trp
145                 150                 155                 160

```
Phe Trp Leu Leu Pro Val Lys Gln Ser Gly Val Pro Leu Ala Lys Gly
                165                 170                 175

Thr Leu Ile Thr His Cys Tyr Lys Asp Leu Gly Phe Met Asp Phe Ile
            180                 185                 190

Cys Ser Leu Val Thr Lys Ser Val Lys Val Phe Ala Glu Tyr Pro Gly
        195                 200                 205

Ser Ser Ala Gln Leu Arg Val Leu Leu Ala Phe Tyr Ala Ser Thr Ile
    210                 215                 220

Val Ser Ala Leu Val Ala Ala Glu Asp Val Ser Asp Asn Ile Ile Ala
225                 230                 235                 240

Lys Leu Phe Pro Tyr Ile Gln Lys Gly Leu Lys Ser Ser Leu Pro Asp
                245                 250                 255

Tyr Arg Ala Ala Thr Tyr Met Ile Ile Cys Gln Ile Ser Val Lys Val
            260                 265                 270

Thr Met Glu Asn Thr Phe Val Asn Ser Leu Ala Ser Gln Ile Ile Lys
        275                 280                 285

Thr Leu Thr Lys Ile Pro Ser Leu Ile Lys Asp Gly Leu Ser Cys Leu
    290                 295                 300

Ile Val Leu Leu Gln Arg Gln Lys Pro Glu Ser Leu Gly Lys Lys Pro
305                 310                 315                 320

Phe Pro His Leu Cys Asn Val Pro Asp Leu Ile Thr Ile Leu His Gly
                325                 330                 335

Ile Ser Glu Thr Tyr Asp Val Ser Pro Leu Leu Arg Tyr Met Leu Pro
            340                 345                 350

His Leu Val Val Ser Ile Ile His His Val Thr Gly Glu Glu Thr Glu
        355                 360                 365

Gly Met Asp Gly Gln Ile Tyr Lys Arg His Leu Glu Ala Ile Leu Thr
    370                 375                 380

Lys Ile Ser Leu Lys Asn Asn Leu Asp His Leu Leu Ala Ser Leu Leu
385                 390                 395                 400

Phe Glu Glu Tyr Ile Ser Tyr Ser Ser Gln Glu Met Asp Ser Asn
                405                 410                 415

Lys Val Ser Leu Leu Asn Glu Gln Phe Leu Pro Leu Ile Arg Leu Leu
            420                 425                 430

Glu Ser Lys Tyr Pro Arg Thr Leu Asp Val Val Leu Glu Glu His Leu
        435                 440                 445

Lys Glu Ile Ala Asp Leu Lys Lys Gln Glu Leu Phe His Gln Phe Val
    450                 455                 460

Ser Leu Ser Thr Ser Gly Gly Lys Tyr Gln Phe Leu Ala Asp Ser Asp
465                 470                 475                 480

Thr Ser Leu Met Leu Ser Leu Asn His Pro Leu Ala Pro Val Arg Ile
                485                 490                 495

Leu Ala Met Asn His Leu Lys Lys Ile Met Lys Thr Ser Lys Glu Gly
            500                 505                 510

Val Asp Glu Ser Phe Ile Lys Glu Ala Val Leu Ala Arg Leu Gly Asp
        515                 520                 525

Asp Asn Ile Asp Val Val Leu Ser Ala Ile Ser Ala Phe Glu Ile Phe
    530                 535                 540

Lys Glu His Phe Ser Ser Glu Val Thr Ile Ser Asn Leu Leu Asn Leu
545                 550                 555                 560

Phe Gln Arg Ala Glu Leu Ser Lys Asn Gly Glu Trp Tyr Glu Val Leu
                565                 570                 575

Lys Ile Ala Ala Asp Ile Leu Ile Lys Glu Glu Ile Leu Ser Glu Asn
            580                 585                 590
```

```
Asp Gln Leu Ser Asn Gln Val Val Cys Leu Leu Pro Phe Val Val
            595                 600                 605

Ile Asn Asn Asp Asp Thr Glu Ser Ala Glu Met Lys Ile Ala Ile Tyr
610                 615                 620

Leu Ser Lys Ser Gly Ile Cys Ser Leu His Pro Leu Leu Arg Gly Trp
625                 630                 635                 640

Glu Glu Ala Leu Glu Asn Val Ile Lys Ser Thr Lys Pro Gly Lys Leu
            645                 650                 655

Ile Gly Val Ala Asn Gln Lys Met Ile Glu Leu Leu Ala Asp Asn Ile
            660                 665                 670

Asn Leu Gly Asp Pro Ser Ser Met Leu Lys Met Val Glu Asp Leu Ile
            675                 680                 685

Ser Val Gly Glu Glu Ser Phe Asn Leu Lys Gln Lys Val Thr Phe
            690                 695                 700

His Val Ile Leu Ser Val Leu Val Ser Cys Cys Ser Ser Leu Lys Glu
705                 710                 715                 720

Thr His Phe Pro Phe Ala Ile Arg Val Phe Ser Leu Leu Gln Lys Lys
            725                 730                 735

Ile Lys Lys Leu Glu Ser Val Ile Thr Ala Val Glu Ile Pro Ser Glu
            740                 745                 750

Trp His Ile Glu Leu Met Leu Asp Arg Gly Ile Pro Val Glu Leu Trp
            755                 760                 765

Ala His Tyr Val Glu Glu Leu Asn Ser Thr Gln Arg Val Ala Val Glu
            770                 775                 780

Asp Ser Val Phe Leu Val Phe Ser Leu Lys Lys Phe Ile Tyr Ala Leu
785                 790                 795                 800

Lys Ala Pro Lys Ser Phe Pro Lys Gly Asp Ile Trp Trp Asn Pro Glu
            805                 810                 815

Gln Leu Lys Glu Asp Ser Arg Asp Tyr Leu His Leu Leu Ile Gly Leu
            820                 825                 830

Phe Glu Met Met Leu Asn Gly Ala Asp Ala Val His Phe Arg Val Leu
            835                 840                 845

Met Lys Leu Phe Ile Lys Val His Leu Glu Asp Val Phe Gln Leu Phe
            850                 855                 860

Lys Phe Cys Ser Val Leu Trp Thr Tyr Gly Ser Ser Leu Ser Asn Pro
865                 870                 875                 880

Leu Asn Cys Ser Val Lys Thr Val Leu Gln Thr Gln Ala Leu Tyr Val
                885                 890                 895

Gly Cys Ala Met Leu Ser Ser Gln Lys Thr Gln Cys Lys His Gln Leu
            900                 905                 910

Ala Ser Ile Ser Ser Pro Val Val Thr Ser Leu Leu Ile Asn Leu Gly
            915                 920                 925

Ser Pro Val Lys Glu Val Arg Arg Ala Ala Ile Gln Cys Leu Gln Ala
            930                 935                 940

Leu Ser Gly Val Ala Ser Pro Phe Tyr Leu Ile Ile Asp His Leu Ile
945                 950                 955                 960

Ser Lys Ala Glu Glu Ile Thr Ser Asp Ala Ala Tyr Val Ile Gln Asp
            965                 970                 975

Leu Ala Thr Leu Phe Glu Glu Leu Gln Arg Gly Lys Lys Leu Lys Ser
            980                 985                 990

His Gln Lys Leu Ser Glu Thr Leu  Lys Asn Leu Leu Ser  Cys Val Tyr
            995                 1000                1005

Ser Cys  Pro Ser Tyr Ile Ala  Lys Asp Leu Met Lys  Val Leu Gln
```

-continued

```
                1010                1015                1020
Gly Val Asn Gly Glu Met Val Leu Ser Gln Leu Leu Pro Met Ala
    1025                1030                1035
Glu Gln Leu Leu Glu Lys Ile Gln Lys Glu Pro Thr Ala Val Leu
    1040                1045                1050
Lys Asp Glu Ala Met Val Leu His Leu Thr Leu Gly Lys Tyr Asn
    1055                1060                1065
Glu Phe Ser Val Ser Leu Leu Asn Glu Asp Pro Lys Ser Leu Asp
    1070                1075                1080
Ile Phe Ile Lys Ala Val His Thr Thr Lys Glu Leu Tyr Ala Gly
    1085                1090                1095
Met Pro Thr Ile Gln Ile Thr Ala Leu Glu Lys Ile Thr Lys Pro
    1100                1105                1110
Phe Phe Ala Ala Ile Ser Asp Glu Lys Val Gln Gln Lys Leu Leu
    1115                1120                1125
Arg Met Leu Phe Asp Leu Leu Val Asn Cys Lys Asn Ser His Cys
    1130                1135                1140
Ala Gln Thr Val Ser Ser Val Phe Lys Gly Ile Ser Val Asn Ala
    1145                1150                1155
Glu Gln Val Arg Ile Glu Leu Glu Pro Pro Asp Lys Ala Lys Pro
    1160                1165                1170
Leu Gly Thr Val Gln Gln Lys Arg Arg Gln Lys Met Gln Gln Lys
    1175                1180                1185
Lys Ser Gln Asp Leu Glu Ser Val Gln Glu Val Gly Gly Ser Tyr
    1190                1195                1200
Trp Gln Arg Val Thr Leu Ile Leu Glu Leu Leu Gln His Lys Xaa
    1205                1210                1215
Lys Leu Arg Ser Pro Gln Ile Leu Val Pro Thr Leu Phe Asn Leu
    1220                1225                1230
Leu Ser Arg Cys Leu Glu Pro Leu Pro Gln Glu Gln Gly Asn Met
    1235                1240                1245
Glu Tyr Thr Lys Gln Leu Ile Leu Ser Cys Leu Leu Asn Ile Cys
    1250                1255                1260
Gln Lys Leu Ser Pro Asp Gly Gly Lys Ile Pro Lys Asp Ile Leu
    1265                1270                1275
Asp Glu Glu Lys Phe Asn Val Glu Leu Ile Val Gln Cys Ile Arg
    1280                1285                1290
Leu Ser Glu Met Pro Gln Thr His His His Ala Leu Leu Leu Leu
    1295                1300                1305
Gly Thr Val Ala Gly Ile Phe Pro Asp Lys Val Leu His Asn Ile
    1310                1315                1320
Met Ser Ile Phe Thr Phe Met Gly Ala Asn Val Met Arg Leu Asp
    1325                1330                1335
Asp Thr Tyr Ser Phe Gln Val Ile Asn Lys Thr Val Lys Met Val
    1340                1345                1350
Ile Pro Ala Leu Ile Gln Ser Asp Ser Gly Asp Ser Ile Glu Val
    1355                1360                1365
Ser Arg Asn Val Glu Glu Ile Val Val Lys Ile Ile Ser Val Phe
    1370                1375                1380
Val Asp Ala Leu Pro His Val Pro Glu His Arg Arg Leu Pro Ile
    1385                1390                1395
Leu Val Gln Leu Val Asp Thr Leu Gly Ala Glu Lys Phe Leu Trp
    1400                1405                1410
```

-continued

```
Ile Leu Leu Ile Leu Leu Phe Glu Gln Tyr Val Thr Lys Thr Val
1415                1420                1425

Leu Ala Ala Ala Tyr Gly Glu Lys Asp Ala Ile Leu Glu Ala Asp
1430                1435                1440

Thr Glu Phe Trp Phe Ser Val Cys Cys Glu Phe Ser Val Gln His
1445                1450                1455

Gln Ile Gln Ser Leu Met Asn Ile Leu Gln Tyr Leu Leu Lys Leu
1460                1465                1470

Pro Glu Glu Lys Glu Glu Thr Ile Pro Lys Ala Val Ser Phe Asn
1475                1480                1485

Lys Ser Glu Ser Gln Glu Glu Met Leu Gln Val Phe Asn Val Glu
1490                1495                1500

Thr His Thr Ser Lys Gln Leu Arg His Phe Lys Phe Leu Ser Val
1505                1510                1515

Ser Phe Met Ser Gln Leu Leu Ser Ser Asn Asn Phe Leu Lys Lys
1520                1525                1530

Val Val Glu Ser Gly Gly Pro Glu Ile Leu Lys Gly Leu Glu Glu
1535                1540                1545

Arg Leu Leu Glu Thr Val Leu Gly Tyr Ile Ser Ala Val Ala Gln
1550                1555                1560

Ser Met Glu Arg Asn Ala Asp Lys Leu Thr Val Lys Phe Trp Arg
1565                1570                1575

Ala Leu Leu Ser Lys Ala Tyr Asp Leu Leu Asp Lys Val Asn Ala
1580                1585                1590

Leu Leu Pro Thr Glu Thr Phe Ile Pro Val Ile Arg Gly Leu Val
1595                1600                1605

Gly Asn Pro Leu Pro Ser Val Arg Arg Lys Ala Leu Asp Leu Leu
1610                1615                1620

Asn Asn Lys Leu Gln Gln Asn Ile Ser Trp Lys Lys Thr Ile Val
1625                1630                1635

Thr Arg Phe Leu Lys Leu Val Pro Asp Leu Leu Ala Ile Val Gln
1640                1645                1650

Arg Lys Lys Lys Glu Gly Glu Glu Glu Gln Ala Ile Asn Arg Gln
1655                1660                1665

Thr Ala Leu Tyr Thr Leu Lys Leu Leu Cys Lys Asn Phe Gly Ala
1670                1675                1680

Glu Asn Pro Asp Pro Phe Val Pro Val Leu Ser Thr Ala Val Lys
1685                1690                1695

Leu Ile Ala Pro Glu Arg Lys Glu Glu Lys Asn Val Leu Gly Ser
1700                1705                1710

Ala Leu Leu Cys Ile Ala Glu Val Thr Ser Thr Leu Glu Ala Leu
1715                1720                1725

Ala Ile Pro Gln Leu Pro Ser Leu Met Pro Ser Leu Leu Thr Thr
1730                1735                1740

Met Lys Asn Thr Ser Glu Leu Val Ser Ser Glu Val Tyr Leu Leu
1745                1750                1755

Ser Ala Leu Ala Ala Leu Gln Lys Val Val Glu Thr Leu Pro His
1760                1765                1770

Phe Ile Ser Pro Tyr Leu Glu Gly Ile Leu Ser Gln Val Ile His
1775                1780                1785

Leu Glu Lys Ile Thr Ser Glu Met Gly Ser Ala Ser Gln Ala Asn
1790                1795                1800

Ile Arg Leu Thr Ser Leu Lys Lys Thr Leu Ala Thr Thr Leu Ala
1805                1810                1815
```

```
Pro Arg Val Leu Leu Pro Ala Ile Lys Lys Thr Tyr Lys Gln Ile
    1820                1825                1830

Glu Lys Asn Trp Lys Asn His Met Gly Pro Phe Met Ser Ile Leu
    1835                1840                1845

Gln Glu His Ile Gly Ala Met Lys Lys Glu Glu Leu Thr Ser His
    1850                1855                1860

Gln Ser Gln Leu Thr Ala Phe Phe Leu Glu Ala Leu Asp Phe Arg
    1865                1870                1875

Ala Gln His Ser Glu Asn Asp Leu Glu Glu Val Gly Lys Thr Glu
    1880                1885                1890

Asn Cys Ile Ile Asp Cys Leu Val Ala Met Val Lys Leu Ser
    1895                1900            1905

Glu Val Thr Phe Arg Pro Leu Phe Phe Lys Leu Phe Asp Trp Ala
    1910                1915                1920

Lys Thr Glu Asp Ala Pro Lys Asp Arg Leu Leu Thr Phe Tyr Asn
    1925                1930                1935

Leu Ala Asp Cys Ile Ala Glu Lys Leu Lys Gly Leu Phe Thr Leu
    1940                1945                1950

Phe Ala Gly His Leu Val Lys Pro Phe Ala Asp Thr Leu Asp Gln
    1955                1960                1965

Val Asn Ile Ser Lys Thr Asp Glu Ala Phe Phe Asp Ser Glu Asn
    1970                1975                1980

Asp Pro Glu Lys Cys Cys Leu Leu Leu Gln Phe Ile Leu Asn Cys
    1985                1990                1995

Leu Tyr Lys Ile Phe Leu Phe Asp Thr Gln His Phe Ile Ser Lys
    2000                2005                2010

Glu Arg Ala Gly Ala Leu Met Met Pro Leu Val Asp Gln Leu Glu
    2015                2020                2025

Asn Arg Leu Gly Gly Glu Glu Lys Phe Gln Glu Arg Val Thr Lys
    2030                2035                2040

His Leu Ile Pro Cys Ile Ala Gln Phe Ser Val Ala Met Ala Asp
    2045                2050                2055

Asp Ser Leu Trp Lys Pro Leu Asn Tyr Gln Ile Leu Leu Lys Thr
    2060                2065                2070

Arg Asp Ser Ser Pro Lys Val Arg Phe Ala Ala Leu Ile Thr Val
    2075                2080                2085

Leu Ala Leu Ala Glu Lys Leu Lys Glu Asn Tyr Ile Val Leu Leu
    2090                2095                2100

Pro Glu Ser Ile Pro Phe Leu Ala Glu Leu Met Glu Asp Glu Cys
    2105                2110                2115

Glu Glu Val Glu His Gln Cys Gln Lys Thr Ile Gln Gln Leu Glu
    2120                2125                2130

Thr Val Leu Gly Glu Pro Leu Gln Ser Tyr Phe
    2135                2140

<210> SEQ ID NO 65
<211> LENGTH: 2096
<212> TYPE: PRT
<213> ORGANISM: Drosophila melanogaster

<400> SEQUENCE: 65

Met Ser Thr Ala Leu Ala Gln Gln Leu Gln Lys Leu Ala Ala Pro Gln
1               5                   10                  15

Ser Ser Val Thr Leu Ala Asp Ala Arg Ser Arg Ala Ser Ile Leu Phe
            20                  25                  30
```

Asp Pro Lys Glu Ala Ala Thr Lys Asp Arg Arg Ser Ile Tyr Glu Ile
         35                  40                  45

Gly Leu Thr Gly Leu Gln Glu Leu Thr Asp Phe Asn Pro Ala Phe Lys
 50                  55                  60

Glu Phe Gln Leu Thr Leu Phe Asp Glu Ala Thr Leu Thr Leu Glu Arg
 65                  70                  75                  80

Ser Val Glu Leu Pro Glu Ile Asn Lys Met Leu Asp Ala Ala Ile Ala
                 85                  90                  95

Lys Phe Leu Arg Leu Leu Ser Pro Tyr Leu Leu Arg Pro Ala His
                100                 105                 110

Met Ala Phe Glu Trp Leu Leu Arg Arg Phe Gln Val His Glu Tyr Asn
                115                 120                 125

Arg Ser Glu Val Met Ala Leu Ile Leu Pro Tyr His Glu Thr Met Ile
                130                 135                 140

Phe Val Gln Ile Val Lys Thr Met Arg Leu Arg Ser Ser Asp Gly Asp
145                 150                 155                 160

Trp Tyr Trp Leu Arg Pro Leu Gln Arg Pro Gly Val Pro Leu Ala Lys
                165                 170                 175

Thr Ala Ile Ile Asn Arg Ala Ala Ser Asn Pro Ala Phe Leu Gly Phe
                180                 185                 190

Ile Cys Gln Ser Thr Gln Lys Ala Val Lys Glu Leu Gly Pro Arg Ala
                195                 200                 205

His Gln Leu Gln Ala Gln Ile Asn Phe Tyr Ala Thr Val Val Gly
                210                 215                 220

Ala Leu Gln Thr Ala Lys Pro Leu Gln Asp Trp His Ile Thr Thr Ile
225                 230                 235                 240

Leu Glu Ser Leu Leu Arg Gly Leu Ile Ser Asp Asn Ile Asp Phe Met
                245                 250                 255

Ala Ala Ala Tyr Val Ile Val Ala Gln Leu Val Ser Arg Thr Lys Leu
                260                 265                 270

Lys Ser Lys Val Cys Asn Ala Leu Leu Glu Arg Val Ala Asn Cys Pro
                275                 280                 285

Phe Glu Arg Leu His Ser Glu Ser Leu Leu Leu Val Cys Ile Tyr
                290                 295                 300

Gly Lys Gln Gln Ala Ala Leu Pro His Phe Lys Pro Glu Thr Ile Leu
305                 310                 315                 320

Asn Leu Val Gly Lys Lys Trp Leu Ile Ser Thr Leu Ser Ser Leu Ala
                325                 330                 335

Lys Gly Asn Ile Ala Ile Gln Ser Ile Cys Met Pro Leu Met Thr Gly
                340                 345                 350

Ala Val Ala Ala Ile Arg Asp Asp Ala Ser Ser Asn Ser Cys Lys
                355                 360                 365

Leu Phe Leu Asp Asn Leu Leu Ser Glu Val Pro Met Pro Lys Pro Thr
370                 375                 380

Ala Gln Gln Leu Ile Asn Cys Phe Leu Asp Thr Tyr Val Glu Thr Ala
385                 390                 395                 400

Ile Asp Ala Pro Glu Pro Met Glu Thr Asn Ser Asn Glu Asp Asp
                405                 410                 415

Thr Ile Val Ile Asp Ser Asp Glu Ile Glu Thr Lys Thr
                420                 425                 430

Phe Gln Ala Trp Tyr Ser Thr Tyr Leu Glu Lys Leu Glu Arg Arg Tyr
                435                 440                 445

Pro Glu Ala Phe Asp Leu Ser Val Lys Glu Ala Leu Arg Ser Lys Ser

```
                450                 455                 460
Ser Thr Ser Asn Arg Gln Lys Ala Leu Lys Leu Ala Leu Gly Phe Arg
465                 470                 475                 480

Leu Asn Thr Thr Asp Glu Lys Ala Lys His Ala Tyr Glu Lys Leu Tyr
                485                 490                 495

His Tyr Ser Ala Asp Trp Arg Leu Ser Ala Val Gln Lys Leu Leu Gln
                500                 505                 510

Asn Leu Asn Val Thr Lys Lys Arg Glu Arg Ser Val Lys Leu Leu Gln
                515                 520                 525

Glu Cys Leu Pro Asp Arg Ile Asn Asp Asp Ser Gly Ala Val Val Ser
530                 535                 540

Thr Leu Leu Ser Leu Pro Thr Glu Glu Leu Ala Glu Met Leu Gly Pro
545                 550                 555                 560

Leu Pro Leu Ala Gln Thr Leu Cys His Leu Leu Tyr Arg Ala Gln Ser
                565                 570                 575

Glu Lys Asp Glu Glu Trp Gln Pro Val Val Pro Leu Ala Val Arg His
                580                 585                 590

Leu Thr Ser Ala Leu Val Ser Gly Ser Tyr Asp Thr Asn Leu Val Leu
                595                 600                 605

Leu Ala Leu Met Pro Leu Leu Phe Pro Gly Glu Ala Leu Ala Glu His
610                 615                 620

Gln His Lys Ala Leu Arg Ile Leu Leu Gly Ser Asp Phe Val Ser Lys
625                 630                 635                 640

Val Pro Phe Leu Ala Glu Leu Lys Val Ser Asn Lys Phe Ser Asp Phe
                645                 650                 655

Asn Val Gly Glu His Arg Gln His Phe Leu Asp Ile Ile Ala Ser Ser
                660                 665                 670

Asn Gln Glu Leu Ser Ser Gln Glu Arg Ala Leu Leu Gln Ser Val Glu
                675                 680                 685

Asp His Gly Gly Glu Leu Tyr Ile Gln Lys Ala Ser Gln Leu Thr His
690                 695                 700

Leu Leu Leu Leu Leu Thr Ala Tyr Ala Lys Arg Glu Leu Gln Pro Arg
705                 710                 715                 720

Glu Ser Leu His Met Leu Glu Lys Ile Gly Leu Tyr Ser Arg Arg Leu
                725                 730                 735

Gln Phe Arg Val Val Asn Gly Ser Gln Asn Thr Gln Asn Cys Ala Pro
                740                 745                 750

Leu Gln Leu Tyr Val Asp Phe Leu Leu Thr Leu Val Lys Asn Thr Lys
                755                 760                 765

Trp Thr Ala Leu Ala Ser Thr Pro Trp Asn Gln Met Thr Asp Glu Leu
770                 775                 780

Arg Leu Cys Leu Arg Leu Leu Glu Ile Ile Cys Ala Gln Val Phe Ser
785                 790                 795                 800

Glu Lys Ala Asp Gln Pro Glu Arg Gln Glu Trp Thr Arg Ala Leu Gln
                805                 810                 815

Gln Ser Leu Gln Leu Ile Leu Pro Glu Ala Gln Asp Arg Leu Glu Val
                820                 825                 830

Leu Ser Asn Phe Tyr Val Phe Glu Arg Leu Pro Glu Leu Trp Pro Arg
                835                 840                 845

Asp Ser Asp Tyr Ala Val Phe Arg Leu Gln Gly Phe Ile Ile Leu Glu
                850                 855                 860

Ala Val Leu Ser Asn Pro Lys Ser Gln Ile Asp Cys Gly Leu Val His
865                 870                 875                 880
```

-continued

```
Val Leu Arg Val Ala Asn Ala Cys Gly Ser Pro Leu Gln Thr Leu Arg
            885                 890                 895

Val Gln Ala Ile Asn Ile Leu Gln Leu Ile Ser Asn Arg Lys Leu Val
            900                 905                 910

Ser His Val Glu Gln Leu Val Arg Ser Leu Leu Gln Arg Lys Ser Glu
            915                 920                 925

Leu Ser Met Asp His Glu Gln Tyr Ala Leu Ile Leu Tyr Thr Ile Leu
            930                 935                 940

Glu Pro Glu Lys Ala Thr Ala Lys Glu Arg Leu Val Leu Ser Lys Leu
945                 950                 955                 960

Lys Arg Ser Val Leu Ala Leu Ala Ser Asp Pro Lys Gln Ser Pro Ile
            965                 970                 975

Cys Thr Ala Ser Leu Leu Ala Ala Leu Lys His Val Asn Asp Glu Asn
            980                 985                 990

Phe Leu Asn Glu Leu Leu Pro Leu Gly Leu Asp Ser Leu Lys Thr Ile
            995                 1000                1005

Thr Ala Gly Glu Asp Asn Gln Asn Ile Lys Gln Leu Pro Trp Pro
    1010                1015                1020

His Ser Glu Ile Tyr Lys Ser Val Ile Glu Arg Phe Glu Gly Arg
    1025                1030                1035

Val Ala Leu Asn Val Leu Leu Arg Lys Asp Leu Ala Trp Lys Leu
    1040                1045                1050

Phe Glu Asp Ser Phe Ala Gln Tyr Asp Thr Tyr Val Gln Leu Glu
    1055                1060                1065

Gln Lys Leu Gln Pro Leu Pro Cys Val Leu Leu Asn Ser Leu Thr
    1070                1075                1080

Pro Glu Thr Phe Glu Gln Met His Ala Lys His Lys Ile Ala Leu
    1085                1090                1095

Ile Lys Leu Ile Val Glu Ser Ala Thr Asn Ser Asp Asn Asp Ser
    1100                1105                1110

Ile Phe Leu Ala Ser His Arg Leu Leu Lys Arg Cys Arg Leu Asp
    1115                1120                1125

Cys Gln Pro Leu Val Pro Ile Leu Leu Glu Met Ala Asn Thr Lys
    1130                1135                1140

Val Glu Lys Lys Gln Pro Val Lys Arg Arg Ser Val Gln Ala Thr
    1145                1150                1155

Gln Leu Asp Leu Thr Ser Pro Tyr Trp Lys Gln Gly Met Thr Leu
    1160                1165                1170

Leu Glu Leu Leu Glu His Lys Lys Gln Leu Val Gly Ala Glu Leu
    1175                1180                1185

Leu Ile Pro Pro Leu Phe Glu Leu Leu Gln Ala Cys Leu Thr Met
    1190                1195                1200

Glu Glu His Ser Ala Ala Glu Tyr Pro Lys Gln Leu Ile Leu Ser
    1205                1210                1215

Ser Leu Leu His Cys Cys Gln Thr Ala Gln Ser Ala Gly Val Gln
    1220                1225                1230

Leu Val Lys Ala Met Pro Glu Ser Ser Phe Arg Ile Glu Leu Val
    1235                1240                1245

Val Gln Ser Leu Arg Asn Thr Arg Asn Pro Gln Thr Gln Gln His
    1250                1255                1260

Ala Leu Leu Phe Leu Thr His Cys Ala Gly Met Tyr Pro Gln Gln
    1265                1270                1275

Val Leu His Lys Ile Val Glu Ile Phe Thr Phe Val Gly Ser Thr
    1280                1285                1290
```

```
Val Ala Arg His Asp Asp Ala Phe Ser Leu His Ile Ile His Asn
        1295                1300                1305

Val Val Glu Ser Ile Ile Pro Ile Leu Leu Leu Asn Thr Gly His
        1310                1315                1320

Asn Glu Leu Val Ile Pro Val Leu Lys Val Phe Ala Asp Ile Cys
        1325                1330                1335

Thr Asp Val Pro Val His Arg Arg Leu Pro Leu Tyr Ala Thr Leu
        1340                1345                1350

Phe Arg Val Leu Glu Pro Lys Glu His Leu Trp Gln Phe Leu Cys
        1355                1360                1365

Ile Ile Phe Glu Ser Gln Val Leu Leu Glu Gln Val Pro Gln Lys
        1370                1375                1380

Val Ser Thr Asp Lys Ser Arg Leu Asp Phe Ala Arg Glu Leu Thr
        1385                1390                1395

Leu Met Phe Glu Asp Pro Thr Val Ala Ile Gln Thr Cys Ile Arg
        1400                1405                1410

Leu Leu Asp Tyr Leu Ala Lys Leu Pro Ala Thr Lys Ser Ser Leu
        1415                1420                1425

Ser Gly Gly Ser Gly Ser Ser Val Leu Ser Thr Glu Gln Gln Leu
        1430                1435                1440

Phe Asp Val Arg Thr Arg Thr Phe Lys Gln Leu Arg His Tyr Lys
        1445                1450                1455

Tyr Leu Ile Met Asp Phe Leu Ser Gly Ile Ser Ser Cys Asn Glu
        1460                1465                1470

Trp Glu Lys Lys Met Lys Arg Pro Asp Pro Asn Glu Leu Leu Pro
        1475                1480                1485

Tyr Tyr Gln Glu Phe Ile Leu Lys Thr Leu Ala Tyr Val Gly Val
        1490                1495                1500

Leu Asn Gly Ala Leu Glu Ala Ser Glu Thr Pro Ser Leu Glu
        1505                1510                1515

Lys Phe Trp Arg Val Leu Ala Asn His Ala His Asp Val Leu Asp
        1520                1525                1530

Asn Ala Ile Gly Leu Leu Ala Pro Gln His Phe Ile Ser Val Ile
        1535                1540                1545

Thr Glu Leu Leu Lys His Asp His Val Tyr Val Arg Ile Lys Val
        1550                1555                1560

Met Asp Leu Leu Val Thr Lys Leu Ser Pro Ser Ser Asp Tyr Phe
        1565                1570                1575

Gln Gln Ser Asn Ala Glu His Phe Gly Val Leu Phe Ala Pro Leu
        1580                1585                1590

Gln Glu Ile Ile Asn Gly Ile Leu Glu Gly Ser Ser Asn Ser Ala
        1595                1600                1605

Gln Gln Ala Lys Leu Gln Gln Thr Ala Leu His Ala Leu Gln Leu
        1610                1615                1620

Leu Ala Leu Arg His Gly Arg Asp Tyr Ile Glu Glu Cys Arg Ser
        1625                1630                1635

Leu Leu Ala Thr Leu Thr Lys Ile Thr Lys Arg Arg Ala Asn Val
        1640                1645                1650

Pro Lys Ala Val Val Gly Asn Val Val Leu Thr Leu Val Glu Ile
        1655                1660                1665

Cys Ala Ser Leu Lys Ala His Ala Leu Ala Gln Leu Pro Lys Phe
        1670                1675                1680

Ala Pro Gln Leu Thr Glu Leu Leu Lys Glu Gln Val His Gln Met
```

-continued

```
            1685                1690                1695

Ala Ser Leu Lys Gln Gly Pro Asp Tyr Val Cys Ser Thr Leu Val
        1700                1705                1710

Thr Ala Leu His Lys Leu Phe Lys Ala Leu Pro Leu Phe Leu Gly
        1715                1720                1725

Pro Tyr Leu Val Asp Ile Ile Gly Gly Leu Ala Arg Leu Ser Val
        1730                1735                1740

Gln Leu Glu Asn Pro Gln Leu Leu Gln Asp Lys Arg Thr Gln Val
        1745                1750                1755

Leu Lys Gln Lys Leu Ala Asp Val Trp Ser Ala Val Ala Gln Gly
        1760                1765                1770

Val Glu Val Arg Ile Leu Val Pro Ser Cys Ala Lys Ala Phe Ser
        1775                1780                1785

Ser Leu Leu Glu Gln Gln Ala Tyr Asp Glu Leu Gly His Leu Met
        1790                1795                1800

Gln Gln Leu Leu Leu Gln Ser Val Arg His Asn Ser Ala Ala Gln
        1805                1810                1815

Leu Gln Pro Val Gln Asp Pro Leu Ser Glu Leu Phe Leu Gln Ala
        1820                1825                1830

Leu Asn Phe Arg Leu Gln Val Arg Gly Leu Gly Leu Gln Arg Gln
        1835                1840                1845

Leu Val Ser Asp Val Glu Ala Ser Ile Thr Glu Thr Phe Val Thr
        1850                1855                1860

Trp Ile Leu Lys Leu Ser Glu Thr Ser Phe Arg Pro Met Tyr Ser
        1865                1870                1875

Arg Val His Lys Trp Ala Leu Glu Ser Thr Ser Arg Glu Thr Arg
        1880                1885                1890

Leu Thr Tyr Phe Leu Leu Thr Asn Arg Ile Ala Glu Ala Leu Lys
        1895                1900                1905

Ser Leu Phe Val Leu Phe Ala Ser Asp Phe Val Glu Asp Ser Ser
        1910                1915                1920

Arg Leu Leu Thr Glu His Asn Ser Ile Arg Pro Glu Phe Glu Val
        1925                1930                1935

Glu Glu Arg Glu Asp Asp Val Asp Leu Leu Met Ala Ile Leu Asn
        1940                1945                1950

Thr Leu His His Val Phe Leu Tyr Cys Ser Glu Asp Phe Ile Asn
        1955                1960                1965

Asp His Arg Phe Asn Val Leu Met Pro Pro Leu Val Asn Gln Leu
        1970                1975                1980

Glu Asn Asp Leu Val Leu Gly Asn Glu Ser Leu Gln Gln Val Leu
        1985                1990                1995

Ser Asn Cys Ile Ala Gln Phe Ala Val Ala Thr Asn Asp Val Met
        2000                2005                2010

Trp Lys Gln Leu Asn Ser Gln Val Leu Leu Lys Thr Arg Thr Ser
        2015                2020                2025

Asn Pro Glu Val Arg Ile Leu Ala Phe Asn Ser Cys Val Ala Ile
        2030                2035                2040

Ala Arg Lys Leu Gly Glu Ser Tyr Ala Ala Leu Leu Pro Glu Thr
        2045                2050                2055

Val Pro Phe Ile Ala Glu Leu Leu Glu Asp Glu His Gln Arg Val
        2060                2065                2070

Glu Lys Asn Thr Arg Thr Gly Val Gln Glu Leu Glu Thr Ile Leu
        2075                2080                2085
```

Gly Glu Ser Val Gln Lys Tyr Leu
    2090            2095

<210> SEQ ID NO 66
<211> LENGTH: 1830
<212> TYPE: PRT
<213> ORGANISM: Arabidopsis thaliana

<400> SEQUENCE: 66

Met Ser Ser Ile Val Ser Gln Leu Gln Ala Leu Lys Ser Val Leu
1               5                   10                  15

Gln Ala Asp Thr Glu Pro Ser Lys Arg Pro Phe Thr Arg Pro Ser Ile
                20                  25                  30

Leu Phe Ser Pro Lys Glu Ala Ala Asp Phe Asp Ile Glu Ser Ile Tyr
            35                  40                  45

Glu Leu Gly Leu Lys Gly Leu Glu Val Leu Gly Asn Lys Asp Glu Arg
    50                  55                  60

Phe Lys Asn Tyr Met Asn Asp Leu Phe Ser His Lys Ser Lys Glu Ile
65                  70                  75                  80

Asp Arg Glu Leu Leu Gly Lys Glu Glu Asn Ala Arg Ile Asp Ser Ser
                85                  90                  95

Ile Ser Ser Tyr Leu Arg Leu Ser Gly Tyr Leu Gln Phe Arg Ala
            100                 105                 110

Ser Leu Glu Thr Leu Glu Tyr Leu Ile Arg Arg Tyr Lys Ile His Ile
        115                 120                 125

Tyr Asn Leu Glu Asp Val Val Leu Cys Ala Leu Pro Tyr His Asp Thr
    130                 135                 140

His Ala Phe Val Arg Ile Val Gln Leu Leu Ser Thr Gly Asn Ser Lys
145                 150                 155                 160

Trp Lys Phe Leu Asp Gly Val Lys Asn Ser Gly Ala Pro Pro Arg
                165                 170                 175

Ser Val Ile Val Gln Gln Cys Ile Arg Asp Lys Gln Val Leu Glu Ala
            180                 185                 190

Leu Cys Asp Tyr Ala Ser Arg Thr Lys Lys Tyr Gln Pro Ser Lys Pro
        195                 200                 205

Val Val Ser Phe Ser Thr Ala Val Val Gly Val Leu Gly Ser Val
    210                 215                 220

Pro Thr Val Asp Gly Asp Ile Val Lys Thr Ile Leu Pro Phe Val Asp
225                 230                 235                 240

Ser Gly Leu Gln Ser Gly Val Lys Gly Cys Leu Asp Gln Gln Ala Gly
                245                 250                 255

Ala Leu Met Val Val Gly Met Leu Ala Asn Arg Ala Val Leu Asn Thr
            260                 265                 270

Asn Leu Ile Lys Arg Leu Met Arg Ser Ile Ile Asp Ile Gly Arg Glu
        275                 280                 285

His Ala Lys Glu Ser Ser Asp Pro His Ser Leu Arg Leu Ser Leu Met
    290                 295                 300

Ala Leu Ile Asn Phe Val Gln Leu Gln Ser Val Asp Leu Ile Pro Arg
305                 310                 315                 320

Lys Ala Leu Asp Leu Phe Asn Glu Ile Ser Ser Ser Asp Lys Cys
                325                 330                 335

Cys Glu Val Leu Ala Ser Ile Ile Glu Thr Val Pro Val Ser Asn Leu
            340                 345                 350

Val Asp His Leu Ile Ser Lys Val Phe Ser Leu Cys Met Thr Gln Tyr
        355                 360                 365

-continued

```
Gln Lys Asn Ser Asp Phe Arg Ser Ser Thr Ser Gly Ser Trp Ala Lys
    370                 375                 380

Lys Phe Leu Val Val Ser Lys Lys Tyr Pro Ala Glu Leu Arg Ala
385                 390                 395                 400

Ala Val Pro Lys Phe Leu Glu Ala Thr Glu Val Gln Ser Lys Lys Glu
                405                 410                 415

Asp Leu Lys Leu Glu Met Leu Ser Cys Met Leu Asp Gly Asn Ser Asp
            420                 425                 430

Met Ser His Pro Phe Val Asp Ser Lys Leu Trp Phe Arg Leu His His
        435                 440                 445

Pro Arg Ala Ala Val Arg Cys Ala Ala Leu Ser Leu Asn Gly Val
    450                 455                 460

Leu Lys Asp Asp Ser Ser Lys Ala Glu Asn Leu Val Thr Ile Gln Asp
465                 470                 475                 480

Ala Ile Leu Arg Gln Leu Trp Asp Asp Leu Ala Val Val Gln Ala
                485                 490                 495

Ala Leu Ser Phe Asp Lys Leu Pro Asn Ile Ile Thr Ser Ser Gly Leu
            500                 505                 510

Leu Asp Ala Leu Leu His Val Val Lys Arg Cys Val Gly Ile Leu Val
        515                 520                 525

Ser Gly Val Ser His Asn Val Gln Leu Ala Val Asp Val Val Ala Leu
    530                 535                 540

Ser Leu Lys Ile Ala Val Ser Ser Phe Gly Asn Gln Thr Asp Ser Thr
545                 550                 555                 560

Glu Lys Val Thr Ser Ala Met Phe Pro Phe Leu Leu Ile Gln Pro Lys
                565                 570                 575

Thr Trp Asn Leu Asn Leu Leu Val Leu Lys Leu Gly Lys Asp Val Asn
            580                 585                 590

Trp Pro Leu Phe Lys Asn Leu Ala Ala Asp Asp Gly Met Lys Lys Leu
        595                 600                 605

Pro Asp Ile Met Ser Thr Asn Leu Ser Ser Ile Ser Met Asp Ile Ile
    610                 615                 620

Asn Asp Leu Gly Glu Ala Leu Ser Leu Asp Pro Asp Glu Arg Arg Ile
625                 630                 635                 640

Glu Leu Ile Glu Arg Ala Cys Asn Tyr Lys Leu Ser Glu Val Leu Glu
                645                 650                 655

Thr Cys Ser Asn Ile Lys Cys Ser Glu Gln Asp Arg Asn Lys Leu Gln
            660                 665                 670

Lys Gly Leu Leu Ile Arg Glu Ser Val Ser Ala Leu Asn Ile Asp Val
        675                 680                 685

Ile Asn Lys Leu Val Glu Ala Phe Met Met His Pro Ala Asp Tyr Ile
    690                 695                 700

Gln Trp Leu Thr Thr Glu Trp Glu Glu Leu Glu Val Glu Val Asp Val
705                 710                 715                 720

Ser Leu Lys Glu Leu Ser Lys Ser Asn Cys Gln Glu Leu Leu Tyr Gln
                725                 730                 735

Leu Leu Asp Thr Ser Asp Phe Thr Ala Leu Asn Ser Lys Asp Val Lys
            740                 745                 750

Ala Ala Ala Ile Asn Cys Ile Glu Ala Leu Phe Asn Leu Arg Ala Ala
        755                 760                 765

Ile Tyr Gly Ser Ser Phe Asp Glu Leu Leu Gly Met Ile Val Gln Gln
    770                 775                 780

Arg Arg Leu Ile Leu Ser Asp Asn Lys Phe Phe Ala Ser Tyr Leu Thr
785                 790                 795                 800
```

```
Ser Leu Leu Ser Ser Thr Thr Asn Asp Leu Leu Val Pro Val Gly Leu
            805                 810                 815

Gln Lys Arg Phe Asp Gln Ser Thr Lys Glu Asn Ile Leu Ser Val Ile
        820                 825                 830

Leu Leu Cys Ala Glu Asp Leu Pro Ala Tyr Gly Lys Leu Arg Val Leu
            835                 840                 845

Ser Leu Leu Lys Asp Leu Gly Ile Met Leu Met Arg Asp Glu Ile Val
        850                 855                 860

Lys Leu Leu Ser Gln Leu Leu Asp Lys Arg Ser Gln Tyr Tyr Tyr Lys
865                 870                 875                 880

Leu Asp Lys Thr Ser Gln Pro Leu Ser Asp Thr Glu Val Asp Leu Leu
            885                 890                 895

Cys Leu Leu Leu Glu Cys Ser Met Met Arg Thr Ser Ser Phe Lys Gly
            900                 905                 910

Gln Ser Leu Asp Asp His Ile Leu Ser Ala Leu Asn Val Asp Cys Met
        915                 920                 925

Ala Ser Glu Arg Pro Ala Val Ile Ser Pro Cys Leu Thr Ile Leu Glu
930                 935                 940

Lys Leu Ser Asn Arg Phe Tyr Asp Glu Leu Gln Thr Asp Val Gln Ile
945                 950                 955                 960

Arg Phe Phe His Lys Leu Val Ser Met Phe Arg Ser Ser Asn Gly Ser
                965                 970                 975

Ile Gln Asn Gly Ala Lys Glu Ala Val Leu Arg Leu Lys Leu Ser Ser
            980                 985                 990

Ser Thr Val Val Leu Ala Leu Asp Arg Ile Thr Gln Gln Asp Thr Leu
        995                 1000                1005

Val Ile Gly Ser Leu Ser Lys Lys Lys Gln Lys Lys Asn Ser
        1010                1015                1020

Lys Ser Cys Pro Glu Glu Asp Ile Asn Ser Glu Glu Phe Arg Ser
        1025                1030                1035

Gly Glu Lys Ala Leu Ser Phe Ile Ala Ser Leu Leu Asp Met Leu
        1040                1045                1050

Leu Leu Lys Lys Asp Leu Thr His Arg Glu Ser Leu Ile Arg Pro
        1055                1060                1065

Leu Phe Lys Leu Leu Gln Arg Ser Met Ser Lys Glu Trp Val Lys
        1070                1075                1080

Ile Ala Phe Ser Ile Glu Glu Thr Ser Leu Gln Pro Pro Gln Asp
        1085                1090                1095

Val Arg Glu Thr Thr Pro Thr Phe Ile Ser Ser Ile Gln Gln Thr
        1100                1105                1110

Leu Leu Leu Ile Leu Lys Asp Ile Phe Asp Ser Leu Asn Met Asn
        1115                1120                1125

Pro Leu Lys Ala Glu Val Ala Asn Glu Ile Asn Val Lys Met Leu
        1130                1135                1140

Val Glu Leu Ala His Ser Ser Asn Asp Gly Val Thr Arg Asn His
        1145                1150                1155

Ile Phe Ser Leu Phe Thr Ala Ile Val Lys Phe Val Pro Asp Lys
        1160                1165                1170

Val Leu Asp His Ile Ile Ser Ile Leu Thr Leu Val Gly Glu Ser
        1175                1180                1185

Thr Val Thr Gln Ile Asp Ser His Ser Lys Ser Ile Phe Glu Gly
        1190                1195                1200

Phe Ile Ser Met Val Ile Pro Phe Trp Leu Ser Lys Thr Lys Ser
```

-continued

```
                 1205                1210                1215

Glu  Glu  Gln  Leu  Leu  Gln  Ile  Phe  Val  Lys  Val  Leu  Pro  Asp  Ile
     1220                1225                1230

Val  Glu  His  Arg  Arg  Ser  Ile  Val  Ala  Tyr  Leu  Leu  Gly  Val
     1235                1240                1245

Val  Thr  Ser  Leu  Leu  Gln  Gln  Gln  Thr  Asp  Tyr  Asn  Gly  Thr  Lys
     1250                1255                1260

Lys  Val  Leu  Gly  Leu  Ile  Ser  Glu  Arg  Ala  Lys  Asp  Thr  Ser  Ser
     1265                1270                1275

Ser  Lys  Met  Lys  His  Lys  Arg  Lys  Ile  Ser  Asn  Gln  Lys  Gly  Arg
     1280                1285                1290

Asn  Ser  Trp  Leu  Asn  Leu  Asp  Glu  Val  Ala  Val  Asp  Ser  Phe  Gly
     1295                1300                1305

Lys  Met  Cys  Glu  Glu  Ile  Val  His  Leu  Ile  Asn  Ala  Thr  Asp  Asp
     1310                1315                1320

Glu  Ser  Gly  Val  Pro  Val  Lys  Arg  Ala  Ala  Ile  Ser  Thr  Leu  Glu
     1325                1330                1335

Val  Leu  Ala  Gly  Arg  Phe  Pro  Ser  Gly  His  Pro  Ile  Phe  Arg  Lys
     1340                1345                1350

Cys  Leu  Ala  Ala  Val  Ala  Glu  Cys  Ile  Ser  Ser  Lys  Asn  Leu  Gly
     1355                1360                1365

Val  Ser  Ser  Ser  Cys  Leu  Arg  Thr  Thr  Gly  Ala  Leu  Ile  Asn  Val
     1370                1375                1380

Leu  Gly  Pro  Lys  Ala  Leu  Ile  Glu  Leu  Pro  Cys  Ile  Met  Lys  Asn
     1385                1390                1395

Leu  Val  Lys  Gln  Ser  Leu  Glu  Val  Ser  Phe  Ala  Ser  Gln  Ser  Gly
     1400                1405                1410

Arg  Asn  Ala  Thr  Ala  Glu  Glu  Gln  Leu  Leu  Met  Leu  Ser  Val  Leu
     1415                1420                1425

Val  Thr  Leu  Glu  Ala  Val  Ile  Asp  Lys  Leu  Gly  Gly  Phe  Leu  Asn
     1430                1435                1440

Pro  His  Leu  Gly  Asp  Ile  Met  Lys  Ile  Met  Val  Leu  His  Pro  Glu
     1445                1450                1455

Tyr  Val  Ser  Asp  Phe  Asp  Lys  Asn  Leu  Lys  Ser  Lys  Ala  Asn  Ala
     1460                1465                1470

Ile  Arg  Arg  Leu  Leu  Thr  Asp  Lys  Ile  Pro  Val  Arg  Leu  Thr  Leu
     1475                1480                1485

Gln  Pro  Leu  Leu  Arg  Ile  Tyr  Asn  Glu  Ala  Val  Ser  Ser  Gly  Asn
     1490                1495                1500

Ala  Ser  Leu  Val  Ile  Ala  Phe  Asn  Met  Leu  Glu  Asp  Leu  Val  Val
     1505                1510                1515

Lys  Met  Asp  Arg  Ser  Ser  Ile  Val  Ser  Ser  His  Gly  Lys  Ile  Phe
     1520                1525                1530

Asp  Gln  Cys  Leu  Val  Ala  Leu  Asp  Ile  Arg  Arg  Leu  Asn  Pro  Ala
     1535                1540                1545

Ala  Ile  Gln  Asn  Ile  Asp  Asp  Ala  Glu  Arg  Ser  Val  Thr  Ser  Ala
     1550                1555                1560

Met  Val  Ala  Leu  Thr  Lys  Lys  Leu  Thr  Glu  Ser  Glu  Phe  Arg  Pro
     1565                1570                1575

Leu  Phe  Ile  Arg  Ser  Ile  Asp  Trp  Ala  Glu  Ser  Asp  Val  Val  Asp
     1580                1585                1590

Gly  Ser  Gly  Ser  Glu  Asn  Lys  Ser  Ile  Asp  Arg  Ala  Ile  Ser  Phe
     1595                1600                1605
```

```
Tyr Gly Leu Val Asp Arg Leu Cys Glu Ser His Arg Ser Ile Phe
1610                1615                1620

Val Pro Tyr Phe Lys Tyr Val Leu Asp Gly Ile Val Ala His Leu
1625                1630                1635

Thr Thr Ala Glu Ala Ser Val Ser Thr Arg Lys Lys Lys Lys Ala
1640                1645                1650

Lys Ile Gln Gln Thr Ser Asp Ser Ile Gln Pro Lys Ser Trp His
1655                1660                1665

Leu Arg Ala Leu Val Leu Ser Cys Leu Lys Asn Cys Phe Leu His
1670                1675                1680

Asp Thr Gly Ser Leu Lys Phe Leu Asp Thr Asn Asn Phe Gln Val
1685                1690                1695

Leu Leu Lys Pro Ile Val Ser Gln Leu Val Val Glu Pro Pro Ser
1700                1705                1710

Ser Leu Lys Glu His Pro His Val Pro Ser Val Asp Glu Val Asp
1715                1720                1725

Asp Leu Leu Val Ser Cys Ile Gly Gln Met Ala Val Ala Ser Gly
1730                1735                1740

Ser Asp Leu Leu Trp Lys Pro Leu Asn His Glu Val Leu Met Gln
1745                1750                1755

Thr Arg Ser Glu Ser Val Arg Ser Arg Met Leu Ser Leu Arg Ser
1760                1765                1770

Val Lys Gln Met Leu Asp Asn Leu Lys Glu Glu Tyr Leu Val Leu
1775                1780                1785

Leu Ala Glu Thr Ile Pro Phe Leu Ala Glu Leu Leu Glu Asp Val
1790                1795                1800

Glu Leu Ser Val Lys Ser Leu Ala Gln Asp Ile Ile Lys Gln Met
1805                1810                1815

Glu Glu Met Ser Gly Glu Ser Leu Ala Glu Tyr Leu
1820                1825                1830

<210> SEQ ID NO 67
<211> LENGTH: 1649
<212> TYPE: PRT
<213> ORGANISM: Schizosaccahromyces pombe

<400> SEQUENCE: 67

Met Ala Ser Ser Leu Gln Lys Gln Leu Lys Asn Ile Gln Ser Asn Asn
1               5                   10                  15

Val Leu Lys Ile Asn Lys Ile Arg Arg Ala Pro Ser Leu Leu Tyr Asp
            20                  25                  30

Pro Lys Val Ala Ala Asp Met Asp Leu Glu Glu Ile Tyr Val Thr Ala
        35                  40                  45

Val Ser Gly Phe His Glu Leu Ala Val His Glu Pro Arg Leu Leu Tyr
    50                  55                  60

Phe Glu Lys Thr Leu Leu Gly Glu Gln Ser Val Gln Val Asp Arg Val
65                  70                  75                  80

Leu Leu Asn Arg Thr Glu Asn Glu Lys Ile Asp Leu Glu Cys Val Gln
                85                  90                  95

Ile Leu Arg Leu Leu Ala Pro Phe Phe Thr Glu Lys Asn Ala Leu Lys
            100                 105                 110

Val Leu Glu Trp Leu Ile Arg Arg Phe Ser Ile His Glu Tyr Val Ser
        115                 120                 125

Asp Glu Phe Ile Leu Ser Phe Leu Pro Phe His Asp His Pro Phe Phe
    130                 135                 140
```

```
Ala Arg Ile Leu Gly Cys Ser Lys Pro Lys Ser Arg Pro Leu Leu Phe
145                 150                 155                 160

Leu Glu Asn Ala Ile Lys Met Pro Val Thr Leu Ser Arg Ala Asp Ile
            165                 170                 175

Val His Ala Leu Ser Arg Asp Lys Glu Phe Phe Ala Met Phe Ala Gln
        180                 185                 190

Phe Val Gln Asn Thr Ala Glu Ser His Asn Met Tyr Pro Glu Leu Ala
    195                 200                 205

Arg Phe Trp Ala Gly Thr Met Met Glu Val Leu Val Ala Trp His Ser
210                 215                 220

Ser Asn Glu Asp Pro Asn Val Leu Leu Asp Arg Phe Phe Leu Arg Val
225                 230                 235                 240

Ser Tyr Ala Val Ser Tyr Val Ser Ser Ile Asp Phe Gln Ile Ala Gly
            245                 250                 255

Phe Met Leu Leu Ser Ser Ile Ala Ala Ser Leu Pro Leu Ser Pro Ser
        260                 265                 270

Ile Ile Pro Pro Leu Val Ser Ala Ile Thr Asp Arg Leu Ser Phe Asp
    275                 280                 285

Asn Ile Lys Pro Ala Leu Ile Cys Val Gly His Leu Leu Gln Phe Cys
290                 295                 300

Ser Ser Phe Glu Phe Asp His Glu Gln Leu Glu Lys Leu Glu Ser Phe
305                 310                 315                 320

Gly Ala Ser Ser Leu Leu Ile Glu Leu Ser Gln Glu His Arg Leu Asp
            325                 330                 335

Glu Phe Phe Val Ser Tyr Trp Val Ser Leu Ile Lys Ser Arg Lys Gln
        340                 345                 350

Lys Asp Lys Lys Arg Leu Ile Ser Leu Leu Asp Thr Ser Ile Ser Gln
355                 360                 365

Ile Arg Val Thr His Glu Gln Ala Lys Phe Leu Leu Ser Val Ile Pro
    370                 375                 380

Val Asn Gln Asp Phe Lys Ala Leu Gln Ser Tyr Arg Arg Ile Leu Asp
385                 390                 395                 400

Ser Val Ile Gln Pro Glu Arg Lys Glu Gly Lys Leu Asp Asn Leu Ile
            405                 410                 415

Asn Thr Leu Gln Asp Lys Lys Lys Ser Ser Thr Phe Ser Lys Lys Asp
        420                 425                 430

Arg Glu Val Leu Leu Lys Lys Ile Ser Glu Ile Asp Ser Gln Thr Ser
    435                 440                 445

Phe Glu Gln Cys Leu Ala Tyr Ala Asp Ser Ala Ala Asp Leu Asp Ser
450                 455                 460

Ser Val Phe Ile Ser Leu Leu Ser Lys Phe Gly Asp Lys Ile Pro Phe
465                 470                 475                 480

Leu Leu Phe Cys Ile Ala Asn Gly Ser Glu Arg Ile Ile Leu Ser
            485                 490                 495

Leu Ile Glu Leu Arg Lys Thr Ile Glu Glu Asn Lys Asp Val Asp Tyr
        500                 505                 510

Gln Ile Ile Leu Pro Val Val Leu Tyr Ser Leu Gln Ser Lys Asp Thr
    515                 520                 525

Glu Val Arg Ser Arg Ala Leu Asn Leu Ile Leu Thr Phe Leu Glu Leu
530                 535                 540

Arg Asn Glu Asn Leu Glu Phe Ser Ile Ile Tyr Gly Met Asp Asp Asn
545                 550                 555                 560

Asp Asn Lys Asn Leu Arg Trp Leu Ser Pro Val Glu Thr Lys Tyr Tyr
            565                 570                 575
```

```
Cys Ser Asp Leu Leu Leu Asp Arg Ser Ser Glu Ile Gly Leu Asp Gly
            580                 585                 590

Thr Tyr Leu Phe Ser Tyr Ile Pro Glu Arg Leu Phe Thr Glu Lys Lys
            595                 600                 605

Pro Lys Asn Ala Ser Lys Glu Ile Ala Val Thr Ser Phe Leu Ser Ser
610                 615                 620

His Ala Ala Cys Ser Lys Leu Ser Asn Val Arg Val Leu Leu Leu Glu
625                 630                 635                 640

Ile Leu Thr Arg Val His Gly Lys Val Glu Asp Ala Lys Met Gln Ile
                645                 650                 655

Leu Leu Pro Arg Leu Glu Gln Leu Ser Glu Phe Asn Ser Glu Lys Phe
                660                 665                 670

Lys Thr Val Ser Lys Arg Glu Val Glu Ala Leu Val Asn Cys Phe Asn
                675                 680                 685

His Thr Ser Phe Thr Ser Leu Leu Ser Phe Leu Ser Ser Asn Ile Val
            690                 695                 700

Leu Ser Gln Ala Ile Cys Arg Arg Ile Val Glu Ile Gln Ser His Leu
705                 710                 715                 720

Lys Asp Pro Gln Arg Leu Glu Phe Val Lys Ala Val Ile Ser Gln Asp
                725                 730                 735

Glu Gln Pro His Tyr Tyr Val Asp Val Leu Asp Ser Ile Lys Ile Pro
                740                 745                 750

Asp Thr Val Phe Lys Lys Leu Ile Gly Ser Val Arg Leu Val Lys Glu
                755                 760                 765

Lys Asn Pro Ala Ile Ala Lys Arg Lys Arg Ile Asp Ser His Ile Phe
770                 775                 780

Asp Gly Asp Val Gln Arg Leu Thr Arg Ile Leu Glu Leu Leu Glu Thr
785                 790                 795                 800

Lys Asn Ala Ala Ser Tyr Pro Lys Leu Ala Ser Pro Leu Phe Glu Val
                805                 810                 815

Leu Asn Ser Val Ile Ala Leu Lys Glu Asp Ile Val Ser Ser Asn Tyr
                820                 825                 830

Leu Leu Gln Leu Leu Gly Leu Leu Tyr Glu Met Ile Gly Ala Ser
                835                 840                 845

Pro Ile Thr Glu Leu Ser Pro Ser Ile Arg Ile Asp Thr Leu Val Gly
                850                 855                 860

Cys Ile Arg Ser Thr Asn Asn Pro Gln Ile Gln Asn Lys Ala Leu Leu
865                 870                 875                 880

Leu Val Ser Ala Leu Ala Asn Ala Ala Pro Glu Ala Val Leu His Gly
                885                 890                 895

Val Met Pro Ile Phe Thr Phe Met Gly Ser Thr Val Leu Ser Arg Asp
                900                 905                 910

Asp Ala Phe Ser Ile His Val Ile Glu Gln Thr Val Lys Thr Val Ile
                915                 920                 925

Ser Ala Leu Ile Arg Leu Gly Lys Asp Phe Asp Ser Ser Leu Leu Val
                930                 935                 940

Ser Cys Phe Val Asn Ala Phe Pro His Ile Pro Gln His Arg Arg Leu
945                 950                 955                 960

Arg Leu Tyr Arg Leu Val Leu Gln Thr Ile Gly Ser Asn Arg Phe Leu
                965                 970                 975

Ser Val Val Leu Ile Gln Phe Ala Glu Lys Met Leu Leu Ala Lys Ser
                980                 985                 990

Thr Asn Val Val Ala Ile His Asp  Phe Cys Leu Thr Leu  Val Gln Ser
```

-continued

```
                995                 1000                1005
      Phe Ser Val Ala Asp Arg Ile Gly Ser Ile Asn Gln Cys Ser Arg
          1010                1015                1020

Phe Cys Leu Lys Ser Leu Glu Glu Gln Ser Asn Ser Asp Ser Asn
          1025                1030                1035

Gly Lys Ala Val Ser Leu Ile Lys Leu Asp Glu Leu Pro Met Asp
          1040                1045                1050

Val Asp Leu Ala Thr Leu Gly Ser Leu Arg Val Lys Val Leu Glu
          1055                1060                1065

Leu Ile Ser Leu Val Ser Lys Ala Lys Asn Phe Ala Phe Asp Leu
          1070                1075                1080

Ala Lys Ile Met Glu Asn Ser Val Asp Ser Phe Val Glu Ile Gln
          1085                1090                1095

Ala Gly Leu Phe Glu Ser Ile Lys Leu Leu Ile Thr Leu Ser Gln
          1100                1105                1110

Gln Ser Ser Asn Glu Met Glu Leu Gly His Val Tyr Val Ala Leu
          1115                1120                1125

Arg Ser Val Ile His Leu Leu Pro Asn Glu Leu Phe Cys Thr Val
          1130                1135                1140

Leu Gly Lys Leu Leu His Asp Glu Arg Ala Leu Leu Arg Arg Lys
          1145                1150                1155

Ala Leu Ser Ile Val Gln Gln Arg Val Gln Gln Gly Ser Lys Val
          1160                1165                1170

Ser Ala Leu Thr Ala Leu Ile Pro Asp Val Thr Tyr Asn Ile Ser
          1175                1180                1185

Asn Tyr Ser Asp Glu Glu Thr Thr Gln Leu Ala Met Asp Cys Leu
          1190                1195                1200

Ala Val Met Ala Lys Arg Phe Ser Ala Ser Pro Glu Leu Phe Ile
          1205                1210                1215

Ser Pro Ile Glu Val Val Ser Gly Pro Tyr Gly Leu Lys Asn Ser
          1220                1225                1230

Ala Arg Asp Val Gln Val Ser Ala Ile Val Cys Ile Thr Val Leu
          1235                1240                1245

Thr Asn Thr Leu Ala Ala Arg Ile Leu Pro Tyr Leu Ala Asp Ile
          1250                1255                1260

Val Asn Tyr Ser Leu Ser Ile Leu Asp Asp Ala Arg Lys Asp Pro
          1265                1270                1275

Glu Gly Asp Leu Leu Glu Leu Ala Cys Phe Ser Met Met Ile Asp
          1280                1285                1290

Phe Phe Lys Val Leu Pro Glu Phe Ser Ser Ser Tyr Val Glu Pro
          1295                1300                1305

Thr Ile Lys Cys Ala Leu Ala Ser Asp Arg Ala Phe Glu His Asp
          1310                1315                1320

Ala Ile Gly Glu Leu Leu Phe Glu Thr Ile Ala Asn Phe Ile Pro
          1325                1330                1335

Thr Arg Leu Leu Met Lys Ser Ile Phe Ala Ala Trp Pro Glu Cys
          1340                1345                1350

Ala Arg Leu Gly Ser Thr Ala Ala Leu Arg Leu Leu Glu Leu Ile
          1355                1360                1365

Glu Leu Ala Leu Gln Asn Ser Ser Arg Ser Ala Ile Gly Thr Val
          1370                1375                1380

Tyr Lys Ser Ile Phe Lys Phe Phe Leu Asp Ser Phe Asp Ser Arg
          1385                1390                1395
```

```
Arg Ser Leu Leu Phe Ala Glu Asp Val Asp Asn Val Glu Thr Gln
    1400            1405                1410

Ala Val Asn Val Phe Leu Lys Phe Val Met Lys Leu Ser Asp Thr
    1415            1420                1425

Thr Phe Arg Pro Leu Phe Leu His Leu His Ser Trp Ala Leu Glu
    1430            1435                1440

Asp Leu Tyr Glu Thr Asp Pro Ser Gly Ile Val Ser Arg Gln Thr
    1445            1450                1455

Phe Phe Tyr Asn Phe Leu Thr Ile Phe Leu Asp Thr Leu Lys Ser
    1460            1465                1470

Ile Val Thr Asn Tyr Tyr Ala Tyr Val Leu Asp Asp Thr Ile Glu
    1475            1480                1485

Leu Leu Ser Ser Lys Asp Thr Asn Ser Glu Val Arg His Leu Val
    1490            1495                1500

Asn Ser Ser Leu Val Ser Ala Phe Glu Asn Asp Thr Glu Glu Phe
    1505            1510                1515

Trp Met Val Pro Ala Arg Phe Gly Lys Ile Ser Pro Val Leu Ile
    1520            1525                1530

Glu Gln Ile Gln Tyr Ala Pro Leu Leu Asp Asp Lys Val Leu Val
    1535            1540                1545

Lys Ala Ile Val Glu Leu Ala Ser Val Ala Ser Ser Ser Asp Asn
    1550            1555                1560

Phe Arg Ser Met Asn Thr Gln Leu Leu Gln Tyr Leu Arg Ser Ser
    1565            1570                1575

Asn Ile Asn Ala Arg Leu Leu Ala Ile Gln Ile Gln Thr Gln Leu
    1580            1585                1590

Tyr Gly Arg Leu Gly Glu Asn Trp Ile Ser Thr Leu Pro Gln Ser
    1595            1600                1605

Val Pro Phe Ile Ala Glu Leu Met Glu Asp Asp Asp Gln Val
    1610            1615                1620

Glu Thr Ala Thr Ala Glu Leu Val Arg Ile Ile Asp Asp Arg Leu
    1625            1630                1635

Gly Glu Asn Glu Ser Leu Gln Asp Tyr Leu Thr
    1640            1645

<210> SEQ ID NO 68
<211> LENGTH: 1769
<212> TYPE: PRT
<213> ORGANISM: Saccharomyces cerevisiae

<400> SEQUENCE: 68

Met Ser Ser Leu Ser Asp Gln Leu Ala Gln Val Ala Ser Asn Asn Ala
1               5                   10                  15

Thr Val Ala Leu Asp Arg Lys Arg Arg Gln Lys Leu His Ser Ala Ser
                20                  25                  30

Leu Ile Tyr Asn Ser Lys Thr Ala Ala Thr Gln Asp Tyr Asp Phe Ile
            35                  40                  45

Phe Glu Asn Ala Ser Lys Ala Leu Glu Glu Leu Ser Gln Ile Glu Pro
        50                  55                  60

Lys Phe Ala Ile Phe Ser Arg Thr Leu Phe Ser Glu Ser Ser Ile Ser
65                  70                  75                  80

Leu Asp Arg Asn Val Gln Thr Lys Glu Glu Ile Lys Asp Leu Asp Asn
                85                  90                  95

Ala Ile Asn Ala Tyr Leu Leu Leu Ala Ser Ser Lys Trp Tyr Leu Ala
            100                 105                 110
```

-continued

```
Pro Thr Leu His Ala Thr Glu Trp Leu Val Arg Arg Phe Gln Ile His
    115                 120                 125

Val Lys Asn Thr Glu Met Leu Leu Ser Thr Leu Asn Tyr Tyr Gln
    130                 135                 140

Thr Pro Val Phe Lys Arg Ile Leu Ser Ile Lys Leu Pro Pro Leu
145                 150                 155                 160

Phe Asn Cys Leu Ser Asn Phe Val Arg Ser Glu Lys Pro Thr Ala
                165                 170                 175

Leu Thr Met Ile Lys Leu Phe Asn Asp Met Asp Phe Leu Lys Leu Tyr
                    180                 185                 190

Thr Ser Tyr Leu Asp Gln Cys Ile Lys His Asn Ala Thr Tyr Thr Asn
        195                 200                 205

Gln Leu Leu Phe Thr Thr Cys Cys Phe Ile Asn Val Val Ala Phe Asn
    210                 215                 220

Ser Asn Asn Asp Glu Lys Leu Asn Gln Leu Val Pro Ile Leu Leu Glu
225                 230                 235                 240

Ile Ser Ala Lys Leu Leu Ala Ser Lys Ser Lys Asp Cys Gln Ile Ala
                245                 250                 255

Ala His Thr Ile Leu Val Val Phe Ala Thr Ala Leu Pro Leu Lys Lys
                    260                 265                 270

Thr Ile Ile Leu Ala Ala Met Glu Thr Ile Leu Ser Asn Leu Asp Ala
275                 280                 285

Lys Glu Ala Lys His Ser Ala Leu Leu Thr Ile Cys Lys Leu Phe Gln
    290                 295                 300

Thr Leu Lys Gly Gln Gly Asn Val Asp Gln Leu Pro Ser Lys Ile Phe
305                 310                 315                 320

Lys Leu Phe Asp Ser Lys Phe Asp Thr Val Ser Ile Leu Thr Phe Leu
                325                 330                 335

Asp Lys Glu Asp Lys Pro Val Cys Asp Lys Phe Ile Thr Ser Tyr Thr
                    340                 345                 350

Arg Ser Ile Ala Arg Tyr Asp Arg Ser Lys Leu Asn Ile Ile Leu Ser
        355                 360                 365

Leu Leu Lys Lys Ile Arg Leu Glu Arg Tyr Glu Val Arg Leu Ile Ile
    370                 375                 380

Thr Asp Leu Ile Tyr Leu Ser Glu Ile Leu Glu Asp Lys Ser Gln Leu
385                 390                 395                 400

Val Glu Leu Phe Glu Tyr Phe Ile Ser Ile Asn Glu Asp Leu Val Leu
                405                 410                 415

Lys Cys Leu Lys Ser Leu Gly Leu Thr Gly Glu Leu Phe Glu Ile Arg
                    420                 425                 430

Leu Thr Thr Ser Leu Phe Thr Asn Ala Asp Val Asn Thr Asp Ile Val
        435                 440                 445

Lys Gln Leu Ser Asp Pro Val Glu Thr Thr Lys Lys Asp Thr Ala Ser
    450                 455                 460

Phe Gln Thr Phe Leu Asp Lys His Ser Glu Leu Ile Asn Thr Thr Asn
465                 470                 475                 480

Val Ser Met Leu Thr Glu Thr Gly Glu Arg Tyr Lys Lys Val Leu Ser
                485                 490                 495

Leu Phe Thr Glu Ala Ile Gly Lys Gly Tyr Lys Ala Ser Ser Phe Leu
                    500                 505                 510

Thr Ser Phe Phe Thr Thr Leu Glu Ser Arg Ile Thr Phe Leu Leu Arg
        515                 520                 525

Val Thr Ile Ser Pro Ala Ala Pro Thr Ala Leu Lys Leu Ile Ser Leu
530                 535                 540
```

-continued

```
Asn Asn Ile Ala Lys Tyr Ile Asn Ser Ile Glu Lys Glu Val Asn Ile
545                 550                 555                 560
Phe Thr Leu Val Pro Cys Leu Ile Cys Ala Leu Arg Asp Ala Ser Ile
                565                 570                 575
Lys Val Arg Thr Gly Val Lys Lys Ile Leu Ser Leu Ile Ala Lys Arg
            580                 585                 590
Pro Ser Thr Lys His Tyr Phe Leu Ser Asp Lys Leu Tyr Gly Glu Asn
        595                 600                 605
Val Thr Ile Pro Met Leu Asn Pro Lys Asp Ser Glu Ala Trp Leu Ser
    610                 615                 620
Gly Phe Leu Asn Glu Tyr Val Thr Glu Asn Tyr Asp Ile Ser Arg Ile
625                 630                 635                 640
Leu Thr Pro Lys Arg Asn Glu Lys Val Phe Leu Met Phe Trp Ala Asn
                645                 650                 655
Gln Ala Leu Leu Ile Pro Ser Pro Tyr Ala Lys Thr Val Leu Leu Asp
            660                 665                 670
Asn Leu Asn Lys Ser Pro Thr Tyr Ala Ser Ser Tyr Ser Ser Leu Phe
        675                 680                 685
Glu Glu Phe Ile Ser His Tyr Leu Glu Asn Arg Ser Ser Trp Glu Lys
    690                 695                 700
Ser Cys Ile Ala Asn Lys Thr Asn Phe Glu His Phe Glu Arg Ser Leu
705                 710                 715                 720
Val Asn Leu Val Ser Pro Lys Glu Lys Gln Ser Phe Met Ile Asp Phe
                725                 730                 735
Val Leu Ser Ala Leu Asn Ser Asp Tyr Glu Gln Leu Ala Asn Ile Ala
            740                 745                 750
Ala Glu Arg Leu Ile Ser Ile Phe Ala Ser Leu Asn Asn Ala Gln Lys
        755                 760                 765
Leu Lys Ile Val Gln Asn Ile Val Asp Ser Ser Asn Val Glu Ser
    770                 775                 780
Ser Tyr Asp Thr Val Gly Val Leu Gln Ser Leu Pro Leu Asp Ser Asp
785                 790                 795                 800
Ile Phe Val Ser Ile Leu Asn Gln Asn Ser Ile Ser Asn Glu Met Asp
                805                 810                 815
Gln Thr Asp Phe Ser Lys Arg Arg Arg Arg Ser Ser Thr Ser Lys
            820                 825                 830
Asn Ala Phe Leu Lys Glu Val Ser Gln Leu Ala Glu Leu His Leu
        835                 840                 845
Arg Lys Leu Thr Ile Ile Leu Glu Ala Leu Asp Lys Val Arg Asn Val
    850                 855                 860
Gly Ser Glu Lys Leu Leu Phe Thr Leu Leu Ser Leu Leu Ser Asp Leu
865                 870                 875                 880
Glu Thr Leu Asp Gln Asp Gly Gly Leu Pro Val Leu Tyr Ala Gln Glu
                885                 890                 895
Thr Leu Ile Ser Cys Thr Leu Asn Thr Ile Thr Tyr Leu Lys Glu His
            900                 905                 910
Gly Cys Thr Glu Leu Thr Asn Val Arg Ala Asp Ile Leu Val Ser Ala
        915                 920                 925
Ile Arg Asn Ser Ala Ser Pro Gln Val Gln Asn Lys Leu Leu Leu Val
    930                 935                 940
Ile Gly Ser Leu Ala Thr Leu Ser Ser Glu Val Ile Leu His Ser Val
945                 950                 955                 960
Met Pro Ile Phe Thr Phe Met Gly Ala His Ser Ile Arg Gln Asp Asp
```

```
                965                 970                 975
Glu Phe Thr Thr Lys Val Val Glu Arg Thr Ile Leu Thr Val Val Pro
            980                 985                 990

Ala Leu Ile Lys Asn Ser Lys Gly Asn Glu Lys Glu Glu Met Glu Phe
        995                1000                1005

Leu Leu Leu Ser Phe Thr Thr Ala Leu Gln His Val Pro Arg His
       1010                1015                1020

Arg Arg Val Lys Leu Phe Ser Thr Leu Ile Lys Thr Leu Asp Pro
       1025                1030                1035

Val Lys Ala Leu Gly Ser Phe Leu Phe Leu Ile Ala Gln Gln Tyr
       1040                1045                1050

Ser Ser Ala Leu Val Asn Phe Lys Ile Gly Glu Ala Arg Ile Leu
       1055                1060                1065

Ile Glu Phe Ile Lys Ala Leu Leu Val Asp Leu His Val Asn Glu
       1070                1075                1080

Glu Leu Ser Gly Leu Asn Asp Leu Leu Asp Ile Ile Lys Leu Leu
       1085                1090                1095

Thr Ser Ser Lys Ser Ser Ser Glu Lys Lys Lys Ser Leu Glu Ser
       1100                1105                1110

Arg Val Leu Phe Ser Asn Gly Val Leu Asn Phe Ser Glu Ser Glu
       1115                1120                1125

Phe Leu Thr Phe Met Asn Asn Thr Phe Glu Phe Ile Asn Lys Ile
       1130                1135                1140

Thr Glu Glu Thr Asp Gln Asp Tyr Tyr Asp Val Arg Arg Asn Leu
       1145                1150                1155

Arg Leu Lys Val Tyr Ser Val Leu Leu Asp Glu Thr Ser Asp Lys
       1160                1165                1170

Lys Leu Ile Arg Asn Ile Arg Glu Glu Phe Gly Thr Leu Leu Glu
       1175                1180                1185

Gly Val Leu Phe Phe Ile Asn Ser Val Glu Leu Thr Phe Ser Cys
       1190                1195                1200

Ile Thr Ser Gln Glu Asn Glu Glu Ala Ser Asp Ser Glu Thr Ser
       1205                1210                1215

Leu Ser Asp His Thr Thr Glu Ile Lys Glu Ile Leu Phe Lys Val
       1220                1225                1230

Leu Gly Asn Val Leu Gln Ile Leu Pro Val Asp Glu Phe Val Asn
       1235                1240                1245

Ala Val Leu Pro Leu Leu Ser Thr Ser Thr Asn Glu Asp Ile Arg
       1250                1255                1260

Tyr His Leu Thr Leu Val Ile Gly Ser Lys Phe Glu Leu Glu Gly
       1265                1270                1275

Ser Glu Ala Ile Pro Ile Val Asn Asn Val Met Lys Val Leu Leu
       1280                1285                1290

Asp Arg Met Pro Leu Glu Ser Lys Ser Val Val Ile Ser Gln Val
       1295                1300                1305

Ile Leu Asn Thr Met Thr Ala Leu Val Ser Lys Tyr Gly Lys Lys
       1310                1315                1320

Leu Glu Gly Ser Ile Leu Thr Gln Ala Leu Thr Leu Ala Thr Glu
       1325                1330                1335

Lys Val Ser Ser Asp Met Thr Glu Val Lys Ile Ser Ser Leu Ala
       1340                1345                1350

Leu Ile Thr Asn Cys Val Gln Val Leu Gly Val Lys Ser Ile Ala
       1355                1360                1365
```

```
Phe Tyr Pro Lys Ile Val Pro Pro Ser Ile Lys Leu Phe Asp Ala
        1370            1375                1380

Ser Leu Ala Asp Ser Ser Asn Pro Leu Lys Glu Gln Leu Gln Val
    1385                1390                1395

Ala Ile Leu Leu Leu Phe Ala Gly Leu Ile Lys Arg Ile Pro Ser
    1400                1405                1410

Phe Leu Met Ser Asn Ile Leu Asp Val Leu His Val Ile Tyr Phe
    1415                1420                1425

Ser Arg Glu Val Asp Ser Ser Ile Arg Leu Ser Val Ile Ser Leu
    1430                1435                1440

Ile Ile Glu Asn Ile Asp Leu Lys Glu Val Leu Lys Val Leu Phe
    1445                1450                1455

Arg Ile Trp Ser Thr Glu Ile Ala Thr Ser Asn Asp Thr Val Ala
    1460                1465                1470

Val Ser Leu Phe Leu Ser Thr Leu Glu Ser Thr Val Glu Asn Ile
    1475                1480                1485

Asp Lys Lys Ser Ala Thr Ser Gln Ser Pro Ile Phe Phe Lys Leu
    1490                1495                1500

Leu Leu Ser Leu Phe Glu Phe Arg Ser Ile Ser Ser Phe Asp Asn
    1505                1510                1515

Asn Thr Ile Ser Arg Ile Glu Ala Ser Val His Glu Ile Ser Asn
    1520                1525                1530

Ser Tyr Val Leu Lys Met Asn Asp Lys Val Phe Arg Pro Leu Phe
    1535                1540                1545

Val Ile Leu Val Arg Trp Ala Phe Asp Gly Glu Gly Val Thr Asn
    1550                1555                1560

Ala Gly Ile Thr Glu Thr Glu Arg Leu Leu Ala Phe Phe Lys Phe
    1565                1570                1575

Phe Asn Lys Leu Gln Glu Asn Leu Arg Gly Ile Ile Thr Ser Tyr
    1580                1585                1590

Phe Thr Tyr Leu Leu Glu Pro Val Asp Met Leu Leu Lys Arg Phe
    1595                1600                1605

Ile Ser Lys Asp Met Glu Asn Val Asn Leu Arg Arg Leu Val Ile
    1610                1615                1620

Asn Ser Leu Thr Ser Ser Leu Lys Phe Asp Arg Asp Glu Tyr Trp
    1625                1630                1635

Lys Ser Thr Ser Arg Phe Glu Leu Ile Ser Val Ser Leu Val Asn
    1640                1645                1650

Gln Leu Ser Asn Ile Glu Asn Ser Ile Gly Lys Tyr Leu Val Lys
    1655                1660                1665

Ala Ile Gly Ala Leu Ala Ser Asn Asn Ser Gly Val Asp Glu His
    1670                1675                1680

Asn Gln Ile Leu Asn Lys Leu Ile Val Glu His Met Lys Ala Ser
    1685                1690                1695

Cys Ser Ser Asn Glu Lys Leu Trp Ala Ile Arg Ala Met Lys Leu
    1700                1705                1710

Ile Tyr Ser Lys Ile Gly Glu Ser Trp Leu Val Leu Leu Pro Gln
    1715                1720                1725

Leu Val Pro Val Ile Ala Glu Leu Leu Glu Asp Asp Glu Glu
    1730                1735                1740

Ile Glu Arg Glu Val Arg Thr Gly Leu Val Lys Val Val Glu Asn
    1745                1750                1755

Val Leu Gly Glu Pro Phe Asp Arg Tyr Leu Asp
    1760                1765
```

<210> SEQ ID NO 69
<211> LENGTH: 1650
<212> TYPE: PRT
<213> ORGANISM: Caenorhabditis elegans

<400> SEQUENCE: 69

```
Met Ala Thr Ser Leu Thr Ser Gln Leu Glu Asn Leu Arg Thr Ser Ala
1               5                   10                  15

Ala Arg His Leu Thr Val Glu Lys Arg His Val Ser Leu Leu Phe Asp
                20                  25                  30

Arg Lys Glu Ala Asn Lys Leu Ser Asn Glu Thr Ala His Arg Ile Gly
            35                  40                  45

Val Ala Gly Leu Glu Gln Met Lys Arg Ile Asp Pro Val Phe Asp Thr
        50                  55                  60

Glu Phe Ala Asn Asp Leu Phe Ser Glu Glu Arg Val Asp Phe Val Arg
65                  70                  75                  80

Ser Met Leu Glu Lys Gly Ala Asn Glu Leu Asn Lys Gln Ile Glu
                85                  90                  95

Lys Leu Leu Leu Glu Leu Ser Pro Tyr Leu Gln His Phe Ala Cys Gln
            100                 105                 110

Gln Val Leu Glu Phe Leu Ile His Thr Tyr Gln Ile Tyr Ser Phe Asn
        115                 120                 125

Ala Glu Thr Leu Leu Leu Thr Phe Leu Pro Phe His Glu Thr Lys Val
    130                 135                 140

Tyr Ser Arg Leu Leu Arg Ile Leu Asp Phe Asp Trp Lys Arg Ser Lys
145                 150                 155                 160

Glu Trp Gln Phe Met Gln Gln Phe Thr Lys Thr Glu Thr Pro Ile Pro
                165                 170                 175

Phe Thr Ser Ile Ala Arg Ala Thr Leu Ser Ser Lys His Ser Ile Ile
            180                 185                 190

Thr Cys Ile Thr Asp His Ile Arg His Ala Val Glu Ile Val Gly Ser
        195                 200                 205

Asp Tyr Leu Glu Ile Lys His Pro Ile Leu Phe Asn Phe His Ala Lys
    210                 215                 220

Leu Leu Leu Ser Met Phe Thr Asp Pro Glu Lys Val Asp Glu Met Met
225                 230                 235                 240

Leu Ala Lys Leu Met Pro Phe Ile Glu Asn Gly Ile Lys Ser Pro Met
                245                 250                 255

Lys Ser Phe Arg Tyr Ser Ala Met Val Val Ile Ser Gln Leu Val Leu
            260                 265                 270

Thr Val Lys Leu Lys Asp Glu Val Leu Asn Ser Met Cys Lys Leu Leu
        275                 280                 285

Ile Thr Lys Met Arg Ser Asp Thr Ala Ala Ser Leu Ser Thr Leu
    290                 295                 300

Met Val Val Phe Gln Gln Gln Asn Val Gln Ser Leu Ser Lys Asn Thr
305                 310                 315                 320

Leu Lys Lys Leu Leu Arg His Glu Glu Gly Ile Asp Val Trp Lys Ile
                325                 330                 335

Leu Lys Glu Leu Ser Glu Arg Thr Asp Thr Thr Lys Phe Phe Asn Val
            340                 345                 350

Leu Trp Lys Glu Leu Ile Val Leu Ser Lys Asp Ala Glu Ser Glu Asp
        355                 360                 365

Asn Thr Leu Ala Ile Asp Val Leu Ile Glu Thr Ile Glu Asp Ala Ser
    370                 375                 380
```

```
Ile Leu Thr Gly Asp Gln Ala Gly Thr Ile Leu Lys Leu Ile Leu Gln
385                 390                 395                 400

Glu Gly Met Asp Gly Asn Ile Phe Asp Asn Lys Lys Leu Lys Ser
            405                 410                 415

Asn Ile Arg Ala Ile Gly Met Arg Phe Ala Lys Gln Phe Asp Ala Ile
            420                 425                 430

His Ala Glu Leu Lys Ala Lys Asp Lys Lys Thr Leu Lys Asn Val Leu
            435                 440                 445

Lys Glu Tyr Gln Ile Glu Asp Ile Val Gln Phe Ala Ser Glu Ala Val
            450                 455                 460

Ala Ala Thr Gln Ser Glu Glu Ser Ile Glu Ile Ile Ser Glu Glu Ala
465                 470                 475                 480

Pro Ser Ser Lys Lys Ile Lys Leu Thr Ala Ser Glu Lys Ala Gln Lys
                    485                 490                 495

Leu Ala Gln Ser Ser Glu Phe Ala Lys Arg Glu Val Phe Ser Gly Asp
            500                 505                 510

Pro Ile Asn Lys Ala Thr Glu Trp Leu Asn Gly Glu Lys Trp Asp Lys
            515                 520                 525

Val Glu Trp Ala Leu Asn Glu Met Ala Gln Arg Gly Glu Lys Tyr Phe
530                 535                 540

Ser Arg Lys Val Glu Asp Asp Val Glu Gln Phe Val Leu Glu Ile Val
545                 550                 555                 560

Lys Val Val Gly Val Gly Gly Val Lys Gln Ile Asp Gly Gly Ser Val
                    565                 570                 575

Lys Ala Ala Leu Ala Gly Ala Asn Leu Asn Pro Gln Phe Val Ala Asp
            580                 585                 590

Leu Leu Thr Lys Phe Asp Gly Val Ser Glu Ile Ala Pro Lys Arg Thr
            595                 600                 605

Lys Gly Ala Gln Lys Lys Asn Leu Val Glu Lys Thr Phe Gly Thr Glu
            610                 615                 620

Glu Ser Trp Glu Ala Phe Asn Gln Arg Val Val Phe Val Leu Asp Leu
625                 630                 635                 640

Leu Asn Ala Arg Gln Ile Ile Pro Ser Ser Glu Lys Val Leu Ala Ala
            645                 650                 655

Leu Phe Ala Val Val Lys Gln Val Asn Ser Lys Ser Asp Val Glu Ser
            660                 665                 670

Ser Ser Tyr Gln Gln His Leu Ala Val Asn Ala Ile Arg Lys Ile Leu
            675                 680                 685

Glu His Pro Glu Lys Thr Lys Ile Gly Ala Ser Glu Val Asp Met Asp
            690                 695                 700

Cys Val Ile Glu Thr Met Arg Ser Thr His Asn His Leu Leu Arg
705                 710                 715                 720

Asp Cys Leu Arg Leu Ile Val Ala Ala Ala Lys His Thr Pro Asn Ser
            725                 730                 735

Val Val Lys His Val Met Ser Val Phe Thr Phe Met Gly Asn Gly Met
            740                 745                 750

Leu Arg Lys Asp Asn Glu Leu Thr Leu Ser Ile Val Glu Lys Thr Val
            755                 760                 765

Glu Ser Leu Phe Ser Thr Ile Ile Asn Ser Ser Gly Gln Ala Val Leu
            770                 775                 780

Thr Lys Gln Gln Gln Thr Glu Lys Leu Ile Glu Leu Ala Arg Leu Phe
785                 790                 795                 800

Ala Ala Ser Ala Ile Asp Ile Pro Ala His Arg Arg Ala Arg Ile Ala
```

-continued

```
            805                 810                 815
Gln Ala Ile Ala Arg Ala Val Gln Ala Glu Asn Ala Ser Thr Val Val
                820                 825                 830
Leu Val Leu Val Ser Ser Phe Cys Ala Arg Trp Gln Arg Ser Ser Asp
                835                 840                 845
Ala Ala Ala Gln Glu Ala Met Lys Arg Gly Ser Asp Gln Asp Ala Tyr
    850                 855                 860
Asp Asp Leu Ala Ile Glu Leu Leu Ser Ala Leu Asn Pro Phe Glu Gln
865                 870                 875                 880
Leu Ser Ser Val Leu Glu Met Cys Glu Tyr Val Arg Arg Leu Gly Gly
                885                 890                 895
Asp Lys Pro Ala Lys Ser Thr Thr Lys Lys Asp Leu Asp Thr Met
                900                 905                 910
Ile Phe Asp Arg Thr Ala Gln Thr Leu Pro Arg Ile Arg His Phe Arg
                915                 920                 925
Tyr Val Val Thr Leu Ile Ser Arg Ile Phe Ser Asn Arg Val Leu
                930                 935                 940
Ile Glu Arg Leu Ala Ala Tyr Asp Asp Glu Glu Leu Leu Lys Asn Ala
945                 950                 955                 960
Leu Pro Leu Gly Lys Arg Leu Ile Glu Cys Ser Val Glu Leu Asp Glu
                965                 970                 975
Phe Ala Asn Lys Glu Ala Asn Asp Gln Asp Gly Ser Asp Pro Gln Ala
                980                 985                 990
Gln Arg Tyr Trp Val Ala Phe Ala Ser Arg Thr Glu Val Val Ser Glu
                995                 1000                1005
Lys Leu Arg His Leu Leu Pro Gly Gly Val Ala Ala Arg Leu Ile
                1010                1015                1020
Ala Asp Val Leu Gln Glu Cys Val Asn Asp Lys Lys Met Ser Tyr
                1025                1030                1035
Lys Met Cys Glu Lys Val Leu Gln Leu Ala Asn Ile Lys Leu Gly
                1040                1045                1050
His Asp Arg Tyr Leu Phe Ala Asp Ser Gly Ile Asn Glu Lys Glu
                1055                1060                1065
Leu Ile Thr Leu Ala Gln Ala Leu Asn Lys Phe Ile Val Ala Glu
                1070                1075                1080
Thr Lys Ser Glu Glu Lys Met Arg Met Cys Gln Asn Ser Ala Tyr
                1085                1090                1095
Thr Leu Lys Leu Ile Ala Lys Asn Leu Pro Ser Gln Ser Glu Ser
                1100                1105                1110
Leu Val Leu Ala Asp Thr Met Gln Arg Cys Val Ser Ile Val Ser
                1115                1120                1125
Gln Tyr Gln Lys Leu Asp Glu Asn Leu Thr Gly Asn Val Leu Leu
                1130                1135                1140
Leu Ala Gly Glu Leu Ile Arg Ser His Asn Met Arg Ser Thr Ile
                1145                1150                1155
His His Ala Thr Ser Leu Leu Lys Thr Cys Leu Ala Thr Val Gln
                1160                1165                1170
Glu Cys Ile Ala Arg Phe Ser Lys Pro Gln Tyr Asp Ser Ala Ala
                1175                1180                1185
Ser Pro Gly Ser Ser Val Ala Gly Gly Arg Gly Asn Arg Gly His
                1190                1195                1200
Arg Ile Arg Gln Gln Ser Leu Gly Gly Asn Lys Phe Gly Ser Asp
                1205                1210                1215
```

-continued

Thr Leu Leu Ile Cys Ser Leu Thr Cys Ile Gln Arg Val Tyr Asp
1220                1225                1230

Gln Phe Ala Ser Phe Val Val Glu Ser Thr Gly Asp Val Ile Ile
1235                1240                1245

Arg Tyr Cys Arg Leu Ile Ala Arg Phe Gly Asp Pro Ser Glu Leu
1250                1255                1260

Leu Ala Leu Asn Gln Pro Ser Ser Ser Thr Thr Ala Ala Phe Gln
1265                1270                1275

Gly Gly Ser Gln Thr Ser Gly Phe Gly Ser Lys Thr Gly Ile His
1280                1285                1290

His Arg Leu Ser Leu Ile Arg Arg Ser Leu Leu Ser Ile Glu Leu
1295                1300                1305

Arg Val Leu Pro Ala His Ile Val Lys Thr Val Gly Glu Leu Lys
1310                1315                1320

Thr Glu Lys Lys Ala Leu Ser Ala Leu Phe Asn Leu Leu Thr Gly
1325                1330                1335

Tyr Ile Glu Thr Gln His Gln Gln Lys Pro Glu Ile Leu Arg Lys
1340                1345                1350

Ser Val Ile Gln Leu Arg Arg Thr Phe Val Ser Asp Val Ile Thr
1355                1360                1365

Pro Thr Leu Ile Val Arg Ser Gln Glu Arg Gln Ser Asp Gln Phe
1370                1375                1380

Glu Asn Val Glu Lys Leu Glu His Thr Val Phe Asn Phe Val Ile
1385                1390                1395

Ser Ile Ala Ser Ile Leu Ser Glu Val Glu Phe Arg Thr Val Val
1400                1405                1410

Asn Glu Leu Val Ala Trp Ala Glu Pro Gly Leu Glu Ala Lys Ala
1415                1420                1425

Asp Leu Ala Ala Arg Leu Arg Leu Val Ser Leu Leu His Phe Ala
1430                1435                1440

Asn Asp Leu Tyr Thr Ser Phe Asn Ser Leu Ala Leu Pro Tyr Phe
1445                1450                1455

Gly Arg Ile Leu Glu Ile Ser Ala Leu Val Leu Lys Lys Cys Asn
1460                1465                1470

Ala Thr Leu Leu Leu Gly Thr Asp Glu Leu Leu Leu Ser Gly Lys
1475                1480                1485

Arg Gly Ser Ile Glu Ala Leu Glu Thr Asp Leu Ala Leu Thr Leu
1490                1495                1500

Ala Ile Asp Val Ile Ser Asn Ala Ala Arg His Arg Asp Phe Phe
1505                1510                1515

Thr Val Asp Arg Cys Gln Leu Val Ser Asp Val Ile Val Asn Glu
1520                1525                1530

Leu Val Asn Thr Lys Val Glu Gly His Glu Lys Arg Cys Ser Asp
1535                1540                1545

His Leu Val Pro Ala Ile Tyr Arg Ile Gly Asn Ala Asp Pro Asp
1550                1555                1560

Ser Phe Pro Glu Leu Leu Asn Lys Ile Met Leu Lys Thr Arg Asp
1565                1570                1575

Ser Arg Ala Lys Ile Arg Tyr Arg Ala Leu Ile Val Leu Glu Leu
1580                1585                1590

Leu Ile Lys Glu Ile Gly Asp Gly Val Gln Pro His Leu Ser Ile
1595                1600                1605

Leu Leu Pro Phe Leu Asn Glu Leu Ile Glu Asp Glu Asn Lys Gln
1610                1615                1620

-continued

```
Val Glu Ala Gln Cys Gln Lys Val Ile Asn Ser Leu Gln His Lys
    1625                1630                1635

Phe Gly Glu Thr Phe Trp Ser Gly Gly Ser Ser Ala
    1640                1645                1650

<210> SEQ ID NO 70
<211> LENGTH: 2204
<212> TYPE: PRT
<213> ORGANISM: Homo sapiens
<220> FEATURE:
<221> NAME/KEY: misc_feature
<222> LOCATION: (1218)..(1218)
<223> OTHER INFORMATION: Xaa can be any naturally occurring amino acid

<400> SEQUENCE: 70

Met Thr Ser Leu Ala Gln Gln Leu Gln Arg Leu Ala Leu Pro Gln Ser
1               5                   10                  15

Asp Ala Ser Leu Leu Ser Arg Asp Glu Val Ala Ser Leu Leu Phe Asp
            20                  25                  30

Pro Lys Glu Ala Ala Thr Ile Asp Arg Asp Thr Ala Phe Ala Ile Gly
        35                  40                  45

Cys Thr Gly Leu Glu Glu Leu Leu Gly Ile Asp Pro Ser Phe Glu Gln
    50                  55                  60

Phe Glu Ala Pro Leu Phe Ser Gln Leu Ala Lys Thr Leu Glu Arg Ser
65                  70                  75                  80

Val Gln Thr Lys Ala Val Asn Lys Gln Leu Asp Glu Asn Ile Ser Leu
                85                  90                  95

Phe Leu Ile His Leu Ser Pro Tyr Phe Leu Leu Lys Pro Ala Gln Lys
            100                 105                 110

Cys Leu Glu Trp Leu Ile His Arg Phe His Ile His Leu Tyr Asn Gln
        115                 120                 125

Asp Ser Leu Ile Ala Cys Val Leu Pro Tyr His Glu Thr Arg Ile Phe
    130                 135                 140

Val Arg Val Ile Gln Leu Leu Lys Ile Asn Asn Ser Lys His Arg Trp
145                 150                 155                 160

Phe Trp Leu Leu Pro Val Lys Gln Ser Gly Val Pro Leu Ala Lys Gly
                165                 170                 175

Thr Leu Ile Thr His Cys Tyr Lys Asp Leu Gly Phe Met Asp Phe Ile
            180                 185                 190

Cys Ser Leu Val Thr Lys Ser Val Lys Val Phe Ala Glu Tyr Pro Gly
        195                 200                 205

Ser Ser Ala Gln Leu Arg Val Leu Leu Ala Phe Tyr Ala Ser Thr Ile
    210                 215                 220

Val Ser Ala Leu Val Ala Ala Glu Asp Val Ser Asp Asn Ile Ile Ala
225                 230                 235                 240

Lys Leu Phe Pro Tyr Ile Gln Lys Gly Leu Lys Ser Ser Leu Pro Asp
                245                 250                 255

Tyr Arg Ala Ala Thr Tyr Met Ile Ile Cys Gln Ile Ser Val Lys Val
            260                 265                 270

Thr Met Glu Asn Thr Phe Val Asn Ser Leu Ala Ser Gln Ile Ile Lys
        275                 280                 285

Thr Leu Thr Lys Ile Pro Ser Leu Ile Lys Asp Gly Leu Ser Cys Leu
    290                 295                 300

Ile Val Leu Leu Gln Arg Gln Lys Pro Glu Ser Leu Gly Lys Lys Pro
305                 310                 315                 320

Phe Pro His Leu Cys Asn Val Pro Asp Leu Ile Thr Ile Leu His Gly
```

```
                    325                 330                 335
Ile Ser Glu Thr Tyr Asp Val Ser Pro Leu Leu Arg Tyr Met Leu Pro
                340                 345                 350

His Leu Val Val Ser Ile Ile His Val Thr Gly Glu Glu Thr Glu
            355                 360                 365

Gly Met Asp Gly Gln Ile Tyr Lys Arg His Leu Glu Ala Ile Leu Thr
            370                 375                 380

Lys Ile Ser Leu Lys Asn Asn Leu Asp His Leu Ala Ser Leu Leu
385                 390                 395                 400

Phe Glu Glu Tyr Ile Ser Tyr Ser Ser Gln Glu Glu Met Asp Ser Asn
                405                 410                 415

Lys Val Ser Leu Leu Asn Glu Gln Phe Leu Pro Leu Ile Arg Leu Leu
            420                 425                 430

Glu Ser Lys Tyr Pro Arg Thr Leu Asp Val Val Leu Glu Glu His Leu
            435                 440                 445

Lys Glu Ile Ala Asp Leu Lys Lys Gln Glu Leu Phe His Gln Phe Val
            450                 455                 460

Ser Leu Ser Thr Ser Gly Gly Lys Tyr Gln Phe Leu Ala Asp Ser Asp
465                 470                 475                 480

Thr Ser Leu Met Leu Ser Leu Asn His Pro Leu Ala Pro Val Arg Ile
                485                 490                 495

Leu Ala Met Asn His Leu Lys Lys Ile Met Lys Thr Ser Lys Glu Gly
                500                 505                 510

Val Asp Glu Ser Phe Ile Lys Glu Ala Val Leu Ala Arg Leu Gly Asp
            515                 520                 525

Asp Asn Ile Asp Val Val Leu Ser Ala Ile Ser Ala Phe Glu Ile Phe
530                 535                 540

Lys Glu His Phe Ser Ser Glu Val Thr Ile Ser Asn Leu Leu Asn Leu
545                 550                 555                 560

Phe Gln Arg Ala Glu Leu Ser Lys Asn Gly Glu Trp Tyr Glu Val Leu
                565                 570                 575

Lys Ile Ala Ala Asp Ile Leu Ile Lys Glu Glu Ile Leu Ser Glu Asn
            580                 585                 590

Asp Gln Leu Ser Asn Gln Val Val Cys Leu Leu Pro Phe Val Val
            595                 600                 605

Ile Asn Asn Asp Asp Thr Glu Ser Ala Glu Met Lys Ile Ala Ile Tyr
            610                 615                 620

Leu Ser Lys Ser Gly Ile Cys Ser Leu His Pro Leu Leu Arg Gly Trp
625                 630                 635                 640

Glu Glu Ala Leu Glu Asn Val Ile Lys Ser Thr Lys Pro Gly Lys Leu
            645                 650                 655

Ile Gly Val Ala Asn Gln Lys Met Ile Glu Leu Leu Ala Asp Asn Ile
            660                 665                 670

Asn Leu Gly Asp Pro Ser Ser Met Leu Lys Met Val Glu Asp Leu Ile
            675                 680                 685

Ser Val Gly Glu Glu Glu Ser Phe Asn Leu Lys Gln Lys Val Thr Phe
            690                 695                 700

His Val Ile Leu Ser Val Leu Ser Cys Cys Ser Ser Leu Lys Glu
705                 710                 715                 720

Thr His Phe Pro Phe Ala Ile Arg Val Phe Ser Leu Leu Gln Lys Lys
                725                 730                 735

Ile Lys Lys Leu Glu Ser Val Ile Thr Ala Val Glu Ile Pro Ser Glu
            740                 745                 750
```

-continued

```
Trp His Ile Glu Leu Met Leu Asp Arg Gly Ile Pro Val Glu Leu Trp
        755                 760                 765

Ala His Tyr Val Glu Glu Leu Asn Ser Thr Gln Arg Val Ala Val Glu
    770                 775                 780

Asp Ser Val Phe Leu Val Phe Ser Leu Lys Lys Phe Ile Tyr Ala Leu
785                 790                 795                 800

Lys Ala Pro Lys Ser Phe Pro Lys Gly Asp Ile Trp Trp Asn Pro Glu
                805                 810                 815

Gln Leu Lys Glu Asp Ser Arg Asp Tyr Leu His Leu Ile Gly Leu
            820                 825                 830

Phe Glu Met Met Leu Asn Gly Ala Asp Ala Val His Phe Arg Val Leu
            835                 840                 845

Met Lys Leu Phe Ile Lys Val His Leu Glu Asp Val Phe Gln Leu Phe
    850                 855                 860

Lys Phe Cys Ser Val Leu Trp Thr Tyr Gly Ser Ser Leu Ser Asn Pro
865                 870                 875                 880

Leu Asn Cys Ser Val Lys Thr Val Leu Gln Thr Ala Leu Tyr Val
                885                 890                 895

Gly Cys Ala Met Leu Ser Ser Gln Lys Thr Gln Cys Lys His Gln Leu
            900                 905                 910

Ala Ser Ile Ser Ser Pro Val Val Thr Ser Leu Leu Ile Asn Leu Gly
    915                 920                 925

Ser Pro Val Lys Glu Val Arg Arg Ala Ala Ile Gln Cys Leu Gln Ala
930                 935                 940

Leu Ser Gly Val Ala Ser Pro Phe Tyr Leu Ile Ile Asp His Leu Ile
945                 950                 955                 960

Ser Lys Ala Glu Glu Ile Thr Ser Asp Ala Ala Tyr Val Ile Gln Asp
                965                 970                 975

Leu Ala Thr Leu Phe Glu Glu Leu Gln Arg Glu Lys Lys Leu Lys Ser
            980                 985                 990

His Gln Lys Leu Ser Glu Thr Leu  Lys Asn Leu Leu Ser  Cys Val Tyr
    995                 1000                1005

Ser Cys  Pro Ser Tyr Ile Ala  Lys Asp Leu Met Lys  Val Leu Gln
    1010                1015                1020

Gly Val  Asn Gly Glu Met Val  Leu Ser Gln Leu Leu  Pro Met Ala
    1025                1030                1035

Glu Gln  Leu Leu Glu Lys Ile  Gln Lys Glu Pro Thr  Ala Val Leu
    1040                1045                1050

Lys Asp  Glu Ala Met Val Leu  His Leu Thr Leu Gly  Lys Tyr Asn
    1055                1060                1065

Glu Phe  Ser Val Ser Leu Leu  Asn Glu Asp Pro Lys  Ser Leu Asp
    1070                1075                1080

Ile Phe  Ile Lys Ala Val His  Thr Thr Lys Glu Leu  Tyr Ala Gly
    1085                1090                1095

Met Pro  Thr Ile Gln Ile Thr  Ala Leu Glu Lys Ile  Thr Lys Pro
    1100                1105                1110

Phe Phe  Ala Ala Ile Ser Asp  Glu Lys Val Gln Gln  Lys Leu Leu
    1115                1120                1125

Arg Met  Leu Phe Asp Leu Leu  Val Asn Cys Lys Asn  Ser His Cys
    1130                1135                1140

Ala Gln  Thr Val Ser Ser Val  Phe Lys Gly Ile Ser  Val Asn Ala
    1145                1150                1155

Glu Gln  Val Arg Ile Glu Leu  Glu Pro Pro Asp Lys  Ala Lys Pro
    1160                1165                1170
```

-continued

```
Leu Gly Thr Val Gln Gln Lys Arg Arg Gln Lys Met Gln Gln Lys
    1175                1180                1185
Lys Ser Gln Asp Leu Glu Ser Val Gln Glu Val Gly Gly Ser Tyr
    1190                1195                1200
Trp Gln Arg Val Thr Leu Ile Leu Glu Leu Leu Gln His Lys Xaa
    1205                1210                1215
Lys Leu Arg Ser Pro Gln Ile Leu Val Pro Thr Leu Phe Asn Leu
    1220                1225                1230
Leu Ser Arg Cys Leu Glu Pro Leu Pro Gln Glu Gln Gly Asn Met
    1235                1240                1245
Glu Tyr Thr Lys Gln Leu Ile Leu Ser Cys Leu Leu Asn Ile Cys
    1250                1255                1260
Gln Lys Leu Ser Pro Asp Gly Gly Lys Ile Pro Lys Asp Ile Leu
    1265                1270                1275
Asp Glu Glu Lys Phe Asn Val Glu Leu Ile Val Gln Cys Ile Arg
    1280                1285                1290
Leu Ser Glu Met Pro Gln Thr His His Ala Leu Leu Leu Leu
    1295                1300                1305
Gly Thr Val Ala Gly Ile Phe Pro Asp Lys Val Leu His Asn Ile
    1310                1315                1320
Met Ser Ile Phe Thr Phe Met Gly Ala Asn Val Met Arg Leu Asp
    1325                1330                1335
Asp Thr Tyr Ser Phe Gln Val Ile Asn Lys Thr Val Lys Met Val
    1340                1345                1350
Ile Pro Ala Leu Ile Gln Ser Asp Ser Gly Asp Ser Ile Glu Val
    1355                1360                1365
Ser Arg Asn Val Glu Glu Ile Val Val Lys Ile Ile Ser Val Phe
    1370                1375                1380
Val Asp Ala Leu Pro His Val Pro Glu His Arg Arg Leu Pro Ile
    1385                1390                1395
Leu Val Gln Leu Val Asp Thr Leu Gly Ala Glu Lys Phe Leu Trp
    1400                1405                1410
Ile Leu Leu Ile Leu Leu Phe Glu Gln Tyr Val Thr Lys Thr Val
    1415                1420                1425
Leu Ala Ala Ala Tyr Gly Glu Lys Asp Ala Ile Leu Glu Ala Asp
    1430                1435                1440
Thr Glu Phe Trp Phe Ser Val Cys Cys Glu Phe Ser Val Gln His
    1445                1450                1455
Gln Ile Gln Ser Leu Met Asn Ile Leu Gln Tyr Leu Leu Lys Leu
    1460                1465                1470
Pro Glu Glu Lys Glu Glu Thr Ile Pro Lys Ala Val Ser Phe Asn
    1475                1480                1485
Lys Ser Glu Ser Gln Glu Glu Met Leu Gln Val Phe Asn Val Glu
    1490                1495                1500
Thr His Thr Ser Lys Gln Leu Arg His Phe Lys Phe Leu Ser Val
    1505                1510                1515
Ser Phe Met Ser Gln Leu Leu Ser Ser Asn Asn Phe Leu Lys Lys
    1520                1525                1530
Val Val Glu Ser Gly Gly Pro Glu Ile Leu Lys Gly Leu Glu Glu
    1535                1540                1545
Arg Leu Leu Asp Lys Met Glu Glu Leu Ile Phe Ser Val Glu Ala
    1550                1555                1560
His Ser Ser Lys Glu Leu Arg His Phe Lys Phe Ile Ser Val Ser
```

-continued

```
            1565               1570                1575

Phe Met Ala Gln Leu Leu Gly Ser Ala Ser Phe Ile Gly Lys Val
        1580                1585                1590

Ser Glu Ile Thr Thr Ser Asn Ser Leu Leu Ser Leu Lys Arg
    1595                1600                1605

Met Leu Leu Glu Thr Val Leu Gly Tyr Ile Ser Ala Val Ala Gln
1610                1615                1620

Ser Met Glu Arg Asn Ala Asp Lys Leu Thr Val Lys Phe Trp Arg
    1625                1630                1635

Ala Leu Leu Ser Lys Ala Tyr Asp Leu Leu Asp Lys Val Asn Ala
    1640                1645                1650

Leu Leu Pro Thr Glu Thr Phe Ile Pro Val Ile Arg Gly Leu Val
    1655                1660                1665

Gly Asn Pro Leu Pro Ser Val Arg Arg Lys Ala Leu Asp Leu Leu
    1670                1675                1680

Asn Asn Lys Leu Gln Gln Asn Ile Ser Trp Lys Lys Thr Ile Val
    1685                1690                1695

Thr Arg Phe Leu Lys Leu Val Pro Asp Leu Leu Ala Ile Val Gln
    1700                1705                1710

Arg Lys Lys Lys Glu Gly Glu Glu Gln Ala Ile Asn Arg Gln
    1715                1720                1725

Thr Ala Leu Tyr Thr Leu Lys Leu Leu Cys Lys Asn Phe Gly Ala
    1730                1735                1740

Glu Asn Pro Asp Pro Phe Val Pro Val Leu Ser Thr Ala Val Lys
    1745                1750                1755

Leu Ile Ala Pro Glu Arg Lys Glu Glu Lys Asn Val Leu Gly Ser
    1760                1765                1770

Ala Leu Leu Cys Ile Ala Glu Val Thr Ser Thr Leu Glu Ala Leu
    1775                1780                1785

Ala Ile Pro Gln Leu Pro Ser Leu Met Pro Ser Leu Leu Thr Thr
    1790                1795                1800

Met Lys Asn Thr Ser Glu Leu Val Ser Ser Glu Val Tyr Leu Leu
    1805                1810                1815

Ser Ala Leu Ala Ala Leu Gln Lys Val Val Glu Thr Leu Pro His
    1820                1825                1830

Phe Ile Ser Pro Tyr Leu Glu Gly Ile Leu Ser Gln Val Ile His
    1835                1840                1845

Leu Glu Lys Ile Thr Ser Glu Met Gly Ser Ala Ser Gln Ala Asn
    1850                1855                1860

Ile Arg Leu Thr Ser Leu Lys Lys Thr Leu Ala Thr Leu Ala
    1865                1870                1875

Pro Arg Val Leu Leu Pro Ala Ile Lys Lys Thr Tyr Lys Gln Ile
    1880                1885                1890

Glu Lys Asn Trp Lys Asn His Met Gly Pro Phe Met Ser Ile Leu
    1895                1900                1905

Gln Glu His Ile Gly Ala Met Lys Lys Glu Glu Leu Thr Ser His
    1910                1915                1920

Gln Ser Gln Leu Thr Ala Phe Phe Leu Glu Ala Leu Asp Phe Arg
    1925                1930                1935

Ala Gln His Ser Glu Asn Asp Leu Glu Glu Val Gly Lys Thr Glu
    1940                1945                1950

Asn Cys Ile Ile Asp Cys Leu Val Ala Met Val Val Lys Leu Ser
    1955                1960                1965
```

```
Glu Val Thr Phe Arg Pro Leu Phe Phe Lys Leu Phe Asp Trp Ala
    1970                1975                1980

Lys Thr Glu Asp Ala Pro Lys Asp Arg Leu Leu Thr Phe Tyr Asn
    1985                1990                1995

Leu Ala Asp Cys Ile Ala Glu Lys Leu Lys Gly Leu Phe Thr Leu
    2000                2005                2010

Phe Ala Gly His Leu Val Lys Pro Phe Ala Asp Thr Leu Asp Gln
    2015                2020                2025

Val Asn Ile Ser Lys Thr Asp Glu Ala Phe Phe Asp Ser Glu Asn
    2030                2035                2040

Asp Pro Glu Lys Cys Cys Leu Leu Leu Gln Phe Ile Leu Asn Cys
    2045                2050                2055

Leu Tyr Lys Ile Phe Leu Phe Asp Thr Gln His Phe Ile Ser Lys
    2060                2065                2070

Glu Arg Ala Gly Ala Leu Met Met Pro Leu Val Asp Gln Leu Glu
    2075                2080                2085

Asn Arg Leu Gly Gly Glu Glu Lys Phe Gln Glu Arg Val Thr Lys
    2090                2095                2100

His Leu Ile Pro Cys Ile Ala Gln Phe Ser Val Ala Met Ala Asp
    2105                2110                2115

Asp Ser Leu Trp Lys Pro Leu Asn Tyr Gln Ile Leu Leu Lys Thr
    2120                2125                2130

Arg Asp Ser Ser Pro Lys Val Arg Phe Ala Ala Leu Ile Thr Val
    2135                2140                2145

Leu Ala Leu Ala Glu Lys Leu Lys Glu Asn Tyr Ile Val Leu Leu
    2150                2155                2160

Pro Glu Ser Ile Pro Phe Leu Ala Glu Leu Met Glu Asp Glu Cys
    2165                2170                2175

Glu Glu Val Glu His Gln Cys Gln Lys Thr Ile Gln Gln Leu Glu
    2180                2185                2190

Thr Val Leu Gly Glu Pro Leu Gln Ser Tyr Phe
    2195                2200

<210> SEQ ID NO 71
<211> LENGTH: 263
<212> TYPE: PRT
<213> ORGANISM: Tetraodon nigroviridis
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (215)..(216)
<223> OTHER INFORMATION: Xaa can be any naturally occurring amino acid

<400> SEQUENCE: 71

Phe Pro Ser Leu Leu Cys Cys Leu Ser Ser Pro Val Gln Glu Val Arg
1               5                   10                  15

Arg Val Ser Leu Gly Ala Leu Gln Ser Leu Ser Arg Ala Arg Ala Ser
                20                  25                  30

Pro Phe Trp Pro Ile Met Glu Lys Leu Leu Arg Thr Thr Asp Glu Leu
            35                  40                  45

Leu Ala Asp Pro Ser Tyr Leu Ser Gln Val Arg Arg Ser Pro Ala
        50                  55                  60

Ser Gly Asp Leu Arg Phe Trp Leu Leu Thr Pro Ser Val Cys Val Cys
65                  70                  75                  80

Cys Leu Gly Tyr Arg Pro Ser Arg Arg Arg Pro Gly Leu Val Leu Ile
```

```
                85                  90                  95
Pro Val Val Val Phe Cys Gln Ser Ile Leu Ser Ala Leu Leu Pro
            100                 105                 110
Leu Leu Glu Arg Leu Leu Glu Gln Ser Ser Pro Asp Thr Pro Asn Gln
        115                 120                 125
Leu Arg Asp Glu Ala Gln Leu Ala Leu Leu Ile Leu Ser Lys Tyr Asn
    130                 135                 140
Glu Ala Ser Ala Pro Leu Leu Ala Lys Asp Glu Asn Cys Leu Asp Leu
145                 150                 155                 160
Phe Ile Arg Ala Leu Arg Asn Ser Thr Gln Gln His Leu Asp Ile Pro
                165                 170                 175
Ser Cys Gln Ile Phe Ala Leu Glu Gln Ile Thr Lys Ser Phe Phe Ser
            180                 185                 190
Ala Ile Glu Ser Glu Thr Val Xaa Gln Lys Leu Leu Ser Val Met Phe
        195                 200                 205
Asp Leu Leu Ala Glu Asn Xaa Xaa Pro Leu Val Ala Ile Thr Ile Gly
    210                 215                 220
Ser Val Phe Lys Arg Ile Thr Val Asp Ala Gln Leu Val Ala Asn Glu
225                 230                 235                 240
Leu Ala Pro Ala Asp Lys Ala Ser Ile Ser Met Thr Val Gln Gln Ser
                245                 250                 255
Arg Arg Ser Arg Met Ile Leu
            260

<210> SEQ ID NO 72
<211> LENGTH: 239
<212> TYPE: PRT
<213> ORGANISM: Tetraodon nigrovifidis

<400> SEQUENCE: 72

Leu Pro Val Leu Val Gln Leu Val Glu Thr Leu Gly Pro Ala Arg Phe
1               5                   10                  15
Leu Trp Val Leu Met Leu Leu Leu Phe Lys Leu His Ala Thr His Thr
            20                  25                  30
Ala Asn Thr Ala Ser Glu Lys Asp Ala Ala Val Glu Lys Asp Val Asp
        35                  40                  45
Phe Trp Ile Ser Leu Cys Ser Gln Phe Lys Val Gly Glu Gln Leu Ala
    50                  55                  60
Ser Leu Asn His Ile Leu Gly Phe Leu Leu Gln Leu Pro Glu Asp Lys
65                  70                  75                  80
Asp Glu Ala Ala Ser Lys His Ala Thr Gly Arg Arg Thr Thr Gln Lys
                85                  90                  95
Lys Glu Lys Glu Glu Gln Gly Asp Lys Met Glu Glu Leu Ile Phe Ser
            100                 105                 110
Val Glu Ala His Ser Ser Lys Glu Leu Arg His Phe Lys Phe Ile Ser
        115                 120                 125
Val Ser Phe Met Ala Gln Leu Leu Gly Ser Ala Ser Phe Ile Gly Lys
    130                 135                 140
Val Ser Glu Ile Thr Thr Ser Asn Ser Leu Leu Leu Ser Leu Lys Arg
145                 150                 155                 160
Met Leu Leu Glu Asp Leu Leu Arg Tyr Ile His Ser Ile Ala Arg Ser
                165                 170                 175
Val Glu Glu Asn Ala Met Lys Pro Thr Ala Lys Phe Trp Arg Val Leu
            180                 185                 190
Leu Asn Lys Ala Tyr Asp Val Leu Asp Lys Val Asn Ser Leu Leu Pro
```

```
                            195                 200                 205
Thr Asp Thr Phe Ile Val Val Met Lys Gly Leu Met Gly Asn Asp Leu
        210                 215                 220

Pro Ser Val Arg Arg Lys Ala Met Glu Leu Leu Asn Asn Lys Leu
225                 230                 235

<210> SEQ ID NO 73
<211> LENGTH: 140
<212> TYPE: PRT
<213> ORGANISM: Tetraodon nigrovifidis
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (93)..(95)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid

<400> SEQUENCE: 73

Glu Val Leu Phe Glu Ser Ser His Ala Asp Gln Lys Val Ala Leu Xaa
1               5                   10                  15

Leu Gln Tyr Val Leu Xaa Cys Leu His Lys Ile Phe Leu Tyr Asp Thr
            20                  25                  30

Gln Arg Phe Leu Ser Lys Glu Arg Ala Asp Thr Leu Met Asn Pro Leu
        35                  40                  45

Leu Asp Gln Leu Glu Asn Thr Ala Gly Gly Pro Gln Thr Tyr Gln Gln
    50                  55                  60

Arg Val Thr Gln His Leu Val Pro Cys Leu Gly Gln Phe Ala Val Ala
65                  70                  75                  80

Leu Ala Asp Asp Thr Gln Trp Lys Thr Leu Asn Tyr Xaa Xaa Xaa Leu
                85                  90                  95

Lys Ser Arg His Ser Asp Ala Lys Val Arg Phe Ser Ser Leu Leu Met
            100                 105                 110

Leu Met Xaa Leu Thr Ser Lys Leu Lys Glu Asn Tyr Met Val Leu Leu
            115                 120                 125

Pro Glu Thr Ile Pro Phe Leu Ala Glu Leu Met Glu
130                 135                 140
```

METHODS OF DETECTING PROSTATE CANCER USING BAP28-RELATED BIALLELIC MARKERS

RELATED APPLICATIONS

This application is a continuation of U.S. patent application Ser. No. 09/603,665, filed Jun. 23, 2000, now abandoned, which claims the benefit of U.S. Provisional Patent Application Ser. No. 60/141,323, filed Jun. 25, 1999 and U.S. Provisional Patent Application Ser. No. 60/176,880, filed Jan. 18, 2000, the disclosures of which are incorporated herein by reference in their entireties.

FIELD OF THE INVENTION

The present invention is directed to polynucleotides encoding a human BAP28 polypeptide as well as a regulatory regions located at the 5'- and 3'-ends of said coding region. The invention also concerns polypeptides encoded by the BAP28 gene. The invention also deals with antibodies directed specifically against such polypeptides that are useful as diagnostic reagents. The invention further encompasses biallelic markers of the BAP28 gene useful in genetic analysis, and more particularly associated with prostate cancer and useful in diagnosis.

BACKGROUND OF THE INVENTION

Prostate Cancer

The incidence of prostate cancer has dramatically increased over the last decades. It averages 30-50/100,000 males in Western European countries as well as within the US White male population. In these countries, it has recently become the most commonly diagnosed malignancy, being one of every four cancers diagnosed in American males. Prostate cancer's incidence is very much population specific, since it varies from 2/100,000 in China, to over 80/100,000 among African-American males.

In France, the incidence of prostate cancer is 35/100,000 males and it is increasing by 10/100,000 per decade. Mortality due to prostate cancer is also growing accordingly. It is the second cause of cancer death among French males, and the first one among French males aged over 70. This makes prostate cancer a serious burden in terms of public health.

Prostate cancel is a latent disease. Many men carry prostate cancer cells without overt signs of disease. Autopsies of individuals dying of other causes show prostate cancer cells in 30% of men at age 50 and in 60% of men at age 80. Furthermore, prostate cancer can take up to 10 years to kill a patient after the initial diagnosis.

The progression of the disease usually goes from a well-defined mass within the prostate to a breakdown and invasion of the lateral margins of the prostate, followed by metastasis to regional lymph nodes, and metastasis to the bone marrow. Cancer metastasis to bone is common and often associated with uncontrollable pain.

Unfortunately, in 80% of cases, diagnosis of prostate cancer is established when the disease has already metastasized to the bones. Of special interest is the observation that prostate cancers frequently grow more rapidly in sites of metastasis than within the prostate itself.

Early-stage diagnosis of prostate cancer mainly relies today on Prostate Specific Antigen (PSA) dosage, and allows the detection of prostate cancer seven years before clinical symptoms become apparent. The effectiveness of PSA dosage diagnosis is however limited, due to its inability to discriminate between malignant and non-malignant affections of the organ and because not all prostate cancers give rise to an elevated serum PSA concentration. Furthermore, PSA dosage and other currently available approaches such as physical examination, tissue biopsy and bone scans are of limited value in predicting disease progression.

Therefore, there is a strong need for a reliable diagnostic procedure which would enable a more systematic early-stage prostate cancer prognosis.

Although an early-stage prostate cancer prognosis is important, the possibility of measuring the period of time during which treatment can be deferred is also interesting as currently available medicaments are expensive and generate important adverse effects. However, the aggressiveness of prostate tumors varies widely. Some tumors are relatively aggressive, doubling every six months whereas others are slow-growing, doubling once every five years. In fact, the majority of prostate cancers grows relatively slowly and never becomes clinically manifest. Very often, affected patients are among the elderly and die from another disease before prostate cancer actually develops. Thus, a significant question in treating prostate carcinoma is how to discriminate between tumors that will progress and those that will not progress during the expected lifetime of the patient.

Hence, there is also a strong need for detection means which may be used to evaluate the aggressiveness or the development potential of prostate cancer tumors once diagnosed.

Furthermore, at the present time, there is no means to predict prostate cancer susceptibility. It would also be very beneficial to detect individual susceptibility to prostate cancer. This could allow preventive treatment and a careful follow up of the development of the tumor.

A further consequence of the slow growth rate of prostate cancer is that few cancer cells are actively dividing at any one time, rendering prostate cancer generally resistant to radiation and chemotherapy. Surgery is the mainstay of treatment but it is largely ineffective and removes the ejaculatory ducts, resulting in impotence. Oral oestrogens and luteinizing releasing hormone analogs are also used for treatment of prostate cancer. These hormonal treatments provide marked improvement for many patients, but they only provide temporary relief. Indeed, most of these cancers soon relapse with the development of hormone-resistant tumor cells and the oestrogen treatment can lead to serious cardiovascular complications. Consequently, there is a strong need for preventive and curative treatment of prostate cancer.

Efficacy/tolerance prognosis could be precious in prostate cancer therapy. Indeed, hormonal therapy, the main treatment currently available, presents important side effects. The use of chemotherapy is limited because of the small number of patients with chemosenisitive tumors. Furthermore the age profile of the prostate cancer patient and intolerance to chemotherapy make the systematic use of this treatment very difficult.

Therefore, a valuable assessment of the eventual efficacy of a medicament to be administered to a prostate cancer patent as well as the patent's eventual tolerance to it may permit to enhance the benefit/risk ratio of prostate cancer treatment.

BAP28

Bowcock et al. (1998) conducted studies to identify proteins interacting with first 304 amino terminal amino acid residues of breast cancer related gene, BRCA1. Bowcock et al. thereby identified a BAP28 cDNA encoding a 515 amino acid protein associating with BRCA1 in a yeast two-hybrid screen, but whose association with BRCA1 could not be confirmed in a two-hybrid screen in mammalian cells.

SUMMARY OF THE INVENTION

The present invention pertains to nucleic acid molecules comprising the genomic sequence of a novel human BAP28 gene and BAP28 protein. The BAP28 genomic sequence comprises regulatory sequences located upstream and downstream of the transcribed portion of said gene, these regulatory sequences being also part of the invention.

The invention also deals with complete cDNA sequences encoding the BAP28 protein, as well as with the corresponding translation product.

Oligonucleotide probes or primers hybridizing specifically with a BAP28 genomic or cDNA sequence are also part of the present invention, as well as DNA amplification and detection methods using said primers and probes.

A further object of the invention consists of recombinant vectors comprising any of the nucleic acid sequences described herein, and in particular of recombinant vectors comprising a BAP28 regulatory sequence or a sequence encoding a BAP28 protein, as well as of cell hosts and transgenic non human animals comprising said nucleic acid sequences or recombinant vectors.

The invention is also directed to BAP28 polymorphisms and BAP28-related biallelic markers as well as use of the of BAP28-related biallelic markers in establishing genetic associations with disease. BAP28-related biallelic markers can be used for diagnosis, staging, prognosis and monitoring of disease, and the efficient design and evaluation of suitable therapeutic solutions including individualized strategies for optimizing drug usage, and screening of potential new medicament candidates. More particularly, the invention concerns an association between BAP28-related biallelic markers and prostate cancer.

Finally, the invention is directed to methods for the screening of substances or molecules that inhibit the expression of BAP28, as well as with methods for the screening of substances or molecules that interact with a BAP28 polypeptide or that modulate the activity of a BAP28 polypeptide.

BRIEF DESCRIPTION OF THE DRAWINGS

FIG. 2 is a diagram showing some alternative cDNA forms of the PCTA-1 gene.

FIG. 3 is an alignment of the human BAP28 protein H (SEQ ID NO: 64) with its homologues from *Drosophila melanogaster* (ORF from AE003615) D(SEQ ID NO: 65), *Arabidopsis thaliana* (AAF63640) A (SEQ ID NO: 66), *Schizosaccahromyces pombe* (060179) S (SEQ ID NO: 67, *Caenorhabditis elegans* (Q23495) C (SEQ ID NO: 69), and *Saccharomyces cerevisiae* (YJK9_YEAST) Y (SEQ ID NO: 68). In C terminal part of the protein alignment, a box indicates the position of a conserved HEAT—REPEAT which is described to be involved in protein-protein interaction. For *Drosophila melanogaster*, the sequence AE003615 describes a gene CG10805 with 6 exons. A new analysis showed that the exons 2, 3, 4, 5, and 6 present an holomoly with BAP28. Therefore, a new cDNA has been generated consisting with 21 bp upstream to exon 2, exon 2, intron 2, exons 3, 4, 5, and 6. This cDNA encodes a protein of 2096 amino acids which is described as D in the FIG. 3.

FIG. 4 is an alignment of the human BAP28 protein (SEQ ID NO: 70) and 3 protein segments from *Tetraodon nigroviridis*, likely part of the same protein. The following sequences from Genbank-have been contigated in order to generate 3 segments of the genomic sequence of Tetraodon (CNS01RV3+CNS03LT9-->tetraodon3, SEQ ID NO: 73; CNS02AXF+CNS03INT-->tetraodon1, SEQ ID NO: 71: CNS02AXG+CNS01RV4+CNS03LTA +CNS03INS-->tetraodon2, SEQ ID NO: 72). The 3 protein fragments which are similar to BAP28 have been found in these contigated regions. Furthermore, the exons encoding the 3 protein segments have the same size and the same structure in human BAP28 and in *Tetraodon*. The amino acid sequences encoding by these exons have been aligned with the human BAP28 protein.

FIG. 7 is a table demonstrating the results of a haplotype association analysis between prostate cancer cases and haplotypes comprising BAP28-related biallelic markers. FIG. 7A a presents the results for the two-marker haplotypes. FIG. 7B presents the results for the three-marker haplotypes.

FIG. 8 is a table demonstrating the results of a haplotype association analysis between familial prostate cancer cases and haplotypes comprising BAP28-related biallelic markers. FIG. 8A a presents the results for the two-marker haplotypes. FIG. 8B presents the results for the three-marker haplotypes.

FIG. 9 is a table demonstrating the results of a haplotype association analysis between early onset familial prostate cancer cases (less than 65 years old) and haplotypes comprising BAP28-related biallelic markers. FIG. 9A a presents the results for the two-marker haplotypes. FIG. 9B presents the results for the three-marker haplotypes.

FIG. 10 is a table demonstrating the results of a haplotype association analysis between sporadic prostate cancer cases and haplotypes comprising BAP28-related biallelic markers. FIG. 10A a presents the results for the two-marker haplotypes. FIG. 10B presents the results for the three-marker haplotypes.

FIG. 11 is a table demonstrating the results of a haplotype association analysis between informative sporadic prostate cancer cases and haplotypes comprising BAP28-related biallelic markers. FIG. 11A a presents the results for the two-marker haplotypes. FIG. 11B presents the results for the three-marker haplotypes.

FIGS. 12A ,12B and 12C are tables summarizing the results of haplotype frequency analyses between prostate cancer and three preferred haplotypes.

FIG. 13 A: Wells 1 and 13: Molecular weight markers X-300 ng; Well 2: Mix PCR water=negative control; Well 3: Marathon Ready cDNA Human Testis: positive Tissue (CLONTECH Lot N°9110553); Well 4: Marathon Ready cDNA Human Brain: negative Tissue; Well 5: Marathon Ready cDNA Human Cerebellum: negative Tissue; Well 6: Marathon Ready cDNA Human Cerebral Cortex: negative Tissue; Well 7: Marathon Ready cDNA Human Hippocampus: positive Tissue (CLONTECH Lot N°9040528); Well 8: Marathon Ready cDNA Human Hypothalamus: negative Tissue: Well 9: Marathon Ready cDNA Human Fetal Kidney: negative Tissue; Well 10: Marathon Ready cDNA Human Thyroid: negative Tissue; Well 11: Marathon Ready cDNA Human Bone Marrow: negative Tissue; Well 11: Marathon Ready cDNA Human Leukemia, promyelocytic HL60: negative Tissue. FIG. 13 B: Wells 1 and 7: Molecular weight markers X–300 ng Well 2: Marathon Ready cDNA Human Leukemia, lymphoblastic MOLT4: negative Tissue; Well 3: Marathon Ready cDNA Human Leukemia, chronic myelogenous K-562: positive Tissue (CLONTECH Lot N°9120565); Well 4: Marathon Ready cDNA Human Fetal Liver: negative Tissue; Well 5: Marathon Ready cDNA Human Stomach: negative Tissue; Well 6: Marathon Ready cDNA Human Prostate: negative Tissue. FIG. 13 D: Wells 1 and 13: Molecular weight markers X–300 ng; Well 2: cDNA Human Kidney: negative Tissue; Well 3 cDNA Human Placenta: negative Tissue; Well 4: cDNA Human Spleen: negative Tissue; Well 5 cDNA Human Fetal Liver: negative Tissue; Well 6: cDNA Human Thyroïd Gland: negative Tissue; Well 7: cDNA Human Leukemia, lymphoblastic: negative Tissue; Well 8: cDNA Human Spinal Cord: positive Tissue (RNA PolyA+ CLONTECH–Lot N°9040709–Réf Cat:6593-1); Well 9: cDNA Human Pituitary Gland: positive Tissue (RNA PolyA+ CLONTECH–Lot N°6080167–Réf Cat:6584-1); Well 10: cDNA Human Adrenal Gland: negative Tissue; Well 11: cDNA Human Trachea: negative Tissue; Well 12: cDNA Human Leukemia, chronic myelogenous: negative Tissue. FIG. 13 E: Wells 1 and 13: Molecular weight markers X–300 ng; Well 2: cDNA Human Salivary Gland: negative Tissue; Well 3: cDNA Human Leukemia, promyelocytic: negative Tissue; Well 4: cDNA Human Small Intestine: negative Tissue; Well 5: cDNA Human Pancreas: negative Tissue; Well 6: cDNA Human Stomach: negative Tissue; Well 7: cDNA Human Mammary Gland: positive Tissue (RNA PolyA+ CLONTECH–Lot N°9031125–Réf Cat:6545-1); Well 8: cDNA Human Bone Marrow: negative Tissue; Well 9: cDNA Human Thymus: negative Tissue; Well 10: cDNA Human Uterus: negative Tissue Well 11: cDNA Human Prostate: negative Tissue; Well 12: cDNA Human Prostate: negative Tissue.

BRIEF DESCRIPTION OF THE SEQUENCES PROVIDED IN THE SEQUENCE LISTING

Figure 1:
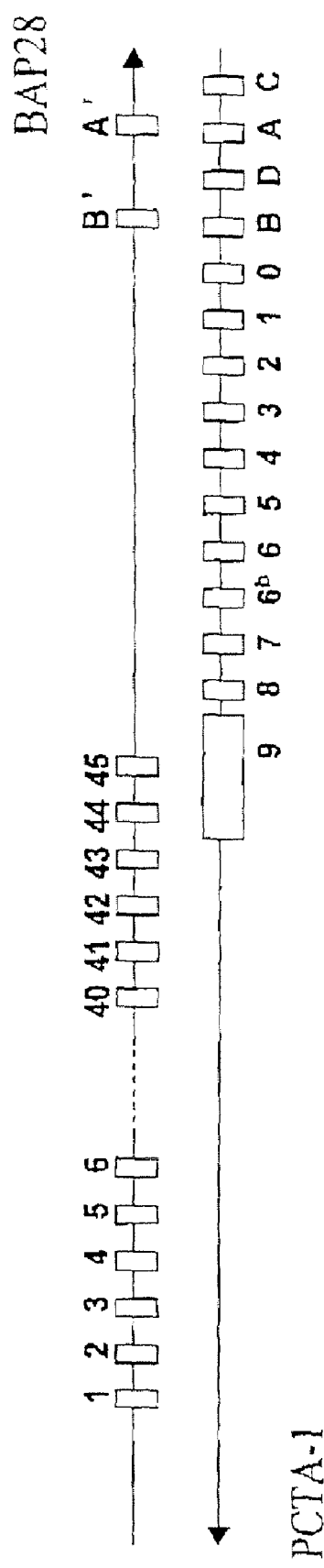
FIG. 1 is a diagram showing the genomic structure of the genes BAP28 and PCTA-1. The arrow represent the DNA with the 5' to 3' direction. The boxes represent the exons.

SEQ ID No 1 contains the genomic sequence of the BAP28 gene comprising the exons and introns, and the 5' and 3' regulatory regions (respectively the upstream and downstream untranscribed regions). Furthermore, SEQ ID No 1 also contains the genomic sequence of the PCTA-1 gene. The coding strand of PCTA-1 gene is on the opposite of the coding strand of BAP28.

SEQ ID No 2 contains a first cDNA sequence of the BAP28 gene consisting of the exons 1 to 45. SEQ ID No 3 contains a second cDNA sequence of the BAP28 gene consisting of the exons 1 to 44, 45b and A'. SEQ ID No 4 contains a sequence of the BAP28 cDNA segment consisting of the exons B'and A'. SEQ ID No 5 contains the BAP28 amino acid sequence encoded by the cDNAs of SEQ ID Nos 2, and 3.

SEQ ID No 6 contains a first cDNA sequence of the PCTA-1 gene consisting of the exons 0 to 9. SEQ ID No 7 contains a second cDNA sequence of the PCTA-1 gene consisting of the exons 0, 1, 2, 3, 4, 5, 6, 6bis, 7, 8, and 9. SEQ ID No 8 contains a third cDNA sequence of the PCTA-1 gene consisting of the exons 0 to 8, 9bis and 9ter. SEQ ID No 9 contains the sequence of a cDNA fragment of the PCTA-1 gene comprising exons C and A. SEQ ID No 10 contains the sequence of a cDNA fragment of the PCTA-1 gene comprising exons B, 0, 1 and 2. SEQ ID No 11 contains the sequence of a cDNA fragment of the PCTA-1 gene comprising exons A, 1 and 2. SEQ ID No 12 contains the sequence of a cDNA fragment of the PCTA-1 gene comprising exons A, D, 0, 1, and 2. SEQ ID No 13 contains a fourth cDNA sequence of the PCTA-1 gene comprising exons A, 0, 1, 2, 3, 9bis and 9ter. SEQ ID No 14 contains the PCTA-1amino acid sequence encoded by the cDNAs of SEQ ID No 6. SEQ ID No 15 contains the PCTA-1 amino acid sequence encoded by the cDNAs of SEQ ID No 7. SEQ ID No 16 contains the PCTA-1 amino acid sequence encoded by the cDNAs of SEQ ID No 8. SEQ ID No 17 contains the PCTA-1 amino acid sequence encoded by the cDNAs of SEQ ID No 13.

SEQ ID Nos 18-31 contain the genomic amplicons respectively designated as 99-7177, 99-7212, 99-7193, 99-7186, 99-7182, 99-1585, 99-1587, 99-13798, 99-1601, 99-13808, 99-13810, 99-13790, 99-13809, and 99-1597.

SEQ ID Nos 31-61 contain the sequence of the following primers: BAP283Ra6283, BAP283Ra6324n, BAP28-exALF7311, BAP28-exALF7311n, PCTAexALF12, PCTAexALF13n, PCTAexALR60, PCTAexALR12n, PCTAexBLF33, PCTAexBLF120n, PCTAexBLR140, PCTAexBLR40n, PCTA5Ra220n, PCTA5Ra230, PCTA__5Ra400, PCTA__5Ran__400, PCTA__5Ra__394, PCTA_exD5Ra, PCTA_exD5Ran, PCTA_exC5Ra, PCTA_exC5Ran, PCTAex9terLR330, PCTAex9terLR325n, PCTAexCLF120, PCTAexCLF130n, BAP28polyTcourt, BAP281LF12.1. BAP28LR6726.1, BAP28LF26SalI and BAP281R6717SalI, respectively.

SEQ ID No 62 contains a primer containing the additional PU 5' sequence described further in Example 2. SEQ ID No 63 contains a primer containing the additional RP 5' sequence described further in Example 2.

In accordance with the regulations relating to Sequence listings, the following codes have been used in the Sequence Listing to indicate the locations of biallelic markers within the sequences and to identify each of the alleles present at the polymorphic base. The code "r" in the sequences indicates that one allele of the polymorphic base is a guanine, while the other allele is an adenine. The code "y" in the sequences indicates that one allele of the polymorphic base is a thymine, while the other allele is a cytosine. The code "m" in the sequences indicates that one allele of the polymorphic base is an adenine, while the other allele is an cytosine. The code "k" in the sequences indicates that one allele of the polymorphic base is a guanine, while the other allele is a thymine. The code "s" in the sequences indicates that one allele of the polymorphic base is a guanine, while the other allele is a cytosine. The code "w" in the sequences indicates that one allele of the polymorphic base is an adenine, while the other allele is an thymine. The nucleotide code of the original allele for each biallelic marker is the following:

| Biallelic marker | Original allele |
|---|---|
| A1 | G |
| A2 | C |
| A3 | T |
| A4 | C |
| A5 | C |
| A6 | T |
| A7 | T |
| A8 | G |
| A9 | T |
| A10 | G |
| A11 | G |
| A12 | A |
| A13 | T |
| A14 | T |
| A15 | A |
| A16 | G |
| A17 | T |
| A18 | T |
| A19 | C |
| A20 | G |
| A21 | G |
| A22 | T |
| A23 | G |
| A24 | G |
| A25 | G |
| A26 | C |
| A27 | A |
| A28 | A |
| A29 | C |
| A30 | A |
| A31 | C |
| A32 | G |
| A33 | G |
| A34 | A |
| A35 | G |
| A36 | G |
| A37 | T |
| A38 | A |
| A39 | C |
| A40 | C |

In some instances, the polymorphic bases of the biallelic markers alter the identity of an amino acids in the encoded polypeptide. This is indicated in the accompanying Sequence listing by use of the feature VARIANT, placement of an Xaa at the position of the polymorphic amino acid, and definition of Xaa as the two alternative amino acids. For example if one allele of a biallelic marker is the codon CAC, which encodes histidine, while the other allele of the biallelic marker is CAA, which encodes glutamine, the Sequence Listing for the encoded polypeptide will contain an Xaa at the location of the polymorphic amino acid. In this instance, Xaa would be defined as being histidine or glutamine.

In other instances, Xaa may indicate an amino acid whose identity is unknown because of nucleotide sequence ambiguity. In this instance, the feature UNSURE is used, placement of an Xaa at the position of the unknown amino acid and definition of Xaa as being any of the 20 amino acids or a limited number of amino acids suggested by the genetic code.

DETAILED DESCRIPTION OF THE INVENTION

The present invention concerns polynucleotides and polypeptides related to the BAP28 gene. Oligonucleotide probes and primers hybridizing specifically with a genomic or the cDNA sequences of BAP28 are also part of the invention. A further object of the invention consists of recombinant vectors comprising any of the nucleic acid sequences described in the present invention, and in particular recombinant vectors comprising a regulatory region of BAP28 or a sequence encoding the BAP28 protein, as well as cell hosts comprising said nucleic acid sequences or recombinant vectors.

The invention also encompasses methods of screening of molecules which inhibit the expression of the BAP28 gene or which modulate the activity of, or interact with, the BAP28 protein. The invention also deals with antibodies directed specifically against such polypeptides that are useful as diagnostic reagents.

The invention also concerns BAP28-related biallelic markers which can be used in any method of genetic analysis including linkage studies in families, linkage disequilibrium studies in populations and association studies of case-control populations. An important aspect of the present invention is that some BAP28-related biallelic markers present an association with the prostate cancer.

DEFINITIONS

Before describing the invention in greater detail, the following definitions are set forth to illustrate and define the meaning and scope of the terms used to describe the invention herein.

The terms "BAP28 gene", when used herein, encompasses genomic, mRNA and cDNA sequences encoding the BAP28 protein, including the untranslated regulatory regions of the genomic DNA.

The term "heterologous protein", when used herein, is intended to designate any protein or polypeptide other than the BAP28 protein. More particularly, the heterologous protein is a compound which can be used as a marker in further experiments with a BAP28 regulatory region.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

As used herein, the term "purified" does not require absolute purity; rather, it is intended as a relative definition. Purification of starting material or natural material is at least one order of magnitude, preferably two or three orders, and more preferably four or five orders of magnitude is expressly contemplated. As an example, purification from 0.1% concentration to 10% concentration is two orders of magnitude.

To illustrate, individual cDNA clones isolated from a cDNA library have been conventionally purified to electrophoretic homogeneity. The sequences obtained from these clones could not be obtained directly either from the library or from total human DNA. The cDNA clones are not naturally occurring as such, but rather are obtained via manipulation of a partially purified naturally occurring substance (messenger RNA). The conversion of mRNA into a cDNA library involves the creation of a synthetic substance (cDNA) and pure individual cDNA clones can be isolated from the synthetic library by clonal selection. Thus, creating a cDNA library from messenger RNA and subsequently isolating individual clones from that library results in an approximately $10^4$-$10^6$ fold purification of the native message.

The term "purified" is further used herein to describe a polypeptide or polynucleotide of the invention which has been separated from other compounds including, but not limited to, polypeptides or polynucleotides, carbohydrates, lipids, etc. The term "purified" may be used to specify the separation of monomeric polypeptides of the invention from oligomeric forms such as homo- or hetero- dimers, trimers, etc. The term "purified" may also be used to specify the separation of covalently closed polynucleotides from linear polynucleotides. A polynucleotide is substantially pure when at least about 50%, preferably 60 to 75% of a sample exhibits a single polynucleotide sequence and conformation (linear versus covalently close). A substantially pure polypeptide or polynucleotide typically comprises about 50%, preferably 60 to 90% weight/weight of a polypeptide or polynucleotide sample, respectively, more usually about 95%, and preferably is over about 99% pure. Polypeptide and polynucleotide purity, or homogeneity, is indicated by a number of means well known in the art, such as agarose or polyacrylamide gel electrophoresis of a sample, followed by visualizing a single band upon staining the gel. For certain purposes higher resolution can be provided by using HPLC or other means well known in the art. As an alternative embodiment, purification of the polypeptides and polynucleotides of the present invention may be expressed as "at least" a percent purity relative to heterologous polypeptides and polynucleotides (DNA, RNA or both). As a preferred embodiment, the polypeptides and polynucleotides of the present invention are at least; 10%, 20%, 30%, 40%, 50%, 60%, 70%, 80%, 90%, 95%, 96%, 96%, 98%, 99%, or 100% pure relative to heterologous polypeptides and polynucleotides, respectively. As a further preferred embodiment the polypeptides and polynucleotides have a purity ranging from any number, to the thousandth position, between 90% and 100% (e.g., a polypeptide or polynucleotide at least 99.995% pure) relative to either heterologous polypeptides or polynucleotides, respectively, or as a weight/weight ratio relative to all compounds and molecules other than those existing in the carrier. Each number representing a percent purity, to the thousandth position, may be claimed as individual species of purity.

The term "polypeptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "recombinant poly peptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

As used herein, the term "non-human animal" refers to any non-human vertebrate, birds and more usually mammals, preferably primates, farm animals such as swine, goats, sheep, donkeys, and horses, rabbits or rodents, more preferably rats or mice. As used herein, the term "animal" is used to refer to any vertebrate, preferable a mammal. Both the terms "animal" and "mammal" expressly embrace human subjects unless preceded with the term "non-human".

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', $F(ab)_2$, and $F(ab')_2$ fragments.

As used herein, an "antigenic determinant" is the portion of an antigen molecule, in this case a BAP28 polypeptide, that determines the specificity of the antigen-antibody reaction. An "epitope" refers to an antigenic determinant of a polypeptide. An epitope can comprise as few as 3 amino acids in a spatial conformation which is unique to the epitope. Generally an epitope consists of at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by Geysen et al. 1984; PCT Publication No WO 84/03564; and PCT Publication No WO 84/03506.

Throughout the present specification, the expression "nucleotide sequence" may be employed to designate indifferently a polynucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule.

As used interchangeably herein, the terms "nucleic acids", "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No WO 95/04064. The polynucleotide sequences of the invention may be prepared by any known method, including synthetic, recombinant, ex vivo generation, or a combination thereof, as well as utilizing any purification methods known in the art.

A sequence which is "operably linked" to a regulatory sequence such as a promoter means that said regulatory element is in the correct location and orientation in relation to the nucleic acid to control RNA polymerase initiation and expression of the nucleic acid of interest.

As used herein, the term "operably linked" refers to a linkage of polynucleotide elements in a functional relationship. For instance, a promoter or enhancer is operably linked to a coding sequence if it affects the transcription of the coding sequence.

The terms "trait" and "phenotype" are used interchangeably herein and refer to any visible, detectable or otherwise measurable property of an organism such as symptoms of, or susceptibility to a disease for example. Typically the terms "trait" or "phenotype" are used herein to refer to symptoms of, or susceptibility to a disease, a beneficial response to or side effects related to a treatment. Preferably, said trait can be, without to be limited to, cancers, developmental diseases, and neurological diseases. More preferably, the term "trait" or "phenotype", when used herein, encompasses, but is not limited to prostate cancer, an early onset of prostate cancer, a beneficial response to or side effects related to treatment or a vaccination against prostate cancer, a susceptibility to prostate cancer, the level of aggressiveness of prostate cancer tumors.

The term "allele" is used herein to refer to variants of a nucleotide sequence. A biallelic polymorphism has two forms. Typically the first identified allele is designated as the original allele whereas other alleles are designated as alternative alleles. The two alleles of a biallelic marker can also be referred to as allele 1 and allele 2. Diploid organisms may be homozygous or heterozygous for an allelic form.

The term "heterozygosity rate" is used herein to refer to the incidence of individuals in a population which are heterozygous at a particular allele. In a biallelic system the heterozygosity rate is on average equal to $2P_a(1-P_a)$, where $P_a$ is the frequency of the least common allele. In order to be useful in genetic studies, a genetic marker should have an adequate level of heterozygosity to allow a reasonable probability that a randomly selected person will be heterozygous.

The term "genotype" as used herein refers the identity of the alleles present in an individual or a sample. In the context of the present invention, a genotype preferably refers to the description of the biallelic marker alleles present in an individual or a sample. The term "genotyping" a sample or an individual for a biallelic marker consists of determining the specific allele or the specific nucleotide carried by an individual at a biallelic marker.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is the replacement of one nucleotide by another nucleotide at the polymorphic site. Deletion of a single nucleotide or insertion of a single nucleotide also gives rise to single nucleotide polymorphisms. In the context of the present invention, "single nucleotide polymorphism" preferably refers to a single nucleotide substitution.

The term "biallelic polymorphism" and "biallelic marker" are used interchangeably herein to refer to a single nucleotide polymorphism having two alleles at a fairly high frequency in the population. A "biallelic marker allele" refers to the nucleotide variants present at a biallelic marker site. Typically, the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker wherein the frequency of the less common allele is 30% or more is termed a "high quality biallelic marker".

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center", and so on.

As used herein the term "BAP28-related biallelic marker" relates to a set of biallelic markers in linkage disequilibrium with the BAP28 gene or a BAP28 nucleotide sequence. The term "BAP28-related biallelic marker" relates to the biallelic markers located in a sequence selected from the group consisting of SEQ ID Nos 1-4, and 18-31, a fragment thereof and/or the complementary sequence thereto. The term BAP28-related biallelic marker encompasses the biallelic markers A1 to A58 disclosed in Table 2 and any biallelic markers in linkage disequilibrium therewith.

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind.

Variants and Fragments

1-Polynucleotides

The invention also relates to variants and fragments of the polynucleotides described herein, particularly of a BAP28 gene containing one or more biallelic markers according to the invention.

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Variants of polynucleotides according to the invention include, without being limited to, nucleotide sequences which are at least 95% identical to a polynucleotide selected from the group consisting of the nucleotide sequences of SEQ ID Nos 1-4, and 9-13 or to any polynucleotide fragment of at least 12, 15, 18, 20, 25, 30, 50, 80, 100, 150, 200, 250, 300, 350, 400, 450, 500, 600 or 1000 consecutive nucleotides of a polynucleotide selected from the group consisting of the nucleotide sequences of SEQ ID Nos 1-4 and 9-13, and preferably at least 99% identical, more particularly at least 99.5% identical, and most preferably at least 99.8% identical to a polynucleotide selected from the group consisting of the nucleotide sequences of SEQ ID Nos 1-4 and 9-13, or to any polynucleotide fragment of at least 12, 15, 18, 20, 25, 30, 50, 80, 100, 150, 200, 250, 300, 350, 400, 450, 500, 600 or 1000 consecutive nucleotides of a polynucleotide selected from the group consisting of the nucleotide sequences of SEQ ID No 1-4 and 9-13.

Nucleotide changes present in a variant polynucleotide may be silent, which means that they do not alter the amino acids encoded by the polynucleotide. However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

In the context of the present invention, particularly preferred embodiments are those in which the polynucleotides encode polypeptides which retain substantially the same biological function or activity as the mature BAP28 protein, or those in which the polynucleotides encode polypeptides which maintain or increase a particular biological activity, while reducing a second biological activity A polynucleotide fragment is a polynucleotide having a sequence that is entirely the same as part but not all of a given nucleotide sequence, preferably the nucleotide sequence of a BAP28 gene, and variants thereof. The fragment can be a portion of an intron or an exon of a BAP28 gene. It can also be a portion of the regulatory regions of BAP28. In some embodiments, the fragments may comprise at least one polymorphism or biallelic marker of the invention.

Such fragments may be "free-standing", i.e. not part of or fused to other polynucleotides, or they may be comprised within a single larger polynucleotide of which they form a part or region. Indeed, several of these fragments may be present within a single larger polynucleotide.

In some embodiments, such fragments may comprise, consist of, or consist essentially of a contiguous span of at least 8, 10, 12, 15, 18, 20, 25, 35, 40, 50, 70, 80, 100, 250, 500 or 1000 nucleotides in length.

2-Polypeptides

The invention also relates to variants, fragments, analogs and derivatives of the polypeptides described herein, including mutated BAP28 proteins.

The variant may be 1) one in which one or more of the amino acid residues are substituted with a conserved or non-conserved amino acid residue and such substituted amino acid residue may or may not be one encoded by the genetic code, or 2) one in which one or more of the amino acid residues includes a substituent group, or 3) one in which the mutated BAP28 is fused with another compound, such as a compound to increase the half-life of the polypeptide (for example, polyethylene glycol), or 4) one in which the additional amino acids are fused to the mutated BAP28, such as a leader or secretory sequence or a sequence which is employed for purification of the mutated BAP28 or a preprotein sequence. Such variants are deemed to be within the scope of those skilled in the art.

A polypeptide fragment is a polypeptide having a sequence that entirely is the same as part but not all of a given polypeptide sequence, preferably a polypeptide encoded by a BAP28 gene and variants thereof.

In the case of an amino acid substitution in the amino acid sequence of a polypeptide according to the invention, one or several amino acids can be replaced by "equivalent" amino acids. The expression "equivalent" amino acid is used herein to designate any amino acid that may be substituted for one of the amino acids having similar properties, such that one skilled in the art of peptide chemistry would expect the secondary structure and hydropathic nature of the polypeptide to be substantially unchanged. Generally, the following groups of amino acids represent equivalent changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; (5) Phe, Tyr, Trp, His.

A specific embodiment of a modified BAP28 peptide molecule of interest according to the present invention, includes, but is not limited to, a peptide molecule which is resistant to proteolysis, is a peptide in which the —CONH— peptide bond is modified and replaced by a (CH2NH) reduced bond, a (NHCO) retro inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH=CH— bond. The invention also encompasses a human BAP28 polypeptide or a fragment or a variant thereof in which at least one peptide bond has been modified as described above.

Such fragments may be "free-standing", i.e. not part of or fused to other polypeptides, or they may be comprised within a single larger polypeptide of which they form a part or region. However, several fragments may be comprised within a single larger polypeptide.

As representative examples of polypeptide fragments of the invention, there may be mentioned those which have at least 6 amino acids, preferably at least 8 to 10 amino acids, more preferably at least 12, 15, 20, 25, 30, 40, 50, 100 or 200 amino acids long. A specific embodiment of a BAP28 fragment is a fragment containing at least one amino acid mutation in the BAP28 protein.

Identity Between Nucleic Acids or Polypeptides

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, FASTA, and CLUSTALW (Pearson and Lipman, 1988; Altschul et al., 1990; Thompson et al., 1994; Higgins et al., 1996; Altschul et al., 1990; Altschul et al., 1993). In a particularly preferred embodiment, protein and nucleic acid sequence homologies are evaluated using the Basic Local Alignment Search Tool ("BLAST") which is well known in the art (see, e.g., Karlin and Altschul, 1990; Altschul et al., 1990, 1993, 1997). In particular, five specific BLAST programs are used to perform the following task: (1) BLASTP and BLAST3 compare an amino acid query sequence against a protein sequence database; (2) BLASTN compares a nucleotide query sequence against a nucleotide sequence database, (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) BLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992; Henikoff and Henikoff, 1993). Less preferably, the PAM or PAM250 matrices may also be used (see, e.g., Schwartz and Dayhoff, eds., 1978). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990).

Stringent Hybridization Conditions

For the purpose of defining such a hybridizing nucleic acid according to the invention, the stringent hybridization conditions are the followings:
the hybridization step is realized at 65° C. in the presence of 6×SSC buffer, 5×Denhardt's solution, 0.5% SDS and 100 µg/ml of salmon sperm DNA.
The hybridization step is followed by four washing steps:
two washings during 5 min. preferably at 65° C. in a 2×SSC and 0.1% SDS buffer.
one washing during 30 min, preferably at 65° C. in a 2×SSC and 0.1% SDS buffer,
one washing during 10 min, preferably at 65° C. in a 0.1×SSC and 0.1% SDS buffer,
these hybridization conditions being suitable for a nucleic acid molecule of about 20 nucleotides in length. There is no need to say that the hybridization conditions described above are to be adapted according to the length of the desired nucleic acid, following techniques well known to the one skilled in the art. The suitable hybridization conditions may for example be adapted according to the teachings disclosed in the book of Hames and Higgins (1985).

TABLE A

| | Position in SEQ ID No 1 | | | Position in SEQ ID No 1 | |
|---|---|---|---|---|---|
| Exon | Beginning | End | Intron | Beginning | End |
| 1 | 4997 | 5076 | 1-2 | 5077 | 5370 |
| 2 | 5371 | 5544 | 2-3 | 5545 | 6120 |
| 3 | 6121 | 6337 | 3-4 | 6338 | 9876 |
| 4 | 9877 | 10018 | 4-5 | 10019 | 11521 |
| 5 | 11522 | 11623 | 5-6 | 11624 | 12520 |
| 6 | 12521 | 12661 | 6-7 | 12662 | 13452 |
| 7 | 13453 | 13664 | 7-8 | 13665 | 13823 |
| 8 | 13824 | 13957 | 8-9 | 13958 | 15375 |
| 9 | 15376 | 15478 | 9-10 | 15479 | 16854 |
| 10 | 16855 | 16965 | 10-11 | 16966 | 17377 |
| 11 | 17378 | 17495 | 11-12 | 17496 | 18534 |
| 12 | 18535 | 18642 | 12-13 | 18643 | 21445 |
| 13 | 21446 | 21541 | 13-14 | 21542 | 21998 |
| 14 | 21999 | 22087 | 14-15 | 22088 | 23035 |
| 15 | 23036 | 23247 | 15-16 | 23248 | 23545 |
| 16 | 23546 | 23667 | 16-17 | 23668 | 24269 |
| 17 | 24270 | 24461 | 17-18 | 24462 | 26286 |
| 18 | 26287 | 26470 | 18-19 | 26471 | 26610 |
| 19 | 26611 | 26747 | 19-20 | 26748 | 28067 |
| 20 | 28068 | 28260 | 20-21 | 28261 | 32539 |
| 21 | 32540 | 32709 | 21-22 | 32710 | 33111 |
| 22 | 33112 | 33270 | 22-23 | 33271 | 34585 |
| 23 | 34586 | 34828 | 23-24 | 34829 | 35155 |
| 24 | 35156 | 35287 | 24-25 | 35288 | 36659 |
| 25 | 36660 | 36763 | 25-26 | 36764 | 36933 |
| 26 | 36934 | 37077 | 26-27 | 37078 | 37802 |
| 27 | 37803 | 37921 | 27-28 | 37922 | 38016 |
| 28 | 38017 | 38138 | 28-29 | 38139 | 40364 |
| 29 | 40365 | 40493 | 29-30 | 40494 | 42617 |
| 30 | 42618 | 42848 | 30-31 | 42849 | 43451 |
| 31 | 43452 | 43578 | 31-32 | 43579 | 44835 |
| 32 | 44836 | 44999 | 32-33 | 45000 | 48222 |
| 33 | 48223 | 48269 | 33-34 | 48270 | 49655 |
| 34 | 49656 | 49779 | 34-35 | 49780 | 50357 |
| 35 | 50358 | 50498 | 35-36 | 50499 | 50963 |
| 36 | 50964 | 51256 | 36-37 | 51257 | 52147 |
| 37 | 52148 | 52298 | 37-38 | 52299 | 53234 |
| 38 | 53235 | 53393 | 38-39 | 53394 | 53553 |
| 39 | 53554 | 53688 | 39-40 | 53689 | 53837 |
| 40 | 53838 | 53942 | 40-41 | 53943 | 54028 |
| 41 | 54029 | 54197 | 41-42 | 54198 | 54740 |
| 42 | 54741 | 54895 | 42-43 | 54896 | 55753 |
| 43 | 55754 | 55912 | 43-44 | 55913 | 57385 |
| 44 | 57386 | 57494 | 44-45 | 57495 | 58503 |
| 45 | 58504 | 58827 | 45-B' | 58828 | 85946 |
| 45b | 58504 | 59354 | 45b-B' | 59355 | 85946 |
| B' | 85947 | 86168 | B'-A' | 86169 | 91228 |
| A' | 91229 | 91851 | | | |

Genomic Sequences of the Human BAP28 Gene

The present invention concerns the genomic sequence of BAP28 comprising the sequence of SEQ ID No 1. The present invention encompasses BAP28 gene, or BAP28 genomic sequence consisting of, consisting essentially of, or comprising a sequence selected from the group consisting of SEQ ID No 1, a sequence complementary thereto, as well as fragments and variants thereof. These polynucleotides may be purified, isolated, or recombinant.

BAP28 was localized by the present inventors to the chromosome 1q43 region.

The human BAP28 genomic nucleic acid comprises at least 47 exons. The exon positions in SEQ ID No 1 are detailed below in the Table A.

The exons B' and A' of the Bap28 gene have been found through the study of the PCTA-1 gene which is described in the PCT application WO 99/64590, incorporated herein by reference. One public cDNA (Genbank Accession Number AF074001) shows an additional 5' exon in comparison of the cDNA described in the above-referenced application. This exon has been called exon B. It does not seem to comprise a splice site in 5'. So this exon will be a first exon. Long range PCR experiments with a first couple of primers PCTAex-BLF33/PCTA5Ra230 (SEQ ID No 40/SEQ ID No 45) and a second one PCTAexBLF120n/PCTA5Ra220n (SEQ ID No 41/SEQ ID No 44) confirm the existence of a cDNA comprising at least the exon B and the exons 0, 1, and 2 (SEQ ID No 10).

Three additional exons have been also identified, namely exons A, C and D. Exon C is the most upstream exon. Exons A and D have a 5' splice site. Long range PCR with a first couple of primers PCTAexALF12/PCTAex9terLR330 (SEQ ID No 36/SEQ ID No 53) and a second one PCTAexALF13n/PCTAex9terLR325n (SEQ ID No 37/SEQ ID No 54) showed an alternative PCTA-1 cDNA consisting with the exons A, 0, 1, 2, 3, 9bis and 9ter (SEQ ID No 13). Other alternative PCTA-1 cDNAs comprise consecutively the exons A, D, 0, 1 and 2 (SEQ ID No 12), the exons A, 1 and 2 (SEQ ID No 11), or the exons C and A (SEQ ID No 9). The form AD012 and A12 have been amplified with the first couple of primers PCTAexALF12/PCTA5Ra230 (SEQ ID No 36/SEQ ID No 45) and the second one PCTAexALF13n/PCTA5Ra220n (SEQ ID No 37/SEQ ID No 44). The exon C have been identified by a RACE experiment with PCTAexALR60 primer (SEQ ID No 38) from the exon A. The FIG. 2 shows the alternative cDNAs of PCTA-1 and the alternative 5' ends of PCTA-1 cDNAs.

The first identified BAP28 cDNAs comprise either the exons 1 to 45 or 1 to 44 and 45b. They are detailed in the section "BAP28 cDNA sequences". The exon 45 of the BAP28 cDNA comprises a polyadenylation site and some RACE experiments failed not show any additional sequence downstream of the exon 45, which was the last identified exon.

The study of the PCTA-1 new exons for an alternative cDNA comprising both the exons A and B provides two additional BAP28 exons, the exons A' and B'. Indeed, two upstream PCR primers were designed; one in the exon A (PCTAexALF12 (SEQ ID No 36 following by PCTAexALF13n (SEQ ID No 37)) and the other in exon B (PCTAexBLF33 (SEQ ID No 40) following by PCTAexBLF120n (SEQ ID No 41)). The downstream primer was generated in previously identified PCTA-1 exons (PCTA5Ra230 (SEQ ID No 45) following by PCTA5Ra220n (SEQ ID No 44)). No alternative cDNA comprising both exons has been observed. Therefore, two couples of primers was designed with the upstream primer in exon A and the downstream primer in exon B. More particularly, the amplification was done with a first couple of primers PCTAexALF12/PCTAexBLR140 (SEQ ID No 36/SEQ ID No 42) and a second one PCTAexALF13n/PCTAexBLR40n (SEQ ID No 37/SEQ ID No 43). An amplification product was obtained. However, the exons were slightly moved and the splice sites were only available on the opposite strand. Therefore, the amplification product was not from the PCTA-1 gene but rather than was supposed to be from the BAP28 gene which is on the opposite strand. This amplification product contains the exons A' and B' (SEQ ID No 4). In order to check that the amplification product comes from BAP28, a PCR amplification was performed with a downstream primer in the exon A and an upstream primer in exon 43 of BAP28 gene. More particularly, the PCR was done with a first couple of primers PCTAexALF12/BAP283Ra6283 (SEQ ID No 36/SEQ ID No 32) and a second one PCTAexALF13n/BAP283Ra6324n (SEQ ID No 37/SEQ ID No 33) The amplification product confirmed that the slightly moved exons A and B are part of the BAP28 eDNA. The sequencing of the amplification product showed a cDNA comprising the exons 44, 45b, and A. The BAP28 cDNA with the exons B' and A' likely consists to an other another alternative cDNA form.

Thus, the invention embodies purified, isolated, or recombinant polynucleotides comprising a nucleotide sequence selected from the group consisting of the exons of the BAP28 gene, or a sequence complementary thereto. Preferred are nucleotide sequences selected from the group consisting of the exons of the BAP28 gene having the nucleotide position ranges listed in Table A, or a complementary sequence thereto or a fragment or a variant thereof.

Encompassed by the invention are purified, isolated, or recombinant nucleic acids comprising a combination of at least two exons of the BAP28 gene, wherein the polynucleotides are arranged within the nucleic acid, from the 5'-end to the 3'-end of said nucleic acid, in the same order as in SEQ ID No 1. The invention further deals with purified, isolated, or recombinant nucleic acids comprising a combination of at least two exons of the BAP28 gene, wherein the nucleic acids comprise at least one exon selected from the group consisting of exons 1 to 45b, 45b. B' and A', wherein the polynucleotides are arranged within the nucleic acid, from the 5'-end to the 3'-end of said nucleic acid, in the same order as in SEQ ID No 1.

Preferred polynucleotides of the invention embody purified, isolated, or recombinant polynucleotides comprising a contiguous span of at least 12, 15, 18, 20, 25, 30, 50, 80, 100, 150, or 200 nucleotides, to the extent that such a length is consistent with the lengths of the particular nucleotide position, of SEQ ID No 1 or the complement thereof, wherein said contiguous span comprises at least 1, 2, 3, 5, 10, 20, 30, 40 or 50 nucleotides selected from the group consisting of the following nucleotide positions of SEQ ID No 1: 4997-5076, 5371-5544, 6121-6337, 9877-10018, 11522-11623, 12521-12661, 13453-13664, 13824-13957, 15376-15478, 16855-16965, 17378-17495, 18535-18642, 21446-21541, 21999-22087, 23036-23247, 23546-23667, 24270-24461, 26287-26470, 26611-26747, 28068-28260, 32540-32709, 33112-33270, 34586-34828, 35156-35287, 36660-36763, 36934-37077, 37803-37921, 38017-38138, 40365-40493, 42618-42848, 43452-43578, 44836-44999, 48223-48269, and 49656-49779.

The position of the introns is detailed in Table A. Thus, the invention embodies purified, isolated, or recombinant polynucleotides comprising a nucleotide sequence selected from the group consisting of the introns of the BAP28 gene, or a sequence complementary thereto.

The invention also encompasses a purified, isolated, or recombinant polynucleotides comprising a nucleotide sequence having at least 70, 75, 80, 85, 90, or 95%/nucleotide identity with a nucleotide sequence of SEQ ID No 1 or a complementary sequence thereto or a fragment thereof. The nucleotide differences as regards to the nucleotide sequences of SEQ ID No 1 may be generally randomly distributed throughout the entire nucleic acid. Nevertheless, preferred nucleic acids are those wherein the nucleotide differences as regards to the nucleotide sequences of SEQ ID No 1 are predominantly located outside the coding sequences contained in the exons. These nucleic acids, as well as their fragments and variants, may be used as oligonucleotide primers or probes in order to detect the presence of a copy of the BAP28 gene in a test sample, or alternatively in order to amplify a target nucleotide sequence within the BAP28 sequences.

Another object of the invention consists of a purified, isolated, or recombinant nucleic acids that hybridizes with a nucleotide sequence selected from the group consisting of SEQ ID No 1 or a complementary sequence thereto or a variant thereof, under the stringent hybridization conditions as defined above.

Particularly preferred nucleic acids of the invention include isolated, purified, or recombinant polynucleotides comprising a contiguous span of at least 12, 15, 18, 20, 25, 30, 50, 80, 100, 150, 200, 250, 300, 350, 400, 450, 500, 600 or 1000 nucleotides, to the extent that such a length is consistent with the lengths of the particular nucleotide position, of SEQ ID No 1 or the complement thereof, wherein said contiguous span comprises at least 1, 2, 3, 5, 10, 20, 30, 40 or 50 of the following nucleotide positions of SEQ ID No 1: 1-50357, 50499-50963, 51257-52147, 52299-53234, 53394-53553, 53689-53837, 53943-54028, 54198-54740, 54896-55753, 55913-57385, 57495-58503, 58828-85946, 59355-85946, 86169-91228, and/or 91852 to 97662.

Further preferred nucleic acids of the invention include isolated, purified, or recombinant polynucleotides comprising a contiguous span of at least 12, 15, 18, 20, 25, 30, 50, 80, 100, 150, 200, 250, 300, 350, 400, 450, 500, 600 or 1000 nucleotides, to the extent that such a length is consistent with the lengths of the particular nucleotide position, of SEQ ID No 1 or the complement thereof, wherein said contiguous span comprises at least 1, 2, 3, 5, 10, 20, 30, 40 or 50 of the following nucleotide positions of SEQ ID No 1: 1-2500, 2501-5000, 5001-7500, 7501-10000, 10001-12500, 12501-15000, 15001-17500, 17501-20000, 20001-22500, 22501-25000, 25001-27500, 27501-30000, 30001-32500, 32501-35000, 35001-37500, 37501-40000, 40001-42500, 42501-45000, 45001-47500, 47501-50000, 50001-50357, 50499-50963, 51257-52147, 52299-53234, 53394-53553, 53689-53837, 53943-54028, 54198-54740, 54896-55753, 55913-57385, 57495-58503, 58828-85946, 59355-85946, 86169-91228, and/or 91852 to 97662.

Other preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides, to the extent that such a length is consistent with the lengths of the particular nucleotide position, of SEQ ID No 1, or the complements thereof, wherein said contiguous span comprises at least one BAP28-related biallelic marker selected from the group consisting of A1 to A58, preferably A1 to A27, A34, A37 to A41, A43 to A49, A52, and A54 to A58, more preferably at least one of the biallelic markers A1, A4, 16, A30, A31, A42, A50, A51, and A53.

It should be noted that nucleic acid fragments of any size and sequence may also be comprised by the polynucleotides described in this section.

In another aspect, the invention concerns polymorphisms of BAP28.

While this section is entitled "Genomic Sequences of BAP28," it should be noted that nucleic acid fragments of any size and sequence may also be comprised by the polynucleotides described in this section, flanking the genomic sequences of BAP28 on either side or between two or more such genomic sequences.

BAP28 cDNA Sequences

Another object of the invention is a purified, isolated, or recombinant nucleic acid comprising a nucleotide sequence selected from the group consisting of SEQ ID Nos 2 and 3, complementary sequences thereto, as well as allelic variants, and fragments thereof. Moreover, preferred polynucleotides of the invention include purified, isolated, or recombinant BAP28 cDNAs consisting of, consisting essentially of, or comprising a nucleotide sequence selected from the group consisting of SEQ ID Nos 2 and 3. The two BAP28 cDNAs have to a different 3' end. The first one, namely the cDNA of the SEQ ID No 2, comprises the exons 1 to 44 and 45. The second one, namely the cDNA of the SEQ ID No 3, comprises the exons 1 to 44, 45b and A'. The cDNA of SEQ ID No 2 or 3 are described in Table B.

Consequently, the invention concerns a purified, isolated, and recombinant nucleic acids comprising a nucleotide sequence of the 5'UTR of the BAP28 cDNA, a sequence complementary thereto, or an allelic variant thereof. The invention also concerns a purified, isolated, and recombinant nucleic acids comprising a nucleotide sequence of the 3'UTR of the BAP28 cDNA, a sequence complementary thereto, or an allelic variant thereof.

TABLE B

| cDNA | Position range of 5UTR | | Position range of ORF | | Position range of 3UTR | |
|---|---|---|---|---|---|---|
| cDNA1 | 1 | 112 | 113 | 6547 | 6548 | 6782 |
| cDNA2 | 1 | 112 | 113 | 6547 | 6548 | 7932 |

As described in the section "Genomic Sequences of the human Bap28 gene", an alternative form of the BAP28 cDNA comprises the exons B' and A'. Therefore, the invention concerns a cDNA of BAP28 comprising the nucleotide sequence of SEQ ID No 4.

Particularly preferred embodiments of the invention include isolated, purified, or recombinant polynucleotides comprising a contiguous span of at least 12, 15, 18, 20, 25, 30, 50, 80, 100, 150, 200, 250, 300, 350, 400, 450, 500, 600 or 1000 nucleotides of a nucleic acid sequence selected from the group consisting of SEQ ID Nos 2 and 3 or the complements thereof, wherein said contiguous span comprises at least 1, 2, 3, 5, or 10 of nucleotide positions 1 to 4995 of SEQ ID No 2 or 3. Further preferred polynucleotides include isolated, purified, or recombinant polynucleotides comprising a contiguous span of at least 12, 15, 18, 20, 25, 30, 50, 80, 100, 150, 200, 250, 300, 350, 400, 450, 500, 600 or 1000 nucleotides of a nucleic acid sequence selected from the group consisting of SEQ ID Nos 2 and 3 or the complements thereof, wherein said contiguous span comprises at least 1, 2, 3, 5, or 10 of the following nucleotide positions of SEQ ID No 2 or 3: 1 to 2033, 2160 to 2348, and 2676 to 4995. Additional preferred nucleic acids of the invention include isolated, purified, or recombinant polynucleotides comprising a contiguous span of at least 12, 15, 18, 20, 25, 30, 50, 80, 100, 150, 200, 250, 300, 350, 400, 450, 500, 600 or 1000 nucleotides of SEQ ID No 2, or the complements thereof, wherein said contiguous span comprises at least 1, 2, 3, 5, or 10 nucleotide positions of any one of the following ranges of nucleotide positions of SEQ ID No 2: 1 to 500, 501 to 1000, 1001 to 1500, 1501 to 2000, 2001 to 2500, 2501 to 3000, 3001 to 3500, 3501 to 4000, 4001 to 4500, 4501 to 4995, 5000 to 5500, 5501 to 6000, 6001 to 6500, and 6501 to 6782. Additional preferred nucleic acids of the invention include isolated, purified, or recombinant polynucleotides comprising a contiguous span of at least 12, 15, 18, 20, 25, 30, 50, 80, 100, 150, 200, 250, 300, 350, 400, 450, 500, 600 or 1000 nucleotides of SEQ ID No 3, or the complements thereof, wherein said contiguous span comprises at least 1, 2, 3, 5, or 10 nucleotide positions of any one of the following ranges of nucleotide positions of SEQ ID No 3: 1 to 500, 501 to 1000, 1001 to 1500, 1501 to 2000, 2001 to 2500, 2501 to 3000, 3001 to 3500, 3501 to 4000, 4001 to 4500, 4501 to 4995, 5000 to 5500, 5501 to 6000, 6001 to 6500, 6501 to 7000, 7001 to 7500, 7501 to 7932.

The invention also pertains to a purified or isolated nucleic acid having at least 95% of nucleotide identity with a nucleotide sequence selected from the group consisting of SEQ ID Nos 2 and 3 or a fragment thereof or a complementary sequence thereto, advantageously 99%, preferably 99.5% nucleotide identity and most preferably 99.8% nucleotide identity with a nucleotide sequence selected from the group consisting of SEQ ID Nos 2 and 3 or a fragment thereof or a complementary sequence thereto.

Another object of the invention consists of a purified, isolated, or recombinant nucleic acids that hybridizes with a nucleotide sequence selected from the group consisting of SEQ ID Nos 2 and 3 or a complementary sequence thereto or a variant thereof, under the stringent hybridization conditions as defined above.

The invention concerns a PCTA-1 cDNA comprising an exon selected from the group consisting of exons A, B, C, and D. More particularly, the invention concerns a PCTA-1 cDNA comprising a polynucleotide sequence selected from the group consisting of SEQ ID Nos 9-13 or a fragment thereof or a complementary sequence thereto.

Encompassed by the invention are purified, isolated, or recombinant nucleic acids comprising a combination of at least two exons of the PCTA-1 gene, wherein the polynucleotides are arranged within the nucleic acid, from the 5'-end to the 3'-end of said nucleic acid, in the same order as in SEQ ID No 1. The invention further deals with purified, isolated, or recombinant nucleic acids comprising a combination of at least two exons of the PCTA-1 gene, wherein the nucleic acids comprise at least one exon selected from the group consisting of exons C, A, D, B, 0, 1, 2, 3, 4, 5, 6, 6bis, 7, 8, 9, 9bis and 9ter, wherein the polynucleotides are arranged within the nucleic acid, from the 5'-end to the 3'-end of said nucleic acid, in the same order as in SEQ ID No 1.

While this section is entitled "BAP28 cDNA Sequences," it should be noted that nucleic acid fragments of any size and sequence may also be comprised by the polynucleotides described in this section, flanking the genomic sequences of BAP28 on either side or between two or more such genomic sequences.

Natural Antisense

Over the last 10 years, an increasing number of natural antisense RNAs has been reported in eukaryotes. Natural antisense RNAs are endogenous transcripts that exhibit complementary sequences to other transcripts, named sense transcripts. Most antisense transcripts are issued from the same locus as sense transcripts. Transcribed from opposite strands of DNA, sense and antisense transcripts overlap each other at least partially, and display perfect complementarity. The reported antisense RNAs are complementary to sense transcripts encoding proteins involved in extremely diverse biological functions: hormonal response, control of proliferation, development, structure, etc. . . .

In some cases, apart from their capability of encoding proteins per se, antisense RNAs were found to regulate, generally downregulate, the expression of their sense counterparts. Often changes in sense gene expression were correlated with the presence of antisense RNA. Indeed, an inverse relationship between levels of accumulation of sense and antisense messengers has been documented in several cases. Some examples have been reported in various pathology such as nervous disorders and cancer.

These characteristics suggest that antisense transcripts are found throughout the whole eukaryotic world and might play a role in general antisense-mediated gene regulation as is the cases in prokaryotes. Indeed, antisense-mediated gene regulation is a way of decreasing the abundance of stable transcripts more rapidly than the cessation of transcription. In addition, natural antisense transcripts are thought to be involved not only in the normal regulation of gene expression but also in the alteration of gene regulation leading to different pathologies.

Indeed, because of their complementarity, antisense transcripts may hybridize to sense transcripts and thus modify the expression of their sense counterparts at any step from transcription to translation.

In the nucleus, antisense RNA may regulate sense expression either at the level of transcription, processing, or nucleocytoplasmic transport. Transcriptional regulation occurs either because the activity of sense and antisense promoters is differentially regulated by cellular conditions or because antisense transcription impedes sense transcription. This interference would involve the collision of two transcription complexes, resulting in premature termination or in reduced elongation of transcription, the transcripts with the highest rate of transcription being predominant. Antisense may also operate at a post-transcriptional level probably by impairing either maturation and/or transport of the sense transcript.

Although some examples have shown that antisense regulation may occur in the nucleus, antisense regulation is generally described as a cytoplasmic event operating mostly at the messenger stability level. Furthermore, the regulation can also be made at the translation stage, particularly when interactions between sense and antisense occur in the 3'UTR.

Two mechanisms of antisense-mediated gene regulation may be envisioned. First, antisense transcripts displaying very similar structural features to sense transcripts may bind proteins actually interacting with their sense counterparts, thus depriving sense messengers from proteins necessary for their functions. The other mechanism of antisense-mediated regulation is thought to operate via duplex formation between complementary sense and antisense transcripts. By simple steric hindrance. RNA duplexes would prevent sense RNA from interacting with diverse cellular components required for normal sense expression, thus impairing maturation, nucleocytoplasmic transport, transcript stability, or translation depending on the cellular components involved. Alternatively, duplexes may represent substrates for double-stranded RNA specific enzymes. It is commonly believed that most duplexes will become targeted for degradation by RNAses and only the most abundant transcripts, either sense or antisense, will persist in the cells. More information on the natural antisense can be found in Vanhee-Brossollet et al. (1998).

BAP28 and PCTA-1 are Natural Antisense

BAP28 transcript has been identified as a natural antisense of the PCTA-1 transcript. Indeed, the coding sequence of PCTA-1 is on the opposite strand of the coding sequence of BAP28. Moreover, the 3'UTR of BAP28 contains some sequences which are complementary of segments of the 5'UTR and 3'UTR of PCTA-1. More particularly, the exons A and B are common for the PCTA-1 and BAP28 genes, the exon 44 of BAP28 gene is antisense of the exons 9 and 9ter of PCTA-1, the exons 45 and 45b of BAP28 gene are antisense of the exon 9 of PCTA-1. Therefore, BAP28 transcript is the antisense of the PCTA-1 RNA. The FIG. 1 presents the general organization of the BAP28 and PCTA-1 genes.

The PCTA-1 protein has been shown to be a specific antigen of prostate cancer cells (WO 96/21671, incorporated herein by reference). Therefore, one can assume that its expression is closely linked to the development of cancer, particularly prostate cancer.

ESTs from the PCTA-1 gene were found in a broad range of tissues. As the protein PCTA-1 is only present in the prostate cancer cells, a regulation of the PCTA-1 RNA will occur, maybe at the stage of the RNA transcription, splicing, stability and/or translation.

The 5'UTR and 3'UTR regions of a gene are of particular importance in that they often comprise regulatory elements which can play a role in providing appropriate expression levels, particularly through the control of mRNA stability.

As the BAP28 transcript is the natural antisense of the PCTA-1 mRNA, the BAP28 mRNA is likely to be involved in the regulation of the PCTA-1 expression and, by consequence, in the process of development of prostate cancer.

The involvement of BAP28 gene in prostate cancer is reported through the clearly significant association of the BAP28-related biallelic markers to prostate cancer. Furthermore, the PCT application WO98/12327, incorporated herein by reference, showed that BAP28 should be involved in interaction with BRCA1. Therefore, BAP28 may be a tumor suppressor. During the process of carcinogenesis, BAP28 would become inactive and its expression could decrease. This expression decrease of BAP28 would lead to an increase of the PCTA-1 mRNA stability and the presence of the PCTA-1 protein at the cell surface. We can hypothesize that these events correspond to a natural defense against the cancer cells.

Consequently, the invention concerns the use of BAP28 nucleotide sequence from the mRNA as antisense in order to control the PCTA-1 expression and preferably to inhibit the PCTA-1 expression. The invention also concerns the use of PCTA-1 nucleotide sequence from the mRNA as an antisense in order to control the BAP28 expression. These antisense can be used in order to avoid cancer development, preferably prostate cancer development.

An embodiment of the invention concerns the polynucleotide segment common in the PCTA-1 and BAP28 cDNAs. More particularly, the invention concerns isolated, purified, or recombinant polynucleotides comprising a contiguous span of at least 12, 15, 18, 20, 25, 30, 50, 80, 100, 150, 200, 250, 300, 350, 400, 450, 500, 600 or 1000 nucleotides of SEQ ID No 1, or the complements thereof, wherein said contiguous span comprises at least 1, 2, 3, 5, or 10 nucleotide positions of any one of the following ranges of nucleotide positions of SEQ ID No 1: 57386-27494, 58504-59354, 85947-86108, and 91259-91325.

An additional embodiment is the use of a polynucleotide according to the invention, more particularly polynucleotides comprising a contiguous span of at least 12, 15, 18, 20, 25, 30, 50, 80, 100, 150, 200, 250, 300, 350, 400, 450, 500, 600 or 1000 nucleotides of SEQ ID No 1, or the complements thereof, wherein said contiguous span comprises at least 1, 2, 3, 5, or 10 nucleotide positions of any one of the following ranges of nucleotide positions of SEQ ID No 1: 57386-27494, 58504-59354, 85947-86108, and 91259-91325, for regulating the expression of PCTA-1 and/or BAP28.

Coding Regions

The BAP28 open reading frame is contained in the corresponding mRNAS of SEQ ID No 2 or 3. More precisely, the effective BAP28 coding sequence (CDS) includes the region between nucleotide position 113 (first nucleotide of the ATG codon) and nucleotide position 6547 (end nucleotide of the TAA codon) of SEQ ID No 2 or 3.

Thus, the present invention deals with a purified or isolated nucleic acid encoding a BAP28 protein or a fragment thereof. More particularly the present invention deals with a purified or isolated nucleic acid encoding a BAP28 protein having the amino acid sequence of SEQ ID No 5 or a peptide fragment or variant thereof. The present invention also embodies isolated, purified, and recombinant polynucleotides which encode a polypeptides comprising a contiguous span of at least 6 amino acids, preferably at least 8 or 10 amino acids, more preferably at least 12, 15, 20, 25, 30, 40, 50, or 100 amino acids of SEQ ID No 5, wherein said contiguous span includes at least 1, 2, 3, 5 or 10 of the amino acid positions 1 to 1629 of the SEQ ID No 5. The present invention further embodies isolated, purified, and recombinant polynucleotides which encode a polypeptides comprising a contiguous span of at least 6 amino acids, preferably at least 8 or 10 amino acids, more preferably at least 12, 15, 20, 25, 30, 40, 50, or 100 amino acids of SEQ ID No 5, wherein said contiguous span contains an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5 and an alanine at the amino acid position 2050 of SEQ ID No 5. The present invention embodies isolated, purified, and recombinant polynucleotides which encode a polypeptides comprising a contiguous span of at least 6 amino acids, preferably at least 8 or 10 amino acids, more preferably at least 12, 15, 20, 25, 30, 40, 50, or 100 amino acids of SEQ ID No 5, wherein said contiguous span includes at least 1, 2, 3, 5 or 10 of the amino acid positions 1 to 200, 201 to 400, 401 to 600, 601 to 800, 801 to 1000, 1001 to 1200, 1201 to 1400 and/or 1401 to 1629 of the SEQ ID No 5.

The above disclosed polynucleotide that contains the coding sequence of the BAP28 gene may be expressed in a desired host cell or a desired host organism, when this polynucleotide is placed Linder the control of suitable expression signals. The expression signals may be either the expression signals contained in the regulatory regions in the BAP28 gene of the invention or in contrast the signals may be exogenous regulatory nucleic sequences. Such a polynucleotide, when placed under the suitable expression signals, may also be inserted in a vector for its expression and/or amplification.

Regulatory Sequences of BAP28

As mentioned, the genomic sequence of the BAP28 gene contains regulatory sequences both in the non-coding 5'-flanking region and in the non-coding 3'-flanking region that border the BAP28 coding region containing the 45 exons of this gene.

The 5'-regulatory sequence of the BAP28 gene is localized between the nucleotide in position 2996 and the nucleotide in position 4996 of the nucleotide sequence of SEQ ID No 1. The 5'-regulatory sequence contains the BAP28 promoter site.

The genomic sequence of the BAP28 gene also contains regulatory sequences in the non-coding 3'-flanking region that border the BAP28 coding region. The 3'-regulatory sequence of the BAP28 gene is localized between nucleotide position 91852 and nucleotide position 97662 of SEQ ID No 1.

Polynucleotides derived from the 5' and 3' regulatory regions are useful in order to detect the presence of at least a copy of a nucleotide sequence of SEQ ID No 1 or a fragment thereof in a test sample.

The promoter activity of the 5' regulatory regions contained in BAP28 can be assessed as described below.

In order to identify the relevant biologically active polynucleotide fragments or variants of SEQ ID No 1, the one skill in the art will refer to the book of Sambrook et al. (1989) which describes the use of a recombinant vector carrying a marker gene (i.e. beta galactosidase, chloramphenicol acetyl transferase, etc.) the expression of which will be detected when placed under the control of a biologically active polynucleotide fragments or variants of SEQ ID No 1. Genomic sequences located upstream of the first exon of the BAP28 gene are cloned into a suitable promoter reporter vector, such as the pSEAP-Basic, pSEAP-Enhancer, pβgal-Basic, pβgal-Enhancer, or pEGFP-1 Promoter Reporter vectors available from Clontech, or pGL2-basic or pGL3-basic promoterless luciferase reporter gene vector from Promega. Briefly, each of these promoter reporter vectors include multiple cloning sites positioned upstream of a reporter gene encoding a readily assayable protein such as secreted alkaline phosphatase, luciferase, β galactosidase, or green fluorescent protein. The sequences upstream the BAP28 coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for increasing transcription levels from weak promoter sequences. A significant level of expression above that observed with the vector lacking an insert indicates that a promoter sequence is present in the inserted upstream sequence.

Promoter sequence within the upstream genomic DNA may be further defined by constructing nested 5' and/or 3' deletions in the upstream DNA using conventional techniques such as Exonuclease III or appropriate restriction endonuclease digestion. The resulting deletion fragments can be inserted into the promoter reporter vector to determine whether the deletion has reduced or obliterated promoter activity, such as described, for example, by Coles et al. (1998). In this way the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into cloning sites in promoter reporter vectors. This type of assay is well-known to those skilled in the art and is described in WO 97/17359, U.S. Pat. No. 5,374,544; EP 582 796; U.S. Pat. Nos. 5,698,389; 5,643,746; 5,502,176; and 5,266,488; incorporated herein by reference.

The strength and the specificity of the promoter of the BAP28 gene can be assessed through the expression levels of a detectable polynucleotide operably linked to the BAP28 promoter in different types of cells and tissues. The detectable polynucleotide may be either a polynucleotide that specifically hybridizes with a predefined oligonucleotide probe, or a polynucleotide encoding a detectable protein, including a BAP28 polypeptide or a fragment or a variant thereof. This type of assay is well-known to those skilled in the art and is described in U.S. Pat. Nos. 5,502,176; and 5,266,488; incorporated herein by reference. Some of the methods are discussed in more detail below.

Polynucleotides carrying the regulatory elements located at the 5' end and at the 3' end of the BAP28 coding region may be advantageously used to control the transcriptional and translational activity of heterologous polynucleotide of interest.

Thus, the present invention also concerns a purified or isolated nucleic acid comprising a polynucleotide which is selected from the group consisting of the 5' and 3' regulatory regions, or a sequence complementary thereto or a biologically active fragment or variant thereof.

The invention also pertains to a purified or isolated nucleic acid comprising a polynucleotide having at least 95% nucleotide identity with a polynucleotide selected from the group consisting of the 5' and 3' regulatory regions, advantageously 99% nucleotide identity, preferably 99.5% nucleotide identity and most preferably 99.8% nucleotide identity with a polynucleotide selected from the group consisting of the 5' and 3' regulatory regions, or a sequence complementary thereto or a variant thereof or a biologically active fragment thereof.

Another object of the invention consists of purified, isolated or recombinant nucleic acids comprising a polynucleotide that hybridizes, under the stringent hybridization conditions defined herein, with a polynucleotide selected from the group consisting of the nucleotide sequences of the 5'- and 3' regulatory regions, or a sequence complementary thereto or a variant thereof or a biologically active fragment thereof.

Preferred fragments of either the 5' or 3' regulatory region have a length of about 1500 or 1000 nucleotides, preferably of about 500 nucleotides, more preferably about 400 nucleotides, even more preferably 300 nucleotides and most preferably about 200 nucleotides.

By "biologically active" polynucleotide derivatives of SEQ ID No 1 are polynucleotides comprising or alternatively consisting in a fragment of said polynucleotide which is functional as a regulatory region for expressing a recombinant polypeptide or a recombinant polynucleotide in a recombinant cell host. It could act either as an enhancer or as a repressor.

For the purpose of the invention, a nucleic acid or polynucleotide is "functional" as a regulatory region for expressing a recombinant polypeptide or a recombinant polynucleotide if said regulatory polynucleotide contains nucleotide sequences which contain transcriptional and translational regulatory information, and such sequences are "operably linked" to nucleotide sequences which encode the desired polypeptide or the desired polynucleotide.

The regulatory polynucleotides of the invention may be prepared from the nucleotide sequence of SEQ ID No 1 by cleavage using suitable restriction enzymes, as described for example in the book of Sambrook et al. (1989). The regulatory polynucleotides may also be prepared by digestion of SEQ ID No 1 by an exonuclease enzyme, such as Bal31 (Wabiko et al. 1986). These regulatory polynucleotides can also be prepared by nucleic acid chemical synthesis, as described elsewhere in the specification.

The regulatory polynucleotides according to the invention may be part of a recombinant expression vector that may be used to express a coding sequence in a desired host cell or host organism. The recombinant expression vectors according to the invention are described elsewhere in the specification.

A preferred 5'-regulatory polynucleotide of the invention thus includes the 5'-UTR of the BAP28 cDNA, or a biologically active fragment or variant thereof.

A preferred 3'-regulatory polynucleotide of the invention includes the 3'-UTR of the BAP28 cDNA, or a biologically active fragment or variant thereof.

A further object of the invention consists of a purified or isolated nucleic acid comprising:

a) a nucleic acid comprising a regulatory nucleotide sequence selected from the group consisting of:
  (i) a nucleotide sequence comprising a polynucleotide of the 5' regulatory region or a complementary sequence thereto;
  (ii) a nucleotide sequence comprising a polynucleotide having at least 95% of nucleotide identity with the nucleotide sequence of the 5' regulatory region or a complementary sequence thereto;
  (iii) a nucleotide sequence comprising a polynucleotide that hybridizes under stringent hybridization conditions with the nucleotide sequence of the 5' regulatory region or a complementary sequence thereto; and
  (iv) a biologically active fragment or variant of the polynucleotides in (i), (ii) and (iii);
b) a polynucleotide encoding a desired polypeptide or a nucleic acid of interest, operably linked to the nucleic acid defined in (a) above;
c) In some embodiments, a nucleic acid comprising a 3'-regulatory polynucleotide, preferably a 3'-regulatory polynucleotide of the BAP28 gene.

In a specific embodiment of the nucleic acid defined above, said nucleic acid includes the 5'-UTR of the BAP28 cDNA, or a biologically active fragment or variant thereof.

In a second specific embodiment of the nucleic acid defined above, said nucleic acid includes the 3'-UTR of the BAP28 cDNA, or a biologically active fragment or variant thereof.

The desired polypeptide encoded by the above-described nucleic acid may be of various nature or origin, encompassing proteins of prokaryotic or eukaryotic origin. Among the polypeptides expressed under the control of a BAP28 regulatory region include bacterial, fungal or viral antigens. Also encompassed are eukaryotic proteins such as intracellular proteins, like "house keeping" proteins, membrane-bound proteins, like receptors, and secreted proteins like endogenous mediators such as cytokines. The desired polypeptide may be the BAP28 protein, especially the protein of the amino acid sequence of SEQ ID No 1, or a fragment or a variant thereof.

The desired nucleic acids encoded by the above-described polynucleotide, usually an RNA molecule, may be complementary to a desired coding polynucleotide, for example to the BAP28 coding sequence, and thus useful as an antisense polynucleotide.

Such a polynucleotide may be included in a recombinant expression vector in order to express the desired polypeptide or the desired nucleic acid in host cell or in a host organism. Suitable recombinant vectors that contain a polynucleotide such as described hereinbefore are disclosed elsewhere in the specification.

Polynucleotide Constructs

The terms "polynucleotide construct" and "recombinant polynucleotide" are used interchangeably herein to refer to linear or circular, purified or isolated polynucleotides that have been artificially designed and which comprise at least two nucleotide sequences that are not found as contiguous nucleotide sequences in their initial natural environment.

DNA Construct that Enables Directing Temporal and Spatial BAP28 Gene Expression in Recombinant Cell Hosts and in Transgenic Animals.

In order to study the physiological and phenotypic consequences of a lack of synthesis of the BAP28 protein, both at the cell level and at the multi cellular organism level, the invention also encompasses DNA constructs and recombinant vectors enabling a conditional expression of a specific allele of the BAP28 genomic sequence or cDNA and also of a copy of this genomic sequence or cDNA harboring substitutions, deletions, or additions of one or more bases as regards to the BAP28 nucleotide sequence of SEQ ID Nos 1-3, or a fragment thereof, these base substitutions, deletions or additions being located either in an exon, an intron or a regulatory sequence, but preferably in an exon of the BAP28 genomic sequence or within the BAP28 cDNA of SEQ ID No 2 or 3. In a preferred embodiment, the BAP28 sequence comprises a biallelic marker of the present invention. In a preferred embodiment, the BAP28 sequence comprises a biallelic marker of the present invention, preferably one of the biallelic markers A1 to A58, preferably A1 to A27, A34, A37 to A41, A43 to A49, A52, and A54 to A58, more preferably one of the biallelic markers A1, A4, 16, A30, A31, A42, A50, A51, and A53.

In an additional embodiment, the invention concerns a DNA construct comprising an exon of PCTA-1 selected from the group consisting of exons A, B, C, and D.

The present invention embodies recombinant vectors comprising any one of the polynucleotides described in the present invention. More particularly, the polynucleotide constructs according to the present invention can comprise any of the polynucleotides described in the "Genomic Sequences Of The Human BAP28 Gene" section, the "BAP28 cDNA Sequences" section, the "Coding Regions" section, and the "Oligonucleotide Probes And Primers" section.

A first preferred DNA construct is based on the tetracycline resistance operon tet from *E. coli* transposon Tn10 for controlling the BAP28 gene expression, such as described by Gossen et al. (1992, 1995) and Furth et al. (1994). Such a DNA construct contains seven tet operator sequences from Tn10 (tetop) that are fused to a minimal promoter, said minimal promoter being operably linked to a polynucleotide of interest that codes either for a sense or an antisense oligonucleotide or for a polypeptide, including a BAP28 polypeptide or a peptide fragment thereof. This DNA construct is functional as a conditional expression system for the nucleotide sequence of interest when the same cell also comprises a nucleotide sequence coding for either the wild type (tTA) or the mutant (rTA) repressor fused to the activating domain of viral protein VP16 of herpes simplex virus, placed under the control of a promoter, such as the HCMVIE1 enhancer/promoter or the MMTV-LTR. Indeed, a preferred DNA construct of the invention comprise both the polynucleotide containing the tet operator sequences and the polynucleotide containing a sequence coding for the tTA or the rTA repressor.

In a specific embodiment, the conditional expression DNA construct contains the sequence encoding the mutant tetracycline repressor rTA, the expression of the polynucleotide of interest is silent in the absence of tetracycline and induced in its presence.

DNA Constructs Allowing Homologous Recombination: Replacement Vectors

A second preferred DNA construct will comprise, from 5'-end to 3'-end: (a) a first nucleotide sequence that is comprised in the BAP28 genomic sequence; (b) a nucleotide sequence comprising a positive selection marker, such as the marker for neomycine resistance (neo); and (c) a second nucleotide sequence that is comprised in the BAP28 genomic sequence, and is located on the genome downstream the first BAP28 nucleotide sequence (a).

In a preferred embodiment, this DNA construct also comprises a negative selection marker located upstream the nucleotide sequence (a) or downstream the nucleotide sequence (c). Preferably, the negative selection marker consists of the thymidine kinase (tk) gene (Thomas et al., 1986), the hygromycine beta gene (Te Riele et al., 1990), the hprt gene (Van der Lugt et al., 1991; Reid et al., 1990) or the Diphtheria toxin A fragment (Dt-A) gene (Nada et al., 1993; Yagi et al. 1990). Preferably, the positive selection marker is located within a BAP28 exon sequence so as to interrupt the sequence encoding a BAP28 protein. These replacement vectors are described, for example, by Thomas et al. (1986; 1987), Mansour et al. (1988) and Koller et al. (1992).

The first and second nucleotide sequences (a) and (c) may be indifferently located within a BAP28 regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb and most preferably from 2 to 4 kb.

DNA Constructs Allowing Homologous Recombination: Cre-LoxP System.

These new DNA constructs make use of the site specific recombination system of the P1 phage. The P1 phage possesses a recombinase called Cre which interacts specifically with a 34 base pairs loxP site. The loxP site is composed of two palindromic sequences of 13 bp separated by a 8 bp conserved sequence (Hoess et al., 1986). The recombination by the Cre enzyme between two loxP sites having an identical orientation leads to the deletion of the DNA fragment.

The Cre-loxP system used in combination with a homologous recombination technique has been first described by Gu et al. (1993, 1994). Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant cell host. The recombinase enzyme may be brought at the desired time either by (a) incubating the recombinant cell hosts in a culture medium containing this enzyme, by injecting the Cre enzyme directly into the desired cell, such as described by Araki et al. (1995), or by lipofection of the enzyme into the cells, such as described by Baubonis et al. (1993); (b) transfecting the cell host with a vector comprising the Cre coding sequence operably linked to a promoter functional in the recombinant cell host (in some embodiments, the promoter may be inducible), said vector being introduced in the recombinant cell host, such as described by Gu et al. (1993) and Sauer et al. (1988); (c) introducing in the genome of the cell host a polynucleotide comprising the Cre coding sequence operably linked to a promoter functional in the recombinant cell host (in some embodiments, the promoter may be inducible), and said polynucleotide being inserted in the genome of the cell host either by a random insertion event or an homologous recombination event, such as described by Gu et al. (1994).

In a specific embodiment, the vector containing the sequence to be inserted in the BAP28 gene by homologous recombination is constructed in such a way that selectable markers are flanked by loxP sites of the same orientation, it is possible, by treatment by the Cre enzyme, to eliminate the selectable markers while leaving the BAP28 sequences of interest that have been inserted by an homologous recombination event. Again, two selectable markers are needed: a positive selection marker to select for the recombination event and a negative selection marker to select for the homologous recombination event. Vectors and methods using the Cre-loxP system are described by Zou et al. (1994).

Thus, a third preferred DNA construct of the invention comprises, from 5'-end to 3'-end: (a) a first nucleotide sequence that is comprised in the BAP28 genomic sequence; (b) a nucleotide sequence comprising a polynucleotide encoding a positive selection marker, said nucleotide sequence comprising additionally two sequences defining a site recognized by a recombinase, such as a loxP site, the two sites being placed in the same orientation; and (c) a second nucleotide sequence that is comprised in the BAP28 genomic sequence, and is located on the genome downstream of the first BAP28 nucleotide sequence (a).

The sequences defining a site recognized by a recombinase, such as a loxP site, are preferably located within the nucleotide sequence (b) at suitable locations bordering the nucleotide sequence for which the conditional excision is sought. In one specific embodiment, two loxP sites are located at each side of the positive selection marker sequence, in order to allow its excision at a desired time after the occurrence of the homologous recombination event.

In a preferred embodiment of a method using the third DNA construct described above, the excision of the polynucleotide fragment bordered by the two sites recognized by a recombinase, preferably two loxP sites, is performed at a desired time, due to the presence within the genome of the recombinant host cell of a sequence encoding the Cre enzyme operably linked to a promoter sequence, preferably an inducible promoter, more preferably a tissue-specific promoter sequence and most preferably a promoter sequence which is both inducible and tissue-specific, such as described by Gu et al. (1994).

The presence of the Cre enzyme within the genome of the recombinant cell host may result of the breeding of two transgenic animals, the first transgenic animal bearing the BAP28-derived sequence of interest containing the loxP sites as described above and the second transgenic animal bearing the Cre coding sequence operably linked to a suitable promoter sequence, such as described by Gu et al. (1994).

Spatio-temporal control of the Cre enzyme expression may also be achieved with an adenovirus based vector that contains the Cre gene thus allowing infection of cells, or in vivo infection of organs, for delivery of the Cre enzyme, such as described by Anton and Graham (1995) and Kanegae et al. (1995).

The DNA constructs described above may be used to introduce a desired nucleotide sequence of the invention, preferably a BAP28 genomic sequence or a BAP28 cDNA sequence, and most preferably an altered copy of a BAP28 genomic or cDNA sequence, within a predetermined location of the targeted genome, leading either to the generation of an altered copy of a targeted gene (knock-out homologous recombination) or to the replacement of a copy of the targeted gene by another copy sufficiently homologous to allow an homologous recombination event to occur (knock-in homologous recombination). In a specific embodiment, the DNA constructs described above may be used to introduce a BAP28 genomic sequence or a BAP28 cDNA sequence. In some embodiments, said sequence comprises at least one biallelic marker of the present invention, preferably at least one biallelic marker selected from the group consisting of A1 to A58, preferably A1 to A27, A34, A37 to A41, A43 to A49, A52, and A54 to A58, more preferably one of the biallelic markers A1, A4, 16, A30, A31, A42, A50, A51, and A53.

Nuclear Antisense DNA Constructs

Other compositions containing a vector of the invention comprising an oligonucleotide fragment of the nucleic sequence SEQ ID No 2 or 3, preferably a fragment including the start codon of the BAP28 gene, as an antisense tool that inhibits the expression of the corresponding BAP28 gene or the expression of the PCTA-1 gene. Preferred methods using antisense polynucleotide according to the present invention are the procedures described by Sczakiel et al. (1995) or those described in PCT Application No WO 95/24223.

Preferably, the antisense tools are chosen among the polynucleotides (15-200 bp long) that are complementary to the 5' end or 3' end of the BAP28 mRNA. In one embodiment, a combination of different antisense polynucleotides complementary to different parts of the desired targeted gene are used.

A preferred antisense according to the invention is a polynucleotide according to the invention, more particularly polynucleotides comprising a contiguous span of at least 12, 15, 18, 20, 25, 30, 50, 80, 100, 150, 200, 250, 300, 350, 400, 450, 500, 600 or 1000 nucleotides of SEQ ID No 1, or the complements thereof, wherein said contiguous span comprises at least 1, 2, 3, 5, or 10 nucleotide positions of any one of the following ranges of nucleotide positions of SEQ ID No 1: 57386-27494, 58504-59354, 85947-86108, and 91259-91325.

Preferred antisense polynucleotides according to the present invention are complementary to a sequence of the mRNAs of BAP28 that contains either the translation initiation codon ATG or a splicing site. Further preferred antisense polynucleotides according to the invention are complementary of the splicing site of the BAP28 mRNA.

The antisense nucleic acids should have a length and melting temperature sufficient to permit formation of an intracellular duplex having sufficient stability to inhibit the expression of the BAP28 mRNA in the duplex. Strategies for designing antisense nucleic acids suitable for use in gene therapy are disclosed in Green et al., (1986) and Izant and Weintraub, (1984), the disclosures of which are incorporated herein by reference.

In some strategies, antisense molecules are obtained by reversing the orientation of the BAP28 coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of BAP28 antisense nucleic acids in vivo by operably linking DNA containing the antisense sequence to a promoter in a suitable expression vector.

Alternatively, suitable antisense strategies are those described by Rossi et al. (1991), in the International Applications Nos. WO 94/23026, WO 95/04141, WO 92/18522 and in the European Patent Application No EP 0 572 287 A2.

Preferably, the antisense polynucleotides of the invention have a 3' polyadenylation signal that has been replaced with a self-cleaving ribozyme sequence, such that RNA polymerase II transcripts are produced without poly(A) at their 3' ends, these antisense polynucleotides being incapable of export from the nucleus, such as described by Liu et al. (1994). In a preferred embodiment, these BAP28 antisense polynucleotides also comprise, within the ribozyme cassette, a histone stem-loop structure to stabilize cleaved transcripts against 3'-5' exonucleolytic degradation, such as the structure described by Eckner et al. (1991).

An alternative to the antisense technology that is used according to the present invention consists in using ribozymes that will bind to a target sequence via their complementary polynucleotide tail and that will cleave the corresponding RNA by hydrolyzing its target site (namely "hammerhead ribozymes"). Briefly, the simplified cycle of a hammerhead ribozyme consists of (1) sequence specific binding to the target RNA via complementary antisense sequences; (2) site-specific hydrolysis of the cleavable motif of the target strand; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposomes as a convenient vector. Preferred antisense ribozymes according to the present invention are prepared as described by Sczakiel et al. (1995), the specific preparation procedures being referred to in said article being herein incorporated by reference.

Oligonucleotide Probes and Primers

Polynucleotides derived from the BAP28 gene are useful in order to detect the presence of at least a copy of a nucleotide sequence of SEQ ID Nos 1-3, or a fragment, complement, or variant thereof in a test sample.

Preferred probes and primers of the invention include isolated, purified, or recombinant polynucleotides comprising a contiguous span of at least 12, 15, 18, 20, 25, 30, 50, 80, 100, 150, or 200 nucleotides, to the extent that such a length is consistent with the lengths of the particular nucleotide position, of SEQ ID No 1 or the complement thereof, wherein said contiguous span comprises at least 1, 2, 3, 5, 10, 20, 30, 40 or 50 nucleotides selected from the group consisting of the following nucleotide positions of SEQ ID No 1: 4997-5076, 5371-5544, 6121-6337, 9877-10018, 11522-11623, 12521-12661, 13453-13664, 13824-13957, 15376-15478, 16855-16965, 17378-17495, 18535-18642, 21446-21541, 21999-22087, 23036-23247, 23546-23667, 24270-24461, 26287-26470, 26611-26747, 28068-28260, 32540-32709, 33112-33270, 34586-34828, 35156-35287, 36660-36763, 36934-37077, 37803-37921, 38017-38138, 40365-40493, 42618-42848, 43452-43578, 44836-44999, 48223-48269, and 49656-49779. Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 a nucleotide of SEQ ID No 1 or the complements thereof, wherein said contiguous span comprises at least 1, 2, 3, 5, or 10 of the following nucleotide positions of SEQ ID No 1: 1-50357, 50499-50963, 51257-52147, 52299-53234, 53394-53553, 53689-53837, 53943-54028, 54198-54740, 54896-55753, 55913-57385, 57495-58503. 58828-85946, 59355-85946, 86169-91228, and/or 91852 to 97662.

Particularly preferred embodiments of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of a nucleic acid sequence selected from the group consisting of SEQ ID Nos 2 and 3 or the complements thereof, wherein said contiguous span comprises at least 1, 2, 3, 5, or 10 of nucleotide positions 1 to 4995 of SEQ ID No 2 or 3. Further embodiments of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of a nucleic acid sequence selected from the group consisting of SEQ ID Nos 2 and 3 or the complements thereof, wherein said contiguous span comprises at least 1, 2, 3, 5, or 10 of the following nucleotide positions of SEQ ID No 2 or 3: 1 to 2033, 2160 to 2348, and 2676 to 4995.

Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of a nucleic acid sequence selected from the group consisting of SEQ ID Nos 1-3, or the complements thereof, wherein said contiguous span comprises at least 1, 2, 3, 5, or 10 nucleotide positions of any one of the following ranges of nucleotide positions of:

(a) SEQ ID No 1: 1-2500, 2501-5000, 5001-7500, 7501-10000, 10001-12500, 12501-15000, 15001-17500, 17501-20000, 20001-22500, 22501-25000, 25001-27500, 27501-30000, 30001-32500, 32501-35000, 35001-37500, 37501-40000, 40001-42500, 42501-45000, 45001-47500, 47501-50000, 50001-50357, 50499-50963, 51257-52147, 52299-53234, 53394-53553, 53689-53837, 53943-54028, 54198-54740, 54896-55753, 55913-57385, 57495-58503, 58828-85946, 59355-85946, 86169-91228, and/or 91852 to 97662;

(b) SEQ ID No 2: 1 to 500, 501 to 1000, 1001 to 1500, 1501 to 2000, 2001 to 2500, 2501 to 3000, 3001 to 3500, 3501 to 4000, 4001 to 4500, 4501 to 4995, 5000 to 5500, 5501 to 6000, 6001 to 6500, and 6501 to 6782; and, (c) SEQ ID No 3: Ito 500, 501 to 1000, 1001 to 1500, 1501 to 2000, 2001 to 2500, 2501 to 3000, 3001 to 3500, 3501 to 4000, 4001 to 4500, 4501 to 4995, 5000 to 5500, 5501 to 6000, 6001 to 6500, 6501 to 7000, 7001 to 7500, 7501 to 7932.

Thus, the invention also relates to nucleic acid probes characterized in that they hybridize specifically, under the stringent hybridization conditions defined above, with a nucleic acid selected from the group consisting of the nucleotide sequences:

a) 1-50357, 50499-50963, 51257-52147, 52299-53234, 53394-53553, 53689-53837, 53943-54028, 54198-54740, 54896-55753, 55913-57385, 57495-58503, 58828-85946, 59355-85946, 86169-91228, and/or 91852 to 97662 of SEQ ID No 1 or a variant thereof or a sequence complementary thereto; or b) 1 to 4995 of SEQ ID No 2 or 3 or a variant thereof or a sequence complementary thereto; and, c) at least one of nucleotide ranges 1 to 2033, 2160 to 2348, 2676 to 4995 of SEQ ID No 2 or 3, or a variant thereof or a sequence complementary thereto.

Additionally, another preferred embodiment of a probe according to the invention consists of a nucleic acid comprising a biallelic marker selected from the group consisting of A1 to A58 or the complements thereto, for which the respective locations in the sequence listing are provided in Table 2. Preferably, a probe according to the present invention consists of a nucleic acid comprising one of the biallelic markers A1 to A27, A34, A37 to A41, A43 to A49, A52, and A54 to A58. More preferably, a probe according to the present invention consists of a nucleic acid comprising one of the biallelic markers A1, A4, 16, A30, A31, A42, A50, A51, and A53.

In one embodiment the invention encompasses isolated, purified, and recombinant polynucleotides comprising, consisting of, or consisting essentially of a contiguous span of 8 to 50 nucleotides of SEQ ID Nos 1, 2, or 3 and the complement thereof, wherein said span includes a BAP28-related biallelic marker in said sequence; In some embodiments said BAP28-related biallelic marker is selected from the group consisting of A1 to A58, and the complements thereof, or the biallelic markers in linkage disequilibrium therewith; In some embodiments said BAP28-related biallelic marker is selected from the group consisting of A1 to A27, A34, A37 to A41, A43 to A49, A52, and A54 to A58, and the complements thereof, or the biallelic markers in linkage disequilibrium therewith; In some embodiments said BAP28-related biallelic marker is selected from the group consisting of A1, A4, 16, A30, A31, A42, A50, A51, and A53, and the complements thereof or the biallelic markers in linkage disequilibrium therewith; In some embodiments said contiguous span is 18 to 35 nucleotides in length and said biallelic marker is within 4 nucleotides of the center of said polynucleotide; In some embodiments, said polynucleotide consists of said contiguous span and said contiguous span is 25 nucleotides in length and said biallelic marker is at the center of said polynucleotide; In some embodiments, the 3' end of said contiguous span is present at the 3' end of said polynucleotide; In some embodiments, the 3' end of said contiguous span is located at the 3' end of said polynucleotide and said biallelic marker is present at the 3' end of said polynucleotide. In a preferred embodiment, said probes comprises, consists of, or consists essentially of a sequence selected from the following sequences: P1 to P58, preferably P1 to P27, P34, P37 to P41. P43 to P49, P52, and P54 to P58, and the complementary sequences thereto.

In another embodiment the invention encompasses isolated, purified and recombinant polynucleotides comprising, consisting of, or consisting essentially of a contiguous span of 8 to 50 nucleotides of SEQ ID Nos 1, 2, or 3 or the complements thereof, wherein the 3' end of said contiguous span is located at the 3' end of said polynucleotide, and wherein the 3' end of said polynucleotide is located within 20 nucleotides upstream of a BAP28-related biallelic marker in said sequence; In some embodiments, said BAP28-related biallelic marker is selected from the group consisting of A1 to A58, and the complements thereof or the biallelic markers in linkage disequilibrium therewith; In some embodiments, said BAP28-related biallelic marker is selected from the group consisting of A1 to A27, A34, A37 to A41, A43 to A49, A52, and A54 to A58, and the complements thereof, or the biallelic markers in linkage disequilibrium therewith; In some embodiments said BAP28-related biallelic marker is selected from the group consisting of A1, A4, 16, A30, A31, A42, A50, A51, and A53, and the complements thereof, or the biallelic markers in linkage disequilibrium therewith; optionally, In some embodiments, the 3' end of said polynucleotide is located 1 nucleotide upstream of said BAP28-related biallelic marker in said sequence; In some embodiments, said polynucleotide consists essentially of a sequence selected from the following sequences: D1 to D58 and E1 to E58, preferably D1 to D27, D34, D37 to D41, D43 to D49, D52, D54 to D58, E1 to E27, E34, E37 to E41, E43 to E49, E52, and E54 to E58.

In a further embodiment, the invention encompasses isolated, purified, or recombinant polynucleotides comprising, consisting of, or consisting essentially of a sequence selected from the following sequences: B1 to B38 and C1 to C38, preferably B1 to B15, B22, B24, B25, B27 to 29, B32, B34 to B38, C1 to C15, C22, C24, C25, C27 to 29, C32, and C34 to C38.

In an additional embodiment, the invention encompasses polynucleotides for use in hybridization assay, sequencing assays, and enzyme-based mismatch detection assays for determining the identity of the nucleotide at a BAP28-related biallelic marker in SEQ ID No 1, or the complements thereof, as well as polynucleotides for use in amplifying segments of nucleotides comprising a BAP28-related biallelic marker in SEQ ID No 1 or the complements thereof; In some embodiments, said BAP28-related biallelic marker is selected from the group consisting of A1 to A58, and the complements thereof, or the biallelic markers in linkage disequilibrium therewith; In some embodiments, said BAP28-related biallelic marker is selected from the group consisting of A1 to A27, A34, A37 to A41, A43 to A49, A52, and A54 to A58, and the complements thereof, or the biallelic markers in linkage disequilibrium therewith; In some embodiments, said BAP28-related biallelic marker is selected from the group consisting of A1, A4, 16, A30, A31, A42, A50, A51, and A53, and the complements thereof, or the biallelic markers in linkage disequilibrium therewith.

Furthermore, the present invention also concerns the use of the oligonucleotide probes and primers according to the invention for determining the identity of the nucleotide at a BAP28-related biallelic marker. The use of these oligonucleotides in diagnostic is contemplated.

The formation of stable hybrids depends on the melting temperature (Tm) of the DNA. The Tm depends on the length of the primer or probe, the ionic strength of the solution and the G+C content. The higher the G+C content of the primer or probe, the higher is the melting temperature because G:C pairs are held by three H bonds whereas A:T pairs have only two. The GC content in the probes of the invention usually ranges between 10 and 75%, preferably between 35 and 60%, and more preferably between 40 and 55%.

A probe or a primer according to the invention has between 8 and 1000 nucleotides in length, or is specified to be at least 12, 15, 18, 20, 25, 35, 40, 50, 60, 70, 80, 100, 250, 500 or 1000 nucleotides in length. More particularly, the length of these probes and primers can range from 8, 10, 15, 20, or 30 to 100 nucleotides, preferably from 10 to 50, more preferably from 15 to 30 nucleotides. Shorter probes and primers tend to lack specificity for a target nucleic acid sequence and generally require cooler temperatures to form sufficiently stable hybrid complexes with the template. Longer probes and primers are expensive to produce and can sometimes self-hybridize to form hairpin structures. The appropriate length for primers and probes under a particular set of assay conditions may be empirically determined by one of skill in the art. A preferred probe or primer consists of a nucleic acid comprising a polynucleotide selected from the group of the nucleotide sequences of P1 to P58 and the complementary sequences thereto, B1 to B38 and C1 to C38, D1 to D58, E1 to E58, for which the respective locations in the sequence listing are provided in Tables 1, 3, and 4, preferably a nucleic acid comprising a polynucleotide selected from the group of the nucleotide sequences of P1 to P27, P34, P37 to P41, P43 to P49, P52, and P54 to P58, and the complementary sequences thereto, B1 to B15, B22, B24, B25, B27 to 29, B32, B34 to B38, C1 to C15, C22, C24, C25, C27 to 29, C32, C34 to C38, D1 to D27, D34, D37 to D41, D43 to D49, D52, D54 to D58, E1 to E27, E34, E37 to E41, E43 to E49, E52, and E54 to E58.

The primers and probes can be prepared by any suitable method, including, for example, cloning and restriction of appropriate sequences and direct chemical synthesis by a method such as the phosphodiester method of Narang et al. (1979), the phosphodiester method of Brown et al. (1979), the diethylphosphoramidite method of Beaucage et al. (1981) and the solid support method described in EP 0 707 592. The disclosures of all these documents are incorporated herein by reference.

Detection probes are generally nucleic acid sequences or uncharged nucleic acid analogs such as, for example peptide nucleic acids which are disclosed in International Patent Application WO 92/20702, morpholino analogs which are described in U.S. Pat. Nos. 5,185,444; 5,034,506 and 5,142,047. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified, U.S. patent application Ser. No. 07/049,061 filed Apr. 19, 1993 describes modifications, which can be used to render a probe non-extendable.

Any of the polynucleotides of the present invention can be labeled, if desired, by incorporating a label detectable by spectroscopic, photochemical, biochemical, immunochemical, or chemical means. For example, useful labels include radioactive substances ($^{32}$P, $^{35}$S, $^{3}$H, $^{125}$I), fluorescent dyes (5-bromodesoxyuridin, fluorescein, acetylaminofluorene, digoxigenin) or biotin. Preferably, polynucleotides are labeled at their 3' and 5' ends. Examples of non-radioactive labeling of nucleic acid fragments are described in the French patent No FR-7810975 or by Urdea et al (1988) or Sanchez-Pescador et al (1988). In addition, the probes according to the present invention may have structural characteristics such that they allow the signal amplification, such structural characteristics being, for example, branched DNA probes as those described by Urdea et al. in 1991 or in the European patent No EP 0 225 807 (Chiron).

A label can also be used to capture the primer, so as to facilitate the immobilization of either the primer or a primer extension product, such as amplified DNA, on a solid support. A capture label is attached to the primers or probes and can be a specific binding member which forms a binding pair with the solid's phase reagent's specific binding member (e.g. biotin and streptavidin). Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA Labeling techniques are well known to the skilled technician.

The probes of the present invention are useful for a number of purposes. They can be notably used in Southern hybridization to genomic DNA. The probes can also be used to detect PCR amplification products. They may also be used to detect mismatches in the BAP28 gene or mRNA using other techniques.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Consequently, the invention also deals with a method for detecting the presence of a nucleic acid comprising a nucleotide sequence selected from a group consisting of SEQ ID Nos 1-4, 9-13, a fragment or a variant thereof and a complementary sequence thereto in a sample, said method comprising the following steps of:

a) bringing into contact a nucleic acid probe or a plurality of nucleic acid probes which can hybridize with a nucleotide sequence included in a nucleic acid selected form the group consisting of the nucleotide sequences of SEQ ID Nos 1-4, 9-13, a fragment or a variant thereof and a complementary sequence thereto and the sample to be assayed; and b) detecting the hybrid complex formed between the probe and a nucleic acid in the sample.

The invention further concerns a kit for detecting the presence of a nucleic acid comprising a nucleotide sequence selected from a group consisting of SEQ ID Nos 1-4, 9-13, a fragment or a variant thereof and a complementary sequence thereto in a sample, said kit comprising:

a) a nucleic acid probe or a plurality of nucleic acid probes which can hybridize with a nucleotide sequence included in a nucleic acid selected form the group consisting of the nucleotide sequences of SEQ ID Nos 1-4, 9-13, a fragment or a variant thereof and a complementary sequence thereto; and b) in some embodiments, the kit also comprises reagents necessary for performing the hybridization reaction.

In a first preferred embodiment of this detection method and kit, said nucleic acid probe or the plurality of nucleic acid probes are labeled with a detectable molecule. In a second preferred embodiment of said method and kit, said nucleic acid probe or the plurality of nucleic acid probes has been immobilized on a substrate In a third preferred embodiment, the nucleic acid probe or the plurality of nucleic acid probes comprise either a sequence which is selected from the group consisting of the nucleotide sequences of P1 to P58 and the complementary sequences thereto, B11 to B38, C1 to C38, D1 to D58, E1 to E58 or a biallelic marker selected from the group consisting of A1 to A58 and the complements thereto, preferably a nucleic acid comprising a polynucleotide selected from the group of the nucleotide sequences of P1 to P27, P34, P37 to P41, P43 to P49, P52, and P54 to P58, and the complementary sequences thereto, B1 to B135, B22, B24, B25, B27 to 29, B32, B34 to B38, C1 to C15, C22, C24, C25, C27 to 29, C32, C34 to C38, D1 to D27, D34, D37 to D41, D43 to D49, D52, D54 to D58, E1 to E27, E34, E37 to E41, E43 to E49, E52, and E54 to E58, or a biallelic marker selected from the group consisting of A1 to A27, A34, A37 to A41, A43 to A49, A52, and A54 to A58, and the complements thereof.

Oligonucleotide Arrays

A substrate comprising a plurality of oligonucleotide primers or probes of the invention may be used either for detecting or amplifying targeted sequences in the BAP28 gene and may also be used for detecting mutations in the coding or in the non-coding sequences of the BAP28 gene.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092. These arrays may generally be produced using mechanical synthesis methods or light directed synthesis methods which incorporate a combination of photolithographic methods and solid phase oligonucleotide synthesis (Fodor et al., 1991). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854; and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256.

In another embodiment of the oligonucleotide arrays of the invention, an oligonucleotide probe matrix may advantageously be used to detect mutations occurring in the BAP28 gene and in its regulatory region. For this particular purpose, probes are specifically designed to have a nucleotide sequence allowing their hybridization to the genes that carry known mutations (either by deletion, insertion or substitution of one or several nucleotides). By known mutations, it is meant, mutations on the BAP28 gene that have been identified according, for example to the technique used by Huang et al. (1996) or Samson et al. (1996).

Another technique that is used to detect mutations in the BAP28 gene is the use of a high-density DNA array. Each oligonucleotide probe constituting a unit element of the high density DNA array is designed to match a specific subsequence of the BAP28 genomic DNA or cDNA. Thus, an array consisting of oligonucleotides complementary to subsequences of the target gene sequence is used to determine the identity of the target sequence with the wild gene sequence, measure its amount, and detect differences between the target sequence and the reference wild gene sequence of the BAP28 gene. In one such design, termed 41 tiled array, is implemented a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4 probes, the whole probe set containing all the possible mutations in the known wild reference sequence. The hybridization signals of the 15-mer probe set tiled array are perturbed by a single base change in the target sequence. As a consequence, there is a characteristic loss of signal or a "footprint" for the probes flanking a mutation position. This technique was described by Chee et al. in 1996, which is herein incorporated by reference.

Consequently, the invention concerns an array of nucleic acid molecules comprising at least one polynucleotide described above as probes and primers. Preferably, the invention concerns all array of nucleic acid comprising at least two polynucleotides described above as probes and primers.

A further object of the invention consists of an array of nucleic acid sequences comprising either at least one of the sequences selected from the group consisting of P1 to P58, B1 to B38, C1 to C38, D1 to D58, E1 to E58, the sequences complementary thereto, a fragment thereof of at least 8, 10, 12, 15, 18, 20, 25, 30, or 40 consecutive nucleotides thereof, or at least one sequence comprising a biallelic marker selected from the group consisting of A1 to A58 and the complements thereto, preferably either at least one of the sequences selected from the group consisting of P1 to P27, P34, P37 to P41, P43 to P49, P52, P54 to P58, B1 to B15, B22, B24, B25, B27 to 29, B32, B34 to B38, C1 to C15, C22, C24, C25, C27 to 29, C32, C34 to C38, D1 to D27, D34, D37 to D41, D43 to D49, D52, D54 to D58, E1 to E27. E34, E37 to E41, E43 to E49, E52, and E54 to E58, or at least one sequence comprising a biallelic marker selected from the group consisting of A1 to A27, A34, A37 to A41, A43 to A49, A52, and A54 to A58, and the complements thereof.

The invention also pertains to an array of nucleic acid sequences comprising either at least two of the sequences selected from the group consisting of P1 to P58, B1 to B338, C1 to C38, D1 to D58, E1 to E58, the sequences complementary thereto, a fragment thereof of at least 8 consecutive nucleotides thereof, or at least two sequences comprising a biallelic marker selected from the group consisting of A1 to A58 and the complements thereof. preferably either at least two of the sequences selected from the group consisting of P1 to P27, P34, P37 to P41, P43 to P49, P52, P54 to P58, B1 to B135, B22, B24, B25, B27 to 29, B32, B34 to B38, C1 to C15, C22, C24, C25, C27 to 29, C32, C34 to C38, D1 to D27, D34, D37 to D41, D43 to D49, D52, D54 to D58, E1 to E27, E34, E37 to E41, E43 to E49, E52, and E54 to E58 or at least two sequences comprising a biallelic marker selected from the group consisting of A1 to A27, A34, A37 to A41, A43 to A49, A52, and A54 to A58, and the complements thereof.

Amplification of the BAP28 Gene

1. DNA Extraction

As for the source of the genomic DNA to be subjected to analysis, any test sample can be foreseen without any particular limitation. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the context of the present invention is from peripheral venous blood of each donor.

The techniques of DNA extraction are well-known to the skilled technician. Such techniques are described notably by Mackey et al. (1998).

2. DNA Amplification

DNA amplification techniques are well-known to those skilled in the art. Amplification techniques that can be used in the context of the present invention include, but are not limited to the ligase chain reaction (LCR) described in EP-A-320 308, WO 9320227 and EP-A-439 182, the disclosures of which are incorporated herein by reference, the polymerase chain reaction (PCR, RT-PCR) and techniques such as the nucleic acid sequence based amplification (NASBA) described in Guatelli J C. et al. (1990) and in Compton J. (1991), Q-beta amplification as described in European Patent Application no 454-4610, strand displacement amplification as described in Walker et al. (1996) and EP A 684 315 and, target mediated amplification as described in PCT Publication WO 9322461, the disclosure of which is incorporated herein by reference.

LCR and Gap LCR are exponential amplification techniques, both depend on DNA ligase to join adjacent primers annealed to a DNA molecule. In Ligase Chain Reaction (LCR), probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate-3'hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. A method for multiplex LCR has also been described (WO 9320227). Gap LCR (GLCR) is a version of LCR where the probes are not adjacent but are separated by 2 to 3 bases.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770 or, to use Asymmetric Gap LCR (RT-AGLCR) as described by Marshall et al. (1994). AGLCR is a modification of GLCR that allows the amplification of RNA.

The PCR technology is the preferred amplification technique used in the present invention. A variety of PCR techniques are familiar to those skilled in the art. For a review of PCR technology see White (1997) and the publication entitled "PCR Methods and Applications" (1991, Cold Spring Harbor Laboratory Press). In each of these PCR procedures, PCR primers oil either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188. Each of these publications is incorporated by reference.

One of the aspects of the present invention is a method for the amplification of the human BAP28 gene, particularly of the genomic sequences of SEQ ID No 1 or of the cDNA sequence of SEQ ID No 2, or a fragment or a variant thereof in a test sample, preferably using the PCR technology. The method comprises the steps of contacting a test sample suspected of containing the target BAP28 encoding sequence or portion thereof with amplification reaction reagents comprising a pair of amplification primers, and eventually in some instances a detection probe that can hybridize with an internal region of amplicon sequences to confirm that the desired amplification reaction has taken place.

Thus, the present invention also relates to a method for the amplification of a human BAP28 gene sequence, particularly of a portion of the genomic sequences of SEQ ID No 1 or of the cDNA sequence of SEQ ID No 2, 3 or 4, or a variant thereof in a test sample, said method comprising the steps of:

a) contacting a test sample suspected of containing the targeted BAP28 gene sequence comprised in a nucleotide sequence selected from a group consisting of SEQ ID Nos 1-4, or fragments or variants thereof with amplification reaction reagents comprising a pair of amplification primers as described above and located on either side of the polynucleotide region to be amplified; and b) in some embodiments, the method also comprises detecting the amplification products.

The invention also concerns a kit for the amplification of a human BAP28 gene sequence, particularly of a portion of the genomic sequence of SEQ ID No 1 or of the cDNA sequence of SEQ ID No 2, 3 or 4, or a variant thereof in a test sample, wherein said kit comprises:

a) a pair of oligonucleotide primers located on either side of the BAP28 region to be amplified; and b) in some embodiments, the kit also comprises the reagents necessary for performing the amplification reaction.

In a first preferred embodiment of the above amplification method or kit, the amplification product is detected by hybridization with a labeled probe having a sequence which is complementary to the amplified region. In another embodiment of the above amplification method and kit, primers comprise a sequence which is selected from the group consisting of the nucleotide sequences of B1 to B38, C1 to C38, D1 to D58, and E1 to E58, preferably B1 to B135, B22, B24, B25, B27 to 29, B32, B34 to B38, C1 to C15, C22, C24, C25, C27 to 29, C32, C34 to C38, D1 to D27, D34, D37 to D41. D43 to D49, D52, D54 to D58, E1 to E27, E34, E37 to E41, E43 to E49, E52, and E54 to E58

The primers are more particularly characterized in that they have sufficient complementarity with any sequence of a strand of the genomic sequence close to the region to be amplified, for example with a non-coding sequence adjacent to exons to amplify.

BAP28 Proteins and Polypeptide Fragments

The BAP28 protein has 2144 amino acids in length. This protein is highly conserved in various species Such as *Drosophila melanogaster, Arabidopsis thaliana, Schizosaccahromyces pombe, Caenorhabditis elegans, Saccharomyces cerevisiae* and *Tetraodon nigroviridis*. The protein alignment between the human BAP28 and the proteins from *Drosophila melanogaster, Arabidopysis thaliana, Schizosaccahromyces pombe, Caenorhabditis elegans, Saccharormyces cerevisiae* is disclosed in the FIG. 3. The protein alignment between the human BAP28 and the protein from *Tetraodon nigroviridis* is disclosed in the FIG. 4. The BAP28 protein is also well conserved among the mammalian. Indeed, several ESTs with a good homolgy with the human BAP28 have been identified. Some examples of ESTs are the following (Genbank Accession Number/species): AW423202/zebrafish; AW481398/*Bos taurus*; AW325866/*Bos taurus*; AW353291/*Bos taurus*; AW315340/*Bos taurus*; AA681616/mouse; AV120680/*Mus musculus* and, D77458/mouse.

Analysis of the BAP28 protein sequence provided several potential phosphorylation sites and N-glycolsylation sites in BAP28. More particularly, protein kinase C phosphorylation sites have been identified in positions 199-201, 269-271, 387-389, 415-417, 508-510, 650-652, 717-719, 778-780, 792-794, 884-886, 903-905, 999-1001, 1091-1093, 1349-1351, 1506-1508, 1573-1575, 1614-1616, 1632-1634, 1673-1675, 1743-1745, 1808-1810, 1829-1831, 1911-1913, and 2077-2079 of SEQ ID No 4; casein kinase II phosphorylation sites have been identified in positions 22-25, 50-53, 253-256, 363-366, 408-411, 409-412, 508-511, 539-542, 590-593, 689-692, 717-720, 745-748, 961-964, 979-982, 1091-1094, 1105-1108, 1195-1198, 1492-1495, 1723-1726, 1882-1885, 1972-1975, and 1981-1984 of SEQ ID No4. Otherwise, several potential N-glycosylation sites have been identified in positions 93-96, 154-157, 776-779, 882-885, 1347-1350, 1488-1491, 1630-1633, 1746-1749, and 1970-1973 of SEQ ID No 5. A conserved HEAT_REPEAT motif has been identified in positions 2106-2139 of SEQ ID No 5. The HEAT_REPEAT motif are generally involved in protein-protein interaction. The PCT application WO98/12327 showed that BAP28 should be involved in interaction with BRCA1.

The term "BAP28 polypeptides" is used herein to embrace all of the proteins and polypeptides of the present invention. Also forming part of the invention are polypeptides encoded by the polynucleotides of the invention, as well as fusion polypeptides comprising such polypeptides. The invention embodies BAP28 proteins from humans, including isolated or purified BAP28 proteins consisting, consisting essentially, or comprising the sequence of SEQ ID No 5 or fragments thereof. The present invention also embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID No 5, wherein said contiguous span includes at least 1, 2, 3, 5 or 10 of the amino acid positions 1 to 1629 of the SEQ ID No 5. The present invention also embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID No 5, wherein said contiguous span include an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an alanine at the amino acid position 2050 of SEQ ID No 5. In other preferred embodiments the BAP28 protein contains an alanine residue at amino acid position 2050 in SEQ ID No 5.

Four biallelic markers of the present invention, namely A16, A19, A21 and A25, provide an amino acid sequence change. Indeed, the biallelic marker A16 encodes a Ser or Asn residue at the position 1694 of the BAP28 protein; the biallelic marker A19 encodes a Ala or Val residue at the position 1854 of the BAP28 protein; the biallelic marker A21 encodes a Asp or Asn at tile position 1967 of the BAP28 protein; and the biallelic marker A25 encodes a Gly or Glu at the position 2017 of the BAP28 protein. The invention encompasses the BAP28 proteins comprising all the combinations of the above-described residues at the positions 1694, 1854, 1967, and 2017.

The variant protein and fragments thereof which contain an asparagine at the amino acid position 1694 of SEQ ID No 5 are collectively referred to herein as "11694-Asn variants". The variant protein and fragments thereof which contain a valine at the amino acid position 1854 of SEQ ID No 5 are collectively referred to herein as "1854-Val variants". The variant protein and fragments thereof which contain an asparagine at the amino acid position 1967 of SEQ ID No 5 are collectively referred to herein as "1967-Asn variants". The variant protein and fragments thereof which contain a glutamic acid at the amino acid position 2017 of SEQ ID No 5 are collectively referred to herein as "2017-Glu variants". The variant protein and fragments thereof which contain an alanine at the amino acid position 2050 of SEQ ID No 5 are collectively referred to herein as "2050-Ala variants". In other preferred embodiments of the polypeptides of the present invention, the contiguous stretch of amino acids comprises the site of a mutation or functional mutation, including a deletion, addition, swap or truncation of the amino acids in the BAP28 protein sequence.

The invention also encompasses a purified, isolated, or recombinant polypeptide comprising an amino acid sequence having at least 70, 75, 80, 85, 90, 95, 98 or 99% amino acid identity with the amino acid sequence of SEQ ID No 5 or a fragment thereof.

The invention concerns the polypeptide which are encoded by a nucleic acid comprising a sequence selected from the group consisting of the sequence SEQ ID Nos 1-3 or fragments thereof.

BAP28 proteins are preferably isolated from human or mammalian tissue samples or expressed from human or mammalian genes. The BAP28 polypeptides of the invention can be made using routine expression methods known in the art. The polynucleotide encoding the desired polypeptide is ligated into an expression vector suitable for any convenient host. Both eukaryotic and prokaryotic host systems may be used in forming recombinant polypeptides, and a summary of some of the more common systems. The polypeptide is then isolated from lysed cells or from the culture medium and purified to the extent needed for its intended use. Purification is by any technique known in the art, for example, differential extraction, salt fractionation, chromatography, centrifugation, and the like. See, for example, Methods in Enzymology for a variety of methods for purifying proteins.

In addition, shorter protein fragments is produced by chemical synthesis. Alternatively the proteins of the invention is extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis.

Any BAP28 cDNA, including SEQ ID Nos 2 and 3, or fragments thereof is used to express BAP28 proteins and polypeptides. The nucleic acid encoding the BAP28 protein or fragments thereof to be expressed is operably linked to a promoter in an expression vector using conventional cloning technology. The BAP28 insert in the expression vector may comprise the full coding sequence for the BAP28 protein or a portion thereof. For example, the BAP28 derived insert may encode a polypeptide comprising at least 10 consecutive amino acids of the BAP28 protein of SEQ ID No 5, wherein said contiguous span includes at least 1, 2, 3, 5 or 10 of the amino acid positions 1 to 1629 of the SEQ ID No 5, or wherein polypeptide is a 2050-Ala variant BAP28 polypeptide.

The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence is optimized for the particular expression organism in which the expression vector is introduced, as explained by Hatfield, et al., U.S. Pat. No. 5,082,767.

In one embodiment, the entire coding sequence of the BAP28 cDNA through the poly A signal of the cDNA are operably linked to a promoter in the expression vector. Alternatively, if the nucleic acid encoding a portion of the BAP28 protein lacks a methionine to serve as the initiation site, an initiating methionine can be introduced next to the first codon of the nucleic acid using conventional techniques. Similarly, if the insert from the BAP28 cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The nucleic acid encoding the BAP28 protein or a portion thereof is obtained by PCR from a bacterial vector containing the BAP28 cDNA of SEQ ID No 2 or 3 using oligonucleotide primers complementary to the BAP28 cDNA or portion thereof and containing restriction endonuclease sequences for Pst I incorporated into the 5'primer and Bgl II at the 5' end of the corresponding cDNA 3' primer, taking care to ensure that the sequence encoding the BAP28 protein or a portion thereof is positioned properly with respect to the poly A signal. The purified fragment obtained from the resulting PCR reaction is digested with PstI, blunt ended with an exonuclease, digested with Bgl II, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.).

Alternatively, the nucleic acids encoding the BAP28 protein or a portion thereof is cloned into pED6dpc2 (Genetics Institute, Cambridge, Mass.). The resulting pED6dpc2 constructs is transfected into a suitable host cell, such as COS 1 cells. Methotrexate resistant cells are selected and expanded.

The above procedures may also be used to express a mutant BAP28 protein responsible for a detectable phenotype or a portion thereof.

The expressed proteins are purified using conventional purification techniques such as ammonium sulfate precipitation or chromatographic separation based on size or charge. The protein encoded by the nucleic acid insert may also be purified using standard immunochromatography techniques. In such procedures, a solution containing the expressed BAP28 protein or portion thereof, such as a cell extract, is applied to a column having antibodies against the BAP28 protein or portion thereof is attached to the chromatography matrix. The expressed protein is allowed to bind the immunochromatography column. Thereafter, the column is washed to remove non-specifically bound proteins. The specifically bound expressed protein is then released from the column and recovered using standard techniques.

To confirm expression of the BAP28 protein or a portion thereof, the proteins expressed from host cells containing an expression vector containing an insert encoding the BAP28 protein or a portion thereof can be compared to the proteins expressed in host cells containing the expression vector without an insert. The presence of a band in samples from cells containing the expression vector with an insert which is absent in samples from cells containing the expression vector without an insert indicates that the BAP28 protein or a portion thereof is being expressed. Generally, the band will have the mobility expected for the BAP28 protein or portion thereof. However, the band may have a mobility different than that expected as a result of modifications such as glycosylation, ubiquitination, or enzymatic cleavage.

Antibodies capable of specifically recognizing the expressed BAP28 protein or a portion thereof are described below.

If antibody production is not possible, the nucleic acids encoding the BAP28 protein or a portion thereof is incorporated into expression vectors designed for use in purification schemes employing chimeric polypeptides. In such strategies the nucleic acid encoding the BAP28 protein or a portion thereof is inserted in frame with the gene encoding the other half of the chimera. The other half of the chimera is β-globin or a nickel binding polypeptide encoding sequence. A chromatography matrix having antibody to β-globin or nickel attached thereto is then used to purify the chimeric protein. Protease cleavage sites is engineered between the β-globin gene or the nickel binding polypeptide and the BAP28 protein or portion thereof. Thus, the two polypeptides of the chimera is separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques are well known to those skilled in the art of molecular biology. Standard methods are published in methods texts such as Davis et al., (1986) and many of the methods are available from Stratagene, Life Technologies, Inc., or Promega. Polypeptide may additionally be produced from the construct using in vitro translation systems such as the In vitro Express™ Translation Kit (Stratagene).

Antibodies that Bind BAP28 Polypeptides of the Invention

Any BAP28 polypeptide or whole protein may be used to generate antibodies capable of specifically binding to expressed BAP28 protein or fragments thereof as described. The antibody compositions of the invention are capable of specifically binding or specifically bind to the BAP28 protein. For an antibody composition to specifically bind to the BAP28 protein it must demonstrate at least a 5%, 10%, 15%, 20%, 25%, 50%, or 100% greater binding affinity for full length BAP28 protein than for any full length protein in an ELISA, RIA, or other antibody-based binding assay. For an antibody composition to specifically bind to the 1694-Asn, 1854-Val, 1967-Asn, 2017-Glu, or 2050-Ala variant BAP28 protein, it must demonstrate at least a 5%, 10%, 15%, 20%, 25%, 50%, or 100% greater binding affinity for full length 1694-Asn, 1854-Val, 1967-Asn, 2017-Glu, or 2050-Ala variant BAP28 protein than for respectively a 1694-Ser, 1854-Ala, 1967-Asp, 2017-Gly or 2050-Val full length protein in an ELISA, RIA, or other antibody-based binding assay. The present invention also contemplates the antibodies which are specific of a protein BAP28 comprising one combination of the above-described residues at the positions 1694, 1854, 1967, and 2017.

In a preferred embodiment of the invention antibody compositions are capable of selectively binding, or selectively bind to an epitope-containing fragment of a polypeptide comprising a contiguous span of at least 6 amino acids, preferably at least 8 to 10 amino acids, more preferably at least 12, 15, 20, 25, 30, 40, 50, or 100 amino acids of SEQ ID No 5, wherein said epitope comprises at least 1, 2, 3, 5 or 10 of the amino acid positions selected from the group consisting of 1 to 1629 and 2050 of SEQ ID No 5, wherein said antibody composition is optionally either polyclonal or monoclonal. In a other preferred embodiment, antibody compositions are capable of selectively binding, or selectively bind to an epitope-containing fragment of a polypeptide comprising a contiguous span of at least 6 amino acids, preferably at least 8 to 10 amino acids, more preferably at least 12, 15, 20, 25, 30, 40, 50, or 100 amino acids of SEQ ID No 5, wherein said epitope comprises an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an alanine at the amino acid position 2050 of SEQ ID No 5, wherein said antibody composition is optionally either polyclonal or monoclonal.

The present invention also contemplates the use of polypeptides comprising a contiguous span of at least 6 amino acids, preferably at least 8 to 10 amino acids, more preferably at least 12, 15, 20, 25, 50, or 100 amino acids of a BAP28 polypeptide in the manufacture of antibodies, wherein said contiguous span comprises at least 1, 2, 3, 5 or 10 of the amino acid positions selected from the group consisting of 1 to 1629 of SEQ ID No 5. The present invention further contemplates the use of polypeptides comprising a contiguous span of at least 6 amino acids, preferably at least 8 to 10 amino acids, more preferably at least 12, 15, 20, 25, 50, or 100 amino acids of a BAP28 polypeptide in the manufacture of antibodies, wherein said contiguous span comprises an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an alanine at the amino acid position 2050 of SEQ ID No 5. In a preferred embodiment such polypeptides are useful in the manufacture of antibodies to detect the presence and absence of the BAP28 protein.

Non-human animals or mammals, whether wild-type or transgenic, which express a different species of BAP28 than the one to which antibody binding is desired, and animals which do not express BAP28 (i.e. a BAP28 knock out animal as described in herein) are particularly useful for preparing antibodies. BAP28 knock out animals will recognize all or most of the exposed regions of BAP28 as foreign antigens, and therefore produce antibodies with a wider array of BAP28 epitopes. Moreover, smaller polypeptides with only 10 to 30 amino acids may be useful in obtaining specific binding to the BAP28 protein. In addition, the humoral immune system of animals which produce a species of BAP28 that resembles the antigenic sequence will preferentially recognize the differences between the animal's native BAP28 species and the antigen sequence, and produce antibodies to these unique sites in the antigen sequence. Such a technique will be particularly useful in obtaining antibodies that specifically bind to the BAP28 protein.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labeled, either by a radioactive, a fluorescent or an enzymatic label.

Consequently, the invention is also directed to a method for detecting specifically the presence of a human BAP28 polypeptide according to the invention in a biological sample, said method comprising the following steps:

a) bringing into contact the biological sample with a polyclonal or monoclonal antibody directed against the BAP28 polypeptide of the amino acid sequence of SEQ ID No 5, or to a peptide fragment or variant thereof;

b) detecting the antigen-antibody complex formed.

The invention also concerns a diagnostic kit for detecting in vitro the presence of a human BAP28 polypeptide according to the present invention in a biological sample, wherein said kit comprises:

a) a polyclonal or monoclonal antibody directed against the BAP28 polypeptide of the amino acid sequence of SEQ ID No 5, or to a peptide fragment or variant thereof. In some embodiments, the antibody may be labeled;

b) a reagent allowing the detection of the antigen-antibody complexes formed, said reagent optionally being labelled, or being able to be recognized itself by a labeled reagent, more particularly in the case when the above-mentioned monoclonal or polyclonal antibody is not labeled by itself.

BAP28-related Biallelic Markers

Advantages of the Biallelic Markers of the Present Invention

The BAP28-related biallelic markers of the present invention offer a number of important advantages over other genetic markers such as RFLP (Restriction fragment length polymorphism) and VNTR (Variable Number of Tandem Repeats) markers.

The first generation of markers, were RFLPs, which are variations that modify the length of a restriction fragment. But methods used to identify and to type RFLPs are relatively wasteful of materials, effort, and time. The second generation of genetic markers were VNTRs, which can be categorized as either minisatellites or microsatellites. Minisatellites are tandemly repeated DNA sequences present in units of 5-50 repeats which are distributed along regions of the human chromosomes ranging from 0.1 to 20 kilobases in length. Since they present many possible alleles, their informative content is very high. Minisatellites are scored by performing Southern blots to identify the number of tandem repeats present in a nucleic acid sample from the individual being tested. However, there are only $10^4$ potential VNTRs that can be typed by Southern blotting. Moreover, both RFLP and VNTR markers are costly and time-consuming to develop and assay in large numbers.

Single nucleotide polymorphism or biallelic markers can be used in the same manner as RFLPs and VNTRs but offer several advantages. SNP are densely spaced in the human genome and represent the most frequent type of variation. An estimated number of more than $10^7$ sites are scattered along the $3 \times 10^9$ base pairs of the human genome. Therefore, SNP occur at a greater frequency and with greater uniformity than RFLP or VNTR markers which means that there is a greater probability that such a marker will be found in close proximity to a genetic locus of interest. SNP are less variable than VNTR markers but are mutationally more stable.

Also, the different forms of a characterized single nucleotide polymorphism, Such as the biallelic markers of the present invention, are often easier to distinguish and can therefore be typed easily on a routine basis. Biallelic markers have single nucleotide based alleles and they have only two common alleles, which allows highly parallel detection and automated scoring. The biallelic markers of the present invention offer the possibility of rapid, high throughput genotyping of a large number of individuals.

Biallelic markers are densely spaced in the genome, sufficiently informative and can be assayed in large numbers. The combined effects of these advantages make biallelic markers extremely valuable in genetic studies. Biallelic markers can be used in linkage studies in families, in allele sharing methods, in linkage disequilibrium studies in populations, in association studies of case-control populations or of trait positive and trait negative populations. An important aspect of the present invention is that biallelic markers allow association studies to be performed to identify genes involved in complex traits. Association studies examine the frequency of marker alleles in unrelated case- and control-populations and are generally employed in the detection of polygenic or sporadic traits. Association studies may be conducted within the general population and are not limited to studies performed on related individuals in affected families (linkage studies). Biallelic markers in different genes can be screened in parallel for direct association with disease or response to a treatment. This multiple gene approach is a powerful tool for a variety of human genetic studies as it provides the necessary statistical power to examine the synergistic effect of multiple genetic factors on a particular phenotype, drug response, sporadic trait, or disease state with a complex genetic etiology.

Although most valuable in association studies, the biallelic markers of the present invention can have a wide range of uses, and may for example also be used in forensic identification of individual humans, such as for identification of descendants, determination of paternity, criminal identification, and the like. For example, a DNA sample is obtained from a person or from a cellular sample (e.g., crime scene evidence such as blood, saliva, semen, and the like) and the identity of the allele present at any one or preferably multiple biallelic markers is determined according to any of the detection methods described herein. On the basis of the allele(s) present at the specified positions, the individual from which the sample originated will be identified with respect to his/her genotype. The biallelic markers of the invention may be used alone or in conjunction with other genetic markers, including RFLP and VNTR to conclusively identify an individual or to rule out the individual as a possible perpetrator.

BAP28-Related Biallelic Markers and Polynucleotides Related Thereto

The invention also concerns BAP28-related biallelic markers. A portion of the biallelic markers of the present invention designated A1 to A58 are disclosed in Table 2, including their location on the BAP28 gene. These biallelic markers are also each listed as a single base polymorphism in the features of SEQ ID No 1.

The invention also relates to a purified and/or isolated nucleotide sequence comprising a polymorphic base of a BAP28-related biallelic marker, preferably of a biallelic marker selected from the group consisting of A1 to A58, more preferably one of the biallelic markers A1 to A27, A34, A37 to A41, A43 to A49, A52, and A54 to A58, still more preferably one of the biallelic markers A1, A4, 16, A30, A31, A42, A50, A51, and A53, and the complements thereof. The sequence has between 8 and 1000 nucleotides in length, and preferably comprises at least 8, 10, 12, 15, 18, 20, 25, 35, 40, 50, 60, 70, 80, 100, 250, 500 or 1000 contiguous nucleotides of a nucleotide sequence selected from the group consisting of SEQ ID Nos 1, 2 or 3, or a variant thereof or a complementary sequence thereto. These nucleotide sequences comprise the polymorphic base of either allele 1 or allele 2 of the respective biallelic marker. In some embodiments, said biallelic marker may be within 6, 5, 4, 3, 2, or 1 nucleotides of the center of said polynucleotide or at the center of said polynucleotide. In some embodiments, the 3' end of said contiguous span may be present at the 3' end of said polynucleotide. In some embodiments, a BAP28-related biallelic marker biallelic marker may be present at the 3' end of said polynucleotide. In some embodiments, the 3' end of said polynucleotide may be located within or at least 2, 4, 6, 8, 10, 12, 15, 18, 20, 25, 50, 100, 250, 500, or 1000 nucleotides upstream of a BAP28-related biallelic marker in said sequence. In some embodiments, the 3' end of said polynucleotide may be located 1 nucleotide upstream of a BAP28-related biallelic marker in said sequence. In some embodiments, said polynucleotide may further comprise a label. In some embodiments, said polynucleotide can be attached to solid support. In a further embodiment, the polynucleotides defined above can be used alone or in any combination.

The invention further concerns a nucleic acid encoding the BAP28 protein, wherein said nucleic acid comprises a polymorphic base of a biallelic marker selected from the group consisting of A1 to A58 and the complements thereof, preferably A1 to A27, A34, A37 to A41, A43 to A49, A52, and A54 to A58.

The invention also encompasses the use of any polynucleotide for, or any polynucleotide for use in, determining the identity of one or more nucleotides at a BAP28-related biallelic marker. In addition, the polynucleotides of the invention for use in determining the identity of one or more nucleotides at a BAP28-related biallelic marker encompass polynucleotides with any further limitation described in this disclosure, or those following, specified alone or in any combination. In some embodiments, said BAP28-related biallelic marker is selected from the group consisting of A1 to A58, and the complements thereof, or the biallelic markers in linkage disequilibrium therewith; In some embodiments, said BAP28-related biallelic marker is selected from the group consisting of A1 to A27, A34, A37 to A41, A43 to A49, A52, and A54 to A58, and the complements thereof, or the biallelic markers in linkage disequilibrium therewith; In some embodiments, said BAP28-related biallelic marker is selected from the group consisting of A1, A4, 16, A30, A31, A42, A50, A51, and A53, and the complements thereof, or the biallelic markers in linkage disequilibrium therewith; In some embodiments, said polynucleotide may comprise a sequence disclosed in the present specification; In some embodiments, said polynucleotide may comprise, consist of, or consist essentially of any polynucleotide described in the present specification; In some embodiments, said determining may be performed in a hybridization assay, sequencing assay, microsequencing assay, or an enzyme-based mismatch detection assay; In some embodiments, said polynucleotide may be attached to a solid Support, array, or addressable array; In some embodiments, said polynucleotide may be labeled. A preferred polynucleotide may be used in a hybridization assay for determining the identity of the nucleotide at a BAP28-related biallelic marker. Another preferred polynucleotide may be used in a sequencing or microsequencing assay for determining the identity of the nucleotide at a BAP28-related biallelic marker. A third preferred polynucleotide may be used in an enzyme-based mismatch detection assay for determining the identity of the nucleotide at a BAP28-related biallelic marker. A fourth preferred polynucleotide may be used in amplifying a segment of polynucleotides comprising a BAP28-related biallelic marker. In some embodiments, any of the polynucleotides described above may be attached to a solid support, array, or addressable array; In some embodiments, said polynucleotide may be labeled.

Additionally, the invention encompasses the use of any polynucleotide for, or any polynucleotide for use in, amplifying a segment of nucleotides comprising a BAP28-related biallelic marker. In addition, the polynucleotides of the invention for use in amplifying a segment of nucleotides comprising a BAP28-related biallelic marker encompass polynucleotides with any further limitation described in this disclosure, or those following, specified alone or in any combination: In some embodiments, said BAP28-related biallelic marker is selected from the group consisting of A1 to A58, and the complements thereof, or the biallelic markers in linkage disequilibrium therewith: In some embodiments, wherein said BAP28-related biallelic marker is selected from the group consisting of A1 to A27, A34. A37 to A41, A43 to A49, A52, and A54 to A58, and the complements thereof, or the biallelic markers in linkage disequilibrium therewith; In some embodiments, said BAP28-related biallelic marker is selected from the group consisting of A1, A4, 16, A30, A31, A42, A50, A51, and A53, and the complements thereof, or the biallelic markers in linkage disequilibrium therewith; In some embodiments, said polynucleotide may comprise a sequence disclosed in the present specification; In some embodiments, said polynucleotide may comprise, consist of, or consist essentially of any polynucleotide described in the present specification; In some embodiments, said amplifying may be performed by a PCR or LCR. In some embodiments, said polynucleotide may be attached to a solid support, array, or addressable array. In some embodiments, said polynucleotide may be labeled.

The primers for amplification or sequencing reaction of a polynucleotide comprising a biallelic marker of the invention may be designed from the disclosed sequences for any method known in the art. A preferred set of primers are fashioned such that the 3' end of the contiguous span of identity with a sequence selected from the group consisting of SEQ ID Nos 1, 2 or 3, or a sequence complementary thereto or a variant thereof is present at the 3' end of the primer. Such a configuration allows the 3' end of the primer to hybridize to a selected nucleic acid sequence and dramatically increases the efficiency of the primer for amplification or sequencing reactions. Allele specific primers may be designed such that a polymorphic base of a biallelic marker is at the 3' end of the contiguous span and the contiguous span is present at the 3' end of the primer. Such allele specific primers tend to selectively prime an amplification or sequencing reaction so long as they are used with a nucleic acid sample that contains one of the two alleles present at a biallelic marker. The 3' end of the primer of the invention may be located within or at least 2, 4, 6, 8, 10, 12, 15, 18, 20, 25, 50, 100, 250, 500, or 1000 nucleotides upstream of a BAP28-related biallelic marker in said sequence or at any other location which is appropriate for their intended use in sequencing, amplification or the location of novel sequences or markers. Thus, another set of preferred amplification primers comprise an isolated polynucleotide consisting essentially of a contiguous span of 8 to 50 nucleotides in a sequence selected from the group consisting of SEQ ID Nos 1, 2 or 3 or a sequence complementary thereto or a variant thereof, wherein the 3' end of said contiguous span is located at the 3' end of said polynucleotide, and wherein the 3' end of said polynucleotide is located upstream of a BAP28-related biallelic marker in said sequence. Preferably, those amplification primers comprise a sequence selected from the group consisting of the sequences B1 to B338 and C1 to C38, preferably B1 to B 15, B22, B24, B25, B27 to 29, B32, B34 to B38, C1 to C15. C22, C24, C25, C27 to 29. C32 and C34 to C38. Primers with their 3' ends located 1 nucleotide upstream of a biallelic marker of BAP28 have a special utility as microsequencing assays. Preferred microsequencing primers are described in Table 4. In some embodiments, microsequencing primers are selected from the group consisting of the nucleotide sequences D1 to D58 and E1 to E58, preferably D1 to D27, D34, D37 to D41, D43 to D49, D52, D54 to D58, E1 to E27, E34, E37 to E41, E43 to E49, E52, and E54 to E58.

The probes of the present invention may be designed from the disclosed sequences for any method known in the art, particularly methods which allow for testing if a marker disclosed herein is present. A preferred set of probes may be designed for use in the hybridization assays of the invention in any manner known in the art such that they selectively bind to one allele of a biallelic marker, but not the other under any particular set of assay conditions. Preferred hybridization probes comprise the polymorphic base of either allele 1 or allele 2 of the considered biallelic marker. In some embodiments, said biallelic marker may be within 6, 5, 4, 3, 2, or 1 nucleotides of the center of the hybridization probe or at the center of said probe. In a preferred embodiment, the probes are selected in the group consisting of the sequences P1 to P58 and the complementary sequence thereto (Table 3), preferably P1 to P27, P34, P37 to P41, P43 to P49, P52, and P54 to P58.

It should be noted that the polynucleotides of the present invention are not limited to having the exact flanking sequences surrounding the polymorphic bases which are enumerated in Sequence Listing. Rather, it will be appreciated that the flanking sequences surrounding the biallelic markers may be lengthened or shortened to any extent compatible with their intended use and the present invention specifically contemplates such sequences. The flanking regions outside of the contiguous span need not be homologous to native flanking sequences which actually occur in human subjects. The addition of any nucleotide sequence which is compatible with the nucleotides intended use is specifically contemplated.

Primers and probes may be labeled or immobilized on a solid support as described in "Oligonucleotide probes and primers". The polynucleotides of the invention which are attached to a solid support encompass polynucleotides with any further limitation described in this disclosure, or those following, specified alone or in any combination: In some embodiments, said polynucleotides may be specified as attached individually or in groups of at least 2, 5, 8, 10, 12, 15, 20, or 25 distinct polynucleotides of the invention to a single solid support. In some embodiments, polynucleotides other than those of the invention may attached to the same solid support as polynucleotides of the invention. In some embodiments, when multiple polynucleotides are attached to a solid support they may be attached at random locations, or in an ordered array. In some embodiments, said ordered array may be addressable.

The present invention also encompasses diagnostic kits comprising one or more polynucleotides of the invention with a portion or all of the necessary reagents and instructions for genotyping a test subject by determining the identity of a nucleotide at a BAP28-related biallelic marker. The polynucleotides of a kit may optionally be attached to a solid support, or be part of an array or addressable array of polynucleotides. The kit may provide for the determination of the identity of the nucleotide at a marker position by any method known in the art including, but not limited to, a sequencing assay method, a microsequencing assay method, a hybridization assay method, or an enzyme-based mismatch detection assay method.

Methods for De Novo Identification of Biallelic Markers

Any of a variety of methods can be used to screen a genomic fragment for single nucleotide polymorphisms such as differential hybridization with oligonucleotide probes, detection of changes in the mobility measured by gel electrophoresis or direct sequencing of the amplified nucleic acid. A preferred method for identifying biallelic markers involves comparative sequencing of genomic DNA fragments from an appropriate number of unrelated individuals.

In a first embodiment, DNA samples from unrelated individuals are pooled together, following which the genomic DNA of interest is amplified and sequenced. The nucleotide sequences thus obtained are then analyzed to identify significant polymorphisms. One of the major advantages of this method resides in the fact that the pooling of the DNA samples substantially reduces the number of DNA amplification reactions and sequencing reactions, which must be carried out. Moreover, this method is sufficiently sensitive so that a biallelic marker obtained thereby usually demonstrates a sufficient frequency of its less common allele to be useful in conducting association studies.

In a second embodiment, the DNA samples are not pooled and are therefore amplified and sequenced individually. This method is usually preferred when biallelic markers need to be identified in order to perform association studies within candidate genes. Preferably, highly relevant gene regions such as promoter regions or exon regions may be screened for biallelic markers. A biallelic marker obtained using this method may show a lower degree of informativeness for conducting association studies, e.g. if the frequency of its less frequent allele may be less than about 10%. Such a biallelic marker will, however, be sufficiently informative to conduct association studies and it will further be appreciated that including less informative biallelic markers in the genetic analysis studies of the present invention, may allow in some cases the direct identification of causal mutations, which may, depending on their penetrance, be rare mutations.

The following is a description of the various parameters of a preferred method used by the inventors for the identification of the biallelic markers of the present invention.

Genomic DNA Samples

The genomic DNA samples from which the biallelic markers of the present invention are generated are preferably obtained from unrelated individuals corresponding to a heterogeneous population of known ethnic background. The number of individuals from whom DNA samples are obtained can vary substantially, preferably from about 10 to about 1000, preferably from about 50 to about 200 individuals. It is usually preferred to collect DNA samples from at least about 100 individuals in order to have sufficient polymorphic diversity in a given population to identify as many markers as possible and to generate statistically significant results.

As for the source of the genomic DNA to be subjected to analysis, any test sample can be foreseen without any particular limitation. These test samples include biological samples, which can be tested by the methods of the present invention described herein, and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants, fixed tissue specimens including tumor and non-tumor tissue and lymph node tissues; bone marrow aspirates and fixed cell specimens. The preferred source of genomic DNA used in the present invention is from peripheral venous blood of each donor. Techniques to prepare genomic DNA from biological samples are well known to the skilled technician. Details of a preferred embodiment are provided in Example 1. The person skilled in the art can choose to amplify pooled or unpooled DNA samples.

DNA Amplification

The identification of biallelic markers in a sample of genomic DNA may be facilitated through the use of DNA amplification methods. DNA samples can be pooled or unpooled for the amplification step. DNA amplification techniques are well known to those skilled in the art. Various methods to amplify DNA fragments carrying biallelic markers are further described hereinbefore in "Amplification of the BAP28 gene". The PCR technology is the preferred amplification technique used to identify new biallelic markers. A typical example of a PCR reaction suitable for the purposes of the present invention is provided in Example 2.

In a first embodiment of the present invention, biallelic markers are identified using genomic sequence information generated by the inventors. Sequenced genomic DNA fragments are used to design primers for the amplification of 500 bp fragments. These 500 bp fragments are amplified from genomic DNA and are scanned for biallelic markers. Primers may be designed using the OSP software (Hillier L. and Green P., 1991). All primers may contain, upstream of the specific target bases, a common oligonucleotide tail that serves as a sequencing primer. Those skilled in the art are familiar with primer extensions, which can be used for these purposes.

Preferred primers, useful for the amplification of genomic sequences encoding the candidate genes, focus on promoters, exons and splice sites of the genes. A biallelic marker presents a higher probability to be an eventual causal mutation if it is located in these functional regions of the gene. Preferred amplification primers of the invention include the nucleotide sequences B1 to B38 and C1 to C38, preferably B1 to B15, B22, B24, B25, B27 to 29, B32, B34 to B38, C1 to C15, C22, C24. C25, C27 to 29, C32, and C34 to C38, detailed further in Example 2, Table 1.

Sequencing of Amplified Genomic DNA and Identification of Single Nucleotide Polymorphisms The amplification products generated as described above, are then sequenced using any method known and available to the skilled technician. Methods for sequencing DNA using either the dideoxy-mediated method (Sanger method) or the Maxam-Gilbert method are widely known to those of ordinary skill in the art. Such methods are for example disclosed in Sambrook et al. (1989). Alternative approaches include hybridization to high-density DNA probe arrays as described in Chee et al. (1996).

Preferably, the amplified DNA is subjected to automated dideoxy terminator sequencing reactions using a dye-primer cycle sequencing protocol. The products of the sequencing reactions are run on sequencing gels and the sequences are determined using gel image analysis. The polymorphism search is based on the presence of superimposed peaks in the electrophoresis pattern resulting from different bases occurring at the same position. Because each dideoxy terminator is labeled with a different fluorescent molecule, the two peaks corresponding to a biallelic site present distinct colors corresponding to two different nucleotides at the same position on the sequence. However, the presence of two peaks can be an artifact due to background noise. To exclude such an artifact, the two DNA strands are sequenced and a comparison between the peaks is carried out. In order to be registered as a polymorphic sequence, the polymorphism has to be detected on both strands.

The above procedure permits those amplification products, which contain biallelic markers to be identified. The detection limit for the frequency of biallelic polymorphisms detected by sequencing pools of 100 individuals is approximately 0.1 for the minor allele, as verified by sequencing pools of known allelic frequencies. However, more than 90% of the biallelic polymorphisms detected by the pooling method have a frequency for the minor allele higher than 0.25. Therefore, the biallelic markers selected by this method have a frequency of at least 0.1 for the minor allele and less than 0.9 for the major allele. Preferably at least 0.2 for the minor allele and less than 0.8 for the major allele, more preferably at least 0.3 for the minor allele and less than 0.7 for the major allele, thus a heterozygosity rate higher than 0.18, preferably higher than 0.32, more preferably higher than 0.42.

In another embodiment, biallelic markers are detected by sequencing individual DNA samples, the frequency of the minor allele of such a biallelic marker may be less than 0.1.

Validation of the Biallelic Markers of the Present Invention

The polymorphisms are evaluated for their usefulness as genetic markers by validating that both alleles are present in a population. Validation of the biallelic mariners is accomplished by genotyping a group of individuals by a method of the invention and demonstrating that both alleles are present. Microsequencing is a preferred method of genotyping alleles. The validation by genotyping step may be performed on individual samples derived from each individual in the group or by genotyping a pooled sample derived from more than one individual. The group can be as small as one individual if that individual is heterozygous for the allele in question. Preferably the group contains at least three individuals, more preferably the group contains five or six individuals, so that a single validation test will be more likely to result in the validation of more of the biallelic markers that are being tested. It should be noted, however, that when the validation test is performed on a small group it may result in a false negative result if as a result of sampling error none of the individuals tested carries one of the two alleles. Thus, the validation process is less useful in demonstrating that a particular initial result is an artifact, than it is at demonstrating that there is a bona fide biallelic marker at a particular position in a sequence. All of the genotyping, haplotyping, association, and interaction study methods of the invention may optionally be performed solely with validated biallelic markers.

Evaluation of the Frequency of the Biallelic Markers of the Present Invention

The validated biallelic markers are further evaluated for their usefulness as genetic mariners by determining the frequency of the least common allele at the biallelic marker site. The higher the frequency of the less common allele the greater the usefulness of the biallelic marker is association and interaction studies. The determination of the least common allele is accomplished by genotyping a group of individuals by a method of the invention and demonstrating that both alleles are present. This determination of frequency by genotyping step may be performed on individual samples derived from each individual in the group or by genotyping a pooled sample derived from more than one individual. The group must be large enough to be representative of the population as a whole. Preferably the group contains at least 20 individuals, more preferably the group contains at least 50 individuals, most preferably the group contains at least 100 individuals. Of course the larger the group the greater the accuracy of the frequency determination because of reduced sampling error. A biallelic marker wherein the frequency of the less common allele is 30% or more is termed a "high quality biallelic marker." All of the genotyping, haplotyping, association, and interaction study methods of the invention may optionally be performed solely with high quality biallelic markers.

Methods for Genotyping an Individual for Biallelic Markers

Methods are provided to genotype a biological sample for one or more biallelic markers of the present invention, all of which may be performed in vitro. Such methods of genotyping comprise determining the identity of a nucleotide at a BAP28 biallelic marker site by any method known in the art. These methods find use in genotyping case-control populations in association studies as well as individuals in the context of detection of alleles of biallelic markers which are known to be associated with a given trait, in which case both copies of the biallelic marker present in individual's genome are determined so that an individual may be classified as homozygous or heterozygous for a particular allele.

These genotyping methods can be performed on nucleic acid samples derived from a single individual or pooled DNA samples.

Genotyping can be performed using similar methods as those described above for the identification of the biallelic markers, or using other genotyping methods such as those further described below. In preferred embodiments, the comparison of sequences of amplified genomic fragments from different individuals is used to identify new biallelic markers whereas microsequencing is used for genotyping known biallelic markers in diagnostic and association study applications.

In one embodiment the invention encompasses methods of genotyping comprising determining the identity of a nucleotide at a BAP28-related biallelic marker or the complement thereof in a biological sample; In some embodiments, said BAP28-related biallelic marker is selected from the group consisting of A1 to A58, and the complements thereof, or the biallelic markers in linkage disequilibrium therewith; In some embodiments, wherein said BAP28-related biallelic marker is selected from the group consisting of A1 to A27, A34, A37 to A41, A43 to A49, A52, and A54 to A58, and the complements thereof, or the biallelic markers in linkage disequilibrium therewith; In some embodiments, said BAP28-related biallelic marker is selected from the group consisting of A1, A4, 16, A30, A31, A42, A50, A51, and A53, and the complements thereof, or the biallelic markers in linkage disequilibrium therewith; In some embodiments, said biological sample is derived from a single subject; In some embodiments, the identity of the nucleotides at said biallelic marker is determined for both copies of said biallelic marker present in said individual's genome; In some embodiments, said biological sample is derived from multiple subjects; In some embodiments, the method further comprises amplifying a portion of said sequence comprising the biallelic marker prior to said determining step; In some embodiments, said amplifying is performed by PCR; In some embodiments, said determining is performed by a hybridization assay, a sequencing assay, a microsequencing assay, or an enzyme-based mismatch detection assay.

Source of DNA for Genotyping

Any source of nucleic acids, in purified or non-purified form, can be utilized as the starting nucleic acid, provided it contains or is suspected of containing the specific nucleic acid sequence desired. DNA or RNA may be extracted from cells, tissues, body fluids and the like as described above. While nucleic acids for use in the genotyping methods of the invention can be derived from any mammalian source, the test subjects and individuals from which nucleic acid samples are taken are generally understood to be human.

Amplification of DNA Fragments Comprising Biallelic Markers

Methods and polynucleotides are provided to amplify a segment of nucleotides comprising one or more biallelic marker of the present invention. It will be appreciated that amplification of DNA fragments comprising biallelic markers may be used in various methods and for various purposes and is not restricted to genotyping. Nevertheless, many genotyping methods, although not all, require the previous amplification of the DNA region carrying the biallelic marker of interest. Such methods specifically increase the concentration or total number of sequences that span the biallelic marker or include that site and sequences located either distal or proximal to it. Diagnostic assays may also rely on amplification of DNA segments carrying a biallelic marker of the present invention. Amplification of DNA may be achieved by any method known in the art. Amplification techniques are described above in the section entitled, "Amplification of the BAP28 gene".

Some of these amplification methods are particularly suited for the detection of single nucleotide polymorphisms and allow the simultaneous amplification of a target sequence and the identification of the polymorphic nucleotide as it is further described below.

The identification of biallelic markers as described above allows the design of appropriate oligonucleotides, which can be used as primers to amplify DNA fragments comprising the biallelic markers of the present invention.

In some embodiments the present invention provides primers for amplifying a DNA fragment containing one or more biallelic markers of the present invention.

The spacing of the primers determines the length of the segment to be amplified. In the context of the present invention, amplified segments carrying biallelic markers can range in size from at least about 25 bp to 35 kbp. Amplification fragments from 25-3000 bp are typical, fragments from 50-1000 bp are preferred and fragments from 100-600 bp are highly preferred. It will be appreciated that amplification primers for the biallelic markers may be any sequence which allow the specific amplification of any DNA fragment carrying the markers. Amplification primers may be labeled or immobilized on a solid support as described in "Oligonucleotide probes and primers".

Methods of Genotyping DNA Samples for Biallelic Markers

Any method known in the art can be used to identify the nucleotide present at a biallelic marker site. Since the biallelic marker allele to be detected has been identified and specified in the present invention, detection will prove simple for one of ordinary skill in the art by employing any of a number of techniques. Many genotyping methods require the previous amplification of the DNA region carrying the biallelic marker of interest. While the amplification of target or signal is often preferred at present, ultrasensitive detection methods which do not require amplification are also encompassed by the present genotyping methods. Methods well-known to those skilled in the art that can be used to detect biallelic polymorphisms include methods such as, conventional dot blot analyzes, single strand conformational polymorphism analysis (SSCP) described by Orita et al. (1989), denaturing gradient gel electrophoresis (DGGE), heteroduplex analysis, mismatch cleavage detection, and other conventional techniques as described in Sheffield et al. (1991), White et al. (1992), Grompe et al. (1989 and 1993). Another method for determining the identity of the nucleotide present at a particular polymorphic site employs a specialized exonuclease-resistant nucleotide derivative as described in U.S. Pat. No. 4,656,127.

Preferred methods involve directly determining the identity of the nucleotide present at a biallelic marker site by sequencing assay, enzyme-based mismatch detection assay, or hybridization assay. The following is a description of some preferred methods. A highly preferred method is the microsequencing technique. The term "sequencing" is used herein to refer to polymerase extension of duplex primer/template complexes and includes both traditional sequencing and microsequencing.

1) Sequencing Assays

The nucleotide present at a polymorphic site can be determined by sequencing methods. In a preferred embodiment, DNA samples are subjected to PCR amplification before sequencing as described above. DNA sequencing methods are described in "Sequencing Of Amplified Genomic DNA And Identification Of Single Nucleotide Polymorphisms".

Preferably, the amplified DNA is subjected to automated dideoxy terminator sequencing reactions using a dye-primer cycle sequencing protocol. Sequence analysis allows the identification of the base present at the biallelic marker site.

2) Microsequencing Assays

In microsequencing methods, the nucleotide at a polymorphic site in a target DNA is detected by a single nucleotide primer extension reaction. This method involves appropriate microsequencing primers which, hybridize just upstream of the polymorphic base of interest in the target nucleic acid. A polymerase is used to specifically extend the 3' end of the primer with one single ddNTP (chain terminator) complementary to the nucleotide at the polymorphic site. Next the identity of the incorporated nucleotide is determined in any suitable way.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883. Alternatively capillary electrophoresis can be used in order to process a higher number of assays simultaneously. An example of a typical microsequencing procedure that can be used in the context of the present invention is provided in Example 4.

Different approaches can be used for the labeling and detection of ddNTPs. A homogeneous phase detection method based on fluorescence resonance energy transfer has been described by Chen and Kwok (1997) and Chen et al. (1997). In this method, amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluorescence changes can be monitored in real time. Alternatively, the extended primer may be analyzed by MALDI-TOF Mass Spectrometry. The base at the polymorphic site is identified by the mass added onto the microsequencing primer (see Haff and Smirnov, 1997).

Microsequencing may be achieved by the established microsequencing method or by developments or derivatives thereof. Alternative methods include several solid-phase microsequencing techniques. The basic microsequencing protocol is the same as described previously, except that the method is conducted as a heterogeneous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator regent. This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template. For example, immobilization can be carried out via an interaction between biotinylated DNA and streptavidin-coated microtitration wells or avidin-coated polystyrene particles. In the same manner, oligonucleotides or templates may be attached to a solid support in a high-density format. In such solid phase microsequencing reactions, incorporated ddNTPs can be radiolabeled (Syvänen, 1994) or linked to fluorescein (Livak and Hainer, 1994). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate). Other possible reporter-detection pairs include: ddNTP linked to dinitrophenyl (DNP) and anti-DNP alkaline phosphatase conjugate (Harju et al., 1993) or biotinylated ddNTP and horseradish peroxidase-conjugated streptavidin with o-phenylenediamine as a substrate (WO 92/15712). As yet another alternative solid-phase microsequencing procedure, Nyren et al. (1993) described a method relying on the detection of DNA polymerase activity by an enzymatic luminometric inorganic pyrophosphate detection assay (ELIDA).

Pastinen et al. (1997) describe a method for multiplex detection of single nucleotide polymorphism in which the solid phase minisequencing principle is applied to an oligonucleotide array format. High-density arrays of DNA probes attached to a solid support (DNA chips) are further described below.

In one aspect the present invention provides polynucleotides and methods to genotype one or more biallelic markers of the present invention by performing a microsequencing assay. Preferred microsequencing primers include the nucleotide sequences D1 to D58 and E1 to E58, preferably D1 to D27, D34, D37 to D41, D43 to D49, D52, D54 to D58 E1 to E27, E34, E37 to E41, E43 to E49, E52, and E54 to E58. It will be appreciated that the microsequencing primers listed in Example 4 are merely exemplary and that, any primer having a 3' end immediately adjacent to the polymorphic nucleotide may be used. Similarly, it will be appreciated that microsequencing analysis may be performed for any biallelic marker or any combination of biallelic markers of the present invention. One aspect of the present invention is a solid support which includes one or more microsequencing primers listed in Example 4, or fragments comprising at least 8, 12, 15, 20, 25, 30, 40, or 50 consecutive nucleotides thereof and having a 3' terminus immediately upstream of the corresponding biallelic marker, for determining the identity of a nucleotide at a biallelic marker site.

3) Mismatch Detection Assays Based on Polymerases and Ligases

In one aspect the present invention provides polynucleotides and methods to determine the allele of one or more biallelic markers of the present invention in a biological sample, by mismatch detection assays based on polymerases and/or ligases. These assays are based on the specificity of polymerases and ligases. Polymerization reactions places particularly stringent requirements on correct base pairing of the 3' end of the amplification primer and the joining of two oligonucleotides hybridized to a target DNA sequence is quite sensitive to mismatches close to the ligation site, especially at the 3' end. Methods, primers and various parameters to amplify DNA fragments comprising biallelic markers of the present invention are further described above in "Amplification Of DNA Fragments Comprising Biallelic Markers".

Allele Specific Amplification Primers

Discrimination between the two alleles of a biallelic marker can also be achieved by allele specific amplification, a selective strategy, whereby one of the alleles is amplified without amplification of the other allele. This is accomplished by placing the polymorphic base at the 3' end of one of the amplification primers. Because the extension forms from the 3' end of the primer, a mismatch at or near this position has an inhibitory effect on amplification. Therefore, under appropriate amplification conditions, these primers only direct amplification on their complementary allele. Determining the precise location of the mismatch and the corresponding assay conditions are well with the ordinary skill in the art.

Ligation/Amplification Based Methods

The "Oligonucleotide Ligation Assay" (OLA) uses two oligonucleotides which are designed to be capable of hybridizing to abutting sequences of a single strand of a target molecules. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and may be advantageously combined with PCR as described by Nickerson et al. (1990). In this method, PCR is used to achieve the exponential amplification of target DNA, which is then detected using OLA.

Other amplification methods which are particularly suited for the detection of single nucleotide polymorphism include LCR (ligase chain reaction), Gap LCR (GLCR) which are described above in "Amplification of the BAP28 gene". LCR uses two pairs of probes to exponentially amplify a specific target. The sequences of each pair of oligonucleotides, is selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that when they hybridize to the target molecule, a "gap" is created as described in WO 90/01069. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

4) Hybridization Assay Methods

A preferred method of determining the identity of the nucleotide present at a biallelic marker site involves nucleic acid hybridization. The hybridization probes, which can be conveniently used in such reactions, preferably include the probes defined herein. Any hybridization assay may be used including Southern hybridization, Northern hybridization, dot blot hybridization and solid-phase hybridization (see Sambrook et al., 1989).

Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms. Allele-specific probes are often used in pairs, one member of a pair showing perfect match to a target sequence containing the original allele and the other showing a perfect match to the target sequence containing the alternative allele. Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., 1989). Stringent conditions are sequence dependent and will be different in different circumstances. Generally, stringent conditions are selected to be about 5° C. lower than the thermal melting point (Tm) for the specific sequence at a defined ionic strength and pH. Although Such hybridizations can be performed in solution, it is preferred to employ a solid-phase hybridization assay. The target DNA comprising a biallelic marker of the present invention may be amplified prior to the hybridization reaction. The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps may be employed to wash away excess target DNA or probe as well as unbound conjugate. Further, standard heterogeneous assay formats are suitable for detecting the hybrids using the labels present on the primers and probes.

Two recently developed assays allow hybridization-based allele discrimination with no need for separations or washes (see Landegren U. et al., 1998). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence energy transfer. Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., 1995). In an alternative homogeneous hybridization based procedure, molecular beacons are used for allele discriminations. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., 1998).

The polynucleotides provided herein can be used to produce probes which can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. A particularly preferred probe is 25 nucleotides in length. Preferably the biallelic marker is within 4 nucleotides of the center of the polynucleotide probe. In particularly preferred probes, the biallelic marker is at the center of said polynucleotide. Preferred probes comprise a nucleotide sequence selected from the group consisting of amplicons listed in Table 1 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. Preferred probes comprise a nucleotide sequence selected from the group consisting of P1 to P58 and the sequences complementary thereto, preferably P1 to P27, P34, P37 to P41, P43 to P49, P52, P54 to P58. In preferred embodiments the polymorphic base(s) are within 5, 4, 3, 2, 1, nucleotides of the center of the said polynucleotide, more preferably at the center of said polynucleotide.

Preferably the probes of the present invention are labeled or immobilized on a solid support. Labels and solid supports are further described in "Oligonucleotide Probes and Primers". The probes can be non-extendable as described in "Oligonucleotide Probes and Primers".

By assaying the hybridization to an allele specific probe, one can detect the presence or absence of a biallelic marker allele in a given sample. High-Throughput parallel hybridizations in array format are specifically encompassed within "hybridization assays" and are described below.

5) Hybridization to Addressable Arrays of Oligonucleotides

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (e.g., the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA1 gene, in *S. cerevisiae* mutant strains, and in the protease gene of HIV-1 virus (Hacia et al., 1996; Shoemaker et al., 1996; Kozal et al., 1996). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual which, target sequences include a polymorphic marker. EP 785280 describes a tiling strategy for the detection of single nucleotide polymorphisms. Briefly, arrays may generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of monomers, i.e. nucleotides. Tiling strategies are further described in PCT application No WO 95/11995. In a particular aspect, arrays are tiled for a number of specific, identified biallelic marker sequences. In particular, the array is tiled to include a number of detection blocks, each detection block being specific for a specific biallelic marker or a set of biallelic markers. For example, a detection block may be tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block. These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the biallelic marker. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT application No WO 92/10092 and WO 95/11995 and U.S. Pat. No. 5,424,186.

Thus, in some embodiments, the chips may comprise an array of nucleic acid sequences of fragments of about 15 nucleotides in length. In further embodiments, the chip may comprise an array including at least one sequences comprising at least about 8 consecutive nucleotides, preferably 10, 15, 20, more preferably 25, 30, 40, 47, or 50 consecutive nucleotides and containing a polymorphic base. In preferred embodiments the polymorphic base is within 5, 4, 3, 2, 1, nucleotides of the center of the said polynucleotide, more preferably at the center of said polynucleotide. In some embodiments, the chip may comprise an array of at least 2, 3, 4, 5, 6, 7, 8 or more of these polynucleotides of the invention. Solid supports and polynucleotides of the present invention attached to solid supports are further described in "oligonucleotide probes and primers".

6) Integrated Systems

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts.

For genotyping biallelic markers, the microfluidic system may integrate nucleic acid amplification, microsequencing, capillary electrophoresis and a detection method such as laser-induced fluorescence detection.

Methods of Genetic Analysis Using the Biallelic Markers of the Present Invention Different methods are available for the genetic analysis of complex traits (see Lander and Schork, 1994). The search for disease-susceptibility genes is conducted using two main methods: the linkage approach in which evidence is sought for cosegregation between a locus and a putative trait locus using family studies, and the association approach in which evidence is sought for a statistically significant association between an allele and a trait or a trait causing allele (Khoury et al., 1993). In general, the biallelic markers of the present invention find use in any method known in the art to demonstrate a statistically significant correlation between a genotype and a phenotype. The biallelic markers may be used in parametric and non-parametric linkage analysis methods. Preferably, the biallelic markers of the present invention are used to identify genes associated with detectable traits using association studies, an approach which does not require the use of affected families and which permits the identification of genes associated with complex and sporadic traits.

The genetic analysis using the biallelic markers of the present invention may be conducted on any scale. The whole set of biallelic markers of the present invention or any subset of biallelic markers of the present invention corresponding to the candidate gene may be used. Further, any set of genetic markers including a biallelic marker of the present invention may be used. A set of biallelic polymorphisms that could be used as genetic markers in combination with the biallelic markers of the present invention has been described in WO 98/20165. As mentioned above, it should be noted that the biallelic markers of the present invention may be included in any complete or partial genetic map of the human genome. These different uses are specifically contemplated in the present invention and claims.

Linkage Analysis

Linkage analysis is based upon establishing a correlation between the transmission of genetic markers and that of a specific trait throughout generations within a family. Thus, the aim of linkage analysis is to detect marker loci that show cosegregation with a trait of interest in pedigrees.

Parametric Methods

When data are available from successive generations there is the opportunity to study the degree of linkage between pairs of loci. Estimates of the recombination fraction enable loci to be ordered and placed onto a genetic map. With loci that are genetic markers, a genetic map can be established, and then the strength of linkage between markers and traits can be calculated and used to indicate the relative positions of markers and genes affecting those traits (Weir, 1996). The classical method for linkage analysis is the logarithm of odds (lod) score method (see Morton, 1955; Ott, 1991). Calculation of lod scores requires specification of the mode of inheritance for the disease (parametric method). Generally, the length of the candidate region identified using linkage analysis is between 2 and 20 Mb. Once a candidate region is identified as described above, analysis of recombinant individuals using additional markers allows further delineation of the candidate region, linkage analysis studies have generally relied on the use of a maximum of 5,000 microsatellite markers, thus limiting the maximum theoretical attainable resolution of linkage analysis to about 600 kb on average.

Linkage analysis has been successfully applied to map simple genetic traits that show clear Mendelian inheritance patterns and which have a high penetrance (i.e., the ratio between the number of trait positive carriers of allele a and the total number of a carriers in the population). However, parametric linkage analysis suffers from a variety of drawbacks. First, it is limited by its reliance on the choice of a genetic model suitable for each studied trait. Furthermore, as already mentioned, the resolution attainable using linkage analysis is limited, and complementary studies are required to refine the analysis of the typical 2 Mb to 20 Mb regions initially identified through linkage analysis. In addition, parametric linkage analysis approaches have proven difficult when applied to complex genetic traits, such as those due to the combined action of multiple genes and/or environmental factors. It is very difficult to model these factors adequately in a lod score analysis. In such cases, too large an effort and cost are needed to recruit the adequate number of affected families required for applying linkage analysis to these situations, as recently discussed by Risch, N. and Merikangas, K. (1996).

Non-Parametric Methods

The advantage of the so-called non-parametric methods for linkage analysis is that they do not require specification of the mode of inheritance for the disease, they tend to be more useful for the analysis of complex traits. In non-parametric methods, one tries to prove that the inheritance pattern of a chromosomal region is not consistent with random Mendelian segregation by showing that affected relatives inherit identical copies of the region more often than expected by chance. Affected relatives should show excess "allele sharing" even in the presence of incomplete penetrance and polygenic inheritance. In non-parametric linkage analysis the degree of agreement at a marker locus in two individuals can be measured either by the number of alleles identical by state (IBS) or by the number of alleles identical by descent (IBD). Affected sib pair analysis is a well-known special case and is the simplest form of these methods.

The biallelic markers of the present invention may be used in both parametric and non-parametric linkage analysis. Preferably biallelic markers may be used in non-parametric methods which allow the mapping of genes involved in complex traits. The biallelic markers of the present invention may be used in both IBD- and IBS-methods to map genes affecting a complex trait. In such studies, taking advantage of the high density of biallelic markers, several adjacent biallelic marker loci may be pooled to achieve the efficiency attained by multi-allelic markers (Zhao et al., 1998).

Population Association Studies

The present invention comprises methods for identifying if the BAP28 gene is associated with a detectable trait using the biallelic markers of the present invention. In one embodiment the present invention comprises methods to detect an association between a biallelic marker allele or a biallelic marker haplotype and a trait. Further, the invention comprises methods to identify a trait causing allele in linkage disequilibrium with any biallelic marker allele of the present invention.

As described above, alternative approaches can be employed to perform association studies: genome-wide association studies, candidate region association studies and candidate gene association studies. In a preferred embodiment, the biallelic markers of the present invention are used to perform candidate gene association studies. The candidate gene analysis clearly provides a short-cut approach to the identification of genes and gene polymorphisms related to a particular trait when some information concerning the biology of the trait is available. Further, the biallelic markers of the present invention may be incorporated in any map of genetic markers of the human genome in order to perform genome-wide association studies. Methods to generate a high-density map of biallelic markers has been described in U.S. Provisional Patent application Ser. No. 60/082,614. The biallelic markers of the present invention may further be incorporated in any map of a specific candidate region of the genome (a specific chromosome or a specific chromosomal segment for example).

As mentioned above, association studies may be conducted within the general population and are not limited to studies performed on related individuals in affected families. Association studies are extremely valuable as they permit the analysis of sporadic or multifactor traits. Moreover, association studies represent a powerful method for fine-scale mapping enabling much finer mapping of trait causing alleles than linkage studies. Studies based on pedigrees often only narrow the location of the trait causing allele. Association studies using the biallelic markers of the present invention can therefore be used to refine the location of a trait causing allele in a candidate region identified by Linkage Analysis methods. Moreover, once a chromosome segment of interest has been identified, the presence of a candidate gene such as a candidate gene of the present invention, in the region of interest can provide a shortcut to the identification of the trait causing allele. Biallelic markers of the present invention can be used to demonstrate that a candidate gene is associated with a trait. Such uses are specifically contemplated in the present invention.

Determining the Frequency of a Biallelic Marker Allele or of a Biallelic Marker Haplotype in a Population Association studies explore the relationships among frequencies for sets of alleles between loci.

Determining the Frequency of an Allele in a Population

Allelic frequencies of the biallelic markers in a populations can be determined using one of the methods described above under the heading "Methods for genotyping an individual for biallelic markers", or any genotyping procedure suitable for this intended purpose. Genotyping pooled samples or individual samples can determine the frequency of a biallelic marker allele in a population. One way to reduce the number of genotypings required is to use pooled samples. A major obstacle in using pooled samples is in terms of accuracy and reproducibility for determining accurate DNA concentrations in setting up the pools. Genotyping individual samples provides higher sensitivity, reproducibility and accuracy and; is the preferred method used in the present invention. Preferably, each individual is genotyped separately and simple gene counting is applied to determine the frequency of an allele of a biallelic marker or of a genotype in a given population.

The invention also relates to methods of estimating the frequency of an allele in a population comprising: a) genotyping individuals from said population for said biallelic marker according to the method of the present invention: b) determining the proportional representation of said biallelic marker in said population. In addition, the methods of estimating the frequency of an allele in a population of the invention encompass methods with any further limitation described in this disclosure, or those following, specified alone or in any combination; In some embodiments, said BAP28-related biallelic marker is selected from the group consisting of A1 to A58, and the complements thereof, or the biallelic markers in linkage disequilibrium therewith; In some embodiments, said BAP28-related biallelic marker is selected from the group consisting of A1 to A27, A34, A37 to A41, A43 to A49, A52, and A54 to A58, and the complements thereof, or the biallelic markers in linkage disequilibrium therewith; In some embodiments, said BAP28-related biallelic marker is selected from the group consisting of A1, A4, 16, A30, A31, A42, A50, A51, and A53, and the complements thereof, or the biallelic markers in linkage disequilibrium therewith; In some embodiments, the step of determining the frequency of a biallelic marker allele in a population may be accomplished by determining the identity of the nucleotides for both copies of said biallelic marker present in the genome of each individual in said population and calculating the proportional representation of said nucleotide at said BAP28-related biallelic marker for the population; In some embodiments, the step of determining the proportional representation may be accomplished by performing a genotyping method of the invention on a pooled biological sample derived from a representative number of individuals, or each individual, in said population, and calculating the proportional amount of said nucleotide compared with the total.

Determining the Frequency of a Haplotype in a Population

The gametic phase of haplotypes is unknown when diploid individuals are heterozygous at more than one locus. Using genealogical information in families gametic phase can sometimes be inferred (Perlin et al., 1994). When no genealogical information is available different strategies may be used. One possibility is that the multiple-site heterozygous diploids can be eliminated from the analysis, keeping only the homozygotes and the single-site heterozygote individuals, but this approach might lead to a possible bias in the sample composition and the underestimation of low-frequency haplotypes. Another possibility is that single chromosomes can be studied independently, for example, by asymmetric PCR amplification (see Newton et al, 1989; Wu et al., 1989) or by isolation of single chromosome by limit dilution followed by PCR amplification (see Ruano et al., 1990). Further, a sample may be haplotyped for sufficiently close biallelic markers by double PCR amplification of specific alleles (Sarkar, G. and Sommer S. S, 1991). These approaches are not entirely satisfying either because of their technical complexity, the additional cost they entail, their lack of generalization at a large scale, or the possible biases they introduce. To overcome these difficulties, an algorithm to infer the phase of PCR-amplified DNA genotypes introduced by Clark. A. G.(1990) may be used. Briefly, the principle is to start filling a preliminary list of haplotypes present in the sample by examining unambiguous individuals, that is, the complete homozygotes and the single-site heterozygotes. Then other individuals in the same sample are screened for the possible occurrence of previously recognized haplotypes. For each positive identification, the complementary haplotype is added to the list of recognized haplotypes, until the phase information for all individuals is either resolved or identified as unresolved. This method assigns a single haplotype to each multiheterozygous individual, whereas several haplotypes are possible when there are more than one heterozygous site. Alternatively, one can use methods estimating haplotype frequencies in a population without assigning haplotypes to each individual. Preferably, a method based on an expectation-maximization (EM) algorithm (Dempster et al., 1977) leading to maximum-likelihood estimates of haplotype frequencies under the assumption of Hardy-Weinberg proportions (random mating) is used (see Excoffier L, and Slatkin M., 1995). The EM algorithm is a generalized iterative maximum-likelihood approach to estimation that is useful when data are ambiguous and/or incomplete. The EM algorithm is used to resolve heterozygotes into haplotypes. Haplotype estimations are further described below under the heading "Statistical Methods." Any other method known in the art to determine or to estimate the frequency of a haplotype in a population may be used.

The invention also encompasses methods of estimating the frequency of a haplotype for a set of biallelic markers in a population, comprising the steps of: a) genotyping at least one BAP28-related biallelic marker according to a method of the invention for each individual in said population; b) genotyping a second biallelic marker by determining the identity of the nucleotides at said second biallelic marker for both copies of said second biallelic marker present in the genome of each individual in said population; and c) applying a haplotype determination method to the identities of the nucleotides determined in steps a) and b) to obtain an estimate of said frequency. In addition, the methods of estimating the frequency of a haplotype of the invention encompass methods with any further limitation described in this disclosure, or those following, specified alone or in any combination: In some embodiments, said BAP28-related biallelic marker is selected from the group consisting of A1 to A58, and the complements thereof, or the biallelic markers in linkage disequilibrium therewith; In some embodiments, said BAP28-related biallelic marker is selected from the group consisting of A1 to A27, A34, A37 to A41, A43 to A49. A52, and A54 to A58, and the complements thereof, or the biallelic markers in linkage disequilibrium therewith; In some embodiments, said BAP28-related biallelic marker is selected from the group consisting of A1, A4, 16, A30, A31, A42, A50, A51, and A53, and the complements thereof or the biallelic markers in linkage disequilibrium therewith; In some embodiments, said haplotype determination method is performed by asymmetric PCR amplification, double PCR amplification of specific alleles, the Clark algorithm, or an expectation-maximization algorithm.

Linkage Disequilibrium Analysis

Linkage disequilibrium is the non-random association of alleles at two or more loci and represents a powerful tool for mapping genes involved in disease traits (see Ajioka R. S. et al., 1997). Biallelic markers, because they are densely spaced in the human genome and can be genotyped in greater numbers than other types of genetic markers (such as RFLP or VNTR markers), are particularly useful in genetic analysis based on linkage disequilibrium.

When a disease mutation is first introduced into a population (by a new mutation or the immigration of a mutation carrier), it necessarily resides on a single chromosome and thus on a single "background" or "ancestral" haplotype of linked markers. Consequently, there is complete disequilibrium between these markers and the disease mutation: one finds the disease mutation only in the presence of a specific set of marker alleles. Through subsequent generations recombination events occur between the disease mutation and these marker polymorphisms, and the disequilibrium gradually dissipates. The pace of this dissipation is a function of the recombination frequency, so the markers closest to the disease gene will manifest higher levels of disequilibrium than those that are further away. When not broken up by recombination, "ancestral" haplotypes and linkage disequilibrium between marker alleles at different loci can be tracked not only through pedigrees but also through populations. Linkage disequilibrium is usually seen as an association between one specific allele at one locus and another specific allele at a second locus.

The pattern or curve of disequilibrium between disease and marker loci is expected to exhibit a maximum that occurs at the disease locus. Consequently, the amount of linkage disequilibrium between a disease allele and closely linked genetic markers may yield valuable information regarding the location of the disease gene. For fine-scale mapping of a disease locus, it is useful to have some knowledge of the patterns of linkage disequilibrium that exist between markers in the studied region. As mentioned above the mapping resolution achieved through the analysis of linkage disequilibrium is much higher than that of linkage studies. The high density of biallelic markers combined with linkage disequilibrium analysis provides powerful tools for fine-scale mapping. Different methods to calculate linkage disequilibrium are described below under the heading "Statistical Methods".

Population-Based Case-Control Studies of Trait-Marker Associations

As mentioned above, the occurrence of pairs of specific alleles at different loci on the same chromosome is not random and the deviation from random is called linkage disequilibrium. Association studies focus on population frequencies and rely on the phenomenon of linkage disequilibrium. If a specific allele in a given gene is directly involved in causing a particular trait, its frequency will be statistically increased in an affected (trait positive) population, when compared to the frequency in a trait negative population or in a random control population. As a consequence of the existence of linkage disequilibrium, the frequency of all other alleles present in the haplotype carrying the trait-causing allele will also be increased in trait positive individuals compared to trait negative individuals or random controls. Therefore, association between the trait and any allele (specifically a biallelic marker allele) in linkage disequilibrium with the trait-causing allele will suffice to suggest the presence of a trait-related gene in that particular region. Case-control populations can be genotyped for biallelic markers to identify associations that narrowly locate a trait causing allele. As any marker in linkage disequilibrium with one given marker associated with a trait will be associated with the trait. Linkage disequilibrium allows the relative frequencies in case-control populations of a limited number of genetic polymorphisms (specifically biallelic markers) to be analyzed as an alternative to screening all possible functional polymorphisms in order to find trait-causing alleles. Association studies compare the frequency of marker alleles in unrelated case-control populations, and represent powerful tools for the dissection of complex traits.

Case-Control Populations (Inclusion Criteria)

Population-based association studies do not concern familial inheritance but compare the prevalence of a particular genetic marker, or a set of markers, in case-control populations. They are case-control studies based on comparison of unrelated case (affected or trait positive) individuals and unrelated control (unaffected, trait negative or random) individuals. Preferably the control group is composed of unaffected or trait negative individuals. Further, the control group is ethnically matched to the case population. Moreover, the control group is preferably matched to the case-population for the main known confusion factor for the trait under study (for example age-matched for an age-dependent trait). Ideally, individuals in the two samples are paired in such a way that they are expected to differ only in their disease status. The terms "trait positive population", "case population" and "affected population" are used interchangeably herein.

An important step in the dissection of complex traits using association studies is the choice of case-control populations (see Lander and Schork, 1994). A major step in the choice of case-control populations is the clinical definition of a given trait or phenotype. Any genetic trait may be analyzed by the association method proposed here by carefully selecting the individuals to be included in the trait positive and trait negative phenotypic groups. Four criteria are often useful: clinical phenotype, age at onset, family history and severity. The selection procedure for continuous or quantitative traits (such as blood pressure for example) involves selecting individuals at opposite ends of the phenotype distribution of the trait under study, so as to include in these trait positive and trait negative populations individuals with non-overlapping phenotypes. Preferably, case-control populations are phenotypically homogeneous populations. Trait positive and trait negative populations consist of phenotypically uniform populations of individuals representing each between 1 and 98%, preferably between 1 and 80%, more preferably between 1 and 50%, and more preferably between 1 and 30%, most preferably between 1 and 20% of the total population under study, and preferably selected among individuals exhibiting non-overlapping phenotypes. The clearer the difference between the two trait phenotypes, the greater the probability of detecting an association with biallelic markers. The selection of those drastically different but relatively uniform phenotypes enables efficient comparisons in association studies and the possible detection of marked differences at the genetic level, provided that the sample sizes of the populations under study are significant enough.

In preferred embodiments, a first group of between 50 and 300 trait positive individuals, preferably about 100 individuals, are recruited according to their phenotypes. A similar number of control individuals are included in such studies.

In the present invention, typical examples of inclusion criteria include, but are not restricted to, prostate cancer or aggressiveness of prostate cancer tumors. In one preferred embodiment of the present invention, association studies are carried out on the basis of a presence (trait positive) or absence (trait negative) of prostate cancer.

Associations studies can be carried out by the skilled technician using the biallelic markers of the invention defined above, with different trait positive and trait negative populations. Suitable further examples of association studies using biallelic markers of the BAP28 gene, including the biallelic markers A1 to A58, preferably A1 to A27, A34, A37 to A41, A43 to A49, A52, and A54 to A58, involve studies on the following populations:

- a trait positive population suffering from a cancer and a healthy unaffected population, or
- a trait positive population suffering from prostate cancer treated with agents acting against prostate cancer and suffering from side-effects resulting from this treatment and an trait negative population suffering from prostate cancer treated with same agents without any substantial side-effects, or
- a trait positive population suffering from prostate cancer treated with agents acting against prostate cancer showing a beneficial response and a trait negative population suffering from prostate cancer treated with same agents without any beneficial response, or
- a trait positive population suffering from prostate cancer presenting highly aggressive prostate cancer tumors and a trait negative population suffering from prostate cancer with prostate cancer tumors devoid of aggressiveness.

Association Analysis

The invention also comprises methods of detecting an association between a genotype and a phenotype, comprising the steps of: a) determining the frequency of at least one BAP28-related biallelic marker in a trait positive population according to a genotyping method of the invention; b) determining the frequency of said BAP28-related biallelic marker in a control population according to a genotyping method of the invention; and c) determining whether a statistically significant association exists between said genotype and said phenotype. In addition, the methods of detecting an association between a genotype and a phenotype of the invention encompass methods with any further limitation described in this disclosure, or those following, specified alone or in any combination: In some embodiments, said BAP28-related biallelic marker is selected from the group consisting of A1 to A58, and the complements thereof, or the biallelic markers in linkage disequilibrium therewith; In some embodiments, said BAP28-related biallelic marker is selected from the group consisting of A1 to A27, A34, A37 to A41, A43 to A49, A52, and A54 to A58, and the complements thereof, or the biallelic markers in linkage disequilibrium therewith; In some embodiments, said BAP28-related biallelic marker is selected from the group consisting of A1, A4, 16, A31, A31, A42, A50, A51, and A53, and the complements thereof, or the biallelic markers in linkage disequilibrium therewith; In some embodiments, said control population may be a trait negative population, or a random population. In some embodiments, each of said genotyping steps a) and b) may be performed on a pooled biological sample derived from each of said populations; In some embodiments, each of said genotyping of steps a) and b) is performed separately on biological samples derived from each individual in said population or a subsample thereof.

The general strategy to perform association studies using biallelic markers derived from a region carrying a candidate gene is to scan two groups of individuals (case-control populations) in order to measure and statistically compare the allele frequencies of the biallelic markers of the present invention in both groups.

If a statistically significant association with a trait is identified for at least one or more of the analyzed biallelic markers, one can assume that: either the associated allele is directly responsible for causing the trait (i.e. the associated allele is the trait causing allele), or more likely the associated allele is in linkage disequilibrium with the trait causing allele. The specific characteristics of the associated allele with respect to the candidate gene function usually give further insight into the relationship between the associated allele and the trait (causal or in linkage disequilibrium). If the evidence indicates that the associated allele within the candidate gene is most probably not the trait causing allele but is in linkage disequilibrium with the real trait causing allele, then the trait causing allele can be found by sequencing the vicinity of the associated marker, and performing further association studies with the polymorphisms that are revealed in an iterative manner.

Association studies are usually run in two successive steps. In a first phase, the frequencies of a reduced number of biallelic markers from the candidate gene are determined in the trait positive and control populations. In a second phase of the analysis, the position of the genetic loci responsible for the given trait is further refined using a higher density of markers from the relevant region. However, if the candidate gene under study is relatively small in length, as is the case for BAP28, a single phase may be sufficient to establish significant associations.

Haplotype Analysis

As described above, when a chromosome carrying a disease allele first appears in a population as a result of either mutation or migration, the mutant allele necessarily resides on a chromosome having a set of linked markers: the ancestral haplotype. This haplotype can be tracked through populations and its statistical association with a given trait can be analyzed. Complementing single point (allelic) association studies with multi-point association studies also called haplotype studies increases the statistical power of association studies. Thus, a haplotype association study allows one to define the frequency and the type of the ancestral carrier haplotype. A haplotype analysis is important in that it increases the statistical power of an analysis involving individual markers.

In a first stage of a haplotype frequency analysis, the frequency of the possible haplotypes based on various combinations of the identified biallelic markers of the invention is determined. The haplotype frequency is then compared for distinct populations of trait positive and control individuals. The number of trait positive individuals, which should be, subjected to this analysis to obtain statistically significant results usually ranges between 30 and 300, with a preferred number of individuals ranging between 50 and 150. The same considerations apply to the number of unaffected individuals (or random control) used in the study. The results of this first analysis provide haplotype frequencies in case-control populations, for each evaluated haplotype frequency a p-value and an odd ratio are calculated. If a statistically significant association is found the relative risk for an individual carrying the given haplotype of being affected with the trait under study can be approximated.

An additional embodiment of the present invention encompasses methods of detecting an association between a haplotype and a phenotype, comprising the steps of: a) estimating the frequency of at least one haplotype in a trait positive population, according to a method of the invention for estimating the frequency of a haplotype; b) estimating the frequency of said haplotype in a control population, according to a method of the invention for estimating the frequency of a haplotype; and c) determining whether a statistically significant association exists between said haplotype and said phenotype. In addition, the methods of detecting an association between a haplotype and a phenotype of the invention encompass methods with any further limitation described in this disclosure, or those following: In some embodiments, said BAP28-related biallelic marker is selected from the group consisting of A1 to A58, and the complements thereof, or the biallelic markers in linkage disequilibrium therewith; In some embodiments, said BAP28-related biallelic marker is selected from the group consisting of A1 to A27, A34, A37 to A41, A43 to A49, A52, and A54 to A58, and the complements thereof, or the biallelic markers in linkage disequilibrium therewith; In some embodiments, said BAP28-related biallelic marker is selected from the group consisting of A1, A4, 16. A30. A3-1, A42. A50, A51, and A53, and the complements thereof, or the biallelic markers in linkage disequilibrium therewith; In some embodiments, said control population is a trait negative population, or a random population. In some embodiments, said method comprises the additional steps of determining the phenotype in said trait positive and said control populations prior to step c).

Interaction Analysis

The biallelic markers of the present invention may also be used to identify patterns of biallelic markers associated with detectable traits resulting from polygenic interactions. The analysis of genetic interaction between alleles at unlinked loci requires individual genotyping using the techniques described herein. The analysis of allelic interaction among a selected set of biallelic markers with appropriate level of statistical significance can be considered as a haplotype analysis. Interaction analysis consists in stratifying the case-control populations with respect to a given haplotype for the first loci and performing a haplotype analysis with the second loci with each subpopulation.

Statistical methods used in association studies are further described below.

Testing for Linkage in the Presence of Association

The biallelic markers of the present invention may further be used in TDT (transmission/disequilibrium test). TDT tests for both linkage and association and is not affected by population stratification. TDT requires data for affected individuals and their parents or data from unaffected sibs instead of from parents (see Spielmann S. et al., 1993. Schaid D. J. et al., 1996, Spielmann S, and Ewens W. J., 1998). Such combined tests generally reduce the false—positive errors produced by separate analyses.

Association of Biallelic Markers of BAP28 with Prostate Cancer

Trait Positive and Control Populations

Two groups of independent individuals were used: the overall trait positive and the control populations included 491 individuals suffering from prostate cancer and 313 individuals without any sign of prostate cancer. A specific protocol for the collection of DNA samples from trait positive and control individuals is described in Example 5. The 491 affected individuals can be subdivided in 197 familial cases and 294 sporadic cases. The sporadic cases comprises 70 sporadic informatives cases. The 491 individuals suffering from prostate cancer can also be subdivided into a population of individuals who developed prostate cancer under 65 years-old and a population of individuals who developed prostate cancer after the age of 65.

In order to have as much certainty as possible on the absence of prostate cancer in control individuals, it is preferred to conduct a PSA dosage analysis on this population. Several commercial assays can be used (WO 96/21042, herein by reference). In one preferred embodiment, a Hybritech assay is used and control individuals must have a level of PSA less than 2.8 ng/ml of serum in order to be selected as such. In a preferred embodiment, the Yang assay is used and trait negative individuals must have a level of PSA of less than 4 ng/ml of serum in order to be included in the population under study. More preferably, the control population is at least 65 year old.

Association Analysis

The association analysis showed an association between BAP28-related biallelic markers and prostate cancer, more particularly both familial prostate cancer and sporadic prostate cancer. The results of the association study were further details in example 5.

Figure 5:
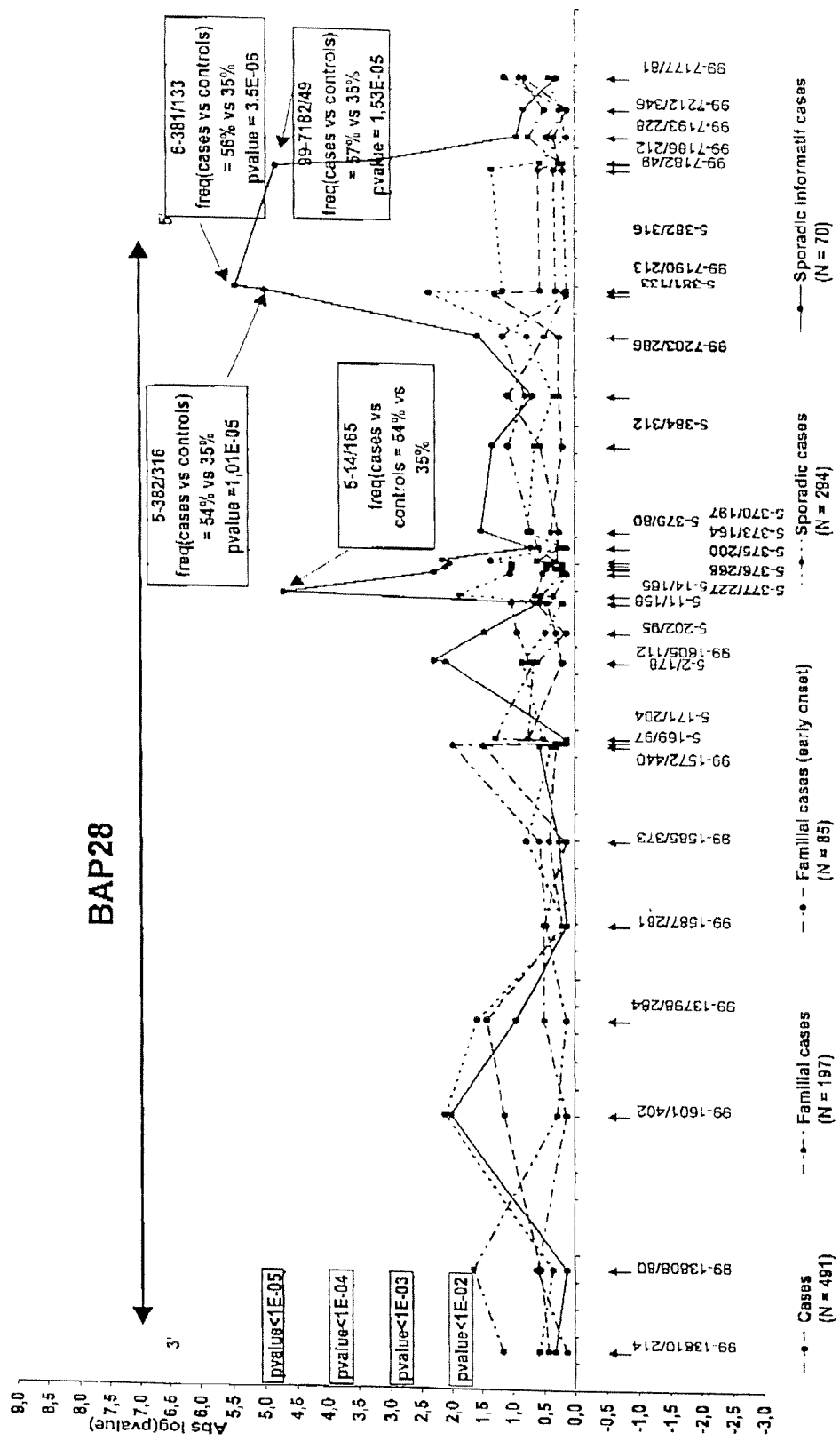
FIG. 5 is a diagram showing the allelic association analysis in chromosomic region 1q43.
Figure 6:
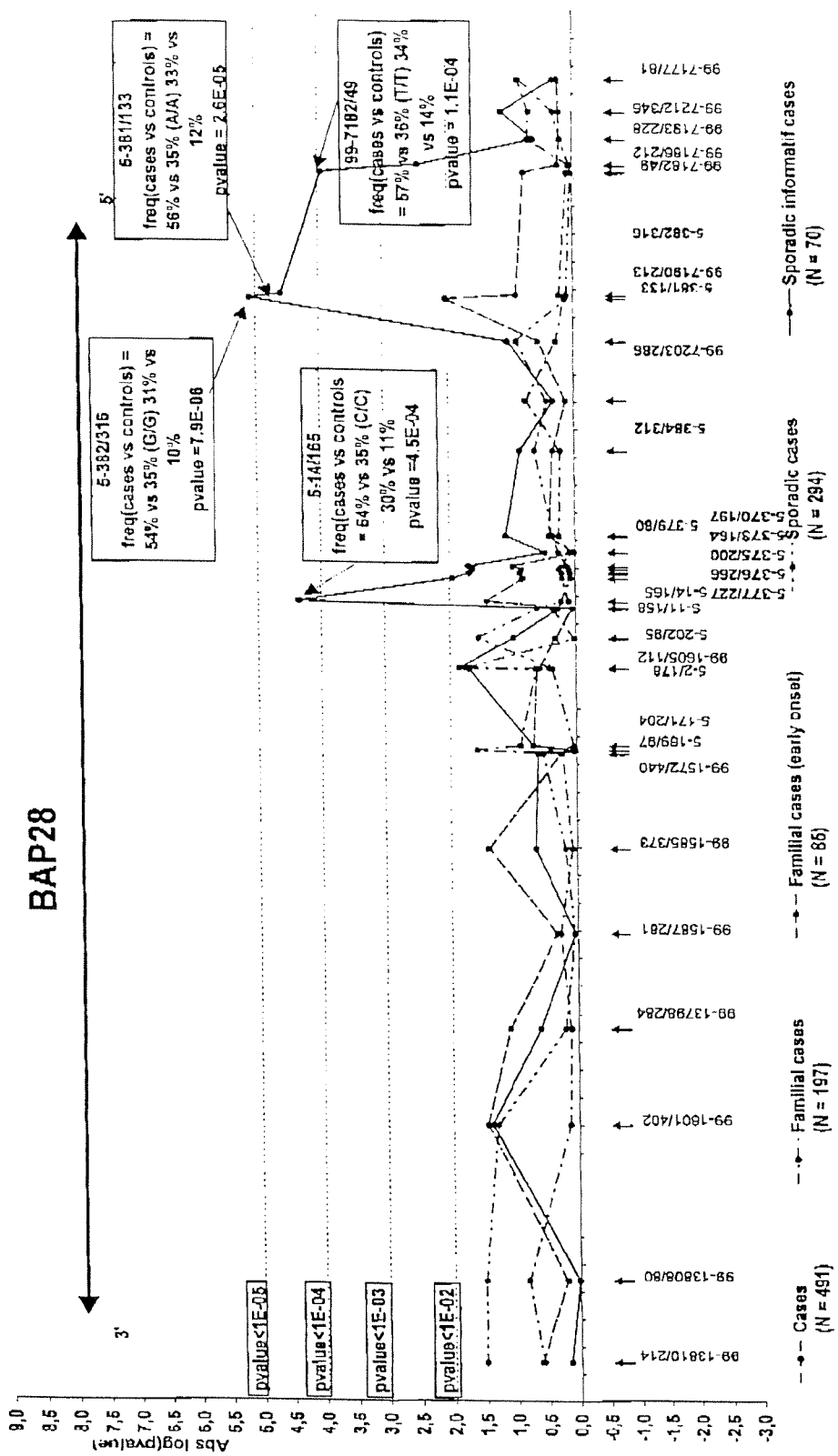
FIG. 6 is a diagram showing the genotypic association analysis in chromosomic region 1q43.
Figure 13A:
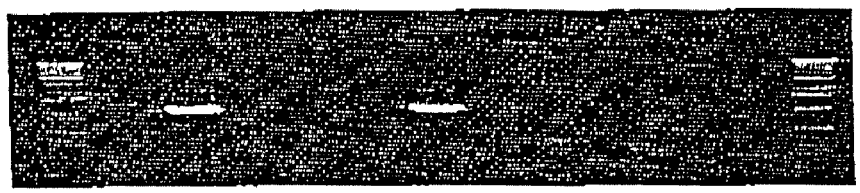
FIG. 13 is a half-tome reproduction of the gels showing the tissular specificity of the BAP28 expression, more particularly the segment comprising the exons 43 to A.
FIG. 13C: Wells 1 and 13: Molecular weight markers X–300 ng; Well 2: cDNA Human Testis: negative Tissue Well 3: cDNA Human Cerebellum: positive Tissue (RNA PolyA+ CLONTECH–Lot N°8070047–Réf Cat:6543-1) Well 4: cDNA Human Corpus Callosum: negative Tissue; Well 5: cDNA Human Substantia Nigra: positive Tissue (RNA PolyA+ CLONTECH–Lot N°8090745–Réf Cat:6580-1); Well 6: cDNA Human Amygdala: negative Tissue Well 7: cDNA Human Thalamus: positive Tissue (RNA PolyA+ CLONTECH–Lot N°9031131–Réf Cat:6582-1); Well 8: cDNA Human Hippocampus positive Tissue (RNA PolyA+ CLONTECH –Lot N°8040059–Réf Cat:6578-1); Well 9: cDNA Human Caudate Nucleus: positive Tissue (RNA PolyA+ CLONTECH–Lot N°6120286–Réf Cat:6575-1); Well 10: cDNA Human Fetal Brain: negative Tissue; Well 11: cDNA Human Skeletal Muscle: negative Tissue; Well 12: cDNA Human Lung: negative Tissue.
Figure 13B:
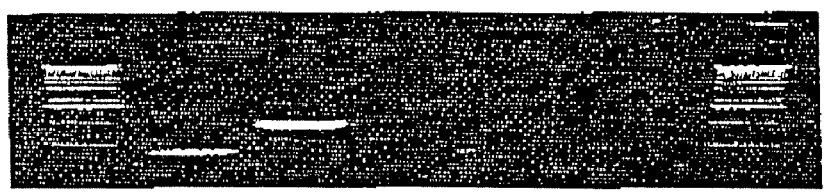
Figure 13C:
Figure 13D:
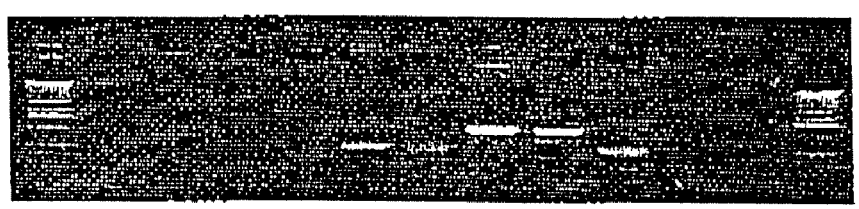
Figure 13E:
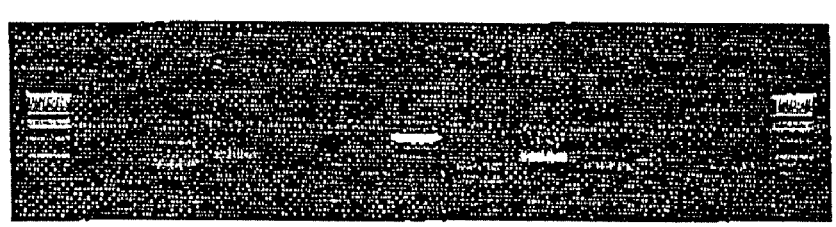
Figure 14:
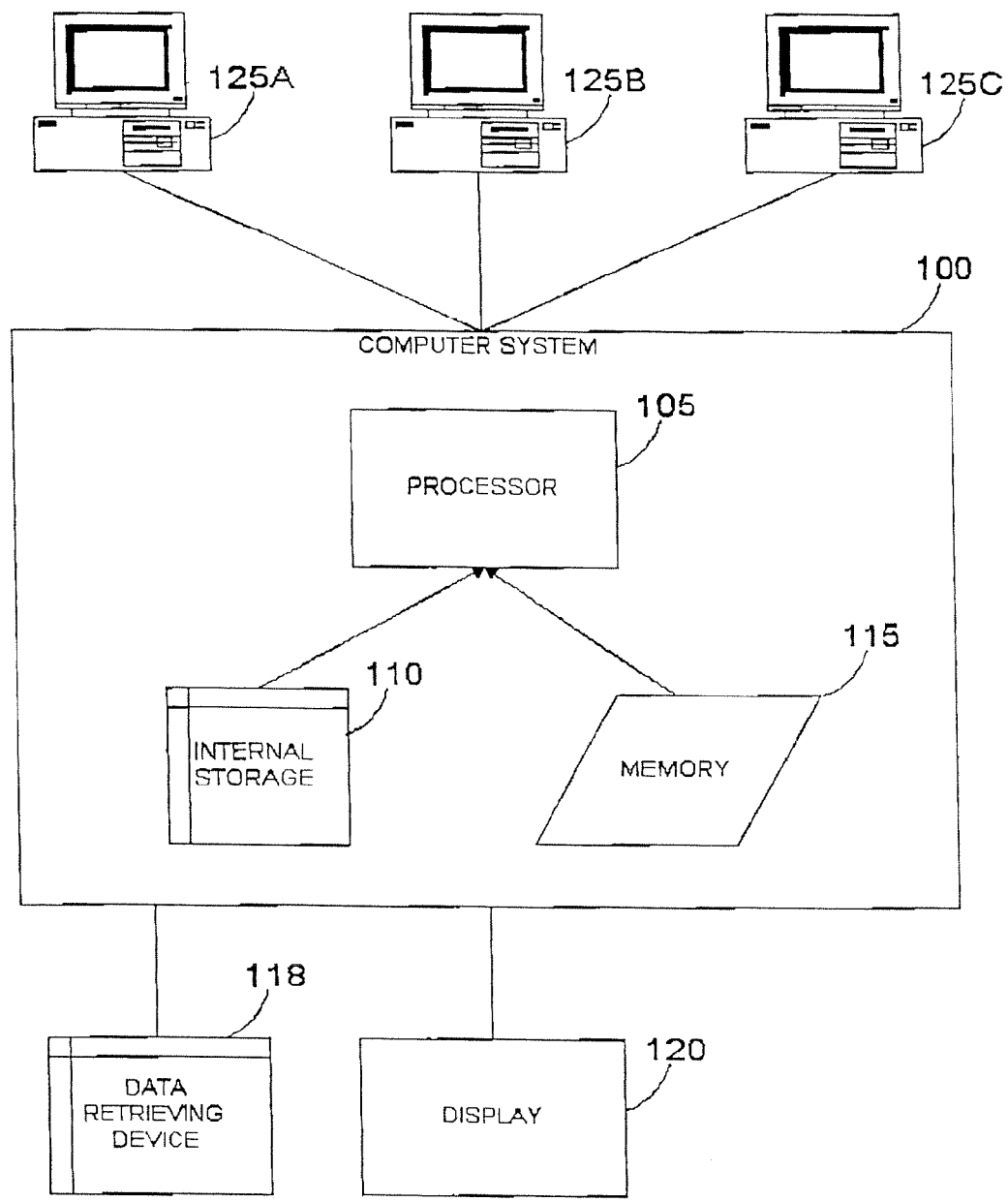
FIG. 14 is a block diagram of an exemplary computer system.
Figure 15:
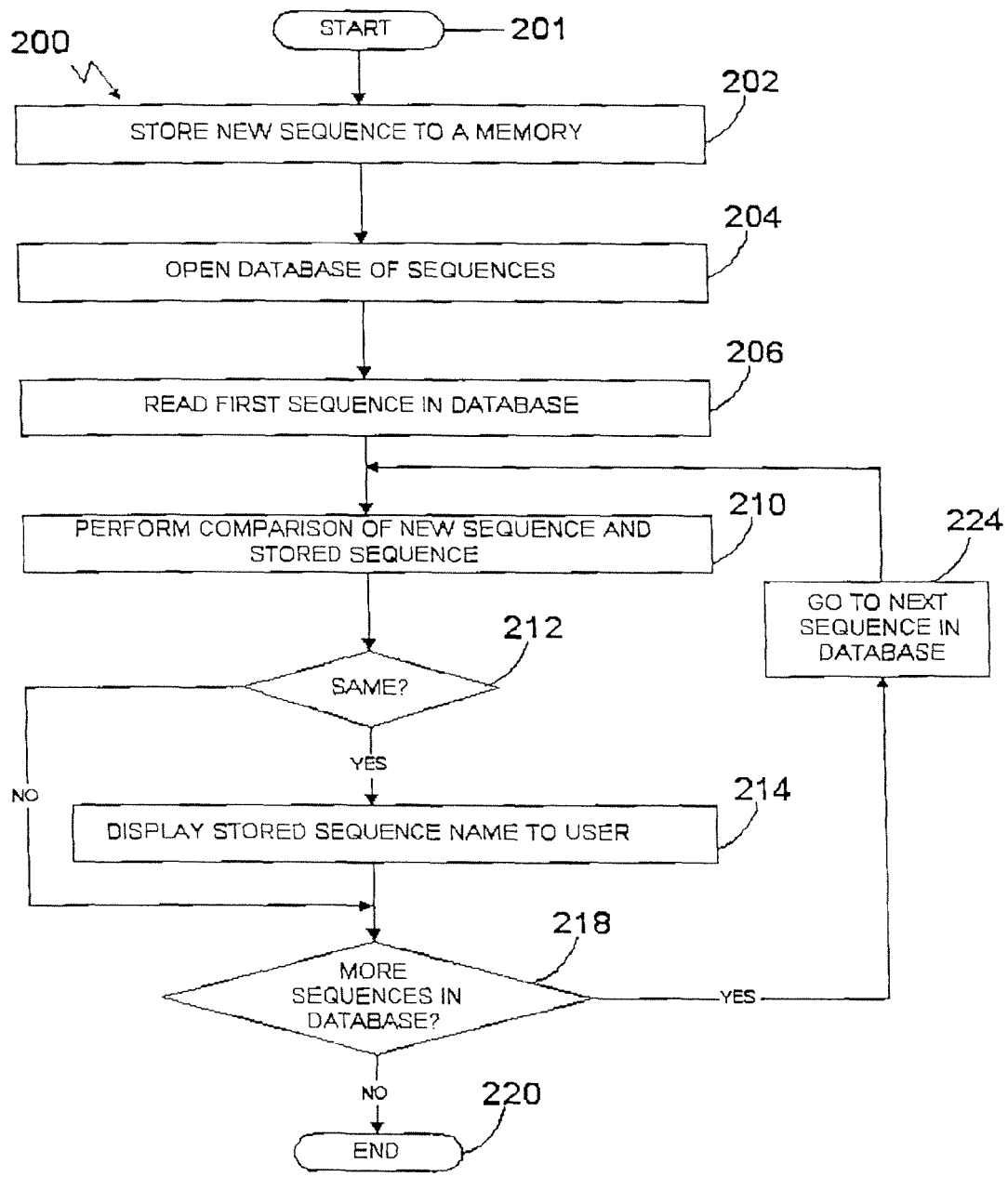
FIG. 15 is a flow diagram illustrating one embodiment of a process 200 for comparing a new nucleotide or protein sequence with a database of sequences in order to determine the homology levels between the new sequence and the sequences in the database.
Figure 16:
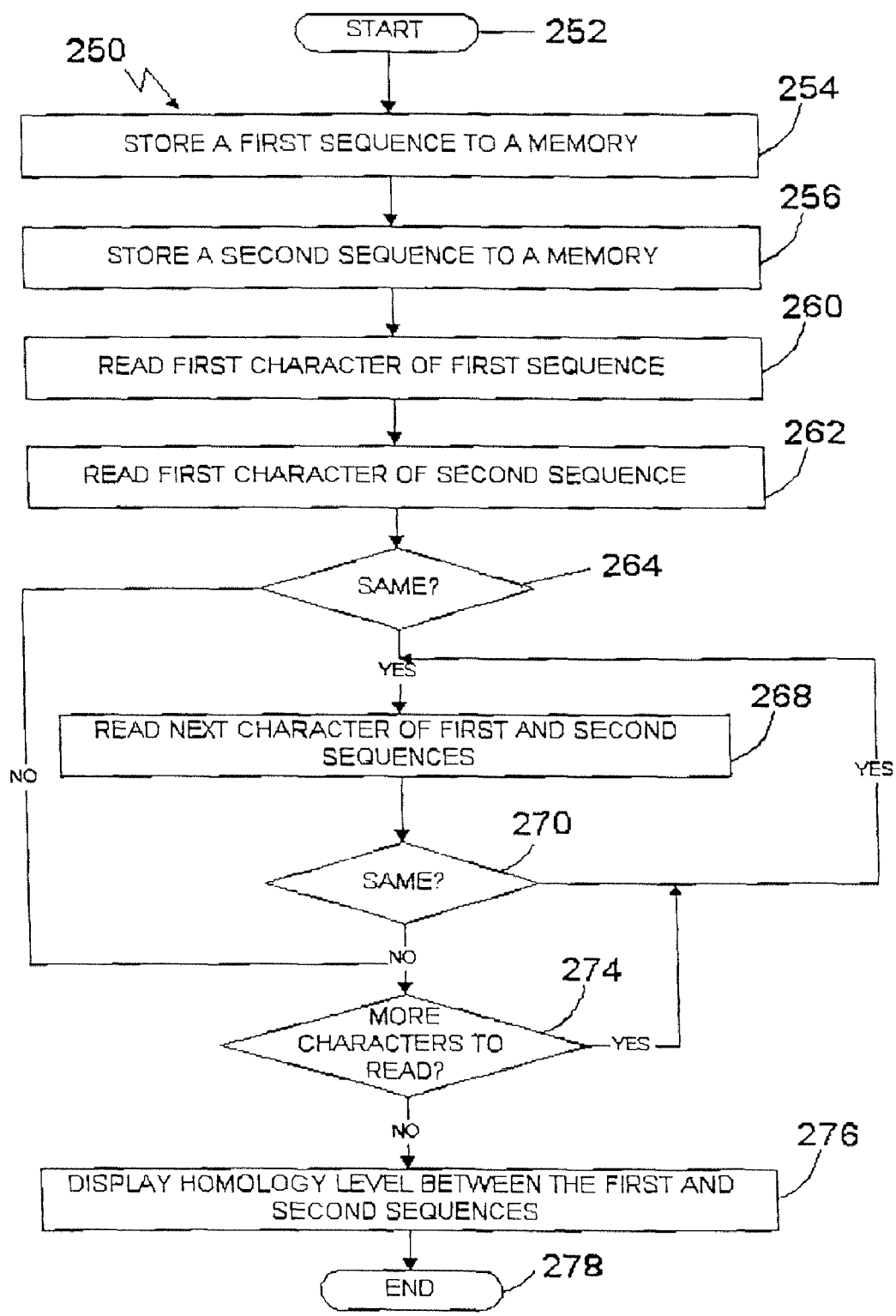
FIG. 16 is a flow diagram illustrating one embodiment of a process 250 in a computer for determining whether two sequences are homologous.
Figure 17:
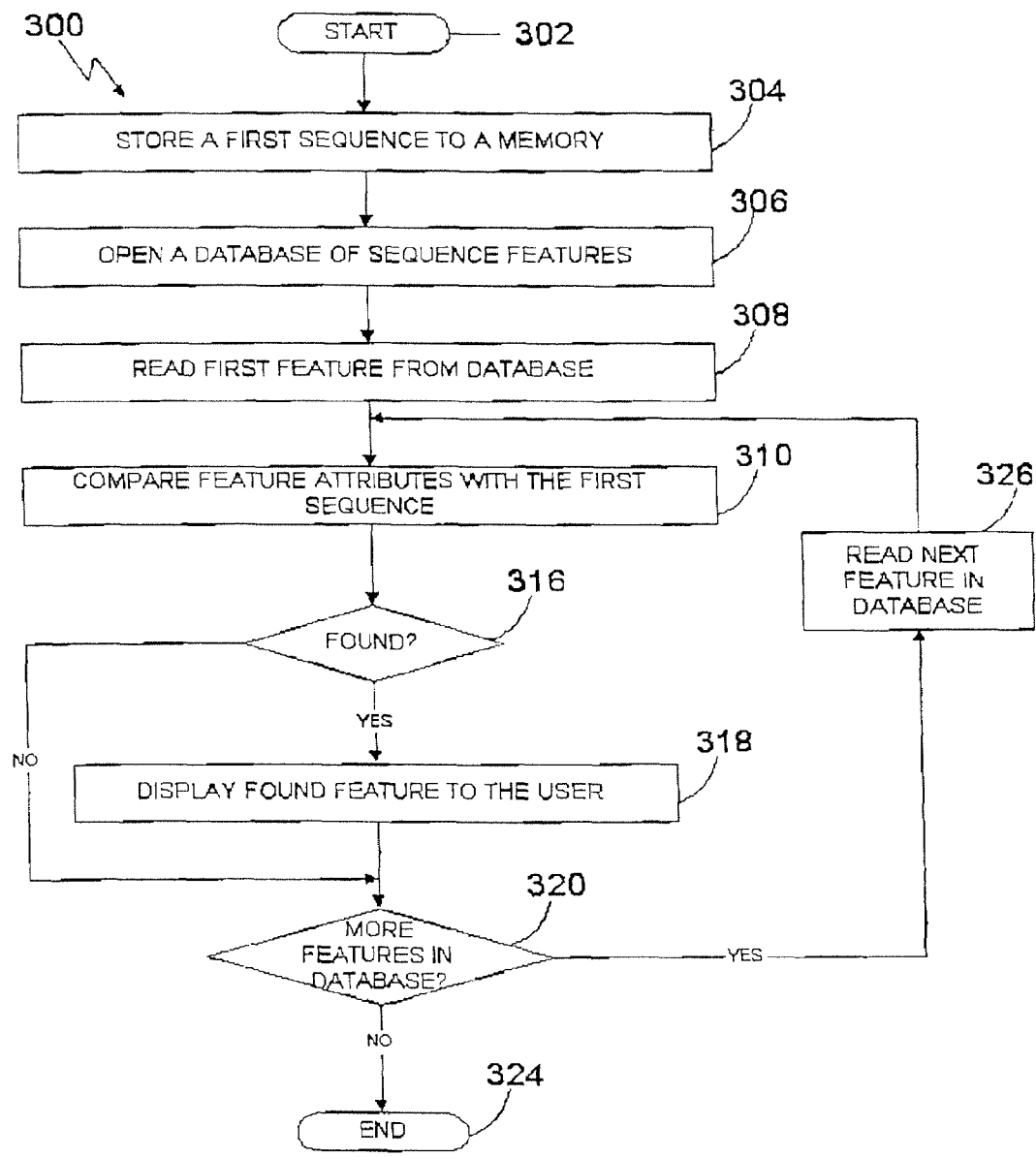
FIG. 17 is a flow diagram illustrating one embodiment of an identifier process 300 for detecting the presence of a feature in a sequence.

A single point analysis of the association study showed an association between biallelic markers of the BAP28 gene and prostate cancer, preferably sporadic prostate cancer is associated most strongly with the biallelic markers A28 (5-14/165), A4 (5-382/316), A1 (5-381/133), and A55 (99-7182/49) which present a particular interest (FIGS. 5 and 6). These association results constitute new elements for studying the genetic susceptibility of individuals to prostate cancer, preferably to sporadic and familial prostate cancer. Further details concerning this association study are provided in FIGS. 5 and 6 and in the example 5.

Similar association studies can also be carried out with other biallelic markers within the scope of the invention, preferably with biallelic markers in linkage disequilibrium with the markers associated with prostate cancer as described above, including the biallelic markers A1 to A58.

Haplotype Analysis

In the context of the present invention, a haplotype can be defined as a combination of biallelic markers found in a given individual and which may be associated more or less significantly, as a result of appropriate statistical analyses, with the expression of a given trait.

The haplotype studies are detailed in Example 5.

Several two-marker haplotypes were significantly associated with familial prostate cancer. One preferred two-marker haplotype including markers A30 (99-1572/440) and A32 (5-171/204), alleles TT respectively, was shown to be significantly associated with prostate cancer, preferably with familial prostate cancer. As shown in FIGS. 8, 9 and 12 A, this haplotype presents a p-value of $2.5 \times 10^{-6}$ for the early onset familial prostate cancer (see Example 5).

Several two-marker haplotypes were significantly associated with sporadic prostate cancer. One preferred two-marker haplotype including markers A16 (5-370/197), and A1 (5-381/133), alleles GA was shown to be significantly associated with sporadic prostate cancer. As shown in FIGS. 10, 11 and 12 B, this haplotype presents a p-value of $9.4 \times 10^{-8}$ for the informative sporadic prostate cancer (see Example 5).

Several two-marker haplotypes were significantly associated with sporadic prostate cancer. One preferred two-marker haplotype including markers A53 (99-1601/402), and A4 (5-382/316), alleles TG, was shown to be significantly associated with sporadic prostate cancer. As shown in FIGS. 10, 11 and 12 C, this haplotype presents a p-value of $1 \times 10^{-5}$ for the informative sporadic prostate cancer (see Example 5).

Several three-biallelic marker haplotypes are described in the Example 5.

The permutation tests clearly validated the statistical significance of the association between these haplotypes and the prostate cancer (see Example 5). All these haplotypes can be used in diagnostic of prostate cancer, more particularly either familial prostate cancer or sporadic prostate cancer.

This information is extremely valuable. The knowledge of a potential genetic predisposition to prostate cancer, even if this predisposition is not absolute, might contribute in a very significant manner to treatment efficacy of prostate cancer and to the development of new therapeutic and diagnostic tools.

The invention concerns a haplotype comprising at least one biallelic marker selected from the group consisting of A1 to A58, preferably A54, A58, A57, A56, A55, A1, A4, A5, A7, A11, A12, A16, A19, A21, A25, A27, A28, A29, A35, A33, A34, A32, A31, A30, A50, A51, A42, A53, A43, and A48, more preferably A1, A4, A30, A31, A42, A51, and A53.

Statistical Methods

In general, any method known in the art to test whether a trait and a genotype show a statistically significant correlation may be used.

1) Methods in Linkage Analysis

Statistical methods and computer programs useful for linkage analysis are well-known to those skilled in the art (see Terwilliger J. D. and Ott J., 1994. Ott J., 1991).

2) Methods to Estimate Haplotype Frequencies in a Population

As described above, when genotypes are scored, it is often not possible to distinguish heterozygotes so that haplotype frequencies cannot be easily inferred. When the gametic phase is not known, haplotype frequencies can be estimated from the multilocus genotypic data. Any method known to person skilled in the art can be used to estimate haplotype frequencies (see Lange K., 1997. Weir, B. S., 1996) Preferably, maximum-likelihood haplotype frequencies are computed using an Expectation-Maximization (EM) algorithm (see Dempster et al., 1977; Excoffier L. and Slatkin M., 1995). This procedure is an iterative process aiming at obtaining maximum-likelihood estimates of haplotype frequencies from multi-locus genotype data when the gametic phase is unknown, haplotype estimations are usually performed by applying the EM algorithm using for example the EM-HAPLO program (Hawley M. E. et al., 1994) or the Arlequin program (Schneider et al., 1997). The EM algorithm is a generalized iterative maximum likelihood approach to estimation and is briefly described below.

Please note that in the present section, "Methods To Estimate Haplotype Frequencies In A Population," of this text, phenotypes will refer to multi-locus genotypes with unknown phase. Genotypes will refer to known-phase multi-locus genotypes.

A sample of N unrelated individuals is typed for K markers. The data observed are the unknown-phase K-locus phenotypes that can categorized in F different phenotypes. Suppose that we have H underlying possible haplotypes (in case of K biallelic markers, $H=2^K$).

For phenotype j, suppose that $c_j$ genotypes are possible. We thus have the following equation $$P_j = \sum_{i=1}^{c_j} pr(genotype_i) = \sum_{i=1}^{c_j} pr(h_k, h_l) \qquad \text{Equation 1}$$

where Pj is the probability of the phenotype j, $h_k$ and $h_l$ are the two haplotypes constituent the genotype i. Under the Hardy-Weinberg equilibrium, $pr(h_k,h_l)$ becomes:

$$pr(h_k,h_l) = pr(h_k)^2 \text{ if } h_k = h_l, pr(h_k, h_l) = 2pr(h_k)\cdot pr(h_l) \text{ if } h_k \neq h_l \qquad \text{Equation 2}$$

The successive steps of the E-M algorithm can be described as follows:

Starting with initial values of the of haplotypes frequencies, noted $p_1^{(0)}, p_2^{(0)}, \ldots p_H^{(0)}$, these initial values serve to estimate the genotype frequencies (Expectation step) and then estimate another set of haplotype frequencies (Maximization step), noted $p_1^{(1)}, p_2^{(1)}, \ldots p_H^{(1)}$, these two steps are iterated until changes in the sets of haplotypes frequency are very small.

A stop criterion can be that the maximum difference between haplotype frequencies between two iterations is less than $10^{-7}$. These values can be adjusted according to the desired precision of estimations.

At a given iteration s, the Expectation step consists in calculating the genotypes frequencies by the following equation:

$$pr(genotype_i)^{(s)} = \qquad \text{Equation 3}$$
$$pr(phenotype_j) \cdot pr(genotype_i \mid phenotype_j)^{(s)} =$$
$$\frac{n_j}{N} \cdot \frac{pr(h_k, h_l)^{(s)}}{P_j^{(s)}}$$

where genotype i occurs in phenotype j, and where $h_k$ and $h_l$ constitute genotype i. Each probability is derived according to eq. 1, and eq. 2 described above.

Then the Maximization step simply estimates another set of haplotype frequencies given the genotypes frequencies. This approach is also known as the gene-counting method (Smith, 1957).

$$p_t^{(s+1)} = \frac{1}{2} \sum_{j=1}^{F} \sum_{i=1}^{c_j} \delta_{it} \cdot pr(genotype_i)^{(s)} \qquad \text{Equation 4}$$

Where $\delta_{it}$ is an indicator variable which count the number of time haplotype t in genotype i. It takes the values of 0, 1 or 2.

To ensure that the estimation finally obtained is the maximum-likelihood estimation several values of departures are required. The estimations obtained are compared and if they are different the estimations leading to the best likelihood are kept.

3) Methods to Calculate Linkage Disequilibrium Between Markers

A number of methods can be used to calculate linkage disequilibrium between any two genetic positions, in practice linkage disequilibrium is measured by applying a statistical association test to haplotype data taken from a population.

Linkage disequilibrium between any pair of biallelic markers comprising at least one of the biallelic markers of the present invention ($M_i$, $M_j$) having alleles ($a_i/b_i$) at marker $M_i$ and alleles ($a_j/b_j$) at marker $M_j$ can be calculated for every allele combination ($a_i,a_j,a_i,b_j,b_i,a_j$ and $b_i,b_j$), according to the Piazza formula:

$\Delta_{aiaj} = \sqrt{\theta 4} - \sqrt{(\theta 4 + \theta 3)(\theta 4 + \theta 2)}$, where:

$\theta 4 = --$ = frequency of genotypes not having allele $a_i$ at $M_i$ and not having allele $a_j$ at $M_j$ $\theta 3 = -+$ = frequency of genotypes not having allele $a_i$ at $M_i$ and having allele $a_j$ at $M_j$ $\theta 2 = +-$ = frequency of genotypes having allele $a_i$ at $M_i$ and not having allele $a_j$ at $M_j$ Linkage disequilibrium (ID) between pairs of biallelic markers ($M_i$, $M_j$) can also be calculated for every allele combination (ai,aj, ai,bj; $b_i,a_j$ and $b_i,b_j$), according to the maximum-likelihood estimate (MLE) for delta (the composite genotypic disequilibrium coefficient), as described by Weir (Weir B. S., 1996). The MLE for the composite linkage disequilibrium is:

$$D_{aiaj} = (2n_1 + n_2 + n_3 + n_4/2)/N - 2(pr(a_i) \cdot pr(a_j))$$

Where $n_1 = \Sigma$ phenotype ($a_i/a_i$, $a_j/a_j$), $n_2 = \Sigma$ phenotype ($a_i/a_i$, $a_j/b_j$), $n_3 = \Sigma$ phenotype ($a_i/b_i$, $a_j/a_j$), $n4 = \Sigma$ phenotype ($a_i/b_i$, $a_j/b_j$) and N is the number of individuals in the sample.

This formula allows linkage disequilibrium between alleles to be estimated when only genotype, and not haplotype, data are available.

Another means of calculating the linkage disequilibrium between markers is as follows. For a couple of biallelic markers, $M_i$ ($a_i/b_i$) and $M_j$ ($a_j/b_j$), fitting the Hardy-Weinberg equilibrium, one can estimate the four possible haplotype frequencies in a given population according to the approach described above.

The estimation of gametic disequilibrium between ai and aj is simply:

$$D_{aiaj} = pr(\text{haplotype}(a_i,a_j)) - pr(a_i) \cdot pr(a_j).$$

Where $pr(a_i)$ is the probability of allele $a_i$ and $pr(a_j)$ is the probability of allele $a_j$ and where pr(haplotype ($a_i$, $a_j$)) is estimated as in Equation 3 above.

For a couple of biallelic marker only one measure of disequilibrium is necessary to describe the association between $M_i$ and $M_j$.

Then a normalized value of the above is calculated as follows:

$D'_{aiaj} = D_{aiaj}/\max(-pr(a_i) \cdot pr(a_j), -pr(b_i) \cdot pr(b_j))$ with $D_{aiaj} < 0$ $D'_{aiaj} = D_{aiaj}/\max(pr(b_i) \cdot pr(a_j), pr(a_i) \cdot pr(b_j))$ with $D_{aiaj} > 0$ The skilled person will readily appreciate that other linkage disequilibrium calculation methods can be used.

Linkage disequilibrium among a set of biallelic markers having an adequate heterozygosity rate can be determined by genotyping between 50 and 1000 unrelated individuals, preferably between 75 and 200, more preferably around 100.

4) Testing for Association

Methods for determining the statistical significance of a correlation between a phenotype and a genotype, in this case an allele at a biallelic marker or a haplotype made up of such alleles, may be determined by any statistical test known in the art and with any accepted threshold of statistical significance being required. The application of particular methods and thresholds of significance are well with in the skill of the ordinary practitioner of the art.

Testing for association is performed by determining the frequency of a biallelic marker allele in case and control populations and comparing these frequencies with a statistical test to determine if their is a statistically significant difference in frequency which would indicate a correlation between the trait and the biallelic marker allele under study. Similarly, a haplotype analysis is performed by estimating the frequencies of all possible haplotypes for a given set of biallelic markers in case and control populations, and comparing these frequencies with a statistical test to determine if their is a statistically significant correlation between the haplotype and the phenotype (trait) under study. Any statistical tool useful to test for a statistically significant association between a genotype and a phenotype may be used. Preferably the statistical test employed is a chi-square test with one degree of freedom. A P-value is calculated (the P-value is the probability that a statistic as large or larger than the observed one would occur by chance).

Statistical Significance

In preferred embodiments, significance for diagnosis purposes, either as a positive basis for further diagnostic tests or as a preliminary starting point for early preventive therapy, the p value related to a biallelic marker association is preferably about $1 \times 10^{-2}$ or less, more preferably about $1 \times 10^{-4}$ or less, for a single biallelic marker analysis and about $1 \times 10^{-3}$ or less, still more preferably $1 \times 10^{-6}$ or less and most preferably of about $1 \times 10^{-8}$ or less, for a haplotype analysis involving two or more markers. These values are believed to be applicable to any association studies involving single or multiple marker combinations.

The skilled person can use the range of values set forth above as a starting point in order to carry out association studies with biallelic markers of the present invention. In doing so, significant associations between the biallelic markers of the present invention and a trait can be revealed and used for diagnosis and drug screening purposes.

Phenotypic Permutation

In order to confirm the statistical significance of the first stage haplotype analysis described above, it might be suitable to perform further analyses in which genotyping data from case-control individuals are pooled and randomized with respect to the trait phenotype. Each individual genotyping data is randomly allocated to two groups, which contain the same number of individuals as the case-control populations used to compile the data obtained in the first stage. A second stage haplotype analysis is preferably run on these artificial groups, preferably for the markers included in the haplotype of the first stage analysis showing the highest relative risk coefficient. This experiment is reiterated preferably at least between 100 and 10000 times. The repeated iterations allow the determination of the probability to obtain the tested haplotype by chance.

Assessment of Statistical Association

To address the problem of false positives similar analysis may be performed with the same case-control populations in random genomic regions. Results in random regions and the candidate region are compared as described in a co-pending US Provisional Patent Application entitled "Methods, Software And Apparati For Identifying Genomic Regions Harboring A Gene Associated With A Detectable Trait," U.S. Ser. No. 60/107,986, filed Nov. 10, 1998, the contents of which are incorporated herein by reference.

5) Evaluation of Risk Factors

The association between a risk factor (in genetic epidemiology the risk factor is the presence or the absence of a certain allele or haplotype at marker loci) and a disease is measured by the odds ratio (OR) and by the relative risk (RR). If $P(R^+)$ is the probability of developing the disease for individuals with R and $P(R^-)$ is the probability for individuals without the risk factor, then the relative risk is simply the ratio of the two probabilities, that is:

$$RR = P(R^+)/P(R^-)$$

In case-control studies, direct measures of the relative risk cannot be obtained because of the sampling design. However, the odds ratio allows a good approximation of the relative risk for low-incidence diseases and can be calculated:

$$OR = \left[\frac{F^+}{1-F^+}\right] / \left[\frac{F^-}{(1-F^-)}\right]$$

$$OR = (F^+/(1-F^+))/(F^-/(1-F^-))$$

$F^+$ is the frequency of the exposure to the risk factor in cases and $F^-$ is the frequency of the exposure to the risk factor in controls. $F^+$ and $F^-$ are calculated using the allelic or haplotype frequencies of the study and further depend on the underlying genetic model (dominant, recessive, additive . . . ).

One can further estimate the attributable risk (AR) which describes the proportion of individuals in a population exhibiting a trait due to a given risk factor. This measure is important in quantifying the role of a specific factor in disease etiology and in terms of the public health impact of a risk factor. The public health relevance of this measure lies in estimating the proportion of cases of disease in the population that could be prevented if the exposure of interest were absent. AR is determined as follows:

$$AR = P_E(RR-1)/(P_E(RR-1)+1)$$

AR is the risk attributable to a biallelic marker allele or a biallelic marker haplotype. $P_E$ is the frequency of exposure to an allele or a haplotype within the population at large; and RR is the relative risk which, is approximated with the odds ratio when the trait under study has a relatively low incidence in the general population.

Identification of Biallelic Markers in Linkage Disequilibrium with the Biallelic Markers of the Invention Once a first biallelic marker has been identified in a genomic region of interest, the practitioner of ordinary skill in the art, using the teachings of the present invention, can easily identify additional biallelic markers in linkage disequilibrium with this first marker. As mentioned before any marker in linkage disequilibrium with a first marker associated with a trait will be associated with the trait. Therefore, once an association has been demonstrated between a given biallelic marker and a trait, the discovery of additional biallelic markers associated with this trait is of great interest in order to increase the density of biallelic markers in this particular region. The causal gene or mutation will be found in the vicinity of the marker or set of markers showing the highest correlation with the trait.

Identification of additional markers in linkage disequilibrium with a given marker involves: (a) amplifying a genomic fragment comprising a first biallelic marker from a plurality of individuals; (b) identifying of second biallelic markers in the genomic region harboring said first biallelic marker: (c) conducting a linkage disequilibrium analysis between said first biallelic marker and second biallelic markers; and (d)

selecting said second biallelic markers as being in linkage disequilibrium with said first marker. Subcombination comprising steps (b) and (c) are also contemplated.

Methods to identify biallelic markers and to conduct linkage disequilibrium analysis are described herein and can be carried out by the skilled person without undue experimentation. The present invention then also concerns biallelic markers which are in linkage disequilibrium with the specific biallelic markers A1 to A58, preferably one of the biallelic markers A1 to A27, A34, A37 to A41, A43 to A49, A52, and A54 to A58, more preferably one of, the biallelic markers A1, A4, 16. A30, A31, A42, A50, A5, and A53, and which are expected to present similar characteristics in terms of their respective association with a given trait. In a preferred embodiment, the invention concerns biallelic markers which are in linkage disequilibrium with the specific biallelic markers

Identification of Functional Mutations

Mutations in the BAP28 gene which are responsible for a detectable phenotype or trait may be identified by comparing the sequences of the BAP28 gene from trait positive and control individuals. Once a positive association is confirmed with a biallelic marker of the present invention, the identified locus can be scanned for mutations. In a preferred embodiment, functional regions such as exons and splice sites, promoters and other regulatory regions of tile BAP28 gene are scanned for mutations. In a preferred embodiment the sequence of the BAP28 gene is compared in trait positive and control individuals. Preferably, trait positive individuals carry the haplotype shown to be associated with the trait and trait negative individuals do not carry the haplotype or allele associated with the trait. The detectable trait or phenotype may comprise a variety of manifestations of altered BAP28 function.

The mutation detection procedure is essentially similar to that used for biallelic marker identification. The method used to detect such mutations generally comprises the following steps:

amplification of a region of the BAP28 gene comprising a biallelic marker or a group of biallelic markers associated with the trait from DNA samples of trait positive patients and trait-negative controls;

sequencing of the amplified region;

comparison of DNA sequences from trait positive and control individuals;

determination of mutations specific to trait-positive patients.

In one embodiment, said biallelic marker is selected from the group consisting of A1 to A58, and the complements thereof. In a preferred embodiment, said biallelic marker is selected from the group consisting of A1 to A27, A34, A37 to A41, A43 to A49, A52, and A54 to A58. In a more preferred embodiment, said biallelic marker is selected from the group consisting of A1, A4, 16, A30, A31, A42, A50, A51, and A53. It is preferred that candidate polymorphisms be then verified by screening a larger population of cases and controls by means of any genotyping procedure such as those described herein, preferably using a microsequencing technique in an individual test format. Polymorphisms are considered as candidate mutations when present in cases and controls at frequencies compatible with the expected association results. Polymorphisms are considered as candidate "trait-causing" mutations when they exhibit a statistically significant correlation with the detectable phenotype.

Biallelic Markers of the Invention in Methods of Genetic Diagnostics

The biallelic markers of the present invention can also be used to develop diagnostics tests capable of identifying individuals who express a detectable trait as the result of a specific genotype or individuals whose genotype places them at risk of developing a detectable trait at a subsequent time. The trait analyzed using the present diagnostics may be any detectable trait, including susceptibility to prostate cancer, the level of aggressiveness of prostate cancer tumors, an early onset of prostate cancer, a beneficial response to or side effects related to treatment against prostate cancer. Such a diagnosis can be useful in the staging, monitoring, prognosis and/or prophylactic or curative therapy of prostate cancer.

The diagnostic techniques of the present invention may employ a variety of methodologies to determine whether a test subject has a biallelic marker pattern associated with an increased risk of developing a detectable trait or whether the individual suffers from a detectable trait as a result of a particular mutation, including methods which enable the analysis of individual chromosomes for haplotyping, such as family studies, single sperm DNA analysis or somatic hybrids.

The present invention provides diagnostic methods to determine whether an individual is at risk of developing a disease or suffers from a disease resulting from a mutation or a polymorphism in the BAP28 gene. The present invention also provides methods to determine whether an individual has a susceptibility to prostate cancer.

These methods involve obtaining a nucleic acid sample from the individual and, determining, whether the nucleic acid sample contains at least one allele or at least one biallelic marker haplotype, indicative of a risk of developing the trait or indicative that the individual expresses the trait as a result of possessing a particular BAP28 polymorphism or mutation (trait-causing allele).

Preferably, in such diagnostic methods, a nucleic acid sample is obtained from the individual and this sample is genotyped using methods described above in "Methods Of Genotyping DNA Samples For Biallelic markers. The diagnostics may be based on a single biallelic marker or a on group of biallelic markers.

In each of these methods, a nucleic acid sample is obtained from the test subject and the biallelic marker pattern of one or more of the biallelic markers A1 to A58, preferably one or more of the biallelic markers A1 to A27, A34, A37 to A41, A43 to A49, A52, and A54 to A58, more preferably one or more of the biallelic markers A1, A4, 16, A30, A31, A42, A50, A51, and A53, is determined.

In one embodiment, a PCR amplification is conducted on the nucleic acid sample to amplify regions in which polymorphisms associated with a detectable phenotype have been identified. The amplification products are sequenced to determine whether the individual possesses one or more BAP28 polymorphisms associated with a detectable phenotype. The primers used to generate amplification products may comprise the primers listed in Table 1. Alternatively, the nucleic acid sample is subjected to microsequencing reactions as described above to determine whether the individual possesses one or more BAP28 polymorphisms associated with a detectable phenotype resulting from a mutation or a polymorphism in the BAP28 gene. The primers used in the microsequencing reactions may include the primers listed in Table 4.

In another embodiment, the nucleic acid sample is contacted with one or more allele specific oligonucleotide probes which, specifically hybridize to one or Inore BAP28 alleles associated with a detectable phenotype. The probes used in the hybridization assay may include the probes listed in Table 3. In another embodiment, the nucleic acid sample is contacted with a second BAP28 oligonucleotide capable of producing an amplification product when used with the allele specific oligonucleotide in an amplification reaction. The presence of an amplification product in the amplification reaction indicates that the individual possesses one or Inore BAP28 alleles associated with a detectable phenotype.

In a preferred embodiment the identity of the nucleotide present at, at least one, biallelic marker selected from the group consisting of A1 to A58 and the complements thereof, preferably A1 to A27, A34, A37 to A41, A43 to A49, A52, and A54 to A58, more preferably A1, A4, 16, A30, A31, A42, A50, A51, and A53, and the complements thereof, is determined and the detectable trait is prostate cancer, more preferably sporadic prostate cancer. Diagnostic kits comprise any of the polynucleotides of the present invention.

These diagnostic methods are extremely valuable as they can, in certain circumstances, be used to initiate preventive treatments or to allow an individual carrying a significant haplotype to foresee warning signs such as minor symptoms.

Diagnostics, which analyze and predict response to a drug or side effects to a drug, may be used to determine whether an individual should be treated with a particular drug. For example, if the diagnostic indicates a likelihood that an individual will respond positively to treatment with a particular drug, the drug may be administered to the individual. Conversely, if the diagnostic indicates that an individual is likely to respond negatively to treatment with a particular drug, an alternative course of treatment may be prescribed. A negative response may be defined as either the absence of an efficacious response or the presence of toxic side effects.

Clinical drug trials represent another application for the markers of the present invention. One or more markers indicative of response to an agent acting against prostate cancer or to side effects to an agent acting against prostate cancer may be identified using the methods described above. Thereafter, potential participants in clinical trials of such an agent may be screened to identify those individuals most likely to respond favorably to the drug and exclude those likely to experience side effects. In that way, the effectiveness of drug treatment may be measured in individuals who respond positively to the drug, without lowering the measurement as a result of the inclusion of individuals who are unlikely to respond positively in the study and without risking undesirable safety problems.

Treatment of Prostate Cancer

As the metastasis of prostate cancer can be fatal, it is important to detect prostate cancer susceptibility of individuals. Consequently, the invention also concerns a method for the treatment of prostate cancer comprising the following steps:
  selecting an individual whose DNA comprises alleles of a biallelic marker or of a group of biallelic markers, preferably BAP28-related markers, associated with prostate cancer;
  following up said individual for the appearance (and optionally the development) of tumors in prostate; and
  administering an effective amount of a medicament acting against prostate cancer to said individual at an appropriate stage of the prostate cancer.

In one embodiment, said biallelic marker is selected from the group consisting of A1 to A58, and the complements thereof. In a preferred embodiment, said biallelic marker is selected from the group consisting of A1 to A27, A34, A37 to A41, A43 to A49, A52, and A54 to A58 and the complements thereof. In a preferred embodiment, said biallelic marker is selected from the group consisting of A1, A4, 16, A30, A31, A42, A50, A51, and A53, and the complements thereof.

The prophylactic administration of a treatment serves to prevent, attenuate or inhibit the growth of cancer cells.

Another embodiment of the present invention consists of a method for the treatment of prostate cancer comprising the following steps:
  selecting an individual whose DNA comprises alleles of a biallelic marker or of a group of biallelic markers, preferably BAP28-related markers, associated with prostate cancer;
  administering to said individual, preferably as a preventive treatment of prostate cancer, an effective amount of a medicament acting against prostate cancer such as 4HPR.

In one embodiment, said biallelic marker is selected from the group consisting of A1 to A58, and the complements thereof. In a preferred embodiment, said biallelic marker is selected from the group consisting of A1 to A27, A34, A37 to A41, A43 to A49, A52, and A54 to A58 and the complements thereof. In a preferred embodiment, said biallelic marker is selected from the group consisting of A1, A4, 16, A30, A31, A42, A50, A54, and A58, and the complements thereof.

In a further embodiment, the present invention concerns a method for the treatment of prostate cancer comprising the following steps:
  selecting an individual whose DNA comprises alleles of a biallelic marker or of a group of biallelic markers, preferably BAP28-related markers, associated with a susceptibility prostate cancer;
  administering to said individual, as a preventive treatment of prostate cancer, an effective amount of a medicament acting against prostate cancer such as 4HPR;
  following up said individual for the appearance and the development of tumors in prostate; and optionally
  administering an effective amount of a medicament acting against prostate cancer to said individual at the appropriate stage of the prostate cancer.

In one embodiment, said biallelic marker is selected from the group consisting of A1 to A58, and the complements thereof. In a preferred embodiment, said biallelic marker is selected from the group consisting of A1 to A27, A34, A37 to A41, A43 to A49, A52, and A54 to A58 and the complements thereof. In a preferred embodiment, said biallelic marker is selected from the group consisting of A1, A4, 16, A30, A31, A42, A50, A51, and A53, and the complements thereof.

To enlighten the choice of the appropriate beginning of the treatment of prostate cancer, the present invention also concerns a method for the treatment of prostate cancer comprising the following steps:
  selecting an individual suffering from a prostate cancer whose DNA comprises alleles of a biallelic marker or of a group of biallelic markers, preferably BAP28-related markers, associated with the aggressiveness of prostate cancer tumors; and
  administering an effective amount of a medicament acting against prostate cancer to said individual.

In one embodiment, said biallelic marker is selected from the group consisting of A1 to A58, and the complements thereof. In a preferred embodiment, said biallelic marker is selected from the group consisting of A1 to A27, A34, A37 to A41, A43 to A49, A52, and A54 to A58 and the complements thereof. In a preferred embodiment, said biallelic marker is selected from the group consisting of A1, A4, 16, A30, A31, A42, A50, A51, and A53, and the complements thereof. In particular embodiments, the individual is selected by genotyping one or more biallelic markers of the present invention.

Recombinant Vectors

The term "vector" is used herein to designate either a circular or a linear DNA or RNA molecule, which is either double-stranded or single-stranded, and which comprise at least one polynucleotide of interest that is sought to be transferred in a cell host or in a unicellular or multicellular host organism.

The present invention encompasses a family of recombinant vectors that comprise a regulatory polynucleotide derived from the BAP28 genomic sequence, and/or a coding polynucleotide from either the BAP28 genomic sequence or the cDNA sequence.

Generally, a recombinant vector of the invention may comprise any of the polynucleotides described herein, including regulatory sequences, coding sequences and polynucleotide constructs, as well as any BAP28 primer or probe as defined above. More particularly, the recombinant vectors of the present invention can comprise any of the polynucleotides described in the "Genomic Sequences Of The BAP28 Gene" section, the "BAP28 cDNA Sequences" section, the "Coding Regions" section, the "Polynucleotide constructs" section, and the "Oligonucleotide Probes And Primers" section.

In a first preferred embodiment, a recombinant vector of the invention is used to amplify the inserted polynucleotide derived from a BAP28 genomic sequence of SEQ ID No 1 or a BAP28 cDNA, for example the cDNA of SEQ ID No 2, 3 or 4 in a suitable cell host, this polynucleotide being amplified at every time that the recombinant vector replicates.

A second preferred embodiment of the recombinant vectors according to the invention consists of expression vectors comprising either a regulatory polynucleotide or a coding nucleic acid of the invention, or both. Within certain embodiments, expression vectors are employed to express the BAP28 polypeptide which can be then purified and, for example be used in ligand screening assays or as an immunogen in order to raise specific antibodies directed against the BAP28 protein. In other embodiments, the expression vectors are used for constructing transgenic animals and also for gene therapy. Expression requires that appropriate signals are provided in the vectors, said signals including various regulatory elements, such as enhances/promoters from both viral and mammalian sources that drive expression of the genes of interest in host cells. Dominant drug selection markers for establishing permanent, stable cell clones expressing the products are generally included in the expression vectors of the invention, as they are elements that link expression of the drug selection markers to expression of the polypeptide.

In a further embodiment, the invention concerns a vector comprising a polynucleotide sequence selected from the group consisting of SEQ ID Nos 4, and 9-13, a complementary sequence thereto or a fragment thereof.

More particularly, the present invention relates to expression vectors which include nucleic acids encoding a BAP28 protein, preferably the BAP28 protein of the amino acid sequence of SEQ ID No 5 or variants or fragments thereof.

The invention also pertains to a recombinant expression vector useful for the expression of the BAP28 coding sequence, wherein said vector comprises a nucleic acid of SEQ ID No 2 or 3.

Recombinant vectors comprising a nucleic acid containing a BAP28-related biallelic marker is also part of the invention. In a preferred embodiment, said biallelic marker is selected from the group consisting of A1 to A58, preferably A1 to A27, A34, A37 to A41, A43 to A49, A52, and A54 to A58, more preferably A1, A4, 16, A30, A31, A42, A50, A51, and A53, and the complements thereof.

Some of the elements which can be found in the vectors of the present invention are described in further detail in the following sections.

The present invention also encompasses primary, secondary, and immortalized homologously recombinant host cells of vertebrate origin, preferably mammalian origin and particularly human origin, that have been engineered to: a) insert exogenous (heterologous) polynucleotides into the endogenous chromosomal DNA of a targeted gene, b) delete endogenous chromosomal DNA, and/or c) replace endogenous chromosomal DNA with exogenous polynucleotides. Insertions, deletions, and/or replacements of polynucleotide sequences may be to the coding sequences of the targeted gene and/or to regulatory regions, such as promoter and enhancer sequences, operably associated with the targeted gene.

The present invention further relates to a method of making a homologously recombinant host cell in vitro or in vivo, wherein the expression of a targeted gene not normally expressed in the cell is altered. Preferably the alteration causes expression of the targeted gene under normal growth conditions or under conditions suitable for producing the polypeptide encoded by the targeted gene. The method comprises the steps of: (a) transfecting the cell in vitro or in vivo with a polynucleotide construct, the a polynucleotide construct comprising; (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination.

The present invention further relates to a method of altering the expression of a targeted gene in a cell in vitro or in vivo wherein the gene is not normally expressed in the cell, comprising the steps of: (a) transfecting the cell in vitro or in vivo with a polynucleotide construct, the a polynucleotide construct comprising: (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination, thereby producing a homologously recombinant cell; and (c) maintaining the homologously recombinant cell in vitro or in vivo under conditions appropriate for expression of the gene.

The present invention further relates to a method of making a polypeptide of the present invention by altering the expression of a targeted endogenous gene in a cell in vitro or in vivo wherein the gene is not normally expressed in the cell, comprising the steps of: a) transfecting the cell in vitro with a polynucleotide construct, the a polynucleotide construct comprising: (i) a targeting sequence; (ii) a regulatory sequence and/or a coding sequence; and (iii) an unpaired splice donor site, if necessary, thereby producing a transfected cell; (b) maintaining the transfected cell in vitro or in vivo under conditions appropriate for homologous recombination, thereby producing a homologously recombinant cell; and c) maintaining the homologously recombinant cell in vitro or in vivo under conditions appropriate for expression of the gene thereby making the polypeptide.

The present invention further relates to a polynucleotide construct which alters the expression of a targeted gene in a cell type in which the gene is not normally expressed. This occurs when the a polynucleotide construct is inserted into the chromosomal DNA of the target cell, wherein the a polynucleotide construct comprises: a) a targeting sequence; b) a regulatory sequence and/or coding sequence; and c) an unpaired splice-donor site, if necessary. Further included are a polynucleotide constructs, as described above, wherein the construct further comprises a polynucleotide which encodes a polypeptide and is in-frame with the targeted endogenous gene after homologous recombination with chromosomal DNA.

The compositions may be produced, and methods performed, by techniques known in the art, such as those described in U.S. Pat. Nos. 6,054,288; 6,048,729; 6,048,724; 6,048,524; 5,994,127; 5,968,502; 5,965,125; 5,869,239; 5,817,789; 5,783,385; 5,733,761; 5,641,670; 5,580,734; International Publication Nos: WO96/29411, WO 94/12650; and scientific articles including 1994; Koller et al., Proc. Natl. Acad. Sci. USA 86:8932-8935 (1989) (the disclosures of each of which are incorporated by reference in their entireties).

1. General Features of the Expression Vectors of the Invention

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may comprise a chromosomal, non-chromosomal, semi-synthetic and synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription.

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation site, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

The in vivo expression of a BAP28 polypeptide of SEQ ID No 5 or fragments or variants thereof may be useful in order to correct a genetic defect related to the expression of the native gene in a host organism or to the production of a biologically inactive BAP28 protein.

Consequently, the present invention also deals with recombinant expression vectors mainly designed for the in vivo production of the BAP28 polypeptide of SEQ ID No 5 or fragments or variants thereof by the introduction of the appropriate genetic material in the organism of the patient to be treated. This genetic material may be introduced in vitro in a cell that has been previously extracted from the organism, the modified cell being subsequently reintroduced in the said organism, directly in vivo into the appropriate tissue.

2. Regulatory Elements

Promoters

The suitable promoter regions used in the expression vectors according to the present invention are chosen taking into account the cell host in which the heterologous gene has to be expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors.

Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., 1983; O'Reilly et al., 1992), the lambda PR promoter or also the trc promoter.

Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

The choice of a promoter is well within the ability of a person skilled in the field of genetic engineering. For example, one may refer to the book of Sambrook et al.(1989) or also to the procedures described by Fuller et al. (1996).

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

3. Selectable Markers

Such markers would confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

4. Preferred Vectors.

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and GEM1 (Promega Biotec, Madison, Wis., USA).

Large numbers of other suitable vectors are known to those of skill in the art, and commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pW1NEO, pSV2CAT, pOG44, pXT1, pSG (Stratagene); pSVK3 pBPV, pMSG, pSVL (Pharmacia); pQE-30 (QIAexpress).

Bacteriophage Vectors

The P1 bacteriophage vector may contain large inserts ranging from about 80 to about 100 kb.

The construction of P1 bacteriophage vectors such as p158 or p158/neo8 are notably described by Sternberg (1992, 1994). Recombinant P1 clones comprising BAP28 nucleotide sequences may be designed for inserting large polynucleotides of more than 40 kb (Linton et al., 1993). To generate P1 DNA for transgenic experiments, a preferred protocol is the protocol described by McCormick et al. (1994). Briefly, *E. coli* (preferably strain NS3529) harboring the P1 plasmid are grown overnight in a suitable broth medium containing 25 µg/ml of kanamycin. The P1 DNA is prepared from the *E. coli* by alkaline lysis using the Qiagen Plasmid Maxi kit (Qiagen, Chatsworth. Calif., USA), according to the manufacturer's instructions. The P1 DNA is purified from the bacterial lysate on two Qiagen-tip 500 columns, using the washing and elution buffers contained in the kit. A phenol/chloroform extraction is then performed before precipitating the DNA with 70% ethanol. After solubilizing the DNA in TE (10 mM Tris-HCl, pH 7.4, 1 mM EDTA), the concentration of the DNA is assessed by spectrophotometry.

When the goal is to express a P1 clone comprising BAP28 nucleotide sequences in a transgenic animal, typically in transgenic mice, it is desirable to remove vector sequences from the P1 DNA fragment, for example by cleaving the P1 DNA at rare-cutting sites within the P1 polylinker (SfiI, NotI or SalI). The P1 insert is then purified from vector sequences on a pulsed-field agarose gel, using methods similar using methods similar to those originally reported for the isolation of DNA from YACs (Schedl et al., 1993a; Peterson et al., 1993). At this stage, the resulting purified insert DNA can be concentrated, if necessary, on a Millipore Ultrafree-MC Filter Unit (Millipore, Bedford, Mass., USA-30,000 molecular weight limit) and then dialyzed against microinjection buffer (10 mM Tris-HCl, pH 7.4; 250 µM EDTA) containing 100 mM NaCl, 30 µM spermine, 70 µM spermidine on a microdyalisis membrane (type VS, 0.025 µM from Millipore). The intactness of the purified P1 DNA insert is assessed by electrophoresis on 1% agarose (Sea Kem GTG; FMC Bio-products) pulse-field gel and staining with ethidium bromide.

Baculovirus Vectors

A suitable vector for the expression of the BAP28 polypeptide of SEQ ID No 5 or fragments or variants thereof is a baculovirus vector that can be propagated in insect cells and in insect cell lines. A specific suitable host vector system is the pVL1392/1393 baculovirus transfer vector (Pharmingen) that is used to transfect the SF9 cell line (ATCC N°RL 1711) which is derived from *Spodoptera frugiperda*.

Other suitable vectors for the expression of the BAP28 polypeptide of SEQ ID No 5 or fragments or variants thereof in a baculovirus expression system include those described by Chai et al. (1993), Viasak et al. (1983) and Lenhard et al. (1996).

Viral Vectors

In one specific embodiment, the vector is derived from an adenovirus. Preferred adenovirus vectors according to the invention are those described by Feldman and Steg (1996) or Ohno et al. (1994). Another preferred recombinant adenovirus according to this specific embodiment of the present invention is the human adenovirus type 2 or 5 (Ad 2 or Ad 5) or an adenovirus of animal origin (French patent application N° FR-93.05954).

Retrovirus vectors and adeno-associated virus vectors are generally understood to be the recombinant gene delivery systems of choice for the transfer of exogenous polynucleotides in vivo particularly to mammals, including humans. These vectors provide efficient delivery of genes into cells, and the transferred nucleic acids are stably integrated into the chromosomal DNA of the host.

Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application No WO 93/25234, PCT Application No WO 94/06920, Roux et al., 1989, Julan et al., 1992 and Neda et al., 1991.

Yet another viral vector system that is contemplated by the invention consists in the adeno-associated virus (AAV). The adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al., 1992; Samulski et al., 1989; McLaughlin et al., 1989). One advantageous feature of AAV derives from its reduced efficacy for transducing primary cells relative to transformed cells.

BAC Vectors

The bacterial artificial chromosome (BAC) cloning system (Shizuya et al., 1992) has been developed to stably maintain large fragments of genomic DNA (100-300 kb) in *E. coli*. A preferred BAC vector consists of pBeloBAC11 vector that has been described by Kim et al. (1996). BAC libraries are prepared with this vector using size-selected genomic DNA that has been partially digested using enzymes that permit ligation into either the Bam HI or HindIII sites in the vector. Flanking these cloning sites are T7 and SP6 RNA polymerase transcription initiation sites that can be used to generate end probes by either RNA transcription or PCR methods. After the construction of a BAC library in *E. coli*, BAC DNA is purified from the host cell as a supercoiled circle. Converting these circular molecules into a linear form precedes both size determination and introduction of the BACs into recipient cells. The cloning site is flanked by two Not I sites, permitting cloned segments to be excised from the vector by Not I digestion. Alternatively, the DNA insert contained in the pBeloBAC11 vector may be linearized by treatment of the BAC vector with the commercially available enzyme lambda terminase that leads to the cleavage at the unique cosN site, but this cleavage method results in a full length BAC clone containing both the insert DNA and the BAC sequences.

5. Delivery of the Recombinant Vectors

In order to effect expression of the polynucleotides and polynucleotide constructs of the inventions these constructs must be delivered into a cell. This delivery may be accomplished in vitro, as in laboratory procedures for transforming cell lines, or in vivo or ex vivo, as in the treatment of certain diseases states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., 1973; Chen et al., 1987), DEAE-dextran (Gopal, 1985), electroporation (Tur-Kaspa et al., 1986; Potter et al., 1984), direct microinjection (Harland et al., 1985), DNA-loaded liposomes (Nicolau et al., 1982; Fraley et al., 1979), and receptor-mediated transfection (Wu and Wu, 1987; 1988). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application N° WO 90/11092 (Vical Inc.) and also in PCT application No WO 95/11307 (Institut Pasteur, INSERM, Université d'Ottawa) as well as in the articles of Tacson et al. (1996) and of Huygen et al. (1996).

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al. (1987).

In a further embodiment, the polynucleotide of the invention may be entrapped in a liposome (Ghosh and Bacchawat, 1991; Wong et al., 1980; Nicolau et al., 1987)

In a specific embodiment, the invention provides a composition for the in vivo production of the BAP28 protein or polypeptide described herein. It comprises a naked polynucleotide operatively coding for this polypeptide, in solution in a physiologically acceptable carrier, and suitable for introduction into a tissue to cause cells of the tissue to express the said protein or polypeptide.

The amount of vector to be injected to the desired host organism varies according to the site of injection. As an indicative dose, it will be injected between 0, 1 and 100 µg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired BAP28 polypeptide or the desired fragment thereof is reintroduced into the animal body in order to deliver the recombinant protein within the body either locally or systemically.

Cell Hosts

Another object of the invention consists of a host cell that has been transformed or transfected with one of the polynucleotides described herein, and in particular a polynucleotide either comprising a BAP28 regulatory polynucleotide or the coding sequence of the BAP28 polypeptide of SEQ ID Nos 1, 2, 3 or 4 or a fragment or a variant thereof. Also included are host cells that are transformed (prokaryotic cells) or that are transfected (eukaryotic cells) with a recombinant vector such as one of those described above. More particularly, the cell hosts of the present invention can comprise any of the polynucleotides described in the "Genomic Sequences Of The BAP28 Gene" section, the "BAP28 cDNA Sequences" section, the "Coding Regions" section, the "Polynucleotide constructs" section, and the "Oligonucleotide Probes And Primers" section.

A further recombinant cell host according to the invention comprises a polynucleotide containing a biallelic marker selected from the group consisting of A1 to A58, preferably A1 to A27, A34. A37 to A41. A43 to A49, A52, and A54 to A58, more preferably A1, A4, 16. A30. A31, A42. A50, A51, and A53, and the complements thereof.

Preferred host cells used as recipients for the expression vectors of the invention are the following:

a) Prokaryotic host cells: *Escherichia coli* strains (I.E.DH5-α strain), *Bacillus subtilis, Salmonella typhimurium*, and strains from species like *Pseudomonas, Streptomyces* and *Staphylococcus*.

b) Eukaryotic host cells: HeLa cells (ATCC N°CCL2; N$_o$CCL2.1; N$_o$CCL2.2), Cv 1 cells (ATCC N°CCL70), COS cells (ATCC N°CRL1650; N°CRL1651), Sf-9 cells (ATCC N°CRL 1711). C127 cells (ATCC N° CRL-1804), 3T3 (ATCC N° CRL-6361), CHO (ATCC N° CCL-61), human kidney 293. (ATCC N° 45504; N° CRL-1573) and BHK (ECACC N° 84100501; N° 84111301).

c) Other Mammalian Host Cells.

The BAP28 gene expression in mammalian, and typically human, cells may be rendered defective, or alternatively it may be proceeded with the insertion of a BAP28 genomic or cDNA sequence with the replacement of the BAP28 gene counterpart in the genome of an animal cell by a BAP28 polynucleotide according to the invention. These genetic alterations may be generated by homologous recombination events using specific DNA constructs that have been previously described.

One kind of cell hosts that may be used are mammal zygotes, such as murine zygotes. For example, murine zygotes may undergo microinjection with a purified DNA molecule of interest, for example a purified DNA molecule that has previously been adjusted to a concentration range from 1 ng/ml—for BAC inserts—3 ng/µl—for P1 bacteriophage inserts—in 10 mM Tris-HCl, ply 7.4, 250 µM EDTA containing 100 mM NaCl, 30 µM spermine, and 70 µM spermidine. When the DNA to be microinjected has a large size, polyamines and high salt concentrations can be used in order to avoid mechanical breakage of this DNA, as described by Schedl et al (1993b).

Anyone of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC n° CRL-1821), ES-D3 (ATCC n° CRL1934 and n° CRL-11632), YS001 (ATCC n° CRL-11776), 36.5 (ATCC n° CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells comprise primary embryonic fibroblasts that are established from tissue of day 13-day 14 embryos of virtually any mouse strain, that are maintained in culture, such as described by Abbondanzo et al. (1993) and are inhibited in growth by irradiation, such as described by Robertson (1987), or by the presence of an inhibitory concentration of LIF, such as described by Pease and Williams (1990).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents.

Such methods are well known by the skill artisan.

Transgenic Animals

The terms "transgenic animals" or "host animals" are used herein designate animals that have their genome genetically and artificially manipulated so as to include one of the nucleic acids according to the invention. Preferred animals are non-human mammals and include those belonging to a genus selected from *Mus* (e.g. mice), *Rattus* (e.g. rats) and *Oryctogalus* (e.g. rabbits) which have their genome artificially and genetically altered by the insertion of a nucleic acid according to the invention. In one embodiment, the invention encompasses non-human host mammals and animals comprising a recombinant vector of the invention or a BAP28 gene disrupted by homologous recombination with a knock out vector.

The transgenic animals of the invention all include within a plurality of their cells a cloned recombinant or synthetic DNA sequence, more specifically one of the purified or isolated nucleic acids comprising a BAP28 coding sequence, a BAP28 regulatory polynucleotide, a polynucleotide construct, or a DNA sequence encoding an antisense polynucleotide such as described in the present specification.

Generally, a transgenic animal according the present invention comprises any one of the polynucleotides, the recombinant vectors and the cell hosts described in the present invention. More particularly, the transgenic animals of the present invention can comprise any of the polynucleotides described in the "Genomic Sequences Of The BAP28 Gene" section, the "BAP28 cDNA Sequences" section, the "Coding Regions" section, the "Polynucleotide constructs" section, the "Oligonucleotide Probes And Primers" section, the "Recombinant Vectors" section and the "Cell Hosts" section.

A further transgenic animals according to the invention contains in their somatic cells and/or in their germ line cells a polynucleotide comprising a biallelic marker selected from the group consisting of A1 to A58, preferably A1 to A27, A34, A37 to A41, A43 to A49, A52, and A54 to A58, more preferably A1, A4, 16, A30, A31, A42, A50, A51, and A53, and the complements thereof.

In a first preferred embodiment, these transgenic animals may be good experimental models in order to study the diverse pathologies related to cell differentiation, in particular concerning the transgenic animals within the genome of which has been inserted one or several copies of a polynucleotide encoding a native BAP28 protein, or alternatively a mutant BAP28 protein.

In a second preferred embodiment, these transgenic animals may express a desired polypeptide of interest under the control of the regulatory polynucleotides of the BAP28 gene, leading to good yields in the synthesis of this protein of interest, and eventually a tissue specific expression of this protein of interest.

The design of the transgenic animals of the invention may be made according to the conventional techniques well known from the one skilled in the art. For more details regarding the production of transgenic animals, and specifically transgenic mice, it may be referred to U.S. Pat. Nos. 4,873,191, issued Oct. 10, 1989; 5,464,764 issued Nov. 7, 1995; and 5,789,215, issued Aug. 4, 1998; these documents being herein incorporated by reference to disclose methods producing transgenic mice.

Transgenic animals of the present invention are produced by the application of procedures which result in an animal with a genome that has incorporated exogenous genetic material. The procedure involves obtaining the genetic material, or a portion thereof, which encodes either a BAP28 coding sequence, a BAP28 regulatory polynucleotide or a DNA sequence encoding a BAP28 antisense polynucleotide such as described in the present specification.

A recombinant polynucleotide of the invention is inserted into an embryonic or ES stem cell line. The insertion is preferably made using electroporation, such as described by Thomas et al. (1987). The cells subjected to electroporation are screened (e.g. by selection via selectable markers, by PCR or by Southern blot analysis) to find positive cells which have integrated the exogenous recombinant polynucleotide into their genome, preferably via an homologous recombination event. An illustrative positive-negative selection procedure that may be used according to the invention is described by Mansour et al. (1988).

Then, the positive cells are isolated, cloned and injected into 3.5 days old blastocysts from mice, such as described by Bradley (1987). The blastocysts are then inserted into a female host animal and allowed to grow to term.

Alternatively, the positive ES cells are brought into contact with embryos at the 2.5 days old 8-16 cell stage (morulae) such as described by Wood et al. (1993) or by Nagy et al. (1993), the ES cells being internalized to colonize extensively the blastocyst including the cells which will give rise to the germ line.

The offspring of the female host are tested to determine which animals are transgenic e.g. include the inserted exogenous DNA sequence and which are wild-type.

Thus, the present invention also concerns a transgenic animal containing a nucleic acid, a recombinant expression vector or a recombinant host cell according to the invention.

Recombinant Cell Lines Derived from the Transgenic Animals of the Invention.

A further object of the invention consists of recombinant host cells obtained from a transgenic animal described herein. In one embodiment the invention encompasses cells derived from non-human host mammals and animals comprising a recombinant vector of the invention or a B4P28 gene disrupted by homologous recombination with a knock out vector.

Recombinant cell lines may be established in vitro from cells obtained from any tissue of a transgenic animal according to the invention, for example by transfection of primary cell cultures with vectors expressing one-genes such as SV40 large T antigen, as described by Chou (1989) and Shay et al. (1991).

Methods for Screening Substances Interacting with a BAP28 Polypeptide

For the purpose of the present invention, a ligand means a molecule, such as a protein, a peptide, an antibody or any synthetic chemical compound capable of binding to the BAP28 protein or one of its fragments or variants or to modulate the expression of the polynucleotide coding for BAP28 or a fragment or variant thereof.

In the ligand screening method according to the present invention, a biological sample or a defined molecule to be tested as a putative ligand of the BAP28 protein is brought into contact with the corresponding purified BAP28 protein, for example the corresponding purified recombinant BAP28 protein produced by a recombinant cell host as described hereinbefore, in order to form a complex between this protein and the putative ligand molecule to be tested.

As an illustrative example, to study the interaction of the BAP28 protein, or a fragment comprising a contiguous span of at least 6 amino acids, preferably at least 8 to 10 amino acids, more preferably at least 12, 15, 20, 25, 30, 40, 50, or 100 amino acids of SEQ ID No 5, wherein said contiguous span includes either at least 1, 2, 3, 5 or 10 of the amino acid positions selected from the group consisting of 1 to 1629 of the SEQ ID No 5, or an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an amino at the amino acid position 2050 of SEQ ID No 5, with drugs or small molecules, such as molecules generated through combinatorial chemistry approaches, the microdialysis coupled to HPLC method described by Wang et al. (1997) or the affinity capillary electrophoresis method described by Bush et al. (1997), the disclosures of which are incorporated by reference, can be used.

In further methods, peptides, drugs, fatty acids, lipoproteins, or small molecules which interact with the BAP28 protein, or a fragment comprising a contiguous span of at least 6 amino acids, preferably at least 8 to 10 amino acids, more preferably at least 12, 15, 20, 25, 30, 40, 50, or 100 amino acids of SEQ ID No 5, wherein said contiguous span includes either at least 1, 2, 3, 5 or 10 of the amino acid positions selected from the group consisting of 1 to 1629 of the SEQ ID No 5 or an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an alanine at the amino acid position 2050 of SEQ ID No 5, may be identified using assays such as the following. The molecule to be tested for binding is labeled with a detectable label, such as a fluorescent, radioactive, or enzymatic tag and placed in contact with immobilized BAP28 protein, or a fragment thereof under conditions which permit specific binding to occur. After removal of non-specifically bound molecules, bound molecules are detected using appropriate means.

Another object of the present invention consists of methods and kits for the screening of candidate substances that interact with BAP28 polypeptide.

The present invention pertains to methods for screening substances of interest that interact with a BAP28 protein or one fragment or variant thereof. By their capacity to bind covalently or non-covalently to a BAP28 protein or to a fragment or variant thereof, these substances or molecules may be advantageously used both in/vitro and in vivo.

In vitro, said interacting molecules may be used as detection means in order to identify the presence of a BAP28 protein in a sample, preferably a biological sample.

A method for the screening of a candidate substance comprises the following steps:

a) providing a polypeptide consisting of a BAP28 protein or a fragment comprising a contiguous span of at least 6 amino acids, preferably at least 8 to 10 amino acids, more preferably at least 12, 15, 20, 25, 30, 40, 50, or 100 amino acids of SEQ ID No 5, wherein said contiguous span includes either at least 1, 2, 3, 5 or 10 of the amino acid positions selected from the group consisting of 1 to 1629 of the SEQ ID No 5 or an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an alanine at the amino acid position 2050 of SEQ ID No 5, or a variant thereof;

b) obtaining a candidate substance;

c) bringing into contact said polypeptide with said candidate substance;

d) detecting the complexes formed between said polypeptide and said candidate substance.

The invention further concerns a kit for the screening of a candidate substance interacting with the BAP28 polypeptide, wherein said kit comprises:

a) a BAP28 protein having an amino acid sequence selected from the group consisting of the amino acid sequences of SEQ ID No 5 or a peptide fragment comprising a contiguous span of at least 6 amino acids, preferably at least 8 to 10 amino acids, more preferably at least 12, 15, 20, 25, 30, 40, 50, or 100 amino acids of SEQ ID No 5, wherein said contiguous span includes either at least 2, 3, 5 or 10 of the amino acid positions selected from the group consisting of 1 to 1629 of the SEQ ID No 5 or an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an alaninie at the amino acid position 2050 of SEQ ID No 5, or a variant thereof:

b) in some embodiments, the kit may also comprise means useful to detect the complex formed between the BAP28 protein or a peptide fragment or a variant thereof and the candidate substance.

In a preferred embodiment of the kit described above, the detection means consist in monoclonal or polyclonal antibodies directed against the BAP28 protein or a peptide fragment or a variant thereof.

Various candidate substances or molecules can be assayed for interaction with a BAP28 polypeptide. These substances or molecules include, without being limited to, natural or synthetic organic compounds or molecules of biological origin such as polypeptides. When the candidate substance or molecule consists of a polypeptide, this polypeptide may be the resulting expression product of a phage clone belonging to a phage-based random peptide library, or alternatively the polypeptide may be the resulting expression product of a cDNA library cloned in a vector suitable for performing a two-hybrid screening assay.

The invention also pertains to kits useful for performing the hereinbefore described screening method. Preferably, such kits comprise a BAP28 polypeptide or a fragment or a variant thereof, and, in some embodiments, means useful to detect the complex formed between the BAP28 polypeptide or its fragment or variant and the candidate substance. In a preferred embodiment the detection means consist in monoclonal or polyclonal antibodies directed against the corresponding BAP28 polypeptide or a fragment or a variant thereof.

A. Candidate Ligands Obtained from Random Peptide Libraries

In a particular embodiment of the screening method, the putative ligand is the expression product of a DNA insert contained in a phage vector (Parmley and Smith, 1988). Specifically, random peptide phages libraries are used. The random DNA inserts encode for peptides of 8 to 20 amino acids in length (Oldenburg K. R. et al., 1992; Valadon P., et al., 1996; Lucas A. H., 1994; Westerink M. A. J., 1995; Felici F. et al., 1991). According to this particular embodiment, the recombinant phages expressing a protein that binds to the immobilized BAP28 protein is retained and the complex formed between the BAP28 protein and the recombinant phage may be subsequently immunoprecipitated by a polyclonal or a monoclonal antibody directed against the BAP28 protein.

Once the ligand library in recombinant phages has been constructed, the phage population is brought into contact with the immobilized BAP28 protein. Then the preparation of complexes is washed in order to remove the non-specifically bound recombinant phages. The phages that bind specifically to the BAP28 protein are then eluted by a buffer (acid pH) or immunoprecipitated by the monoclonal antibody produced by the hybridoma anti-BAP28, and this phage population is subsequently amplified by an over-infection of bacteria (for example E. coli). The selection step may be repeated several times, preferably 2-4 times, in order to select the more specific recombinant phage clones. The last step consists in characterizing the peptide produced by the selected recombinant phage clones either by expression in infected bacteria and isolation, expressing the phage insert in another host-vector system, or sequencing the insert contained in the selected recombinant phages.

B. Candidate Ligands Obtained by Competition Experiments.

Alternatively, peptides, drugs or small molecules which bind to the BAP28 protein, or a fragment comprising a contiguous span of at least 6 amino acids, preferably at least 8 to 10 amino acids more preferably at least 12, 15, 20, 25, 30, 40, 50, or 100 amino acids of SEQ ID No 5, wherein said contiguous span includes either at least 1, 2, 3, 5 or 10 of the amino acid positions selected from the group consisting of 1 to 1629 of the SEQ ID No 5 or an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an alanine at the amino acid position 2050 of SEQ ID No 5, may be identified in competition experiments. In such assays, the BAP28 protein, or a fragment thereof, is immobilized to a surface, such as a plastic plate. Increasing amounts of the peptides, drugs or small molecules are placed in contact with the immobilized BAP28 protein, or a fragment thereof, in the presence of a detectable labeled known BAP28 protein ligand. For example, the BAP28 ligand may be detectably labeled with a fluorescent, radioactive, or enzymatic tag. The ability of the test molecule to bind the BAP28 protein, or a fragment thereof, is determined by measuring the amount of detectably labeled known ligand bound in the presence of the test molecule. A decrease in the amount of known ligand bound to the BAP28 protein, or a fragment thereof, when the test molecule is present indicated that the test molecule is able to bind to the BAP28 protein, or a fragment thereof.

C. Candidate Ligands Obtained by Affinity Chromatography.

Proteins or other molecules interacting with the BAP28 protein, or a fragment comprising a contiguous span of at least 6 amino acids, preferably at least 8 to 10 amino acids, more preferably at least 12, 15, 20, 25, 30, 40, 50, or 100 amino acids of SEQ ID No 5, wherein said contiguous span includes either at least 1, 2, 3, 5 or 10 of the amino acid positions selected from the group consisting of 1 to 1629 of the SEQ ID No 5 or an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an alanine at the amino acid position 2050 of SEQ ID No 5, can also be found using affinity columns which contain the BAP28 protein, or a fragment thereof. The BAP28 protein, or a fragment thereof, may be attached to the column using conventional techniques including chemical coupling to a suitable column matrix such as agarose, Affi Gel®, or other matrices familiar to those of skill in art. In some embodiments of this method, the affinity column contains chimeric proteins in which the BAP28 protein, or a fragment thereof, is fused to glutathion S transferase (GST). A mixture of cellular proteins or pool of expressed proteins as described above is applied to the affinity column.

Proteins or other molecules interacting with the BAP28 protein, or a fragment thereof, attached to the column can then be isolated and analyzed on 2-D electrophoresis gel as described in Ramunsen et al. (1997), the disclosure of which is incorporated by reference. Alternatively, the proteins retained on the affinity column can be purified by electrophoresis based methods and sequenced. The same method can be used to isolate antibodies, to screen phage display products, or to screen phage display human antibodies.

D. Candidate Ligands Obtained by Optical Biosensor Methods

Proteins interacting with the BAP28 protein, or a fragment comprising a contiguous span of at least 6 amino acids, preferably at least 8 to 10 amino acids, more preferably at least 12, 15, 20, 25, 30, 40, 50, or 100 amino acids of SEQ ID No 5, wherein said contiguous span includes either at least 1, 2, 3, 5 or 10 of the amino acid positions selected from the group consisting of 1 to 1629 of the SEQ ID No 5 or an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an alanine at the amino acid position 2050 of SEQ ID No 5, can also be screened by using an Optical Biosensor as described in Edwards and Leatherbarrow (1997) and also in Szabo et al. (1995), the disclosure of which is incorporated by reference. This technique permits the detection of interactions between molecules in real time, without the need of labeled molecules. This technique is based on the surface plasmon resonance (SPR) phenomenon. Briefly, the candidate ligand molecule to be tested is attached to a surface (such as a carboxymethyl dextran matrix). A light beam is directed towards the side of the surface that does not contain the sample to be tested and is reflected by said surface. The SPR phenomenon causes a decrease in the intensity of the reflected light with a specific association of angle and wavelength. The binding of candidate ligand molecules cause a change in the refraction index on the surface, which change is detected as a change in the SPR signal. For screening of candidate ligand molecules or substances that are able to interact with the BAP28 protein, or a fragment thereof, the BAP28 protein, or a fragment thereof, is immobilized onto a surface. This surface consists of one side of a cell through which flows the candidate molecule to be assayed. The binding of the candidate molecule on the BAP28 protein, or a fragment thereof, is detected as a change of the SPR signal. The candidate molecules tested may be proteins, peptides, carbohydrates, lipids, or small molecules generated by combinatorial chemistry. This technique may also be performed by immobilizing eukaryotic or prokaryotic cells or lipid vesicles exhibiting an endogenous or a recombinantly expressed BAP28 protein at their Surface.

The main advantage of the method is that it allows the determination of the association rate between the BAP28 protein and molecules interacting with the BAP28 protein. It is thus possible to select specifically ligand molecules interacting with the BAP28 protein, or a fragment thereof, through strong or conversely weak association constants.

E. Candidate Ligands Obtained Through a Two-Hybrid Screening Assay.

The yeast two-hybrid system is designed to study protein-protein interactions in vivo (Fields and Song, 1989), and relies upon the fusion of a bait protein to the DNA binding domain of the yeast Ga14 protein. This technique is also described in the U.S. Pat. No. 5,667,973 and the U.S. Pat. No. 5,283,173 (Fields et al.) the technical teachings of both patents being herein incorporated by reference.

The general procedure of library screening by the two-hybrid assay may be performed as described by Harper et al. (1993) or as described by Cho et al. (1998) or also Fromont-Racine et al. (1997).

The bait protein or polypeptide consists of a BAP28 polypeptide or a fragment comprising a contiguous span of at least 6 amino acids, preferably at least 8 to 10 amino acids, more preferably at least 12, 15, 20, 25, 30, 40, 50, or 100 amino acids of SEQ ID No 5, wherein said contiguous span includes either at least 1, 2, 3, 5 or 10 of the amino acid positions selected from the group consisting of 1 to 1629 of the SEQ ID No 5 or an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an alanine at the amino acid position 2050 of SEQ ID No 5, or a variant thereof.

More precisely, the nucleotide sequence encoding the BAP28 polypeptide or a fragment or variant thereof is fused to a polynucleotide encoding the DNA binding domain of the GAL4 protein, the fused nucleotide sequence being inserted in a suitable expression vector, for example pAS2 or pM3.

Then, a human cDNA library is constructed in a specially designed vector, such that the human cDNA insert is fused to a nucleotide sequence in the vector that encodes the transcriptional domain of the GAL4 protein. Preferably, the vector used is the pACT vector. The polypeptides encoded by the nucleotide inserts of the human cDNA library are termed "pray" polypeptides.

A third vector contains a detectable marker gene, such as beta galactosidase gene or CAT gene that is placed under the control of a regulation sequence that is responsive to the binding of a complete Ga14 protein containing both the transcriptional activation domain and the DNA binding domain. For example, the vector pG5EC may be used.

Two different yeast strains are also used. As an illustrative but non limiting example the two different yeast strains may be the followings:

Y190, the phenotype of which is (MATa, Lez2-3, 112 ura3-12, trp1-901, his3-D200, ade2-101, gal4Dgall80D URA3 GAL-LacZ, LYS GAL-HIS3, cyh');

Y187, the phenotype of which is (MATa gal gal80 his3 trp1-901 ade2-101 ura3-52 leu2-3, -112 URA3 GAL-lacZmet$^-$), which is the opposite mating type of Y190.

Briefly, 20 μg of pAS2/BAP28 and 20 μg of pACT-cDNA library are co-transformed into yeast strain Y190. The transformants are selected for growth on minimal media lacking histidine, leucine and tryptophan, but containing the histidine synthesis inhibitor 3-AT (50 mM). Positive colonies are screened for beta galactosidase by filter lift assay. The double positive colonies (His, bela-gal$^-$) are then grown on plates lacking histidine, leucine, but containing tryptophan and cycloheximide (10 mg/ml) to select for loss of pAS2/BAP28 plasmids bu retention of pACT-cDNA library plasmids. The resulting Y190 strains are mated with Y187 strains expressing BAP28 or non-related control proteins; such as cyclophilin B, lamin, or SNF1, as Gal4 fusions as described by Harper et al. (1993) and by Bram et al. (Bram R J et al., 1993), and screened for beta galactosidase by filter lift assay. Yeast clones that are beta gal-after mating with the control Gal4 fusions are considered false positives.

In another embodiment of the two-hybrid method according to the invention, interaction between the BAP28 or a fragment or variant thereof with cellular proteins may be assessed using the Matchmaker Two Hybrid System 2 (Catalog No K1604-1, Clontech). As described in the manual accompanying the Matchmaker Two Hybrid System 2 (Catalog No K1604-1, Clontech), the disclosure of which is incorporated herein by reference, nucleic acids encoding the BAP28 protein or a portion thereof, are inserted into an expression vector such that they are in frame with DNA encoding the DNA binding domain of the yeast transcriptional activator GAL4. A desired cDNA, preferably human cDNA, is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain interaction between BAP28 and the protein or peptide encoded by the initially selected cDNA insert.

Methods for Screening Substances Modulating the Activity of the BAP28 Protein

The invention also concerns a method for screening new agents, or candidate substances which modulate the activity of the BAP28 protein or a fragment thereof. Preferably, the BAP28 protein or a fragment thereof is a polypeptide code comprising a contiguous span of at least 6 amino acids of SEQ ID No 5, wherein said contiguous span includes either at least 1, 2, 3, 5 or 10 of the amino acid positions selected from the group consisting of 1 to 1629 of the SEQ ID No 5 or an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an alanine at the amino acid position 2050 of SEQ ID No 5. Preferably, the candidate substance is mixed with the BAP28 protein and the activity of the BAP28 protein is measured. Candidate substances include, without being limited to, natural or synthetic organic compounds or molecules of biological origin such as polypeptides.

Method for Screening Substances Interacting with the Regulatory Sequences of the BAP28 Gene The present invention also concerns a method for screening substances or molecules that are able to interact with the regulatory sequences of the BAP28 gene, such as for example promoter or enhancer sequences.

Nucleic acids encoding proteins which are able to interact with the regulatory sequences of the BAP28 gene, more particularly a nucleotide sequence selected from the group consisting of the polynucleotides of the 5' and 3' regulatory region or a fragment or variant thereof, and preferably a variant comprising one of the biallelic markers of the invention, may be identified by using a one-hybrid system, such as that described in the booklet enclosed in the Matchmaker One-Hybrid System kit from Clontech (Catalog Ref. n° K1603-1), the technical teachings of which are herein incorporated by reference. Briefly, the target nucleotide sequence is cloned upstream of a selectable reporter sequence and the resulting DNA construct is integrated in the yeast genome (*Saccharomyces cerevisiae*). The yeast cells containing the reporter sequence in their genome are then transformed with a library consisting of fusion molecules between cDNAs encoding candidate proteins for binding onto the regulatory sequences of the BAP28 gene and sequences encoding the activator domain of a yeast transcription factor such as GAL4. The recombinant yeast cells are plated in a culture broth for selecting cells expressing the reporter sequence. The recombinant yeast cells thus selected contain a fusion protein that is able to bind onto the target regulatory sequence of the BAP28 gene. Then, the cDNAs encoding the fusion proteins are sequenced and may be cloned into expression or transcription vectors in vitro. The binding of the encoded polypeptides to the target regulatory sequences of the BAP28 gene may be confirmed by techniques familiar to the one skilled in the art, such as gel retardation assays or DNAse protection assays.

Gel retardation assays may also be performed independently in order to screen candidate molecules that are able to inter-act with the regulatory sequences of the BAP28 gene, such as described by Fried and Crothers (1981), Garner and Revzin (1981) and Dent and Latchman (1993), the teachings of these publications being herein incorporated by reference. These techniques are based on the principle according to which a DNA fragment which is bound to a protein migrates slower than the same unbound DNA fragment. Briefly, the target nucleotide sequence is labeled. Then the labeled target nucleotide sequence is brought into contact with either a total nuclear extract from cells containing transcription factors, or with different candidate molecules to be tested. The interaction between the target regulatory sequence of the BAP28 gene and the candidate molecule or the transcription factor is detected after gel or capillary electrophoresis through a retardation in the migration.

Method for Screening Ligands that Modulate the Expression of the BAP28 Protein

Another subject of the present invention is a method for screening molecules that modulate the expression of the BAP28 protein. Such a screening method comprises the steps of:

a) cultivating a prokaryotic or an eukaryotic cell that has been transfected with a nucleotide sequence encoding the BAP28 protein or a variant or a fragment thereof, placed under the control of its own promoter;

b) bringing into contact the cultivated cell with a molecule to be tested;

c) quantifying the expression of the BAP28 protein or a variant or a fragment thereof.

Using DNA recombination techniques well known by the one skill in the art, the BAP28 protein encoding DNA sequence is inserted into an expression vector, downstream from its promoter sequence. As an illustrative example, the promoter sequence of the BA P28 gene is contained in the nucleic acid of the 5' regulatory region.

The quantification of the expression of the BAP28 protein may be realized either at the mRNA level or at the protein level. In the latter case, polygonal or monoclonal antibodies may be used to quantify the amounts of the BAP28 protein that have been produced, for example in an ELISA or a RIA assay.

In a preferred embodiment, the quantification of the BAP28 mRNA is realized by a quantitative PCR amplification of the cDNA obtained by a reverse transcription of the total mRNA of the cultivated BAP28-transfected host cell, using a pair of primers specific for BAP28.

The present invention also concerns a method for screening substances or molecules that are able to increase, or in contrast to decrease, the level of expression of the BAP28 gene. Such a method may allow the one skilled in the art to select substances exerting a regulating effect on the expression level of the BAP28 gene and which may be useful as active ingredients included in pharmaceutical compositions for treating patients suffering from prostate cancer.

Thus, is also part of the present invention a method for screening of a candidate substance or molecule that modulated the expression of the BAP28 gene, this method comprises the following steps:

providing a recombinant cell host containing a nucleic acid, wherein said nucleic acid comprises a nucleotide sequence of the 5' regulatory region or a biologically active fragment or variant thereof located upstream a polynucleotide encoding a detectable protein;

obtaining a candidate substance; and determining the ability of the candidate substance to modulate the expression levels of the polynucleotide encoding the detectable protein.

In a further embodiment, the nucleic acid comprising the nucleotide sequence of the 5' regulatory region or a biologically active fragment or variant thereof also includes a 5'UTR region of the BAP28 cDNA of SEQ ID No 2 or 3, or one of its biologically active fragments or variants thereof.

Among the preferred polynucleotides encoding a detectable protein, there may be cited polynucleotides encoding beta galactosidase, green fluorescent protein (GFP) and chloramphenicol acetyl transferase (CAT). In some embodiments, the detectable protein can be BAP28 or a fragment thereof.

The invention also pertains to kits useful for performing the hereinbefore described screening method. Preferably, such kits comprise a recombinant vector that allows the expression of a nucleotide sequence of the 5' regulatory region or a biologically active fragment or variant thereof located upstream and operably linked to a polynucleotide encoding a detectable protein or the BAP28 protein or a fragment or a variant thereof.

In another embodiment of a method for the screening of a candidate substance or molecule that modulates the expression of the BAP28 gene, wherein said method comprises the following steps:

a) providing a recombinant host cell containing a nucleic acid, wherein said nucleic acid comprises a 5'UTR sequence of the BAP28 cDNA of SEQ ID No 2 or 3, or one of its biologically active fragments or variants, the 5'UTR sequence or its biologically active fragment or variant being operably linked to a polynucleotide encoding a detectable protein;

b) obtaining a candidate substance; and c) determining the ability of the candidate substance to modulate the expression levels of the polynucleotide encoding the detectable protein.

In a specific embodiment of the above screening method, the nucleic acid that comprises a nucleotide sequence selected from the group consisting of the 5'UTR sequence of the BAP28 cDNA of SEQ ID No 2 or 3 or one of its biologically active fragments or variants, includes a promoter sequence which is endogenous with respect to the BAP28 5'UTR sequence.

In another specific embodiment of the above screening method, the nucleic acid that comprises a nucleotide sequence selected from the group consisting of the 5'UTR sequence of the BAP28 cDNA of SEQ ID No 2 or 3 or one of its biologically active fragments or variants, includes a promoter sequence which is exogenous with respect to the BAP28 5'UTR sequence defined therein.

In a further preferred embodiment, the nucleic acid comprising the 5'-UTR sequence of the BAP28 cDNA or SEQ ID No 2 or 3 or the biologically active fragments thereof includes a biallelic marker selected from the group consisting of A1 to A58, preferably A1 to A27, A34, A37 to A41, A43 to A49, A52, and A54 to A58, more preferably one of the biallelic markers A1, A4, 16, A30, A31, A42. A50, A51, and A53, or the complements thereof.

The invention further deals with a kit for the screening of a candidate substance modulating the expression of the BAP28 gene, wherein said kit comprises a recombinant vector that comprises a nucleic acid including a 5'UTR sequence of the BAP28 cDNA of SEQ ID No 2 or 3, or one of their biologically active fragments or variants, the 5'UTR sequence or its biologically active fragment or variant being operably linked to a polynucleotide encoding a detectable protein.

For the design of suitable recombinant vectors useful for performing the screening methods described above, it will be referred to the section of the present specification wherein the preferred recombinant vectors of the invention are detailed.

Expression levels and patterns of BAP28 may be analyzed by solution hybridization with long probes as described in International Patent Application No WO 97/05277, the entire contents of which are incorporated herein by reference. Briefly, the BAP28 cDNA or the BAP28 genomic DNA described above, or fragments thereof, is inserted at a cloning site immediately downstream of a bacteriophage (T3, T7 or SP6) RNA polymerase promoter to produce antisense RNA. Preferably, the BAP28 insert comprises at least 100 or more consecutive nucleotides of the genomic DNA sequence or the cDNA sequences. The plasmid is linearized and transcribed in the presence of ribonucleotides comprising modified riboniucleotides (i.e. biotin-UTP and DIG-UTP). An excess of this doubly labeled RNA is hybridized in solution with mRNA isolated from cells or tissues of interest. The hybridizations are performed under standard stringent conditions (40-50° C. for 16 hours in an 80% formamide, 0.4 M NaCl buffer, pH 7-8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Quantitative analysis of BAP28 gene expression may also be performed using arrays. As used herein, the term array means a one dimensional, two dimensional, or multidimensional arrangement of a plurality of nucleic acids of sufficient length to permit specific detection of expression of mRNAs capable of hybridizing thereto. For example, the arrays may contain a plurality of nucleic acids derived from genes whose expression levels are to be assessed. The arrays may include the BAP28 genomic DNA, the BAP28 cDNA sequences or the sequences complementary thereto or fragments thereof, particularly those comprising at least one of the biallelic markers according the present invention, preferably at least one of the biallelic markers A1 to A58, preferably A1 to A27, A34, A37 to A41, A43 to A49, A52, and A54 to A58, more preferably at least one of the biallelic markers A1, A4, 16, A30, A31, A42, A50, A51, and A53. Preferably, the fragments are at least 15 nucleotides in length. In other embodiments, the fragments are at least 25 nucleotides in length. In some embodiments, the fragments are at least 50 nucleotides in length. More preferably, the fragments are at least 100 nucleotides in length. In another preferred embodiments the fragments are more than 100 nucleotides in length. In some embodiments the fragments may be more than 500 nucleotides in length.

For example, quantitative analysis of BAP28 gene expression may be performed with a complementary DNA microarray as described by Schena et al. (1995 and 1996). Full length BAP28 cDNAs or fragments thereof are amplified by PCR and arrayed from a 96-well microtiter plate onto silylated microscope slides using high-speed robotics. Printed arrays are incubated in a humid chamber to allow rehydration of the array elements and rinsed, once in 0.2% SDS for 1 min, twice in water for 1 mill and once for 5 min in sodium borohydride solution. The arrays are submerged in water for 2 min at 95° C. transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 cm² microarrays under a 14×14 mm glass coverslip for 6-12 hours at 60° C. Arrays are washed for 5 min at 25° C. in low stringency wash buffer (1×SSC/0.2% SDS), then for 10 ml at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of BAP28 gene expression may also be performed with full length BAP28 cDNAs or fragments thereof in complementary DNA arrays as described by Pietu et al. (1996). The full length BAP28 cDNA or fragments thereof is PCR amplified and spotted on membranes.

Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis using the BAP28 genomic DNA, the BAP28 cDNA, or fragments thereof can be done through high density nucleotide arrays as described by Lockhart et al. (1996) and Sosnowsky et al. (1997). Oligonucleotides of 15-50 nucleotides from the sequences of the BAP28 genomic DNA, the BAP28 cDNA sequences particularly those comprising at least one of biallelic markers according the present invention, preferably at least one biallelic marker selected from the group consisting of A1 to A58, preferably A1 to A27, A34, A37 to A41, A43 to A49, A52, and A54 to A58, more preferably at least one of the biallelic markers A1, A4, 16, A30, A31. A42. A50, A51, and A53, or the sequences complementary thereto, are synthesized directly on the chip (Lockhart et al., supra) or synthesized and then addressed to the chip (Sosnowski et al., supra). Preferably, the oligonucleotides are about 20 nucleotides in length.

BAP28 cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., 1997), the dyes or labeling compounds are detected and quantified. Duplicate hybridizations are performed. Comparative analysis of the intensity of the signal originating from cDNA probes on the same target oligonucleotide in different cDNA samples indicates a differential expression of BAP28 mRNA.

COMPUTER-RELATED EMBODIMENTS

As used herein the term "nucleic acid codes of the invention" encompass the nucleotide sequences comprising, consisting essentially of, or consisting of any one of the following:

a) a contiguous span of at least 12, 15, 18, 20, 25, 30, 35, 40, 50, 60, 70, 80, 90, 100, 150, 200, 500, or 1000 nucleotides of SEQ ID No 1, wherein said contiguous span comprises at least 1.2, 3, 5, or 10 of the following nucleotide positions of SEQ ID No 1: 1-50357, 50499-50963, 51257-52147, 52299-53234, 53394-53553, 53689-53837, 53943-54028, 54198-54740, 54896-55753, 55913-57385, 57495-58503, 58828-85946, 59355-85946, 86169-91228, and/or 91852 to 97662;

b) a contiguous span of at least 12, 15, 18, 20, 25, 30, 50, 80, 100, 150, 200, 250, 300, 350, 400, 450, or 500 nucleotides of SEQ ID No 1 or the complement thereof, wherein said contiguous span comprises at least 1, 2, 3, 5, 10, 20, 30, 40 or 50 nucleotides selected from the group consisting of the following nucleotide positions of SEQ ID No 1: 4997-5076, 5371-5544, 6121-6337, 9877-10018, 11522-11623, 12521-12661, 13453-13664, 13824-13957, 15376-15478, 16855-16965, 17378-17495, 18535-18642, 21446-21541, 21999-22087, 23036-23247, 23546-23667, 24270-24461, 26287-26470, 26611-26747, 28068-28260, 32540-32709, 33112-33270, 34586-34828, 35156-35287, 36660-36763, 36934-37077, 37803-37921, 38017-38138, 40365-40493, 42618-42848, 43452-43578, 44836-44999, 48223-48269, and 49656-49779;

c) a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least one BAP28-related biallelic marker selected from the group consisting of A1 to A58, preferably A1 to A27, A34, A37 to A41, A43 to A49, A52, and A54 to A58, more preferably one of the biallelic markers A1, A4, 16, A30, A31, A42, A50, A51, and A53;

d) a contiguous span of at least 12, 15, 18, 20, 25, 30, 35, 40, 50, 60, 70, 80, 90, 100, 150, 200, 500, or 1000 nucleotides of a nucleic acid sequence selected from the group consisting of SEQ ID Nos 2 and 3 or the complements thereof, wherein said contiguous span comprises at least 1, 2, 3, 5 or 10 of nucleotide positions 1 to 4995 of SEQ ID No 2 or 3;

e) a contiguous span of at least 12, 15, 18, 20, 25, 30, 35, 40, 50, 60, 70, 80, 90, 100, 150, 200, 500, or 1000 nucleotides of a nucleic acid sequence selected from the group consisting of SEQ ID Nos 2 and 3 or the complements thereof, wherein said contiguous span comprises at least 1, 2, 3, 5, or 10 of nucleotide positions 1 to 2033, 2160 to 2348 and 2676 to 4995 of SEQ ID No 2 or 3;

f) a contiguous span of at least 12, 15, 18, 20, 25, 30, 35, 40, 50, 60, 70, 80, 90, 100, 150, 200, 500, or 1000 nucleotides of a nucleic acid sequence selected from the group consisting of SEQ ID Nos 1-3 or the complements thereof, wherein said contiguous span comprises at least 1, 2, 3, 5, or 10 of any one of the following ranges of nucleotide positions of:

(1) SEQ ID No 1: 1-2500, 2501-5000, 5001-7500, 7501-10000, 10001-12500, 12501-15000, 15001-17500, 17501-20000, 20001-22500, 22501-25000, 25001-27500, 27501-30000, 30001-32500, 32501-35000, 35001-37500, 37501-40000, 40001-42500, 42501-45000, 45001-47500, 47501-50000, 50001-50357, 50499-50963, 51257-52147, 52299-53234, 53394-53553, 53689-53837, 53943-54028, 54198-54740, 54896-55753, 55913-57385, 57495-58503, 58828-85946, 59355-85946, 86169-91228, and/or 91852 to 97662;

(2) SEQ ID No 2: to 500, 501 to 1000, 1001 to 1500, 1501 to 2000, 2001 to 2500, 2501 to 3000, 3001 to 3500, 3501 to 4000, 4001 to 4500, 4501 to 4995, 5000 to 5500, 5501 to 6000, 6001 to 6500, and 6501 to 6782; and, (3) SEQ ID No 3: 1 to 500, 501 to 1000, 1001 to 1500, 1501 to 2000, 2001 to 2500, 2501 to 3000, 3001 to 3500, 3501 to 4000, 4001 to 4500, 4501 to 4995, 5000 to 5500, 5501 to 6000, 6001 to 6500, 6501 to 7000, 7001 to 7500, 7501 to 7932; and g) a nucleotide sequence selected from the group consisting of SEQ ID Nos 4, and 9-13; and, h) a nucleotide sequence complementary to any one of the preceding nucleotide sequences.

The "nucleic acid codes of the invention" further encompass nucleotide sequences homologous to:

a) a contiguous span of at least 12, 15, 18, 20, 25, 30, 35, 40, 50, 60, 70, 80, 90, 100, 150, 200, 500, or 1000 nucleotides of SEQ ID No 1, wherein said contiguous span comprises at least 1, 2, 3, 5, or 10 of the following nucleotide positions of SEQ ID No 1: 1-50357, 50499-50963, 51257-52147, 52299-53234, 53394-53553, 53689-53837, 53943-54028, 54198-54740, 54896-55753, 55913-57385, 57495-58503, 58828-85946, 59355-85946, 86169-91228, and/or 91852 to 97662;

b) a contiguous span of at least 12, 15, 18, 20, 25, 30, 50, 80, 100, 150, 200, 250, 300, 350, 400, 450, or 500 nucleotides of SEQ ID No 1 or the complement thereof, wherein said contiguous span comprises at least 1, 2, 3, 5, 10, 20, 30, 40 or 50 nucleotides selected from the group consisting of the following nucleotide positions of SEQ ID No 1: 4997-5076, 5371-5544, 6121-6337, 9877-10018, 11522-11623, 12521-12661, 13453-13664, 13824-13957, 15376-15478, 16855-16965, 17378-17495, 18535-18642, 21446-21541, 21999-22087, 23036-23247, 23546-23667, 24270-24461, 26287-26470, 26611-26747, 28068-28260, 32540-32709, 33112-33270, 34586-34828, 35156-35287, 36660-36763, 36934-37077, 37803-37921, 38017-38138, 40365-40493, 42618-42848, 43452-43578, 44836-44999, 48223-48269, and 49656-49779;

c) a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least one BAP28-related biallelic marker selected from the group consisting of A1 to A58, preferably A1 to A27, A34, A37 to A41, A43 to A49, A52, and A54 to A58, more preferably one of the biallelic markers A1, A4, 16, A30, A31, A42, A50, A51, and A53;

d) a contiguous span of at least 12, 15, 18, 20, 25, 30, 35, 40, 50, 60, 70, 80, 90, 100, 150, 200, 500, or 1000 nucleotides of a nucleic acid sequence selected from the group consisting of SEQ ID Nos 2 and 3 or the complements thereof, wherein said contiguous span comprises at least 1, 2, 3, 5, or 10 of nucleotide positions 1 to 4995 of SEQ ID No 2 or 3;

e) a contiguous span of at least 12, 15, 18, 20, 25, 30, 35, 40, 50, 60, 70, 80, 90, 100, 150, 200, 500, or 1000 nucleotides of a nucleic acid sequence selected from the group consisting of SEQ ID Nos 2 and 3 or the complements thereof, wherein said contiguous span comprises at least 1, 2, 3, 5, or 10 of nucleotide positions 1 to 2033, 2160 to 2348 and 2676 to 4995 of SEQ ID No 2 or 3;

f) a contiguous span of at least 12, 15, 18, 20, 25, 30, 35, 40, 50, 60, 70, 80, 90, 100, 150, 200, 500, or 1000 nucleotides of a nucleic acid sequence selected from the group consisting of SEQ ID Nos 1-3 or the complements thereof, wherein said contiguous span comprises at least 1, 2, 3, 5, or of any one of the following ranges of nucleotide positions of:

(1) SEQ ID No 1: 1-2500, 2501-5000, 5001-7500, 7501-10000, 10001-12500, 12501-15000, 15001-17500, 17501-20000, 20001-22500, 22501-25000, 25001-27500, 27501-30000, 30001-32500, 32501-35000, 35001-37500, 37501-40000, 40001-42500, 42501-45000, 45001-47500, 47501-50000, 50001-50357, 50499-50963, 51257-52147, 52299-53234, 53394-53553, 53689-53837, 53943-54028, 54198-54740, 54896-55753, 55913-57385, 57495-58503, 58828-85946, 59355-85946, 86169-91228, and/or 91852 to 97662;

(2) SEQ ID No 2: 1 to 500, 501 to 1000, 1001 to 1500, 1501 to 2000, 2001 to 2500, 2501 to 3000, 3001 to 3500, 3501 to 4000, 4001 to 4500, 4501 to 4995, 5000 to 5500, 5501 to 6000, 6001 to 6500, and 6501 to 6782; and, (3) SEQ ID No 3: 1 to 500, 501 to 1000, 1001 to 1500, 1501 to 2000, 2001 to 2500, 2501 to 3000, 3001 to 3500, 3501 to 4000, 4001 to 4500, 4501 to 4995, 5000 to 5500, 5501 to 6000, 6001 to 6500, 6501 to 7000, 7001 to 7500, 7501 to 7932; and g) a nucleotide sequence selected from the group consisting of SEQ ID Nos 4, and 9-13; and, h) a nucleotide sequence complementary to any one of the preceding nucleotide sequences.

Homologous sequences refer to a sequence having at least 99%, 98%, 97%, 96%, 95%, 90%, 85%, 80%, or 75% homology to these contiguous spans. Homology may be determined using any method described herein, including BLAST2N with the default parameters or with any modified parameters. Homologous sequences also may include RNA sequences in which uridines replace the thymines in the nucleic acid codes of the invention. It will be appreciated that the nucleic acid codes of the invention can be represented in the traditional single character format (See the inside back cover of Stryer, Lubert. *Biochemistry*, 3$^{rd}$ edition. W. H Freeman & Co., New York.) or in any other format or code which records the identity of the nucleotides in a sequence.

As used herein the term "polypeptide codes of the invention" encompass the polypeptide sequences comprising a contiguous span of at least 6, 8, 10, 12, 15, 20, 25, 30, 40, 50, or 100 amino acids of SEQ ID No 5, wherein said contiguous span includes either at least 1, 2, 3, 5 or 10 of the amino acid positions selected from the group consisting of 1 to 1629 of the SEQ ID No 5 or an amino acid selected from the group consisting of an asparagine at the amino acid position 1694 of SEQ ID No 5, a valine at the amino acid position 1854 of SEQ ID No 5, an asparagine at the amino acid position 1967 of SEQ ID No 5, a glutamic acid at the amino acid position 2017 of SEQ ID No 5, and an alanine at the amino acid position 2050 of SEQ ID No 5. It will be appreciated that the polypeptide codes of the invention can be represented in the traditional single character format or three letter format (See the inside back cover of Stryer, Lubert. *Biochemistry*, 3$^{rd}$ edition. W.H. Freeman & Co., New York.) or in any other format or code which records the identity of the polypeptides in a sequence.

It will be appreciated by those skilled in the art that the nucleic acid codes of the invention and polypeptide codes of the invention can be stored, recorded, and manipulated on any medium which can be read and accessed by a computer. As used herein, the words "recorded" and "stored" refer to a process for storing information on a computer medium. A skilled artisan can readily adopt any of the presently known methods for recording information oil a computer readable medium to generate manufactures comprising one or more of the nucleic acid codes of the invention, or one or more of the polypeptide codes of the invention. Another aspect of the present invention is a computer readable medium having recorded thereon at least 2, 5, 10, 15, 20, 25, 30, or 50 nucleic acid codes of the invention. Another aspect of the present invention is a computer readable medium having recorded thereon at least 2, 5, 10, 15, 20, 25, 30, or 50 polypeptide codes of the invention.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Embodiments of the present invention include systems, particularly computer systems which store and manipulate the sequence information described herein. One example of a computer system 100 is illustrated in block diagram form in FIG. 7. As used herein, "a computer system" refers to the hardware components, software components, and data storage components used to analyze the nucleotide sequences of the nucleic acid codes of the invention or the amino acid sequences of the polypeptide codes of the invention. In one embodiment, the computer system 100 is a Sun Enterprise 1000 server (Sun Microsystems, Palo Alto, Calif.). The computer system 100 preferably includes a processor for processing, accessing and manipulating the sequence data. The processor 105 can be any well-known type of central processing unit, such as the Pentium III from Intel Corporation, or similar processor from Sun, Motorola, Compaq or International Business Machines.

Preferably, the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the nucleotide sequences of the nucleic acid codes of the invention or the amino acid sequences of the polypeptide codes of the invention (such as search tools, compare tools, and modeling tools etc.) may reside in main memory 115 during execution.

In some embodiments, the computer system 100 may further comprise a sequence comparer for comparing the above-described nucleic acid codes of the invention or the polypeptide codes of the invention stored on a computer readable medium to reference nucleotide or polypeptide sequences stored on a computer readable medium. A "sequence comparer" refers to one or more programs which are implemented on the computer system 100 to compare a nucleotide or polypeptide sequence with other nucleotide or polypeptide sequences and/or compounds including but not limited to peptides, peptidomimetics, and chemicals stored within the data storage means. For example, the sequence comparer may compare the nucleotide sequences of nucleic acid codes of the invention or the amino acid sequences of the polypeptide codes of the invention stored on a computer readable medium to reference sequences stored on a computer readable medium to identify homologies, motifs implicated in biological function, or structural motifs. The various sequence comparer programs identified elsewhere in this patent specification are particularly contemplated for use in this aspect of the invention.

FIG. 8 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK, PIR OR SWISSPROT that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the present invention is a computer system comprising a processor, a data storage device having stored thereon a nucleic acid code of the invention or a polypeptide code of the invention, a data storage device having retrievably stored thereon reference nucleotide sequences or polypeptide sequences to be compared to the nucleic acid code of the invention or polypeptide code of the invention and a sequence comparer for conducting the comparison. The sequence comparer may indicate a homology level between the sequences compared or identify structural motifs in the nucleic acid code of the invention and polypeptide codes of the invention or it may identify structural motifs in sequences which are compared to these nucleic acid codes and polypeptide codes. In some embodiments, the data storage device may have stored thereon the sequences of at least 2, 5, 10, 15, 20, 25, 30, or 50 of the nucleic acid codes of the invention or polypeptide codes of the invention.

Another aspect of the present invention is a method for determining the level of homology between a nucleic acid code of the invention and a reference nucleotide sequence, comprising the steps of reading the nucleic acid code and the reference nucleotide sequence through the use of a computer program which determines homology levels and determining homology between the nucleic acid code and the reference nucleotide sequence with the computer program. The computer program may be any of a number of computer programs for determining homology levels, including those specifically enumerated herein, including BLAST2N with the default parameters or with any modified parameters. The method may be implemented using the computer systems described above. The method may also be performed by reading 2, 5, 10, 15, 20, 25, 30, or 50 of the above described nucleic acid codes of the invention through the use of the computer program and determining homology between the nucleic acid codes and reference nucleotide sequences.

FIG. 9 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it should be in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there aren't any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of the nucleic acid codes of the present invention, to reference nucleotide sequences in order to determine whether the nucleic acid code of the invention differs from a reference nucleic acid sequence at one or more positions. In some embodiments, such a program records the length and identity of inserted, deleted or substituted nucleotides with respect to the sequence of either the reference polynucleotide or the nucleic acid code of the invention. In one embodiment, the computer program may be a program which determines whether the nucleotide sequences of the nucleic acid codes of the invention contain one or more single nucleotide polymorphisms (SNP) with respect to a reference nucleotide sequence. These single nucleotide polymorphisms may each comprise a single base substitution, insertion, or deletion.

Another aspect of the present invention is a method for determining the level of homology between a polypeptide code of the invention and a reference polypeptide sequence, comprising the steps of reading the polypeptide code of the invention and the reference polypeptide sequence through use of a computer program which determines homology levels and determining homology between the polypeptide code and the reference polypeptide sequence using the computer program.

Accordingly, another aspect of the present invention is a method for determining whether a nucleic acid code of the invention differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms The method may be implemented by the computer systems described above and the method illustrated in FIG. 9. The method may also be performed by reading at least 2, 5, 10, 15, 20, 25, 30, or 50 of the nucleic acid codes of the invention and the reference nucleotide sequences through the use of the computer program and identifying differences between the nucleic acid codes and the reference nucleotide sequences with the computer program.

In other embodiments the computer based system may further comprise an identifier for identifying features within the nucleotide sequences of the nucleic acid codes of the invention or the amino acid sequences of the polypeptide codes of the invention.

An "identifier" refers to one or more programs which identifies certain features within the above-described nucleotide sequences of the nucleic acid codes of the invention or the amino acid sequences of the polypeptide codes of the invention. In one embodiment, the identifier may comprise a program which identifies an open reading frame in the cDNAs codes of the invention.

FIG. 10 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group (www.gcg.com).

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

In another embodiment, the identifier may comprise a molecular modeling program which determines the 3-dimensional structure of the polypeptides codes of the invention. In some embodiments, the molecular modeling program identifies target sequences that are most compatible with profiles representing the structural environments of the residues in known three-dimensional protein structures. (See, e.g., Eisenberg et al., U.S. Pat. No. 5,436,850 issued Jul. 25, 1995). In another technique, the known three-dimensional structures of proteins in a given family are superimposed to define the structurally conserved regions in that family. This protein modeling technique also uses the known three-dimensional structure of a homologous protein to approximate the structure of the polypeptide codes of the invention. (See e.g., Srinivasan, et al., U.S. Pat. No. 5,557,535 issued Sep. 17, 1996). Conventional homology modeling techniques have been used routinely to build models of proteases and antibodies. (Sowdhamini et al., Protein Engineering 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods now enables the identification of likely folding patterns in a number of situations where the structural relatedness between target and template(s) is not detectable at the sequence level. Hybrid methods, in which fold recognition is performed using Multiple Sequence Threading (MST), structural equivalencies are deduced from the threading output using a distance geometry program DRAGON to construct a low resolution model, and a full-atom representation is constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalencies obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszodi et al., Proteins:Structure, Function, and Genetics, Supplement 1:38-42 (1997)).

The results of the molecular modeling analysis may then be used in rational drug design techniques to identify agents which modulate the activity of the polypeptide codes of the invention.

Accordingly, another aspect of the present invention is a method of identifying a feature within the nucleic acid codes of the invention or the polypeptide codes of the invention comprising reading the nucleic acid code(s) or the polypeptide code(s) through the use of a computer program which identifies features therein and identifying features within the nucleic acid code(s) or polypeptide code(s) with the computer program. In one embodiment, computer program comprises a computer program which identifies open reading frames. In a further embodiment, the computer program identifies structural motifs in a polypeptide sequence. In another embodiment, the computer program comprises a molecular modeling program. The method may be performed by reading a single sequence or at least 2, 5, 10, 15, 20, 25, 30, or 50 of the nucleic acid codes of the invention or the polypeptide codes of the invention through the use of the computer program and identifying features within the nucleic acid codes or polypeptide codes with the computer program.

The nucleic acid codes of the invention or the polypeptide codes of the invention may be stored and manipulated in a variety of data processor programs in a variety of formats. For example, they may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide or polypeptide sequences to be compared to the nucleic acid codes of the invention or the polypeptide codes of the invention. The following list is intended not to limit the invention but to provide guidance to programs and databases which are useful with the nucleic acid codes of the invention or the polypeptide codes of the invention. The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, 1990), FASTA (Pearson and Lipman, 1988). FASTDB (Brutlag et al., 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.). Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), Quante M M, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.). WebLab Diversity Explorer (Molecular Simulations Inc.). Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the alt given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Throughout this application, various publications, patents and published patent applications are cited. The disclosures of these publications, patents and published patent specification referenced in this application are hereby incorporated by reference into the present disclosure to more fully describe the sate of the art to which this invention pertains.

EXAMPLES

Example 1

Identification of Biallelic Markers—DNA Extraction

Blood donors were from French Caucasian origin. They presented a sufficient diversity for being representative of a French heterogeneous population. The DNA from 100 unrelated and healthy individuals was extracted, pooled and tested for the detection of biallelic markers. The pool was constituted by mixing equivalent quantities of DNA from each individual.

30 ml of peripheral venous blood were taken from each donor in the presence of EDTA. Cells (pellet) were collected after centrifugation for 10 minutes at 2000 rpm. Red cells were lysed by a lysis solution (50 ml final volume: 10 mM Tris pH7.6; 5 mM $MgCl_2$; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:
  3 ml TE 10-2 (Tris-HCl 10 mM, EDTA 2 mM)/NaCl 0.4 M
  200 µl SDS 10%
  500 µl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD=50 µg/ml DNA).

To determine the presence of proteins in the DNA solution, the OD 260/OD 280 ratio was determined. Only DNA preparations having a OD 260/OD 280 ratio between 1.8 and 2 were used in the subsequent examples described below.

Example 2

Identification of Biallelic Markers: Amplification of Genomic DNA by PCR

The amplification of specific genomic sequences of the DNA samples of example 1 was carried out on the pool of DNA obtained previously. In addition, 10 individual samples were similarly amplified.

PCR assays were performed using the following protocol:

| | |
|---|---|
| Final volume | 25 µl |
| DNA | 2 ng/µl |
| $MgCl_2$ | 2 mM |
| dNTP (each) | 200 µM |
| primer (each) | 2.9 ng/µl |
| Ampli Taq Gold DNA polymerase | 0.05 unit/µl |
| PCR buffer (10x = 0.1 M TrisHCl pH8.3 0.5M KCl) | 1x |

Each pair of first primers is designed using the sequence information of the BAP28 gene disclosed herein and the OSP software (Hillier & Green, 1991). This first pair of primers were about 20 nucleotides in length.

TABLE 1

| Amplicon | Position range of the amplicon in SEQ ID No 1 | | Primer name | Position range of amplification primer in SEQ ID No 1 | | Primer name | Complementary position range of amplification primer in SEQ ID No 1 | |
|---|---|---|---|---|---|---|---|---|
| 5-381 | 4840 | 5266 | B1 | 4840 | 4859 | C1 | 5249 | 5266 |
| 5-382 | 5307 | 5729 | B2 | 5307 | 5324 | C2 | 5710 | 5729 |
| 99-7190 | 12946 | 13488 | B3 | 12946 | 12963 | C3 | 13471 | 13488 |
| 99-7203 | 23482 | 23929 | B4 | 23482 | 23501 | C4 | 23909 | 23929 |
| 5-383 | 27887 | 28315 | B5 | 27887 | 27904 | C5 | 28296 | 28315 |
| 99-7205 | 29833 | 30288 | B6 | 29833 | 29853 | C6 | 30270 | 30288 |
| 5-384 | 32439 | 32877 | B7 | 32439 | 32457 | C7 | 32858 | 32877 |
| 5-379 | 48110 | 48460 | B8 | 48110 | 48127 | C8 | 48441 | 48460 |
| 5-380 | 49558 | 49977 | B9 | 49558 | 49577 | C9 | 49958 | 49977 |
| 5-366 | 50162 | 50583 | B10 | 50162 | 50180 | C10 | 50564 | 50583 |
| 5-370 | 50937 | 51359 | B11 | 50937 | 50955 | C11 | 51341 | 51359 |
| 5-373 | 53437 | 53858 | B12 | 53437 | 53455 | C12 | 53840 | 53858 |
| 5-375 | 53974 | 54394 | B13 | 53974 | 53993 | C13 | 54375 | 54394 |
| 5-376 | 54602 | 55021 | B14 | 54602 | 54619 | C14 | 55002 | 55021 |
| 5-377 | 55608 | 56043 | B15 | 55608 | 55625 | C15 | 56025 | 56043 |

TABLE 1-continued

| Amplicon | Position range of the amplicon in SEQ ID No 1 | | Primer name | Position range of amplification primer in SEQ ID No 1 | | Primer name | Complementary position range of amplification primer in SEQ ID No 1 | |
|---|---|---|---|---|---|---|---|---|
| 5-14 | 59673 | 60100 | B16 | 59673 | 59692 | C16 | 60083 | 60100 |
| 5-11 | 60718 | 61137 | B17 | 60718 | 60737 | C17 | 61119 | 61137 |
| 5-202 | 66177 | 66608 | B23 | 66177 | 66194 | C23 | 66589 | 66608 |
| 99-1605 | 71723 | 72170 | B21 | 71723 | 71743 | C21 | 72150 | 72170 |
| 5-2 | 71735 | 72169 | B22 | 71735 | 71754 | C22 | 72150 | 72169 |
| 5-171 | 85485 | 85905 | B20 | 85485 | 85502 | C20 | 85887 | 85905 |
| 5-169 | 86184 | 86600 | B19 | 86184 | 86203 | C19 | 86581 | 86600 |
| 99-1572 | 86932 | 87574 | B18 | 86932 | 86952 | C18 | 87556 | 87574 |
| 5-403 | 91068 | 91417 | B24 | 91068 in SEQ ID No 29 | 91085 | C24 | 91398 | 91417 |
| 99-13790 | 1 | 454 | B25 | 1 in SEQ ID No 25 | 20 | C25 | 434 | 454 |
| 99-13798 | 1 | 447 | B26 | 1 in SEQ ID No 27 | 20 | C26 | 427 | 447 |
| 99-13808 | 1 | 546 | B27 | 1 in SEQ ID No 30 | 20 | C27 | 526 | 546 |
| 99-13809 | 1 | 444 | B28 | 1 in SEQ ID No 28 | 21 | C28 | 424 | 444 |
| 99-13810 | 1 | 476 | B29 | 1 in SEQ ID No 23 | 18 | C29 | 458 | 476 |
| 99-1585 | 1 | 546 | B30 | 1 in SEQ ID No 24 | 20 | C30 | 527 | 546 |
| 99-1587 | 1 | 396 | B31 | 1 in SEQ ID No 31 | 21 | C31 | 377 | 396 |
| 99-1597 | 1 | 693 | B32 | 1 in SEQ ID No 26 | 19 | C32 | 675 | 693 |
| 99-1601 | 1 | 506 | B33 | 1 in SEQ ID No 18 | 18 | C33 | 486 | 506 |
| 99-7177 | 1 | 504 | B34 | 1 in SEQ ID No 22 | 20 | C34 | 484 | 504 |
| 99-7182 | 1 | 531 | B35 | 1 in SEQ ID No 21 | 20 | C35 | 511 | 531 |
| 99-7186 | 1 | 528 | B36 | 1 in SEQ ID No 20 | 19 | C36 | 510 | 528 |
| 99-7193 | 1 | 542 | B37 | 1 in SEQ ID No 19 | 20 | C37 | 522 | 542 |
| 99-7212 | 1 | 492 | B38 | 1 | 20 | C38 | 472 | 492 |

Preferably, the primers contained a common oligonucleotide tail upstream of the specific bases targeted for amplification which was useful for sequencing.

Primers PU contain the following additional PU 5' sequence: TGTAAAACGACGGCCAGT (SEQ ID NO: 62); primers RP contain the following RP 5' sequence: CAGGAAACAGCTATGACC (SEQ ID NO: 63). The primer containing the additional PU 5' sequence is listed in SEQ ID No 11. The primer containing the additional RP 5' sequence is listed in SEQ ID No 12.

The synthesis of these primers was performed following the phosphoramidite method on a GENSET UFPS 24.1 synthesizer.

DNA amplification was performed on a Genius II thermocycler. After heating at 95° C. for 10 min, 40 cycles were performed. Each cycle comprised: 30 sec at 95° C., 54° C. for 1 min. and 30 sec at 72° C. For final elongation, 10 min at 72° C. ended the amplification. The quantities of the amplification products obtained were determined on 96-well microtiter plates, using a fluorometer and Picogreen as intercalant agent (Molecular Probes).

Example 3

Identification of Biallelic Markers—Sequencing of Amplified Genomic DNA and Identification of Polymorphisms The sequencing of the amplified DNA obtained in example 2 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined using gel image analysis (ABI Prism DNA Sequencing Analysis software (2.1.2 version)).

The sequence data were further evaluated to detect the presence of biallelic markers within the amplified fragments. The polymorphism search was based on the presence of superimposed peaks in the electrophoresis pattern resulting from different bases occurring at the same position as described previously.

The localization of the biallelic markers on SEQ ID Nos 1, and 18 to 31 are as shown above in Table 2.

Also encompassed by the present invention are BAP28-related biallelic markers A1 to A58 described below in Table 2.

TABLE 2

| Amplicon | BM | Marker Name | Localization in BAP28 gene | Polymorphism all1 | all2 | BM position in SEQ ID No 1 | BM position in SEQ ID Nos 2, 3 & 4 |
|---|---|---|---|---|---|---|---|
| 5-381 | A1 | 5-381-133 | 5' regulatory region | A | G | 4972 | |
| 5-382 | A2 | 5-382-162 | Exon 2 | C | T | 5468 | 178 |
| 5-382 | A3 | 5-382-310 | Intron 2-3 | C | T | 5616 | |
| 5-382 | A4 | 5-382-316 | Intron 2-3 | G | C | 5622 | |
| 99-7190 | A5 | 99-7190-213 | Intron 6-7 | C | T | 13158 | |
| 99-7203 | A6 | 99-7203-282 | Intron 16-17 | A | T | 23761 | |
| 99-7203 | A7 | 99-7203-286 | Intron 16-17 | C | T | 23765 | |
| 5-383 | A8 | 5-383-42 | Intron 19-20 | A | G | 27928 | |
| 5-383 | A9 | 5-383-184 | Exon 20 | G | T | 28070 | 2677 |
| 99-7205 | A10 | 99-7205-228 | Intron 20-21 | A | G | 30061 | |
| 5-384 | A11 | 5-384-312 | Intron 21-22 | G | C | 32750 | |
| 5-379 | A12 | 5-379-80 | Intron 32-33 | A | C | 48189 | |
| 5-380 | A13 | 5-380-58 | Intron 33-34 | G | T | 49615 | |
| 5-380 | A14 | 5-380-59 | Intron 33-34 | C | T | 49616 | |
| 5-366 | A15 | 5-366-143 | Intron 34-35 | A | G | 50304 | |
| 5-370 | A16 | 5-370-197 | Exon 36 | A | G | 51133 | 5193 |
| 5-370 | A17 | 5-370-247 | Exon 36 | C | T | 51183 | 5243 |
| 5-373 | A18 | 5-373-98 | Intron 38-39 | C | T | 53534 | |
| 5-373 | A19 | 5-373-164 | Exon 39 | C | T | 53600 | 5673 |
| 5-373 | A20 | 5-373-222 | Exon 39 | A | G | 53658 | 5731 |
| 5-375 | A21 | 5-375-200 | Exon 41 | A | G | 54173 | 6011 |
| 5-375 | A22 | 5-375-259 | Intron 41-42 | C | T | 54232 | |
| 5-375 | A23 | 5-375-296 | Intron 41-42 | G | C | 54269 | |
| 5-375 | A24 | 5-375-399 | Intron 41-42 | G | C | 54372 | |
| 5-376 | A25 | 5-376-266 | Exon 42 | A | G | 54867 | 6162 |
| 5-377 | A26 | 5-377-82 | Intron 42-43 | C | T | 55689 | |
| 5-377 | A27 | 5-377-227 | Exon 43 | A | G | 55834 | 6271 |
| 5-14 | A28 | 5-14-165 | Intron 45-B' | A | G | 59937 | |
| 5-11 | A29 | 5-11-158 | Intron 45-B' | C | T | 60980 | |
| 5-202 | A36 | 5-202-117 | Intron 45-B' | A | T | 66492 | |
| 5-202 | A35 | 5-202-95 | Intron 45-B' | A | C | 66514 | |
| 99-1605 | A33 | 99-1605-112 | Intron 45-B' | A | G | 71834 | |
| 5-2 | A34 | 5-2-178 | Intron 45-B' | A | G | 71993 | |
| 5-171 | A32 | 5-171-204 | Intron 45-B' | A | G | 85702 | |
| 5-169 | A31 | 5-169-97 | Intron B'-A' | G | C | 86504 | |
| 99-1572 | A30 | 99-1572-440 | Intron B'-A' | A | G | 87135 | |
| 5-403 | A37 | 5-403-325 | Intron B'-A' | C | T | 91093 | |
| 5-403 | A38 | 5-403-294 | Intron B'-A' | A | G | 91124 | |
| 5-403 | A39 | 5-403-209 | Intron B'-A' | C | T | 91209 | |
| 5-403 | A40 | 5-403-156 | Exon A' | C | T | 91262 | 7935 in SEQ ID No 3<br>256 in SEQ ID No 4 |

| Amplicon | BM | Marker Name | Polymorphism all1 | all2 | BM position |
|---|---|---|---|---|---|
| 99-13790 | A41 | 99-13790-129 | C | T | 127 in SEQ ID No 29 |
| 99-13798 | A42 | 99-13798-284 | A | G | 283 in SEQ ID No 25 |
| 99-13808 | A43 | 99-13808-80 | A | T | 79 in SEQ ID No 27 |
| 99-13808 | A44 | 99-13808-268 | A | C | 266 in SEQ ID No 27 |
| 99-13808 | A45 | 99-13808-425 | G | C | 419 in SEQ ID No 27 |
| 99-13808 | A46 | 99-13808-455 | A | G | 453 in SEQ ID No 27 |
| 99-13809 | A47 | 99-13809-153 | A | G | 153 in SEQ ID No 30 |
| 99-13810 | A48 | 99-13810-214 | C | T | 212 in SEQ ID No 28 |
| 99-13810 | A49 | 99-13810-170 | A | T | 168 in SEQ ID No 28 |
| 99-1585 | A50 | 99-1585-373 | C | T | 372 in SEQ ID No 23 |
| 99-1587 | A51 | 99-1587-281 | A | G | 278 in SEQ ID No 24 |
| 99-1597 | A52 | 99-1597-162 | A | G | 162 in SEQ ID No 31 |
| 99-1601 | A53 | 99-1601-402 | A | T | 402 in SEQ ID No 26 |
| 99-7177 | A54 | 99-7177-81 | C | T | 81 in SEQ ID No 18 |
| 99-7182 | A55 | 99-7182-49 | C | T | 49 in SEQ ID No 22 |

TABLE 2-continued

| | | | | | |
|---|---|---|---|---|---|
| 99-7186 | A56 | 99-7186-212 | A | G | 212 in SEQ ID No 21 |
| 99-7193 | A57 | 99-7193-228 | G | C | 226 in SEQ ID No 20 |
| 99-7212 | A58 | 99-7212-346 | C | T | 345 in SEQ ID No 19 |

BM refers to "biallelic marker". All1 and all2 refer respectively to allele 1 and allele 2 of the biallelic marker.

The biallelic markers A16, A19, A21 and A25 are located in exonic sequence and give amino acid polymorphisms. Indeed, the codon comprising the marker A16 encodes either a serine or an asparagine in position 1694 of the SEQ ID No 5; the codon comprising the marker A19 encodes either an alanine or a valine in position 1854 of the SEQ ID No 5; the codon comprising the marker A21 encodes either an aspartic acid or an asparagine in position 1967 of the SEQ ID No 5; the codon comprising the marker A25 encodes either a glycine or a glutamic acid in position 2017 of the SEQ ID No 5.

The Table 3 discloses the probes specific of each biallelic markers.

TABLE 3

| BM | Marker Name | Position range of probes in SEQ ID No 1 | | Probes |
|---|---|---|---|---|
| A1 | 5-381-133 | 4960 | 4984 | P1 |
| A2 | 5-382-162 | 5456 | 5480 | P2 |
| A3 | 5-382-310 | 5604 | 5628 | P3 |
| A4 | 5-382-316 | 5610 | 5634 | P4 |
| A5 | 99-7190-213 | 13146 | 13170 | P5 |
| A6 | 99-7203-282 | 23749 | 23773 | P6 |
| A7 | 99-7203-286 | 23753 | 23777 | P7 |
| A8 | 5-383-42 | 27916 | 27940 | P8 |
| A9 | 5-383-184 | 28058 | 28082 | P9 |
| A10 | 99-7205-228 | 30049 | 30073 | P10 |
| A11 | 5-384-312 | 32738 | 32762 | P11 |
| A12 | 5-379-80 | 48177 | 48201 | P12 |
| A13 | 5-380-58 | 49603 | 49627 | P13 |
| A14 | 5-380-59 | 49604 | 49628 | P14 |
| A15 | 5-366-143 | 50292 | 50316 | P15 |
| A16 | 5-370-197 | 51121 | 51145 | P16 |
| A17 | 5-370-247 | 51171 | 51195 | P17 |
| A18 | 5-373-98 | 53522 | 53546 | P18 |
| A19 | 5-373-164 | 53588 | 53612 | P19 |
| A20 | 5-373-222 | 53646 | 53670 | P20 |
| A21 | 5-375-200 | 54161 | 54185 | P21 |
| A22 | 5-375-259 | 54220 | 54244 | P22 |
| A23 | 5-375-296 | 54257 | 54281 | P23 |
| A24 | 5-375-399 | 54360 | 54384 | P24 |
| A25 | 5-376-266 | 54855 | 54879 | P25 |
| A26 | 5-377-82 | 55677 | 55701 | P26 |
| A27 | 5-377-227 | 55822 | 55846 | P27 |
| A28 | 5-14-165 | 59925 | 59949 | P28 |
| A29 | 5-11-158 | 60968 | 60992 | P29 |
| A36 | 5-202-117 | 66480 | 66504 | P36 |

TABLE 3-continued

| BM | Marker Name | Position range of probes | | Probes |
|---|---|---|---|---|
| A35 | 5-202-95 | 66502 | 66526 | P35 |
| A33 | 99-1605-112 | 71822 | 71846 | P33 |
| A34 | 5-2-178 | 71981 | 72005 | P34 |
| A32 | 5-171-204 | 85690 | 85714 | P32 |
| A31 | 5-169-97 | 86492 | 86516 | P31 |
| A30 | 99-1572-440 | 87123 | 87147 | P30 |
| A37 | 5-403-325 | 91081 | 91105 | P37 |
| A38 | 5-403-294 | 91112 | 91136 | P38 |
| A39 | 5-403-209 | 91197 | 91221 | P39 |
| A40 | 5-403-156 | 91250 | 91274 | P40 |
| BM | Marker Name | Position range of probes | | Probes |
| A41 | 99-13790-129 | 115-139 in SEQ ID No 29 | | P41 |
| A42 | 99-13798-284 | 271-295 in SEQ ID No 25 | | P42 |
| A43 | 99-13808-80 | 67-91 in SEQ ID No 27 | | P43 |
| A44 | 99-13808-268 | 254-278 in SEQ ID No 27 | | P44 |
| A45 | 99-13808-425 | 407-431 in SEQ ID No 27 | | P45 |
| A46 | 99-13808-455 | 441-465 in SEQ ID No 27 | | P46 |
| A47 | 99-13809-153 | 141-165 in SEQ ID No 30 | | P47 |
| A48 | 99-13810-214 | 200-224 in SEQ ID No 28 | | P48 |
| A49 | 99-13810-170 | 156-180 in SEQ ID No 28 | | P49 |
| A50 | 99-1585-373 | 360-384 in SEQ ID No 23 | | P50 |
| A51 | 99-1587-281 | 266-290 in SEQ ID No 24 | | P51 |
| A52 | 99-1597-162 | 150-174 in SEQ ID No 31 | | P52 |
| A53 | 99-1601-402 | 390-414 in SEQ ID No 26 | | P53 |
| A54 | 99-7177-81 | 69-93 in SEQ ID No 18 | | P54 |
| A55 | 99-7182-49 | 37-61 in SEQ ID No 22 | | P55 |
| A56 | 99-7186-212 | 200-224 in SEQ ID No 21 | | P56 |
| A57 | 99-7193-228 | 214-238 in SEQ ID No 20 | | P57 |
| A58 | 99-7212-346 | 333-357 in SEQ ID No 19 | | P58 |

Example 4

Validation of the Polymorphisms Through Microsequencing

The biallelic markers identified in example 3 were further confirmed and their respective frequencies were determined through microsequencing. Microsequencing was carried out for each individual DNA sample described in Example 1.

Amplification from genomic DNA of individuals was performed by PCR as described above for the detection of the biallelic markers with the same set of PCR primers.

The preferred primers used in microsequencing were about 19 nucleotides in length and hybridized just upstream of the considered polymorphic base. According to the invention, the primers used in microsequencing are detailed in Table 4.

TABLE 4

| Marker Name | BM | Mis1 | Position range of microsequencing primer mis 1 in SEQ ID No 1 | | Mis2 | Complementary position range of microsequencing primer mis. 2 in SEQ ID No 1 | |
|---|---|---|---|---|---|---|---|
| 5-381-133 | A1 | D1 | 4953 | 4971 | E1 | 4973 | 4991 |
| 5-382-162 | A2 | D2 | 5449 | 5467 | E2 | 5469 | 5487 |
| 5-382-310 | A3 | D3 | 5597 | 5615 | E3 | 5617 | 5635 |
| 5-382-316 | A4 | D4 | 5603 | 5621 | E4 | 5623 | 5641 |
| 99-7190-213 | A5 | D5 | 13139 | 13157 | E5 | 13159 | 13177 |
| 99-7203-282 | A6 | D6 | 23742 | 23760 | E6 | 23762 | 23780 |
| 99-7203-286 | A7 | D7 | 23746 | 23764 | E7 | 23766 | 23784 |
| 5-383-42 | A8 | D8 | 27909 | 27927 | E8 | 27929 | 27947 |
| 5-383-184 | A9 | D9 | 28051 | 28069 | E9 | 28071 | 28089 |
| 99-7205-228 | A10 | D10 | 30042 | 30060 | E10 | 30062 | 30080 |

TABLE 4-continued

| Marker Name | BM | Mis1 | | | Mis2 | | |
|---|---|---|---|---|---|---|---|
| 5-384-312 | A11 | D11 | 32731 | 32749 | E11 | 32751 | 32769 |
| 5-379-80 | A12 | D12 | 48170 | 48188 | E12 | 48190 | 48208 |
| 5-380-58 | A13 | D13 | 49596 | 49614 | E13 | 49616 | 49634 |
| 5-380-59 | A14 | D14 | 49597 | 49615 | E14 | 49617 | 49635 |
| 5-366-143 | A15 | D15 | 50285 | 50303 | E15 | 50305 | 50323 |
| 5-370-197 | A16 | D16 | 51114 | 51132 | E16 | 51134 | 51152 |
| 5-370-247 | A17 | D17 | 51164 | 51182 | E17 | 51184 | 51202 |
| 5-373-98 | A18 | D18 | 53515 | 53533 | E18 | 53535 | 53553 |
| 5-373-164 | A19 | D19 | 53581 | 53599 | E19 | 53601 | 53619 |
| 5-373-222 | A20 | D20 | 53639 | 53657 | E20 | 53659 | 53677 |
| 5-375-200 | A21 | D21 | 54154 | 54172 | E21 | 54174 | 54192 |
| 5-375-259 | A22 | D22 | 54213 | 54231 | E22 | 54233 | 54251 |
| 5-375-296 | A23 | D23 | 54250 | 54268 | E23 | 54270 | 54288 |
| 5-375-399 | A24 | D24 | 54353 | 54371 | E24 | 54373 | 54391 |
| 5-376-266 | A25 | D25 | 54848 | 54866 | E25 | 54868 | 54886 |
| 5-377-82 | A26 | D26 | 55670 | 55688 | E26 | 55690 | 55708 |
| 5-377-227 | A27 | D27 | 55815 | 55833 | E27 | 55835 | 55853 |
| 5-14-165 | A28 | D28 | 59918 | 59936 | E28 | 59938 | 59956 |
| 5-11-158 | A29 | D29 | 60961 | 60979 | E29 | 60981 | 60999 |
| 5-202-117 | A36 | D36 | 66473 | 66491 | E36 | 66493 | 66511 |
| 5-202-95 | A35 | D35 | 66495 | 66513 | E35 | 66515 | 66533 |
| 99-1605-112 | A33 | D33 | 71815 | 71833 | E33 | 71835 | 71853 |
| 5-2-178 | A34 | D34 | 71974 | 71992 | E34 | 71994 | 72012 |
| 5-171-204 | A32 | D32 | 85683 | 85701 | E32 | 85703 | 85721 |
| 5-169-97 | A31 | D31 | 86485 | 86503 | E31 | 86505 | 86523 |
| 99-1572-440 | A30 | D30 | 87116 | 87134 | E30 | 87136 | 87154 |
| 5-403-325 | A37 | D37 | 91074 | 91092 | E37 | 91094 | 91112 |
| 5-403-294 | A38 | D38 | 91105 | 91123 | E38 | 91125 | 91143 |
| 5-403-209 | A39 | D39 | 91190 | 91208 | E39 | 91210 | 91228 |
| 5-403-156 | A40 | D40 | 91243 | 91261 | E40 | 91263 | 91281 |

| Marker Name | BM | Mis1 | Position range of microsequencing primer mis 1 | Mis2 | Complementary position range of microsequencing primer mis. 2 |
|---|---|---|---|---|---|
| 99-13790-129 | A41 | D41 | 108-126 in SEQ ID No 29 | E41 | 128-146 in SEQ ID No 29 |
| 99-13798-284 | A42 | D42 | 264-282 in SEQ ID No 25 | E42 | 284-302 in SEQ ID No 25 |
| 99-13808-80 | A43 | D43 | 60-78 in SEQ ID No 27 | E43 | 80-98 in SEQ ID No 27 |
| 99-13808-268 | A44 | D44 | 247-265 in SEQ ID No 27 | E44 | 267-285 in SEQ ID No 27 |
| 99-13808-425 | A45 | D45 | 400-418 in SEQ ID No 27 | E45 | 420-438 in SEQ ID No 27 |
| 99-13808-455 | A46 | D46 | 434-452 in SEQ ID No 27 | E46 | 454-472 in SEQ ID No 27 |
| 99-13809-153 | A47 | D47 | 134-152 in SEQ ID No 30 | E47 | 154-172 in SEQ ID No 30 |
| 99-13810-214 | A48 | D48 | 193-211 in SEQ ID No 28 | E48 | 213-231 in SEQ ID No 28 |
| 99-13810-170 | A49 | D49 | 149-167 in SEQ ID No 28 | E49 | 169-187 in SEQ ID No 28 |
| 99-1585-373 | A50 | D50 | 353-371 in SEQ ID No 23 | E50 | 373-391 in SEQ ID No 23 |
| 99-1587-281 | A51 | D51 | 259-277 in SEQ ID No 24 | E51 | 279-297 in SEQ ID No 24 |
| 99-1597-162 | A52 | D52 | 143-161 in SEQ ID No 31 | E52 | 163-181 in SEQ ID No 31 |
| 99-1601-402 | A53 | D53 | 383-401 in SEQ ID No 26 | E53 | 403-421 in SEQ ID No 26 |
| 99-7177-81 | A54 | D54 | 62-80 in SEQ ID No 18 | E54 | 82-100 in SEQ ID No 18 |
| 99-7182-49 | A55 | D55 | 30-48 in SEQ ID No 22 | E55 | 50-68 in SEQ ID No 22 |
| 99-7186-212 | A56 | D56 | 193-211 in SEQ ID No 21 | E56 | 213-231 in SEQ ID No 21 |
| 99-7193-228 | A57 | D57 | 207-225 in SEQ ID No 20 | E57 | 227-245 in SEQ ID No 20 |
| 99-7212-346 | A58 | D58 | 326-344 in SEQ ID No 19 | E58 | 346-364 in SEQ ID No 19 |

Mis 1 and Mis 2 respectively refer to microsequencing primers which hybridized with the non-coding strand of the BAP28 gene or with the coding strand of the BAP28 gene.

The microsequencing reaction was performed as follows:

After purification of the amplification products, the microsequencing reaction mixture was prepared by adding, in a 20 µl final volume: 10 pmol microsequencing oligonucleotide, 1 U Thermosequenase (Amersham E79000G), 1.25 µl Thermosequenase buffer (260 mM Tris HCl pH 9.5, 65 mM $MgCl_2$), and the two appropriate fluorescent ddNTPs (Perkin Elmer, Dye Terminator Set 401095) complementary to the nucleotides at the polymorphic site of each biallelic marker tested, following the manufacturer's recommendations. After 4 minutes at 94° C., 20 PCR cycles of 15 sec at 55° C., 5 sec at 72° C., and 10 sec at 94° C. were carried out in a Tetrad PTC-225 thermocycler (MJ Research). The unincorporated dye terminators were then removed by ethanol precipitation. Samples were finally resuspended in formamide-EDTA loading buffer and heated for 2 min at 95° C. before being loaded on a polyacrylamide sequencing gel. The data were collected by an ABI PRISM 377 DNA sequencer and processed using the GENESCAN software (Perkin Elmer).

Following gel analysis, data were automatically processed with software that allows the determination of the alleles of biallelic markers present in each amplified fragment.

The software evaluates such factors as whether the intensities of the signals resulting from the above microsequencing procedures are weak, normal, or saturated, or whether the signals are ambiguous. In addition, the software identifies significant peaks (according to shape and height criteria). Among the significant peaks, peaks corresponding to the targeted site are identified based on their position. When two significant peaks are detected for the same position, each sample is categorized classification as homozygous or heterozygous type based on the height ratio.

Example 5

Association Study Between Prostate Cancer and the Biallelic Markers of the PCTA-1 Gene Collection of DNA Samples from Affected and Non-Affected Individuals Affected Population:

The positive trait followed in this association study was prostate cancer. Prostate cancer patients were recruited according to a combination of clinical, histological and biological inclusion criteria. Clinical criteria can include rectal examination and prostate biopsies. Biological criteria can include PSA assays. The affected individuals were recorded as familial forms when at least two persons affected by prostate cancer have been diagnosed in the family. Remaining cases were classified as sporadic cases, and more particularly in informative cases (at least two sibs of the case both aged over 50 years old are unaffected), or sporadic uninformative cases (no information about sibs over 50 years old is available). All affected individuals included in the statistical analysis of this patent were unrelated. Cases were also separated following the criteria of diagnosis age: early onset prostate cancer (under 65 years old) and late onset prostate cancer (65 years old or more).

Unaffected Population:

Control individuals included in this study were checked for both the absence of all clinical and biological criteria defining the presence or the risk of prostate cancer (PSA <4) (WO 96/21042), and for their age (aged 65 years old or more). All unaffected individuals included in the statistical analysis of this patent were unrelated.

The affected group was composed by 491 unrelated individuals, comprising:

197 familial cases; and
294 sporadic cases, 70 of which are sporadic informative cases.

The unaffected group contained 313 individuals which were 65 years or older.

Genotyping of Affected and Control Individuals

The general strategy to perform the association studies was to individually scan the DNA samples from all individuals in each of the populations described above in order to establish the allele frequencies of the above described biallelic markers in each of these populations. More particularly, the 30 biallelic markers used in the present association study are described in Table 5.

Allelic frequencies of the biallelic markers of the Table 5 in each population were determined by performing microsequencing reactions on amplified fragments obtained by genomic PCR performed on the DNA samples from each individual. Genomic PCR and microsequencing were performed as detailed above in examples 2 and 4 using the described PCR and microsequencing primers.

TABLE 5

| BM | Marker Name | Position in BAP28 gene | Position in PCTA-1 gene | Nb of controls | Frequency (allele) |
|---|---|---|---|---|---|
| A54 | 99-7177/81 | 5' of gene | 3' of gene | 257 | 69.07 (C) |
| A58 | 99-7212/346 | 5' of gene | 3' of gene | 259 | 66.99 (C) |
| A57 | 99-7193/228 | 5' of gene | 3' of gene | 250 | 59.2 (C) |
| A56 | 99-7186/212 | 5' of gene | 3' of gene | 292 | 66.1 (A) |
| A55 | 99-7182/49 | 5' of gene | 3' of gene | 287 | 63.59 (C) |
| A1 | 5-381/133 | 5' regulatory region | 3' of gene | 304 | 65.46 (G) |
| A4 | 5-382/316 | intron 2-3 | 3' of gene | 304 | 65.79 (C) |
| A5 | 99-7190/213 | intron 6-7 | 3' of gene | 297 | 72.9 (C) |
| A7 | 99-7203/286 | intron 16-17 | 3' of gene | 257 | 68.09 (T) |
| A11 | 5-384/312 | intron 21-22 | 3' of gene | 211 | 73.22 (G) |
| A12 | 5-379/80 | intron 32-33 | 3' of gene | 294 | 73.98 (A) |
| A16 | 5-370/197 | Exon 36 | 3' of gene | 287 | 76.31 (G) |
| A19 | 5-373/164 | Exon 39 | 3' of gene | 298 | 68.62 (C) |
| A21 | 5-375/200 | exon 41 | 3' of gene | 307 | 68.73 (G) |
| A25 | 5-376/266 | exon 42 | 3' of gene | 298 | 68.96 (G) |
| A27 | 5-377/227 | exon 43 | 3' of gene | 307 | 68.73 (A) |
| A28 | 5-14/165 | intron 45-B' | 3' UTR | 307 | 65.15 (T) |
| A29 | 5-11/158 | intron 45-B' | 3' UTR | 303 | 75.41 (G) |
| A35 | 5-202/95 | intron 45-B' | Exon 6b | 308 | 95.13 (G) |
| A33 | 99-1605/112 | intron 45-B' | intron 2 | 304 | 68.75 (G) |
| A34 | 5-2/178 | intron 45-B' | Exon 2 | 306 | 68.3 (C) |
| A32 | 5-171/204 | intron 45-B' | intron B | 307 | 70.85 (T) |
| A31 | 5-169/97 | intron B'-A' | intron D | 305 | 82.3 (C) |
| A30 | 99-1572/440 | intron B'-A' | intron D | 304 | 65.79 (T) |
| A50 | 99-1585/373 | 3' of gene | 5' of gene | 300 | 78 (C) |
| A51 | 99-1587/281 | 3' of gene | 5' of gene | 286 | 67.31 (G) |
| A42 | 99-13798/284 | 3' of gene | 5' of gene | 278 | 53.42 (A) |
| A53 | 99-1601/402 | 3' of gene | 5' of gene | 305 | 67.21 (A) |
| A43 | 99-13808/80 | 3' of gene | 5' of gene | 214 | 59.58 (T) |
| A48 | 99-13810/214 | 3' of gene | 5' of gene | 289 | 59.86 (T) |

Association Study Between Prostate Cancer and the Biallelic Markers of the BAP28 Gene: Single Marker Association Frequencies of biallelic alleles were compared in case-control populations described above. We compare different sub-populations in function of phenotypes (sporadic and familial cases vs controls) to determine the characterisation of association.

The FIG. 5 shows the results of allelic association analysis for markers localized in and around BAP28 gene. This analysis tests the difference of allelic frequency for each marker between population. The statistical significance of this difference is assessed by performing a Pearson chi-square test with one degree of freedom.

The genotyped markers A55 (99-7182/49). A4 (5-382/316), A19 (5-373/164), A28 (5-14/165), A42 (99-13798/284), and A53 (99-1601/402) are significant at the 5% level for allelic test (respectively, pvalue=$4\times10^{-2}$, $4\times10^{-3}$, $4\times10^{-2}$, $1\times10^{-2}$, $2\times10^{-2}$, and $7\times10^{-3}$) for sporadic cases. The 4 markers A28 (5-14/165), A4 (5-382/316), A1 (5-381/133), and A55 (99-7182/49) present a high significant association for allelic test (respectively, pvalue=$4\times10^{-5}$, $8\times10^{-6}$, $3\times10^{-5}$, and $1\times10^{-4}$) between informatif sporadic cases and controls. The marker A30 (99-1572/440) is significant for familial cases (allelic pvalue=$3\times10^{-2}$).

Frequencies of the genotypes for one biallelic marker were compared in case-control populations described above. We compare different sub-populations in function of phenotypes (sporadic and familial cases vs controls) to determine the characterisation of association. The FIG. 6 shows the results of genotypic association analysis for markers localized in and around BAP28 gene. This analysis compares the three genotype frequencies between the two studied population. The statistical test used is a Pearson chi-square with 2 degree of freedom.

The genotyped markers A4(5-382/316), A19 (5-373/164), A28 (5-14/165), A50 (99-1585/373), A42 (99-13798/284), and A53 (99-1601/402) are significant at the 5% level for allelic test (respectively, pvalue=$9\times10^{-3}$, $9\times10^{-2}$, $4\times10^{-2}$, $4\times10^{-2}$, $8\times10^{-2}$ and $3\times10^{-2}$) for sporadic cases. The 4 markers A28 (5-14/165), A4 (5-382/316), A1 (5-381/133), and A55 (99-7182/49) present a high significant association for allelic test (respectively, pvalue=$1\times10^{-5}$, $2\times10^{-5}$, $3\times10^{-6}$, and $1\times10^{-5}$) between informatif sporadic cases and controls. The 2 markers A31 (5-169/97) and A33 (99-1605/112) are significant for familial cases (respectively, pvalue=$3\times10^{2}$ and $2\times10^{-2}$).

The results of the association studies show that a polymorphism of the BAP28 gene is related to sporadic and/or familial association. The biallelic markers A55 (99-7182/49), A1 (5-381/133), A4 (5-382/316), A19 (5-373/164), A28 (5-14/165), A50 (99-1585/373), A42 (99-13798/284), A31 (5-169/97), A33 (99-1605/112), and A53 (99-1601/402) can be then used in diagnostics with a test based on these markers.

Haplotype Frequency Analysis

One way of increasing the statistical power of individual markers, is by performing haplotype association analysis.

Haplotype analysis for association of BAP28 markers and prostate cancer was performed by estimating the frequencies of all possible haplotypes comprising biallelic markers of the Table 5 in the cases and control populations described in Example 5, and comparing these frequencies by means of a chi square statistical test (one degree of freedom). Haplotype estimations were performed by applying the Expectation-Maximization (EM) algorithm (Excoffier L & Slatkin M, 1995), using the EM-HAPLO program (Hawley M E, Pakstis A J & Kidd K K, 1994). More particularly, two tests were performed, namely a haplo-max test and an Omnibus L R test which compares the profile of haplotype frequencies were also performed.

The haplo-max test, which is based on haplotype frequencies differences, selects the difference showing the maximum positive (maxM) or negative (maxS) test value between cases versus controls (rejecting test values based on rare haplotype frequencies, i.e, with an estimated number of haplotypes carriers inferior to 10); for one combination of markers there is therefore one Max-M and one Max-S test values.

For one combination of 2, 3 or 4 markers, the Omnibus Likelihood ratio test allows to compare the profile of haplotype frequency differences between the two populations under study. The null hypothesis is that both cases and controls are samples derived from the same population, i.e. the haplotypes frequencies are close. Using the E-M algorithm, one can calculate the haplotype frequencies in cases, in controls and in the overall population. Once the haplotype frequencies are estimated, a likelihood ratio test (LR test) can be derived. It has to be underlined that for one combination of markers, only one LR test is obtained. If the data at hand would be observed haplotypes frequencies, provided there are no rare haplotypes, the LR test should follows a Chi-square distribution with h-1 degree of freedom, h being the number of possible haplotypes. This is to say: for two markers, a chi-square with 4 degree of freedom; for 3 markers, a chi-square with 7 degree of freedom; and for 4-markers, a chi-square with 15 degree of freedom. As haplotype frequencies are only inferred via the E-M algorithm and that rare haplotypes occur, a permutation procedure is more suitable.

The results of haplotype analysis using all combinations of 2 or 3 biallelic markers from the BAP28-related biallelic markers of the Table 5 are represented in the FIGS. 7 to 11. As above-mentioned, the profile of haplotypes frequencies have been compared by two main approaches: Individual haplotype tests and Omnibus Likelihood ratio tests. A permutation procedure allowed assessment of the significance of the tests. The most significant haplotypes obtained are shown in FIG. 12. We analyzed separately the familial cases and sporadic cases, because the singlepoint analyses showed the different significant SNPs pattern.

Haplotype Frequency Analysis for Prostate Cancer Cases

The most significant haplotypes obtained with the cases of prostate cancer are shown in FIG. 7 a and b.

The two-markers haplotypes comprise the biallelic markers A1 (5-381/133), A4 (5-382/316), A19 (5-373/164), A21 (5-375/200), A25 (5-376/266), A27 (5-377/227), A53 (99-1601/402), A42 (99-13798/284), and A55 (99-7182/49).

The preferred two-markers haplotypes are described in FIG. 7a as H1 to H8. All these haplotypes comprise either the biallelic marker A53 (99-1601/402) or A42 (99-13798/284). One of the more preferred haplotype is the haplotype H1 and it comprises the biallelic markers A53 (99-1601/402) and A27 (5-377/227), alleles TG respectively. This haplotype presented a p-value for the haplotype frequency test of $3.9\times10^{-4}$ and an odd-ratio of 1.80. Estimated haplotype frequencies were 15.6% in the cases and 9.3% in the controls. This haplotype presented a p-value for the likelihood ratio test of T $0.7\times10^{-2}$. The pvalue by permutation test is $<1\times10^{-2}$ and the pvalue for this group of markers is $5\times10^{-2}$ by omnibus Lr test.

The three-markers haplotypes comprise the biallelic markers A53 (99-1601/402), A42 (99-13798/284), A51 (99-1587/281), A31 (5-169/97), A34 (5-2/178), A33 (99-1605/112), A28 (5-14/165), A27 (5-377/227), A25 (5-376/266), A21 (5-375/200), A19 (5-373/164), A7 (99-7203/286), A4 (5-382/3T16), A55 (99-7182/49), A56 (99-7186/212), A57 (99-7193/228), A58 (99-7212/346).

Figure 7B:
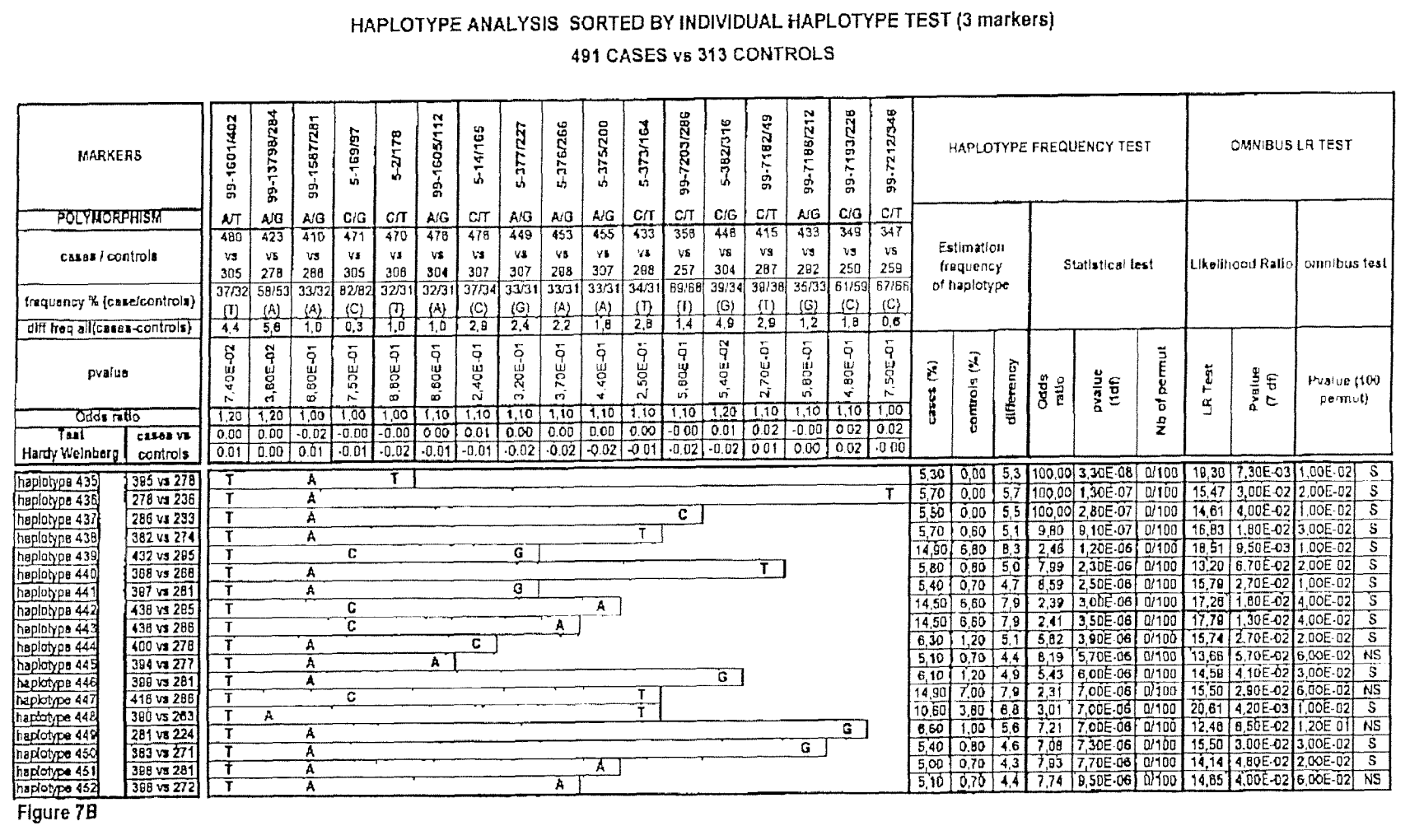

The preferred three-markers haplotypes are described in FIG. 7b as H435 to H452. All these haplotypes comprise the biallelic marker A53 (99-1601/402). Most of them comprise the biallelic marker A51 (99-1587/281). The more preferred haplotype is the haplotype H435 and comprises the biallelic markers A53 (99-1601/402), A51 (99-1587/281) and A34 (5-2/178), alleles TAT, respectively. This haplotype presented a p-value for the haplotype frequency test of $3.3\times10^{-8}$ and an odd-ratio of 100. Estimated haplotype frequencies were 5.3% in the cases and 0% in the controls. This haplotype presented a pvalue for the likelihood ratio test of $7.3\times10^{-3}$. The p-value by permutation test is $<1\times10^{-2}$ and the p-value for this group of markers is $1\times10^{-2}$ by omnibus Lr test.

In conclusion, most preferred haplotypes for the cases of prostate cancer comprise the biallelic marker A53 (99-1601/402). Some other preferred haplotypes for the cases of prostate cancer comprise the biallelic markers A42 (99-13798/

284) and/or A51 (99-1587/281). These haplotypes can be used in diagnostic, more particularly in diagnostics of prostate cancer susceptibility.

Haplotype Frequency Analysis for Familial Cases of Prostate Cancer

The most significant haplotypes obtained with the familial cases of prostate cancer are shown in FIG. 8 *a* and *b*.

The two-markers haplotypes comprise the biallelic markers A51 (99-1587/281), A30 (99-1572/440), A32 (5-171/204), A34 (5-2/178), A33 (99-1605/112), A29 (5-11/158), A27 (5-377/227), A19 (5-373/164), A5 (99-7190/213), A56 (99-7186/212), and A54 (99-7177/81).

Figure 8A:
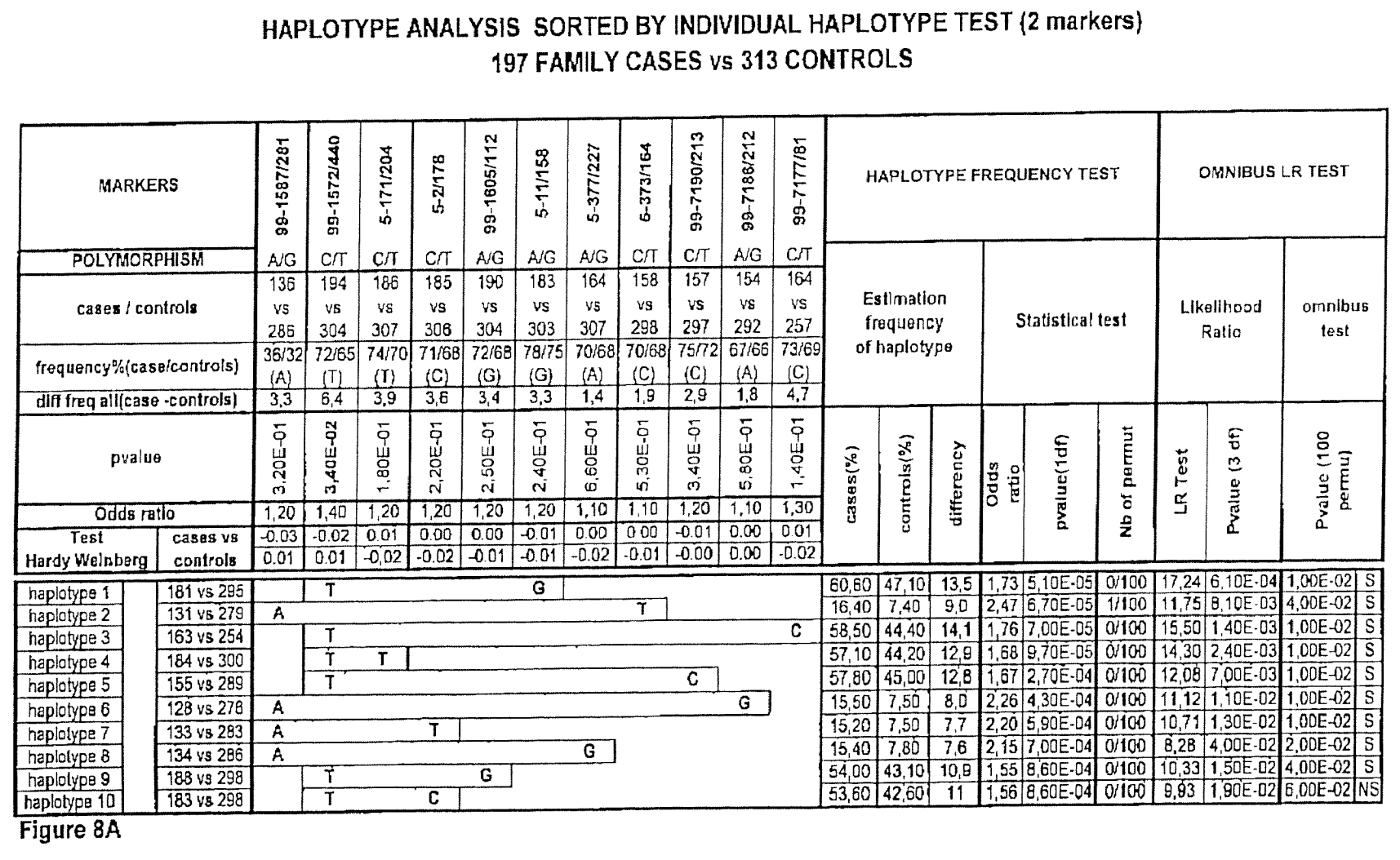

The preferred two-markers haplotypes are described in FIGS. 8*a* as H1 to H10. All these haplotypes comprise either the biallelic marker A51 (99-1587/281) or A30 (99-1572/440). One of the more preferred haplotype is the haplotype H4. The pvalue of haplotype H4 obtained by a chi-square distribution with 2 ddl for this combination of 2 markers with A30 (99-1572/440) and A32 (5-171/204) is $2.4 \times 10^{-3}$ by omnibus test. These markers are not in disequilibrium linkage. In concerning the individual haplotype test, this haplotype consisting of 2 biallelic markers presented a $9.7 \times 10^{-5}$ p-value of and an odd-ratio of 1.7, for alleles TT respectively. The pvalue by permutation test is $<1 \times 10^{-2}$ and the pvalue for this group of markers is $1 \times 10^{-2}$ by omnibus Lr test. This haplotype tested on all cases-controls population gives estimated haplotype frequencies for sporadic cases (n=197) of 57.1% and for controls (n=313) of 44.1%. The trend about of estimations of haplotype frequencies are not identical between familial and sporadic cases, but the trend of sporadics are same for controls.

The three-markers haplotypes comprise the biallelic markers A48 (99-13810/214), A53 (99-1601/402), A42 (99-13798/284), A51 (99-1587/281), A30 (99-1572/440), A32 (5-171/204), A34 (5-2/178), A33 (99-1605/112), A29 (5-11/158), A27 (5-377/227), A19 (5-373/164), A7 (99-7203/286), A5 (99-7190/213), A56 (99-7186/212) and A54 (99-7177/81).

Figure 8B:
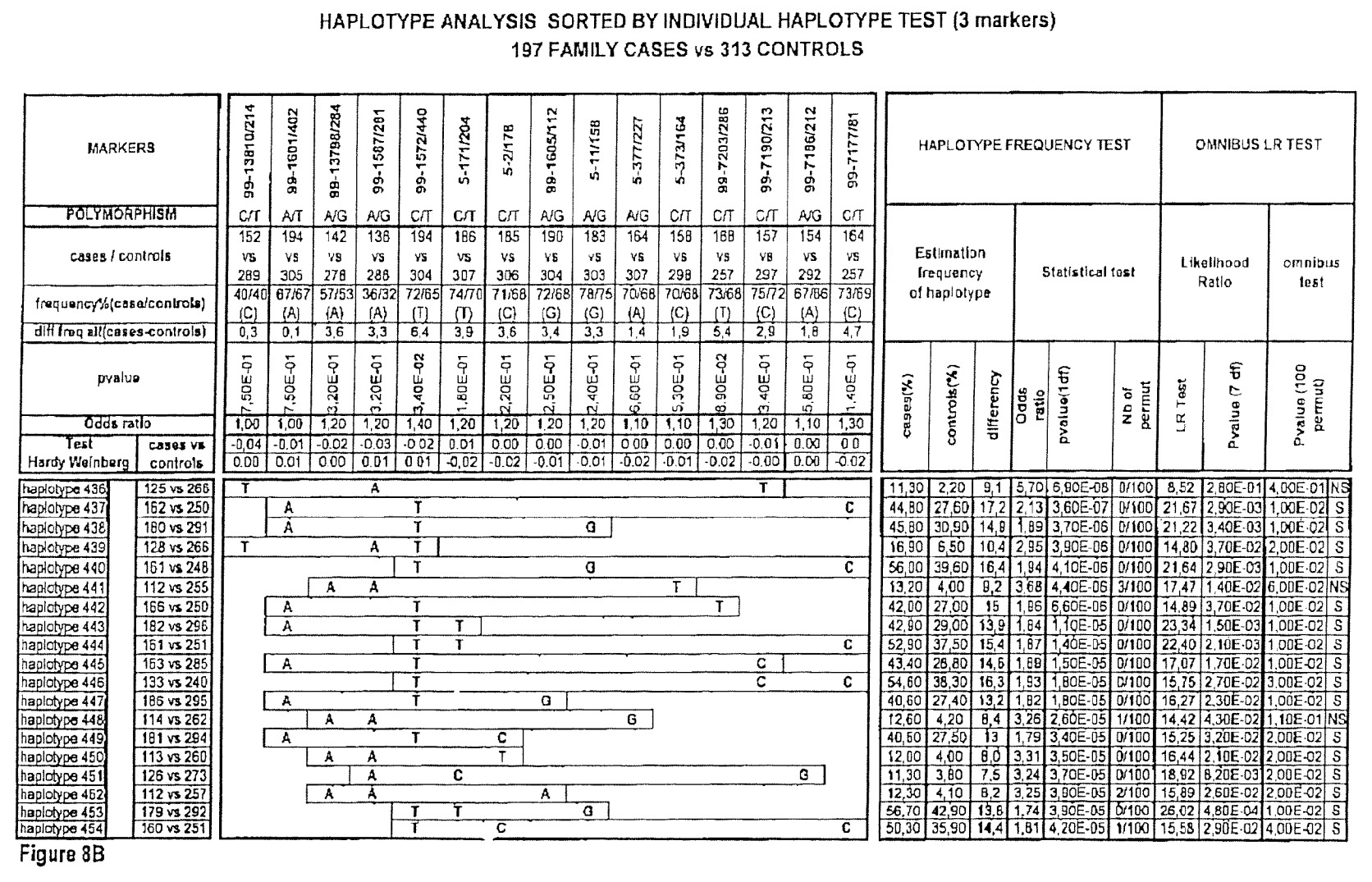

The preferred three-markers haplotypes are described in FIG. 8*b* as H436 to H454. Most of them comprise the biallelic marker A30 (99-1572/440), A51 (99-1587/281) and A53 (99-1601/402). One of the more preferred haplotype is the haplotype H437 and comprises the biallelic markers A53 (99-1601/402), A30 (99-1572/440) and A54 (99-7177/81), alleles ATC, respectively. This haplotype presented a p-value for the haplotype frequency test of $3.6 \times 10^{-7}$ and an odd-ratio of 2.13. Estimated haplotype frequencies were 44.8% in the cases and 27.6% in the controls. This haplotype presented a p-value for the likelihood ratio test of $2.9 \times 10^{-3}$. The pvalue by permutation test is $<1 \times 10^{-2}$ and the pvalue for this group of markers is $1 \times 10^{-2}$ by omnibus Lr test.

In conclusion, most preferred haplotypes for the familial cases of prostate cancer comprise the biallelic markers A30 (99-1572/440), and A51 (99-1587/281). These haplotypes can be used in diagnostic, more particularly in diagnostics of familial prostate cancer susceptibility.

The most significant haplotypes obtained with the early onset familial cases of prostate cancer are shown in FIG. 9 *a* and *b*.

The two-markers haplotypes comprise the biallelic markers A42 (99-13798/284), A51 (99-1587/281), A50 (99-1585/373), A30 (99-1572/440), A32 (5-171/204), A34 (5-2/178), A33 (99-1605/112), A29 (5-11/158), A19 (5-373/164), A16 (5-370/197), A12 (5-379/80), A11 (5-384/312), A7 (99-7203/286), A5 (99-7190/213), A4 (5-382/316), and A54 (99-7177/81).

The preferred two-markers haplotypes are described in FIG. 7*a* as H1 to H13. Most of these haplotypes comprise the biallelic marker A30 (99-1572/440). One of the more preferred haplotype is the haplotype H1 and it comprises the biallelic markers A30 (99-1572/440) and A32 (5-171/204), alleles TT respectively. This haplotype presented a p-value for the haplotype frequency test of $2.5 \times 0$-6 and an odd-ratio of 2.28. Estimated haplotype frequencies were 64.4% in the cases and 44.2% in the controls. This haplotype presented a p-value for the likelihood ratio test of $8.3 \times 10^{-5}$. The pvalue by permutation test is $<1 \times 10^{-2}$ and the p-value for this group of markers is $5 \times 10^{-2}$ by omnibus Lr test.

The three-markers haplotypes comprise the biallelic markers A53 (99-1601/402), A30 (99-1572/440), A32 (5-171/204), A34 (5-2/178), A33 (99-1605/112), A29 (5-11/158), A21 (5-375/200), A19 (5-373/164), A12 (5-379/80), A11 (5-384/312), A7 (99-7203/286), A5 (99-7190/213), A56 (99-7186/212), and A54 (99-7177/81).

Figure 9B:
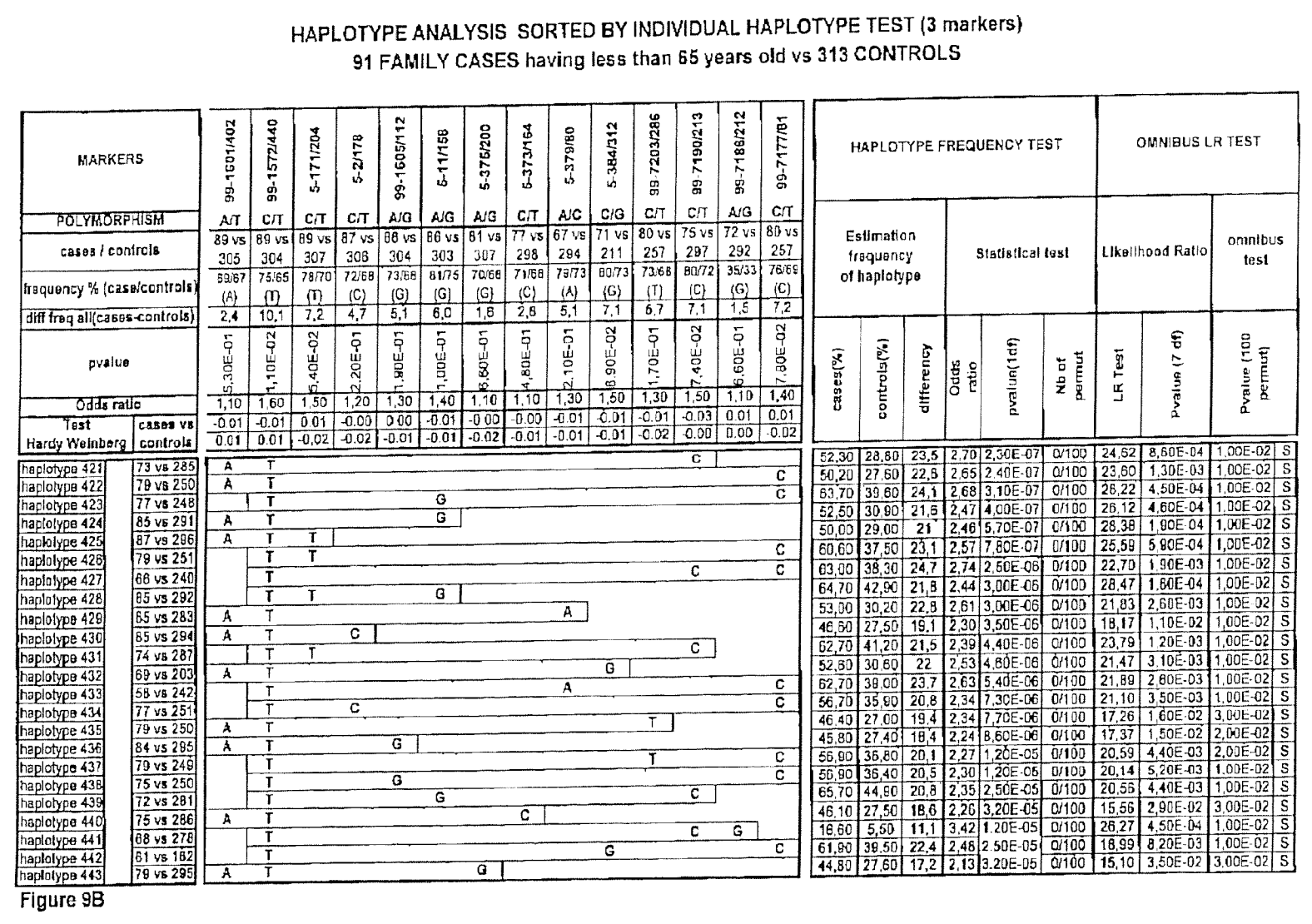

The preferred three-markers haplotypes are described in FIG. 9*b* as H421 to H1443. All of them comprise the biallelic marker A30 (99-1572/440) and almost all of them comprise the biallelic marker A53 (99-1601/402). One of the more preferred haplotype is the haplotype H421 and comprises the biallelic markers A53 (99-1601/402), A30 (99-1572/440) and A5 (99-7190/213), alleles ATC, respectively. This haplotype presented a p-value for the haplotype frequency test of $2.3 \times 10^{-7}$ and an odd-ratio of 2.7. Estimated haplotype frequencies were 52.3% in the cases and 28.8% in the controls. This haplotype presented a pvalue for the likelihood ratio test of $8.6 \times 10^{-2}$. The pvalue by permutation test is $<1 \times 10^{-2}$ and the pvalue for this group of markers is $1 \times 0$-2 by omnibus Lr test.

In conclusion, most preferred haplotypes for the early onset familial cases of prostate cancer comprise the biallelic markers A30 (99-1572/440), and A53 (99-1601/402). These haplotypes can be used in diagnostic, more particularly in diagnostics of early onset familial prostate cancer susceptibility.

Haplotype Frequency Analysis for Sporadic Cases of Prostate Cancer

The most significant haplotypes obtained with the sporadic cases of prostate cancel are shown in FIG. 10 *a* and *b*.

The two-markers haplotypes comprise the biallelic markers A53 (99-1601/402), A42 (99-13798/284), A32 (5-171/204), A29 (5-11/158), A28 (5-14/165), A27 (5-377/227), A25 (5-376/266), A19 (5-373/164), A16 (5-370/197), A4 (5-382/316), and A55 (99-7182/49).

Figure 10A:
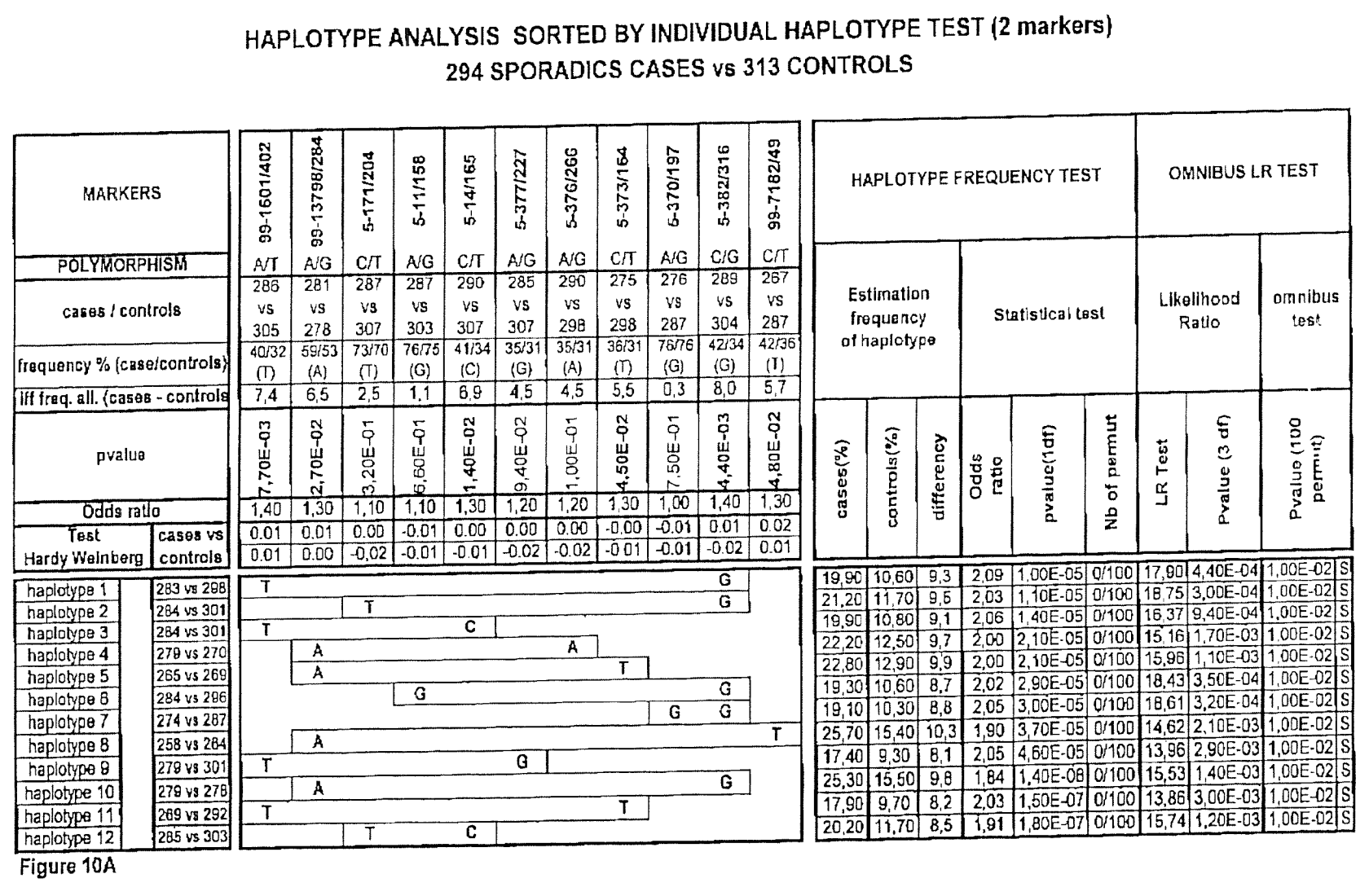

The preferred two-markers haplotypes are described in FIGS. 10*a* as H1 to H12. The more usual biallelic markers in these haplotypes are A4 (5-382/316), A53 (99-1601/402), and A42 (99-13798/284). One of the more preferred haplotype is the haplotype H1 and comprises the biallelic markers A53 (99-1601/402), and A4 (5-382/316), alleles TG respectively. This haplotype presented a p-value for the haplotype frequency test of $1 \times 10^{-5}$ and an odd-ratio of 2.09. Estimated haplotype frequencies were 19.9% in the cases and 10.6% in the controls. This haplotype presented a p-value for the likelihood ratio test of $4.4 \times 10^{-4}$. The pvalue by permutation test is $<1 \times 10^{-2}$ and the pvalue for this group of markers is $1 \times 10^{-2}$ by omnibus Lr test. The results of allelic association which show that these markers are associated are significant. The haplotype analysis by combining the informativeness of a set of biallelic markers increases the power of the association analysis, allowing false positive and/or negative data that may result from the single marker studies to be. eliminated-. The significant trend for singlepoint analysis seems to be identical for multipoint analysis. This haplotype tested on all cases-controls population gives estimated haplotype frequencies for sporadic cases (n=294) of 19.6% and for controls (n=313) of 10.6%. For the same haplotype, any significant results for familial cases can be found. Therefore, the association for sporadic cases is different for familial cases.

The three-markers haplotypes comprise the biallelic markers A53 (99-1601/402), A42 (99-13798/284), A51 (99-1587/281), A31 (5-169/97), A34 (5-2/178), A27 (5-377/227), A25 (5-376/266). A21 (5-375/200), A19 (5-373/164), and A55 (99-7182/49).

Figure 10B:
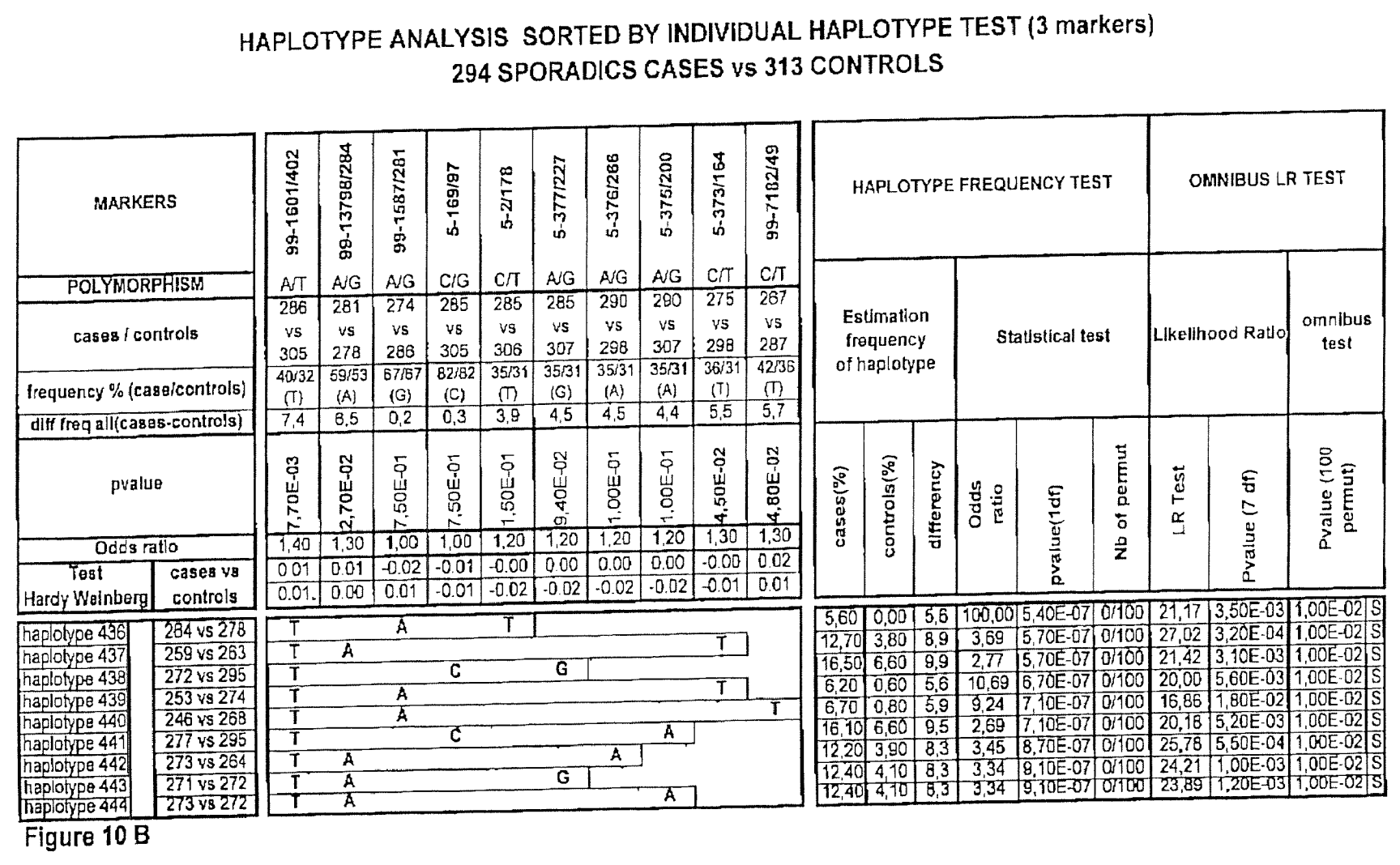

The preferred three-markers haplotypes are described in FIG. 10b as 11436 to H1444. All the haplotypes comprise the biallelic marker A53 (99-1601/402). The biallelic markers A42 (99-13798/284) and A51 (99-1587/281) are frequently found in these haplotypes. One of the more preferred haplotype is the haplotype H436 and comprises the biallelic markers A53 (99-1601/402), A51 (99-1587/281) and A34 (5-2/178), alleles TAT respectively. This haplotype presented a p-value for the haplotype frequency test of $5.4 \times 10^{-7}$ and an odd-ratio of 100. Estimated haplotype frequencies were 5.6% in the cases and 0% in the controls. This haplotype presented a p-value for the likelihood ratio test of $3.5 \times 10^{-3}$. The pvalue by permutation test is $<1 \times 10^{-2}$ and the pvalue for this group of markers is $1 \times 10^{-2}$ by omnibus Lr test.

In conclusion, most preferred haplotypes for the sporadic cases of prostate cancer comprise the biallelic marker A53 (99-1601/402). The biallelic markers A42 (99-13798/284), A51 (99-1587/281) and A4 (5-382/316) are frequently found in the preferred haplotypes. These haplotypes can be used in diagnostic, more particularly in diagnostics of sporadic prostate cancer susceptibility.

The most significant haplotypes obtained with the informative sporadic cases of prostate cancer are shown in FIG. 11 a and b.

The two-markers haplotypes comprise the biallelic markers A53 (99-1601/402), A30 (99-1572/440), A32 (5-171/204), A29 (5-11/158), A16 (5-370/197), A4 (5-382/316), A1 (5-381/133), and A55 (99-7182/49).

Figure 11A:
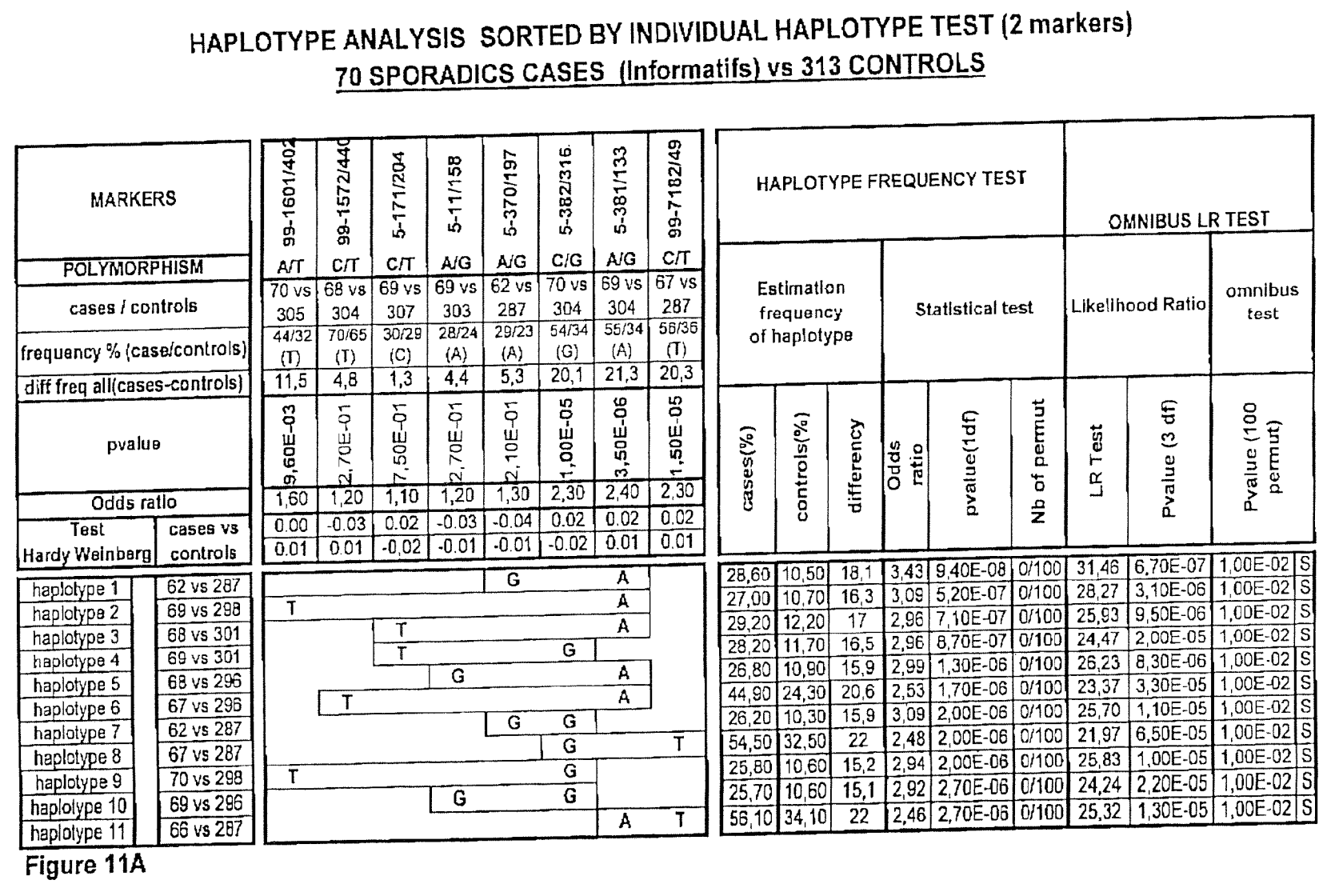

The preferred two-markers haplotypes are described in FIG. 11a as H1 to H11. The more usual biallelic markers in these haplotypes are A4 (5-382/316), and A1 (5-381/133). One of the more preferred haplotype is the haplotype H1 and comprises the biallelic markers A16 (5-370/197), and A1 (5-381/133), alleles GA respectively. This haplotype presented a p-value for the haplotype frequency test of $9.4 \times 10^{-8}$ and an odd-ratio of 3.43. Estimated haplotype frequencies were 28.6% in the cases and 10.5% in the controls. This haplotype presented a p-value for the likelihood ratio test of $6.7 \times 10^{-7}$. The pvalue by permutation test is $<1 \times 10^{-2}$ and the pvalue for this group of markers is 1×0-2 by omnibus Lr test.

The three-markers haplotypes comprise the biallelic markers A53 (99-1601/402), A50 (99-1585/373), A30 (99-1572/440), A31 (5-169/97), A34 (5-2/178), A33 (99-1605/112), A29 (5-11/158), A28 (5-14/165), A27 (5-377/227), A25 (5-376/266), A21 (5-375/200), A16 (5-370/197), A4 (5-382/316), A1 (5-381/133), and A55 (99-7182/49).

Figure 11B:
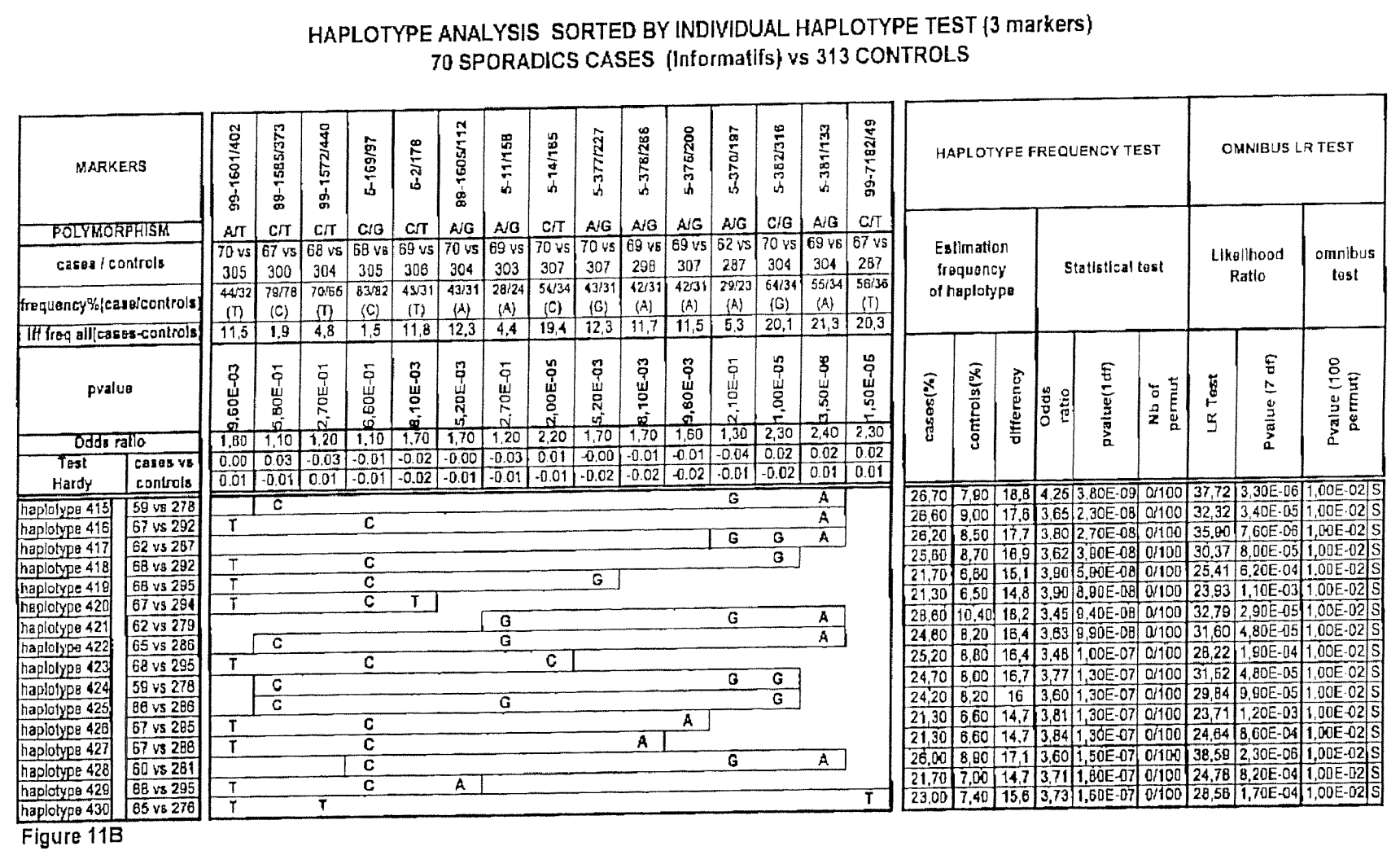

The preferred three-markers haplotypes are described in FIG. 11b as H415 to H430. Most of the haplotypes comprise the biallelic markers A53 (99-1601/402) and A31 (5-169/97). The biallelic markers A50 (99-1585/373), A16 (5-370/197), A4 (5-382/316), and A1 (5-381/133) are frequently found in these haplotypes. One of the more preferred haplotype is the haplotype H415 and comprises the biallelic markers A50 (99-1585/373), A16 (5-370/197), and A1 (5-381/133), alleles CGA respectively. This haplotype presented a p-value for the haplotype frequency test of $3.8 \times 10^{-9}$ and an odd-ratio of 4.25. Estimated haplotype frequencies were 26.7% in the cases and 7.9% in the controls. This haplotype presented a p-value for the likelihood ratio test of $3.3 \times 10^{-6}$. The pvalue by permutation test is $<1 \times 10^{-2}$ and the pvalue for this group of markers is $1 \times 10^{-2}$ by omnibus Lr test.

In conclusion, most preferred haplotypes for the informative sporadic cases of prostate cancer comprise the biallelic markers A53 (99-1601/402), A31 (5-169/97), A4 (5-382/316), and A1 (5-381/133). The biallelic markers A50 (99-1585/373), A16 (5-370/197) are also frequently found in the preferred haplotypes. These haplotypes can be used in diagnostic, more particularly in diagnostics of informative sporadic prostate cancer susceptibility.

Summary of Haplotype Frequency Analysis

The most preferred two-biallelic markers haplotypes for the familial and sporadic prostate cancer are summarized in FIG. 12. This haplotype can be used in diagnostic of prostate cancer susceptibility.

The statistical significance of the results obtained for the haplotype analysis was evaluated by a phenotypic permutation test reiterated 1000 times on a computer. For this computer simulation, data from the cases and control individuals were pooled and randomly allocated to two groups which contained the same number of individuals as the case-control populations used to produce the haplotype frequency analysis data. A haplotype analysis was then run on these artificial groups for the preferred haplotypes which presented a strong association with prostate cancer. This experiment was reiterated 1000 times and the results are shown in FIG. 12.

FIG. 12A shows the association results the preferred haplotype with A30 (99-1572/440) and A32 (5-171/204), alleles TT, for each population and with 1000 permutations. This haplotype is specific of familial prostate cancer, and more particularly of early onset prostate cancer. This haplotype is highly significant and could be used in diagnostic.

FIG. 12B shows the association results the preferred haplotype with A16 (5-370/197), and A1 (5-381/133), alleles GA, for each population and with 1000 permutations. This haplotype is specific of sporadic prostate cancer. This haplotype is highly significant and could be used in diagnostic.

FIG. 12C shows the association results the preferred haplotype with A53 (99-1601/402), and A4 (5-382/316), alleles TG, for each population and with 1000 permutations. This haplotype is specific of prostate cancer, and more particularly of sporadic prostate cancer. This haplotype is highly significant and could be used in diagnostic.

Example 6

Preparation of Antibody Compositions to the BAP28 Protein

Substantially pure protein or polypeptide is isolated from transfected or transformed cells containing an expression vector encoding the BAP28 protein or a portion thereof. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes in the BAP28 protein or a portion thereof can be prepared from murine hybridomas according to the classical method of Kohler, G. and Milstein, C. Nature 256:495 (1975) or derivative methods thereof. Also see Harlow, E., and D. Lane. 1988. Antibodies A Laboratory Manual. Cold Spring Harbor Laboratory. pp. 53-242.

Briefly, a mouse is repetitively inoculated with a few micrograms of the BAP28 protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2.

B. Polyclonal Antibody Production by Immunization

Polyclonal antiserum containing antibodies to heterogeneous epitopes in the BAP28 protein or a portion thereof can be prepared by immunizing suitable non-human animal with the BAP28 protein or a portion thereof, which can be unmodified or modified to enhance immunogenicity. A suitable non-human animal is preferably a non-human mammal is selected, usually a mouse, rat, rabbit, goat, or horse. Alternatively, a crude preparation which has been enriched for BAP28 concentration can be used to generate antibodies. Such proteins, fragments or preparations are introduced into the non-human mammal in the presence of an appropriate adjuvant (e.g. aluminum hydroxide. RIBI., etc.) which is known in the art. In addition the protein, fragment or preparation can be pretreated with an agent which will increase antigenicity, such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. Techniques for producing and processing polyclonal antisera are known in the art, see for example, Mayer and Walker (1987). An effective immunization protocol for rabbits can be found in Vaitukaitis., J. et al. J. Clin. Endocrinol. Metab. 33:988-991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., (11973). Plateau concentration of antibody is usually in the range of 0.1 to 0.2 mg/ml of serum (about 12 µM). Affinity of the antisera for the antigen is determined by preparing competitive binding curves, as described, for example, by Fisher, D., Chap. 42 in: Manual of Clinical Immunology, 2d Ed. (Rose and Friedman, Eds.) Amer. Soc. For Microbiol., Washington, D.C. (1980).

Antibody preparations prepared according to either the monoclonal or the polyclonal protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

Example 7

Tissular Specificity of the BAP28 Expression

Synthesis of the cDNA

The mRNA used are human RNA from CLONTECH.

11.5 µl water treated with DEPC (diethyl pyrocarbonate) with 1 µl of human RNA (1 µg/µl) and 1 µl of oligo dT primer random (oligo dT hexamer) (20 pmol/µl) were heated at 74° C. for 2 min 30 s. Then the enzymatic mixture was added. The enzymatic mixture comprised 4 µL 5× Reaction Buffer, 1 µL dNTP 10 mM each, 0.5 µL Recombinant RNase Inibitor 40 U/µL and 1 µL MMLV Reverse Transcriptase 200 U/µL. The sample was heated 1 h at 42° C., and 5 min at 94° C. Then 80 µl of water treated with DEPC were added. (kit Advantage RT-for-PCR. CLONTECH K1402-2) The synthezised cDNAs were stocked at −20° C.

Amplification of the BAP28 Amplicon

The cDNAs used in this experiment come from the cDNA preparation described above and from Marathon Ready cDNA from CLONTECH.

For each tissue, the following PCR reactions were done.

First PCR reaction: The couple of primers used in this PCR was PCTAexALF12 (SEQ ID No 36)/BAP283Ra6283 (SEQ ID No 32). There were located in exon A' and exon 43 of the BAP28 gene, respectively.

The PCR assay was performed using the following protocol

| Final volume | 50 µl |
|---|---|
| Water | 19.8 µL |
| Buffer 3.3X | 15 µL |
| Mix dNTP (25 mM each) | 4 µL |
| rttHXL PERKIN ELMER (2 U/µL) | 1 µL |
| Primer PCTAexALF12 (20 pmol/µL) | 1 µL |
| Primer BAP283Ra6283 (20 pmol/µL) | 1 µL |
| cDNA | 6 µL |

After 3 min of denaturation, 2.2 µl of Mg(OAc)$_2$ 25 mM were added. The PCR was performed with 10 min at 94° C.; 34 cycles of 30 sec at 94° C., and 3 min at 67° C.; and 10 min at 72° C.

* Second PCR reaction (Nested PCR): The couple of primers used in this PCR was PCTAexALF13n (SEQ ID No 37)/BAP283Ra6324n (SEQ ID No 33). There were also located in exon A' and exon 43 of the BAP28 gene, respectively, and they were more downstream than the first couple of primers.

The PCR assay was performed using the following protocol

| Final volume | 50 µl |
|---|---|
| Water | 20.8 µL |
| Buffer 3.3X | 15 µL |
| Mix dNTP (25 mM each) | 4 µL |
| rttHXL PERKIN ELMER (2 U/µL) | 1 µL |
| Primer PCTAexALF13n (20 pmol/µL) | 1 µL |
| Primer BAP283Ra6324n (20 pmol/µL) | 1 µL |
| Product of PCR N°1 | 5 µL |

After 3 min of denaturation, 2.2 μl of Mg(OAc)₂ 25 mM were added. The PCR was proceeded performed with 10 min at 94° C.; 34 cycles of 30 sec at 94° C., and 3 min at 67° C.; and 10 min at 72° C.

The PCR products of the second PCR were analyzed on a 1% TAE1X gel.

The results are shown in FIG. 13. The segment comprising the exons 43 to A has been observed in the following tissues : Marathon testis, Marathon hippocampus, Marathon leukemia (chronic myelogenous K-562), cDNA cerebellum, cDNA substantia nigra, cDNA thalamus, cDNA caudate nucleus, cDNA spinal cord, cDNA pituitary gland and cDNA mammary gland.

In contract, this cDNA segment has not been observed in Marathon Brain, Marathon Cerebellum, Marathon Cerebral Cortex, Marathon Hypothalamus, Marathon Fetal Kidney. Marathon Thyroid, Marathon Bone Marrow, Marathon HL60, Marathon MOLT4, Marathon Fetal liver, Marathon Stomach, Marathon Prostate, cDNA Testis, cDNA Corpus Callosum, cDNA Amygdala, cDNA Fetal Brain, cDNA Skeletal Muscle, cDNA Lung, cDNA Kidney, cDNA Placenta, cDNA Spleen, cDNA Fetal Liver, cDNA Thyroid Gland, cDNA MOLT4, cDNA Adrenal Gland, cDNA Trachea, cDNA Salivary Gland, cDNA HL60, cDNA Small Intestine, cDNA Pancreas, cDNA Stomach, cDNA Bone Marrow, cDNA Thymus, cDNA Uterus, and cDNA Prostate.

An additional analysis of the expression pattern in the tissue has been done by the search of ESTs in Genbank database which show homology with the BAP28 cDNA. The results are shown in Table 6.

TABLE 6

| Tissue | Accession number in Genbank |
| --- | --- |
| placenta | AK001857; AI277866 |
| colon | AW858897; AW858960 |
| colon tumor metastasis | AW962967 |
| HeLa cell | AA098827 |
| Adipose tissue white | AA320776 |
| LNCAP cells | AA357743 |
| Total fetus | AA424101; AA460031; AA992680 |
| germinal center B cell | AA814857; AA814859 |
| testis | AI023607; AL040338; AA437086 |
| Fetal liver spleen | AI033328 |
| Fetal liver | AI114709 |
| Fetal heart | AI150773 |
| lung | AI348668; AW450486 |
| kidney | AI582623 |
| colon tumor | AI738790 |
| pooled fetal lung testis B-cell | AI827817 |
| stomach | AW389900 |
| Multiple sclerosis | N77431 |
| fetal liver spleen | T85649 |
| anaplastic oligodendroglioma Organ: brain | AI356180 |
| breast | AI905672 |

Example 8

Cloning of a BAP28 cDNA

We cloned the BAP28 cDNA consisting to the exons 1 to 45.

Synthesis of cDNAs mRNAs were total human prostate RNA from CLONTECH (Lot N°8040072—Ref Cat:64038).

11.5 μL water treated with DEPC with 1 μL Total Human Prostate RNA (1 μg/μL) and 1 μL primer oligodT BAP28polyTcourt (20 pmol/μl) (tttttttttttttttgtata: SEQ ID No 57) were heated 2 min 30 sec at 74° C. Then the enzymatic mixture was added. The enzymatic mixture comprised 4 μL 5× Reaction Buffer, 1 μL mix dNTP10mM each, 0.5 μL Recombinant RNase Inibitor 40 U/μL and 1 μL MMLV Reverse Transcriptase 200 U/μL. The sample was heated 1 h at 42° C. and 5 min at 94° C. Then, 80 μl water treated with DEPC were added. The obtained cDNAs were stocked −20° C.

Amplification of the BAP28 Segment to be Cloned: (Double PCR Reaction)

A first PCR with a couple of primer BAP281LF12.1 (SEQ ID No 58)/BAP28LR6726.1 (SEQ ID No 59) was performed using the following protocol

| | |
| --- | --- |
| Final volume | 50 μl |
| Water | 19.8 μL |
| Buffer 3.3X | 15 μL |
| Mix dNTP (25 mM each) | 4 μL |
| rttHXL PERKIN ELMER (2 U/μL) | 1 μL |
| Primer BAP281LF12.1 (20 pmol/μL) | 1 μL |
| Primer BAP28LR6726.1 (20 pmol/μL) | 1 μL |
| Preparation of cDNA | 6 μL |

After 3 min of denaturation, 2.2 μl of Mg(OAc)₂ 25 mM were added. The PCR was performed with 10 min at 94° C.; 34 cycles of 30 sec at 94° C., and 8 min at 67° C.; and 10 min at 72° C.

A second PCR reaction (Nested PCR) with a couple of primers BAP28LF26SalI (SEQ ID No 60)/BAP28LR6717SalI (SEQ ID No 61) was performed using the following protocol:

| | |
| --- | --- |
| Final volume | 50 μl |
| Water | 18.3 μL |
| Buffer 3.3X | 15 μL |
| Mix dNTP (25 mM each) | 4 μL |
| VENT BIOLABS (2 U/μL) | 3.5 μL |
| Primer BAP281LF12.1 (20 pmol/μL) | 1 μL |
| Primer BAP28LR6726.1 (20 pmol/μL) | 1 μL |
| Product of PCR N°1 | 5 μL |

After 3 min of denaturation, 2.2 μl of Mg(OAc)₂ 25 mM were added. The PCR was performed with 10 min at 94° C.; 34 cycles of 30 sec at 94° C., and 8 min at 67° C.; and 10 min at 72° C.

As soon as the end of PCR, the phenol/chloroform extraction was performed in order to avoid in degradation. Finally, the PCR product was precipitated with NaCl and ethanol.

The PCR product and the cloning vector pGEM11Zf(+) were both digested by the restriction endonuclease SalI. The digested vector was then dephosphorylated. The digested PCR product was ligated with the digested and dephosphorylated pGEM11Zf(+) vector. E. coli DH10B was transformed by the obtained vector and the bacteria containing the recombinant vector were selected. The positive clones contained an 6.8 kb insert which is the expected size for the entire BAP28 cDNA. The sequencing of the insert showed a cDNA consisting of the exons 1 to 45 of BAP28.

Example 9

Natural Antisense Structure

The natural antisense structure observed in the BAP28 gene related to the PCTA-1 gene is conserved in the Droso-

*phila*. Indeed, the new CDS generated from the Genbank sequence AE00315 (gene CG10805) is located between the positions 97601 and 104127 of the sequence. Another CDS is described on the opposite strand as the gene CG10806. This CDS is located between the positions 107695 and 104389 of the sequence. Then, the distance between the two CDS is about 262 bp. Therefore, as the 3'UTR of the 2 genes are likely overlapping, the new gene CG010805 is a natural antisense of the gene CG10806 and the natural antisense organization of BAP28 is conserved in *Drosphila*.

While the preferred embodiment of the invention has been illustrated and described, it will be appreciated that various changes can be made therein by the one skilled in the art without departing from the spirit and scope of the invention.

The Sequence Listing for this application is labeled "seqlist-replace2.txt", which was created on Aug. 3, 2010 and is 404 KB. The entire content of the sequence listing is incorporated herein by reference in its entirety.

REFERENCES

The following references cited herein are incorporated herein by reference in their entireties Abbondanzo S J et al., 1993, Methods in Enzymology, Academic Press, New York. pp. 803-823 /Ajioka R. S. et al., *Am. J. Hum. Genet.*, 60: 439-1447, 1997 /Altschul et al., 1990, J. Mol. Biol. 215(3):403-410 /Altschul et al., 1993, Nature Genetics 3:266-272 /Altschul et al., 1997, Nuc. Acids Res. 25:3389-3402 /Anton M. et al., 1995, J. Virol., 69: 4600-4606 /Araki K et al. (1995) *Proc. Natl. Acad. Sci. USA.* 92(1):160-4. /Ausubel et al. (1989) Current Protocols in Molecular Biology, Green Publishing Associates and Wiley Interscience, N.Y. /Baubonis W. (1993) *Nucleic Acids Res.* 21(9):2025-9. /Beaucage et al., *Tetrahedron Lett* 1981, 22: 1859-1862 /Bowcock et al., 1998, International Patent Publication No WO98/12327)/Bradley A., 1987, Production and analysis of chimeric mice. In: E. J. Robertson (Ed.), Teratocarcinomas and embryonic stem cells: A practical approach. IRL Press, Oxford, pp. 113. /Bram R J et al., 1993, Mol . Cell Biol., 13: 4760-4769 /Brown E L, Belagaje R, Ryan M J, Khorania H G, Methods Enzymol 1979; 68:109-151 /Brurtlag et al. Comp. App. Biosci. 6:237-245, 1990 /Bush et al., 1997, J. Chromatogr., 777: 311-328. /Capecchi, M R. (1989a) *Science,* 244:1288-1292 /Capecchi, M. R. (1989b) *Trends Genet.,* 5:70-76 /Chai H. et al. (1993) *Biotechnol. Appl. Biochem.* 18:259-273. /Chee et al. (1996) *Science.* 274:610-614. /Chen et al. (1987) *Mol. Cell. Biol.* 7:2745-2752. /Chen et al. Proc. Natl. Acad. Sci. USA 94/20 10756-10761, 1997 /Chen and Kwok *Nucleic Acids Research* 25:347-353 1997 /Chen and Kwok *Nucleic Acids Research* 25:347-353 1997 /Cho R J et al., 1998, Proc. Natl. Acad. Sci. USA, 95(7): 3752-3757. /Chou J. Y., 1989, Mol. Endocrinol., 3: 1511-1514. /Clark A. G. (1990) *Mol. Biol. Evol.* 7:111-122. /Coles R, Caswell R, Rubinsztein D C, *Hum Mol Genet.* 1998; 7:791-800 /Compton J. (1991) *Nature.* 350(6313):91-92. /Davis E. G., M. D. Dibner, and J. F. Battey, Basic Methods in Molecular Biology, ed., Elsevier Press, NY, 1986 /Dempster et al., (1977) *J. R. Stat. Soc.* 39B: 1-38. /Dent D S & Latchman D S (1993) The DNA mobility shift assay. In: *Transcription Factors. A Practical Approach* (Latchman D S, ed.) pp 1-26. Oxford: IRL Press/Eckner R. et al. (1991) *EMBO. J* 10:3513-3522. /Edwards et Leatherbarrow, *Analytical Biochemistry,* 246, 1-6 (1997)/Engvall, E., Meth. Enzymol. 70:419 (1980)/Excoffier L. and Slatkin M. (1995) *Mol. Biol. Evol.,* 12(5): 921-927. /Feldman and Steg, 1996, Medicine/Sciences, synthese, 12:47-55 /Felici F., 1991, J. Mol. Biol., Vol. 222:301-310 /Fields and Song, 1989, Nature, 340: 245-246 /Fisher, D., Chap. 42 in: Manual of Clinical Immunology, 2d Ed. (Rose and Friedman, Eds.) Amer. Soc. For Microbiol., Washington, D.C. (1980)/Flotte et al. (1992) *Am. J. Respir. Cell Mol. Biol.* 7:349-356. /Fodor et al. (1991) *Science* 251:767-777. /Fraley et al. (1979) *Proc. Natl. Acad. Sci. USA.* 76:3348-3352. /Fried M, Crothers D M. *Nucleic Acids Res* 1981; 9:6505-6525 /Fromont-Racilne M. et al., 1997, Nature Genetics, 16(3): 277-282. /Fuller S. A. et al. (1996) *Immunology in Current Protocol, in Molecular Biology*, Ausubel et al. Eds, John Wiley & Sons, Inc., USA. /Furth P. A. et al. (1994) *Proc. Natl. Acad. Sci USA* 91:9302-9306. /Garner M M, Revzin A, *Nucleic Acids Res* 1981; 9:3047-3060 /Geysen H. Mario et al. 1984. Proc. Natl. Acad. Sci. U.S.A. 81:3998-4002 /Ghosh and Bacchawat, 1991, *Targeting liposomes to hepatoytes*, IN: *Liver Diseases, Targeted diagnosis and therapy using specific receptors and ligands*. Wu et al. Eds., Marcel Dekeker, N.Y., pp. 87-104. /Gonnet et al., 1992, Science 256:1443-1445 /Gopal (1985) *Mol. Cell. Biol.,* 5:1188-1190. /Gossen M. et al. (1992) *Proc. Natl. Acad. Sci. USA* 89:5547-5551. /Gossen M. et al. (1995) *Science.* 268:1766-1769. /Graham et al. (1973) *Virology* 52:456-457. /Green et al., *Ann. Rev. Biochem.* 55:569-597 (1986)/Grompe, M. (1993) *Nature Genetics.* 5:111-117. /Grompe, M. et al. (1989) *Proc. Natl. Acad. Sci. U.S.A.* 86:5855-5892. /Gu H. et al. (1993) *Cell* 173:1155-1164. /Gu L H. et al. (1994) *Science* 265:103-106. /Guatelli J C et al. *Proc. Natl. Acad. Sci. USA.* 35:273-286. /Hacia J G, Brody L C, Chee M S, Fodor S P, Collins F S, *Nat Genet.* 1996; 14(4):441-447 /Haff L. A. and Smirnov I. P. (1997) *Genome Research,* 7:378-388. /Hames B. D. and Higgins S. J. (1985) *Nucleic Acid Hybridization. A Practical Approach*. Hames and Higgins Ed., IRL Press, Oxford. /Harju L, Weber T, Alexandrova L, Lukin M, Ranki M, Jalanko A, *Clin Chem* 1993; 39(11Pt 1):2282-2287 /Harland et al. (1985) *J. Cell. Biol.* 101:1094-1095. /Harlow, E., and D. Lane. 1988. Antibodies A Laboratory Manual. Cold Spring Harbor Laboratory. pp. 53-242 /Harper J W et al., 1993, Cell, 75: 805-816 /Hawley M. E. et al. (1994) *Am. J. Phys. Anthropol.* 18:104. /Henikoff and Henikoff, 1993, Proteins 17:49-61 /Higgins et al., 1996, Methods Enzymol. 266:383-402 /Hillier L. and Green P. *Methods Appl.,* 1991, 1: 124-8. /Hoess et al. (1986) Nucleic Acids Res. 14: 2287-2300. /Huang L. et al. (1996) Cancer Res 56(5):1137-1141. /Huygen et al. (1996) Nature Medicine. 2(8):893-898. /Izant J G, Weintraub H, Cell 1984 April; 36(4):1007-15 /Julan et al. (1992) J. Gen. Virol. 73:3251-3255. /Kanegae Y. et al., Nucl. Acids Res. 23:3816-3821. /Karlin and Altschul, 1990, Proc. Natl. Acad. Sci. USA 87:2267-2268 /Khoury J. et al., *Fundamentals of Genetic Epidemiology*, Oxford University Press, NY, 1993 /Kim U-J. et al. (1996) *Genomics* 34:213-218. /Klein et al. (1987) *Nature.* 327:70-73. /Kohler, G. and Milstein, C., Nature 256: 495 (1975)/Koller et al. (1992) *Annu. Rev. Immunol.* 10:705-730. /Kozal M J, Shah N, Shen N, Yang R, Fucini R, Merigan T C, Richman D D, Morris D, Hubbell E, Chee M, Gingeras T R, Nat Med 1996; 2(7):753-759 /Landegren U. et al. (1998) *Genome Research,* 8:769-776. /Lander and Schork, *Science,* 265, 2037-2048, 1994 /Lange K. (1997) *Mathematical and Statistical Methods for Genetic Analysis*. Springer, N.Y. /Lenhard T. et al. (1996) *Gene.* 169:187-190. /Linton M. F. et al. (1993) *J Clin. Invest.* 92:3029-3037. /Liu Z. et al. (1994) *Proc. Natl. Acad. Sci. USA.* 91:4528-4262. /Livak et al., *Nature Genetics,* 9:341-342, 1995 /Livak K J, Hainer J W, *Hum Mutat* 1994; 3(4):379-385 /Lockhart et al. *Nature Biotechnology* 14: 1675-1680, 1996 /Lucas A. H., 1994, In: Development and Clinical Uses of Haemophilus b Conjugate; /Mackey K, Steinkamp A, Chomezynski P, 1998, *Mol Biotechnol,* 9(1):1-5 /Mansour S. L. et al. (1988) *Nature.* 336:348-352. /Marshall R. L. et al. (1994) *PCR Methods and*

Applications. 4:80-84. /McCormick et al. (1994) *Genet. Anal. Tech. Appl.* 11:158-164. /McLaughlin B. A. et al. (1996) *Am. J. Hum. Genet.* 59:561-569. /Morton N. E., *Am. J. Hum. Genet.*, 7:277-318, 1955 /Muzyczka et al. (1992) *Curr. Topics in Micro. and Immunol.* 158:97-129. /Nada S. et al. (1993) *Cell* 73:1125-1135. /Nagy A. et al., 1993, Proc. Natl. Acad. Sci. USA. 90: 8424-8428. /Nangaku M. (1994) Cell 79, 1209-1220 /Narang S A, Hsiung H M, Brousseau R, *Methods Enzymol* 1979; 68:90-98 /Neda et al. (1991) *J. Biol. Chem.* 266:14143-14146. /Newton et al. (1989) *Nucleic Acids Res.* 17:2503-2516. /Nickerson D. A. et al. (1990) *Proc. Natl. Acad. Sci. U.S.A* 87:8923-8927. /Nicolau C. et al., 1987, Methods Enzymol., 149:157-76. /Nicolau et al. (1982) *Biochim. Biophys. Acta.* 721:185-190. /Nyren P, Pettersson B, Uhlen M, Anal Biochem 1993; 208(1):171-175 /O'Reilly et al. (1992) *Baculovirus Expression Vectors: A Laboratory Manual.* W.H. Freeman and Co., New York. /Obno et al. (1994) *Science.* 265:781-784. /Oldenburg K. R. et al., 1992. Proc. Natl. Acad. Sci., 89:5393-5397. /Orita et al. (1989) *Proc. Natl. Acid. Sci. U.S.A.* 86: 2776-2770. /Ott J., *Analysis of Hunan Genetic Linkage*, John Hopkins University Press., Baltimore, 1991 /Ouchterlony, O. et al., Chap. 19 in: Handbook of Experimental Immunology D. Wier (ed) Blackwell (1973)/Parmley and Smith, Gene, 1988, 73:305-318 /Pastinen et al., *Genome Research* 1997; 7:606-614 /Pearson and Lipman, 1988, Proc. Natl. Acad. Sci. USA 85(8):2444-2448 /Pease S. and William R. S., 1990, Exp. Cell. Res., 190: 209-211. /Perlin et al. (1994) *Am. J. Hum. Genet.* 55:777-787. /Peterson et al., 1993, Proc. Natl. Acad. Sci. USA, 90: 7593-7597. /Pietu et al. *Genome Research* 6:492-503, 1996 /Potter et al. (1984) *Proc. Natl. Acad. Sci. U.S.A.* 81(22):7161-7165. /Ramunsen et al., 1997, Electrophoresis, 18: 588-598. /Reid L. H. et al. (1990) *Proc. Natl. Acad. Sci. U.S.A.* 87:4299-4303. /Risch, N. and Merikangas, K. (*Science*, 273:1516-1517, 1996 /Robertson E., 1987, Embryo-derived stem cell lines. In: E. J. Robertson Ed. *Teratocarcinomas and embrionic stem cells. a practical approach. IRL Press, Oxford, pp.* 71. /Rossi et al., *Pharmacol. Ther.* 50:245-254, (1991)/Roth J. A. et al. (1996) *Nature Medicine.* 2(9):985-991. /Roux et al. (1989) *Proc. Natl. Acad. Sci. U.S.A.* 86:9079-9083. /Ruano et al. (1990) *Proc. Natl. Acad. Sci. U.S.A.* 87:6296-6300. /Sambrook, J., Fritsch, E. F., and T. Maniatis. (1989) *Molecular Cloning. A Laboratory Manual.* 2ed. Cold Spring Harbor Laboratory, Cold Spring Harbor, N.Y. /Samson M, et al. (1996) *Nature,* 382(6593):722-725. /Samulski et al. (1989) *J. Virol.* 63:3822-3828. /Sanchez-Pescador R. (1988) *J. Clin. Microbiol.* 26(10):1934-1938. /Sarkar, G. and Sommer S. S. (1991) *Biotechniques.* /Sauer B. et al. (1988) *Proc. Natl. Acad. Sci. U.S.A.* 85:5166-5170. /Schaid D. J. et al., *Genet. Epidemiol.*, 13:423-450, 1996 /Schedl A. et al., 1993a, Nature, 362: 258-261. /Schedl et al., 1993b, Nucleic Acids Res., 21: 4783-4787. /Schena et al. *Science* 270:467-470, 1995 /Schena et al., 1996, Proc Natl Acad Sci USA. 93(20): 10614-10619. /Schneider et al. (11997) *Arlequin. A Software For Population Genetics Data Analysis.* University of Geneva. /Schwartz and Dayhoff, eds., 1978, Matrices for Detecting Distance Relationships: Atlas of Protein Sequence and Structure, Washington: National Biomedical Research Foundation/Sczakiel G. et al. (1995) *Trends Microbiol.* 3(6): 213-217. /Shay J. W. et al., 1991, Biochem. Biophys. Acta, 1072: 1-7. /Sheffield, V. C. et al. (1991) *Proc. Natl. Acad. Sci. U.S.A.* 49:699-706. /Shizuya et al. (1992) *Proc. Natl. Acad. Sci. U.S.A.* 89:8794-8797. /Shoemaker D D, et al., *Nat Genet.* 1996; 14(4):450-456 /Smith (1957) *Ann. Hum. Genet.* 21:254-276. /Smith et al. (1983) *Mol. Cell. Biol.* 3:2156-2165. /Sosnowski R G, et al., *Proc Natl Acad Sci USA* 1997; 94:1119-1123 /Spielmann S. and Ewens W. J., *Am. J. Hum. Genet.,* 62:450-458, 1998 /Spielmann S. et al., *Am. J. Hum. Genet.,* 52:506-516, 1993 /Sternberg N. L. (1994) *Mamm. Genome.* 5:397-404. /Sternberg N. L. (1992) Trends Genet. 8:1-16. /Stryer, L., *Biochemistry,* 4th edition, 1995 /Syvanen A C, *Clin Chim Acta* 1994; 226(2):225-236 /Szabo A. et al. *Curr Opin Struct Biol* 5, 699-705 (1995)/Tacson et al. (1996) *Nature Medicine.* 2(8):888-892. /Tatusov, R. L. & Koonin, E. V. (1994), CABIOS 10, No 4 /Te Riele et al. (1990) Nature. 348:649-651. /Terwilliger J. D. and Ott J., *Handbook of Human Genetic Linkage,* John I-Hopkins University Press, London, 1994 /Thomas K. R. et al. (1986) *Cell.* 44:419-428. /Thomas K. R. et al. (1987) *Cell.* 51:503-512. /Thompson et al., 1994, Nucleic Acids Res. 22(2):4673-4680 /TurKaspa et al. (1986) *Mol. Cell. Biol.* 6:716-718. /Tyagi et al. (1998) *Nature Biotechnology.* 16:49-53. /Urdea M. S. (1988) *Nucleic Acids Research.* 11:4937-4957. /Urdea M. S. et al. (1991) *Nucleic Acids Symp. Ser.* 24:197-200. /Vaitukaitis, J. et al. J. Clin. Endocrinol. Metab. 33:988-991 (1971)/Valadon P., et al., 1996, J. Mol. Biol., 261:11-22. /Van der Lugt et al. (1991) *Gene.* 105:263-267. /Vanhee-Brossollet and Vaquero. (1998) Gene; 211(1):1-9 /Vlasak R. et al. (1983) *Eur. J. Biochem.* 135:123-126. /Von Heijne, G., J. Mol. Biol. (1992) 225, 487-494 /Wabiko et al. (1986) *DNA.* 5(4):305-314. /Walker et al. (1996) *Clin. Chem.* 42:9-13. /Wang et al., 1997, Chromatographia, 44: 205-208. /Weir, B. S. (1996) *Genetic data Analysis II. Methods for Discrete population genetic Data,* Sinauer Assoc., Inc., Sunderland, Mass., U.S.A. /Westerink M. A. J., 1995, Proc. Natl. Acad. Sci., 92:4021-4025 /White, M. B. et al. (1992) *Genomics.* 12:301-306. /White, M. B. et al. (1997) *Genomics.* 12:301-306. /Wong et al. (1980) *Gene.* 10:87-94. /Wood S. A. et al. 1993, Proc. Natl. Acad. Sci. USA, 90: 4582-4585. /Wu and Wu (1987) *J. Biol. Chem.* 262:4429-4432. /Wu and Wu (1988) *Biochemistry.* 27:887-892. /Wu et al. (1989) *Proc. Natl. Acad. Sci, U.S.A.* 86:2757. /Yagi T. et al. (1990) *Proc. Nail. Acad. Sci. U.S.A.* 87:9918-9922. /Zhao et al., *Am. J. Hum. Genet.,* 63:225-240, 1998 /Zou Y. R. et al. (1994) *Curr. Biol.* 4:1099-1103.

What is claimed is:

1. A method of detecting a risk of developing prostate cancer in an individual, comprising:
   a) genotyping a biological sample from the individual to determine the identity of a combination of three BAP28-related biallelic markers (BM) or the complements thereof, said combination of three BAP28-related biallelic markers being the allele combination of TAT at biallelic markers A53, A51 and A34; and
   b) detecting the presence of the allele combination of TAT at biallelic markers A53, A51 and A34 in said biological sample as indicative of a risk of developing prostate cancer in said individual, said biallelic markers being located at the following positions: nucleotide 402 in SEQ ID NO: 26 (A53); nucleotide 278 in SEQ ID NO: 24 (A51); and nucleotide 71993 in SEQ ID NO: 1 (A34), wherein the T of the A34 biallelic marker is the complement of the A depicted at nucleotide 71993 in SEQ ID NO: 1.

* * * * *

UNITED STATES PATENT AND TRADEMARK OFFICE
CERTIFICATE OF CORRECTION

PATENT NO. : 7,998,671 B2  
APPLICATION NO. : 11/776964  
DATED : August 16, 2011  
INVENTOR(S) : Caroline Barry et al.

It is certified that error appears in the above-identified patent and that said Letters Patent is hereby corrected as shown below:

Title Page,
Item (57) Abstract, Lines 1-2, "polypeptides. BAP28" should read
--polypeptides, BAP28--.

Column 1,
Line 18, "as a regulatory" should read --as regulatory--.

Column 2,
Line 19, "cancers grows" should read --cancers grow--.
Lines 58-59, "cancer patent as well as the patent's" should read
--cancer patient as well as the patient's--.
Line 65, "with first 304" should read --with the first 304--.

Column 3,
Line 47, "arrow represent" should read --arrows represent--.

Column 4,
Line 7, "NO: 71:" should read --NO: 71;--.

Column 6,
Line 46, "BAP28-exALF7311n" should read --BAP28-exALF7319n--.
Line 55, "BAP281R6717SalI" should read --BAP28LR6717SalI--.

Column 7,
Line 51, "of an amino acids" should read --of amino acids--.

Column 9,
Line 64, "poly peptide" should read --polypeptide--.

Signed and Sealed this
Twenty-first Day of February, 2012

David J. Kappos
*Director of the United States Patent and Trademark Office*

Column 10,
Line 8, "preferable a mammal" should read --preferably a mammal--.

Column 11,
Line 18, "without to be limited to" should read --without being limited to--.

Column 15,
Line 5, "FASTA, FASTA" should read --FASTA, TFASTA--.
Line 54, "5 min." should read --5 min,--.

Column 17,
Line 67, "eDNA" should read --cDNA--.

Column 18,
Lines 2-3, "to an other another" should read --to another--.
Line 21, "1 to 45b, 45b." should read --1 to 45, 45b,--.

Column 25,
Lines 8-9, "one skill in the art" should read --one skilled in the art--.

Column 33,
Line 26, "No 3: Ito" should read --No 3: 1 to--.

Column 37,
Line 39, "selected form" should read --selected from--.
Line 52, "selected form" should read --selected from--.
Line 62, "substrate In a" should read --substrate. In a--.

Column 38,
Line 5, "B1 to B135" should read --B1 to B15--.

Column 39,
Line 14, "termed 41" should read --termed 4L--.
Line 19, "4 probes" should read --4L probes--.
Line 31, "concerns all" should read --concerns an--.
Line 53, "B1 to B338" should read --B1 to B38--.
Line 58, "thereof. preferably" should read --thereof, preferably--.
Lines 60-61, "B1 to B135" should read --B1 to B15--.

Column 40,
Line 33, "no 454-4610" should read --no 4544610--.

CERTIFICATE OF CORRECTION (continued)
U.S. Pat. No. 7,998,671 B2

Column 41,
Line 11, "primers oil" should read --primers on--.
Line 67, "B1 to B135" should read --B1 to B15--.

Column 42,
Line 14, "species Such as" should read --species such as--.

Column 43,
Line 20, "at tile position" should read --at the position--.

Column 51,
Line 34, "B1 to B338" should read --B1 to B38--.

Column 52,
Line 17, "may attached" should read --may be attached--.

Column 54,
Line 60, "biallelic mariners" should read --biallelic markers--.

Column 55,
Line 20, "genetic mariners" should read --genetic markers--.

Column 60,
Line 2, "well with the" should read --well within the--.

Column 64,
Line 47, "region, linkage" should read --region. Linkage--.
Lines 54-55, "allele a and the total number of a carriers" should read
--allele α and the total number of α carriers--.

Column 72,
Line 27, "16. A30. A3-1, A42. A50" should read --A16, A30, A31, A42, A50--.

Column 74,
Lines 43-44, "known to person" should read --known to a person--.
Line 52, "unknown, haplotype" should read --unknown. Haplotype--.
Line 65, "can categorized" should read --can be categorized--.

Column 75,
Line 2, "the following equation" should read --the following equation:--.

Column 76,
Line 17, "(ID) between" should read --(LD) between--.
Line 19, "(ai,aj, ai,bj;" should read --($a_i,a_j$; $a_i,b_j$;--.
Line 45, "marker" should read --markers--.

Column 77,
Line 1, "well with in" should read --well within--.
Line 6, "if their is" should read --if there is--.
Line 12, "if their is" should read --if there is--.

Column 78,
Line 17, "$OR=(F^+/(1-F^-))/(F^-/(1-F^-))$" should read --OR= $(F^+/(1-F^+))/(F^-/(1-F^-))$--.

Column 79,
Line 2, "Subcombination" should read --Subcombinations--.
Lines 17-18, "markers" should read --markers.--.

Column 80,
Lines 45-46, "or a on group" should read --or on a group--.

Column 83,
Line 53, "enhances/promoters" should read --enhancers/promoters--.

Column 84,
Line 62, "the a polynucleotide" should read --the polynucleotide--.

Column 85,
Line 8, "the a polynucleotide" should read --the polynucleotide--.
Lines 9-10, "the a polynucleotide" should read --the polynucleotide--.
Lines 12-13, "included are a polynucleotide constructs" should read
 --included are polynucleotide constructs--.

Column 86,
Line 26, "are chosen taking" should read --are chosen, taking--.

Column 87,
Line 29, "pW1NEO" should read --pWLNEO--.
Lines 60-61, "gel, using methods similar using methods similar to those" should read
 --gel, using methods similar to those--.

Column 88,
Line 12, "ATCC N°RL" should read --ATCC N°CRL--.
Line 17, "Viasak et al." should read --Vlasak et al.--.

Column 91,
Line 60, "the skill artisan" should read --the skilled artisan--.
Line 65, "herein designate" should read --herein to designate--.

Column 92,
Line 27, "A further transgenic animals" should read --A further transgenic animal--.

Column 93,
Line 36, "one-genes" should read --*onc*-genes--.

Column 94,
Line 40, "in/vitro" should read --in vitro--.

Column 97,
Line 52, "their Surface" should read --their surface--.

Column 98,
Line 40, "Lez2-3" should read --Leu2-3--.
Line 43, "gal gal80" should read --gal4 gal80--.
Line 52, "($His^+$, beta-gal$^-$)" should read --($His^+$, *beta-gal$^+$*)--.
Line 55, "plasmids bu retention" should read --plasmids but retention--.

Column 100,
Line 47, "BA P28" should read --BAP28--.

Column 103,
Line 6, "for 1 mill" should read --for 1 min--.

Column 105,
Line 59, "1, 2, 3, 5, or of any" should read --1, 2, 3, 5, or 10 of any--.

Column 106,
Line 55, "information oil a" should read --information on a--.

Column 109,
Lines 50-51, "first and sequence sequences" should read --first and second sequences--.
Line 61, "characters either" should read --characters in either--.

Column 111,
Line 18, "move features" should read --more features--.

Column 113,
Line 25, "the sate of the art" should read --the state of the art--.

Column 125,
Line 29, "$3 \times 10^2$ and" should read --$3 \times 10^{-2}$ and--.

Column 126,
Lines 41-42, "test of T $0.7 \times 10^{-2}$" should read --test of $1.7 \times 10^{-2}$--.
Lines 48-49, "A4 (5-382/3T16)" should read --A4 (5-382/316)--.

Column 128,
Line 7, "2.5 × 0-6" should read --2.5 × $10^{-6}$--.
Line 31, "is 1 × 0-2" should read --is 1 × $10^{-2}$--.
Line 41, "prostate cancel" should read --prostate cancer--.

Column 129,
Line 11, "as 11436 to H1444" should read --a H436 to H444--.
Line 49, "1 × 0-2" should read --1 × $10^{-2}$--.

Column 132,
Lines 34-35, "protocol" should read --protocol:--.
Lines 55-56, "protocol" should read --protocol:--.

Column 133,
Line 2, "was proceeded performed" should read --was performed--.
Line 17, "Fetal Kidney." should read --Fetal Kidney,--.
Line 60, "consisting to the" should read --consisting of the--.

Column 134,
Line 14, "protocol" should read --protocol:--.

Column 135,
Line 8, "CG010805" should read --CG10805--.
Line 26, "60: 439-1447" should read --60: 1439-1447--.
Line 41, "Khorania HG," should read --Khorana HG,--.

Column 136,
Line 10, "*Protocol, in*" should read --*Protocols in*--.
Line 65, "Chomezynski P," should read --Chomczynski P,--.

Column 137,
Line 17, "Obno et al." should read --Ohno et al.--.

Column 138,
Line 3, "(11997)" should read --(1997)--.